US010550401B2

(12) United States Patent
Flasinski et al.

(10) Patent No.: US 10,550,401 B2
(45) Date of Patent: Feb. 4, 2020

(54) PLANT REGULATORY ELEMENTS AND USES THEREOF

(71) Applicant: Monsanto Technology LLC, St. Louis, MO (US)

(72) Inventors: Stanislaw Flasinski, Ballwin, MO (US); Barrett C. Foat, St. Louis, MO (US); Mohammed Oufattole, Wildwood, MO (US); Randall W. Shultz, St. Louis, MO (US); Xiaoping Wei, St. Louis, MO (US); Wei Wu, Chesterfield, MO (US); Shiaw-Pyng Yang, St. Louis, MO (US)

(73) Assignee: Monsanto Technology LLC, St. Louis, MO (US)

( * ) Notice: Subject to any disclaimer, the term of this patent is extended or adjusted under 35 U.S.C. 154(b) by 29 days.

(21) Appl. No.: 15/802,843

(22) Filed: Nov. 3, 2017

(65) Prior Publication Data

US 2018/0148731 A1 May 31, 2018

Related U.S. Application Data

(62) Division of application No. 14/117,342, filed as application No. PCT/US2012/037561 on May 11, 2012, now Pat. No. 9,845,477.

(60) Provisional application No. 61/485,876, filed on May 13, 2011.

(51) Int. Cl.
*C12N 15/82* (2006.01)

(52) U.S. Cl.
CPC ................................ *C12N 15/8216* (2013.01)

(58) Field of Classification Search
None
See application file for complete search history.

(56) References Cited

U.S. PATENT DOCUMENTS

2004/0055039 A1 3/2004 Yamagata et al.
2010/0058495 A1 3/2010 Abbitt
2012/0084885 A1 4/2012 Alexandrov et al.

FOREIGN PATENT DOCUMENTS

| | | | |
|---|---|---|---|
| CN | 101880657 A | | 11/2010 |
| CN | 101952435 A | | 1/2011 |
| CN | 102016049 A | | 4/2011 |
| JP | 2001-346580 A | | 12/2001 |
| JP | 2003-516753 | | 4/2006 |
| WO | WO 01/44457 | * | 6/2001 |
| WO | WO 2001/044457 | | 6/2001 |
| WO | WO 2005/098007 | | 10/2005 |
| WO | WO 2006/039449 | | 4/2006 |

OTHER PUBLICATIONS

Dolferus et al. (1994) Plant Physiol 105:1075-87.*
Donald & Cashmore (1990) EMBO J 9:1717-26.*
Kim et al. (1994) Plant Mol Biol 24:105-17.*
Potenza et al. (2004) In Vitro Cell Dev Biol Plant 40:1-22.*
Saha et al. (2007) in Silico Biol 7(1):7-19.*
Liu et al. (2013) "Advanced genetic tools for plant biotechnology," Nat Rev Genet 14:781-93.*
Cho & Cosgrove (2002) Plant Cell 14:3237-53.*
Callis et al., "Introns increase gene expression in cultured maize cells," *Genes Dev.* 1:1183-1200, 1987.
Chee et al., "Expression of a bean storage protein 'phaseolin minigene' in foreign plant tissues," *Gene* 41:47-57, 1986.
Cho and Cosgrove, *Plant Cell* 14:3237-53 (2002).
Christiansen et al., "Maize polyubiquitin genes: structure, thermal perturbation of expression and transcript splicing, and promoter activity following transfer to protoplasts by electroporation," *Plant Mol. Biol.* 18:675-689, 1992.
Clancy et al., "Splicing of the maize Sh1 first intron is essential for enhancement of gene expression, and a T-rich motif increases expression without affecting splicing," *Plant Physiol.* 130(2):918-929, 2002.
Dean et al., "Sequences downstream of translation start regulate quantitative expression of two petunia rbcS genes," *Plant Cell* 1(2):201-208, 1989.
Dolferus et al., *Plant Physiol.* 105:1075-87 (1994).
Donald & Cashmore, EMBO J. 9:1717-26 (1990).
International Preliminary Report on Patentability regarding PCT Application No. PCT/US2012/037561, dated Nov. 19, 2013.
International Search Report regarding PCT Application No. PCT/US2012/037561, dated Sep. 12, 2012.
Jeon et al., "Tissue-preferential expression of a rice alpha-tubulin gene, OsTubA1, mediated by the first intron," *Plant Physiol.* 123(3):1005-1014, 2000.
Kim et al., Plant Mol. Biol. 24:105-17 (1994).
Kuhlemeier et al., "Upstream sequences determine the difference in transcript abundance of pea rbcS genes," *Mol. Gen. Genet.* 212:405-411, 1988.
Lasserre et al., "Differential activation of two ACC oxidase gene promoters from melon during plant development and in response to pathogen attack," *Mol. Gen. Genet.* 256(3):211-222, 1997.
Leon et al., "Transient gene expression in protoplasts of *Phaseolus vulgaris* isolated from a cell suspension culture," *Plant Physiol.* 95(3):968-972, 1991.
Loganantharaj, *Int. J. Bioinf. Res. Appl.* 2:36-51 (2006).
Mascarenhas et al., "Intron-mediated enhancement of heterologous gene expression in maize," *Plant Mol. Biol.* 15(6):913-920, 1990.
Mcelroy et al., "Isolation of an efficient actin promoter for use in rice transformation," *Plant Cell*2(2):163-171, 1990.

(Continued)

*Primary Examiner* — Russell T Boggs
(74) *Attorney, Agent, or Firm* — Dentons US LLP; Carine Doyle

(57) ABSTRACT

The invention provides DNA molecules and constructs, including their nucleotide sequences, useful for modulating gene expression in plants and plant cells. Transgenic plants, plant cells, plant parts, seeds, and commodity products comprising the DNA molecules operably linked to heterologous transcribable polynucleotides are also provided, as are methods of their use.

16 Claims, 6 Drawing Sheets

Specification includes a Sequence Listing.

(56) References Cited

OTHER PUBLICATIONS

Norris et al., "The intron of *Arabidopsis thaliana* polyubiquitin genes is conserved in location and is a quantitative determinant of chimeric gene expression," *Plant Mol. Biol.* 21(5):895-906, 1993.
Piechulla et al., Plant Mol. Biol. 38:655-62 (1998).
Potenza et al., *In Vitro Cell Dev. Biol. Plant* 40:1-22 (2004).
Rose et al., "Introns act post-transcriptionally to increase expression of the *Arabidopsis thaliana* tryptophan pathway gene PAT1," *Plant J.* 11(3):455-464, 1997.
Rose et al., "Intron-mediated enhancement of gene expression independent of unique intron sequences and splicing," *Plant Physiol.* 122(2):535-542, 2000.
Saha et al., *In Silico. Biol.* 7(1):7-19 (2007).
Sherf et al., "Dual-luciferase reporter assay: an advanced co-reporter technology integrating firefly and Renilla luciferase assays," *Promega Notes Magazine* No. 57, p. 2, 1996.
Sinibaldi et al., "Intron splicing and intron-mediated enhanced expression in monocots," *Prog. Nucleic Acid Res. Mol. Biol.* (42):229-257, 1992.
Vancanneyt et al., "Construction of an intron-containing marker gene: splicing of the intron in transgenic plants and its use in monitoring early events in Agrobacterium-mediated plant transformation," *Mol. Gen. Genet.* 220(2):245-250, 1990.
Vasil et al., "Increased gene expression by the first intron of maize shrunken-1 locus in grass species," *Plant Physiol.* 91(4):1575-1579, 1989.
Welsch et al., Planta 216:523-34 (2003).
Xu et al., "Rice triosephosphate isomerase gene 5' sequence directs β-glucuronidase activity in transgenic tobacco but requires an intron for expression in rice," *Plant Physiol.* 106(2):459-467, 1994.
Yamagata et al., "TGTCACA motif is a novel cis-regulatory enhancer element involved in fruit-specific expression of the cucumisin gene," *J. Biol. Chem.* 227(13):11582-11590, 2002.
GenBank Accession No. HN314561, dated Nov. 24, 2010.
GenBank Accession No. JG468661, dated Mar. 16, 2011.
GenBank Accession No. HN298588, dated Nov. 24, 2010.
GenBank Accession No. JG469358, dated Mar. 16, 2011.
GenBank Accession No. HN327993, dated Nov. 24, 2010.
GenBank Accession No. JG467489, dated Mar. 16, 2011.
GenBank Accession No. HN319913, dated Nov. 24, 2010.
GenBank Accession No. JG480182, dated Mar. 16, 2011.
Office Action regarding Chilean Application No. 201601540, dated Jun. 14, 2017.
GenBank Accession No. LN713263, dated Mar. 5, 2015.
Office Action regarding Eurasian Application No. 201690416, dated Jul. 28, 2017.
GenBank Accession No. HN320890, dated Nov. 23, 2010.
USPTO Written Description Guidelines. (2008).
China Office Action and Search Report regarding China Application No. 201710186179.8, dated Nov. 7, 2019, 13 pages.

* cited by examiner

```
P-CUCme.Ubq1-1:1:15 (SEQ ID NO: 2)     ATCTGAAAGGAACACCTAGCAAGGGGCTACTCTACAAGCATACTAAGTCTACAAAGCTAG
P-CUCme.Ubq1-1:1:16 (SEQ ID NO: 6)     ------------------------------------------------------------
P-CUCme.Ubq1-1:1:17 (SEQ ID NO: 8)     ------------------------------------------------------------
P-CUCme.Ubq1-1:1:18 (SEQ ID NO: 10)    ------------------------------------------------------------
P-CUCme.Ubq1-1:1:19 (SEQ ID NO: 12)    ------------------------------------------------------------

P-CUCme.Ubq1-1:1:15 (SEQ ID NO: 2)     AGTTGTATGGTTATGCAGAAGACCTGGACAAAAGAAGATCACTCGCTGCTTTTACTTTTA
P-CUCme.Ubq1-1:1:16 (SEQ ID NO: 6)     ------------------------------------------------------------
P-CUCme.Ubq1-1:1:17 (SEQ ID NO: 8)     ------------------------------------------------------------
P-CUCme.Ubq1-1:1:18 (SEQ ID NO: 10)    ------------------------------------------------------------
P-CUCme.Ubq1-1:1:19 (SEQ ID NO: 12)    ------------------------------------------------------------

P-CUCme.Ubq1-1:1:15 (SEQ ID NO: 2)     TCCTAAGAGGAAATGTGATTTTATGGAAGTTTAACCTATAGCCTGTAGTGGCACTATTCA
P-CUCme.Ubq1-1:1:16 (SEQ ID NO: 6)     ------------------------------------------------------------
P-CUCme.Ubq1-1:1:17 (SEQ ID NO: 8)     ------------------------------------------------------------
P-CUCme.Ubq1-1:1:18 (SEQ ID NO: 10)    ------------------------------------------------------------
P-CUCme.Ubq1-1:1:19 (SEQ ID NO: 12)    ------------------------------------------------------------

P-CUCme.Ubq1-1:1:15 (SEQ ID NO: 2)     CAACAAAAGTAAAGTTTATAGCCATGACTGAAGTTGTTAAAGAAGTCGTCTGGCTAAAAG
P-CUCme.Ubq1-1:1:16 (SEQ ID NO: 6)     ------------------------------------------------------------
P-CUCme.Ubq1-1:1:17 (SEQ ID NO: 8)     ------------------------------------------------------------
P-CUCme.Ubq1-1:1:18 (SEQ ID NO: 10)    ------------------------------------------------------------
P-CUCme.Ubq1-1:1:19 (SEQ ID NO: 12)    ------------------------------------------------------------

P-CUCme.Ubq1-1:1:15 (SEQ ID NO: 2)     GACTACTTGAAGAACTTGGCTTCTTTTAACAGTCAGTAAACATCATGTGTGATAGTTAAA
P-CUCme.Ubq1-1:1:16 (SEQ ID NO: 6)     ------------------------------------------------------------
P-CUCme.Ubq1-1:1:17 (SEQ ID NO: 8)     ------------------------------------------------------------
P-CUCme.Ubq1-1:1:18 (SEQ ID NO: 10)    ------------------------------------------------------------
P-CUCme.Ubq1-1:1:19 (SEQ ID NO: 12)    ------------------------------------------------------------

P-CUCme.Ubq1-1:1:15 (SEQ ID NO: 2)     GTGCAATACACTTGTCTAAAAATCTGCAATATCACGAAAGAACTAAGCATATTGATGTGA
P-CUCme.Ubq1-1:1:16 (SEQ ID NO: 6)     ------------------------------------------------------------
P-CUCme.Ubq1-1:1:17 (SEQ ID NO: 8)     ------------------------------------------------------------
P-CUCme.Ubq1-1:1:18 (SEQ ID NO: 10)    ------------------------------------------------------------
P-CUCme.Ubq1-1:1:19 (SEQ ID NO: 12)    ------------------------------------------------------------
```

FIG. 1a

```
P-CUCme.Ubq1-1:1:15 (SEQ ID NO: 2)      AGCTATATGTCATTAGAGAAGTCATAGCAAAGAGAAAAGTAACAGTATCAAAGGTTCAGA
P-CUCme.Ubq1-1:1:16 (SEQ ID NO: 6)      ------------------------------------------------------------
P-CUCme.Ubq1-1:1:17 (SEQ ID NO: 8)      ------------------------------------------------------------
P-CUCme.Ubq1-1:1:18 (SEQ ID NO: 10)     ------------------------------------------------------------
P-CUCme.Ubq1-1:1:19 (SEQ ID NO: 12)     ------------------------------------------------------------

P-CUCme.Ubq1-1:1:15 (SEQ ID NO: 2)      CAAAAGAAAATGCAGCAGATATGTTGACTAAAATAGTTACTAATGCTAAACTCGAGCACT
P-CUCme.Ubq1-1:1:16 (SEQ ID NO: 6)      ------------------------------------------------------------
P-CUCme.Ubq1-1:1:17 (SEQ ID NO: 8)      ------------------------------------------------------------
P-CUCme.Ubq1-1:1:18 (SEQ ID NO: 10)     ------------------------------------------------------------
P-CUCme.Ubq1-1:1:19 (SEQ ID NO: 12)     ------------------------------------------------------------

P-CUCme.Ubq1-1:1:15 (SEQ ID NO: 2)      GCCTACAGTTGCTCAAGGTAATAGACTACTTAAAAGAATAGAATCAGAAGAAATAGTCAT
P-CUCme.Ubq1-1:1:16 (SEQ ID NO: 6)      ------------------------------------------------------------
P-CUCme.Ubq1-1:1:17 (SEQ ID NO: 8)      ------------------------------------------------------------
P-CUCme.Ubq1-1:1:18 (SEQ ID NO: 10)     ------------------------------------------------------------
P-CUCme.Ubq1-1:1:19 (SEQ ID NO: 12)     ------------------------------------------------------------

P-CUCme.Ubq1-1:1:15 (SEQ ID NO: 2)      TGGTAGCAATAAAATTCAAGGTGGAGGATTGTTAAAAAGAAGAGTGAATTTTATTACTTA
P-CUCme.Ubq1-1:1:16 (SEQ ID NO: 6)      ------------------------------------------------------------
P-CUCme.Ubq1-1:1:17 (SEQ ID NO: 8)      ------------------------------------------------------------
P-CUCme.Ubq1-1:1:18 (SEQ ID NO: 10)     ------------------------------------------------------------
P-CUCme.Ubq1-1:1:19 (SEQ ID NO: 12)     ------------------------------------------------------------

P-CUCme.Ubq1-1:1:15 (SEQ ID NO: 2)      AAGAAAATCTCGGTGAAACTCGAAAGATCTCGATTCGAAACTCTATTGCTTAAGAACCTG
P-CUCme.Ubq1-1:1:16 (SEQ ID NO: 6)      ---------TCGGTGAAACTCGAAAGATCTCGATTCGAAACTCTATTGCTTAAGAACCTG
P-CUCme.Ubq1-1:1:17 (SEQ ID NO: 8)      ------------------------------------------------------------
P-CUCme.Ubq1-1:1:18 (SEQ ID NO: 10)     ------------------------------------------------------------
P-CUCme.Ubq1-1:1:19 (SEQ ID NO: 12)     ------------------------------------------------------------

P-CUCme.Ubq1-1:1:15 (SEQ ID NO: 2)      GTGAAGCTCGAGAGATCTTGATACAATCCCAGTGCCCTAACTCTTCAACAAGCTAAGCAA
P-CUCme.Ubq1-1:1:16 (SEQ ID NO: 6)      GTGAAGCTCGAGAGATCTTGATACAATCCCAGTGCCCTAACTCTTCAACAAGCTAAGCAA
P-CUCme.Ubq1-1:1:17 (SEQ ID NO: 8)      ------------------------------------------------------------
P-CUCme.Ubq1-1:1:18 (SEQ ID NO: 10)     ------------------------------------------------------------
P-CUCme.Ubq1-1:1:19 (SEQ ID NO: 12)     ------------------------------------------------------------
```

FIG. 1b

```
P-CUCme.Ubq1-1:1:15 (SEQ ID NO: 2)     GTTGTACTGTGGGGCTCAATCTCGGTTCAATCTCGACGCACCTGATGCTTTGTTCCCTGT
P-CUCme.Ubq1-1:1:16 (SEQ ID NO: 6)     GTTGTACTGTGGGGCTCAATCTCGGTTCAATCTCGACGCACCTGATGCTTTGTTCCCTGT
P-CUCme.Ubq1-1:1:17 (SEQ ID NO: 8)     ------------------------------------------------------------
P-CUCme.Ubq1-1:1:18 (SEQ ID NO: 10)    ------------------------------------------------------------
P-CUCme.Ubq1-1:1:19 (SEQ ID NO: 12)    ------------------------------------------------------------

P-CUCme.Ubq1-1:1:15 (SEQ ID NO: 2)     CTACTCGATGAAGAAGCAATTACTTCTCAGGACAACTCGGTACCCCTAAATACAGATTTT
P-CUCme.Ubq1-1:1:16 (SEQ ID NO: 6)     CTACTCGATGAAGAAGCAATTACTTCTCAGGACAACTCGGTACCCCTAAATACAGATTTT
P-CUCme.Ubq1-1:1:17 (SEQ ID NO: 8)     ------------------------------------------------------------
P-CUCme.Ubq1-1:1:18 (SEQ ID NO: 10)    ------------------------------------------------------------
P-CUCme.Ubq1-1:1:19 (SEQ ID NO: 12)    ------------------------------------------------------------

P-CUCme.Ubq1-1:1:15 (SEQ ID NO: 2)     GAGCTTCGTGATCCTACAACTGAAATCAAATAGAAAAACTAATAAGTTAGTTAGAGTTTG
P-CUCme.Ubq1-1:1:16 (SEQ ID NO: 6)     GAGCTTCGTGATCCTACAACTGAAATCAAATAGAAAAACTAATAAGTTAGTTAGAGTTTG
P-CUCme.Ubq1-1:1:17 (SEQ ID NO: 8)     ------------------------------------------------------------
P-CUCme.Ubq1-1:1:18 (SEQ ID NO: 10)    ------------------------------------------------------------
P-CUCme.Ubq1-1:1:19 (SEQ ID NO: 12)    ------------------------------------------------------------

P-CUCme.Ubq1-1:1:15 (SEQ ID NO: 2)     TTATATTTACTGCCATTAAATAACTCTGTAATGTAAATAATAAACCATTTAACTCAATAT
P-CUCme.Ubq1-1:1:16 (SEQ ID NO: 6)     TTATATTTACTGCCATTAAATAACTCTGTAATGTAAATAATAAACCATTTAACTCAATAT
P-CUCme.Ubq1-1:1:17 (SEQ ID NO: 8)     ------------------------------------------------------------
P-CUCme.Ubq1-1:1:18 (SEQ ID NO: 10)    ------------------------------------------------------------
P-CUCme.Ubq1-1:1:19 (SEQ ID NO: 12)    ------------------------------------------------------------

P-CUCme.Ubq1-1:1:15 (SEQ ID NO: 2)     GAAATATAGAATGAGAAAAAGAAAAAGAAAAAGTTAAAGAGAGAGAGGAAGAAAACTCAT
P-CUCme.Ubq1-1:1:16 (SEQ ID NO: 6)     GAAATATAGAATGAGAAAAAGAAAAAGAAAAAGTTAAAGAGAGAGAGGAAGAAAACTCAT
P-CUCme.Ubq1-1:1:17 (SEQ ID NO: 8)     ------------------------------------------------------------
P-CUCme.Ubq1-1:1:18 (SEQ ID NO: 10)    ------------------------------------------------------------
P-CUCme.Ubq1-1:1:19 (SEQ ID NO: 12)    ------------------------------------------------------------

P-CUCme.Ubq1-1:1:15 (SEQ ID NO: 2)     TTTCAAATTCTCTATACTTGTTTGATCCTTGAATAAGTTGAATAAAAGCTCTATGGCGGC
P-CUCme.Ubq1-1:1:16 (SEQ ID NO: 6)     TTTCAAATTCTCTATACTTGTTTGATCCTTGAATAAGTTGAATAAAAGCTCTATGGCGGC
P-CUCme.Ubq1-1:1:17 (SEQ ID NO: 8)     ------------------------------------------------------------
P-CUCme.Ubq1-1:1:18 (SEQ ID NO: 10)    ------------------------------------------------------------
P-CUCme.Ubq1-1:1:19 (SEQ ID NO: 12)    ------------------------------------------------------------
```

FIG. 1c

```
P-CUCme.Ubq1-1:1:15 (SEQ ID NO: 2)     TTCAAAGTGGATGTAGGCACTATTAGTCGAACCACAATAAATTTGTTATGTTCTTTTGCT
P-CUCme.Ubq1-1:1:16 (SEQ ID NO: 6)     TTCAAAGTGGATGTAGGCACTATTAGTCGAACCACAATAAATTTGTTATGTTCTTTTGCT
P-CUCme.Ubq1-1:1:17 (SEQ ID NO: 8)     ------------------------AGTCGAACCACAATAAATTTGTTATGTTCTTTTGCT
P-CUCme.Ubq1-1:1:18 (SEQ ID NO: 10)    ------------------------------------------------------------
P-CUCme.Ubq1-1:1:19 (SEQ ID NO: 12)    ------------------------------------------------------------

P-CUCme.Ubq1-1:1:15 (SEQ ID NO: 2)     ATTCCTTGTAATCTCCATAAATATTTTCTTACTAAGCTCTAGAAATCTGCTTGTCAAGAG
P-CUCme.Ubq1-1:1:16 (SEQ ID NO: 6)     ATTCCTTGTAATCTCCATAAATATTTTCTTACTAAGCTCTAGAAATCTGCTTGTCAAGAG
P-CUCme.Ubq1-1:1:17 (SEQ ID NO: 8)     ATTCCTTGTAATCTCCATAAATATTTTCTTACTAAGCTCTAGAAATCTGCTTGTCAAGAG
P-CUCme.Ubq1-1:1:18 (SEQ ID NO: 10)    ------------------------------------------------------------
P-CUCme.Ubq1-1:1:19 (SEQ ID NO: 12)    ------------------------------------------------------------

P-CUCme.Ubq1-1:1:15 (SEQ ID NO: 2)     ATTAGGTATCATTTATGCCTTTTATATTTCCTTTCGGTTGCATATCTTGAGCTAGTTAAG
P-CUCme.Ubq1-1:1:16 (SEQ ID NO: 6)     ATTAGGTATCATTTATGCCTTTTATATTTCCTTTCGGTTGCATATCTTGAGCTAGTTAAG
P-CUCme.Ubq1-1:1:17 (SEQ ID NO: 8)     ATTAGGTATCATTTATGCCTTTTATATTTCCTTTCGGTTGCATATCTTGAGCTAGTTAAG
P-CUCme.Ubq1-1:1:18 (SEQ ID NO: 10)    ------------------------------------------------------------
P-CUCme.Ubq1-1:1:19 (SEQ ID NO: 12)    ------------------------------------------------------------

P-CUCme.Ubq1-1:1:15 (SEQ ID NO: 2)     ATCGAGAGGTTACTGTTGTTGAAACCGAGATTAGTATCTTTGGATTAACACGTGCCTACC
P-CUCme.Ubq1-1:1:16 (SEQ ID NO: 6)     ATCGAGAGGTTACTGTTGTTGAAACCGAGATTAGTATCTTTGGATTAACACGTGCCTACC
P-CUCme.Ubq1-1:1:17 (SEQ ID NO: 8)     ATCGAGAGGTTACTGTTGTTGAAACCGAGATTAGTATCTTTGGATTAACACGTGCCTACC
P-CUCme.Ubq1-1:1:18 (SEQ ID NO: 10)    ------------------------------------------------------------
P-CUCme.Ubq1-1:1:19 (SEQ ID NO: 12)    ------------------------------------------------------------

P-CUCme.Ubq1-1:1:15 (SEQ ID NO: 2)     AAAATTTGAAATTTTGTATTTACCCCATTCATTGGATAATAAGCAATTCTTATAGTGTTA
P-CUCme.Ubq1-1:1:16 (SEQ ID NO: 6)     AAAATTTGAAATTTTGTATTTACCCCATTCATTGGATAATAAGCAATTCTTATAGTGTTA
P-CUCme.Ubq1-1:1:17 (SEQ ID NO: 8)     AAAATTTGAAATTTTGTATTTACCCCATTCATTGGATAATAAGCAATTCTTATAGTGTTA
P-CUCme.Ubq1-1:1:18 (SEQ ID NO: 10)    ------------------------------------------------------------
P-CUCme.Ubq1-1:1:19 (SEQ ID NO: 12)    ------------------------------------------------------------

P-CUCme.Ubq1-1:1:15 (SEQ ID NO: 2)     TCAATTAAACTCCTATAAAGTGTAATAATTGAATCCATGAACTATTTTCATATGTAATCT
P-CUCme.Ubq1-1:1:16 (SEQ ID NO: 6)     TCAATTAAACTCCTATAAAGTGTAATAATTGAATCCATGAACTATTTTCATATGTAATCT
P-CUCme.Ubq1-1:1:17 (SEQ ID NO: 8)     TCAATTAAACTCCTATAAAGTGTAATAATTGAATCCATGAACTATTTTCATATGTAATCT
P-CUCme.Ubq1-1:1:18 (SEQ ID NO: 10)    ------------------------------------------------------------
P-CUCme.Ubq1-1:1:19 (SEQ ID NO: 12)    ------------------------------------------------------------
```

FIG. 1d

```
P-CUCme.Ubq1-1:1:15 (SEQ ID NO: 2)     TAATAAAATGAATTTAGAAGTTTAATTAAAATAATATATTTTGTATGCTATTTTTCAAAG
P-CUCme.Ubq1-1:1:16 (SEQ ID NO: 6)     TAATAAAATGAATTTAGAAGTTTAATTAAAATAATATATTTTGTATGCTATTTTTCAAAG
P-CUCme.Ubq1-1:1:17 (SEQ ID NO: 8)     TAATAAAATGAATTTAGAAGTTTAATTAAAATAATATATTTTGTATGCTATTTTTCAAAG
P-CUCme.Ubq1-1:1:18 (SEQ ID NO: 10)    ------------------------------------------------------------
P-CUCme.Ubq1-1:1:19 (SEQ ID NO: 12)    ------------------------------------------------------------

P-CUCme.Ubq1-1:1:15 (SEQ ID NO: 2)     TTTGAAGAATGTGTTAATTGATACACATACAAAAAATCTAGGTTTTACATGAAAAACTAT
P-CUCme.Ubq1-1:1:16 (SEQ ID NO: 6)     TTTGAAGAATGTGTTAATTGATACACATACAAAAAATCTAGGTTTTACATGAAAAACTAT
P-CUCme.Ubq1-1:1:17 (SEQ ID NO: 8)     TTTGAAGAATGTGTTAATTGATACACATACAAAAAATCTAGGTTTTACATGAAAAACTAT
P-CUCme.Ubq1-1:1:18 (SEQ ID NO: 10)    ------------------------------------------------------------
P-CUCme.Ubq1-1:1:19 (SEQ ID NO: 12)    ------------------------------------------------------------

P-CUCme.Ubq1-1:1:15 (SEQ ID NO: 2)     GGAAGTGAAAGATAGCATCTAATATTTTATGACACAAAATGCAAACTAATATATAAAGGA
P-CUCme.Ubq1-1:1:16 (SEQ ID NO: 6)     GGAAGTGAAAGATAGCATCTAATATTTTATGACACAAAATGCAAACTAATATATAAAGGA
P-CUCme.Ubq1-1:1:17 (SEQ ID NO: 8)     GGAAGTGAAAGATAGCATCTAATATTTTATGACACAAAATGCAAACTAATATATAAAGGA
P-CUCme.Ubq1-1:1:18 (SEQ ID NO: 10)    -----------------------------TGACACAAAATGCAAACTAATATATAAAGGA
P-CUCme.Ubq1-1:1:19 (SEQ ID NO: 12)    ------------------------------------------------------------

P-CUCme.Ubq1-1:1:15 (SEQ ID NO: 2)     TTTAATTAATTTTTATAGGTTTCAAATTTGTTAGACTTGTCAAATACAAAATTTTATTGA
P-CUCme.Ubq1-1:1:16 (SEQ ID NO: 6)     TTTAATTAATTTTTATAGGTTTCAAATTTGTTAGACTTGTCAAATACAAAATTTTATTGA
P-CUCme.Ubq1-1:1:17 (SEQ ID NO: 8)     TTTAATTAATTTTTATAGGTTTCAAATTTGTTAGACTTGTCAAATACAAAATTTTATTGA
P-CUCme.Ubq1-1:1:18 (SEQ ID NO: 10)    TTTAATTAATTTTTATAGGTTTCAAATTTGTTAGACTTGTCAAATACAAAATTTTATTGA
P-CUCme.Ubq1-1:1:19 (SEQ ID NO: 12)    ------------------------------------------------------------

P-CUCme.Ubq1-1:1:15 (SEQ ID NO: 2)     ACCAAATACATACAAACATCAAAATTAAGAACAGAAAATCTAAATTCAAATGAAATTTAT
P-CUCme.Ubq1-1:1:16 (SEQ ID NO: 6)     ACCAAATACATACAAACATCAAAATTAAGAACAGAAAATCTAAATTCAAATGAAATTTAT
P-CUCme.Ubq1-1:1:17 (SEQ ID NO: 8)     ACCAAATACATACAAACATCAAAATTAAGAACAGAAAATCTAAATTCAAATGAAATTTAT
P-CUCme.Ubq1-1:1:18 (SEQ ID NO: 10)    ACCAAATACATACAAACATCAAAATTAAGAACAGAAAATCTAAATTCAAATGAAATTTAT
P-CUCme.Ubq1-1:1:19 (SEQ ID NO: 12)    ------------------------------------------------------------

P-CUCme.Ubq1-1:1:15 (SEQ ID NO: 2)     TAATAGAAAAATTAGAAAAAAGAAAAAGAAAATAAAAGGAATCGTATTGTTTTTTCCTTC
P-CUCme.Ubq1-1:1:16 (SEQ ID NO: 6)     TAATAGAAAAATTAGAAAAAAGAAAAAGAAAATAAAAGGAATCGTATTGTTTTTTCCTTC
P-CUCme.Ubq1-1:1:17 (SEQ ID NO: 8)     TAATAGAAAAATTAGAAAAAAGAAAAAGAAAATAAAAGGAATCGTATTGTTTTTTCCTTC
P-CUCme.Ubq1-1:1:18 (SEQ ID NO: 10)    TAATAGAAAAATTAGAAAAAAGAAAAAGAAAATAAAAGGAATCGTATTGTTTTTTCCTTC
P-CUCme.Ubq1-1:1:19 (SEQ ID NO: 12)    ------------------------------------------------------------
```

FIG. 1e

```
P-CUCme.Ubq1-1:1:15 (SEQ ID NO: 2)     CTTTTTCCCATTTGAGAGGTGAATAAAGCTAATTGAGCTGCTCTAACTTCCTAATCTTTA
P-CUCme.Ubq1-1:1:16 (SEQ ID NO: 6)     CTTTTTCCCATTTGAGAGGTGAATAAAGCTAATTGAGCTGCTCTAACTTCCTAATCTTTA
P-CUCme.Ubq1-1:1:17 (SEQ ID NO: 8)     CTTTTTCCCATTTGAGAGGTGAATAAAGCTAATTGAGCTGCTCTAACTTCCTAATCTTTA
P-CUCme.Ubq1-1:1:18 (SEQ ID NO: 10)    CTTTTTCCCATTTGAGAGGTGAATAAAGCTAATTGAGCTGCTCTAACTTCCTAATCTTTA
P-CUCme.Ubq1-1:1:19 (SEQ ID NO: 12)    ------------------------------------------------------------

P-CUCme.Ubq1-1:1:15 (SEQ ID NO: 2)     TGCTTTCCCCATAAAGCTTTCCCAACTGCGCGTAATCGTATAAATGGAAAATTGACCTTT
P-CUCme.Ubq1-1:1:16 (SEQ ID NO: 6)     TGCTTTCCCCATAAAGCTTTCCCAACTGCGCGTAATCGTATAAATGGAAAATTGACCTTT
P-CUCme.Ubq1-1:1:17 (SEQ ID NO: 8)     TGCTTTCCCCATAAAGCTTTCCCAACTGCGCGTAATCGTATAAATGGAAAATTGACCTTT
P-CUCme.Ubq1-1:1:18 (SEQ ID NO: 10)    TGCTTTCCCCATAAAGCTTTCCCAACTGCGCGTAATCGTATAAATGGAAAATTGACCTTT
P-CUCme.Ubq1-1:1:19 (SEQ ID NO: 12)    -----------------------------------TCGTATAAATGGAAAATTGACCTTT

P-CUCme.Ubq1-1:1:15 (SEQ ID NO: 2)     CCAACTAGATTCTTCCAGAACTAAACAATACGTAACACGCAAGTAATCAAAGACACGTTT
P-CUCme.Ubq1-1:1:16 (SEQ ID NO: 6)     CCAACTAGATTCTTCCAGAACTAAACAATACGTAACACGCAAGTAATCAAAGACACGTTT
P-CUCme.Ubq1-1:1:17 (SEQ ID NO: 8)     CCAACTAGATTCTTCCAGAACTAAACAATACGTAACACGCAAGTAATCAAAGACACGTTT
P-CUCme.Ubq1-1:1:18 (SEQ ID NO: 10)    CCAACTAGATTCTTCCAGAACTAAACAATACGTAACACGCAAGTAATCAAAGACACGTTT
P-CUCme.Ubq1-1:1:19 (SEQ ID NO: 12)    CCAACTAGATTCTTCCAGAACTAAACAATACGTAACACGCAAGTAATCAAAGACACGTTT

P-CUCme.Ubq1-1:1:15 (SEQ ID NO: 2)     CATTTTCCTATAGAATATTATAGTTATTCGTGATTAACGGAAGTCGGCAATTTTAGGTAT
P-CUCme.Ubq1-1:1:16 (SEQ ID NO: 6)     CATTTTCCTATAGAATATTATAGTTATTCGTGATTAACGGAAGTCGGCAATTTTAGGTAT
P-CUCme.Ubq1-1:1:17 (SEQ ID NO: 8)     CATTTTCCTATAGAATATTATAGTTATTCGTGATTAACGGAAGTCGGCAATTTTAGGTAT
P-CUCme.Ubq1-1:1:18 (SEQ ID NO: 10)    CATTTTCCTATAGAATATTATAGTTATTCGTGATTAACGGAAGTCGGCAATTTTAGGTAT
P-CUCme.Ubq1-1:1:19 (SEQ ID NO: 12)    CATTTTCCTATAGAATATTATAGTTATTCGTGATTAACGGAAGTCGGCAATTTTAGGTAT

P-CUCme.Ubq1-1:1:15 (SEQ ID NO: 2)     AAATACGTGAATTCTCGAGCGCTAATTT
P-CUCme.Ubq1-1:1:16 (SEQ ID NO: 6)     AAATACGTGAATTCTCGAGCGCTAATTT
P-CUCme.Ubq1-1:1:17 (SEQ ID NO: 8)     AAATACGTGAATTCTCGAGCGCTAATTT
P-CUCme.Ubq1-1:1:18 (SEQ ID NO: 10)    AAATACGTGAATTCTCGAGCGCTAATTT
P-CUCme.Ubq1-1:1:19 (SEQ ID NO: 12)    AAATACGTGAATTCTCGAGCGCTAATTT
```

FIG. 1f

PLANT REGULATORY ELEMENTS AND USES THEREOF

REFERENCE TO RELATED APPLICATIONS

This application is a divisional of co-pending U.S. application Ser. No. 14/117,342, filed Oct. 23, 2014, which is a 371 National Stage application of International Application No. PCT/US12/037561, filed May 11, 2012, which claims the benefit of U.S. Provisional Application No. 61/485,876 filed May 13, 2011 each of which is herein incorporated by reference in its entirety.

INCORPORATION OF SEQUENCE LISTING

The sequence listing that is contained in the file named "MONS304WO.txt", which is 463 kilobytes (as measured in Microsoft Windows®) and was created on May 9, 2012, is filed herewith by electronic submission and is incorporated by reference herein.

FIELD OF THE INVENTION

The invention relates to the field of plant molecular biology and plant genetic engineering, and DNA molecules useful for modulating gene expression in plants.

BACKGROUND

Regulatory elements are genetic elements that regulate gene activity by modulating the transcription of an operably linked transcribable polynucleotide molecule. Such elements include promoters, leaders, introns, and 3' untranslated regions and are useful in the field of plant molecular biology and plant genetic engineering.

SUMMARY OF THE INVENTION

The present invention provides novel gene regulatory elements such as promoters, leaders and introns derived from *Cucumis melo*, a plant species commonly referred to as muskmelon, for use in plants. The present invention also provides DNA constructs, transgenic plant cells, plants, and seeds comprising the regulatory elements. The sequences may be provided operably linked to a transcribable polynucleotide molecule which may be heterologous with respect to a regulatory sequence provided herein. The present invention also provides methods of making and using the regulatory elements, the DNA constructs comprising the regulatory elements, and the transgenic plant cells, plants, and seeds comprising the regulatory elements operably linked to a transcribable polynucleotide molecule.

Thus, in one aspect, the present invention provides a DNA molecule, such as a transcriptional regulatory expression element group, or promoter, or leader, or intron, comprising a polynucleotide sequence selected from the group consisting of: a) a sequence with at least 85 percent sequence identity to any of SEQ ID NOs: 1-199, 211 and 212; b) a sequence comprising any of SEQ ID NOs: 1-199, 211 and 212; and c) a fragment of any of SEQ ID NOs: 1-199, 211 and 212 exhibiting gene-regulatory activity, wherein said DNA molecule is operably linked to a heterologous transcribable polynucleotide molecule. In specific embodiments, a transcriptional regulatory expression element group, or promoter, or leader, or intron is at least 90 percent, at least 95 percent, at least 98 percent, or at least 99 percent identical to any of SEQ ID NOs: 1-199, 211 and 212. In particular embodiments, the heterologous transcribable polynucleotide molecule comprises a gene of agronomic interest, a gene capable of providing herbicide resistance in plants, or a gene capable of providing plant pest resistance in plants.

The invention also provides a transgenic plant cell containing a DNA molecule such as a transcriptional regulatory expression element group, or promoter, or leader, or intron, comprising a polynucleotide sequence selected from the group consisting of: a) a sequence with at least 85 percent sequence identity to any of SEQ ID NOs: 1-199, 211 and 212; b) a sequence comprising any of SEQ ID NOs: 1-199, 211 and 212; and c) a fragment of any of SEQ ID NOs: 1-199, 211 and 212 exhibiting gene-regulatory activity, wherein said DNA molecule is operably linked to a heterologous transcribable polynucleotide molecule. Further, the transcriptional regulatory expression element group, or promoter, or leader, or intron regulates the expression of a gene. The transgenic plant cell can be a monocotyledonous or dicotyledonous plant cell.

Further provided by the invention is a transgenic plant, or part of the transgenic plant containing a DNA molecule such as a transcriptional regulatory expression element group, or promoter, or leader, or intron, comprising a polynucleotide sequence selected from the group consisting of: a) a sequence with at least 85 percent sequence identity to any of SEQ ID NOs: 1-199, 211 and 212; b) a sequence comprising any of SEQ ID NOs: 1-199, 211 and 212; and c) a fragment of any of SEQ ID NOs: 1-199, 211 and 212 exhibiting gene-regulatory activity, wherein said DNA molecule is operably linked to a heterologous transcribable polynucleotide molecule. In specific embodiments, the transgenic plant may be a progeny plant of any generation that contains the transcriptional regulatory expression element group, or promoter, or leader, or intron.

Still further provided is a transgenic seed containing a DNA molecule such as a transcriptional regulatory expression element group, or promoter, or leader, or intron, comprising a polynucleotide sequence selected from the group consisting of: a) a sequence with at least 85 percent sequence identity to any of SEQ ID NOs: 1-199, 211 and 212; b) a sequence comprising any of SEQ ID NOs: 1-199, 211 and 212; and c) a fragment of any of SEQ ID NOs: 1-199, 211 and 212 exhibiting gene-regulatory activity, wherein said DNA molecule is operably linked to a heterologous transcribable polynucleotide molecule.

In yet another aspect, the invention provides a method of producing a commodity product from the transgenic plant, transgenic plant part or transgenic seed which contains a DNA molecule such as a transcriptional regulatory expression element group, or promoter, or leader, or intron, comprising a polynucleotide sequence selected from the group consisting of: a) a sequence with at least 85 percent sequence identity to any of SEQ ID NOs: 1-199, 211 and 212; b) a sequence comprising any of SEQ ID NOs: 1-199, 211 and 212; and c) a fragment of any of SEQ ID NOs: 1-199, 211 and 212 exhibiting gene-regulatory activity, wherein said DNA molecule is operably linked to a heterologous transcribable polynucleotide molecule. In one embodiment, the commodity product is protein concentrate, protein isolate, grain, starch, seeds, meal, flour, biomass, or seed oil.

In another aspect, the invention provides a commodity product comprising a DNA molecule such as a transcriptional regulatory expression element group, or promoter, or leader, or intron, comprising a polynucleotide sequence selected from the group consisting of: a) a sequence with at least 85 percent sequence identity to any of SEQ ID NOs: 1-199, 211 and 212; b) a sequence comprising any of SEQ ID NOs: 1-199, 211 and 212; and c) a fragment of any of SEQ ID NOs: 1-199, 211 and 212 exhibiting gene-regulatory activity, wherein said DNA molecule is operably linked to a heterologous transcribable polynucleotide molecule.

In still yet another aspect, the invention provides a method of expressing a transcribable polynucleotide molecule in a transgenic plant using a DNA molecule such as a transcriptional regulatory expression element group, or promoter, or leader, or intron which has a DNA sequence which is at least 85 percent identical to that of any of SEQ ID NOs: 1-199, 211 and 212, or contains any of SEQ ID NOs: 1-199, 211 and 212, or consists of a fragment of any of SEQ ID NOs: 1-199, 211 and 212; and cultivating the transgenic plant.

BRIEF DESCRIPTION OF THE SEQUENCES

SEQ ID NOs: 1, 5, 7, 9, 11, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 159, 162, 167, 168, 172, 175, 176, 177, 178, 181, 182, 183, 184, 185, 188, 189, 190, 191, 192, 193, 194, 195, 196, 197, 198, 199, 211 and 212 are *Cucumis* transcriptional regulatory expression element groups or EXP sequences which are comprised of either a promoter element, operably linked to a leader element; or a promoter element, operably linked to a leader element and an intron element, or a promoter element, operably linked to a leader element, operably linked to an intron element, operably linked to a leader element.

SEQ ID NOs: 2, 6, 8, 10, 12, 163 and 169 are promoter elements.

SEQ ID NOs: 3, 164, 166 and 170 are leader sequences.

SEQ ID NOs: 4, 165 and 171 are intron sequences.

SEQ ID NOs: 157, 160, 173, 179 and 186 are sequences wherein a promoter is operably linked to a leader element.

SEQ ID NOs: 158, 161, 174, 180 and 187 are sequences wherein an intron is operably linked to a leader element.

BRIEF DESCRIPTION OF THE DRAWINGS

FIGS. 1*a*-1*f* depict alignment of promoter variant segments corresponding to promoter elements isolated from the *Cucumis melo*. In particular, FIGS. 1*a*-1*f* show alignment of the 2068 bp promoter sequence P-CUCme.Ubq1-1:1:15 (SEQ ID NO: 2), found in the transcriptional regulatory expression element group EXP-CUCme.Ubq1:1:1 (SEQ ID NO: 1), vs. promoter sequences derived via 5' deletions of the promoter, P-CUCme.Ubq1-1:1:15. Deletion, for instance of the 5' end of P-CUCme.Ubq1-1:1:15, produced the promoters, P-CUCme.Ubq1-1:1:16 (SEQ ID NO: 6) a 1459 bp promoter which is found within EXP-CUCme.Ubq1:1:2 (SEQ ID NO: 5); P-CUCme.Ubq1-1:1:17 (SEQ ID NO: 8), a 964 bp sequence comprised within EXP-CUCme.Ubq1:1:3 (SEQ ID NO: 7); P-CUCme.Ubq1-1:1:18 (SEQ ID NO: 10), a 479 bp sequence comprised within EXP-CUCme.Ubq1:1:4 (SEQ ID NO: 9); and P-CUCme.Ubq1-1:1:19 (SEQ ID NO: 12), a 173 bp sequence comprised within EXP-CUCme.Ubq1:1:5 (SEQ ID NO: 11).

DETAILED DESCRIPTION OF THE INVENTION

The invention disclosed herein provides polynucleotide molecules obtained from *Cucumis melo* having beneficial gene regulatory activity. The design, construction, and use of these polynucleotide molecules are described. The nucleotide sequences of these polynucleotide molecules are provided among SEQ ID NOs: 1-199, 211 and 212. These polynucleotide molecules are, for instance, capable of affecting the expression of an operably linked transcribable polynucleotide molecule in plant tissues, and therefore selectively regulating gene expression, or activity of an encoded gene product, in transgenic plants. The present invention also provides methods of modifying, producing, and using the same. The invention also provides compositions, transformed host cells, transgenic plants, and seeds containing the promoters and/or other disclosed nucleotide sequences, and methods for preparing and using the same.

The following definitions and methods are provided to better define the present invention and to guide those of ordinary skill in the art in the practice of the present invention. Unless otherwise noted, terms are to be understood according to conventional usage by those of ordinary skill in the relevant art.

DNA Molecules

As used herein, the term “DNA” or “DNA molecule” refers to a double-stranded DNA molecule of genomic or synthetic origin, i.e. a polymer of deoxyribonucleotide bases or a polynucleotide molecule, read from the 5' (upstream) end to the 3' (downstream) end. As used herein, the term “DNA sequence” refers to the nucleotide sequence of a DNA molecule.

As used herein, the term “isolated DNA molecule” refers to a DNA molecule at least partially separated from other molecules normally associated with it in its native or natural state. In one embodiment, the term “isolated” refers to a DNA molecule that is at least partially separated from some of the nucleic acids which normally flank the DNA molecule in its native or natural state. Thus, DNA molecules fused to regulatory or coding sequences with which they are not normally associated, for example as the result of recombinant techniques, are considered isolated herein. Such molecules are considered isolated when integrated into the chromosome of a host cell or present in a nucleic acid solution with other DNA molecules, in that they are not in their native state.

Any number of methods are known in the to isolate and manipulate a DNA molecule, or fragment thereof, disclosed in the present invention. For example, PCR (polymerase chain reaction) technology can be used to amplify a particular starting DNA molecule and/or to produce variants of the original molecule. DNA molecules, or fragment thereof, can also be obtained by other techniques such as by directly synthesizing the fragment by chemical means, as is commonly practiced by using an automated oligonucleotide synthesizer.

As used herein, the term “sequence identity” refers to the extent to which two optimally aligned polynucleotide sequences or two optimally aligned polypeptide sequences are identical. An optimal sequence alignment is created by manually aligning two sequences, e.g. a reference sequence and another sequence, to maximize the number of nucleotide matches in the sequence alignment with appropriate internal nucleotide insertions, deletions, or gaps. As used herein, the term "reference sequence" refers to a sequence provided as the polynucleotide sequences of SEQ ID NOs: 1-199, 211 and 212.

As used herein, the term "percent sequence identity" or "percent identity" or "% identity" is the identity fraction times 100. The "identity fraction" for a sequence optimally aligned with a reference sequence is the number of nucleotide matches in the optimal alignment, divided by the total number of nucleotides in the reference sequence, e.g. the total number of nucleotides in the full length of the entire reference sequence. Thus, one embodiment of the invention is a DNA molecule comprising a sequence that when optimally aligned to a reference sequence, provided herein as SEQ ID NOs: 1-199, 211 and 212, has at least about 85 percent identity at least about 90 percent identity at least about 95 percent identity, at least about 96 percent identity, at least about 97 percent identity, at least about 98 percent identity, or at least about 99 percent identity to the reference sequence. In particular embodiments such sequences may be defined as having gene-regulatory activity or encoding a peptide that functions to localize an operably linked polypeptide within a cell.

Regulatory Elements

A regulatory element is a DNA molecule having gene regulatory activity, i.e. one that has the ability to affect the transcription and/or translation of an operably linked transcribable polynucleotide molecule. The term "gene regulatory activity" thus refers to the ability to affect the expression pattern of an operably linked transcribable polynucleotide molecule by affecting the transcription and/or translation of that operably linked transcribable polynucleotide molecule. As used herein, a transcriptional regulatory expression element group (EXP) may be comprised of expression elements, such as enhancers, promoters, leaders and introns, operably linked. Thus a transcriptional regulatory expression element group may be comprised, for instance, of a promoter operably linked 5' to a leader sequence, which is in turn operably linked 5' to an intron sequence. The intron sequence may be comprised of a sequence beginning at the point of the first intron/exon splice junction of the native sequence and further may be comprised of a small leader fragment comprising the second intron/exon splice junction so as to provide for proper intron/exon processing to facilitate transcription and proper processing of the resulting transcript. Leaders and introns may positively affect transcription of an operably linked transcribable polynucleotide molecule as well as translation of the resulting transcribed RNA. The pre-processed RNA molecule comprises leaders and introns, which may affect the post-transcriptional processing of the transcribed RNA and/or the export of the transcribed RNA molecule from the cell nucleus into the cytoplasm. Following post-transcriptional processing of the transcribed RNA molecule, the leader sequence may be retained as part of the final messenger RNA and may positively affect the translation of the messenger RNA molecule.

Regulatory elements such as promoters, leaders, introns, and transcription termination regions are DNA molecules that have gene regulatory activity and play an integral part in the overall expression of genes in living cells. The term "regulatory element" refers to a DNA molecule having gene regulatory activity, i.e. one that has the ability to affect the transcription and/or translation of an operably linked transcribable polynucleotide molecule. Isolated regulatory elements, such as promoters and leaders that function in plants are therefore useful for modifying plant phenotypes through the methods of genetic engineering.

Regulatory elements may be characterized by their expression pattern effects (qualitatively and/or quantitatively), e.g. positive or negative effects and/or constitutive or other effects such as by their temporal, spatial, developmental, tissue, environmental, physiological, pathological, cell cycle, and/or chemically responsive expression pattern, and any combination thereof, as well as by quantitative or qualitative indications. A promoter is useful as a regulatory element for modulating the expression of an operably linked transcribable polynucleotide molecule.

As used herein, a "gene expression pattern" is any pattern of transcription of an operably linked DNA molecule into a transcribed RNA molecule. The transcribed RNA molecule may be translated to produce a protein molecule or may provide an antisense or other regulatory RNA molecule, such as a dsRNA, a tRNA, an rRNA, a miRNA, and the like.

As used herein, the term "protein expression" is any pattern of translation of a transcribed RNA molecule into a protein molecule. Protein expression may be characterized by its temporal, spatial, developmental, or morphological qualities as well as by quantitative or qualitative indications.

As used herein, the term "promoter" refers generally to a DNA molecule that is involved in recognition and binding of RNA polymerase II and other proteins (trans-acting transcription factors) to initiate transcription. A promoter may be initially isolated from the 5' untranslated region (5' UTR) of a genomic copy of a gene. Alternately, promoters may be synthetically produced or manipulated DNA molecules. Promoters may also be chimeric, that is a promoter produced through the fusion of two or more heterologous DNA molecules. Promoters useful in practicing the present invention include any of SEQ ID NOs: 2, 6, 8, 10, 12, 163 and 169, or the promoter elements comprised within any of SEQ ID NOs: 13 through 199, 211 and 212, or fragments or variants thereof. In specific embodiments of the invention, such molecules and any variants or derivatives thereof as described herein, are further defined as comprising promoter activity, i.e., are capable of acting as a promoter in a host cell, such as in a transgenic plant. In still further specific embodiments, a fragment may be defined as exhibiting promoter activity possessed by the starting promoter molecule from which it is derived, or a fragment may comprise a "minimal promoter" which provides a basal level of transcription and is comprised of a TATA box or equivalent sequence for recognition and binding of the RNA polymerase II complex for intiation of transcription.

In one embodiment, fragments of a promoter molecule are provided. Promoter fragments provide promoter activity, as described above, and may be useful alone or in combination with other promoters and promoter fragments, such as in constructing chimeric promoters. In specific embodiments, fragments of a promoter are provided comprising at least about 50, 95, 150, 250, 500, 750, or at least about 1000 contiguous nucleotides, or longer, of a polynucleotide molecule having promoter activity disclosed herein.

Compositions derived from any of the promoters presented as SEQ ID NOs: 2, 6, 8, 10, 12, 163 and 169, or the promoter elements comprised within SEQ ID NOs: 13 through 199, 211 and 212, such as internal or 5' deletions, for example, can be produced to improve or alter expression, including by removing elements that have either positive or negative effects on expression; duplicating elements that have positive or negative effects on expression; and/or duplicating or removing elements that have tissue or cell specific effects on expression. Compositions derived from any of the promoters presented as SEQ ID NOs: 2, 6, 8, 10, 12, 163 and 169, or the promoter elements comprised within SEQ ID NOs: 13 through 199, 211 and 212 comprised of 3' deletions in which the TATA box element or equivalent sequence thereof and downstream sequence is removed can be used, for example, to make enhancer elements. Further deletions can be made to remove any elements that have positive or negative; tissue specific; cell specific; or timing specific (such as, but not limited to, circadian rhythms) effects on expression. Any of the promoters presented as SEQ ID NOs: 2, 6, 8, 10, 12, 163 and 169, or the promoter elements comprised within SEQ ID NOs: 13 through 199, 211 and 212, and fragments or enhancers derived there from can be used to make chimeric transcriptional regulatory element compositions comprised of any of the promoters presented as SEQ ID NOs: 2, 6, 8, 10, 12, 163 and 169, or the promoter elements comprised within SEQ ID NOs: 13 through 199, 211 and 212, and the fragments or enhancers derived therefrom operably linked to other enhancers and promoters. The efficacy of the modifications, duplications or deletions described herein on the desired expression aspects of a particular transgene may be tested empirically in stable and transient plant assays, such as those described in the working examples herein, so as to validate the results, which may vary depending upon the changes made and the goal of the change in the starting molecule.

As used herein, the term “leader” refers to a DNA molecule isolated from the untranslated 5' region (5' UTR) of a genomic copy of a gene and defined generally as a nucleotide segment between the transcription start site (TSS) and the protein coding sequence start site. Alternately, leaders may be synthetically produced or manipulated DNA elements. A leader can be used as a 5' regulatory element for modulating expression of an operably linked transcribable polynucleotide molecule. Leader molecules may be used with a heterologous promoter or with their native promoter. Promoter molecules of the present invention may thus be operably linked to their native leader or may be operably linked to a heterologous leader. Leaders useful in practicing the present invention include SEQ ID NOs: 3, 164, 166 and 170, or the leader element comprised within SEQ ID NOs: 13 through 199, 211 and 212, or fragments or variants thereof. In specific embodiments, such sequences may be provided defined as being capable of acting as a leader in a host cell, including, for example, a transgenic plant cell. In one embodiment such sequences are decoded as comprising leader activity.

The leader sequences (5' UTR) presented as SEQ ID NOs: 3, 164, 166 and 170, or the leader element comprised within any of SEQ ID NOs: 13 through 199, 211 and 212 may be comprised of regulatory elements or may adopt secondary structures that can have an effect on transcription or translation of a transgene. The leader sequences presented as SEQ ID NOs: 3, 164, 166 and 170, or the leader element comprised within SEQ ID NOs: 13 through 199, 211 and 212 can be used in accordance with the invention to make chimeric regulatory elements that affect transcription or translation of a transgene. In addition, the leader sequences presented as SEQ ID NOs: 3, 164, 166 and 170, or the leader element comprised within any of SEQ ID NOs: 13 through 199, 211 and 212 can be used to make chimeric leader sequences that affect transcription or translation of a transgene.

The introduction of a foreign gene into a new plant host does not always result in a high expression of the incoming gene. Furthermore, if dealing with complex traits, it is sometimes necessary to modulate several genes with spatially or temporarily different expression pattern. Introns can principally provide such modulation. However, multiple use of the same intron in one transgenic plant has shown to exhibit disadvantages. In those cases it is necessary to have a collection of basic control elements for the construction of appropriate recombinant DNA elements. As the available collection of introns known in the art with expression enhancing properties is limited, alternatives are needed.

Compositions derived from any of the introns presented as SEQ ID NOs: 4, 165 and 171 or the intron element comprised within SEQ ID NOs: 13 through 199, 211 and 212 can be comprised of internal deletions or duplications of cis regulatory elements; and/or alterations of the 5' and 3' sequences comprising the intron/exon splice junctions can be used to improve expression or specificity of expression when operably linked to a promoter+leader or chimeric promoter+leader and coding sequence. Alterations of the 5' and 3' regions comprising the intron/exon splice junction can also be made to reduce the potential for introduction of false start and stop codons being produced in the resulting transcript after processing and splicing of the messenger RNA. The introns can be tested empirically as described in the working examples to determine the intron's effect on expression of a transgene.

In accordance with the invention a promoter or promoter fragment may be analyzed for the presence of known promoter elements, i.e. DNA sequence characteristics, such as a TATA-box and other known transcription factor binding site motifs. Identification of such known promoter elements may be used by one of skill in the art to design variants having a similar expression pattern to the original promoter.

As used herein, the term “enhancer” or “enhancer element” refers to a cis-acting transcriptional regulatory element, a.k.a. cis-element, which confers an aspect of the overall expression pattern, but is usually insufficient alone to drive transcription, of an operably linked polynucleotide sequence. Unlike promoters, enhancer elements do not usually include a transcription start site (TSS) or TATA box or equivalent sequence. A promoter may naturally comprise one or more enhancer elements that affect the transcription of an operably linked polynucleotide sequence. An isolated enhancer element may also be fused to a promoter to produce a chimeric promoter.cis-element, which confers an aspect of the overall modulation of gene expression. A promoter or promoter fragment may comprise one or more enhancer elements that effect the transcription of operably linked genes. Many promoter enhancer elements are believed to bind DNA-binding proteins and/or affect DNA topology, producing local conformations that selectively allow or restrict access of RNA polymerase to the DNA template or that facilitate selective opening of the double helix at the site of transcriptional initiation. An enhancer element may function to bind transcription factors that regulate transcription. Some enhancer elements bind more than one transcription factor, and transcription factors may interact with different affinities with more than one enhancer domain. Enhancer elements can be identified by a number of techniques, including deletion analysis, i.e. deleting one or more nucleotides from the 5' end or internal to a promoter; DNA binding protein analysis using DNase I footprinting, methylation interference, electrophoresis mobility-shift assays, in vivo genomic footprinting by ligation-mediated PCR, and other conventional assays; or by DNA sequence similarity analysis using known cis-element motifs or enhancer elements as a target sequence or target motif with conventional DNA sequence comparison methods, such as BLAST. The fine structure of an enhancer domain can be further studied by mutagenesis (or substitution) of one or more nucleotides or by other conventional methods.

Enhancer elements can be obtained by chemical synthesis or by isolation from regulatory elements that include such elements, and they can be synthesized with additional flanking nucleotides that contain useful restriction enzyme sites to facilitate subsequence manipulation. Thus, the design, construction, and use of enhancer elements according to the methods disclosed herein for modulating the expression of operably linked transcribable polynucleotide molecules are encompassed by the present invention.

In plants, the inclusion of some introns in gene constructs leads to increased mRNA and protein accumulation relative to constructs lacking the intron. This effect has been termed "intron mediated enhancement" (IME) of gene expression (Mascarenhas et al., (1990) *Plant Mol. Biol.* 15:913-920). Introns known to stimulate expression in plants have been identified in maize genes (e.g. tubA1, Adh1, Sh1, Ubi1 (Jeon et al. (2000) *Plant Physiol.* 123:1005-1014; Callis et al. (1987) *Genes Dev.* 1:1183-1200; Vasil et al. (1989) *Plant Physiol.* 91:1575-1579; Christiansen et al. (1992) *Plant Mol. Biol.* 18:675-689) and in rice genes (e.g. salt, tpi: McElroy et al., *Plant Cell* 2:163-171 (1990); Xu et al., *Plant Physiol.* 106:459-467 (1994)). Similarly, introns from dicotyledonous plant genes like those from *petunia* (e.g. rbcS), potato (e.g. st-ls1) and from *Arabidopsis thaliana* (e.g. ubq3 and pat1) have been found to elevate gene expression rates (Dean et al. (1989) *Plant Cell* 1:201-208; Leon et al. (1991) *Plant Physiol.* 95:968-972; Norris et al. (1993) *Plant Mol Biol* 21:895-906; Rose and Last (1997) *Plant J.* 11:455-464). It has been shown that deletions or mutations within the splice sites of an intron reduce gene expression, indicating that splicing might be needed for IME (Mascarenhas et al. (1990) *Plant Mol Biol.* 15:913-920; Clancy and Hannah (2002) *Plant Physiol.* 130:918-929). However, that splicing per se is not required for a certain IME in dicotyledonous plants has been shown by point mutations within the splice sites of the pat1 gene from *A. thaliana* (Rose and Beliakoff (2000) *Plant Physiol.* 122:535-542).

Enhancement of gene expression by introns is not a general phenomenon because some intron insertions into recombinant expression cassettes fail to enhance expression (e.g. introns from dicot genes (rbcS gene from pea, phaseolin gene from bean and the stls-1 gene from *Solanum tuberosum*) and introns from maize genes (adh1 gene the ninth intron, hsp81 gene the first intron)) (Chee et al. (1986) *Gene* 41:47-57; Kuhlemeier et al. (1988) *Mol Gen Genet* 212:405-411; Mascarenhas et al. (1990) *Plant Mol. Biol.* 15:913-920; Sinibaldi and Mettler (1992) In W E Cohn, K Moldave, eds, *Progress in Nucleic Acid Research and Molecular Biology*, Vol 42. Academic Press, New York, pp 229-257; Vancanneyt et al. 1990 *Mol. Gen. Genet.* 220:245-250). Therefore, not each intron can be employed in order to manipulate the gene expression level of non-endogenous genes or endogenous genes in transgenic plants. What characteristics or specific sequence features must be present in an intron sequence in order to enhance the expression rate of a given gene is not known in the prior art and therefore from the prior art it is not possible to predict whether a given plant intron, when used heterologously, will cause IME.

As used herein, the term "chimeric" refers to a single DNA molecule produced by fusing a first DNA molecule to a second DNA molecule, where neither first nor second DNA molecule would normally be found in that configuration, i.e. fused to the other. The chimeric DNA molecule is thus a new DNA molecule not otherwise normally found in nature. As used herein, the term "chimeric promoter" refers to a promoter produced through such manipulation of DNA molecules. A chimeric promoter may combine two or more DNA fragments; an example would be the fusion of a promoter to an enhancer element. Thus, the design, construction, and use of chimeric promoters according to the methods disclosed herein for modulating the expression of operably linked transcribable polynucleotide molecules are encompassed by the present invention.

As used herein, the term "variant" refers to a second DNA molecule that is in composition similar, but not identical to, a first DNA molecule and yet the second DNA molecule still maintains the general functionality, i.e. same or similar expression pattern, of the first DNA molecule. A variant may be a shorter or truncated version of the first DNA molecule and/or an altered version of the sequence of the first DNA molecule, such as one with different restriction enzyme sites and/or internal deletions, substitutions, and/or insertions. A "variant" can also encompass a regulatory element having a nucleotide sequence comprising a substitution, deletion and/or insertion of one or more nucleotides of a reference sequence, wherein the derivative regulatory element has more or less or equivalent transcriptional or translational activity than the corresponding parent regulatory molecule. The regulatory element "variants" may also encompass variants arising from mutations that naturally occur in bacterial and plant cell transformation. In the present invention, a polynucleotide sequence provided as SEQ ID NOs: 1-199, 211 and 212 may be used to create variants similar in composition, but not identical to, the polynucleotide sequence of the original regulatory element, while still maintaining the general functionality of, i.e. same or similar expression pattern, the original regulatory element. Production of such variants of the present invention is well within the ordinary skill of the art in light of the disclosure and is encompassed within the scope of the present invention. "Variants" of chimeric regulatory element comprise the same constituent elements as a reference chimeric regulatory element sequence but the constituent elements comprising the chimeric regulatory element may be operatively linked by various methods known in the art such as, restriction enzyme digestion and ligation, ligation independent cloning, modular assembly of PCR products during amplification, or direct chemical synthesis of the chimeric regulatory element as well as other methods known in the art. The resulting "variant" chimeric regulatory element is comprised of the same, or variants of the same, constituent elements as the reference sequence but differ in the sequence or sequences that are used to operably link the constituent elements. In the present invention, the polynucleotide sequences provided as SEQ ID NOs: 1-199, 211 and 212 each provide a reference sequence wherein the constituent elements of the reference sequence may be joined by methods known in the art and may consist of substitutions, deletions and/or insertions of one or more nucleotides or mutations that naturally occur in bacterial and plant cell transformation.

Constructs

As used herein, the term "construct" means any recombinant polynucleotide molecule such as a plasmid, cosmid, virus, autonomously replicating polynucleotide molecule, phage, or linear or circular single-stranded or double-stranded DNA or RNA polynucleotide molecule, derived from any source, capable of genomic integration or autonomous replication, comprising a polynucleotide molecule where one or more polynucleotide molecule has been linked in a functionally operative manner, i.e. operably linked. As used herein, the term "vector" means any recombinant polynucleotide construct that may be used for the purpose of transformation, i.e. the introduction of heterologous DNA into a host cell. The term includes an expression cassette isolated from any of the aforementioned molecules.

As used herein, the term "operably linked" refers to a first molecule joined to a second molecule, wherein the molecules are so arranged that the first molecule affects the function of the second molecule. The two molecules may or may not be part of a single contiguous molecule and may or may not be adjacent. For example, a promoter is operably linked to a transcribable polynucleotide molecule if the promoter modulates transcription of the transcribable polynucleotide molecule of interest in a cell. A leader, for example, is operably linked to coding sequence when it is capable of serving as a leader for the polypeptide encoded by the coding sequence.

The constructs of the present invention may be provided, in one embodiment, as double Ti plasmid border DNA constructs that have the right border (RB or AGRtu.RB) and left border (LB or AGRtu.LB) regions of the Ti plasmid isolated from *Agrobacterium tumefaciens* comprising a T-DNA, that along with transfer molecules provided by the *A. tumefaciens* cells, permit the integration of the T-DNA into the genome of a plant cell (see, for example, U.S. Pat. No. 6,603,061). The constructs may also contain the plasmid backbone DNA segments that provide replication function and antibiotic selection in bacterial cells, for example, an *Escherichia coli* origin of replication such as ori322, a broad host range origin of replication such as oriV or oriRi, and a coding region for a selectable marker such as Spec/Strp that encodes for Tn7 aminoglycoside adenyltransferase (aadA) conferring resistance to spectinomycin or streptomycin, or a gentamicin (Gm, Gent) selectable marker gene. For plant transformation, the host bacterial strain is often *A. tumefaciens* ABI, C58, or LBA4404; however, other strains known in the art of plant transformation can function in the present invention.

Methods are available for assembling and introducing constructs into a cell in such a manner that the transcribable polynucleotide molecule is transcribed into a functional mRNA molecule that is translated and expressed as a protein product. For the practice of the present invention, conventional compositions and methods for preparing and using constructs and host cells can be found in, for example, *Molecular Cloning: A Laboratory Manual, 3rd edition* Volumes 1, 2, and 3 (2000) J. F. Sambrook, D. W. Russell, and N. Irwin, Cold Spring Harbor Laboratory Press. Methods for making recombinant vectors particularly suited to plant transformation include, without limitation, those described in U.S. Pat. Nos. 4,971,908; 4,940,835; 4,769,061; and 4,757,011 in their entirety. These types of vectors have also been reviewed in the scientific literature (see, for example, Rodriguez, et al., *Vectors: A Survey of Molecular Cloning Vectors and Their Uses*, Butterworths, Boston, (1988) and Glick, et al., *Methods in Plant Molecular Biology and Biotechnology*, CRC Press, Boca Raton, Fla. (1993)). Typical vectors useful for expression of nucleic acids in higher plants are well known in the art and include vectors derived from the tumor-inducing (Ti) plasmid of *Agrobacterium tumefaciens* (Rogers, et al., *Methods in Enzymology* 153: 253-277 (1987)). Other recombinant vectors useful for plant transformation, including the pCaMVCN transfer control vector, have also been described in the scientific literature (see, for example, Fromm, et al., *Proc. Natl. Acad. Sci.* USA 82: 5824-5828 (1985)).

Various regulatory elements may be included in a construct including any of those provided herein. Any such regulatory elements may be provided in combination with other regulatory elements. Such combinations can be designed or modified to produce desirable regulatory features. In one embodiment, constructs of the present invention comprise at least one regulatory element operably linked to a transcribable polynucleotide molecule operably linked to a 3' transcription termination molecule.

Constructs of the present invention may include any promoter or leader provided herein or known in the art. For example, a promoter of the present invention may be operably linked to a heterologous non-translated 5' leader such as one derived from a heat shock protein gene (see, for example, U.S. Pat. Nos. 5,659,122 and 5,362,865). Alternatively, a leader of the present invention may be operably linked to a heterologous promoter such as the Cauliflower Mosaic Virus 35S transcript promoter (see, U.S. Pat. No. 5,352,605). The expression properties imparted by such operable linkages of heterologous elements is not necessarily additive of the elucidated properties of each promoter and leader, but rather is determined through empirical analysis of expression driven by the operably linked heterologous promoter and leader.

As used herein, the term "intron" refers to a DNA molecule that may be isolated or identified from the genomic copy of a gene and may be defined generally as a region spliced out during mRNA processing prior to translation. Alternately, an intron may be a synthetically produced or manipulated DNA element. An intron may contain enhancer elements that effect the transcription of operably linked genes. An intron may be used as a regulatory element for modulating expression of an operably linked transcribable polynucleotide molecule. A DNA construct may comprise an intron, and the intron may or may not be heterologous with respect to the transcribable polynucleotide molecule sequence. Examples of introns in the art include the rice actin intron (U.S. Pat. No. 5,641,876) and the corn HSP70 intron (U.S. Pat. No. 5,859,347). Introns useful in practicing the present invention include SEQ ID NOs: 4, 165 and 171 or the intron element comprised within any of SEQ ID NOs: 13 through 199, 211 and 212.

As used herein, the term "3' transcription termination molecule" or "3' UTR" refers to a DNA molecule that is used during transcription to produce the 3' untranslated region (3' UTR) of an mRNA molecule. The 3' untranslated region of an mRNA molecule may be generated by specific cleavage and 3' polyadenylation, a.k.a. polyA tail. A 3' UTR may be operably linked to and located downstream of a transcribable polynucleotide molecule and may include polynucleotides that provide a polyadenylation signal and other regulatory signals capable of affecting transcription, mRNA processing, or gene expression. PolyA tails are thought to function in mRNA stability and in initiation of translation. Examples of 3' transcription termination molecules are the nopaline synthase 3' region (see, Fraley, et al., *Proc. Natl. Acad. Sci.* USA, 80: 4803-4807 (1983)); wheat hsp17 3' region; pea rubisco small subunit 3' region; cotton E6 3' region (U.S. Pat. No. 6,096,950); 3' regions disclosed in WO0011200A2; and the coixin 3' UTR (U.S. Pat. No. 6,635,806).

3' UTRs typically find beneficial use for the recombinant expression of specific genes. In animal systems, a machinery of 3' UTRs has been well defined (e.g. Zhao et al., *Microbiol Mol Biol Rev* 63:405-445 (1999); Proudfoot, *Nature* 322: 562-565 (1986); Kim et al., *Biotechnology Progress* 19:1620-1622 (2003); Yonaha and Proudfoot, *EMBO J.* 19:3770-3777 (2000); Cramer et al., *FEBS Letters* 498:179-182 (2001); Kuerstem and Goodwin, *Nature Reviews Genetics* 4:626-637 (2003)). Effective termination of RNA transcription is required to prevent unwanted transcription of trait-unrelated (downstream) sequences, which may interfere with trait performance. Arrangement of multiple gene expression cassettes in local proximity to one another (e.g. within one T-DNA) may cause suppression of gene expression of one or more genes in said construct in comparison to independent insertions (Padidam and Cao, *BioTechniques* 31:328-334 (2001). This may interfere with achieving adequate levels of expression, for instance in cases were strong gene expression from all cassettes is desired.

In plants, clearly defined polyadenylation signal sequences are not known. Hasegawa et al., *Plant J.* 33:1063-1072, (2003)) were not able to identify conserved polyadenylation signal sequences in both in vitro and in vivo systems in *Nicotiana sylvestris* and to determine the actual length of the primary (non-polyadenylated) transcript. A weak 3' UTR has the potential to generate read-through, which may affect the expression of the genes located in the neighboring expression cassettes (Padidam and Cao, *BioTechniques* 31:328-334 (2001)). Appropriate control of transcription termination can prevent read-through into sequences (e.g. other expression cassettes) localized downstream and can further allow efficient recycling of RNA polymerase, to improve gene expression. Efficient termination of transcription (release of RNA Polymerase II from the DNA) is pre-requisite for re-initiation of transcription and thereby directly affects the overall transcript level. Subsequent to transcription termination, the mature mRNA is released from the site of synthesis and template to the cytoplasm. Eukaryotic mRNAs are accumulated as poly(A) forms in vivo, so that it is difficult to detect transcriptional termination sites by conventional methods. However, prediction of functional and efficient 3' UTRs by bioinformatics methods is difficult in that there are no conserved sequences which would allow easy prediction of an effective 3' UTR.

From a practical standpoint, it is typically beneficial that a 3' UTR used in a transgene cassette possesses the following characteristics. The 3' UTR should be able to efficiently and effectively terminate transcription of the transgene and prevent read-through of the transcript into any neighboring DNA sequence which can be comprised of another transgene cassette as in the case of multiple cassettes residing in one T-DNA, or the neighboring chromosomal DNA into which the T-DNA has inserted. The 3' UTR should not cause a reduction in the transcriptional activity imparted by the promoter, leader and introns that are used to drive expression of the transgene. In plant biotechnology, the 3' UTR is often used for priming of amplification reactions of reverse transcribed RNA extracted from the transformed plant and used to (1) assess the transcriptional activity or expression of the transgene cassette once integrated into the plant chromosome; (2) assess the copy number of insertions within the plant DNA; and (3) assess zygosity of the resulting seed after breeding. The 3' UTR is also used in amplification reactions of DNA extracted from the transformed plant to characterize the intactness of the inserted cassette.

3' UTRs useful in providing expression of a transgene in plants may be identified based upon the expression of expressed sequence tags (ESTs) in cDNA libraries made from messenger RNA isolated from seed, flower and other tissues derived from Foxtail millet (*Setaria italica* (L.) Beauv). Libraries of cDNA are made from tissues isolated from selected plant species using flower tissue, seed, leaf and root. The resulting cDNAs are sequenced using various sequencing methods. The resulting ESTs are assembled into clusters using bioinformatics software such as clc_ref_assemble_complete version 2.01.37139 (CLC bio USA, Cambridge, Mass. 02142). Transcript abundance of each cluster is determined by counting the number of cDNA reads for each cluster. The identified 3' UTRs may be comprised of sequence derived from cDNA sequence as well as sequence derived from genomic DNA. The cDNA sequence is used to design primers, which are then used with GenomeWalker™ (Clontech Laboratories, Inc, Mountain View, Calif.) libraries constructed following the manufacturer's protocol to clone the 3' region of the corresponding genomic DNA sequence to provide a longer termination sequence. Analysis of relative transcript abundance either by direct counts or normalized counts of observed sequence reads for each tissue library can be used to infer properties about patters of expression. For example, some 3' UTRs may be found in transcripts seen in higher abundance in root tissue as opposed to leaf. This is suggestive that the transcript is highly expressed in root and that the properties of root expression may be attributable to the transcriptional regulation of the promoter, the lead, the introns or the 3' UTR. Empirical testing of 3' UTRs identified by the properties of expression within specific organs, tissues or cell types can result in the identification of 3' UTRs that enhance expression in those specific organs, tissues or cell types.

Constructs and vectors may also include a transit peptide coding sequence that expresses a linked peptide that is useful for targeting of a protein product, particularly to a chloroplast, leucoplast, or other plastid organelle; mitochondria; peroxisome; vacuole; or an extracellular location. For descriptions of the use of chloroplast transit peptides, see U.S. Pat. Nos. 5,188,642 and 5,728,925. Many chloroplast-localized proteins are expressed from nuclear genes as precursors and are targeted to the chloroplast by a chloroplast transit peptide (CTP). Examples of such isolated chloroplast proteins include, but are not limited to, those associated with the small subunit (SSU) of ribulose-1,5-bisphosphate carboxylase, ferredoxin, ferredoxin oxidoreductase, the light-harvesting complex protein I and protein II, thioredoxin F, enolpyruvyl shikimate phosphate synthase (EPSPS), and transit peptides described in U.S. Pat. No. 7,193,133. It has been demonstrated in vivo and in vitro that non-chloroplast proteins may be targeted to the chloroplast by use of protein fusions with a heterologous CTP and that the CTP is sufficient to target a protein to the chloroplast. Incorporation of a suitable chloroplast transit peptide such as the *Arabidopsis thaliana* EPSPS CTP (CTP2) (See, Klee et al., *Mol. Gen. Genet.* 210:437-442 (1987)) or the *Petunia hybrida* EPSPS CTP (CTP4) (See, della-Cioppa et al., *Proc. Natl. Acad. Sci.* USA 83:6873-6877 (1986)) has been show to target heterologous EPSPS protein sequences to chloroplasts in transgenic plants (See, U.S. Pat. Nos. 5,627,061; 5,633,435; and 5,312,910 and EP 0218571; EP 189707; EP 508909; and EP 924299).

Transcribable Polynucleotide Molecules

As used herein, the term "transcribable polynucleotide molecule" refers to any DNA molecule capable of being transcribed into a RNA molecule, including, but not limited to, those having protein coding sequences and those producing RNA molecules having sequences useful for gene suppression. A "transgene" refers to a transcribable polynucleotide molecule heterologous to a host cell at least with respect to its location in the genome and/or a transcribable polynucleotide molecule artificially incorporated into a host cell's genome in the current or any prior generation of the cell.

A promoter of the present invention may be operably linked to a transcribable polynucleotide molecule that is heterologous with respect to the promoter molecule. As used herein, the term "heterologous" refers to the combination of two or more polynucleotide molecules when such a combination is not normally found in nature. For example, the two molecules may be derived from different species and/or the two molecules may be derived from different genes, e.g. different genes from the same species or the same genes from different species. A promoter is thus heterologous with respect to an operably linked transcribable polynucleotide molecule if such a combination is not normally found in nature, i.e. that transcribable polynucleotide molecule is not naturally occurring operably linked in combination with that promoter molecule.

The transcribable polynucleotide molecule may generally be any DNA molecule for which expression of a RNA transcript is desired. Such expression of an RNA transcript may result in translation of the resulting mRNA molecule and thus protein expression. Alternatively, for example, a transcribable polynucleotide molecule may be designed to ultimately cause decreased expression of a specific gene or protein. In one embodiment, this may be accomplished by using a transcribable polynucleotide molecule that is oriented in the antisense direction. Briefly, as the antisense transcribable polynucleotide molecule is transcribed, the RNA product hybridizes to and sequesters a complimentary RNA molecule inside the cell. This duplex RNA molecule cannot be translated into a protein by the cell's translational machinery and is degraded in the cell. Any gene may be negatively regulated in this manner.

Thus, one embodiment of the invention is a regulatory element of the present invention, such as those provided as SEQ ID NOs: 1-199, 211 and 212, operably linked to a transcribable polynucleotide molecule so as to modulate transcription of the transcribable polynucleotide molecule at a desired level or in a desired pattern when the construct is integrated in the genome of a plant cell. In one embodiment, the transcribable polynucleotide molecule comprises a protein-coding region of a gene, and the promoter affects the transcription of an RNA molecule that is translated and expressed as a protein product. In another embodiment, the transcribable polynucleotide molecule comprises an antisense region of a gene, and the promoter affects the transcription of an antisense RNA molecule, double stranded RNA or other similar inhibitory RNA molecule in order to inhibit expression of a specific RNA molecule of interest in a target host cell.

Genes of Agronomic Interest

Transcribable polynucleotide molecules may be genes of agronomic interest. As used herein, the term "gene of agronomic interest" refers to a transcribable polynucleotide molecule that when expressed in a particular plant tissue, cell, or cell type confers a desirable characteristic, such as associated with plant morphology, physiology, growth, development, yield, product, nutritional profile, disease or pest resistance, and/or environmental or chemical tolerance. Genes of agronomic interest include, but are not limited to, those encoding a yield protein, a stress resistance protein, a developmental control protein, a tissue differentiation protein, a meristem protein, an environmentally responsive protein, a senescence protein, a hormone responsive protein, an abscission protein, a source protein, a sink protein, a flower control protein, a seed protein, an herbicide resistance protein, a disease resistance protein, a fatty acid biosynthetic enzyme, a tocopherol biosynthetic enzyme, an amino acid biosynthetic enzyme, a pesticidal protein, or any other agent such as an antisense or RNAi molecule targeting a particular gene for suppression. The product of a gene of agronomic interest may act within the plant in order to cause an effect upon the plant physiology or metabolism or may be act as a pesticidal agent in the diet of a pest that feeds on the plant.

In one embodiment of the invention, a promoter of the present invention is incorporated into a construct such that the promoter is operably linked to a transcribable polynucleotide molecule that is a gene of agronomic interest. The expression of the gene of agronomic interest is desirable in order to confer an agronomically beneficial trait. A beneficial agronomic trait may be, for example, but is not limited to, herbicide tolerance, insect control, modified yield, fungal disease resistance, virus resistance, nematode resistance, bacterial disease resistance, plant growth and development, starch production, modified oils production, high oil production, modified fatty acid content, high protein production, fruit ripening, enhanced animal and human nutrition, biopolymers, environmental stress resistance, pharmaceutical peptides and secretable peptides, improved processing traits, improved digestibility, enzyme production, flavor, nitrogen fixation, hybrid seed production, fiber production, and biofuel production. Examples of genes of agronomic interest include those for herbicide resistance (U.S. Pat. Nos. 6,803,501; 6,448,476; 6,248,876; 6,225,114; 6,107,549; 5,866,775; 5,804,425; 5,633,435; and 5,463,175), increased yield (U.S. Pat. Nos. RE38,446; 6,716,474; 6,663,906; 6,476,295; 6,441,277; 6,423,828; 6,399,330; 6,372,211; 6,235,971; 6,222,098; and 5,716,837), insect control (U.S. Pat. Nos. 6,809,078; 6,713,063; 6,686,452; 6,657,046; 6,645,497; 6,642,030; 6,639,054; 6,620,988; 6,593,293; 6,555,655; 6,538,109; 6,537,756; 6,521,442; 6,501,009; 6,468,523; 6,326,351; 6,313,378; 6,284,949; 6,281,016; 6,248,536; 6,242,241; 6,221,649; 6,177,615; 6,156,573; 6,153,814; 6,110,464; 6,093,695; 6,063,756; 6,063,597; 6,023,013; 5,959,091; 5,942,664; 5,942,658, 5,880,275; 5,763,245; and 5,763,241), fungal disease resistance (U.S. Pat. Nos. 6,653,280; 6,573,361; 6,506,962; 6,316,407; 6,215,048; 5,516,671; 5,773,696; 6,121,436; 6,316,407; and 6,506,962), virus resistance (U.S. Pat. Nos. 6,617,496; 6,608,241; 6,015,940; 6,013,864; 5,850,023; and 5,304,730), nematode resistance (U.S. Pat. No. 6,228,992), bacterial disease resistance (U.S. Pat. No. 5,516,671), plant growth and development (U.S. Pat. Nos. 6,723,897 and 6,518,488), starch production (U.S. Pat. Nos. 6,538,181; 6,538,179; 6,538,178; 5,750,876; 6,476,295), modified oils production (U.S. Pat. Nos. 6,444,876; 6,426,447; and 6,380,462), high oil production (U.S. Pat. Nos. 6,495,739; 5,608,149; 6,483,008; and 6,476,295), modified fatty acid content (U.S. Pat. Nos. 6,828,475; 6,822,141; 6,770,465; 6,706,950; 6,660,849; 6,596,538; 6,589,767; 6,537,750; 6,489,461; and 6,459,018), high protein production (U.S. Pat. No. 6,380,466), fruit ripening (U.S. Pat. No. 5,512,466), enhanced animal and human nutrition (U.S. Pat. Nos. 6,723,837; 6,653,530; 6,5412,59; 5,985,605; and 6,171,640), biopolymers (U.S. Pat. Nos. RE37,543; 6,228,623; and U.S. Pat. Nos. 5,958,745, and 6,946,588), environmental stress resistance (U.S. Pat. No. 6,072,103), pharmaceutical peptides and secretable peptides (U.S. Pat. Nos. 6,812,379; 6,774,283; 6,140,075; and 6,080,560), improved processing traits (U.S. Pat. No. 6,476,295), improved digestibility (U.S. Pat. No. 6,531,648) low raffinose (U.S. Pat. No. 6,166,292), industrial enzyme production (U.S. Pat. No. 5,543,576), improved flavor (U.S. Pat. No. 6,011,199), nitrogen fixation (U.S. Pat. No. 5,229,114), hybrid seed production (U.S. Pat. No. 5,689,041), fiber production (U.S. Pat. Nos. 6,576,818; 6,271,443; 5,981,834; and 5,869,720) and biofuel production (U.S. Pat. No. 5,998,700).

Alternatively, a gene of agronomic interest can affect the above mentioned plant characteristic or phenotype by encoding a RNA molecule that causes the targeted modulation of gene expression of an endogenous gene, for example via antisense (see e.g. U.S. Pat. No. 5,107,065); inhibitory RNA ("RNAi", including modulation of gene expression via miRNA-, siRNA-, trans-acting siRNA-, and phased sRNA-mediated mechanisms, e.g. as described in published applications US 2006/0200878 and US 2008/0066206, and in U.S. patent application Ser. No. 11/974,469); or cosuppression-mediated mechanisms. The RNA could also be a catalytic RNA molecule (e.g. a ribozyme or a riboswitch; see e.g. US 2006/0200878) engineered to cleave a desired endogenous mRNA product. Thus, any transcribable polynucleotide molecule that encodes a transcribed RNA molecule that affects an agronomically important phenotype or morphology change of interest may be useful for the practice of the present invention. Methods are known in the art for constructing and introducing constructs into a cell in such a manner that the transcribable polynucleotide molecule is transcribed into a molecule that is capable of causing gene suppression. For example, posttranscriptional gene suppression using a construct with an anti-sense oriented transcribable polynucleotide molecule to regulate gene expression in plant cells is disclosed in U.S. Pat. Nos. 5,107,065 and 5,759,829, and posttranscriptional gene suppression using a construct with a sense-oriented transcribable polynucleotide molecule to regulate gene expression in plants is disclosed in U.S. Pat. Nos. 5,283,184 and 5,231,020. Expression of a transcribable polynucleotide in a plant cell can also be used to suppress plant pests feeding on the plant cell, for example, compositions isolated from coleopteran pests (U.S. Patent Publication No. US20070124836) and compositions isolated from nematode pests (U.S. Patent Publication No. US20070250947). Plant pests include, but are not limited to arthropod pests, nematode pests, and fungal or microbial pests. Exemplary transcribable polynucleotide molecules for incorporation into constructs of the present invention include, for example, DNA molecules or genes from a species other than the target species or genes that originate with or are present in the same species, but are incorporated into recipient cells by genetic engineering methods rather than classical reproduction or breeding techniques. The type of polynucleotide molecule can include, but is not limited to, a polynucleotide molecule that is already present in the plant cell, a polynucleotide molecule from another plant, a polynucleotide molecule from a different organism, or a polynucleotide molecule generated externally, such as a polynucleotide molecule containing an antisense message of a gene, or a polynucleotide molecule encoding an artificial, synthetic, or otherwise modified version of a transgene.

Selectable Markers

As used herein the term "marker" refers to any transcribable polynucleotide molecule whose expression, or lack thereof, can be screened for or scored in some way. Marker genes for use in the practice of the present invention include, but are not limited to transcribable polynucleotide molecules encoding ß-glucuronidase (GUS described in U.S. Pat. No. 5,599,670), green fluorescent protein and variants thereof (GFP described in U.S. Pat. Nos. 5,491,084 and 6,146,826), proteins that confer antibiotic resistance, or proteins that confer herbicide tolerance. Useful antibiotic resistance markers include those encoding proteins conferring resistance to kanamycin (nptII), hygromycin B (aph IV), streptomycin or spectinomycin (aad, spec/strep) and gentamycin (aac3 and aacC4). Herbicides for which transgenic plant tolerance has been demonstrated and the method of the present invention can be applied, include, but are not limited to: amino-methyl-phosphonic acid, glyphosate, glufosinate, sulfonylureas, imidazolinones, bromoxynil, delapon, dicamba, cyclohezanedione, protoporphyrinogen oxidase inhibitors, and isoxasflutole herbicides. Transcribable polynucleotide molecules encoding proteins involved in herbicide tolerance include, but are not limited to, a transcribable polynucleotide molecule encoding 5-enolpyruvylshikimate-3-phosphate synthase (EPSPS for glyphosate tolerance described in U.S. Pat. Nos. 5,627,061; 5,633,435; 6,040,497; and 5,094,945); a transcribable polynucleotide molecule encoding a glyphosate oxidoreductase and a glyphosate-N-acetyl transferase (GOX described in U.S. Pat. No. 5,463,175; GAT described in U.S. Patent publication No. 20030083480, and dicamba monooxygenase U.S. Patent publication No. 20030135879); a transcribable polynucleotide molecule encoding bromoxynil nitrilase (Bxn for Bromoxynil tolerance described in U.S. Pat. No. 4,810,648); a transcribable polynucleotide molecule encoding phytoene desaturase (crtI) described in Misawa, et al., *Plant Journal* 4:833-840 (1993) and Misawa, et al., *Plant Journal* 6:481-489 (1994) for norflurazon tolerance; a transcribable polynucleotide molecule encoding acetohydroxyacid synthase (AHAS, aka ALS) described in Sathasiivan, ei al., *Nucl. Acids Res.* 18:2188-2193 (1990) for tolerance to sulfonylurea herbicides; and the bar gene described in DeBlock, et al., *EMBO Journal* 6:2513-2519 (1987) for glufosinate and bialaphos tolerance. The promoter molecules of the present invention can express linked transcribable polynucleotide molecules that encode for phosphinothricin acetyltransferase, glyphosate resistant EPSPS, aminoglycoside phosphotransferase, hydroxyphenyl pyruvate dehydrogenase, hygromycin phosphotransferase, neomycin phosphotransferase, dalapon dehalogenase, bromoxynil resistant nitrilase, anthranilate synthase, aryloxyalkanoate dioxygenases, acetyl CoA carboxylase, glyphosate oxidoreductase, and glyphosate-N-acetyl transferase.

Included within the term "selectable markers" are also genes which encode a secretable marker whose secretion can be detected as a means of identifying or selecting for transformed cells. Examples include markers that encode a secretable antigen that can be identified by antibody interaction, or even secretable enzymes which can be detected catalytically. Selectable secreted marker proteins fall into a number of classes, including small, diffusible proteins which are detectable, (e.g. by ELISA), small active enzymes which are detectable in extracellular solution (e.g, alpha-amylase, beta-lactamase, phosphinothricin transferase), or proteins which are inserted or trapped in the cell wall (such as proteins which include a leader sequence such as that found in the expression unit of extension or tobacco pathogenesis related proteins also known as tobacco PR-S). Other possible selectable marker genes will be apparent to those of skill in the art and are encompassed by the present invention.

Cell Transformation

The invention is also directed to a method of producing transformed cells and plants which comprise a promoter operably linked to a transcribable polynucleotide molecule.

The term "transformation" refers to the introduction of nucleic acid into a recipient host. As used herein, the term "host" refers to bacteria, fungi, or plant, including any cells, tissue, organs, or progeny of the bacteria, fungi, or plant. Plant tissues and cells of particular interest include protoplasts, calli, roots, tubers, seeds, stems, leaves, seedlings, embryos, and pollen.

As used herein, the term "transformed" refers to a cell, tissue, organ, or organism into which a foreign polynucleotide molecule, such as a construct, has been introduced. The introduced polynucleotide molecule may be integrated into the genomic DNA of the recipient cell, tissue, organ, or organism such that the introduced polynucleotide molecule is inherited by subsequent progeny. A "transgenic" or "transformed" cell or organism also includes progeny of the cell or organism and progeny produced from a breeding program employing such a transgenic organism as a parent in a cross and exhibiting an altered phenotype resulting from the presence of a foreign polynucleotide molecule. The term "transgenic" refers to a bacteria, fungi, or plant containing one or more heterologous polynucleic acid molecules.

There are many methods for introducing polynucleic acid molecules into plant cells. The method generally comprises the steps of selecting a suitable host cell, transforming the host cell with a recombinant vector, and obtaining the transformed host cell. Suitable methods include bacterial infection (e.g. *Agrobacterium*), binary bacterial artificial chromosome vectors, direct delivery of DNA (e.g. via PEG-mediated transformation, desiccation/inhibition-mediated DNA uptake, electroporation, agitation with silicon carbide fibers, and acceleration of DNA coated particles, etc. (reviewed in Potrykus, et al., *Ann. Rev. Plant Physiol. Plant Mol. Biol.* 42: 205 (1991)).

Any transformation methods may be utilized to transform a host cell with one or more promoters and/or constructs of the present invention. Host cells may be any cell or organism such as a plant cell, algae cell, algae, fungal cell, fungi, bacterial cell, or insect cell. Preferred hosts and transformed cells include cells from: plants, *Aspergillus*, yeasts, insects, bacteria and algae.

Regenerated transgenic plants can be self-pollinated to provide homozygous transgenic plants. Alternatively, pollen obtained from the regenerated transgenic plants may be crossed with non-transgenic plants, preferably inbred lines of agronomically important species. Descriptions of breeding methods that are commonly used for different traits and crops can be found in one of several reference books, see, for example, Allard, *Principles of Plant Breeding,* John Wiley & Sons, NY, U. of CA, Davis, Calif., 50-98 (1960); Simmonds, *Principles of crop improvement*, Longman, Inc., NY, 369-399 (1979); Sneep and Hendriksen, Plant breeding perspectives, Wageningen (ed), Center for Agricultural Publishing and Documentation (1979); Fehr, *Soybeans: Improvement, Production and Uses,* 2nd Edition, Monograph, 16:249 (1987); Fehr, *Principles of variety development, Theory and Technique*, (Vol. 1) and *Crop Species Soybean* (Vol 2), Iowa State Univ., Macmillan Pub. Co., NY, 360-376 (1987). Conversely, pollen from non-transgenic plants may be used to pollinate the regenerated transgenic plants.

The transformed plants may be analyzed for the presence of the genes of interest and the expression level and/or profile conferred by the regulatory elements of the present invention. Those of skill in the art are aware of the numerous methods available for the analysis of transformed plants. For example, methods for plant analysis include, but are not limited to Southern blots or northern blots, PCR-based approaches, biochemical analyses, phenotypic screening methods, field evaluations, and immunodiagnostic assays. The expression of a transcribable polynucleotide molecule can be measured using TaqMan® (Applied Biosystems, Foster City, Calif.) reagents and methods as described by the manufacturer and PCR cycle times determined using the TaqMan® Testing Matrix. Alternatively, the Invader® (Third Wave Technologies, Madison, Wis.) reagents and methods as described by the manufacturer can be used transgene expression.

The seeds of the plants of this invention can be harvested from fertile transgenic plants and be used to grow progeny generations of transformed plants of this invention including hybrid plant lines comprising the construct of this invention and expressing a gene of agronomic interest.

The present invention also provides for parts of the plants of the present invention. Plant parts, without limitation, include leaves, stems, roots, tubers, seeds, endosperm, ovule, and pollen. The invention also includes and provides transformed plant cells which comprise a nucleic acid molecule of the present invention.

The transgenic plant may pass along the transgenic polynucleotide molecule to its progeny. Progeny includes any regenerable plant part or seed comprising the transgene derived from an ancestor plant. The transgenic plant is preferably homozygous for the transformed polynucleotide molecule and transmits that sequence to all offspring as a result of sexual reproduction. Progeny may be grown from seeds produced by the transgenic plant. These additional plants may then be self-pollinated to generate a true breeding line of plants. The progeny from these plants are evaluated, among other things, for gene expression. The gene expression may be detected by several common methods such as western blotting, northern blotting, immunoprecipitation, and ELISA.

Having now generally described the invention, the same will be more readily understood through reference to the following examples which are provided by way of illustration, and are not intended to be limiting of the present invention, unless specified. It should be appreciated by those of skill in the art that the techniques disclosed in the following examples represent techniques discovered by the inventors to function well in the practice of the invention. However, those of skill in the art should, in light of the present disclosure, appreciate that many changes can be made in the specific embodiments that are disclosed and still obtain a like or similar result without departing from the spirit and scope of the invention, therefore all matter set forth or shown in the accompanying drawings is to be interpreted as illustrative and not in a limiting sense.

EXAMPLES

Example 1: Identification and Cloning of Regulatory Elements

Novel transcriptional regulatory elements, or transcriptional regulatory expression element group (EXP) sequences were identified and isolated from genomic DNA of the dicot species *Cucumis melo* WSH-39-1070AN.

Transcriptional regulatory elements were selected based upon proprietary and public microarray data derived from transcriptional profiling experiments conducted in soybean (*Glycine max*) and *Arabidopsis* as well as homology based searches using known dicot sequences as query against proprietary *Cucumis melo* sequences.

Using the identified sequences, a bioinformatic analysis was conducted to identify regulatory elements within the amplified DNA, followed by identification of the transcriptional start site (TSS) and any bi-directionality, introns, or upstream coding sequence present in the sequence. Using the results of this analysis, regulatory elements were defined within the DNA sequences and primers designed to amplify the regulatory elements. The corresponding DNA molecule for each regulatory element was amplified using standard polymerase chain reaction conditions with primers containing unique restriction enzyme sites and genomic DNA isolated from *Cucumis melo*. The resulting DNA fragments were ligated into base plant expression vectors using standard restriction enzyme digestion of compatible restriction sites and DNA ligation methods.

Analysis of the regulatory element TSS and intron/exon splice junctions can be performed using transformed plant protoplasts. Briefly, the protoplasts are transformed with the plant expression vectors comprising the cloned DNA fragments operably linked to a heterologous transcribable polynucleotide molecule and the 5' RACE System for Rapid Amplification of cDNA Ends, Version 2.0 (Invitrogen, Carlsbad, Calif. 92008) is used to confirm the regulatory element TSS and intron/exon splice junctions by analyzing the sequence of the mRNA transcripts produced thereby.

Sequences encoding ubiquitin 1 transcriptional regulatory expression element groups (EXP) were analyzed as described above and each transcriptional regulatory expression element groups ("EXP's") was also broken down into the corresponding promoters, leaders and introns comprising each transcriptional regulatory expression element group. Sequences of the identified ubiquitin 1 transcriptional regulatory expression element groups ("EXP's") are provided herein as SEQ ID NOs: 1, 5, 7, 9 and 11 and is listed in Table 1 below. The corresponding ubiquitin 1 promoters are provided herein as SEQ ID NOs: 2, 6, 8, 10 and 12. The ubiquitin 1 leader and intron are herein provided as SEQ ID NOs: 3 and 4, respectively.

Sequences encoding other *Cucumis* transcriptional regulatory expression element groups or EXP sequences which are comprised of either a promoter element, operably linked to a leader element; or a promoter element, operably linked to a leader element and an intron element, or a promoter element, operably linked to a leader element, operably linked to an intron element, operably linked to a leader element are provided as SEQ ID NOs: 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 159, 162, 167, 168, 172, 175, 176, 177, 178, 181, 182, 183, 184, 185, 188, 189, 190, 191, 192, 193, 194, 195, 196, 197, 198, 199, 211 and 212 and are also listed in Table 1 below. Additional promoter elements are provided as SEQ ID NOs: 163 and 169. Additional leader elements are provided as SEQ ID NOs: 164, 166 and 170. Additional intron elements are provided as SEQ ID NOs: 165 and 171. Elements wherein a promoter is operably linked to a leader element are provided as SEQ ID NOs: 157, 160, 173, 179 and 186. Elements wherein an intron is operably linked to a leader element are provided as SEQ ID NOs: 158, 161, 174, 180 and 187. With respect to the subset of sequences provided as SEQ ID NOs: 13 through 199, 211 and 212, these sequences were selected and cloned based upon the results of experiments such as transcript profiling or expression driven by promoters from homologous genes of a different species suggesting desirable patterns of expression such as constitutive expression, root expression, above ground expression or seed expression. The actual activity imparted by the *Cucumis* sequences is determined empirically and is not necessarily the same as that of a regulatory element derived from a homologous gene from a species other than *Cucumis melo* when used in a transformed plant host cell and whole transgenic plant.

TABLE 1

Transcriptional regulatory expression element groups, promoters, leaders and introns isolated from *Cucumis melo*.

| Annotation | SEQ ID NO: | Description | Composition Type | Size (bp) | Composition | Coordinates of Elements within EXP |
|---|---|---|---|---|---|---|
| EXP-CUCme.Ubq1:1:1 | 1 | Ubiquitin 1 | EXP | 2611 | Promoter; Leader; Intron | 1-2068; 2069-2150; 2151-2608 |
| P-CUCme.Ubq1-1:1:15 | 2 | Ubiquitin 1 | P | 2068 | Promoter | |
| L-CUCme.Ubq1-1:1:1 | 3 | Ubiquitin 1 | L | 82 | Leader | |
| I-CUCme.Ubq1-1:1:1 | 4 | Ubiquitin 1 | I | 461 | Intron | |
| EXP-CUCme.Ubq1:1:2 | 5 | Ubiquitin 1 | EXP | 2002 | Promoter; Leader; Intron | 1-1459; 1460-1541; 1542-1999 |
| P-CUCme.Ubq1-1:1:16 | 6 | Ubiquitin 1 | P | 1459 | Promoter | |
| EXP-CUCme.Ubq1:1:3 | 7 | Ubiquitin 1 | EXP | 1507 | Promoter; Leader; Intron | 1-964; 965-1046; 1047-1504 |
| P-CUCme.Ubq1-1:1:17 | 8 | Ubiquitin 1 | P | 964 | Promoter | |
| EXP-CUCme.Ubq1:1:4 | 9 | Ubiquitin 1 | EXP | 1022 | Promoter; Leader; Intron | 1-479; 480-561; 562-1019 |
| P-CUCme.Ubq1-1:1:18 | 10 | Ubiquitin 1 | P | 479 | Promoter | |
| EXP-CUCme.Ubq1:1:5 | 11 | Ubiquitin 1 | EXP | 716 | Promoter; Leader; Intron | 1-173; 174-255; 256-713 |
| P-CUCme.Ubq1-1:1:19 | 12 | Ubiquitin 1 | P | 173 | Promoter | |
| P-CUCme.1-1:1:1 | 13 | Phosphatase 2A | EXP | 2000 | Promoter; Leader; Intron; Leader | Reverse compliment; see SEQ ID NO: 155 |
| P-CUCme.2-1:1:1 | 14 | Actin 1 | EXP | 2000 | Promoter; Leader; Intron; Leader | 1-964; 965-1028; 1029-1991; 1992-2003 |
| P-CUCme.3-1:1:3 | 15 | Actin 2 | EXP | 1990 | Promoter; Leader; Intron; Leader | 1-1243; 1244-1319; 1320-1982; 1983-1990 |
| P-CUCme.4-1:1:2 | 16 | Ubiquitin 2 | EXP | 2005 | Promoter; Leader; Intron; Leader | 1-1646; 1647-1704; 1705-2005; 2006-2008 |
| P-CUCme.5-1:1:2 | 17 | Ubiquitin 3 | EXP | 2004 | Promoter; Leader; Intron | 1-748; 749-819; 820-2004 |

TABLE 1-continued

Transcriptional regulatory expression element groups, promoters, leaders and introns isolated from *Cucumis melo*.

| Annotation | SEQ ID NO: | Description | Composition Type | Size (bp) | Composition | Coordinates of Elements within EXP |
|---|---|---|---|---|---|---|
| P-CUCme.6-1:1:1 | 18 | Tubulin beta chain | EXP | 1935 | Promoter; Leader; Intron; Leader | 1-1436; 1437-1482; 1483-1919; 1920-1935 |
| P-CUCme.8-1:1:2 | 19 | Tubulin beta chain | EXP | 1606 | Promoter; Leader | 1-1527; 1528-1606 |
| P-CUCme.9-1:1:2 | 20 | Tubulin beta chain | EXP | 1487 | Promoter; Leader | 1-1384; 1385-1487 |
| P-CUCme.10-1:1:1 | 21 | Tubulin beta chain | EXP | 1448 | Promoter; Leader | 1-1363; 1364-1448 |
| P-CUCme.11-1:1:2 | 22 | Elongation Factor 1 alpha | EXP | 1235 | Promoter; Leader; Intron | 1-617; 618-677; 678-1213; 1214-1235 |
| P-CUCme.15-1:1:2 | 23 | Elongation Factor 1 alpha | EXP | 2003 | Promoter; Leader; Intron; Leader | 1-1330; 1331-1435; 1430-1975; 1976-2002 |
| P-CUCme.16a-1:1:2 | 24 | Ubiquitin 7 | EXP | 2015 | Promoter; Leader | |
| P-CUCme.16b-1:1:1 | 25 | Ubiquitin 6 | EXP | 2006 | Promoter; Leader | |
| P-CUCme.17-1:1:2 | 26 | ubiquitin-40S ribosomal protein S27a | EXP | 2017 | Promoter; Leader | 1-1969; 1970-2017 |
| P-CUCme.18-1:1:2 | 27 | ubiquitin-40S ribosomal protein S27a | EXP | 1353 | Promoter; Leader | 1-1308; 1309-1353 |
| P-CUCme.19-1:1:2 | 28 | Chloropyll a/b binding protein | EXP | 2005 | Promoter; Leader | 1-1960; 1961-2005 |
| P-CUCme.20-1:1:2 | 29 | Chloropyll a/b binding protein | EXP | 1445 | Promoter; Leader | 1-1390; 1391-1445 |
| P-CUCme.21-1:1:1 | 30 | Chloropyll a/b binding protein | EXP | 1282 | Promoter; Leader | 1-1233; 1234-1282 |
| P-CUCme.22-1:1:3 | 31 | Elongation Factor 4 alpha | EXP | 2002 | | |
| P-CUCme.24-1:1:2 | 32 | S-Adenosylmethionine Synthetase | EXP | 2003 | Promoter; Leader; Intron; Leader | 1-1067; 1068-1165; 1166-2001; 2002-2003 |
| P-CUCme.26-1:1:2 | 33 | Stress responsive protein | EXP | 1372 | Promoter; Leader; Intron; Leader | 1-577; 578-654; 655-1366; 1367-1372 |
| P-CUCme.28-1:1:2 | 34 | Ribosomal protein S5a | EXP | 1122 | | |
| P-CUCme.29-1:1:2 | 35 | Ribosomal protein S5a | EXP | 2017 | Promoter; Leader; Intron; Leader | 1-490; 491-571; 572-2012; 2013-2017 |
| CumMe_WSM_SF143981. G5150 | 36 | LHCB6 (LIGHT HARVESTING COMPLEX PSII SUBUNIT 6) | EXP | 2000 | | |
| CumMe_WSM_SF144839. G5080 | 37 | EIF2 GAMMA translation initiation factor | EXP | 1760 | | |
| CumMe_WSM_SF146040. G5050 | 38 | EIF2 translation initiation factor | EXP | 1767 | | |
| CumMe_WSM_SF16408. G5350 | 39 | elongation factor Tu | EXP | 2000 | | |
| CumMe_WSM_SF16429. G5670 | 40 | unknown protein | EXP | 2000 | | |
| CumMe_WSM_SF16444. G5140 | 41 | histone H4 | EXP | 2000 | Promoter; Leader | 1-1947; 1948-2000 |
| CumMe_WSM_SF16530. G6000 | 42 | HMGB2 (HIGH MOBILITY GROUP B 2) transcription factor | EXP | 2000 | | |
| CumMe_WSM_SF16553. G5090 | 43 | PBG1; threonine-type endopeptidase | EXP | 1115 | | |
| CumMe_WSM_SF16563. G5560 | 44 | ATARFB1A (ADP-ribosylation factor B1A) | EXP | 2000 | Promoter; Leader; Intron; Leader | 1-1329; 1330-1427; 1428-1988; 1989-2000 |
| CumMe_WSM_SF16675. G5720 | 45 | chromatin protein family | EXP | 2000 | | |
| CumMe_WSM_SF16920. G5650 | 46 | CSD1 (COPPER/ZINC SUPEROXIDE DISMUTASE 1) | EXP | 2000 | | |
| CumMe_WSM_SF16953. G5180 | 47 | SCE1 (SUMO CONJUGATION ENZYME 1); SUMO ligase | EXP | 2000 | | |
| CumMe_WSM_SF17051. G5470 | 48 | 60S ribosomal protein L9 (RPL90D) | EXP | 2000 | | |
| CumMe_WSM_SF17111. G5790 | 49 | ubiquinol-cytochrome C reductase complex ubiquinone-binding protein | EXP | 2000 | Promoter; Leader | 1-1895; 1896-2000 |

TABLE 1-continued

Transcriptional regulatory expression element groups, promoters, leaders and introns isolated from *Cucumis melo*.

| Annotation | SEQ ID NO: | Description | Composition Type | Size (bp) | Composition | Coordinates of Elements within EXP |
|---|---|---|---|---|---|---|
| CumMe_WSM_SF17142.G5920 | 50 | peptidyl-prolyl cis-trans isomerase, chloroplast | EXP | 2000 | | |
| CumMe_WSM_SF17190.G6200 | 51 | PRK (PHOSPHORIBULOKINASE) | EXP | 2000 | | |
| CumMe_WSM_SF17250.G5910 | 52 | LHCB5 (LIGHT HARVESTING COMPLEX OF PHOTOSYSTEM II 5) | EXP | 2000 | | |
| CumMe_WSM_SF17252.G7330 | 53 | nascent polypeptide-associated complex (NAC) domain-containing protein | EXP | 2000 | Promoter; Leader; Intron | 1-1195; 1196-1297; 1298-2000 |
| CumMe_WSM_SF17253.G5150 | 54 | RPS9 (RIBOSOMAL PROTEIN S9) | EXP | 1547 | | |
| CumMe_WSM_SF17322.G5110 | 55 | 60S ribosomal protein L22 (RPL22A) | EXP | 2000 | | |
| CumMe_WSM_SF17349.G5770 | 56 | PGRL1B (PGR5-Like B) | EXP | 2000 | | |
| CumMe_WSM_SF17357.G5630 | 57 | 40S ribosomal protein S10 (RPS10B) | EXP | 2000 | | |
| CumMe_WSM_SF17494.G5140 | 58 | MEE34 (maternal effect embryo arrest 34) | EXP | 1591 | | |
| CumMe_WSM_SF17524.G6410 | 59 | SUS2 (ABNORMAL SUSPENSOR 2) | EXP | 2000 | | |
| CumMe_WSM_SF17672.G5610 | 60 | PSAK (photosystem I subunit K) | EXP | 2000 | | |
| CumMe_WSM_SF17773.G6620 | 61 | aconitase C-terminal domain-containing protein | EXP | 2000 | | |
| CumMe_WSM_SF17866.G6050 | 62 | ATPDIL5-1 (PDI-like 5-1) | EXP | 2000 | | |
| CumMe_WSM_SF18004.G6600 | 63 | hydroxyproline-rich glycoprotein family protein | EXP | 2000 | | |
| CumMe_WSM_SF18045.G6670 | 64 | | EXP | 2000 | | |
| CumMe_WSM_SF18053.G5410 | 65 | endomembrane protein 70 | EXP | 2000 | | |
| CumMe_WSM_SF18287.G5380 | 66 | CP12-1 | EXP | 2000 | | |
| CumMe_WSM_SF18488.G5340 | 67 | caffeoyl-CoA 3-O-methyltransferase | EXP | 2000 | Promoter; Leader | 1-1923; 1924-2000 |
| CumMe_WSM_SF18504.G5090 | 68 | vacuolar ATP synthase subunit H family protein | EXP | 2000 | | |
| CumMe_WSM_SF18530.G5750 | 69 | GUN5 (GENOMES UNCOUPLED 5); magnesium chelatase | EXP | 2000 | | |
| CumMe_WSM_SF18536.G6480 | 70 | MBF1A (MULTIPROTEIN BRIDGING FACTOR 1A) transcription coactivator | EXP | 2000 | | |
| CumMe_WSM_SF18575.G6410 | 71 | unknown protein | EXP | 2000 | | |
| CumMe_WSM_SF18634.G5190 | 72 | 60S ribosomal protein L23 (RPL23A) | EXP | 2000 | Promoter; Leader | 1-1971; 1972-2000 |
| CumMe_WSM_SF18645.G5380 | 73 | GS2 (GLUTAMINE SYNTHETASE 2) | EXP | 2000 | | |
| CumMe_WSM_SF18716.G5860 | 74 | 40S ribosomal protein S12 (RPS12A); reverse compliment: Auxin-induced protein x10A-like | EXP | 2000 | Promoter; Leader | Reverse compliment; see SEQ ID NO: 184 |
| CumMe_WSM_SF18801.G5040 | 75 | | EXP | 2000 | | |
| CumMe_WSM_SF18806.G6220 | 76 | unknown protein | EXP | 2000 | | |
| CumMe_WSM_SF18850.G5630 | 77 | PAC1; threonine-type endopeptidase | EXP | 2000 | | |
| CumMe_WSM_SF18863.G7550 | 78 | ATP synthase gamma chain, mitochondrial (ATPC) | EXP | 2000 | | |

TABLE 1-continued

Transcriptional regulatory expression element groups, promoters, leaders and introns isolated from *Cucumis melo*.

| Annotation | SEQ ID NO: | Description | Composition Type | Size (bp) | Composition | Coordinates of Elements within EXP |
|---|---|---|---|---|---|---|
| CumMe_WSM_SF18986. G6110 | 79 | GER1 (GERMIN-LIKE PROTEIN 1); oxalate oxidase | EXP | 2000 | | |
| CumMe_WSM_SF19064. G5690 | 80 | histone H3.2 | EXP | 2000 | Promoter; Leader; Intron | 1-1581; 1582-1670; 1671-2000 |
| CumMe_WSM_SF19323. G5120 | 81 | chloroplast outer envelope GTP-binding protein, putative | EXP | 2000 | | |
| CumMe_WSM_SF19452. G5090 | 82 | glucan phosphorylase, putative | EXP | 1072 | | |
| CumMe_WSM_SF19631. G5170 | 83 | RuBisCO activase, putative | EXP | 1730 | | |
| CumMe_WSM_SF19647. G5760 | 84 | 6-phosphogluconate dehydrogenase family protein | EXP | 2000 | Promoter; Leader; Intron; Leader | 1-936; 937-1021; 1022-1992; 1993-2000 |
| CumMe_WSM_SF19839. G5090 | 85 | ATPDX1.1 (pyridoxine biosynthesis 1.1) | EXP | 1020 | Promoter; Leader | 1-928; 929-1020 |
| CumMe_WSM_SF19850. G5130 | 86 | HMGB2 (HIGH MOBILITY GROUP B 2) transcription factor | EXP | 2000 | | |
| CumMe_WSM_SF19902. G5260 | 87 | universal stress protein (USP) family protein/ early nodulin ENOD18 family protein | EXP | 2000 | | |
| CumMe_WSM_SF19992. G6100 | 88 | unknown protein | EXP | 2000 | | |
| CumMe_WSM_SF20132. G5560 | 89 | peroxidase 21 | EXP | 2000 | Promoter; Leader | 1-1962; 1963-2000 |
| CumMe_WSM_SF20147. G7910 | 90 | CSD1 (COPPER/ZINC SUPEROXIDE DISMUTASE 1) | EXP | 2000 | | |
| CumMe_WSM_SF20355. G5130 | 91 | ATP synthase family | EXP | 2000 | | |
| CumMe_WSM_SF20359. G5870 | 92 | NADH-ubiquinone oxidoreductase 20 kDa subunit, mitochondrial | EXP | 2000 | | |
| CumMe_WSM_SF20368. G5700 | 93 | PGR5 (proton gradient regulation 5) | EXP | 2000 | | |
| CumMe_WSM_SF20409. G5240 | 94 | elongation factor 1B alpha-subunit 1 (eEF1Balpha1) | EXP | 2000 | | |
| CumMe_WSM_SF20431. G6340 | 95 | DHS2 (3-deoxy-d-arabino-heptulosonate 7-phosphate synthase) | EXP | 2000 | | |
| CumMe_WSM_SF20505. G5440 | 96 | THIC (ThiaminC); ADP-ribose pyrophosphohydrolase | EXP | 1373 | | |
| CumMe_WSM_SF20509. G5920 | 97 | Y14; RNA binding/ protein binding | EXP | 2000 | | |
| CumMe_WSM_SF206458. G5970 | 98 | FAD2 (FATTY ACID DESATURASE 2) | EXP | 2000 | Promoter | 1-2000 |
| CumMe_WSM_SF206534. G5200 | 99 | unknown protein | EXP | 2000 | | |
| CumMe_WSM_SF20997. G6990 | 100 | ALD1 (AGD2-LIKE DEFENSE RESPONSE PROTEIN1) | EXP | 2000 | | |
| CumMe_WSM_SF21035. G5090 | 101 | sodium/calcium exchanger family protein | EXP | 1078 | | |
| CumMe_WSM_SF21117. G5370 | 102 | 30S ribosomal protein, putative | EXP | 2000 | | |
| CumMe_WSM_SF21141. G5630 | 103 | 40S ribosomal protein S24 (RPS24A) | EXP | 2000 | | |
| CumMe_WSM_SF21198. G5180 | 104 | | EXP | 1974 | | |
| CumMe_WSM_SF21366. G5980 | 105 | GRF12 (GENERAL REGULATORY FACTOR 12) | EXP | 2000 | | |
| CumMe_WSM_SF21828. G5150 | 106 | cpHsc70-1 (chloroplast heat shock protein 70-1) | EXP | 1643 | | |
| CumMe_WSM_SF21886. G5080 | 107 | NPQ4 (NONPHOTOCHEMICAL QUENCHING) | EXP | 2000 | | |

TABLE 1-continued

Transcriptional regulatory expression element groups, promoters, leaders and introns isolated from *Cucumis melo*.

| Annotation | SEQ ID NO: | Description | Composition Type | Size (bp) | Composition | Coordinates of Elements within EXP |
|---|---|---|---|---|---|---|
| CumMe_WSM_SF22008. G5670 | 108 | NAP1; 2 (NUCLEOSOME ASSEMBLY PROTEIN 1; 2) | EXP | 2000 | | |
| CumMe_WSM_SF22070. G5280 | 109 | fructose-bisphosphate aldolase, putative | EXP | 2000 | | |
| CumMe_WSM_SF22097. G5540 | 110 | APX3 (ASCORBATE PEROXIDASE 3) | EXP | 2000 | | |
| CumMe_WSM_SF22254. G5760 | 111 | 40S ribosomal protein S7 (RPS7B) | EXP | 2000 | | |
| CumMe_WSM_SF22275. G5780 | 112 | ribosomal protein L17 family protein | EXP | 1027 | | |
| CumMe_WSM_SF22355. G5310 | 113 | | EXP | 2000 | | |
| CumMe_WSM_SF22531. G5120 | 114 | eukaryotic translation initiation factor 1A, putative | EXP | 2000 | Promoter; Leader; Intron; Leader | 1-759; 760-858; 859-1979; 1980-2000 |
| CumMe_WSM_SF22870. G5370 | 115 | ATSARA1A (*ARABIDOPSIS THALIANA* SECRETION-ASSOCIATED RAS SUPER FAMILY 1) | EXP | 2000 | | |
| CumMe_WSM_SF22934. G5290 | 116 | T-complex protein 1 epsilon subunit, putative | EXP | 2000 | | |
| CumMe_WSM_SF23181. G5100 | 117 | CEV1 (CONSTITUTIVE EXPRESSION OF VSP 1) | EXP | 1025 | | |
| CumMe_WSM_SF23186. G6160 | 118 | ubiquinol-cytochrome C reductase complex 14 kDa protein, putative | EXP | 2000 | | |
| CumMe_WSM_SF23397. G5210 | 119 | RPL27 (RIBOSOMAL PROTEIN LARGE SUBUNIT 27) | EXP | 2000 | | |
| CumMe_WSM_SF23760. G5200 | 120 | NDPK1; ATP binding/nucleoside diphosphate kinase | EXP | 2000 | Promoter; Leader | 1-1901; 1902-2000 |
| CumMe_WSM_SF23906. G6180 | 121 | PSBX (photosystem II subunit X) | EXP | 2000 | | |
| CumMe_WSM_SF24040. G5450 | 122 | RPS17 (RIBOSOMAL PROTEIN S17) | EXP | 2000 | | |
| CumMe_WSM_SF24045. G5400 | 123 | EXL3 (EXORDIUM LIKE 3) | EXP | 2000 | | |
| CumMe_WSM_SF24117. G5600 | 124 | 60S ribosomal protein L26 (RPL26A) | EXP | 2000 | | |
| CumMe_WSM_SF25084. G5580 | 125 | | EXP | 2000 | | |
| CumMe_WSM_SF25141. G5160 | 126 | isocitrate dehydrogenase, putative | EXP | 1397 | Promoter; Leader | 1-1322; 1323-1397 |
| CumMe_WSM_SF25355. G5000 | 127 | LOS1; copper ion binding translation elongation factor | EXP | 2000 | Promoter; Leader; Intron; Leader; CDS | 1-734; 735-811; 812-1340; 1341-1360; 1361-2000 |
| CumMe_WSM_SF25370. G5000 | 128 | PSBP-1 (PHOTOSYSTEM II SUBUNIT P-1) | EXP | 1657 | | |
| CumMe_WSM_SF25455. G5370 | 129 | GLY3 (GLYOXALASE II 3) | EXP | 2000 | | |
| CumMe_WSM_SF25936. G5450 | 130 | mitochondrial substrate carrier family protein | EXP | 2000 | Promoter; Leader | 1-1878; 1879-2000 |
| CumMe_WSM_SF27080. G5510 | 131 | LIP1 (LIPOIC ACID SYNTHASE 1) | EXP | 2000 | | |
| CumMe_WSM_SF27222. G5150 | 132 | DRT112; copper ion binding/electron carrier | EXP | 2000 | | |
| CumMe_WSM_SF27957. G5450 | 133 | SMAP1 (SMALL ACIDIC PROTEIN 1) | EXP | 2000 | | |
| CumMe_WSM_SF28729. G5340 | 134 | RNA-binding protein cp29, putative | EXP | 1696 | | |
| CumMe_WSM_SF28805. G6200 | 135 | unknown protein | EXP | 2000 | | |
| CumMe_WSM_SF31264. G5380 | 136 | ATPH1 (*ARABIDOPSIS THALIANA* PLECKSTRIN HOMOLOGUE 1) | EXP | 2000 | | |

TABLE 1-continued

Transcriptional regulatory expression element groups, promoters, leaders and introns isolated from *Cucumis melo*.

| Annotation | SEQ ID NO: | Description | Composition Type | Size (bp) | Composition | Coordinates of Elements within EXP |
|---|---|---|---|---|---|---|
| CumMe_WSM_SF35856.G5150 | 137 | TIP4; 1 (tonoplast intrinsic protein 4; 1) | EXP | 1575 | | |
| CumMe_WSM_SF40859.G5250 | 138 | SMT2 (STEROL METHYLTRANSFERASE 2) | EXP | 2000 | | |
| CumMe_WSM_SF41124.G5080 | 139 | 40S ribosomal protein S2 (RPS2C) | EXP | 1006 | Promoter; Leader | 1-883; 884-1006 |
| CumMe_WSM_SF41128.G5410 | 140 | CRY2 (CRYPTOCHROME 2) | EXP | 2000 | | |
| CumMe_WSM_SF41254.G5160 | 141 | GDP-D-glucose Phosphorylase | EXP | 1556 | | |
| CumMe_WSM_SF41588.G5470 | 142 | PRPL11 (PLASTID RIBOSOMAL PROTEIN L11) | EXP | 2000 | | |
| CumMe_WSM_SF41644.G6400 | 143 | SHD (SHEPHERD) | EXP | 2000 | | |
| CumMe_WSM_SF41983.G5000 | 144 | catalytic/coenzyme binding | EXP | 1337 | | |
| CumMe_WSM_SF42075.G5100 | 145 | CPN60B (CHAPERONIN 60 BETA) | EXP | 2000 | | |
| CumMe_WSM_SF42141.G5110 | 146 | cathepsin B-like cysteine protease, putative | EXP | 1212 | | |
| CumMe_WSM_SF44933.G5290 | 147 | EBF1 (EIN3-BINDING F BOX PROTEIN 1) ubiquitin-protein ligase | EXP | 2000 | | |
| CumMe_WSM_SF44977.G5000 | 148 | PAP26 (PURPLE ACID PHOSPHATASE 26) | EXP | 1254 | | |
| CumMe_WSM_SF45441.G5510 | 149 | GAPA-2 (GLYCERALDEHYDE 3-PHOSPHATE DEHYDROGENASE A SUBUNIT 2) | EXP | 2000 | | |
| CumMe_WSM_SF45882.G5120 | 150 | fructose-1,6-bisphosphatase, putative | EXP | 1680 | | |
| CumMe_WSM_SF47806.G5070 | 151 | ATP synthase epsilon chain, mitochondrial | EXP | 1524 | | |
| CumMe_WSM_SF53106.G5190 | 152 | CPN60A (CHAPERONIN-60ALPHA) | EXP | 1851 | | |
| CumMe_WSM_SF65588.G5230 | 153 | vacuolar calcium-binding protein-related | EXP | 2000 | | |
| CumMe_WSM_SF9060.G5120 | 154 | APE2 (ACCLIMATION OF PHOTOSYNTHESIS TO ENVIRONMENT 2) | EXP | 1288 | | |
| P-CUCme.1-1:1:1rc | 155 | Phosphatase 2A | EXP | 2000 | Promoter; Leader; Intron; Leader | 1-1135; 1136-1249; 1250-1990; 1991-2000 |
| EXP-CUCme.4:1:1 | 156 | Ubiquitin 2 | EXP | 2011 | Promoter; Leader; Intron; Leader | 1-1646; 1647-1704; 1705-2005; 2006-2008 |
| P-CUCme.4-1:1:4 | 157 | Ubiquitin 2 | P; L | 1698 | Promoter; Leader | |
| I-CUCme.4-1:1:1 | 158 | Ubiquitin 2 | I; L | 313 | Intron; Leader | |
| EXP-CUCme.5:1:1 | 159 | Ubiquitin 3 | EXP | 2010 | Promoter; Leader; Intron; Leader | 1-748; 749-819; 820-2004; 2005-2007 |
| P-CUCme.5-1:1:3 | 160 | Ubiquitin 3 | P; L | 1107 | Promoter; Leader | |
| I-CUCme.5-1:1:1 | 161 | Ubiquitin 3 | I; L | 903 | Intron; Leader | |
| EXP-CUCme.eEF1a:1:1 | 162 | Elongation Factor 1 alpha | EXP | 1235 | Promoter; Leader; Intron; Leader | 1-617; 618-677; 678-1213; 1214-1235 |
| P-CUCme.eEF1a-1:1:1 | 163 | Elongation Factor 1 alpha | P | 617 | Promoter | |
| L-CUCme.eEF1a-1:1:1 | 164 | Elongation Factor 1 alpha | L | 54 | Leader | |
| I-CUCme.eEF1a-1:1:1 | 165 | Elongation Factor 1 alpha | I | 545 | Intron | |
| L-CUCme.eEF1a-1:1:2 | 166 | Elongation Factor 1 alpha | L | 19 | Leader | |
| P-CUCme.19-1:1:3 | 167 | Chloropyll a/b binding protein | EXP | 2003 | Promoter; Leader | 1-1958; 1959-2003 |
| EXP-CUCme.SAMS2:1:1 | 168 | S-Adenosylmethionine Synthetase | EXP | 2004 | Promoter; Leader; Intron | 1-1067; 1068-1165; 1166-2003 |

TABLE 1-continued

Transcriptional regulatory expression element groups, promoters, leaders and introns isolated from *Cucumis melo*.

| Annotation | SEQ ID NO: | Description | Composition Type | Size (bp) | Composition | Coordinates of Elements within EXP |
|---|---|---|---|---|---|---|
| P-CUCme.SAMS2-1:1:1 | 169 | S-Adenosylmethionine Synthetase | P | 1067 | Promoter | |
| L-CUCme.SAMS2-1:1:1 | 170 | S-Adenosylmethionine Synthetase | L | 92 | Leader | |
| I-CUCme.SAMS2-1:1:1 | 171 | S-Adenosylmethionine Synthetase | I | 845 | Intron | |
| EXP-CUCme.29:1:1 | 172 | Ribosomal protein S5a | EXP | 2018 | Promoter; Leader; Intron; Leader | 1-490; 491-571; 572-2012; 2013-2018 |
| P-CUCme.29-1:1:4 | 173 | Ribosomal protein S5a | P; L | 565 | Promoter; Leader | |
| I-CUCme.29-1:1:1 | 174 | Ribosomal protein S5a | I; L | 1453 | Intron; Leader | |
| P-CUCme.CumMe_WSM_SF16444.G5140-1:1:1 | 175 | histone H4 | EXP | 1999 | Promoter; Leader; Intron | 1-1946; 947-1999 |
| P-CUCme.CumMe_WSM_SF16563.G5560-1:1:1 | 176 | ATARFB1A (ADP-ribosylation factor B1A) | EXP | 2004 | Promoter; Leader; Intron; Leader | 1-1331; 1332-1429; 1430-1992; 1993-2004 |
| P-CUCme.CumMe_WSM_SF17111.G5790-1:1:1 | 177 | ubiquinol-cytochrome C reductase complex ubiquinone-binding protein | EXP | 2005 | Promoter; Leader | 1-1901; 1902-2005 |
| EXP-CumMe.WSM_SF17252.G7330:1:1 | 178 | nascent polypeptide-associated complex (NAC) domain-containing protein | EXP | 1978 | Promoter; Leader; Intron; Leader | 1-1167; 1168-1269; 1270-1972; 1973-1975 |
| P-CUCme.WSM_SF17252.G7330-1:1:1 | 179 | nascent polypeptide-associated complex (NAC) domain-containing protein | P; L | 1263 | Promoter; Leader | |
| I-CUCme.WSM_SF17252.G7330-1:1:1 | 180 | nascent polypeptide-associated complex (NAC) domain-containing protein | I; L | 715 | Intron; Leader | |
| P-CUCme.CumMe_WSM_SF18488.G5340-1:1:1 | 181 | caffeoyl-CoA 3-O-methyltransferase | EXP | 2000 | Promoter; Leader | 1-923; 1924-2000 |
| P-CUCme.CumMe_WSM_SF18536.G6480-1:1:1 | 182 | MBF1A (MULTIPROTEIN BRIDGING FACTOR 1A) transcription coactivator | EXP | 2000 | Promoter; Leader; Intron | |
| P-CUCme.CumMe_WSM_SF18634.G5190-1:1:1 | 183 | 60S ribosomal protein L23 (RPL23A) | EXP | 1989 | Promoter; Leader | 1-1960; 1961-1989 |
| P-CUCme.CumMe_WSM_SF18716.G5860-1:1:1 | 184 | Auxin-induced prtoein X10A-like | EXP | 1463 | Promoter; Leader | 1-1392; 1393-1463 |
| EXP-CUCme.WSM_SF19064.G5690:1:1 | 185 | histone H3.2 | EXP | 2006 | Promoter; Leader; Intron; Leader | 1-1581; 1582-1670; 1671-2000; 2001-2003 |
| P-CUCme.WSM_SF19064.G5690-1:1:1 | 186 | histone H3.2 | P; L | 1664 | Promoter; Leader | |
| I-CUCme.WSM_SF19064.G5690-1:1:1 | 187 | histone H3.2 | I; L | 342 | Intron; Leader | |
| P-CUCme.CumMe_WSM_SF19647.G5760-1:1:1 | 188 | 6-phosphogluconate dehydrogenase family protein | EXP | 2003 | Promoter; Leader; Intron; Leader | 1-939; 940-1024; 1025-1995; 1996-2003 |
| P-CUCme.CumMe_WSM_SF19839.G5090-1:1:1 | 189 | ATPDX1.1 (pyridoxine biosynthesis 1.1) | EXP | 1024 | Promoter; Leader | 1-904; 905-1024 |
| P-CUCme.CumMe_WSM_SF20132.G5560-1:1:1 | 190 | peroxidase 21 | EXP | 2001 | Promoter; Leader | 1-1962; 1963-2001 |
| P-CUCme.CumMe_WSM_SF206458.G5970-1:1:1 | 191 | FAD2 (FATTY ACID DESATURASE 2) | EXP | 4175 | Promoter; Leader; Intron; Leader | 1-2171; 2172-2325; 2326-4155; 4156-4175 |
| P-CUCme.CumMe_WSM_SF22531.G5120-1:1:1 | 192 | eukaryotic translation initiation factor 1A, putative | EXP | 1999 | Promoter; Leader; Intron; Leader | 1-759; 760-858; 859-1978; 1979-1999 |
| P- | 193 | NDPK1; ATP binding/ | EXP | 2000 | Promoter; Leader | 1-1901; 1902-2000 |

TABLE 1-continued

Transcriptional regulatory expression element groups, promoters, leaders and introns isolated from *Cucumis melo*.

| Annotation | SEQ ID NO: | Description | Composition Type | Size (bp) | Composition | Coordinates of Elements within EXP |
|---|---|---|---|---|---|---|
| CUCme.CumMe_WSM_SF23760.G5200-1:1:1 | | nucleoside diphosphate kinase | | | | |
| P-CUCme.CumMe_WSM_SF23906.G6180-1:1:1 | 194 | PSBX (photosystem II subunit X) | EXP | 2000 | Promoter; Leader | |
| P-CUCme.CumMe_WSM_SF25141.G5160-1:1:2 | 195 | isocitrate dehydrogenase, putative | EXP | 1400 | Promoter; Leader | 1-1325; 1326-1400 |
| P-CUCme.CumMe_WSM_SF25355.G5000-1:1:1 | 196 | LOS1; copper ion binding translation elongation factor | EXP | 2019 | Promoter; Leader; Intron; Leader; CDS | 1-734; 735-811; 812-1340; 1341-1360; 1361-2019 |
| P-CUCme.CumMe_WSM_SF25936.G5450-1:1:1 | 197 | mitochondrial substrate carrier family protein | EXP | 1999 | Promoter; Leader | 1-1877; 1878-1999 |
| P-CUCme.CumMe_WSM_SF35856.G5150-1:1:1 | 198 | TIP4; 1 (tonoplast intrinsic protein 4; 1) | EXP | 1578 | | |
| P-CUCme.CumMe_WSM_SF41124.G5080-1:1:1 | 199 | 40S ribosomal protein S2 (RPS2C) | EXP | 1023 | Promoter; Leader | 1-945; 946-1023 |
| P-CUCme.20-1:3 | 211 | Chloropyll a/b binding protein | EXP | 1446 | Promoter; Leader | 1-1390; 1391-1446 |
| EXP-CUCme.29:1:2 | 212 | Ribosomal protein S5a | EXP | 2018 | Promoter; Leader; Intron; Leader | 1-490; 491-571; 572-2011; 2013-2018 |

As shown in Table 1, for example, the transcriptional regulatory expression element group (EXP) designated EXP-CUCme.Ubq1:1:1 (SEQ ID NO: 1), with components isolated from *C. melo*, comprises a 2068 base pair sized (bp) promoter element, P-CUCme.Ubq1-1:1:15 (SEQ ID NO: 2), operably linked 5' to a leader element, L-CUCme.Ubq1-1:1:1 (SEQ ID NO: 3), operably linked 5' to an intron element, I-CUCme.Ubq1-1:1:1 (SEQ ID NO: 4). The transcriptional regulatory expression element group (EXP) designated EXP-CUCme.Ubq1:1:2 (SEQ ID NO: 5), with components isolated from *C. melo*, comprises a 1459 bp promoter element, P-CUCme.Ubq1-1:1:16 (SEQ ID NO: 6), operably linked 5' to a leader element, L-CUCme.Ubq1-1:1:1 (SEQ ID NO: 3), operably linked 5' to an intron element, I-CUCme.Ubq1-1:1:1 (SEQ ID NO: 4). The transcriptional regulatory expression element group (EXP) designated EXP-CUCme.Ubq1:1:3 (SEQ ID NO: 7), with components isolated from *C. melo*, comprises a 964 bp promoter element, P-CUCme.Ubq1-1:1:17 (SEQ ID NO: 8), operably linked 5' to a leader element, L-CUCme.Ubq1-1:1:1 (SEQ ID NO: 3), operably linked 5' to an intron element, I-CUCme.Ubq1-1:1:1 (SEQ ID NO: 4). The transcriptional regulatory expression element group (EXP) designated EXP-CUCme.Ubq1:1:4 (SEQ ID NO: 9), with components isolated from *C. melo*, comprises a 479 bp promoter element, P-CUCme.Ubq1-1:1:18 (SEQ ID NO: 10), operably linked 5' to a leader element, L-CUCme.Ubq1-1:1:1 (SEQ ID NO: 3), operably linked 5' to an intron element, I-CUCme.Ubq1-1:1:1 (SEQ ID NO: 4). The transcriptional regulatory expression element group (EXP) designated EXP-CUCme.Ubq1:1:5 (SEQ ID NO: 11), with components isolated from *C. melo*, comprises a 173 bp promoter element, P-CUCme.Ubq1-1:1:19 (SEQ ID NO: 12), operably linked 5' to a leader element, L-CUCme.Ubq1-1:1:1 (SEQ ID NO: 3), operably linked 5' to an intron element, I-CUCme.Ubq1-1:1:1 (SEQ ID NO: 4).

An alignment of the ubiquitin 1 promoter sequences is provided in FIGS. 1*a*-1*f*. The promoter elements, P-CUCme.Ubq1-1:1:16 (SEQ ID NO: 6), P-CUCme.Ubq1-1:1:17 (SEQ ID NO: 8), P-CUCme.Ubq1-1:1:18 (SEQ ID NO: 10) and P-CUCme.Ubq1-1:1:19 (SEQ ID NO: 12) were built by introducing varying lengths of deletions from the 5' end of the promoter, P-CUCme.Ubq1-1:1:15 (SEQ ID NO: 2).

Example 2: Analysis of Regulatory Elements Driving GUS in Soy Cotyledon Protoplasts Soybean cotyledon protoplasts were transformed with plant expression vectors containing a test transcriptional regulatory expression element group driving expression of the ß-glucuronidase (GUS) transgene and compared to GUS expression in leaf protoplasts in which expression of GUS is driven by known constitutive promoters.

Expression of a transgene driven by EXP-CUCme.Ubq1:1:1 (SEQ ID NO: 1), EXP-CUCme.Ubq1:1:2 (SEQ ID NO: 5), EXP-CUCme.Ubq1:1:3 (SEQ ID NO: 7), EXP-CUCme.Ubq1:1:4 (SEQ ID NO: 9) and EXP-CUCme.Ubq1:1:5 (SEQ ID NO: 11) was compared with expression from known constitutive promoters. Each plant expression vector was comprised of a right border region from *Agrobacterium tumefaciens*, a first transgene cassette comprised of an EXP sequence or known constitutive promoter operably linked 5' to a coding sequence for ß-glucuronidase (GUS, SEQ ID NO: 206) containing a processable intron derived from the potato light-inducible tissue-specific ST-LS1 gene (Genbank Accession: X04753), operably linked 5' to a 3' termination region from the *Gossypium barbadense* E6 gene (T-Gb.E6-3b:1:1, SEQ ID NO: 204), the *Pisum sativum* RbcS2-E9 gene (T-Ps.RbcS2-E9-1:1:6, SEQ ID NO: 203), or the *Gossypium barbadense* FbLate-2 gene (T-Gb.FbL2-1:1:1, SEQ ID NO: 205); a second transgene selection cassette used for selection of transformed plant cells that either confers resistance to the herbicide glyphosate (driven by the *Arabidopsis* Actin 7 promoter) or the antibiotic, kanamycin and a left border region from *A. tumefaciens*. A promoterless control plant expression vector (pMON124912) served as a negative control for expression. The foregoing test and constitutive expression element groups were cloned into plant expression vectors as shown in Table 2 below.

TABLE 2

Plant expression vectors and corresponding expression element group and 3' UTR.

| Expression Vector | Regulatory Element | SEQ ID NO: | 3' UTR |
|---|---|---|---|
| pMON80585 | EXP-At.Atntt1:1:2 | 200 | T-Ps.RbcS2-E9-1:1:6 |
| pMON109584 | EXP-CaMV.35S-enh+Ph.DnaK:1:3 | 201 | T-Gb.E6-3b:1:1 |
| pMON118756 | EXP-At.Act7:1:11 | 202 | T-Gb.E6-3b:1:1 |
| pMON124912 | No promoter | | T-Gb.FbL2-1:1:1 |
| pMON138776 | EXP-CUCme.Ubq1:1:1 | 1 | T-Gb.FbL2-1:1:1 |
| pMON138777 | EXP-CUCme.Ubq1:1:2 | 5 | T-Gb.FbL2-1:1:1 |
| pMON138778 | EXP-CUCme.Ubq1:1:3 | 7 | T-Gb.FbL2-1:1:1 |
| pMON138779 | EXP-CUCme.Ubq1:1:4 | 9 | T-Gb.FbL2-1:1:1 |
| pMON138780 | EXP-CUCme.Ubq1:1:5 | 11 | T-Gb.FbL2-1:1:1 |

Two plasmids, for use in co-transformation and normalization of data, were also constructed. One transformation control plasmid was comprised of a constitutive promoter, driving the expression of the firefly (*Photinus pyralis*) luciferase coding sequence (FLuc, SEQ ID NO: 207), operably linked 5' to a 3' termination region from the *Agrobacterium tumefaciens* nopaline synthase gene (T-AGRtu.nos-1:1:13, SEQ ID NO: 209). The other transformation control plasmid was comprised of a constitutive promoter, driving the expression of the sea pansy (*Renilla reniformis*) luciferase coding sequence (RLuc, SEQ ID NO: 208), operably linked 5' to a 3' termination region from the *Agrobacterium tumefaciens* nopaline synthase gene.

The plant expression vectors, pMON80585, pMON109584, pMON118756, pMON124912, pMON138776, pMON138777, pMON138778, pMON138779 and pMON138780 were used to transform soybean cotyledon protoplast cells using PEG transformation methods. Protoplast cells were transformed with equimolar amounts of each of the two transformation control plasmids and a test plant expression vector. GUS and luciferase activity was assayed. Measurements of both GUS and luciferase were conducted by placing aliquots of a lysed preparation of cells transformed as above into two different small-well trays. One tray was used for GUS measurements, and a second tray was used to perform a dual luciferase assay using the dual luciferase reporter assay system (Promega Corp., Madison, Wis.; see for example, Promega Notes Magazine, No: 57, 1996, p. 02). Sample measurements were made using 3 or 4 replicates per transformation. The average GUS and luciferase values are presented in Table 3 below.

TABLE 3

Average GUS and luciferase expression values and GUS/luciferase ratios.

| Construct | Regulatory Element | SEQ ID NO: | Average GUS | Average FLuc | Average RLuc | GUS/FLuc | GUS/RLuc |
|---|---|---|---|---|---|---|---|
| pMON80585 | EXP-At.Atntt1:1:2 | 200 | 55173 | 6498 | 30503 | 8.49 | 1.81 |
| pMON109584 | EXP-CaMV.35S-enh + Ph.DnaK:1:3 | 200 | 24940 | 5050.75 | 35495 | 4.94 | 0.70 |
| pMON118756 | EXP-At.Act7:1:11 | 201 | 9871 | 6880 | 40850 | 1.43 | 0.24 |
| pMON124912 | No promoter | | 2000 | 11670 | 73187 | 0.17 | 0.03 |
| pMON138776 | EXP-CUCme.Ubq1:1:1 | 1 | 26972 | 6467.25 | 37200 | 4.17 | 0.73 |
| pMON138777 | EXP-CUCme.Ubq1:1:2 | 5 | 41307 | 5902.5 | 24396 | 7.00 | 1.69 |
| pMON138778 | EXP-CUCme.Ubq1:1:3 | 7 | 90140 | 10710.5 | 60983 | 8.42 | 1.48 |
| pMON138779 | EXP-CUCme.Ubq1:1:4 | 9 | 35526 | 5590 | 28001 | 6.36 | 1.27 |
| pMON138780 | EXP-CUCme.Ubq1:1:5 | 11 | 23298 | 4483.25 | 19075 | 5.20 | 1.22 |

To compare the relative activity of each promoter in soybean cotyledon protoplasts, GUS values were expressed as a ratio of GUS to luciferase activity and normalized with respect to the expression levels observed for the constitutive expression element groups, EXP-At.Act7:1:11 and EXP-CaMV.35S-enh+Ph.DnaK:1:3. Table 4 below shows the GUS to firefly luciferase (FLuc) ratios normalized with respect to EXP-At.Act7:1:11 and EXP-CaMV.35S-enh+Ph.DnaK:1:3. Table 5 below shows the GUS to *renilla* luciferase (RLuc) ratios normalized with respect to EXP-At.Act7:1:11 and EXP-CaMV.35S-enh+Ph.DnaK:1:3.

TABLE 4

GUS to firefly luciferase (FLuc) ratios normalized with respect to EXP-At.Act7:1:11 and EXP-CaMV.35S-enh+Ph.DnaK:1:3.

| Construct | Regulatory Element | SEQ ID NO: | GUS/FLuc normalized with respect to EXP-At.Act7:1:11 | GUS/FLuc normalized with respect to EXP-CaMV.35S-enh+Ph.DnaK:1:3 |
|---|---|---|---|---|
| pMON80585 | EXP-At.Atntt1:1:2 | 200 | 5.92 | 1.72 |
| pMON109584 | EXP-CaMV.35S-enh+Ph.DnaK:1:3 | 201 | 3.44 | 1.00 |
| pMON118756 | EXP-At.Act7:1:11 | 202 | 1.00 | 0.29 |
| pMON124912 | No promoter | | 0.12 | 0.03 |
| pMON138776 | EXP-CUCme.Ubq1:1:1 | 1 | 2.91 | 0.84 |
| pMON138777 | EXP-CUCme.Ubq1:1:2 | 5 | 4.88 | 1.42 |
| pMON138778 | EXP-CUCme.Ubq1:1:3 | 7 | 5.87 | 1.70 |

TABLE 4-continued

GUS to firefly luciferase (FLuc) ratios normalized with respect to EXP-At.Act7:1:11 and EXP-CaMV.35S-enh+Ph.DnaK:1:3.

| Construct | Regulatory Element | SEQ ID NO: | GUS/FLuc normalized with respect to EXP-At.Act7:1:11 | GUS/FLuc normalized with respect to EXP-CaMV.35S-enh+Ph.DnaK:1:3 |
|---|---|---|---|---|
| pMON138779 | EXP-CUCme.Ubq1:1:4 | 9 | 4.43 | 1.29 |
| pMON138780 | EXP-CUCme.Ubq1:1:5 | 11 | 3.62 | 1.05 |

TABLE 5

GUS to renilla luciferase (RLuc) ratios normalized with respect to EXP-At.Act7:1:11 and EXP-CaMV.35S-enh+Ph.DnaK:1:3.

| Construct | Regulatory Element | SEQ ID NO: | GUS/RLuc normalized with respect to EXP-At.Act7:1:11 | GUS/RLuc normalized with respect to EXP-CaMV.35S-enh+Ph.DnaK:1:3 |
|---|---|---|---|---|
| pMON80585 | EXP-At.Atntt1:1:2 | 200 | 7.49 | 2.57 |
| pMON109584 | EXP-CaMV.35S-enh+Ph.DnaK:1:3 | 201 | 2.91 | 1.00 |
| pMON118756 | EXP-At.Act7:1:11 | 202 | 1.00 | 0.34 |
| pMON124912 | No promoter | | 0.11 | 0.04 |
| pMON138776 | EXP-CUCme.Ubq1:1:1 | 1 | 3.00 | 1.03 |
| pMON138777 | EXP-CUCme.Ubq1:1:2 | 5 | 7.01 | 2.41 |
| pMON138778 | EXP-CUCme.Ubq1:1:3 | 7 | 6.12 | 2.10 |
| pMON138779 | EXP-CUCme.Ubq1:1:4 | 9 | 5.25 | 1.81 |
| pMON138780 | EXP-CUCme.Ubq1:1:5 | 11 | 5.05 | 1.74 |

As can be seen in Tables 4 and 5 above, each of the expression element groups EXP-CUCme.Ubq1:1:1 (SEQ ID NO: 1), EXP-CUCme.Ubq1:1:2 (SEQ ID NO: 5), EXP-CUCme.Ubq1:1:3 (SEQ ID NO: 7), EXP-CUCme.Ubq1:1:4 (SEQ ID NO: 9) and EXP-CUCme.Ubq1:1:5 (SEQ ID NO: 11) demonstrated the ability of driving transgene expression in soybean cotyledon protoplasts. Expression levels were greater than that of EXP-At.Act7:1:11 and was 2.9 to 5.8 (FLuc) or 3 to 7 (RLuc) fold higher than EXP-At.Act7:1:11 in this assay. Expression was equivalent or higher than expression observed for EXP-CaMV.35S-enh+Ph.DnaK:1:3. Expression levels were 0.8 to 1.7 (FLuc) or 1 to 2.4 (RLuc) fold higher than expression observed for EXP-CaMV.35S-enh+Ph.DnaK:1:3.

Example 3: Analysis of Regulatory Elements Driving GUS in Bombarded Soybean Leaves and Roots Soybean leaves and roots were transformed with plant expression vectors containing a test transcriptional regulatory expression element group driving expression of the ß-glucuronidase (GUS) transgene and compared to GUS expression in roots and leaves in which expression of GUS is driven by known constitutive promoters.

Expression of a transgene driven by EXP-CUCme.Ubq1:1:1 (SEQ ID NO: 1), EXP-CUCme.Ubq1:1:2 (SEQ ID NO: 5), EXP-CUCme.Ubq1:1:3 (SEQ ID NO: 7), EXP-CUCme.Ubq1:1:4 (SEQ ID NO: 9) and EXP-CUCme.Ubq1:1:5 (SEQ ID NO: 11) was compared with expression from known constitutive promoters in particle bombarded soybean leaves and roots. The plant expression vectors used for transformation of leaves and roots was the same as those presented in Table 2 of Example 2 above.

The plant expression vectors, pMON80585, pMON109584, pMON118756, pMON124912, pMON138776, pMON138777, pMON138778, pMON138779 and pMON138780 were used to transform soybean leaves and roots using particle bombardment transformation methods.

Briefly, A3244 soybean seeds were surface sterilized and allowed to germinate in trays with a photoperiod of 16 hours light and 8 hours of darkness. After approximately 13 days, leaf and root tissue was harvested under sterile conditions from the seedlings and used for bombardment. The tissue samples were randomly placed on a petri dish containing plant culture medium. Ten micrograms of plasmid DNA was used to coat 0.6 micron gold particles (Catalog #165-2262 Bio-Rad, Hercules, Calif.) for bombardment. Macro-carriers were loaded with the DNA-coated gold particles (Catalog #165-2335 Bio-Rad, Hercules Calif.). A PDS 1000/He biolistic gun was used for transformation (Catalog #165-2257 Bio-Rad, Hercules Calif.). The bombarded root and leaf tissues were allowed to incubate in the dark for 24 hours at 26 degrees Celsius. Following this overnight incubation, the tissues were stained in solution for GUS expression overnight at 37 degrees Celsius. After staining overnight, the tissues were soaked in 70% ethanol overnight to remove chlorophyll and reveal the GUS staining. The tissues were then photographed and a rating scale of "0", "+" to "++++++" reflecting the level of GUS expression is assigned to each construct (0—no expression, + to ++++++—low to high, respectively).

Expression of the GUS transgene demonstrated in each tissue is used to infer the relative potential level and specificity of each element's capacity to drive transgene expression in stably transformed corn plants. Average GUS expression ratings are provided in Table 6 below.

TABLE 6

GUS expression ratings for particle bombarded leaf and root.

| Construct | Regulatory Element | SEQ ID NO: | Leaf Expression Rating | Root Expression Rating |
|---|---|---|---|---|
| pMON80585 | EXP-At.Atntt1:1:2 | 200 | ++++ | ++ |
| pMON109584 | EXP-CaMV.35S-enh+Ph.DnaK:1:3 | 201 | +++++ | +++ |
| pMON118756 | EXP-At.Act7:1:11 | 202 | ++++ | ++ |
| pMON124912 | No promoter | | 0 | 0 |
| pMON138776 | EXP-CUCme.Ubq1:1:1 | 1 | ++++ | +++ |
| pMON138777 | EXP-CUCme.Ubq1:1:2 | 5 | +++ | ++ |
| pMON138778 | EXP-CUCme.Ubq1:1:3 | 7 | +++ | ++ |
| pMON138779 | EXP-CUCme.Ubq1:1:4 | 9 | +++ | ++ |
| pMON138780 | EXP-CUCme.Ubq1:1:5 | 11 | ++ | + |

As can be seen in Table 6 above, each of the expression element groups EXP-CUCme.Ubq1:1:1 (SEQ ID NO: 1), EXP-CUCme.Ubq1:1:2 (SEQ ID NO: 5), EXP-CUCme.Ubq1:1:3 (SEQ ID NO: 7), EXP-CUCme.Ubq1:1:4 (SEQ ID NO: 9) and EXP-CUCme.Ubq1:1:5 (SEQ ID NO: 11) demonstrated the ability of driving transgene expression in particle bombarded transformed leaf and root tissues.

Example 4: Analysis of Regulatory Elements Driving GUS in Soy Cotyledon Protoplasts Soybean cotyledon protoplasts were transformed with plant expression vectors containing a test transcriptional regulatory expression element group driving expression of the ß-glucuronidase (GUS) transgene and compared to GUS expression in leaf protoplasts in which expression of GUS is driven by known constitutive promoters.

Expression of a transgene driven by P-CUCme.1-1:1:1rc (SEQ ID NO: 155), P-CUCme.2-1:1:1 (SEQ ID NO: 14), P-CUCme.3-1:1:3 (SEQ ID NO: 15), EXP-CUCme.4:1:1 (SEQ ID NO: 156), EXP-CUCme.5:1:1 (SEQ ID NO: 159), P-CUCme.6-1:1:1 (SEQ ID NO: 18), P-CUCme.8-1:1:2 (SEQ ID NO: 19), P-CUCme.9-1:1:2 (SEQ ID NO: 20), P-CUCme.10-1:1:1 (SEQ ID NO: 21), EXP-CUCme.eEF1a:1:1 (SEQ ID NO: 162), P-CUCme.15-1:1:2 (SEQ ID NO: 23), P-CUCme.16a-1:1:2 (SEQ ID NO: 24), P-CUCme.17-1:1:2 (SEQ ID NO: 26), P-CUCme.18-1:1:2 (SEQ ID NO: 27), P-CUCme.19-1:1:3 (SEQ ID NO: 167), P-CUCme.20-1:3 (SEQ ID NO: 211), P-CUCme.21-1:1:1 (SEQ ID NO: 30), P-CUCme.22-1:1:3 (SEQ ID NO: 31), EXP-CUCme.SAMS2:1:1 (SEQ ID NO: 168), P-CUCme.26-1:1:2 (SEQ ID NO: 33), P-CUCme.28-1:1:2 (SEQ ID NO: 34) and EXP-CUCme.29:1:2 (SEQ ID NO: 212) was compared with expression from known constitutive expression element groups. Each plant expression vector was comprised of a right border region from *Agrobacterium tumefaciens*, a first transgene cassette comprised of a test promoter or known constitutive promoter operably linked 5' to a coding sequence for ß-glucuronidase (GUS, SEQ ID NO: 206) containing a processable intron derived from the potato light-inducible tissue-specific ST-LS1 gene (Genbank Accession: X04753), operably linked 5' to a 3' termination region from the *Gossypium barbadense* E6 gene (T-Gb.E6-3b:1:1, SEQ ID NO: 204), the *Pisum sativum* RbcS2-E9 gene (T-Ps.RbcS2-E9-1:1:6, SEQ ID NO: 203), or the *Gossypium barbadense* FbLate-2 gene (T-Gb.FbL2-1:1:1, SEQ ID NO: 205); a second transgene selection cassette used for selection of transformed plant cells that either confers resistance to the herbicide glyphosate (driven by the *Arabidopsis* Actin 7 promoter) or the antibiotic, kanamycin and a left border region from *A. tumefaciens*. A promoterless control plant expression vector (pMON124912) served as a negative control for expression. The foregoing test and constitutive expression element groups were cloned into plant expression vectors as shown in Table 7 below.

TABLE 7

Plant expression vectors and corresponding expression element group and 3' UTR.

| Construct | Regulatory Element | SEQ ID NO: | 3' UTR |
|---|---|---|---|
| pMON80585 | EXP-At.Atntt1:1:2 | 200 | T-Ps.RbcS2-E9-1:1:6 |
| pMON109584 | EXP-CaMV.35S-enh+Ph.DnaK:1:3 | 201 | T-Gb.E6-3b:1:1 |
| pMON118756 | EXP-At.Act7:1:11 | 202 | T-Gb.E6-3b:1:1 |
| pMON124912 | Promoterless | | T-Gb.FbL2-1:1:1 |
| pMON140818 | P-CUCme.1-1:1:1rc | 155 | T-Gb.FbL2-1:1:1 |
| pMON140819 | P-CUCme.2-1:1:1 | 14 | T-Gb.FbL2-1:1:1 |
| pMON140820 | P-CUCme.3-1:1:3 | 15 | T-Gb.FbL2-1:1:1 |
| pMON140821 | EXP-CUCme.4:1:1 | 156 | T-Gb.FbL2-1:1:1 |
| pMON140822 | EXP-CUCme.5:1:1 | 159 | T-Gb.FbL2-1:1:1 |
| pMON140823 | P-CUCme.6-1:1:1 | 18 | T-Gb.FbL2-1:1:1 |
| pMON140824 | P-CUCme.8-1:1:2 | 19 | T-Gb.FbL2-1:1:1 |
| pMON140825 | P-CUCme.9-1:1:2 | 20 | T-Gb.FbL2-1:1:1 |
| pMON140826 | P-CUCme.10-1:1:1 | 21 | T-Gb.FbL2-1:1:1 |
| pMON140827 | EXP-CUCme.eEF1a:1:1 | 162 | T-Gb.FbL2-1:1:1 |
| pMON140828 | P-CUCme.15-1:1:2 | 23 | T-Gb.FbL2-1:1:1 |
| pMON140829 | P-CUCme.16a-1:1:2 | 24 | T-Gb.FbL2-1:1:1 |
| pMON140830 | P-CUCme.17-1:1:2 | 26 | T-Gb.FbL2-1:1:1 |
| pMON140831 | P-CUCme.18-1:1:2 | 27 | T-Gb.FbL2-1:1:1 |
| pMON140832 | P-CUCme.19-1:1:3 | 167 | T-Gb.FbL2-1:1:1 |
| pMON140833 | P-CUCme.20-1:3 | 211 | T-Gb.FbL2-1:1:1 |
| pMON140834 | P-CUCme.21-1:1:1 | 30 | T-Gb.FbL2-1:1:1 |
| pMON140835 | P-CUCme.22-1:1:3 | 31 | T-Gb.FbL2-1:1:1 |
| pMON140836 | EXP-CUCme.SAMS2:1:1 | 168 | T-Gb.FbL2-1:1:1 |
| pMON140837 | P-CUCme.26-1:1:2 | 33 | T-Gb.FbL2-1:1:1 |
| pMON140838 | P-CUCme.28-1:1:2 | 34 | T-Gb.FbL2-1:1:1 |
| pMON140839 | EXP-CUCme.29:1:2 | 212 | T-Gb.FbL2-1:1:1 |

Two plasmids, for use in co-transformation and normalization of data, were also constructed. One transformation control plasmid was comprised of a constitutive promoter, driving the expression of the firefly (*Photinus pyralis*) luciferase coding sequence (FLuc, SEQ ID NO: 207), operably linked 5' to a 3' termination region from the *Agrobacterium tumefaciens* nopaline synthase gene (T-AGRtu.nos-1:1:13, SEQ ID NO: 209). The other transformation control plasmid was comprised of a constitutive promoter, driving the expression of the sea pansy (*Renilla reniformis*) luciferase coding sequence (RLuc, SEQ ID NO: 208), operably linked 5' to a 3' termination region from the *Agrobacterium tumefaciens* nopaline synthase gene.

The plant expression vectors, pMON80585, pMON109584, pMON118756, pMON124912, pMON140818, pMON140819, pMON140820, pMON140821, pMON140822, pMON140823, pMON140824, pMON140825, pMON140826, pMON140827, pMON140828, pMON140829, pMON140830, pMON140831, pMON140832, pMON140833, pMON140834, pMON140835, pMON140836, pMON140837, pMON140838 and pMON140839 were used to transform soybean cotyledon protoplast cells using PEG transformation methods. Protoplast cells were transformed with equimolar amounts of each of the two transformation control plasmids and a test plant expression vector. GUS and luciferase activity was assayed. Measurements of both GUS and luciferase were conducted by placing aliquots of a lysed preparation of cells transformed as above into two different small-well trays. One tray was used for GUS measurements, and a second tray was used to perform a dual luciferase assay using the dual luciferase reporter assay system (Promega Corp., Madison, Wis.; see for example, Promega Notes Magazine, No: 57, 1996, p. 02). Sample measurements were made using 3 or 4 replicates per transformation. The average GUS and luciferase values are presented in Table 8 below.

TABLE 8

Average GUS and luciferase expression values and GUS/luciferase ratios.

| Construct | Regulatory Element | SEQ ID NO: | Average GUS | Average FLuc | Average RLuc | GUS/ FLuc | GUS/ RLuc |
|---|---|---|---|---|---|---|---|
| pMON80585 | EXP-At.Atntt1:1:2 | 200 | 586 | 5220.7 | 8323 | 0.1100 | 0.0700 |
| pMON109584 | EXP-CaMV.35S-enh + Ph.DnaK:1:3 | 201 | 5768 | 4275 | 15098 | 1.3500 | 0.3800 |
| pMON118756 | EXP-At.Act7:1:11 | 202 | 773 | 7722 | 10545 | 0.1000 | 0.0700 |
| pMON124912 | Promoterless | | 48 | 9746.5 | 13905 | 0.0000 | 0.0000 |
| pMON140818 | P-CUCme.1-1:1:1rc | 155 | 194 | 4772 | 6363 | 0.0400 | 0.0300 |
| pMON140819 | P-CUCme.2-1:1:1 | 14 | 171 | 6855 | 10123 | 0.0200 | 0.0200 |
| pMON140820 | P-CUCme.3-1:1:3 | 15 | 37 | 7089.3 | 9593 | 0.0100 | 0.0000 |
| pMON140821 | EXP-CUCme.4:1:1 | 156 | 4211 | 7626.8 | 13935 | 0.5500 | 0.3000 |
| pMON140822 | EXP-CUCme.5:1:1 | 159 | 626 | 15609.3 | 21140 | 0.0400 | 0.0300 |
| pMON140823 | P-CUCme.6-1:1:1 | 18 | 331 | 15178.5 | 22818 | 0.0200 | 0.0100 |
| pMON140824 | P-CUCme.8-1:1:2 | 19 | 238 | 17514.5 | 28429 | 0.0100 | 0.0100 |
| pMON140825 | P-CUCme.9-1:1:2 | 20 | 510 | 13208 | 19567 | 0.0400 | 0.0300 |
| pMON140826 | P-CUCme.10-1:1:1 | 21 | 352 | 14805.3 | 22200 | 0.0200 | 0.0200 |
| pMON140827 | EXP-CUCme.eEF1a:1:1 | 162 | 724 | 9326.8 | 14476 | 0.0800 | 0.0500 |
| pMON140828 | P-CUCme.15-1:1:2 | 23 | 304 | 11798 | 17486 | 0.0300 | 0.0200 |
| pMON140829 | P-CUCme.16a-1:1:2 | 24 | 88 | 5429 | 9596 | 0.0200 | 0.0100 |
| pMON140830 | P-CUCme.17-1:1:2 | 26 | 180 | 10477.8 | 15291 | 0.0200 | 0.0100 |
| pMON140831 | P-CUCme.18-1:1:2 | 27 | 111 | 5059.3 | 6778 | 0.0200 | 0.0200 |
| pMON140832 | P-CUCme.19-1:1:3 | 167 | 121 | 3765 | 6032 | 0.0300 | 0.0200 |
| pMON140833 | P-CUCme.20-1:3 | 211 | 155 | 10458.8 | 14748 | 0.0100 | 0.0100 |
| pMON140834 | P-CUCme.21-1:1:1 | 30 | 582 | 7760 | 11440 | 0.0800 | 0.0500 |
| pMON140835 | P-CUCme.22-1:1:3 | 31 | 400 | 11393.8 | 18654 | 0.0400 | 0.0200 |
| pMON140836 | EXP-CUCme.SAMS2:1:1 | 168 | 568 | 9466.3 | 13962 | 0.0600 | 0.0400 |
| pMON140837 | P-CUCme.26-1:1:2 | 33 | 87 | 6683 | 8494 | 0.0100 | 0.0100 |
| pMON140838 | P-CUCme.28-1:1:2 | 34 | 171 | 19104.8 | 29619 | 0.0100 | 0.0100 |
| pMON140839 | EXP-CUCme.29:1:2 | 212 | 90 | 11247.3 | 15919 | 0.0100 | 0.0057 |

To compare the relative activity of each promoter in soybean cotyledon protoplasts, GUS values were expressed as a ratio of GUS to luciferase activity and normalized with respect to the expression levels observed for the constitutive expression element groups, EXP-At.Act7:1:11 and EXP-CaMV.35S-enh+Ph.DnaK:1:3. Table 9 below shows the GUS to firefly luciferase (FLuc) ratios normalized with respect to EXP-At.Act7:1:11 and EXP-CaMV.35S-enh+Ph-.DnaK:1:3. Table 10 below shows the GUS to *renilla* luciferase (RLuc) ratios normalized with respect to EXP-At.Act7:1:11 and EXP-CaMV.35S-enh+Ph.DnaK:1:3.

TABLE 9

GUS to firefly luciferase (FLuc) ratios normalized with respect to EXP-At.Act7:1:11 and EXP-CaMV.35S-enh+Ph.DnaK:1:3.

| Construct | Regulatory Element | SEQ ID NO: | GUS/FLuc normalized with respect to EXP-At.Act7:1:11 | GUS/FLuc normalized with respect to EXP-CaMV.35S-enh+Ph.DnaK:1:3 |
|---|---|---|---|---|
| pMON80585 | EXP-At.Atntt1:1:2 | 200 | 1.12 | 0.08 |
| pMON109584 | EXP-CaMV.355-enh+Ph.DnaK:1:3 | 201 | 13.48 | 1.00 |
| pMON118756 | EXP-At.Act7:1:11 | 202 | 1.00 | 0.07 |
| pMON124912 | Promoterless | | 0.05 | 0.00 |
| pMON140818 | P-CUCme.1-1:1:1rc | 155 | 0.41 | 0.03 |
| pMON140819 | P-CUCme.2-1:1:1 | 14 | 0.25 | 0.02 |
| pMON140820 | P-CUCme.3-1:1:3 | 15 | 0.05 | 0.00 |
| pMON140821 | EXP-CUCme.4:1:1 | 156 | 5.52 | 0.41 |
| pMON140822 | EXP-CUCme.5:1:1 | 159 | 0.40 | 0.03 |
| pMON140823 | P-CUCme.6-1:1:1 | 18 | 0.22 | 0.02 |

TABLE 9-continued

GUS to firefly luciferase (FLuc) ratios normalized with respect to EXP-At.Act7:1:11 and EXP-CaMV.35S-enh+Ph.DnaK:1:3.

| Construct | Regulatory Element | SEQ ID NO: | GUS/FLuc normalized with respect to EXP-At.Act7:1:11 | GUS/FLuc normalized with respect to EXP-CaMV.35S-enh+Ph.DnaK:1:3 |
|---|---|---|---|---|
| pMON140824 | P-CUCme.8-1:1:2 | 19 | 0.14 | 0.01 |
| pMON140825 | P-CUCme.9-1:1:2 | 20 | 0.39 | 0.03 |
| pMON140826 | P-CUCme.10-1:1:1 | 21 | 0.24 | 0.02 |
| pMON140827 | EXP-CUCme.eEF1a:1:1 | 162 | 0.78 | 0.06 |
| pMON140828 | P-CUCme.15-1:1:2 | 23 | 0.26 | 0.02 |
| pMON140829 | P-CUCme.16a-1:1:2 | 24 | 0.16 | 0.01 |
| pMON140830 | P-CUCme.17-1:1:2 | 26 | 0.17 | 0.01 |
| pMON140831 | P-CUCme.18-1:1:2 | 27 | 0.22 | 0.02 |
| pMON140832 | P-CUCme.19-1:1:3 | 167 | 0.32 | 0.02 |
| pMON140833 | P-CUCme.20-1:3 | 211 | 0.15 | 0.01 |
| pMON140834 | P-CUCme.21-1:1:1 | 30 | 0.75 | 0.06 |
| pMON140835 | P-CUCme.22-1:1:3 | 31 | 0.35 | 0.03 |
| pMON140836 | EXP-CUCme.SAMS2:1:1 | 168 | 0.60 | 0.04 |
| pMON140837 | P-CUCme.26-1:1:2 | 33 | 0.13 | 0.01 |
| pMON140838 | P-CUCme.28-1:1:2 | 34 | 0.09 | 0.01 |
| pMON140839 | EXP-CUCme.29:1:2 | 212 | 0.08 | 0.01 |

TABLE 10

GUS to renilla luciferase (RLuc) ratios normalized with respect to EXP-At.Act7:1:11 and EXP-CaMV.35S-enh+Ph.DnaK:1:3.

| Construct | Regulatory Element | SEQ ID NO: | GUS/RLuc normalized with respect to EXP-At.Act7:1:11 | GUS/RLuc normalized with respect to EXP-CaMV.35S-enh+Ph.DnaK:1:3 |
|---|---|---|---|---|
| pMON80585 | EXP-At.Atntt1:1:2 | 200 | 0.96 | 0.18 |
| pMON109584 | EXP-CaMV.35S-enh+Ph.DnaK:1:3 | 201 | 5.21 | 1.00 |
| pMON118756 | EXP-At.Act7:1:11 | 202 | 1.00 | 0.19 |
| pMON124912 | Promoterless | | 0.05 | 0.01 |
| pMON140818 | P-CUCme.1-1:1:1rc | 155 | 0.42 | 0.08 |
| pMON140819 | P-CUCme.2-1:1:1 | 14 | 0.23 | 0.04 |
| pMON140820 | P-CUCme.3-1:1:3 | 15 | 0.05 | 0.01 |
| pMON140821 | EXP-CUCme.4:1:1 | 156 | 4.12 | 0.79 |
| pMON140822 | EXP-CUCme.5:1:1 | 159 | 0.40 | 0.08 |
| pMON140823 | P-CUCme.6-1:1:1 | 18 | 0.20 | 0.04 |
| pMON140824 | P-CUCme.8-1:1:2 | 19 | 0.11 | 0.02 |
| pMON140825 | P-CUCme.9-1:1:2 | 20 | 0.36 | 0.07 |
| pMON140826 | P-CUCme.10-1:1:1 | 21 | 0.22 | 0.04 |
| pMON140827 | EXP-CUCme.eEF1a:1:1 | 162 | 0.68 | 0.13 |
| pMON140828 | P-CUCme.15-1:1:2 | 23 | 0.24 | 0.05 |
| pMON140829 | P-CUCme.16a-1:1:2 | 24 | 0.13 | 0.02 |
| pMON140830 | P-CUCme.17-1:1:2 | 26 | 0.16 | 0.03 |
| pMON140831 | P-CUCme.18-1:1:2 | 27 | 0.22 | 0.04 |
| pMON140832 | P-CUCme.19-1:1:3 | 167 | 0.27 | 0.05 |
| pMON140833 | P-CUCme.20-1:3 | 211 | 0.14 | 0.03 |
| pMON140834 | P-CUCme.21-1:1:1 | 30 | 0.69 | 0.13 |
| pMON140835 | P-CUCme.22-1:1:3 | 31 | 0.29 | 0.06 |
| pMON140836 | EXP-CUCme.SAMS2:1:1 | 168 | 0.55 | 0.11 |
| pMON140837 | P-CUCme.26-1:1:2 | 33 | 0.14 | 0.03 |
| pMON140838 | P-CUCme.28-1:1:2 | 34 | 0.08 | 0.02 |
| pMON140839 | EXP-CUCme.29:1:2 | 212 | 0.08 | 0.01 |

As can be seen in Tables 9 and 10, most of the expression element groups tested, demonstrated the ability to drive transgene expression in soybean cotyledon protoplast cells. One expression element group, EXP-CUCme.4:1:1 (SEQ ID NO: 156) demonstrated levels of transgene expression higher than that of EXP-At.Act7:1:11 in this assay.

Example 5: Analysis of Regulatory Elements Driving GUS in Bombarded Soybean Leaves and Roots Soybean leaves and roots were transformed with plant expression vectors containing a test transcriptional regulatory expression element group driving expression of the ß-glucuronidase (GUS) transgene and compared to GUS expression in roots and leaves in which expression of GUS is driven by known constitutive promoters.

Expression of a transgene driven by P-CUCme.1-1:1:1rc (SEQ ID NO: 155), P-CUCme.2-1:1:1 (SEQ ID NO: 14), P-CUCme.3-1:1:3 (SEQ ID NO: 15), EXP-CUCme.4:1:1 (SEQ ID NO: 156), EXP-CUCme.5:1:1 (SEQ ID NO: 159), P-CUCme.6-1:1:1 (SEQ ID NO: 18), P-CUCme.8-1:1:2 (SEQ ID NO: 19), P-CUCme.9-1:1:2 (SEQ ID NO: 20), P-CUCme.10-1:1:1 (SEQ ID NO: 21), EXP-CUCme.eEF1a:1:1 (SEQ ID NO: 162), P-CUCme.15-1:1:2 (SEQ ID NO: 23), P-CUCme.16a-1:1:2 (SEQ ID NO: 24), P-CUCme.17-1:1:2 (SEQ ID NO: 26), P-CUCme.18-1:1:2 (SEQ ID NO: 27), P-CUCme.19-1:1:3 (SEQ ID NO: 167), P-CUCme.20-1:3 (SEQ ID NO: 211), P-CUCme.21-1:1:1 (SEQ ID NO: 30), P-CUCme.22-1:1:3 (SEQ ID NO: 31), EXP-CUCme.SAMS2:1:1 (SEQ ID NO: 168), P-CUCme.26-1:1:2 (SEQ ID NO: 33), P-CUCme.28-1:1:2 (SEQ ID NO: 34) and EXP-CUCme.29:1:2 (SEQ ID NO: 212) was compared with expression from known constitutive expression element groups in particle bombarded soybean leaves and roots. The plant expression vectors used for transformation of leaves and roots was the same as those presented in Table 7 of Example 4 above.

The plant expression vectors, pMON80585, pMON109584, pMON118756, pMON124912, pMON140818, pMON140819, pMON140820, pMON140821, pMON140822, pMON140823, pMON140824, pMON140825, pMON140826, pMON140827, pMON140828, pMON140829, pMON140830, pMON140831, pMON140832, pMON140833, pMON140834, pMON140835, pMON140836, pMON140837, pMON140838 and pMON140839 were used to transform soybean leaves and roots using particle bombardment transformation methods.

Briefly, A3244 soybean seeds were surface sterilized and allowed to germinate in trays with a photoperiod of 16 hours light and 8 hours of darkness. After approximately 13 days, leaf and root tissue was harvested under sterile conditions from the seedlings and used for bombardment. The tissue samples were randomly placed on a petri dish containing plant culture medium. Ten micrograms of plasmid DNA was used to coat 0.6 micron gold particles (Catalog #165-2262 Bio-Rad, Hercules, Calif.) for bombardment. Macro-carriers were loaded with the DNA-coated gold particles (Catalog #165-2335 Bio-Rad, Hercules Calif.). A PDS 1000/He biolistic gun was used for transformation (Catalog #165-2257 Bio-Rad, Hercules Calif.). The bombarded root and leaf tissues were allowed to incubate in the dark for 24 hours at 26 degrees Celsius. Following this overnight incubation, the tissues were stained in solution for GUS expression overnight at 37 degrees Celsius. After staining overnight, the tissues were soaked in 70% ethanol overnight to remove chlorophyll and reveal the GUS staining. The tissues were then photographed and a rating scale of “0”, “+” to “++++++” reflecting the level of GUS expression is assigned to each construct (0—no expression, + to ++++++—low to high, respectively).

Expression of the GUS transgene demonstrated in each tissue is used to infer the relative potential level and specificity of each element’s capacity to drive transgene expression in stably transformed corn plants. Average GUS expression ratings are provided in Table 11 below.

TABLE 11

GUS expression ratings for particle bombarded leaf and root.

| Construct | Regulatory Element | SEQ ID NO: | Leaf Expression | Root Expression |
|---|---|---|---|---|
| pMON80585 | EXP-At.Atntt1:1:2 | 200 | +++ | +++ |
| pMON109584 | EXP-CaMV.35S-enh+Ph.DnaK:1:3 | 201 | +++++ | ++ |
| pMON118756 | EXP-At.Act7:1:11 | 202 | ++++ | +++ |
| pMON124912 | Promoterless | | 0 | 0 |
| pMON140818 | P-CUCme.1-1:1:1rc | 155 | +++ | + |
| pMON140819 | P-CUCme.2-1:1:1 | 14 | ++ | + |
| pMON140820 | P-CUCme.3-1:1:3 | 15 | 0 | 0 |
| pMON140821 | EXP-CUCme.4:1:1 | 156 | ++++++ | +++ |
| pMON140822 | EXP-CUCme.5:1:1 | 159 | ++ | + |
| pMON140823 | P-CUCme.6-1:1:1 | 18 | ++ | + |
| pMON140824 | P-CUCme.8-1:1:2 | 19 | + | + |
| pMON140825 | P-CUCme.9-1:1:2 | 20 | ++ | + |
| pMON140826 | P-CUCme.10-1:1:1 | 21 | +++ | +++ |
| pMON140827 | EXP-CUCme.eEF1a:1:1 | 162 | ++++ | +++ |
| pMON140828 | P-CUCme.15-1:1:2 | 23 | + | + |
| pMON140829 | P-CUCme.16a-1:1:2 | 24 | + | − |
| pMON140830 | P-CUCme.17-1:1:2 | 26 | ++++ | + |
| pMON140831 | P-CUCme.18-1:1:2 | 27 | +++ | + |
| pMON140832 | P-CUCme.19-1:1:3 | 167 | + | + |
| pMON140833 | P-CUCme.20-1:3 | 211 | + | + |
| pMON140834 | P-CUCme.21-1:1:1 | 30 | + | + |
| pMON140835 | P-CUCme.22-1:1:3 | 31 | ++++ | + |
| pMON140836 | EXP-CUCme.SAMS2:1:1 | 168 | +++++ | +++ |
| pMON140837 | P-CUCme.26-1:1:2 | 33 | + | + |
| pMON140838 | P-CUCme.28-1:1:2 | 34 | + | + |
| pMON140839 | EXP-CUCme.29:1:2 | 212 | + | + |

As can be seen in Table 11 above, all but one of the expression element groups demonstrated the ability to drive transgene expression in particle bombarded soybean leaf and root tissue. Two expression element groups, P-CUCme.28-1:1:2 (SEQ ID NO: 34) and EXP-CUCme.4:1:1 (SEQ ID NO: 156) demonstrated similar or higher levels of expression relative to expression driven by EXP-CaMV.35S-enh+Ph.DnaK:1:3 in this assay.

Example 6: Analysis of Regulatory Elements Driving GUS in Soy Cotyledon Protoplast Using Transgene Cassette Amplicons Soybean cotyledon protoplasts were transformed with transgene cassette amplicons containing a transcriptional regulatory expression element group driving expression of the ß-glucuronidase (GUS) transgene and compared to GUS expression in leaf protoplasts in which expression of GUS is driven by known constitutive promoters. The transgene cassette amplicons were comprised of an EXP sequence, operably linked to a GUS coding sequence (GUS, SEQ ID NO: 206), operably linked to a 3' UTR (T-Gb.FbL2-1:1:1, SEQ ID NO: 205). Average GUS expression was compared to the control EXP elements, P-CaMV.35S-enh-1:1:102/L-CaMV.35S-1:1:2 (SEQ ID NO: 210) and EXP-At.Atntt1:1:2 (SEQ ID NO: 200).

A plasmid, for use in co-transformation and normalization of data was also used in a similar manner as that described above in Example 2. The transformation control plasmid was comprised of a constitutive promoter, driving the expression of the firefly (*Photinus pyralis*) luciferase coding sequence (FLuc, SEQ ID NO: 205), operably linked 5' to a 3' termination region from the *Agrobacterium tumefaciens* nopaline synthase gene (T-AGRtu.nos-1:1:13, SEQ ID NO: 209).

Table 12 below shows the mean GUS expression values conferred by each transgene amplicon. Table 13 below shows the GUS to firefly luciferase (FLuc) ratios normalized with respect to EXP-At.Atntt1:1:2 and P-CaMV.35S-enh-1:1:102/L-CaMV.35S-1:1:2

TABLE 12

Average GUS and luciferase expression values and GUS/luciferase ratios.

| Amplicon ID | Regulatory Element | SEQ ID NO: | Mean GUS | Mean Fluc | GUS/Fluc |
|---|---|---|---|---|---|
| No DNA | | | 0.00 | 0.00 | 0.00 |
| pMON124912 | No promoter | | 54.67 | 34905.00 | 0.00 |
| pMON33449 | P-CaMV.35S-enh-1:1:102/L-CaMV.35S-1:1:2 | 210 | 107064.67 | 21757.67 | 4.92 |
| pMON80585 | EXP-At.Atntt1:1:2 | 200 | 4962.33 | 40778.67 | 0.12 |
| 56969 | CumMe_WSM_SF16429.G5670 | 40 | 283.67 | 53452.00 | 0.01 |
| 56877 | P-CUCme.CumMe_WSM_SF16444.G5140-1:1:1 | 175 | 5297.67 | 46576.67 | 0.11 |
| 56749 | P-CUCme.CumMe_WSM_SF16563.G5560-1:1:1 | 176 | 280.67 | 41958.33 | 0.01 |
| 56918 | CumMe_WSM_SF17051.G5470 | 48 | 1088.00 | 36321.00 | 0.03 |
| 56849 | P-CUCme.CumMe_WSM_SF17111.G5790-1:1:1 | 177 | 196.00 | 48128.00 | 0.00 |
| 56754 | P-CUCme.WSM_SF17252.G7330-1:1:1 | 179 | 175.67 | 45427.00 | 0.00 |
| 56892 | CumMe_WSM_SF17349.G5770 | 56 | 34.00 | 38016.00 | 0.00 |
| 56477 | CumMe_WSM_SF17866.G6050 | 62 | 862.00 | 52203.33 | 0.02 |
| 56842 | P-CUCme.CumMe_WSM_SF18488.G5340-1:1:1 | 181 | 2892.67 | 49144.33 | 0.06 |
| 56852 | P-CUCme.CumMe_WSM_SF18536.G6480-1:1:1 | 182 | 3462.67 | 46549.33 | 0.07 |
| 56497 | CumMe_WSM_SF18575.G6410 | 71 | 92.67 | 47628.33 | 0.00 |
| 56847 | P-CUCme.CumMe_WSM_SF18634.G5190-1:1:1 | 183 | 122.33 | 36815.33 | 0.00 |
| 56746 | P-CUCme.CumMe_WSM_SF18716.G5860-1:1:1 | 184 | 14.33 | 62483.33 | 0.00 |
| 56883 | CumMe_WSM_SF18986.G6110 | 79 | 863.33 | 54379.33 | 0.02 |
| 56734 | EXP-CUCme.WSM_SF19064.G5690:1:1 | 185 | 142.00 | 46962.67 | 0.00 |
| 56912 | P-CUCme.CumMe_WSM_SF19647.G5760-1:1:1 | 188 | 7659.00 | 46935.67 | 0.16 |
| 56482 | P-CUCme.CumMe_WSM_SF19839.G5090-1:1:1 | 189 | 3279.00 | 37070.67 | 0.09 |
| 56963 | CumMe_WSM_SF19902.G5260 | 87 | 1629.00 | 55649.00 | 0.03 |
| 56747 | P-CUCme.CumMe_WSM_SF20132.G5560-1:1:1 | 190 | 340.33 | 40577.00 | 0.01 |
| 56479 | CumMe_WSM_SF20359.G5870 | 92 | 192.00 | 61341.67 | 0.00 |
| 56744 | CumMe_WSM_SF206458.G5970 | 98 | 154.67 | 33139.33 | 0.00 |
| 56948 | CumMe_WSM_SF206534.G5200 | 99 | 62.00 | 52118.00 | 0.00 |
| 56896 | CumMe_WSM_SF22008.G5670 | 108 | 1585.00 | 53540.00 | 0.03 |
| 56919 | CumMe_WSM_SF22275.G5780 | 112 | 8.33 | 48546.33 | 0.00 |
| 56967 | CumMe_WSM_SF22355.G5310 | 113 | 74.33 | 36202.67 | 0.00 |
| 56837 | P-CUCme.CumMe_WSM_SF22531.G5120-1:1:1 | 192 | 1526.67 | 52799.33 | 0.03 |
| 56940 | CumMe_WSM_SF22870.G5370 | 115 | 14.67 | 53663.33 | 0.00 |
| 56495 | P-CUCme.CumMe_WSM_SF23760.G5200-1:1:1 | 193 | 196.33 | 49870.67 | 0.00 |
| 56868 | P-CUCme.CumMe_WSM_SF23906.G6180-1:1:1 | 194 | 1584.33 | 42532.33 | 0.04 |
| 56998 | CumMe_WSM_SF24045.G5400 | 123 | 80.67 | 47553.00 | 0.00 |
| 56976 | P-CUCme.CumMe_WSM_SF25141.G5160-1:1:2 | 195 | 4506.00 | 57213.00 | 0.08 |
| 56742 | P-CUCme.CumMe_WSM_SF25355.G5000-1:1:1 | 196 | 4.00 | 41114.33 | 0.00 |
| 56915 | P-CUCme.CumMe_WSM_SF25936.G5450-1:1:1 | 197 | 965.33 | 34494.67 | 0.03 |
| 56854 | CumMe_WSM_SF28729.G5340 | 134 | 208.33 | 53956.00 | 0.00 |
| 56936 | CumMe_WSM_SF31264.G5380 | 136 | 292.67 | 42320.67 | 0.01 |
| 56863 | P-CUCme.CumMe_WSM_SF35856.G5150-1:1:1 | 198 | 125.00 | 48705.33 | 0.00 |
| 56751 | P-CUCme.CumMe_WSM_SF41124.G5080-1:1:1 | 199 | 31.33 | 53595.00 | 0.00 |
| 56921 | CumMe_WSM_SF41254.G5160 | 141 | 11.67 | 52643.67 | 0.00 |
| 56884 | CumMe_WSM_SF42141.G5110 | 146 | 48.33 | 40556.67 | 0.00 |

TABLE 13

GUS to firefly luciferase (FLuc) ratios normalized with respect to EXP-At.Atntt1:1:2 and P-CaMV.35S-enh-1:1:102/L-CaMV.355-1:1:2.

| Amplicon ID | Regulatory Element | SEQ ID NO: | GUS/Fluc normalized with respect to EXP-At.Atntt1:1:2 | GUS/Fluc normalized with respect to P-CaMV.35S-enh-1:1:102/L-CaMV.35S-1:1:2 |
|---|---|---|---|---|
| No DNA | | | 0.00 | 0.00 |
| pMON124912 | No promoter | | 0.01 | 0.00 |
| pMON33449 | P-CaMV.35S-enh-1:1:102/L-CaMV.35S-1:1:2 | 210 | 40.44 | 1.00 |
| pMON80585 | EXP-At.Atntt1:1:2 | 200 | 1.00 | 0.02 |
| 56969 | CumMe_WSM_SF16429.G5670 | 40 | 0.04 | 0.00 |
| 56877 | P-CUCme.CumMe_WSM_SF16444.G5140-1:1:1 | 175 | 0.93 | 0.02 |
| 56749 | P-CUCme.CumMe_WSM_SF16563.G5560-1:1:1 | 176 | 0.05 | 0.00 |
| 56918 | CumMe_WSM_SF17051.G5470 | 48 | 0.25 | 0.01 |
| 56849 | P-CUCme.CumMe_WSM_SF17111.G5790-1:1:1 | 177 | 0.03 | 0.00 |
| 56754 | P-CUCme.WSM_SF17252.G7330-1:1:1 | 179 | 0.03 | 0.00 |
| 56892 | CumMe_WSM_SF17349.G5770 | 56 | 0.01 | 0.00 |
| 56477 | CumMe_WSM_SF17866.G6050 | 62 | 0.14 | 0.00 |
| 56842 | P-CUCme.CumMe_WSM_SF18488.G5340-1:1:1 | 181 | 0.48 | 0.01 |
| 56852 | P-CUCme.CumMe_WSM_SF18536.G6480-1:1:1 | 182 | 0.61 | 0.02 |
| 56497 | CumMe_WSM_SF18575.G6410 | 71 | 0.02 | 0.00 |

TABLE 13-continued

GUS to firefly luciferase (FLuc) ratios normalized with respect to EXP-At.Atntt1:1:2 and P-CaMV.35S-enh-1:1:102/L-CaMV.355-1:1:2.

| Amplicon ID | Regulatory Element | SEQ ID NO: | GUS/Fluc normalized with respect to EXP-At.Atntt1:1:2 | GUS/Fluc normalized with respect to P-CaMV.35S-enh-1:1:102/L-CaMV.35S-1:1:2 |
|---|---|---|---|---|
| 56847 | P-CUCme.CumMe_WSM_SF18634.G5190-1:1:1 | 183 | 0.03 | 0.00 |
| 56746 | P-CUCme.CumMe_WSM_SF18716.G5860-1:1:1 | 184 | 0.00 | 0.00 |
| 56883 | CumMe_WSM_SF18986.G6110 | 79 | 0.13 | 0.00 |
| 56734 | EXP-CUCme.WSM_SF19064.G5690:1:1 | 185 | 0.02 | 0.00 |
| 56912 | P-CUCme.CumMe_WSM_SF19647.G5760-1:1:1 | 188 | 1.34 | 0.03 |
| 56482 | P-CUCme.CumMe_WSM_SF19839.G5090-1:1:1 | 189 | 0.73 | 0.02 |
| 56963 | CumMe_WSM_SF19902.G5260 | 87 | 0.24 | 0.01 |
| 56747 | P-CUCme.CumMe_WSM_SF20132.G5560-1:1:1 | 190 | 0.07 | 0.00 |
| 56479 | CumMe_WSM_SF20359.G5870 | 92 | 0.03 | 0.00 |
| 56744 | CumMe_WSM_SF206458.G5970 | 98 | 0.04 | 0.00 |
| 56948 | CumMe_WSM_SF206534.G5200 | 99 | 0.01 | 0.00 |
| 56896 | CumMe_WSM_SF22008.G5670 | 108 | 0.24 | 0.01 |
| 56919 | CumMe_WSM_SF22275.G5780 | 112 | 0.00 | 0.00 |
| 56967 | CumMe_WSM_SF22355.G5310 | 113 | 0.02 | 0.00 |
| 56837 | P-CUCme.CumMe_WSM_SF22531.G5120-1:1:1 | 192 | 0.24 | 0.01 |
| 56940 | CumMe_WSM_SF22870.G5370 | 115 | 0.00 | 0.00 |
| 56495 | P-CUCme.CumMe_WSM_SF23760.G5200-1:1:1 | 193 | 0.03 | 0.00 |
| 56868 | P-CUCme.CumMe_WSM_SF23906.G6180-1:1:1 | 194 | 0.31 | 0.01 |
| 56998 | CumMe_WSM_SF24045.G5400 | 123 | 0.01 | 0.00 |
| 56976 | P-CUCme.CumMe_WSM_SF25141.G5160-1:1:2 | 195 | 0.65 | 0.02 |
| 56742 | P-CUCme.CumMe_WSM_SF25355.G5000-1:1:1 | 196 | 0.00 | 0.00 |
| 56915 | P-CUCme.CumMe_WSM_SF25936.G5450-1:1:1 | 197 | 0.23 | 0.01 |
| 56854 | CumMe_WSM_SF28729.G5340 | 134 | 0.03 | 0.00 |
| 56936 | CumMe_WSM_SF31264.G5380 | 136 | 0.06 | 0.00 |
| 56863 | P-CUCme.CumMe_WSM_SF35856.G5150-1:1:1 | 198 | 0.02 | 0.00 |
| 56751 | P-CUCme.CumMe_WSM_SF41124.G5080-1:1:1 | 199 | 0.00 | 0.00 |
| 56921 | CumMe_WSM_SF41254.G5160 | 141 | 0.00 | 0.00 |
| 56884 | CumMe_WSM_SF42141.G5110 | 146 | 0.01 | 0.00 |

As can be seen in Table 12 above, not all EXP sequences demonstrated the ability to drive transgene expression when compared to the promoterless control. However, the EXP sequences, CumMe_WSM_SF16429.G5670 (SEQ ID NO: 40), P-CUCme.CumMe_WSM_SF16444.G5140-1:1:1 (SEQ ID NO: 175), P-CUCme.CumMe_WSM_SF16563.G5560-1:1:1 (SEQ ID NO: 176), CumMe_WSM_SF17051.G5470 (SEQ ID NO: 48), P-CUCme.CumMe_WSM_SF17111.65790-1:1:1 (SEQ ID NO: 177), P-CUCme.WSM_SF17252.G7330-1:1:1 (SEQ ID NO: 179), CumMe_WSM_SF17866.G6050 (SEQ ID NO: 62), P-CUCme.CumMe_WSM_SF18488.G5340-1:1:1 (SEQ ID NO: 181), P-CUCme.CumMe_WSM_SF18536.G6480-1:1:1 (SEQ ID NO: 182), CumMe_WSM_SF18575.G6410 (SEQ ID NO: 71), P-CUCme.CumMe_WSM_SF18634.G5190-1:1:1 (SEQ ID NO: 183), CumMe_WSM_SF18986.G6110 (SEQ ID NO: 79), EXP-CUCme.WSM_SF19064.G5690:1:1 (SEQ ID NO: 185), P-CUCme.CumMe_WSM_SF19647.G5760-1:1:1 (SEQ ID NO: 188), P-CUCme.CumMe_WSM_SF19839.G5090-1:1:1 (SEQ ID NO: 189), CumMe_WSM_SF19902.G5260 (SEQ ID NO: 87), P-CUCme.CumMe_WSM_SF20132.G5560-1:1:1 (SEQ ID NO: 190), CumMe_WSM_SF20359.G5870 (SEQ ID NO: 92), CumMe_WSM_SF206458.G5970 (SEQ ID NO: 98), CumMe_WSM_SF206534.G5200 (SEQ ID NO: 99), CumMe_WSM_SF22008.G5670 (SEQ ID NO: 108), CumMe_WSM_SF22355.G5310 (SEQ ID NO: 113), P-CUCme.CumMe_WSM_SF22531.G5120-1:1:1 (SEQ ID NO: 192), EXP-CUCme.WSM_SF19064.G5690:1:1 (SEQ ID NO: 193), P-CUCme.CumMe_WSM_SF23906.G6180-1:1:1 (SEQ ID NO: 194), CumMe_WSM_SF24045.G5400 (SEQ ID NO: 123), P-CUCme.CumMe_WSM_SF25141.G5160-1:1:2 (SEQ ID NO: 195), P-CUCme.CumMe_WSM_SF25936.G5450-1:1:1 (SEQ ID NO: 197), CumMe_WSM_SF28729.G5340 (SEQ ID NO: 134), CumMe_WSM_SF31264.G5380 (SEQ ID NO: 136) and P-CUCme.CumMe_WSM_SF35856.G5150-1:1:1 (SEQ ID NO: 198) demonstrated the ability to drive transgene expression in soybean cotyledon protoplasts at a level similar or greater than EXP-At.Atntt1:1:2. As shown in Table 13 above, the EXP sequence P-CUCme.CumMe_WSM_SF19647.G5760-1:1:1 (SEQ ID NO: 188) demonstrated the ability to drive transgene expression in this assay at a level greater than EXP-At.Atntt1:1:2.

Example 7: Analysis of Regulatory Elements Driving GUS in Cotton Leaf Protoplasts Cotton leaf protoplasts were transformed with plant expression vectors containing a test transcriptional regulatory expression element group driving expression of the ß-glucuronidase (GUS) transgene and compared to GUS expression in leaf protoplasts in which expression of GUS is driven by known constitutive promoters.

Expression of a transgene driven by P-CUCme.1-1:1:1rc (SEQ ID NO: 155), P-CUCme.2-1:1:1 (SEQ ID NO: 14), P-CUCme.3-1:1:3 (SEQ ID NO: 15), EXP-CUCme.4:1:1 (SEQ ID NO: 156), P-CUCme.6-1:1:1 (SEQ ID NO: 18), P-CUCme.8-1:1:2 (SEQ ID NO: 19), P-CUCme.9-1:1:2 (SEQ ID NO: 20), P-CUCme.10-1:1:1 (SEQ ID NO: 21), EXP-CUCme.eEF1a:1:1 (SEQ ID NO: 162), P-CUCme.15-

1:1:2 (SEQ ID NO: 23), P-CUCme.16a-1:1:2 (SEQ ID NO: 24), P-CUCme.17-1:1:2 (SEQ ID NO: 26), P-CUCme.18-1:1:2 (SEQ ID NO: 27), P-CUCme.19-1:1:3 (SEQ ID NO: 167), P-CUCme.20-1:3 (SEQ ID NO: 211), P-CUCme.21-1:1:1 (SEQ ID NO: 30), P-CUCme.22-1:1:3 (SEQ ID NO: 31), EXP-CUCme.SAMS2:1:1 (SEQ ID NO: 168), P-CUCme.26-1:1:2 (SEQ ID NO: 33), P-CUCme.28-1:1:2 (SEQ ID NO: 34) and EXP-CUCme.29:1:2 (SEQ ID NO: 212) was compared with expression from known constitutive expression element groups. Each plant expression vector was comprised of a right border region from *Agrobacterium tumefaciens*, a first transgene cassette comprised of a test promoter or known constitutive promoter operably linked 5' to a coding sequence for ß-glucuronidase (GUS, SEQ ID NO: 206) containing a processable intron derived from the potato light-inducible tissue-specific ST-LS1 gene (Genbank Accession: X04753), operably linked 5' to a 3' termination region from the *Gossypium barbadense* E6 gene (T-Gb.E6-3b:1:1, SEQ ID NO: 204), the *Pisum sativum* RbcS2-E9 gene (T-Ps.RbcS2-E9-1:1:6, SEQ ID NO: 203), or the *Gossypium barbadense* FbLate-2 gene (T-Gb.FbL2-1:1:1, SEQ ID NO: 205); a second transgene selection cassette used for selection of transformed plant cells that either confers resistance to the herbicide glyphosate (driven by the *Arabidopsis* Actin 7 promoter) or the antibiotic, kanamycin and a left border region from *A. tumefaciens*. A promoterless control plant expression vector (pMON124912) served as a negative control for expression. The foregoing test and constitutive expression element groups were cloned into plant expression vectors as shown in Table 14 below.

TABLE 14

Plant expression vectors and corresponding expression element group and 3' UTR.

| Construct | Regulatory Element | SEQ ID NO: | 3' UTR |
|---|---|---|---|
| pMON109584 | EXP-CaMV.35S-enh+Ph.DnaK:1:3 | 201 | T-Gb.E6-3b:1:1 |
| pMON118756 | EXP-At.Act7:1:11 | 202 | T-Gb.E6-3b:1:1 |
| pMON124912 | Promoterless | | T-Gb.FbL2-1:1:1 |
| pMON140818 | P-CUCme.1-1:1:1rc | 155 | T-Gb.FbL2-1:1:1 |
| pMON140819 | P-CUCme.2-1:1:1 | 14 | T-Gb.FbL2-1:1:1 |
| pMON140820 | P-CUCme.3-1:1:3 | 15 | T-Gb.FbL2-1:1:1 |
| pMON140821 | EXP-CUCme.4:1:1 | 156 | T-Gb.FbL2-1:1:1 |
| pMON140823 | P-CUCme.6-1:1:1 | 18 | T-Gb.FbL2-1:1:1 |
| pMON140824 | P-CUCme.8-1:1:2 | 19 | T-Gb.FbL2-1:1:1 |
| pMON140825 | P-CUCme.9-1:1:2 | 20 | T-Gb.FbL2-1:1:1 |
| pMON140826 | P-CUCme.10-1:1:1 | 21 | T-Gb.FbL2-1:1:1 |
| pMON140827 | EXP-CUCme.eEF1a:1:1 | 162 | T-Gb.FbL2-1:1:1 |
| pMON140828 | P-CUCme.15-1:1:2 | 23 | T-Gb.FbL2-1:1:1 |
| pMON140829 | P-CUCme.16a-1:1:2 | 24 | T-Gb.FbL2-1:1:1 |

TABLE 14-continued

Plant expression vectors and corresponding expression element group and 3' UTR.

| Construct | Regulatory Element | SEQ ID NO: | 3' UTR |
|---|---|---|---|
| pMON140830 | P-CUCme.17-1:1:2 | 26 | T-Gb.FbL2-1:1:1 |
| pMON140831 | P-CUCme.18-1:1:2 | 27 | T-Gb.FbL2-1:1:1 |
| pMON140832 | P-CUCme.19-1:1:3 | 167 | T-Gb.FbL2-1:1:1 |
| pMON140833 | P-CUCme.20-1:3 | 211 | T-Gb.FbL2-1:1:1 |
| pMON140834 | P-CUCme.21-1:1:1 | 30 | T-Gb.FbL2-1:1:1 |
| pMON140835 | P-CUCme.22-1:1:3 | 31 | T-Gb.FbL2-1:1:1 |
| pMON140836 | EXP-CUCme.SAMS2:1:1 | 168 | T-Gb.FbL2-1:1:1 |
| pMON140837 | P-CUCme.26-1:1:2 | 33 | T-Gb.FbL2-1:1:1 |
| pMON140838 | P-CUCme.28-1:1:2 | 34 | T-Gb.FbL2-1:1:1 |
| pMON140839 | EXP-CUCme.29:1:2 | 212 | T-Gb.FbL2-1:1:1 |

Two plasmids, for use in co-transformation and normalization of data, were also constructed. One transformation control plasmid was comprised of a constitutive promoter, driving the expression of the firefly (*Photinus pyralis*) luciferase coding sequence (FLuc, SEQ ID NO: 205), operably linked 5' to a 3' termination region from the *Agrobacterium tumefaciens* nopaline synthase gene (T-AGRtu.nos-1:1:13, SEQ ID NO: 209). The other transformation control plasmid was comprised of a constitutive promoter, driving the expression of the sea pansy (*Renilla reniformis*) luciferase coding sequence (RLuc, SEQ ID NO: 206), operably linked 5' to a 3' termination region from the *Agrobacterium tumefaciens* nopaline synthase gene.

The plant expression vectors, pMON80585, pMON109584, pMON118756, pMON124912, pMON140818, pMON140819, pMON140820, pMON140821, pMON140823, pMON140824, pMON140825, pMON140826, pMON140827, pMON140828, pMON140829, pMON140830, pMON140831, pMON140832, pMON140833, pMON140834, pMON140835, pMON140836, pMON140837, pMON140838 and pMON140839 were used to transform cotton leaf protoplast cells using PEG transformation methods. Protoplast cells were transformed with equimolar amounts of each of the two transformation control plasmids and a test plant expression vector. GUS and luciferase activity was assayed. Measurements of both GUS and luciferase were conducted by placing aliquots of a lysed preparation of cells transformed as above into two different small-well trays. One tray was used for GUS measurements, and a second tray was used to perform a dual luciferase assay using the dual luciferase reporter assay system (Promega Corp., Madison, Wis.; see for example, Promega Notes Magazine, No: 57, 1996, p. 02). Sample measurements were made using 4 replicates per transformation. The average GUS and luciferase values are presented in Table 15 below.

TABLE 15

Average GUS and luciferase expression values and GUS/luciferase ratios.

| Construct | Regulatory Element | SEQ ID NO: | Average GUS | Average FLuc | Average RLuc | GUS/ FLuc | GUS/ RLuc |
|---|---|---|---|---|---|---|---|
| pMON109584 | EXP-CaMV.35S-enh + Ph.DnaK:1:3 | 201 | 5322.8 | 14842.8 | 27990.5 | 0.3586 | 0.1902 |
| pMON118756 | EXP-At.Act7:1:11 | 202 | 1006.3 | 19746.8 | 25582.3 | 0.0510 | 0.0393 |
| pMON124912 | Promoterless | | 21 | 19248.5 | 25012 | 0.0011 | 0.0008 |
| pMON140818 | P-CUCme.1-1:1:1rc | 155 | 170.3 | 17796.8 | 22026.3 | 0.0096 | 0.0077 |
| pMON140819 | P-CUCme.2-1:1:1 | 14 | 34.8 | 16326.3 | 21407.5 | 0.0021 | 0.0016 |
| pMON140820 | P-CUCme.3-1:1:3 | 15 | 51.5 | 17356.8 | 21523.8 | 0.0030 | 0.0024 |
| pMON140821 | EXP-CUCme.4:1:1 | 156 | 3497.8 | 18745.3 | 26065.3 | 0.1866 | 0.1342 |

TABLE 15-continued

Average GUS and luciferase expression values and GUS/luciferase ratios.

| Construct | Regulatory Element | SEQ ID NO: | Average GUS | Average FLuc | Average RLuc | GUS/ FLuc | GUS/ RLuc |
|---|---|---|---|---|---|---|---|
| pMON140823 | P-CUCme.6-1:1:1 | 18 | 40.8 | 19533.8 | 26361.5 | 0.0021 | 0.0015 |
| pMON140824 | P-CUCme.8-1:1:2 | 19 | 22 | 19701 | 26278 | 0.0011 | 0.0008 |
| pMON140825 | P-CUCme.9-1:1:2 | 20 | 372.5 | 21972.3 | 28755 | 0.0170 | 0.0130 |
| pMON140826 | P-CUCme.10-1:1:1 | 21 | 198 | 21362.8 | 28902 | 0.0093 | 0.0069 |
| pMON140827 | EXP-CUCme.eEF1a:1:1 | 162 | 725 | 21589 | 27635.3 | 0.0336 | 0.0262 |
| pMON140828 | P-CUCme.15-1:1:2 | 23 | 55.3 | 17706 | 28846 | 0.0031 | 0.0019 |
| pMON140829 | P-CUCme.16a-1:1:2 | 24 | 14 | 23289.5 | 30190 | 0.0006 | 0.0005 |
| pMON140830 | P-CUCme.17-1:1:2 | 26 | 155.5 | 23178.3 | 31602.8 | 0.0067 | 0.0049 |
| pMON140831 | P-CUCme.18-1:1:2 | 27 | 86.8 | 19085.8 | 22396.5 | 0.0045 | 0.0039 |
| pMON140832 | P-CUCme.19-1:1:3 | 167 | 130 | 21520.3 | 27270.5 | 0.0060 | 0.0048 |
| pMON140833 | P-CUCme.20-1:3 | 211 | 88.5 | 22223.8 | 30786 | 0.0040 | 0.0029 |
| pMON140834 | P-CUCme.21-1:1:1 | 30 | 98.5 | 18579 | 20506.3 | 0.0053 | 0.0048 |
| pMON140835 | P-CUCme.22-1:1:3 | 31 | 363 | 21780.3 | 28816.3 | 0.0167 | 0.0126 |
| pMON140836 | EXP-CUCme.SAMS2:1:1 | 168 | 515 | 17906 | 23031 | 0.0288 | 0.0224 |
| pMON140837 | P-CUCme.26-1:1:2 | 33 | 125 | 15529.3 | 15169.3 | 0.0080 | 0.0082 |
| pMON140838 | P-CUCme.28-1:1:2 | 34 | 115.8 | 17013.5 | 22236.5 | 0.0068 | 0.0052 |
| pMON140839 | EXP-CUCme.29:1:2 | 212 | 15.5 | 16370.3 | 20409 | 0.0009 | 0.0008 |

To compare the relative activity of each promoter in cotton leaf protoplasts, GUS values were expressed as a ratio of GUS to luciferase activity and normalized with respect to the expression levels observed for the constitutive expression element groups, EXP-At.Act7:1:11 and EXP-CaMV.35S-enh+Ph.DnaK:1:3. Table 16 below shows the GUS to firefly luciferase (FLuc) ratios normalized with respect to EXP-At.Act7:1:11 and EXP-CaMV.35S-enh+Ph-.DnaK:1:3. Table 17 below shows the GUS to *renilla* luciferase (RLuc) ratios normalized with respect to EXP-At.Act7:1:11 and EXP-CaMV.35S-enh+Ph.DnaK:1:3.

TABLE 16

GUS to firefly luciferase (FLuc) ratios normalized with respect to EXP-At.Act7:1:11 and EXP-CaMV.35S-enh+Ph.DnaK:1:3.

| Construct | Regulatory Element | SEQ ID NO: | GUS/FLuc normalized with respect to EXP-At.Act7:1:11 | GUS/FLuc normalized with respect to EXP-CaMV.355-enh+Ph.DnaK:1:3 |
|---|---|---|---|---|
| pMON109584 | EXP-CaMV.35S-enh+Ph.DnaK:1:3 | 201 | 7.037 | 1.000 |
| pMON118756 | EXP-At.Act7:1:11 | 202 | 1.000 | 0.142 |
| pMON124912 | Promoterless | | 0.021 | 0.003 |
| pMON140818 | P-CUCme.1-1:1:1rc | 155 | 0.188 | 0.027 |
| pMON140819 | P-CUCme.2-1:1:1 | 14 | 0.042 | 0.006 |
| pMON140820 | P-CUCme.3-1:1:3 | 15 | 0.058 | 0.008 |
| pMON140821 | EXP-CUCme.4:1:1 | 156 | 3.662 | 0.520 |
| pMON140823 | P-CUCme.6-1:1:1 | 18 | 0.041 | 0.006 |
| pMON140824 | P-CUCme.8-1:1:2 | 19 | 0.022 | 0.003 |
| pMON140825 | P-CUCme.9-1:1:2 | 20 | 0.333 | 0.047 |
| pMON140826 | P-CUCme.10-1:1:1 | 21 | 0.182 | 0.026 |
| pMON140827 | EXP-CUCme.eEF1a:1:1 | 162 | 0.659 | 0.094 |
| pMON140828 | P-CUCme.15-1:1:2 | 23 | 0.061 | 0.009 |
| pMON140829 | P-CUCme.16a-1:1:2 | 24 | 0.012 | 0.002 |
| pMON140830 | P-CUCme.17-1:1:2 | 26 | 0.132 | 0.019 |
| pMON140831 | P-CUCme.18-1:1:2 | 27 | 0.089 | 0.013 |
| pMON140832 | P-CUCme.19-1:1:3 | 167 | 0.119 | 0.017 |
| pMON140833 | P-CUCme.20-1:3 | 211 | 0.078 | 0.011 |
| pMON140834 | P-CUCme.21-1:1:1 | 30 | 0.104 | 0.015 |
| pMON140835 | P-CUCme.22-1:1:3 | 31 | 0.327 | 0.046 |
| pMON140836 | EXP-CUCme.SAMS2:1:1 | 168 | 0.564 | 0.080 |
| pMON140837 | P-CUCme.26-1:1:2 | 33 | 0.158 | 0.022 |
| pMON140838 | P-CUCme.28-1:1:2 | 34 | 0.134 | 0.019 |
| pMON140839 | EXP-CUCme.29:1:2 | 212 | 0.019 | 0.003 |

TABLE 17

GUS to renilla luciferase (RLuc) ratios normalized with respect to EXP-At.Act7:1:11 and EXP-CaMV.35S-enh+Ph.DnaK:1:3.

| Construct | Regulatory Element | SEQ ID NO: | GUS/RLuc normalized with respect to EXP-At.Act7:1:11 | GUS/RLuc normalized with respect to EXP-CaMV.35S-enh+Ph.DnaK:1:3 |
|---|---|---|---|---|
| pMON109584 | EXP-CaMV.35S-enh+Ph.DnaK:1:3 | 201 | 4.83 | 1.00 |
| pMON118756 | EXP-At.Act7:1:11 | 202 | 1.00 | 0.21 |
| pMON124912 | Promoterless | | 0.02 | 0.00 |
| pMON140818 | P-CUCme.1-1:1:1rc | 155 | 0.20 | 0.04 |
| pMON140819 | P-CUCme.2-1:1:1 | 14 | 0.04 | 0.01 |
| pMON140820 | P-CUCme.3-1:1:3 | 15 | 0.06 | 0.01 |
| pMON140821 | EXP-CUCme.4:1:1 | 156 | 3.41 | 0.71 |
| pMON140823 | P-CUCme.6-1:1:1 | 18 | 0.04 | 0.01 |
| pMON140824 | P-CUCme.8-1:1:2 | 19 | 0.02 | 0.00 |
| pMON140825 | P-CUCme.9-1:1:2 | 20 | 0.33 | 0.07 |
| pMON140826 | P-CUCme.10-1:1:1 | 21 | 0.17 | 0.04 |
| pMON140827 | EXP-CUCme.eEF1a:1:1 | 162 | 0.67 | 0.14 |
| pMON140828 | P-CUCme.15-1:1:2 | 23 | 0.05 | 0.01 |
| pMON140829 | P-CUCme.16a-1:1:2 | 24 | 0.01 | 0.00 |
| pMON140830 | P-CUCme.17-1:1:2 | 26 | 0.13 | 0.03 |
| pMON140831 | P-CUCme.18-1:1:2 | 27 | 0.10 | 0.02 |
| pMON140832 | P-CUCme.19-1:1:3 | 167 | 0.12 | 0.03 |
| pMON140833 | P-CUCme.20-1:3 | 211 | 0.07 | 0.02 |
| pMON140834 | P-CUCme.21-1:1:1 | 30 | 0.12 | 0.03 |
| pMON140835 | P-CUCme.22-1:1:3 | 31 | 0.32 | 0.07 |
| pMON140836 | EXP-CUCme.SAMS2:1:1 | 168 | 0.57 | 0.12 |
| pMON140837 | P-CUCme.26-1:1:2 | 33 | 0.21 | 0.04 |
| pMON140838 | P-CUCme.28-1:1:2 | 34 | 0.13 | 0.03 |
| pMON140839 | EXP-CUCme.29:1:2 | 212 | 0.02 | 0.00 |

As can be seen in Tables 16 and 17, most of the expression element groups tested, demonstrated the ability to drive transgene expression in cotton leaf protoplast cells. One expression element group, EXP-CUCme.4:1:1 (SEQ ID NO: 156) demonstrated levels of transgene expression higher than that of EXP-At.Act7:1:11 in this assay.

Example 8: Analysis of Regulatory Elements Driving GUS in Cotton Leaf Protoplasts Using Transgene Cassette Amplicons Cotton leaf protoplasts were transformed with transgene cassette amplicons containing a transcriptional regulatory expression element group driving expression of the ß-glucuronidase (GUS) transgene and compared to GUS expression in leaf protoplasts in which expression of GUS is driven by known constitutive promoters. The transgene cassette amplicons were comprised of an EXP sequence, operably linked to a GUS coding sequence (GUS, SEQ ID NO: 206), operably linked to a 3' UTR (T-Gb.FbL2-1:1:1, SEQ ID NO: 205). Average GUS expression was compared to the control EXP elements, P-CaMV.35S-enh-1:1:102/L-CaMV.35S-1:1:2 (SEQ ID NO: 210) and EXP-At.Atntt1:1:2 (SEQ ID NO: 200).

A plasmid, for use in co-transformation and normalization of data was also used in a similar manner as that described above in Example 2. The transformation control plasmid was comprised of a constitutive promoter, driving the expression of the firefly (*Photinus pyralis*) luciferase coding sequence (FLuc, SEQ ID NO: 205), operably linked 5' to a 3' termination region from the *Agrobacterium tumefaciens* nopaline synthase gene (T-AGRtu.nos-1:1:13, SEQ ID NO: 209).

Table 18 below shows the mean GUS expression values conferred by each transgene amplicon. Table 19 below shows the GUS to firefly luciferase (FLuc) ratios normalized with respect to EXP-At.Atntt1:1:2 and P-CaMV.35S-enh-1:1:102/L-CaMV.35S-1:1:2.

TABLE 18

Average GUS and luciferase expression values and GUS/luciferase ratios.

| Amplicon ID | Regulatory Element | SEQ ID NO: | Mean GUS | Mean Fluc | GUS/Fluc |
|---|---|---|---|---|---|
| Empty Vector | No DNA | | 32.8 | 14087.5 | 0.002 |
| pMON124912 | No promoter | | 12 | 20486.3 | 0.001 |
| pMON80585 | EXP-At.Atntt1:1:2 | 200 | 55.5 | 18811 | 0.003 |
| pMON33449 | P-CaMV.35S-enh-1:1:102/L-CaMV.35S-1:1:2 | 210 | 12472.5 | 19126.3 | 0.652 |
| 56741 | CumMe_WSM_SF143981.G5150 | 36 | 5.8 | 17449.5 | 0.000 |
| 56492 | CumMe_WSM_SF144839.G5080 | 37 | 27.5 | 16674 | 0.002 |
| 56877 | P-CUCme.CumMe_WSM_SF16444.G5140-1:1:1 | 175 | 96.3 | 17237.8 | 0.006 |
| 56485 | CumMe_WSM_SF16530.G6000 | 42 | 27.3 | 17858.5 | 0.002 |
| 56844 | CumMe_WSM_SF16953.G5180 | 47 | 22.3 | 19398.5 | 0.001 |

TABLE 18-continued

Average GUS and luciferase expression values and GUS/luciferase ratios.

| Amplicon ID | Regulatory Element | SEQ ID NO: | Mean GUS | Mean Fluc | GUS/Fluc |
|---|---|---|---|---|---|
| 56500 | CumMe_WSM_SF17250.G5910 | 52 | 12.3 | 23980.3 | 0.001 |
| 56754 | P-CUCme.WSM_SF17252.G7330-1:1:1 | 179 | 16 | 13848.8 | 0.001 |
| 56740 | CumMe_WSM_SF17672.G5610 | 60 | 12 | 16646.8 | 0.001 |
| 56870 | CumMe_WSM_SF18287.G5380 | 66 | 39.3 | 13930.5 | 0.003 |
| 56478 | CumMe_WSM_SF18504.G5090 | 68 | 11.8 | 15830.5 | 0.001 |
| 56481 | CumMe_WSM_SF18530.G5750 | 69 | 6.5 | 15211.3 | 0.000 |
| 56498 | CumMe_WSM_SF18645.G5380 | 73 | 36 | 14569.8 | 0.002 |
| 56746 | P-CUCme.CumMe_WSM_SF18716.G5860-1:1:1 | 184 | 11 | 18054.5 | 0.001 |
| 56490 | CumMe_WSM_SF18801.G5040 | 75 | 21.5 | 14147.3 | 0.002 |
| 56488 | CumMe_WSM_SF19323.G5120 | 81 | 15.3 | 11985.3 | 0.001 |
| 56499 | CumMe_WSM_SF19631.G5170 | 83 | 12.5 | 20140.5 | 0.001 |
| 56482 | P-CUCme.CumMe_WSM_SF19839.G5090-1:1:1 | 189 | 75 | 18690.5 | 0.004 |
| 56489 | CumMe_WSM_SF19850.G5130 | 86 | 38.3 | 19756.5 | 0.002 |
| 56476 | CumMe_WSM_SF20355.G5130 | 91 | 10.5 | 27901.8 | 0.000 |
| 56895 | CumMe_WSM_SF20431.G6340 | 95 | 34.8 | 16283.8 | 0.002 |
| 56744 | CumMe_WSM_SF206458.G5970 | 98 | 11 | 19659 | 0.001 |
| 56480 | CumMe_WSM_SF21366.G5980 | 105 | 10.8 | 17367 | 0.001 |
| 56930 | CumMe_WSM_SF22070.G5280 | 109 | 25.3 | 14210.5 | 0.002 |
| 56484 | CumMe_WSM_SF23181.G5100 | 117 | 20.3 | 13506 | 0.002 |
| 56495 | P-CUCme.CumMe_WSM_SF23760.G5200-1:1:1 | 193 | 7.8 | 15138.5 | 0.001 |
| 56971 | CumMe_WSM_SF25084.G5580 | 125 | 16 | 16135.3 | 0.001 |
| 56742 | P-CUCme.CumMe_WSM_SF25355.G5000-1:1:1 | 196 | 18 | 13782.8 | 0.001 |
| 56494 | CumMe_WSM_SF25455.G5370 | 129 | 10.5 | 16089.8 | 0.001 |
| 56751 | P-CUCme.CumMe_WSM_SF41124.G5080-1:1:1 | 199 | 24.3 | 17884.3 | 0.001 |
| 56483 | CumMe_WSM_SF41644.G6400 | 143 | 14.5 | 13130.5 | 0.001 |
| 56904 | CumMe_WSM_SF44933.G5290 | 147 | 33 | 13369 | 0.002 |
| 56743 | CumMe_WSM_SF9060.G5120 | 154 | 11.3 | 15230.8 | 0.001 |

TABLE 19

GUS to firefly luciferase (FLuc) ratios normalized with respect to EXP-At.Atntt1:1:2 and P-CaMV.35S-enh-1:1:102/L-CaMV.35S-1:1:2.

| Amplicon ID | Regulatory Element | SEQ ID NO: | GUS/Fluc normalized with respect to EXP-At.Atntt1:1:2 | GUS/Fluc normalized with respect to P-CaMV.35S-enh-1:1:102/L-CaMV.35S-1:1:2 |
|---|---|---|---|---|
| Empty Vector | No DNA | | | |
| pMON124912 | No promoter | | | |
| pMON80585 | EXP-At.Atntt1:1:2 | 200 | 1.000 | 0.005 |
| pMON33449 | P-CaMV.35S-enh-1:1:102/L-CaMV.35S-1:1:2 | 210 | 221.025 | 1.000 |
| 56741 | CumMe_WSM_SF143981.G5150 | 36 | 0.113 | 0.001 |
| 56492 | CumMe_WSM_SF144839.G5080 | 37 | 0.559 | 0.003 |
| 56877 | P-CUCme.CumMe_WSM_SF16444.G5140-1:1:1 | 175 | 1.893 | 0.009 |
| 56485 | CumMe_WSM_SF16530.G6000 | 42 | 0.518 | 0.002 |
| 56844 | CumMe_WSM_SF16953.G5180 | 47 | 0.390 | 0.002 |
| 56500 | CumMe_WSM_SF17250.G5910 | 52 | 0.174 | 0.001 |
| 56754 | P-CUCme.WSM_SF17252.G7330-1:1:1 | 179 | 0.392 | 0.002 |
| 56740 | CumMe_WSM_SF17672.G5610 | 60 | 0.244 | 0.001 |
| 56870 | CumMe_WSM_SF18287.G5380 | 66 | 0.956 | 0.004 |
| 56478 | CumMe_WSM_SF18504.65090 | 68 | 0.253 | 0.001 |
| 56481 | CumMe_WSM_SF18530.G5750 | 69 | 0.145 | 0.001 |
| 56498 | CumMe_WSM_SF18645.G5380 | 73 | 0.837 | 0.004 |
| 56746 | P-CUCme.CumMe_WSM_SF18716.G5860-1:1:1 | 184 | 0.207 | 0.001 |
| 56490 | CumMe_WSM_SF18801.G5040 | 75 | 0.515 | 0.002 |
| 56488 | CumMe_WSM_SF19323.G5120 | 81 | 0.433 | 0.002 |
| 56499 | CumMe_WSM_SF19631.G5170 | 83 | 0.210 | 0.001 |
| 56482 | P-CUCme.CumMe_WSM_SF19839.G5090-1:1:1 | 189 | 1.360 | 0.006 |
| 56489 | CumMe_WSM_SF19850.G5130 | 86 | 0.657 | 0.003 |

TABLE 19-continued

GUS to firefly luciferase (FLuc) ratios normalized with respect to EXP-At.Atntt1:1:2 and P-CaMV.35S-enh-1:1:102/L-CaMV.35S-1:1:2.

| Amplicon ID | Regulatory Element | SEQ ID NO: | GUS/Fluc normalized with respect to EXP-At.Atntt1:1:2 | GUS/Fluc normalized with respect to P-CaMV.35S-enh-1:1:102/L-CaMV.35S-1:1:2 |
|---|---|---|---|---|
| 56476 | CumMe_WSM_SF20355.G5130 | 91 | 0.128 | 0.001 |
| 56895 | CumMe_WSM_SF20431.G6340 | 95 | 0.724 | 0.003 |
| 56744 | CumMe_WSM_SF206458.G5970 | 98 | 0.190 | 0.001 |
| 56480 | CumMe_WSM_SF21366.G5980 | 105 | 0.211 | 0.001 |
| 56930 | CumMe_WSM_SF22070.G5280 | 109 | 0.603 | 0.003 |
| 56484 | CumMe_WSM_SF23181.G5100 | 117 | 0.509 | 0.002 |
| 56495 | P-CUCme.CumMe_WSM_SF23760.G5200-1:1:1 | 193 | 0.175 | 0.001 |
| 56971 | CumMe_WSM_SF25084.G5580 | 125 | 0.336 | 0.002 |
| 56742 | P-CUCme.CumMe_WSM_SF25355.G5000-1:1:1 | 196 | 0.443 | 0.002 |
| 56494 | CumMe_WSM_SF25455.G5370 | 129 | 0.221 | 0.001 |
| 56751 | P-CUCme.CumMe_WSM_SF41124.G5080-1:1:1 | 199 | 0.461 | 0.002 |
| 56483 | CumMe_WSM_SF41644.G6400 | 143 | 0.374 | 0.002 |
| 56904 | CumMe_WSM_SF44933.G5290 | 147 | 0.837 | 0.004 |
| 56743 | CumMe_WSM_SF9060.G5120 | 154 | 0.251 | 0.001 |

As can be seen in Table 18 above, not all EXP sequences demonstrated the ability to drive transgene expression when compared to the promoterless control. However, the EXP sequences, P-CUCme.CumMe_WSM_SF16444.G5140-1:1:1 (SEQ ID NO: 175) and P-CUCme.CumMe_WSM_SF19839.G5090-1:1:1 (SEQ ID NO: 189) demonstrated the ability to drive transgene expression in soybean cotyledon protoplasts at a level similar or greater than EXP-At.Atntt1:1:2. As shown in Table 19 above, the EXP sequence, P-CUCme.CumMe_WSM_SF19839.G5090-1:1:1 (SEQ ID NO: 189) demonstrated the ability to drive transgene expression in this assay at a level greater than EXP-At.Atntt1:1:2.

Example 9: Analysis of Regulatory Elements Driving GUS in Stably Transformed Soybean Soybean plants were transformed with plant expression vectors containing an EXP sequence driving expression of the ß-glucuronidase (GUS) transgene.

Expression of the GUS transgene driven by EXP-CUCme.Ubq1:1:1 (SEQ ID NO: 1), EXP-CUCme.Ubq1:1:3 (SEQ ID NO: 7), P-CUCme.1-1:1:1rc (SEQ ID NO: 155), P-CUCme.2-1:1:1 (SEQ ID NO: 14), P-CUCme.3-1:1:3 (SEQ ID NO: 15), EXP-CUCme.4:1:1 (SEQ ID NO: 156), EXP-CUCme.5:1:1 (SEQ ID NO: 159), P-CUCme.6-1:1:1 (SEQ ID NO: 18), P-CUCme.8-1:1:2 (SEQ ID NO: 19), P-CUCme.9-1:1:2 (SEQ ID NO: 20), P-CUCme.10-1:1:1 (SEQ ID NO: 21), EXP-CUCme.eEF1a:1:1 (SEQ ID NO: 162), P-CUCme.15-1:1:2 (SEQ ID NO: 23), P-CUCme.17-1:1:2 (SEQ ID NO: 26), P-CUCme.18-1:1:2 (SEQ ID NO: 27), P-CUCme.19-1:1:3 (SEQ ID NO: 167), P-CUCme.20-1:3 (SEQ ID NO: 211), P-CUCme.21-1:1:1 (SEQ ID NO: 30), EXP-CUCme.SAMS2:1:1 (SEQ ID NO: 168), P-CUCme.26-1:1:2 (SEQ ID NO: 33), EXP-CUCme.29:1:2 (SEQ ID NO: 212), P-CUCme.CumMe_WSM_SF25355.G5000-1:1:1 (SEQ ID NO: 196), P-CUCme.CumMe_WSM_SF17111.G5790-1:1:1 (SEQ ID NO: 177), P-CUCme.CumMe_WSM_SF22531.G5120-1:1:1 (SEQ ID NO: 192), P-CUCme.CumMe_WSM_SF18488.G5340-1:1:1 (SEQ ID NO: 181), P-CUCme.CumMe_WSM_SF23760.G5200-1:1:1 (SEQ ID NO: 193), EXP-CUCme.WSM_SF19064.G5690:1:1 (SEQ ID NO: 185), P-CUCme.WSM_SF17252.G7330-1:1:1 (SEQ ID NO: 179), P-CUCme.CumMe_WSM_SF18634.G5190-1:1:1 (SEQ ID NO: 183), P-CUCme.CumMe_WSM_SF19647.G5760-1:1:1 (SEQ ID NO: 188), P-CUCme.CumMe_WSM_SF25936.G5450-1:1:1 (SEQ ID NO: 197), P-CUCme.CumMe_WSM_SF19839.G5090-1:1:1 (SEQ ID NO: 189), CumMe_WSM_SF206458.G5970 (SEQ ID NO: 98) and P-CUCme.CumMe_WSM_SF18716.G5860-1:1:1 (SEQ ID NO: 184) assayed both qualitatively through inspection of stained tissue sections and quantitatively. Each plant expression vector was comprised of a right border region from *Agrobacterium tumefaciens*, a first transgene cassette comprised of an EXP sequence operably linked 5' to a coding sequence for ß-glucuronidase (GUS, SEQ ID NO: 206) containing a processable intron derived from the potato light-inducible tissue-specific ST-LS1 gene (Genbank Accession: X04753), operably linked 5' to a 3' termination region from the the *Gossypium barbadense* FbLate-2 gene (T-Gb.FbL2-1:1:1, SEQ ID NO: 205); a second transgene selection cassette used for selection of transformed plant cells that conferred resistance to the herbicide glyphosate (driven by the *Arabidopsis* Actin 7 promoter) and a left border region from *A. tumefaciens*.

The foregoing EXP sequences were cloned into plant expression constructs as shown in Tables 20 through 23 below and used to transform soybean plants using an *agrobacterium* mediated transformation method. Expression of GUS was assayed qualitatively using histological sections of selected tissues and quantitatively.

Histochemical GUS analysis was used for qualitative expression analysis of transformed plants. Whole tissue sections were incubated with GUS staining solution X-Gluc (5-bromo-4-chloro-3-indolyl-b-glucuronide) (1 milligram/milliliter) for an appropriate length of time, rinsed, and visually inspected for blue coloration. GUS activity was qualitatively determined by direct visual inspection or inspection under a microscope using selected plant organs and tissues. The $R_0$ generation plants were inspected for expression in Vn5 Root, R1 Root, Vn5 Sink Leaf, Vn5 Source Leaf, R1 Source Leaf, R1 Petiole, Yellow Pod Embryo, Yellow Pod Cotyledon, R3 Immature Seed, R3 Pod, R5 Cotyledon and R1 Flower.

For quantitative analysis, total protein was extracted from selected tissues of transformed corn plants. One microgram of total protein was used with the fluorogenic substrate 4-methyleumbelliferyl-β-D-glucuronide (MUG) in a total reaction volume of 50 microliters. The reaction product, 4-methlyumbelliferone (4-MU), is maximally fluorescent at high pH, where the hydroxyl group is ionized. Addition of a basic solution of sodium carbonate simultaneously stops the assay and adjusts the pH for quantifying the fluorescent product. Fluorescence was measured with excitation at 365 nm, emission at 445 nm using a Fluoromax-3 (Horiba; Kyoto, Japan) with Micromax Reader, with slit width set at excitation 2 nm and emission 3 nm.

Tables 20 and 21 below show the mean quantitative expression levels measured in the $R_0$ generation plant tissues. Those tissued not assayed are shown as blank cells in both tables.

TABLE 20

Mean GUS expression in Vn5 Root, R1 Root, Vn5 Sink Leaf, Vn5 Source Leaf, R1 Source Leaf and R1 Petiole of $R_0$ generation transformed soybean plants

| Construct | Regulatory Element | SEQ ID NO: | Vn5_Root | R1_Root |
|---|---|---|---|---|
| pMON138776 | EXP-CUCme.Ubq1:1:1 | 1 | 4 | |
| pMON138778 | EXP-CUCme.Ubq1:1:3 | 7 | 16 | |
| pMON140818 | P-CUCme.1-1:1:1rc | 155 | 48.21 | |
| pMON140819 | P-CUCme.2-1:1:1 | 14 | | |
| pMON140820 | P-CUCme.3-1:1:3 | 15 | | |
| pMON140821 | EXP-CUCme.4:1:1 | 156 | 96.82 | |
| pMON140822 | EXP-CUCme.5:1:1 | 159 | 28.88 | |
| pMON140823 | P-CUCme.6-1:1:1 | 18 | 23.94 | |
| pMON140824 | P-CUCme.8-1:1:2 | 19 | | |
| pMON140825 | P-CUCme.9-1:1:2 | 20 | 22.06 | |
| pMON140826 | P-CUCme.10-1:1:1 | 21 | | |
| pMON140827 | EXP-CUCme.eEF1a:1:1 | 162 | 189.24 | 153.52 |
| pMON140828 | P-CUCme.15-1:1:2 | 23 | 30.53 | |
| pMON140830 | P-CUCme.17-1:1:2 | 26 | 51.62 | |
| pMON140831 | P-CUCme.18-1:1:2 | 27 | 57.38 | |
| pMON140832 | P-CUCme.19-1:1:3 | 167 | 23.07 | |
| pMON140833 | P-CUCme.20-1:3 | 211 | 23.15 | |
| pMON140834 | P-CUCme.21-1:1:1 | 30 | | |
| pMON140836 | EXP-CUCme.SAMS2:1:1 | 168 | 230.89 | 184.88 |
| pMON140837 | P-CUCme.26-1:1:2 | 33 | 56.21 | |
| pMON140839 | EXP-CUCme.29:1:2 | 212 | 82.17 | |
| pMON144926 | P-CUCme.CumMe_WSM_SF25355.G5000-1:1:1 | 196 | 28.53 | |
| pMON144927 | P-CUCme.CumMe_WSM_SF17111.G5790-1:1:1 | 177 | 23.62 | |
| pMON144928 | P-CUCme.CumMe_WSM_SF22531.G5120-1:1:1 | 192 | 75.62 | |
| pMON144931 | P-CUCme.CumMe_WSM_SF18488.G5340-1:1:1 | 181 | 43.2 | |
| pMON144933 | P-CUCme.CumMe_WSM_SF23760.G5200-1:1:1 | 193 | 25.61 | |
| pMON146941 | EXP-CUCme.WSM_SF19064.G5690:1:1 | 185 | 33.5 | |
| pMON144932 | P-CUCme.WSM_SF17252.G7330-1:1:1 | 179 | 32.54 | |
| pMON146940 | P-CUCme.CumMe_WSM_SF18634.G5190-1:1:1 | 183 | 0 | |
| pMON147340 | P-CUCme.CumMe_WSM_SF19647.G5760-1:1:1 | 188 | 28.9 | |
| pMON147342 | P-CUCme.CumMe_WSM_SF25936.G5450-1:1:1 | 197 | 50.15 | |
| pMON147343 | P-CUCme.CumMe_WSM_SF19839.G5090-1:1:1 | 189 | 36.05 | |
| pMON144929 | CumMe_WSM_SF206458.G5970 | 98 | | |
| pMON147304 | P-CUCme.CumMe_WSM_SF18716.G5860-1:1:1 | 184 | 35.01 | |

| Construct | Vn5_Sink_Leaf | Vn5_Source Leaf | R1_Source_Leaf | R1_Petiole |
|---|---|---|---|---|
| pMON138776 | | | 4 | 4 |
| pMON138778 | 1 | 2 | 13 | 23 |
| pMON140818 | 22.35 | 20.24 | 33.01 | 78.17 |
| pMON140819 | | | | |
| pMON140820 | | | | |
| pMON140821 | 28.32 | 39.17 | 322.98 | 280.03 |
| pMON140822 | | | 41.11 | |
| pMON140823 | | | 32.14 | 30.22 |
| pMON140824 | | | | |
| pMON140825 | | | 21.22 | 23.08 |
| pMON140826 | | | | |
| pMON140827 | 59.6 | 37.44 | 103.01 | 130.6 |
| pMON140828 | | | | |
| pMON140830 | 30.07 | 31.08 | 30.49 | 60.14 |
| pMON140831 | | | | 30.03 |
| pMON140832 | 50.21 | 59.73 | 65.58 | 137.42 |
| pMON140833 | 61.6 | 118.76 | 502.55 | 119.46 |
| pMON140834 | | | 25.49 | |
| pMON140836 | 65.44 | 53.36 | 118.82 | 351.49 |
| pMON140837 | 26.81 | 45.07 | 51.61 | 47.42 |
| pMON140839 | 45.2 | 28.27 | 64.96 | 109.9 |
| pMON144926 | | | | |

TABLE 20-continued

Mean GUS expression in Vn5 Root, R1 Root, Vn5 Sink Leaf, Vn5 Source Leaf, R1 Source Leaf and R1 Petiole of $R_0$ generation transformed soybean plants

| | | | | |
|---|---|---|---|---|
| pMON144927 | | | | |
| pMON144928 | 23 | 20.46 | 21.78 | 39.77 |
| pMON144931 | | | | 52.55 |
| pMON144933 | 20.45 | 0 | 0 | 28.69 |
| pMON146941 | 0 | 0 | 24.27 | 47.82 |
| pMON144932 | 23.76 | 21.5 | 0 | 22.21 |
| pMON146940 | 0 | 0 | 0 | 0 |
| pMON147340 | 0 | 0 | 29.77 | 25.82 |
| pMON147342 | 24.26 | 0 | 29.38 | 29.91 |
| pMON147343 | 25.7 | 27.54 | 22.85 | 37.15 |
| pMON144929 | | | | |
| pMON147304 | 21.17 | 21.23 | 22 | 44.57 |

TABLE 21

Mean GUS expression in Yellow Pod Embryo, Yellow Pod Cotyledon, R3 Immature Seed, R3 Pod, R5 Cotyledon and R1 Flower of $R_0$ generation transformed soybean plants

| Construct | Regulatory Element | SEQ ID NO: | Yellow_Pod_Embryo | Yellow_Pod_Cotyledon |
|---|---|---|---|---|
| pMON138776 | EXP-CUCme.Ubq1:1:1 | 1 | 12 | 9 |
| pMON138778 | EXP-CUCme.Ubq1:1:3 | 7 | 3 | 1 |
| pMON140818 | P-CUCme.1-1:1:1rc | 155 | 100.79 | 117.5 |
| pMON140819 | P-CUCme.2-1:1:1 | 14 | | |
| pMON140820 | P-CUCme.3-1:1:3 | 15 | | |
| pMON140821 | EXP-CUCme.4:1:1 | 156 | 86.68 | 225.53 |
| pMON140822 | EXP-CUCme.5:1:1 | 159 | 21.48 | 32.27 |
| pMON140823 | P-CUCme.6-1:1:1 | 18 | 38.75 | |
| pMON140824 | P-CUCme.8-1:1:2 | 19 | | |
| pMON140825 | P-CUCme.9-1:1:2 | 20 | 132.04 | |
| pMON140826 | P-CUCme.10-1:1:1 | 21 | | |
| pMON140827 | EXP-CUCme.eEF1a:1:1 | 162 | 200.28 | 291.26 |
| pMON140828 | P-CUCme.15-1:1:2 | 23 | | |
| pMON140830 | P-CUCme.17-1:1:2 | 26 | 343.34 | 302.94 |
| pMON140831 | P-CUCme.18-1:1:2 | 27 | 103.17 | 135.97 |
| pMON140832 | P-CUCme.19-1:1:3 | 167 | 30.96 | 64.46 |
| pMON140833 | P-CUCme.20-1:3 | 211 | 174.62 | 524.88 |
| pMON140834 | P-CUCme.21-1:1:1 | 30 | | |
| pMON140836 | EXP-CUCme.SAMS2:1:1 | 168 | 110.23 | 159.43 |
| pMON140837 | P-CUCme.26-1:1:2 | 33 | 56.73 | 50.06 |
| pMON140839 | EXP-CUCme.29:1:2 | 212 | 251.76 | 237.2 |
| pMON144926 | P-CUCme.CumMe_WSM_SF25355.G5000-1:1:1 | 196 | | |
| pMON144927 | P-CUCme.CumMe_WSM_SF17111.G5790-1:1:1 | 177 | 58.84 | 28.94 |
| pMON144928 | P-CUCme.CumMe_WSM_SF22531.G5120-1:1:1 | 192 | 135.62 | 152.48 |
| pMON144931 | P-CUCme.CumMe_WSM_SF18488.G5340-1:1:1 | 181 | 866.94 | |
| pMON144933 | P-CUCme.CumMe_WSM_SF23760.G5200-1:1:1 | 193 | | |
| pMON146941 | EXP-CUCme.WSM_SF19064.G5690:1:1 | 185 | | |
| pMON144932 | P-CUCme.WSM_SF17252.G7330-1:1:1 | 179 | | |
| pMON146940 | P-CUCme.CumMe_WSM_SF18634.G5190-1:1:1 | 183 | | |
| pMON147340 | P-CUCme.CumMe_WSM_SF19647.G5760-1:1:1 | 188 | | |
| pMON147342 | P-CUCme.CumMe_WSM_SF25936.G5450-1:1:1 | 197 | | |
| pMON147343 | P-CUCme.CumMe_WSM_SF19839.G5090-1:1:1 | 189 | | |
| pMON144929 | CumMe_WSM_SF206458.G5970 | 98 | | |
| pMON147304 | P-CUCme.CumMe_WSM_SF18716.G5860-1:1:1 | 184 | | |

| Construct | R3_Immature_Seed | R3_Pod | R5_Cotyledon | R1_Flower |
|---|---|---|---|---|
| pMON138776 | 13 | 11 | 10 | 7 |
| pMON138778 | 13 | 9 | 13 | 27 |
| pMON140818 | 38.31 | 84.72 | 132.27 | 66.8 |
| pMON140819 | | | 20.35 | 36.18 |
| pMON140820 | | | | |
| pMON140821 | 105.62 | 342.07 | 119.08 | 184.92 |
| pMON140822 | 21.47 | 21.66 | | 36.88 |
| pMON140823 | 23.03 | | 25.32 | 58.7 |
| pMON140824 | | | 90.33 | 25.77 |
| pMON140825 | | 20.56 | 34.78 | |
| pMON140826 | | | 22.34 | |
| pMON140827 | 58.21 | 131.17 | 114.29 | 130.38 |
| pMON140828 | 142.24 | 26.2 | | |
| pMON140830 | 65.55 | 80.94 | 137.02 | 62.7 |
| pMON140831 | 30 | 34.62 | 88.14 | 23.73 |
| pMON140832 | | 316.66 | | 53.46 |
| pMON140833 | | 222.04 | 59.43 | 124.68 |

TABLE 21-continued

Mean GUS expression in Yellow Pod Embryo, Yellow Pod Cotyledon, R3 Immature Seed, R3 Pod, R5 Cotyledon and R1 Flower of $R_0$ generation transformed soybean plants

| | | | | |
|---|---|---|---|---|
| pMON140834 | 28.15 | 20.52 | 23.89 | |
| pMON140836 | 61.99 | 248.96 | 49.17 | 224.24 |
| pMON140837 | 70 | 143.05 | 25.06 | 49.92 |
| pMON140839 | 49.16 | 89.28 | 114.92 | 57.84 |
| pMON144926 | 21.41 | | 22.23 | |
| pMON144927 | | | 20.97 | |
| pMON144928 | 30.45 | 51.71 | 129.72 | 42.2 |
| pMON144931 | 23.26 | 21.49 | | |
| pMON144933 | 29.03 | 34.9 | 69.63 | 24.42 |
| pMON146941 | 36.69 | 83.08 | 89.81 | 33.99 |
| pMON144932 | 34.29 | 39.89 | 113.83 | 0 |
| pMON146940 | 30.25 | 0 | 0 | 0 |
| pMON147340 | 25.73 | 28.28 | 24.04 | 23.35 |
| pMON147342 | 104.02 | 80.27 | 31.06 | 26.8 |
| pMON147343 | | | | 29.09 |
| pMON144929 | 24.42 | 25.33 | | |
| pMON147304 | | 283.49 | | 61.43 |

As can be seen in Tables 20 and 21, the EXP sequences, EXP-CUCme.Ubq1:1:1 (SEQ ID NO: 1), EXP-CUCme.Ubq1:1:3 (SEQ ID NO: 7), P-CUCme.1-1:1:1rc (SEQ ID NO: 155), P-CUCme.2-1:1:1 (SEQ ID NO: 14), EXP-CUCme.4:1:1 (SEQ ID NO: 156), EXP-CUCme.5:1:1 (SEQ ID NO: 159), P-CUCme.6-1:1:1 (SEQ ID NO: 18), P-CUCme.8-1:1:2 (SEQ ID NO: 19), P-CUCme.9-1:1:2 (SEQ ID NO: 20), P-CUCme.10-1:1:1 (SEQ ID NO: 21), EXP-CUCme.eEF1a:1:1 (SEQ ID NO: 162), P-CUCme.15-1:1:2 (SEQ ID NO: 23), P-CUCme.17-1:1:2 (SEQ ID NO: 26), P-CUCme.18-1:1:2 (SEQ ID NO: 27), P-CUCme.19-1:1:3 (SEQ ID NO: 167), P-CUCme.20-1:3 (SEQ ID NO: 211), P-CUCme.21-1:1:1 (SEQ ID NO: 30), EXP-CUCme.SAMS2:1:1 (SEQ ID NO: 168), P-CUCme.26-1:1:2 (SEQ ID NO: 33), EXP-CUCme.29:1:2 (SEQ ID NO: 212), P-CUCme.CumMe_WSM_SF25355.G5000-1:1:1 (SEQ ID NO: 196), P-CUCme.CumMe_WSM_SF17111.G5790-1:1:1 (SEQ ID NO: 177), P-CUCme.CumMe_WSM_SF22531.G5120-1:1:1 (SEQ ID NO: 192), P-CUCme.CumMe_WSM_SF18488.G5340-1:1:1 (SEQ ID NO: 181), P-CUCme.CumMe_WSM_SF23760.G5200-1:1:1 (SEQ ID NO: 193), EXP-CUCme.WSM_SF19064.G5690:1:1 (SEQ ID NO: 185), P-CUCme.WSM_SF17252.G7330-1:1:1 (SEQ ID NO: 179), P-CUCme.CumMe_WSM_SF18634.G5190-1:1:1 (SEQ ID NO: 183), P-CUCme.CumMe_WSM_SF19647.G5760-1:1:1 (SEQ ID NO: 188), P-CUCme.CumMe_WSM_SF25936.G5450-1:1:1 (SEQ ID NO: 197), P-CUCme.CumMe_WSM_SF19839.G5090-1:1:1 (SEQ ID NO: 189), CumMe_WSM_SF206458.G5970 (SEQ ID NO: 98) and P-CUCme.CumMe_WSM_SF18716.G5860-1:1:1 (SEQ ID NO: 184) demonstrated quantitatively the capacity to drive transgene expression in some or all tissues assayed, depending upon the EXP sequence used to drive expression.

Histological analysis of selected tissue sections provided further evidence of expression for many of the EXP sequences. EXP-CUCme.Ubq1:1:1 (SEQ ID NO: 1) and EXP-CUCme.Ubq1:1:3 (SEQ ID NO: 7) demonstrated a constitutive expression pattern with staining observed in all tissues, even though quantitative analysis showed fairly low levels of expression. This type of expression pattern can be most adventitious to driving expression of transgenes that require a low level of constitutive expression. Expression driven by P-CUCme.1-1:1:1rc (SEQ ID NO: 155) demonstrated expression in sink and source leaf vascular bundles and xylem and in the root cortex, phloem, xylem, endodermis, stele and tip. Expression driven by EXP-CUCme.4:1:1 (SEQ ID NO: 156) was observed in all tissues with the highest expression observed in the reproductive phase of the plant. Expression driven by P-CUCme.10-1:1:1 (SEQ ID NO: 21) was observed only in in V5 Sink Leaf and R1 Flower anthers. Expression driven by EXP-CUCme.eEF1a:1:1 (SEQ ID NO: 162) demonstrated a constitutive expression pattern with highest expression being observed in yellow pod embryo and cotyledon. The yellow pod embryo activity was 5fold higher in the R1 generation than in the R0 generation (see Table 23 below). Expression driven by P-CUCme.15-1:1:2 (SEQ ID NO: 23), P-CUCme.17-1:1:2 (SEQ ID NO: 26) and P-CUCme.18-1:1:2 (SEQ ID NO: 27) demonstrated a constitutive level of expression histologically. Expression driven by P-CUCme.19-1:1:3 (SEQ ID NO: 167) demonstrated a constitutive pattern of expression histologically with the exception of the V5 root and R1 petiole. R3 pod showed the highest expression.

Expression driven by P-CUCme.20-1:3 (SEQ ID NO: 211) demonstrated a constitutive expression pattern histologically with the exception of expression in V5 root. Expression was highest in the R8 stage cotyledon. Expression driven by EXP-CUCme.SAMS2:1:1 (SEQ ID NO: 168) demonstrated a constitutive pattern of expression with expression observed histologically in all tissues. GUS expression was observed to increase in the R1 generation (see Tables 22 and 23 below). The R1 stage flowers and petioles demonstrated the highest levels of expression in soybean. Expression driven by P-CUCme.CumMe_WSM_SF22531.G5120-1:1:1 (SEQ ID NO: 192) demonstrated a constitutive pattern of expression histologically with highest expression in the R8 stage cotyledon and embryo. Expression driven by P-CUCme.CumMe_WSM_SF18488.G5340-1:1:1 (SEQ ID NO: 181) demonstrated a constitutive level of expression while quantitatively high expression was observed in the yellow pod embryo.

$R_0$ generation plants transformed with the plasmid constructs comprising EXP-CUCme.eEF1a:1:1 (SEQ ID NO: 162) and EXP-CUCme.SAMS2:1:1 (SEQ ID NO: 168) were allowed to set seed and the $R_1$ generation plants analyzed for GUS expression. The $R_1$ generation plants were analyzed for expression in Vn5 Root, Vn5 Sink Leaf, Vn5 Source Leaf, R1 Source Leaf, R1 Petiole Yellow Pod Embryo, Yellow Pod Cotyledon, R3 Immature Seed, R3 Pod, R5 Cotyledon and R1 Flower. Tables 22 and 23 show the mean GUS expression measured in each tissue of the $R_1$ generation transformed plants.

TABLE 22

| Mean GUS expression in Vn5 Root, Vn5 Sink Leaf, Vn5 Source Leaf, R1 Source Leaf, R1 Petiole of $R_1$ generation transformed soybean plants | | | | | | | |
|---|---|---|---|---|---|---|---|
| Construct | Regulatory Element | SEQ ID NO: | Vn5_Root | Vn5_Sink_Leaf | Vn5_Source Leaf | R1_Source_Leaf | R1_Petiole |
| pMON140827 | EXP-CUCme.eEF1a:1:1 | 162 | 145.84 | 50.24 | 43.73 | 107.98 | 357.67 |
| pMON140836 | EXP-CUCme.SAMS2:1:1 | 168 | 260.41 | 65.52 | 51.12 | 129.86 | 623.42 |

TABLE 23

| Mean GUS expression in Yellow Pod Embryo, Yellow Pod Cotyledon, R3 Immature Seed, R3 Pod, R5 Cotyledon, R1 Flower of $R_1$ generation transformed soybean plants | | | | |
|---|---|---|---|---|
| Construct | Regulatory Element | SEQ ID NO: | Yellow_Pod_Embryo | Yellow_Pod_Cotyledon |
| pMON140827 | EXP-CUCme.eEF1a:1:1 | 162 | 1098.51 | 764.83 |
| pMON140836 | EXP-CUCme.SAMS2:1:1 | 168 | 219.04 | 291.58 |

| Construct | R3_Immature_Seed | R3_Pod | R5_Cotyledon | R1_Flower |
|---|---|---|---|---|
| pMON140827 | 288.77 | 214.6 | 459.62 | 394.77 |
| pMON140836 | 241.48 | 382.73 | 397.91 | 653.23 |

As can be seen in Tables 22 and 23 above expression driven in $R_1$ generation by EXP-CUCme.eEF1a:1:1 (SEQ ID NO: 162) and EXP-CUCme.SAMS2:1:1 (SEQ ID NO: 168) shows a constitutive level of expression with increase in expression observed in many tissues at $R_1$ generation relative to $R_0$ generation.

Having illustrated and described the principles of the present invention, it should be apparent to persons skilled in the art that the invention can be modified in arrangement and detail without departing from such principles. All modifications that are within the spirit and scope of the claims are intended to be included within the scope of the present invention. All publications and published patent documents cited herein are hereby incorporated by reference to the same extent as if each individual publication or patent application is specifically and individually indicated to be incorporated by reference.

What is claimed is:

1. A DNA molecule exhibiting a gene regulatory functional activity comprising a polynucleotide sequence selected from the group consisting of:

a) a sequence with at least 95 percent sequence identity to SEQ ID NO: 29, and exhibiting promoter activity;

b) a sequence comprising SEQ ID NO: 29; and c) a fragment comprising at least 250 contiguous nucleotides of SEQ ID NO: 29 exhibiting promoter activity;

wherein said DNA molecule is operably linked to a heterologous transcribable polynucleotide molecule.

2. The DNA molecule of claim 1, wherein said polynucleotide sequence has at least 97 percent sequence identity to the polynucleotide sequence as set forth in SEQ ID NO: 29.

3. The DNA molecule of claim 1, wherein said polynucleotide sequence has at least 99 percent sequence identity to the polynucleotide sequence as set forth in SEQ ID NO: 29.

4. The DNA molecule of claim 1, wherein the heterologous transcribable polynucleotide molecule comprises a gene of agronomic interest.

5. The DNA molecule of claim 4, wherein the gene of agronomic interest confers herbicide tolerance in plants.

6. The DNA molecule of claim 4, wherein the gene of agronomic interest confers pest resistance in plants.

7. A transgenic plant cell comprising a DNA molecule exhibiting a gene regulatory functional activity comprising a polynucleotide sequence selected from the group consisting of:

a) a sequence with at least 95 percent sequence identity to SEQ ID NO: 29, and exhibiting promoter activity;

b) a sequence comprising SEQ ID NO: 29; and c) a fragment comprising at least 250 contiguous nucleotides of SEQ ID NO: 29 exhibiting promoter activity;

wherein said DNA molecule is operably linked to a heterologous transcribable polynucleotide molecule.

8. The transgenic plant cell of claim 7, wherein said transgenic plant cell is a monocotyledonous plant cell.

9. The transgenic plant cell of claim 7, wherein said transgenic plant cell is a dicotyledonous plant cell.

10. A transgenic plant, or part thereof, comprising a DNA molecule exhibiting a gene-regulatory functional activity comprising a polynucleotide sequence selected from the group consisting of:

a) a sequence with at least 95 percent sequence identity to SEQ ID NO: 29, and exhibiting promoter activity;

b) a sequence comprising SEQ ID NO: 29; and c) a fragment comprising at least 250 contiguous nucleotides of SEQ ID NO: 29 exhibiting promoter activity;

wherein said DNA molecule is operably linked to a heterologous transcribable polynucleotide molecule.

11. A progeny plant of the transgenic plant of claim 10, or part thereof, wherein the progeny plant or part thereof comprises said DNA molecule exhibiting a gene regulatory functional activity.

12. A transgenic seed comprising a DNA molecule exhibiting a gene regulatory functional activity comprising a polynucleotide sequence selected from the group consisting of:

a) a sequence with at least 95 percent sequence identity to SEQ ID NO: 29, and exhibiting promoter activity;

b) a sequence comprising SEQ ID NO: 29; and c) a fragment comprising at least 250 contiguous nucleotides of SEQ ID NO: 29 exhibiting promoter activity;

wherein said DNA molecule is operably linked to a heterologous transcribable polynucleotide molecule.

13. A method of producing a commodity product comprising:

a) obtaining a transgenic plant or part thereof comprising a DNA molecule exhibiting a gene regulatory functional activity comprising a polynucleotide sequence selected from the group consisting of:

1) a sequence with at least 95 percent sequence identity to SEQ ID NO: 29, and exhibiting promoter activity;

2) a sequence comprising SEQ ID NO: 29; and 3) a fragment comprising at least 250 contiguous nucleotides of SEQ ID NO: 29 exhibiting promoter activity;

wherein said DNA molecule is operably linked to a heterologous transcribable polynucleotide molecule; and b) producing the commodity product from the transgenic plant or part thereof.

14. The method of claim 13, wherein the commodity product is protein concentrate, protein isolate, grain, starch, seeds, meal, flour, biomass, or seed oil.

15. A commodity product comprising a DNA molecule exhibiting a gene regulatory functional activity comprising a polynucleotide sequence selected from the group consisting of:

a) a sequence with at least 95 percent sequence identity to SEQ ID NO: 29, and exhibiting promoter activity;

b) a sequence comprising SEQ ID NO: 29; and c) a fragment comprising at least 250 contiguous nucleotides of SEQ ID NO: 29 exhibiting promoter activity;

wherein said DNA molecule is operably linked to a heterologous transcribable polynucleotide molecule.

16. A method of expressing a transcribable polynucleotide molecule comprising:

a) obtaining a transgenic plant comprising a DNA molecule exhibiting a gene regulatory functional activity comprising a polynucleotide sequence selected from the group consisting of:

1) a sequence with at least 95 percent sequence identity to SEQ ID NO: 29, and exhibiting promoter activity;

2) a sequence comprising SEQ ID NO: 29; and 3) a fragment comprising at least 250 contiguous nucleotides of SEQ ID NO: 29 exhibiting promoter activity;

wherein said DNA molecule is operably linked to a heterologous transcribable polynucleotide molecule; and b) cultivating said transgenic plant, wherein the transcribable polynucleotide is expressed.

* * * * *

SEQUENCE LISTING

```
<160> NUMBER OF SEQ ID NOS: 212

<210> SEQ ID NO 1
<211> LENGTH: 2611
<212> TYPE: DNA
<213> ORGANISM: Cucumis melo

<400> SEQUENCE: 1

atctgaaagg aacacctagc aaggggctac tctacaagca tactaagtct acaaagctag      60

agttgtatgg ttatgcagaa gacctggaca aaagaagatc actcgctgct tttactttta     120

tcctaagagg aaatgtgatt ttatggaagt ttaacctata gcctgtagtg gcactattca     180

caacaaaagt aaagtttata gccatgactg aagttgttaa agaagtcgtc tggctaaaag     240

gactacttga agaacttggc ttcttttaac agtcagtaaa catcatgtgt gatagttaaa     300

gtgcaataca cttgtctaaa aatctgcaat atcacgaaag aactaagcat attgatgtga     360

agctatatgt cattagagaa gtcatagcaa agagaaaagt aacagtatca aaggttcaga     420

caaaagaaaa tgcagcagat atgttgacta aaatagttac taatgctaaa ctcgagcact     480

gcctacagtt gctcaaggta atagactact taaaagaata gaatcagaag aaatagtcat     540

tggtagcaat aaaattcaag gtggaggatt gttaaaaaga agagtgaatt ttattactta     600

aagaaaatct cggtgaaact cgaaagatct cgattcgaaa ctctattgct taagaacctg     660

gtgaagctcg agagatcttg atacaatccc agtgccctaa ctcttcaaca agctaagcaa     720

gttgtactgt ggggctcaat ctcggttcaa tctcgacgca cctgatgctt tgttccctgt     780

ctactcgatg aagaagcaat tacttctcag gacaactcgg tacccctaaa tacagatttt     840
```

-continued gagcttcgtg atcctacaac tgaaatcaaa tagaaaaact aataagttag ttagagtttg 900
ttatatttac tgccattaaa taactctgta atgtaaataa taaaccattt aactcaatat 960
gaaatataga atgagaaaaa gaaaaagaaa aagttaaaga gagagaggaa gaaaactcat 1020
tttcaaattc tctatacttg tttgatcctt gaataagttg aataaaagct ctatggcggc 1080
ttcaaagtgg atgtaggcac tattagtcga accacaataa atttgttatg ttcttttgct 1140
attccttgta atctccataa atattttctt actaagctct agaaatctgc ttgtcaagag 1200
attaggtatc atttatgcct tttatatttc ctttcggttg catatcttga gctagttaag 1260
atcgagaggt tactgttgtt gaaaccgaga ttagtatctt tggattaaca cgtgcctacc 1320
aaaatttgaa attttgtatt taccccattc attggataat aagcaattct tatagtgtta 1380
tcaattaaac tcctataaag tgtaataatt gaatccatga actattttca tatgtaatct 1440
taataaaatg aatttagaag tttaattaaa ataatatatt ttgtatgcta tttttcaaag 1500
tttgaagaat gtgttaattg atacacatac aaaaaatcta ggttttacat gaaaaactat 1560
ggaagtgaaa gatagcatct aatattttat gacacaaaat gcaaactaat atataaagga 1620
tttaattaat ttttataggt ttcaaatttg ttagacttgt caaatacaaa attttattga 1680
accaaataca tacaaacatc aaaattaaga acagaaaatc taaattcaaa tgaaatttat 1740
taatagaaaa attagaaaaa agaaaaagaa aataaaagga atcgtattgt tttttccttc 1800
ctttttccca tttgagaggt gaataaagct aattgagctg ctctaacttc ctaatcttta 1860
tgctttcccc ataaagcttt cccaactgcg cgtaatcgta taaatggaaa attgaccttt 1920
ccaactagat tcttccagaa ctaaacaata cgtaacacgc aagtaatcaa agacacgttt 1980
cattttccta tagaatatta tagttattcg tgattaacgg aagtcggcaa ttttaggtat 2040
aaatacgtga attctcgagc gctaatttc catacagact cgaaatactc taaactttct 2100
catcgcgctt tattcctatt tcgtaattcg ctcttcttca acctctcaag gttttcatct 2160
tttctctatc ttctgtttc agattgcatc ttttccccct cctgttcgat taattgatgt 2220 ttgaatttc gagaaacgat ttgaagtctt tgttgtattt ttcatttctg ttcgttaggt 2280
aggtcgattt ttaatcgtga tgtccgacgt tgttcggatg attcacattt ggtttttgtc 2340
atcttctttc tatgttgtga ttatcatgat ttttatcttt ttttcttctc aagatttgta 2400
atttatcgat tccccatggt tcttggtttt ttatacatgt attgaatctg gttactagaa 2460
ttatgttctt cgacggacgt ctttcagatt taaattgcat tgtaggaaat atgatttgct 2520
atctgagtaa cgtttttcca gagtattctt gattgcgcga tctatcttca attgttaaat 2580
tgtttttgtt taattggggt catgacaggt g 2611

<210> SEQ ID NO 2
<211> LENGTH: 2068
<212> TYPE: DNA
<213> ORGANISM: Cucumis melo

<400> SEQUENCE: 2
atctgaaagg aacacctagc aaggggctac tctacaagca tactaagtct acaaagctag 60
agttgtatgg ttatgcagaa gacctggaca aaagaagatc actcgctgct tttactttta 120
tcctaagagg aaatgtgatt ttatggaagt ttaacctata gcctgtagtg gcactattca 180
caacaaaagt aaagtttata gccatgactg aagttgttaa agaagtcgtc tggctaaaag 240
gactacttga agaacttggc ttcttttaac agtcagtaaa catcatgtgt gatagttaaa 300

-continued

```
gtgcaataca cttgtctaaa aatctgcaat atcacgaaag aactaagcat attgatgtga    360

agctatatgt cattagagaa gtcatagcaa agagaaaagt aacagtatca aaggttcaga    420

caaaagaaaa tgcagcagat atgttgacta aaatagttac taatgctaaa ctcgagcact    480

gcctacagtt gctcaaggta atagactact taaaagaata gaatcagaag aaatagtcat    540

tggtagcaat aaaattcaag gtggaggatt gttaaaaaga agagtgaatt ttattactta    600

aagaaaatct cggtgaaact cgaaagatct cgattcgaaa ctctattgct taagaacctg    660

gtgaagctcg agagatcttg atacaatccc agtgccctaa ctcttcaaca agctaagcaa    720

gttgtactgt ggggctcaat ctcggttcaa tctcgacgca cctgatgctt tgttccctgt    780

ctactcgatg aagaagcaat tacttctcag gacaactcgg taccccctaaa tacagatttt    840

gagcttcgtg atcctacaac tgaaatcaaa tagaaaaact aataagttag ttagagtttg    900

ttatatttac tgccattaaa taactctgta atgtaaataa taaaccattt aactcaatat    960

gaaatataga atgagaaaaa gaaaaagaaa aagttaaaga gagagaggaa gaaaactcat   1020

tttcaaattc tctatacttg tttgatcctt gaataagttg aataaaagct ctatggcggc   1080

ttcaaagtgg atgtaggcac tattagtcga accacaataa atttgttatg ttcttttgct   1140

attccttgta atctccataa atattttctt actaagctct agaaatctgc ttgtcaagag   1200

attaggtatc atttatgcct tttatatttc ctttcggttg catatcttga gctagttaag   1260

atcgagaggt tactgttgtt gaaaccgaga ttagtatctt tggattaaca cgtgcctacc   1320

aaaatttgaa attttgtatt taccccattc attggataat aagcaattct tatagtgtta   1380

tcaattaaac tcctataaag tgtaataatt gaatccatga actattttca tatgtaatct   1440

taataaaatg aatttagaag tttaattaaa ataatatatt ttgtatgcta tttttcaaag   1500

tttgaagaat gtgttaattg atacacatac aaaaaatcta ggttttacat gaaaaactat   1560

ggaagtgaaa gatagcatct aatattttat gacacaaaat gcaaactaat atataaagga   1620

tttaattaat ttttataggt ttcaaatttg ttagacttgt caaatacaaa attttattga   1680

accaaataca tacaaacatc aaaattaaga acagaaaatc taaattcaaa tgaaatttat   1740

taatagaaaa attagaaaaa agaaaaagaa aataaaagga atcgtattgt tttttccttc   1800

ctttttccca tttgagaggt gaataaagct aattgagctg ctctaacttc ctaatcttta   1860

tgctttcccc ataaagcttt cccaactgcg cgtaatcgta taaatggaaa attgaccttt   1920

ccaactagat tcttccagaa ctaaacaata cgtaacacgc aagtaatcaa agacacgttt   1980

cattttccta tagaatatta tagttattcg tgattaacgg aagtcggcaa ttttaggtat   2040

aaatacgtga attctcgagc gctaattt                                       2068
```

<210> SEQ ID NO 3
<211> LENGTH: 82
<212> TYPE: DNA
<213> ORGANISM: Cucumis melo

<400> SEQUENCE: 3

```
tccatacaga ctcgaaatac tctaaacttt ctcatcgcgc tttattccta tttcgtaatt     60

cgctcttctt caacctctca ag                                               82
```

<210> SEQ ID NO 4
<211> LENGTH: 461
<212> TYPE: DNA
<213> ORGANISM: Cucumis melo

<400> SEQUENCE: 4

```
gttttcatct tttctctatc ttctgttttc agattgcatc ttttcccct cctgttcgat     60

taattgatgt ttgaattttc gagaaacgat ttgaagtctt tgttgtattt ttcatttctg   120

ttcgttaggt aggtcgattt ttaatcgtga tgtccgacgt tgttcggatg attcacattt   180

ggtttttgtc atcttctttc tatgttgtga ttatcatgat ttttatcttt ttttcttctc   240

aagatttgta atttatcgat tccccatggt tcttggtttt ttatacatgt attgaatctg   300

gttactagaa ttatgttctt cgacggacgt ctttcagatt taaattgcat tgtaggaaat   360

atgatttgct atctgagtaa cgtttttcca gagtattctt gattgcgcga tctatcttca   420

attgttaaat tgtttttgtt taattggggt catgacaggt g                       461
```

<210> SEQ ID NO 5
<211> LENGTH: 2002
<212> TYPE: DNA
<213> ORGANISM: Cucumis melo

<400> SEQUENCE: 5

```
tcggtgaaac tcgaaagatc tcgattcgaa actctattgc ttaagaacct ggtgaagctc     60

gagagatctt gatacaatcc cagtgcccta actcttcaac aagctaagca agttgtactg   120

tggggctcaa tctcggttca atctcgacgc acctgatgct ttgttccctg tctactcgat   180

gaagaagcaa ttacttctca ggacaactcg gtacccctaa atacagattt tgagcttcgt   240

gatcctacaa ctgaaatcaa atagaaaaac taataagtta gttagagttt gttatattta   300

ctgccattaa ataactctgt aatgtaaata ataaaccatt taactcaata tgaaatatag   360

aatgagaaaa agaaaaagaa aaagttaaag agagagagga agaaaactca ttttcaaatt   420

ctctatactt gtttgatcct tgaataagtt gaataaaagc tctatggcgg cttcaaagtg   480

gatgtaggca ctattagtcg aaccacaata aatttgttat gttcttttgc tattccttgt   540

aatctccata aatatttctt tactaagctc tagaaatctg cttgtcaaga gattaggtat   600

catttatgcc ttttatattt cctttcggtt gcatatcttg agctagttaa gatcgagagg   660

ttactgttgt tgaaaccgag attagtatct ttggattaac acgtgcctac caaaatttga   720

aattttgtat ttaccccatt cattggataa taagcaattc ttatagtgtt atcaattaaa   780

ctcctataaa gtgtaataat tgaatccatg aactattttc atatgtaatc ttaataaaat   840

gaatttagaa gtttaattaa aataatatat tttgtatgct atttttcaaa gtttgaagaa   900

tgtgttaatt gatacacata caaaaaatct aggttttaca tgaaaaacta tggaagtgaa   960

agatagcatc taatatttta tgacacaaaa tgcaaactaa tatataaagg atttaattaa  1020

tttttatagg tttcaaattt gttagacttg tcaaatacaa aattttattg aaccaaatac  1080

atacaaacat caaaattaag aacagaaaat ctaaattcaa atgaaattta ttaatagaaa  1140

aattagaaaa aagaaaaaga aaataaaagg aatcgtattg tttttttcctt cctttttccc  1200

atttgagagg tgaataaagc taattgagct gctctaactt cctaatcttt atgctttccc  1260

cataaagctt tcccaactgc gcgtaatcgt ataaatggaa aattgacctt tccaactaga  1320

ttcttccaga actaaacaat acgtaacacg caagtaatca aagacacgtt tcattttcct  1380

atagaatatt atagttattc gtgattaacg gaagtcggca attttaggta taaatacgtg  1440

aattctcgag cgctaatttt ccatacagac tcgaaatact ctaaactttc tcatcgcgct  1500

ttattcctat ttcgtaattc gctcttcttc aacctctcaa ggttttcatc ttttctctat  1560

cttctgtttt cagattgcat cttttccccc tcctgttcga ttaattgatg tttgaatttt  1620
```

-continued

```
cgagaaacga tttgaagtct ttgttgtatt tttcatttct gttcgttagg taggtcgatt   1680

tttaatcgtg atgtccgacg ttgttcggat gattcacatt tggtttttgt catcttcttt   1740

ctatgttgtg attatcatga tttttatctt tttttcttct caagatttgt aatttatcga   1800

ttccccatgg ttcttggttt tttatacatg tattgaatct ggttactaga attatgttct   1860

tcgacggacg tctttcagat ttaaattgca ttgtaggaaa tatgatttgc tatctgagta   1920

acgtttttcc agagtattct tgattgcgcg atctatcttc aattgttaaa ttgtttttgt   1980

ttaattgggg tcatgacagg tg                                            2002
```

<210> SEQ ID NO 6
<211> LENGTH: 1459
<212> TYPE: DNA
<213> ORGANISM: Cucumis melo

<400> SEQUENCE: 6

```
tcggtgaaac tcgaaagatc tcgattcgaa actctattgc ttaagaacct ggtgaagctc     60

gagagatctt gatacaatcc cagtgcccta actcttcaac aagctaagca agttgtactg    120

tggggctcaa tctcggttca atctcgacgc acctgatgct ttgttccctg tctactcgat    180

gaagaagcaa ttacttctca ggacaactcg gtacccctaa atacagattt tgagcttcgt    240

gatcctacaa ctgaaatcaa atagaaaaac taataagtta gttagagttt gttatattta    300

ctgccattaa ataactctgt aatgtaaata ataaaccatt taactcaata tgaaatatag    360

aatgagaaaa agaaaaagaa aaagttaaag agagagagga agaaaactca ttttcaaatt    420

ctctatactt gtttgatcct tgaataagtt gaataaaagc tctatggcgg cttcaaagtg    480

gatgtaggca ctattagtcg aaccacaata aatttgttat gttcttttgc tattccttgt    540

aatctccata aatattttct tactaagctc tagaaatctg cttgtcaaga gattaggtat    600

catttatgcc ttttatattt cctttcggtt gcatatcttg agctagttaa gatcgagagg    660

ttactgttgt tgaaaccgag attagtatct ttggattaac acgtgcctac caaaatttga    720

aattttgtat ttaccccatt cattggataa taagcaattc ttatagtgtt atcaattaaa    780

ctcctataaa gtgtaataat tgaatccatg aactattttc atatgtaatc ttaataaaat    840

gaatttagaa gtttaattaa aataatatat tttgtatgct atttttcaaa gtttgaagaa    900

tgtgttaatt gatacacata caaaaaatct aggttttaca tgaaaaacta tggaagtgaa    960

agatagcatc taatatttta tgacacaaaa tgcaaactaa tatataaagg atttaattaa   1020

tttttatagg tttcaaattt gttagacttg tcaaatacaa aattttattg aaccaaatac   1080

atacaaacat caaaattaag aacagaaaat ctaaattcaa atgaaattta ttaatagaaa   1140

aattagaaaa aagaaaaaga aaataaaagg aatcgtattg ttttttcctt ccttttttccc   1200

atttgagagg tgaataaagc taattgagct gctctaactt cctaatcttt atgctttccc   1260

cataaagctt tcccaactgc gcgtaatcgt ataaatggaa aattgacctt tccaactaga   1320

ttcttccaga actaaacaat acgtaacacg caagtaatca aagacacgtt tcattttcct   1380

atagaatatt atagttattc gtgattaacg gaagtcggca attttaggta taaatacgtg   1440

aattctcgag cgctaattt                                                1459
```

<210> SEQ ID NO 7
<211> LENGTH: 1507
<212> TYPE: DNA
<213> ORGANISM: Cucumis melo

<400> SEQUENCE: 7

-continued agtcgaacca caataaattt gttatgttct tttgctattc cttgtaatct ccataaatat 60
tttcttacta agctctagaa atctgcttgt caagagatta ggtatcattt atgcctttta 120
tatttccttt cggttgcata tcttgagcta gttaagatcg agaggttact gttgttgaaa 180
ccgagattag tatctttgga ttaacacgtg cctaccaaaa tttgaaattt tgtatttacc 240
ccattcattg gataataagc aattcttata gtgttatcaa ttaaactcct ataaagtgta 300
ataattgaat ccatgaacta ttttcatatg taatcttaat aaaatgaatt tagaagttta 360
attaaaataa tatattttgt atgctatttt tcaaagtttg aagaatgtgt taattgatac 420
acatacaaaa aatctaggtt ttacatgaaa aactatggaa gtgaaagata gcatctaata 480
ttttatgaca caaaatgcaa actaatatat aaaggattta attaattttt ataggtttca 540
aatttgttag acttgtcaaa tacaaaattt tattgaacca aatacataca aacatcaaaa 600
ttaagaacag aaaatctaaa ttcaaatgaa atttattaat agaaaaatta gaaaaaagaa 660
aaagaaaata aaaggaatcg tattgttttt tccttccttt ttcccatttg agaggtgaat 720
aaagctaatt gagctgctct aacttcctaa tctttatgct ttccccataa agctttccca 780
actgcgcgta atcgtataaa tggaaaattg acctttccaa ctagattctt ccagaactaa 840
acaatacgta acacgcaagt aatcaaagac acgtttcatt ttcctataga atattatagt 900
tattcgtgat taacggaagt cggcaatttt aggtataaat acgtgaattc tcgagcgcta 960
attttccata cagactcgaa atactctaaa ctttctcatc gcgctttatt cctatttcgt 1020
aattcgctct tcttcaacct ctcaaggttt tcatcttttc tctatcttct gttttcagat 1080
tgcatctttt ccccctcctg ttcgattaat tgatgtttga attttcgaga aacgatttga 1140
agtctttgtt gtatttttca tttctgttcg ttaggtaggt cgatttttaa tcgtgatgtc 1200
cgacgttgtt cggatgattc acatttggtt tttgtcatct tctttctatg ttgtgattat 1260
catgattttt atcttttttt cttctcaaga tttgtaattt atcgattccc catggttctt 1320
ggttttttat acatgtattg aatctggtta ctagaattat gttcttcgac ggacgtcttt 1380
cagatttaaa ttgcattgta ggaaatatga tttgctatct gagtaacgtt tttccagagt 1440
attcttgatt gcgcgatcta tcttcaattg ttaaattgtt tttgtttaat tggggtcatg 1500
acaggtg 1507

<210> SEQ ID NO 8
<211> LENGTH: 964
<212> TYPE: DNA
<213> ORGANISM: Cucumis melo

<400> SEQUENCE: 8
agtcgaacca caataaattt gttatgttct tttgctattc cttgtaatct ccataaatat 60
tttcttacta agctctagaa atctgcttgt caagagatta ggtatcattt atgcctttta 120
tatttccttt cggttgcata tcttgagcta gttaagatcg agaggttact gttgttgaaa 180
ccgagattag tatctttgga ttaacacgtg cctaccaaaa tttgaaattt tgtatttacc 240
ccattcattg gataataagc aattcttata gtgttatcaa ttaaactcct ataaagtgta 300
ataattgaat ccatgaacta ttttcatatg taatcttaat aaaatgaatt tagaagttta 360
attaaaataa tatattttgt atgctatttt tcaaagtttg aagaatgtgt taattgatac 420
acatacaaaa aatctaggtt ttacatgaaa aactatggaa gtgaaagata gcatctaata 480
ttttatgaca caaaatgcaa actaatatat aaaggattta attaattttt ataggtttca 540

-continued aatttgttag acttgtcaaa tacaaaattt tattgaacca aatacataca aacatcaaaa 600
ttaagaacag aaaatctaaa ttcaaatgaa atttattaat agaaaaatta gaaaaaagaa 660
aaagaaaata aaaggaatcg tattgttttt tccttccttt ttcccatttg agaggtgaat 720
aaagctaatt gagctgctct aacttcctaa tctttatgct ttccccataa agctttccca 780
actgcgcgta atcgtataaa tggaaaattg acctttccaa ctagattctt ccagaactaa 840
acaatacgta acacgcaagt aatcaaagac acgtttcatt ttcctataga atattatagt 900
tattcgtgat taacggaagt cggcaatttt aggtataaat acgtgaattc tcgagcgcta 960
attt 964

<210> SEQ ID NO 9
<211> LENGTH: 1022
<212> TYPE: DNA
<213> ORGANISM: Cucumis melo

<400> SEQUENCE: 9
tgacacaaaa tgcaaactaa tatataaagg atttaattaa tttttatagg tttcaaattt 60
gttagacttg tcaaatacaa aattttattg aaccaaatac atacaaacat caaaattaag 120
aacagaaaat ctaaattcaa atgaaattta ttaatagaaa aattagaaaa aagaaaaaga 180
aaataaaagg aatcgtattg tttttttcctt cctttttccc atttgagagg tgaataaagc 240
taattgagct gctctaactt cctaatcttt atgctttccc cataaagctt tcccaactgc 300
gcgtaatcgt ataaatggaa aattgacctt tccaactaga ttcttccaga actaaacaat 360
acgtaacacg caagtaatca aagacacgtt tcattttcct atagaatatt atagttattc 420
gtgattaacg gaagtcggca attttaggta taaatacgtg aattctcgag cgctaatttt 480
ccatacagac tcgaaatact ctaaactttc tcatcgcgct ttattcctat ttcgtaattc 540
gctcttcttc aacctctcaa ggttttcatc ttttctctat cttctgtttt cagattgcat 600
cttttccccc tcctgttcga ttaattgatg tttgaatttt cgagaaacga tttgaagtct 660
ttgttgtatt tttcatttct gttcgttagg taggtcgatt tttaatcgtg atgtccgacg 720
ttgttcggat gattcacatt tggtttttgt catcttcttt ctatgttgtg attatcatga 780
tttttatctt tttttcttct caagatttgt aatttatcga ttccccatgg ttcttggttt 840
tttatacatg tattgaatct ggttactaga attatgttct tcgacggacg tctttcagat 900
ttaaattgca ttgtaggaaa tatgatttgc tatctgagta acgtttttcc agagtattct 960
tgattgcgcg atctatcttc aattgttaaa ttgtttttgt ttaattgggg tcatgacagg 1020
tg 1022

<210> SEQ ID NO 10
<211> LENGTH: 479
<212> TYPE: DNA
<213> ORGANISM: Cucumis melo

<400> SEQUENCE: 10
tgacacaaaa tgcaaactaa tatataaagg atttaattaa tttttatagg tttcaaattt 60
gttagacttg tcaaatacaa aattttattg aaccaaatac atacaaacat caaaattaag 120
aacagaaaat ctaaattcaa atgaaattta ttaatagaaa aattagaaaa aagaaaaaga 180
aaataaaagg aatcgtattg tttttttcctt cctttttccc atttgagagg tgaataaagc 240
taattgagct gctctaactt cctaatcttt atgctttccc cataaagctt tcccaactgc 300
gcgtaatcgt ataaatggaa aattgacctt tccaactaga ttcttccaga actaaacaat 360
acgtaacacg caagtaatca aagacacgtt tcattttcct atagaatatt atagttattc 420
gtgattaacg gaagtcggca attttaggta taaatacgtg aattctcgag cgctaattt 479

<210> SEQ ID NO 11
<211> LENGTH: 716
<212> TYPE: DNA
<213> ORGANISM: Cucumis melo

<400> SEQUENCE: 11
tcgtataaat ggaaaattga cctttccaac tagattcttc cagaactaaa caatacgtaa 60
cacgcaagta atcaaagaca cgtttcattt tcctatagaa tattatagtt attcgtgatt 120
aacggaagtc ggcaatttta ggtataaata cgtgaattct cgagcgctaa ttttccatac 180
agactcgaaa tactctaaac tttctcatcg cgctttattc ctatttcgta attcgctctt 240
cttcaacctc tcaaggtttt catcttttct ctatcttctg ttttcagatt gcatcttttc 300
cccctcctgt tcgattaatt gatgtttgaa ttttcgagaa acgatttgaa gtctttgttg 360
tatttttcat ttctgttcgt taggtaggtc gatttttaat cgtgatgtcc gacgttgttc 420
ggatgattca catttggttt ttgtcatctt ctttctatgt tgtgattatc atgattttta 480
tctttttttc ttctcaagat ttgtaattta tcgattcccc atggttcttg gtttttttata 540 catgtattga atctggttac tagaattatg ttcttcgacg gacgtctttc agatttaaat 600
tgcattgtag gaaatatgat ttgctatctg agtaacgttt ttccagagta ttcttgattg 660
cgcgatctat cttcaattgt taaattgttt ttgtttaatt ggggtcatga caggtg 716

<210> SEQ ID NO 12
<211> LENGTH: 173
<212> TYPE: DNA
<213> ORGANISM: Cucumis melo

<400> SEQUENCE: 12
tcgtataaat ggaaaattga cctttccaac tagattcttc cagaactaaa caatacgtaa 60
cacgcaagta atcaaagaca cgtttcattt tcctatagaa tattatagtt attcgtgatt 120
aacggaagtc ggcaatttta ggtataaata cgtgaattct cgagcgctaa ttt 173

<210> SEQ ID NO 13
<211> LENGTH: 2000
<212> TYPE: DNA
<213> ORGANISM: Cucumis melo

<400> SEQUENCE: 13
cttattcagc gctttcctgt aaaattaaag acttgatgag ggagaaaaag aaaaccggtt 60
cgcagcttca agaagacggc ttccgaataa gaatcagata ctcgatgatg gggaaacaat 120
aacaaagata tcaaaagaaa tcatgaaaca tagcataaga acgaaaaccc agaggtgaag 180
aacagtgccc aaacgcaact ttacccaaag aacatgtata aaacgtcttc cagacgttca 240
aaataagaaa gtggacaaaa tcaaagctac aaacgatctc caataactag atggaaaaca 300
ctaattgcac tagagatttt gaatgctttg ttgttgattt ataatcctcg acttccaaga 360
aaaagtaaca agtagaaatg aacgaatcag atccgcaatc gaagatctga aggcaagata 420
aggtaaggct aaagaaccat aggaaaacgg taaaaacgtc caaaacagtg tgagaaatat 480
cgcagattca aaggtccgaa ccctaagaac ggtgttatgc agctataaag gtgagaatca 540
aaaccctcta tccataacgt ggacggcgcg gttgaatcat tgtcttgttc cttgaaactg 600

-continued

```
aaggtatgcg agacatagaa ttcgatctca ctattatctt ctaatcaacg acgaagtaaa    660
gaagtgaaat ccagaacaaa gaatggagaa ttggaaatga caagaaaaac ggcagaggaa    720
agtggaaaag tgaaagcgga ctcacctaga tcaatgccct tggctggtcg agcttcagga    780
acctgtcgtc ggagagaaag agaaagagaa aagagcaaga gagagagaga gagagcacaa    840
ggagaagaga acgaggacaa tggaggcttt tgtttcgata ctccctgatc tggaattcta    900
taataacata actataaact tctctgggtt ggcccatcat cacgtatatt gggcttttag    960
cccaattatt tgttcactgc tcatgggccg gtgattttgg gctttcttct gggccttggt   1020
acataacaac ccagtatatg acgtattttc ggtgatagct attttcaaga acaccaactt   1080
ttttgttcaa caatgtggag atcaaataac agtatgtata tatacacaaa catatgctca   1140
tttatgaaaa atagaaagaa aaagaatgtt ggtaatttgt tacaaaatta taatttctct   1200
ctctttgttt gatttcatga acggtgtgtt ctatataaaa caatgaaata acataattat   1260
taaaatgatt cttaaaacat gatgatttca atattcatgg tttacatttg gtgggatgat   1320
tcgtttaatt attattgata atgtatagtt attgtgtgtc ccgttttctt tttctttggt   1380
ggaagaaaag aaaaaagtag gaaggcatgt aatattgcga tccttcacgg gacagatcca   1440
ttttccaatg tgatcgagta ctagttaggt ggagagtgga agaatcttcg tgcatgcata   1500
aatcaagtca caacttgcca atttggaaag aatcatgtta tattctacct ttactttcaa   1560
gtagggttaa gtgaattaga ccacaacgaa gcaatcaagt ccaaccaaac tcacttaggt   1620
caagcagttt agtgatatag acaggtcagt ggtcgttttt ttaatactaa gaaatgtcaa   1680
ttctatctag ttgactatta ttcatataga aggagaaaaa tgataactat gattgtccca   1740
caaacaacaa ctaccgatcg atctaaacca acaagtcgat gattggtgcc actttaaatt   1800
taaatctgac gccactcaat tgatgatcac ccctattcaa gcacacaaga acgcatgctc   1860
ttaaaacatt tggtaatatg attggaatta gtacaaaatg tttattcgat ctatacaaac   1920
aactcctttt taacacaaat gttttattgt actttcccgt gaaatggggt tagtaaaact   1980
atggagttaa taaaacataa                                                2000
```

<210> SEQ ID NO 14
<211> LENGTH: 2000
<212> TYPE: DNA
<213> ORGANISM: Cucumis melo

<400> SEQUENCE: 14

```
tataacaaaa tatgtgaaat tagccattat gtttgtcctt tcgttcttct tattcacttc     60
gttgcgattt ctttctatcg tctatcgtct ttcttctttt ttctgttgaa atttattttc    120
atcgtttttc ttctttttcc atcgtgaaaa aaatagtcaa atctaaatga tcgtgtataa    180
agaataaacg atcgtgtaga caaatctaaa tggtcgaata ttaagaaaat tgataggaaa    240
atttattcat tagaaaaatt ttagtaagaa aaattagaaa tgaaagggtt gaaccagaaa    300
gaaataaaag taatagacaa atgaaaattt taaataaaaa gaaatttggg atgggtgcat    360
ttactattta gtcttgagtt ttaattcttt tattacttta cataagatgt attaaattaa    420
agaggtaaga tagaattttt ttttaaaaaa aactatcatt agtaaattta acaaaagtga    480
catagcacca ttttcgttaa aagaataatt gttttatgta gtaaaattgg tagaaatatt    540
ttttaagtat agcaaaatat ctttgtcttt ttatatcttt cactgacaga taataataat    600
ttattaatat atcatttata tagtcccatt ttcggtaaat tttaatattt gaacataaaa    660
cactatttaa aataatgaaa aaaaacttta caaacttttt tatttttatt atatttgtaa    720
```

```
atatttctaa aaaattttac atttaaaata atattttcaa ggttaataca gaagaaaaaa    780
aacaaaaaaa gaggaaaagg caatttaaga agaatgacaa gaaaatcggg aggtggtgtg    840
gctaagagga agaagggacc ggttcttcaa gatccaacgc tccacattca atctcacttc    900
cttcttcaat tccgtcttct ccgtttcctc ctttatatgc ttctctcttt ccctcccttt    960
ctttctctcc ttcaatcaat caatcaatca atcaatcaat cctcccattc ccattacatt   1020
gccaaaaggt tctattctca ttctctacat ccatttccct ttctttcctt cttcttcctc   1080
tgtttcttct tcgtttcctt gattcatttc tctttgtacg ttccttcctt ccttctgcat   1140
tttgattatt ttcttttgtt ttacgtccgg aattgcaatg tggtttatct ttatttctgt   1200
ttttggacgt caagatgcct gttgttttta acattttgat ttgattcatc gttcatggcg   1260
taatcatgtc ttttggaatt gtttgaaatc caaggatcac attgatttca ctattgtttc   1320
atttgttctt ttttgttaat tttgtataat gaatcgtata ggggatcatt tttccattgg   1380
ttctcttgaa aatctttaag agttgcatta tgtatactaa gtctctctta tggcgtctgt   1440
ttgagtgaga attgataaaa gatccatggg aggaagaagt tttctttcat gaggcttggt   1500
tttattcagc tgtttcttct cgttgcaatt tgttgaagaa gggacatggg tatcttttac   1560
atcaaagtat aactaactat ataattcaat ttggttgata aagtagatac atgtaggagt   1620
caaccgattt gagtgtataa taatgttgtt atgtcccttg caacttaatg tagtgcatat   1680
ttgggagtga ttataaaatt gtataaatca ttttatgttt agaatcatct tgaaacacgt   1740
tttttagtat ttaaaaacta atttaatatt tagttttgca cttttaaatg aaatttttgt   1800
ttcactaata ttagttttga ttcattaaat gcatgctcca tcgtaatatt aaaagtaact   1860
agtgatttta accattttat aatcacatgt ctgtgatata gtgaagtgta cggctgcctt   1920
gttgagaatt gttacccttt agaagaaaca caggatgtat ttgatgttta acttgcattt   1980
tcttctggca ggcttagaaa                                                2000
```

<210> SEQ ID NO 15
<211> LENGTH: 1990
<212> TYPE: DNA
<213> ORGANISM: Cucumis melo

<400> SEQUENCE: 15

```
tatttgtaca atgaaaatat ttatttcttt tctcgattct ttaacaaaag ttcaaaatct     60
tttatcataa atacaaatat ttagtaattt aagtttagac taggtgtatc agatgtgcac    120
caagtgtata ttacgtgcat caagtatata tcaaatgtgt accaaacgta tatcacgtgt    180
atcaagtgtg tatcaagtgt ctatttgaag tcaagtgcat taagaatata tcacatgtgt    240
accaaatata tcaaaataaa tactgattga gcatcaagta tgtctattag tagtgtatca    300
agtgtattaa ttaagtttgt agcaaaggtg tatcatgatg tataacgtgt attatgtggg    360
ttggtttttt tttttttttg tcatttttgc aaaagtaatt aagtttgtgt tatgaaccta    420
attttttaaa tttcttttttg tcacgtataa gagacttgaa aataggttta aaaggtctta    480
agggtatttt agtttgactt ttttaaaaag tatttatatg atatttaaaa attagaattt    540
tttagaaaga ataggagttt tataaattat tcttttaaga aaaattgcat cagatgacaa    600
aaaaaattta gaaataagca gcccataata actctttaaa tttgctatca gacgactatc    660
cgagggttat catcttttaa atttgctact tttacaattt agaaaatgta gtgacatgga    720
ccctattatc ataagatttt tttttgctat ttttgcaaac acatgttctt ttaaaatgac    780
```

-continued

```
ataattattt aaaataaaaa tataaagtta tttgatggat cttttgaacc tatttttaaa    840
agctaaagta ctaaaaagat acatattgaa aacttgaggt caaatgggct attattataa    900
atatgtggac taaaaatgta catttctaaa acttagagac taaatgcaca tatttaaaaa    960
agcatgtgaa ctaaaaaagt cgtttttcct aatatttttt tacaacaatg actaaattga   1020
acctcaaatt tgaagggtgg aaaaccatac taattattca ctaatgaact aaactcattt   1080
gatgatttca agacatatga ggttcattga gtagttgggt ttgaggggat gaaatgagtg   1140
gtggaagaaa gtttatgtaa cgacccaacg aaataggaag gtcatcccaa ggaagtcgca   1200
catccaatga gtaattacca caaaacaacc tctccttttt tctcaaattc ccttttaata   1260
aataatttga ttccccattc cttcctttct cccttggcag ccttctcctt ttttcaaagg   1320
tttttgtttt ttcttttctt ttttaaattt cattcctttg tttctctctt tctttcttca   1380
ttaacattct tcttatttcc tcattactga tcatctcctt ttcttggtat tattcttctt   1440
tcttttctca aagttttgtt tttcattgat gtagatgttt ttgtatcaat caatggaaat   1500
ttgagttttt cttatctcat tgtatcatca ttgagtgtgt gtttatgtta gggatccatt   1560
attaggatgg atgagaatca taatttcatt gctaatctat gaaccatgaa taaagaaatc   1620
taaatccaac atagaagata gaacatttgc attgtgttat gagtaaccag ctctgtcact   1680
tcaattggtt cttctacaca tttgatggca atggctttgt ttgatattcg tgatggcatc   1740
taagcattgg ttcttcctat gtttttcgtt ggctcttggt ttgatttgca attagtgaag   1800
agcatgtttg gaatgaatga gttgaaatca cctttaacat ttttaaaatc actttaaata   1860
ttaaattaat tttgagtgat aaaagtaatt ttaacaatga taaaattact ttcaaatgtg   1920
ggccgaatca aattgtctag aatgtttagg gttctccaac taatagcaat ttatccaaac   1980
agggtaaaaa                                                          1990
```

<210> SEQ ID NO 16
<211> LENGTH: 2005
<212> TYPE: DNA
<213> ORGANISM: Cucumis melo

<400> SEQUENCE: 16

```
ttgttagagg agttagcttt tcagggagtc ggttacaact tacaagacag acaaccatac     60
tgtacaatca atcactactg cctcaaagtc gaaaccattt aataccagtt gagcctcatt    120
gtgactgcat aattttgacc cctaccacga ggtaatttca gttcaaatca attgtatctc    180
tcttctggat atcagtcaag aatctcatgt tctcaagtta tagtacattg ataattactg    240
tgcattttta ttaatttatg agttaaaatc ctgctgatta attcaactaa aggaataaaa    300
tagttattgg catttggatg agaatagaat gtgaatccca tcattcatcg ctagattgga    360
ccgtaattat aagtgagagg gagaaacttc tgttgctatt cccttttttat ttcttaattc    420
atttataaat tgtttttagg ccttttatat atatatattt ctaccatttt tacatttaaa    480
attcttttaa ctttattatg tatggactca aactaacaag ctttatttga taaaattgtt    540
caaactatta tattagtttt atatttgtaa accataaaac aaatccataa aattccacct    600
gcatcactca ctcatgttgt tgaatggtac gaaataaaca atacatgtga aagatgaaaa    660
taagaattgt tctcttatta aatctaaaat ctagattttc tttttagtac atttaacact    720
tcaatgaaag gtctaaaaca ttattgaatg acgtcacgaa ctattacaaa agattattcc    780
gatttatctc aaaaggggtc tatttcacta attttggtgt cccacatctg taaagagaat    840
tttcgtgata tgtgtagata tttaaatata attgaattcg atgaaagcaa agcaagaatc    900
```

```
gatatccgta gttattttga tatagatcgg tgataaataa aagacaatat gcataaagtt    960
tgtgggtaca gagtcggcta gttgcaatga ggggtatggc cccaagactt ttccccaacc   1020
ccaacggtca attaatcacc ccaatggggc atcgaatctt ccccaccatt ttccttttct   1080
tcgccgactc ttctacccat ctcttttgcc gactctttct cacaggtttg attaaatccc   1140
attcatattc agatacacta tttcaaaata actcgcaaat taatttgttt tttaaatatt   1200
ggtataataa taaaattaat tataaattgt gacctaaaaa gtactttgtg gaagagggga   1260
tatagtctgt ctaatatatt attgattaaa tatataatag aaccataaat gcaaaccact   1320
agaattgtta ataaaaatca acgctctttt aagtctttcc atagaaagaa aggcaaagac   1380
gcgcaacgtc tagaatttc tttataacgg aagctaactc tgttataacg gccgtccaca   1440
taatatggta gatttaaaat gacgtcagca tgtcgcttct aaatttgggt ccaaaggggg   1500
gattcattta tagggaaggg aaacggcaaa tgcaagcata gtgagtaaat acgtggcggc   1560
aaagtaatgg ataattctgc ctctgccgtg acgacattgc ccttccattt cactataaat   1620
acacctcctc tatccctcga tttcttcgca attgaatttc tcttctcatc tctgtcgtag   1680
caaaccaaat cgatttcttc aaaggtattt cttcctttcc tttttttttt tttttttttt   1740
tttttaaatc atgttgttca aactttgaga gatgaaatga ttaggggctt tcaaagtggt   1800
tttcgtttga tatgtttctt agatcgatag ggtttagaat cgagcatcct tgtaggtatc   1860
ctgaggtttg gtggttggat ctgcttaatt tttatgtggt tgcatggaaa attgggattt   1920
ttttttctta attacgtgat tctggaaata ttgatctgtg gttcagatgg aattgaatct   1980
gatctttctg ttttgttctg tatag                                         2005
```

<210> SEQ ID NO 17
<211> LENGTH: 2004
<212> TYPE: DNA
<213> ORGANISM: Cucumis melo

<400> SEQUENCE: 17

```
tagaaaaaaa ttgaagatct tcttaatgct aataataaaa gcatatataa aaaggcttca     60
tattacacaa gcatcttaaa accaaaccga acttgatttg aaattatccc actaattctg    120
tagatttcac caaagtcctt aacctttata ctaacatctg catttgactc tttcatttga    180
cctccaacat attctttctc attttccttc cattcaccac aaaaaccaac aaatacaaaa    240
aaccacaaat acatagaaaa ttaataaaaa aatcaaaatt tcgagatgaa atcattataa    300
actcatccga taactttgag atttgaaacc ttacactata taaagaaact catccgataa    360
ctttgaattc gcatcgaaat tacgtaagtg aagacgaaaa tgtaaatgat tagatgcgaa    420
taacaaaaaa aacataattt ctaaacgtaa aacactatat tcaccttatt atacttgatt    480
attttggaaa agtatgaaat ttgagtgtgg gagaggagcc aaagaattgg aaacttgtta    540
ttaggagtcg ttatgaaaca ttttcaacaa gccaatattc tttcacatac tataatgata    600
tacatagaaa taatacaata atatttttga aattgaggca tttttgtcgt aatttatcta    660
aaaatgtcag ggtagattca tcatgtatac aaatctctcg ctatcaaaac tatataaaaa    720
tcttgtgaat gatttcaatc gaaatggacc gagaaaaaac atcgtaacca cctctaaaat    780
cgataaattt gtttcaattt caaatcccta aaactaaagg tgctactttg tacaatttcc    840
cctgattagg gtgctaaagt taaaccctaa ataaaggtgt gtacgtttcc ggaagtttct    900
agaatcccca gcgaagttct ccaaatcgtg gcttgcagac caaggacccc cattaaaatt    960
```

-continued

```
cgtttcttcc tctaaacctc ctcccttaat tttggcattt tggtattttg gctcctataa   1020

attcaccccc tccttatccc taatcctttg tcttccaaat tttccttcaa agcctgcttt   1080

tcccatttcg tcgtgctttt tcttcatcta aaggtatatt tcagttctag ttttctttct   1140

ctgttgatct cttggatttg agggacgttt gaagttggct ttgtttaatt ctttgttatt   1200

caatctcttt ttttgttaga gttgttgttt aatcgtttcc cttgttgttt ttctcccttc   1260

tagttcgatt ttagaacgct ttttgtgggt tgattttaat ttctccgttt tcttacatct   1320

ttcacaaaga aacgattgaa atcgtgtttg tttttttttcc cacggcatac gttattagat   1380

cttgtagata atgatctcaa tctattgttt agtttttgca aataagaagt tggtttttta   1440

tctccaactt ttatatattc gattcgatga gatgttctac accgttagga tggaaccaag   1500

aagtgaggta agggtgtttg attgaaaaat tgaactgaga agttaaagtt ccttcctaac   1560

tttttaatgg attgtataat tcgttcaatt ccttgtcgtt ccatttttat ttctgtttcg   1620

tttttcgtgt tgctgcgtat cgcttccctt gttgttttcc tcccctattg attttgcgtt   1680

tcttggagtt tctctgtttt ctctcttcat ttttctacaa aaatcaattc tatttttatt   1740

cgttttcaat tcccgagctc cttggaatgt tatccttttc tcctgtgtaa ataagaaccc   1800

gtattcaatc ccagttcata gtttggcttt cccaaataag agcaaaaaga ttgtactgag   1860

aagttgaaga tttcaaaatt ttgtacatga tttcttctaa tttatcaatt tgattggact   1920

ttttgtatat agatttggtt cttgagctat ttatgttatg acgttttcat attgaggcca   1980

tgcgttgaat tggtttctta acag                                          2004
```

<210> SEQ ID NO 18
<211> LENGTH: 1935
<212> TYPE: DNA
<213> ORGANISM: Cucumis melo

<400> SEQUENCE: 18

```
tatacaaatg acaaaatatc gttgaagtcc aaaaaagatt tattgttggt aaatatcgtt     60

aaagttagta aatagatttt agagaaagga gatatagccc ttgtagtaga aacacacaca    120

caaattgaat tagatgtgtt taatgtttaa ttaaattaga tatgagtcaa cttatatcta    180

atataggaca ttattaaaca aataagaaat aagaaacatg aaacaagaaa aacaagaaat    240

agaaacaata tcaaacacat tcctatttct tgttctaaaa aaagaaaaaa catggtacaa    300

gaaataggaa acggaaaaga ggaaacaagg aacaaatgct accaaacggg cctaagtttc    360

taacaaaatg agctaggtgt agtttattgg tatagatagt gactttcaat tattttaaat    420

ttttttatcc atacctccac gtctttagaa tctttcttat ttatatgtga tcttaattca    480

ttcatgtctc aatcttaaaa ttagaacatt acatgttcat catttttttcc ttttgttact    540

gtgtttaatc tttcctaaca agacaaatag tttaacctta atccacacat tattataacc    600

aaattaaaat aatctacctt caaagaaaac attattataa tcttatatta accacaaatt    660

ataataccaa actctaacgc tccaacccaa cctaggaaga atgacaaggc tgtcataatt    720

tagttggttt ggcacgttgt tggaagttct caaaattatg gaaatattta tttccttctt    780

ctttatccat catcctcctt gggagggtga atttgtgtta aaaaagaata gaaactaaag    840

tctaagtggc aggacttaca ttatgtgtgt atgtggaagt aaaattgcag taacagttta    900

caaaaacaac tcatccatga ttcataacca acttaaatga atataatttt ttgcctaaag    960

attttaaatt aatatataag cggaagaatt aacctataac ttcaagttta acaacacaaa   1020

tattatatca tactgattaa ttattggaat gatgtttagg ctttaaacat aaagtattga   1080
```

```
gaggctaatt tgagtttaac tcactaaact atcattaccc tttcaaaata gatccaatca   1140
tccatttatt ataatactca atgaaataaa gcaaaagatg agtaaaataa ttcaccatga   1200
acattgataa ttaattttcc cactaagata aactactact cctcaaatct tcatatgtgt   1260
ttttcctttt tgagttgcac tcaaattttc atagttgaaa tttacccatc aaaacaacca   1320
acaatctttc aaattcaaca aacatttgac cttacaccct ttgatgccaa atccttaccc   1380
tctccctctt ccataaaaat tcttatataa accaccatca ctctcacttc tcaattcact   1440
ctcttctcta ctcccaatca cctgacttgc ctcttactcc accgccaggt tccgccccaa   1500
cttccccggt aagttccagt tcttcagatc tggttaccac atttgatttc ttgcttgtat   1560
ttgacgtggg aattttcata tcggcgtttt ttcgaactgg gttttgcttt atgatcatat   1620
tcttgtagta aaatgccatg aatctgttat ttgattccgt ttttttgga gatcggtcta   1680
gctttatggc catattctgg catttaaatg ccatgaatcc gtgatttggt tgaatttcac   1740
ttccgatcca atgtttatgc tgatattgac atctttgcat tcaatgcaga ggagttttgt   1800
ttcgatttat tactgatctc atcacactga tcttgaattt tttatacttt tatgtgtgtg   1860
tgtgtatttt ctttaatatc tatgccaatt gaactatgtg gttaacttca gagtgttctt   1920
gtgggcagtg agaag                                                     1935
```

<210> SEQ ID NO 19
<211> LENGTH: 1606
<212> TYPE: DNA
<213> ORGANISM: Cucumis melo

<400> SEQUENCE: 19

```
atatattgta tcgattcttt agttgctcta tgtttttgtt tgcttcattt gtcgattaaa     60
ctgtaaaatt aatttctttg acaaggaaaa agatataatt taattctata atttattaca    120
atctaatcca tatggtttaa taaaacactg aaaattgttt atgaaaattt tatcgaacta    180
caagaactat taataaagtt tttttaaacc gtaaattgaa tgaattttct ccacggtgta    240
aatttgaaaa cattaattaa ttaattaatt aattttaatt tcaaggtttt ttctgaccca    300
tgaacctatt ttatgatata agttgttcag gggttgcaat agtaaccaaa taaagttgat    360
cagaaaaggt taacaactca tgaaaacttc caaatgcatt tgtgtttcaa ttattttctt    420
aaccctcttt ttttggtaat tttagtttaa aaagtgagtc ggttgatcat tattgttctt    480
taatttcttg ggagaaaaat attaatgttg attatggtga tgagttaagt ccaattcttc    540
atcaaatcat accaaattag gaacaaaaaa aacatcaatt ttaaggtgca aatccatttc    600
taatggctaa aatgtcaagc atcccaccaa accaacaatc tctaaaccca tttttactcc    660
actaatctaa tgtttaataa taatcaacaa ggtttttgctc attccttttt tagttaataa    720
tcatttaaca ccaaagctca aaagtaccca cccaatggat caaaatcgag aatatatagc    780
atttaaggat ataaagacta gagataataa taacctagct tagagcttaa agggatacac    840
tagccatcaa gtcaatttgg tagacaatct aaaaacaaat aattcgatga aaataaagtt    900
gtatttttgt gttttcaaac atgttttaag acgaaggttt ttgataaatt tgatctcaat    960
aggtaaacaa tggtaattac tcgattataa ttactcacta aataccaaat cgaatataaa   1020
ttattactaa ttaattatga acatgtttta cattttaaaa aatgaataat ttttttttta   1080
gaatttgtgt tattgaaaat aattttcaaa acaatattga atgaatctta agtgaaatca   1140
atgtattaaa agaacataaa acataatcta gatggtctat cgaacaagct agaaaatatc   1200
```

-continued

```
ttccataaat ccaatgatta agacaggcag gcaggcatga agataagagg attggattaa   1260

ttggtgattt taagttatga ataaagacac aagaactagc agctctcctc ttcttgtcac   1320

cttcctttgt catccagctc acacaactcc aacttggaat ttgacaggtc tctcttcact   1380

catacattcc cacatgaaat tattaattga atcttcaaca ttgtctttga ttcttcagct   1440

gcactgtcct tttccaccat ttttttcttc aagataaaga ctaataaact ccttatatat   1500

tcctctcttc ccattcacct gtgcatactc acaaagcaac tgccatttcc ttcttgttta   1560

tctctgtttt tttcttacac atttgttgaa ctttccctct gaaaaa                  1606
```

```
<210> SEQ ID NO 20
<211> LENGTH: 1487
<212> TYPE: DNA
<213> ORGANISM: Cucumis melo

<400> SEQUENCE: 20

taatgaattt gtatttgtta gtggattgag tttatatgat attaattttg acccaaacag     60

ttgagtacgt aattaatgtg gcttgcattg aaagtgatat gggcatatag tatgtgtaga    120

atgtagctga cacaacacat taacaaaacc caattttaac tttttctttt tctttttctt    180

ttaattttat atggatcaga tcacatgtca ttttccatta caactcactc tctaccaatc    240

atcccatccc ataggccata ccccataaca tccctttcta aatatctaaa tcatctccct    300

aaattattac atttttttc tctcaaatat aactattcaa ttcataaata ttattctttt     360

tttagctctt attatttcaa ttatgatttt aaatattcct tttcaattta cgacctttta    420

tttaccatat caacatttta attctactca attaaagatc attataatga aatttcaggt    480

ataacaaaat aaataggtgt gatataatga tggactacta atttcactaa tttcgtcatc    540

tgaaataagg acaagttcca actatcacta ttgtgaaaac ctcataactc ctaaaagtgt    600

taaaattgga ccctcaagtt tataataatt ttgcaaattg aatcccaaaa ttaaataatc    660

agtataattt atacgttttg agagtcaaat ttaatatttg aataagcttg aatacttaac    720

ttctaatttt gaaaatttaa aaatgcaact gcgagagtaa cttttgcaat tagccgtcga    780

aacaattaat tatattggtt aatttatgtc tcattctctt ttgatgacca taaagataaa    840

cccatttata atataaatat caagcaaagc taaaacaaaa tcttttttt ttcaaattag     900

atctaaatat gaataaaagc agaactttct agaagtacaa atttgattat ttttcttgag    960

ataaaatttt cgctatgaac ctttttataa taggaaaaag agaaaaagga tggttttata   1020

taaatgtatg ataaaaaggt aataatatcc attgtaatag taaaaaagaa aaaaagaaaa   1080

aaagaaaaag caattttctt tttcatgatt aggaaatata aaaacaaaaa ttggctccca   1140

attgacatct ttaatcttct ttttcttttt cttagaaaat aaaattagtg agagaaggaa   1200

aaaaacgaag ggttgagaga tagagagaga aaaaattgat ttttaattta gtttattttc   1260

ctttttgga gcacaaaata aatagataaa taaaatatta gtttgcaaaa aagcccctcg    1320

agtttatctt atttgctcaa aaaagcaagg ataaatacct cccgacatcc ctgtttatcc   1380

ctctcagttt cataattcca ttggttcgat aagaaaacaa ttctcccaat attcccgctg   1440

tagatctcgt cgattttccg tttgtttccc gggaagatca atcaaag                 1487
```

```
<210> SEQ ID NO 21
<211> LENGTH: 1448
<212> TYPE: DNA
<213> ORGANISM: Cucumis melo

<400> SEQUENCE: 21
```

-continued

```
ggtgtcttgt tgtaaggaaa tggaaagaaa agagaaaggc tcttgttgtt gtccttgttc     60
tgtgtatcga tgaaaatgga tcgacgcgaa gaagatgaag gacgagagtg gggattataa    120
gacagagaaa ctccgaaatt tgagggctaa tatggtaata acaaatggcg ggatactttc    180
aatggacgtg gacccattgc ttctttaact caccgtctga tctttatttt acggtcatga    240
tttccctctt tccccaatat ttttgggagg gaaaaccaac tttgtttttg taattttaat    300
catttttcct caaatcgtaa aaaaaaaatt atagattttt tcaaaaatag aaaaaattca    360
tataagaaaa ccaagataaa atattttgaa aaatatccta ttttttactt cttaaaaata    420
attcataaaa gaattattat aaatattaaa aaatatcagt accactatag acaactattt    480
atatagcaca tatagatata tttgttggtt tttctattta gtatttgaaa acaactccaa    540
aaacaataca tttcaatata cctacgaagc atacaaatat aattattaat tttaataagt    600
tcaaaaatat ctaatggcat ccttatttaa tcaatttttt catcgacgtt atacacggta    660
aggatgtcct aatccttgac cattgaaaga cgtttgtttt gataattata tcttttgata    720
tatacaaaca tttatctcat gattagaata gtcacctttt tatttgattt aacgattata    780
cataatattt gaaaattttt aaatccatca acacaatcaa accaaaaatt tcctaactac    840
ataatctaca agagatttac catcttcttt aaacaattgg tcattacgtt tgttaatgtt    900
taaaattaaa tgcaaccata ttgggtgtaa aagccaaaca ttgatttgat tattaaagtt    960
ttttctatat agacttgatg tgtaaaccta ataaccaact tgagctaaat aactttaatt   1020
tctaaaattc attaaactgt cctcatccaa attataatat caaagatttt tgaaatattt   1080
aaaaattccg aacatgggaa ctactggaac ttggcaataa attcaagcaa gaaagaggaa   1140
aacgatataa tcaaacaatt aaaaaacaac agaaatttat ttaatcaaag gaataatctc   1200
atcttttatt tattgggttt tacttttaat actgtgagtg atgattggaa cattaattaa   1260
catttaagac attaatttgc aacaatcaat caaaattgta taaatccact tgttttgatt   1320
tatttgaacc atcacttttt tttttatata tatatataat atgggagtga aagatcaaac   1380
gtataatcat gaaatgaaag atgggatatc attgaactta attaaatatc attgaactgc   1440
aatttttt                                                            1448
```

<210> SEQ ID NO 22
<211> LENGTH: 1235
<212> TYPE: DNA
<213> ORGANISM: Cucumis melo

<400> SEQUENCE: 22

```
aaattttaat aattaaaatg aacaattttt caagagtaat agagtttgag agatgtcaga     60
gaagtttgag gaagaagata acaagtggga gaagagaata agtttgttgt gtgaaagaga    120
aggggaaatt tcattcaagg gtatattgaa ctttttactc aaattttgta agtctatttt    180
ttccgatcaa tcctaaaatc acacacaccc ttaaaaaatg gattatattt ggcaattttc    240
catgataaac tcatttttaa tttagagtta ttttttcaac gagatattaa cagttttagt    300
tcatatacta attgtaagaa tagtttcttt taagttgaat agaatttttg aaacttttaa    360
tagttcaaaa ggtatttttg aaacaaaata agaatgtttt tgaacttttt ataaaaagaa    420
ttgagatttt tttgaaattt ttgataaaga gaaaagaaaa gaagaaagaa aaaagaaaaa    480
caagtttgta gaactccgtg ggaaaatcgt cgagggccct gtgaaggaat tttgaaatta    540
taatgagggt attttcgtca acaagggaat ttagacatcg tatataagca tcctcaaacc    600
```

ctataattaa gcccttcaat ccaattgcca ttctccatct ctcgccgcaa gggtttaaga 660
gcagcttctc tcctcaggtt ggggtttccc cctatcttct tcattcttcc tcttctcgat 720
ttctttcttc tatttgctcg atagtctctt atttcttgag cttttgctgt ttttctcctg 780
tacatcctaa catgaattat aacttggttt tgattttgtc ttttacttct gtattaaaca 840
acttttctta cccttttatt cttctcttct tcttcgtgtc cctgcccttt tgtttttatg 900
ctaattttat gtttctgttt atcaatctat cgaggcgtga cctgtcgttc ttccaatagc 960
gtagatctgc acttaatcta ttctagctga ttggattggt cgtttttcgt ttttttaatt 1020
tattttctct gttctagttc cgataaattt ttttatatat aattaacaag ttctccagcc 1080
aaaagggtta atattgcgtt ggatatttta atttttacgt tatttagatg tgtgaatcta 1140
ataaaattag ggttattcat aaatttcagt aatgatattt tggttatctg ttcttgctgt 1200
tcctgtttcg cagttctttt acctaatatt caagc 1235

<210> SEQ ID NO 23
<211> LENGTH: 2003
<212> TYPE: DNA
<213> ORGANISM: Cucumis melo

<400> SEQUENCE: 23
ctagacattt ttgtctaacc tttcaaatgt tttgttttaa tcttccctct cccaaatagt 60
gaaggacatc cagtgtcaac cgtgaacgca tactgtgtca ttcatgaaac aaatcttttt 120
tgtagtgggc attgtcagca tacatagcat gtagaagcta tagacagatg ttgctttgag 180
ttgtatttag ttctctttaa aggaactttg tacaaagtac tgaatgtact ctgttatttg 240
aaatatcaat gaagtcctct taattctttt gagttcccat tccacgttta agttgttagt 300
tgtattcatt ttcgcttact aggtgttctg catgtatctc acagagagac tcacgtgaaa 360
tgtttaggcg gtcacatccc taatgacttt tgaaggggtg tgacacgatc atttgaatat 420
atcacttatc taatagtgac agtggtctat atctttgtct atctgtatag atcattggtt 480
gtttagatat tggtacacta ttgtgtagtg aaaaaagaag aagaagaaga aaaatataat 540
acttgataat gagaaaagaa taagaaaaaa tattgtcttt atgaaagatg aaaaaatgat 600
gctgaagacg agaaatgacg gaaaaggaat aaattctaga tgaagagatg aagaaattct 660
agaagaacaa atctagaatt tataaatggg ataacaataa agataaatgg gataacaaag 720
aaaaaaaatc aagaaattac ctaaatgttt caatcttgct acgccttaat tagaaaaaga 780
aaagaaacaa aaaagaaaat gcacaaaaat atctatatat atatacacac acaagcacaa 840
gaaaaaaatg aatattggaa aaagacgaaa atgcattatt ttttatttgc gttagcgagt 900
tgttgtgatt ttgtgagcaa gaaaaggata tgcaggagaa ttaagataaa taaggaagat 960
tgaatagaga ttaaaagaga aatatgggaa tagagtgggg atgaaaggtt taaagatagg 1020
gagggaggga gcgagagaga ggagaaacaa acataccttg agaaagggag aatgagagag 1080
ataataaata aatacggtga tttggaactc ataaaaagat taaaaaaaaa aaccttagag 1140
taaagacttt tccatgcatt tcgagaaaat ggaaaagaat attctattct atttgcttgg 1200
acaccaagtt ccttttttgtc gcatgcatac gtctatttat ttctgcttgc ttgcataggc 1260
agtttttgtc caaggaaatt cagcaaaggc ggtatcaatt tcgtcaactt agaatccact 1320
cagtactatt tgaagttcct cactaccaat ttgcaccatc caatctcttc tctctccaac 1380
ttcctgccag ggcttaacct ctcttaattc cttatcctta cttgttacct tacctggttc 1440
cactcttcac gtctctctat tctatattgt ttttttttca ttcataattt tgttactctc 1500
ttctctgtcc cctttgtctt ggattttatc tctccatata ttcattggaa taatttaagt 1560
tctttgtaga ttttatgaaa ttaccaattt aatttttcaa acagtttttg gatttgttta 1620
atttctcctt ctctaaatcg cgttgacttt atgttatttc gcccttgctc tgttttctct 1680
gatcataaag tatgtacttg attttatggt gaatgctttc ttgatttaac aaccctggtg 1740
ctgaaatctt ttttaaatcc tacttttgtt gttttacata tgttcttact ctaaaatgag 1800
cgacttattt ccttttattc ttccttcttg attaaggatt taatcgttga agtatgctta 1860
tattgtggaa atttggtttt aattgatcat acgagctagt attactagct tctcggtttc 1920
tttggatgag ttatatgcat atgatgattt caattccaat ttttattttg caacagattg 1980
ttttttgtgg ctgaaattca agt 2003

<210> SEQ ID NO 24
<211> LENGTH: 2015
<212> TYPE: DNA
<213> ORGANISM: Cucumis melo

<400> SEQUENCE: 24
gatcagagta gcagttgagc aaacccaaac caaacccttt atctatacaa tcctctcaaa 60
ataaaattat tgtttaatta ttcccatatc tattatcatt tttccataat tgcattgaga 120
gaaaaaaaaa aaattctagg agacctaaat acaacaacaa ctatttaata atagccccat 180
gtcacattaa ataaaactaa caaaaagttt aatacgtcaa gaaacgatac ttgtggatat 240
tgaggcatgg gtccctcctt ctttgtatat tcaaatctgt ggtctgccat cagataaggc 300
ctttaccata taataagttt tcaaaaaagt aagcaccact tgctgctttt ttaatttaat 360
tatatttaat ctaattattg aaacttatag ttgttttcta tccttattct tttcttctct 420
tcaaacaccc tcctattaat ttaaaataac caaacaacct ttttctttac atagacaaac 480
ttaattagat taaatataac ttgtaattag attaataata tagtttaaaa agaattttat 540
tttaagtaga attattagta aaaatgaatt ttgtggatag atacttggaa tttaagagaa 600
agttaaaaga gagaaaaata tgaaaaggaa ttaaatgatt aaagttgaat gtaagaaatc 660
aataaacata aattccatgt attaaatttt tgtcggtgtg tgaataaata aatatctatt 720
actattagat tacccagctt tgtttataaa aagaaaaaga aaaagttttt aaaatattgg 780
aaaattttgt ataattattg aagaaattgc gtggtctttg caatttgggc atcgttctta 840
tcgcttccaa tgaaggggcc gtttacctcc accactattt ccaacttgtt tttgtaccat 900
tctctatatt tctttgacac ctatattaca cgtgtcttta atccattgga ccttcgtcct 960
actatatttt tacccgaaat gacgaatctg tccttctcat ccacctataa attcacctct 1020
ccggctcctt ccctttcatt cagttttcct ctattcttct ctctatacgt catattcatt 1080
tcttccaagg ttcgtcctcc ttttatcttt cttctttctt tcactttttt tcgctttttt 1140
cttttctttc ggtttttgtt cttttaattt cattcgtttc tttttgttat atggtatgtg 1200
gtatttgttg aattgagatg ttttagggtt tcgatttagg ttttatttct tatcctactt 1260
aagggctatt gtgattttgg agaaaggagt tcttatttgt tttttttttt ttccttttttc 1320 ttatctggca gatgcaaatc ttcgttaaaa ccctaaccgg taagacaatc acccttgagg 1380
ttgagtcgtc tgatacgatc gacaacgtca aggccaagat ccaggacaag gaagggattc 1440
ccccggatca gcaacgtctc atcttcgccg gtaaacaact cgaggatggc cgtaccttgg 1500
ccgactacaa catccagaag gagtccaccc tccaccttgt cctccgtctt cgtggtggca 1560

-continued

```
tgcagatttt cgtgaagacc ctgaccggaa agaccatcac ccttgaggtt gagtcgtctg   1620

acaccattga caacgtgaag gccaagatcc aggacaaaga aggcattccc ccagaccaac   1680

agcgtcttat cttcgctgga aagcaactcg aggatggccg cactttggcc gactacaaca   1740

tccagaagga gtctaccctc cacttggtcc tccgtcttcg tggtggtatg caaattttcg   1800

ttaagaccct gacgggtaaa accatcaccc tcgaggtcga atcctctgat accatcgata   1860

acgtcaaggc aaagatccag gacaaggagg gaattccccc agaccaacaa agactcatct   1920

ttgctggtaa gcaattagag gacggccgta cccttgccga ttacaacatc cagaaggagt   1980

ccaccctcca ccttgtgttg cgtcttcgtg gtggt                              2015
```

<210> SEQ ID NO 25
<211> LENGTH: 2006
<212> TYPE: DNA
<213> ORGANISM: Cucumis melo

<400> SEQUENCE: 25

```
accaccacga agacgcaaca caaggtggag ggtggactcc ttctggatgt tgtaatcggc     60

aagggtacgg ccgtcctcta attgcttacc agcaaagatg agtctttgtt ggtctggggg    120

aattccctcc ttgtcctgga tctttgcctt gacgttatcg atggtatcag aggattcgac    180

ctcgagggtg atggttttac ccgtcagggt cttaacgaaa atttgcatac caccacgaag    240

acggaggacc aagtggaggg tagactcctt ctggatgttg tagtcggcca aagtgcggcc    300

atcctcgagt tgctttccag cgaagataag acgctgttgg tctgggggaa tgccttcttt    360

gtcctggatc ttggccttca cgttgtcaat ggtgtcagac gactcaacct caagggtgat    420

ggtctttccg gtcagggtct tcacgaaaat ctgcatgcca ccacgaagac gcaacacaag    480

gtggagggtg gactccttct ggatgttgta atcggcaagg gtacggccgt cctctaattg    540

cttaccagca aagatgagtc tttgttggtc tgggggaatt ccctccttgt cctggatctt    600

tgccttgacg ttatcgatgg tatcagagga ttcgacctcg agggtgatgg ttttacccgt    660

cagggtctta acgaaatttg cataccacca cgaagacgga ggaccaagtg gagggtagac    720

tccttctgga tgttgtagtc ggccaaagtg cggccatcct cgagttgctt ttccagcgaa    780

gataagacgc tgtttggtct gggggaatgc ctttctttgt cctgggatct tggccttaaa    840

agaacaaaaa ccgaaagaaa agaaaaaagc gaaaaaaagt gaaagaaaga agaaagataa    900

aaggaggacg aaccttggaa gaaatgaata tgacgtatag agagaagaat agaggaaaac    960

tgaatgaaag ggaaggagcc ggagaggtga atttataggt ggatgagaag gacagattcg   1020

tcatttcggg taaaaatata gtaggacgaa ggtccaatgg attaaagaca cgtgtaatat   1080

aggtgtcaaa gaaatataga gaatggtaca aaaacaagtt ggaaatagtg gtggaggtaa   1140

acggcccctt caattggaaa gcgataagaa cgatgcccaa aattgcaaaa gacccacgca   1200

atttcttcaa taattataca aaattttccc aatattaaaa acttttcttt ttctttttat   1260

aaacaaagct gggtaatcta atagtaatag atatttattt attcacacac cgacaaaaat   1320

ttaatacatg gaatttatgt ttattgattt cttacattca actttaatca tttaattcct   1380

tttcatattt ttctctcttt taactttctc ttaaattcca agtatctatc cacaaaattc   1440

atttttacta ataattctac ttaaaataaa attcttttta aactatatta ttaatctaat   1500

tacaagttat atttaatcta attaagtttg tctatgtaaa gaaaaaggtt gtttggttat   1560

tttaaattaa taggagggtg tttgaagaga agaaaagaat aaggatagaa aacaactata   1620

agtttcaata attagattaa atataattaa attaaaaaag cagcaagtgg tgcttacttt   1680
```

tttgaaaact tattatatgg taaaggcctt atctgatggc agaccacaga tttgaatata 1740
caaagaagga gggacccatg cctcaatatc cacaagtatc ggtttcttga cgtattaaac 1800
tttttgttag ttttatttaa tgtgacatgg ggctattatt aaatagttgt tgttgtattt 1860
aggtctccta gaattttttt tttttctctc aatgcaatta tggaaaaatg ataatagata 1920
tgggaataat taaacaataa ttttattttg agaggattgt atagataaag ggtttggttt 1980
gggtttgctc aactgctact ctgatc 2006

<210> SEQ ID NO 26
<211> LENGTH: 2017
<212> TYPE: DNA
<213> ORGANISM: Cucumis melo

<400> SEQUENCE: 26
atggataagg cagagcttac cactaacctt ctaagatatt ttcgtcgctc ggcatttatt 60
cttggaggga accacaccaa ctccaaaata cccatgaaac ataggaaaaa atggttcata 120
gtctaagttt ccatttcgat tcggtttggt tcggtctttt attttaaaaa caataaatat 180
aaacctacta atttgatgat gacaagttta ctaatgttaa gtaagaattc atcaatacct 240
aagaatttgc aagtttttct taagtttgat ggtaaggatt tcgtaatcct tgaaatacaa 300
caattgtata gaaatgaagc gttgcatttt taacgtctat ataggaacac tattttactc 360
caatcaagtt gtaatttgat agataatagt ttgtataact taatgatgaa gagctttttt 420
ttttatatat aatttttatt aatacgtata gttcaaaatt ggaattagct atcactaaca 480
cgtgcttgcg atagaaacaa caataaattc aattagtgtc gcatgtattt catatggtat 540
tgatgacata agagtagttt gatacgatgg gttacatgga gtgacatgat aattgtatta 600
aatttcaata gttatgatct caagtttggg ttgtgtctca ctttgagctt tttgagaaat 660
tggcctcaag actcgcctaa tttaatgttg cttcaagcta tagatgctta catcgtgtgt 720
atgaaacata ttgcactttg atgcttaaag ttaatatagt gagtaactaa ccagatatta 780
cacgctactc ttttaaaatg gtcaaataag aacatttatt agtatgtgat ataacacgta 840
ccctccaatt acatacaata attgatcaac ccaaatcttg aggtatttaa taataacaaa 900
tacaaaatag atggattata tatctgaata gctaaagaat aaagaatatg tgttatgttg 960
tagttacata gtacaataag tcctctcaaa attagaatgg tataataaaa aataagaggt 1020
acattcttaa agaaaatgtt atcaaaactg ttgcatcata ggcattttgg caggaagaat 1080
agtggaagaa aattcttaaa cctaaattct atcgatatta aatagatttt ataagggata 1140
attgcaaatg tagcaattat atttaaaata attaagtata tagcaacatt ttaaaaaaat 1200
ggcaaatata gcaaaatttg tcaaaatcta tcgatgaccg atagatcatg taagtctatc 1260
actgataaac cataggagtt tatcaacgat agaagtctat caccgataaa ttttgttata 1320
tttataattt ttttaaaata ttgctacata gttaataatt attctaaaaa ttgctattac 1380
caccggtttt taaataggac ctaaatttaa ggtatttgac ataaattttg atgaaccaaa 1440
ctagcccaaa tcaaagaagt ttgggcccaa agcccaacga atccacaaca aacaaagccc 1500
acacaacact tcatgaaaat gattttttca aattttagaa aaaggttata aaatataaaa 1560
aaaataatca aactatccct ggtagctaag tagttattat tatttttatg gatacgaatt 1620
gagtagtatt tattttaaaa taggataatt gatcttagtt tcacttgtga tgaactattt 1680
cactttatta tttgtttgta attcaataaa attagggttt gattgtcaat gataattatt 1740
acaacctcaa tattatactc agtaaagaaa aataaaaatt taaaattgag aaattaatac 1800
caattttttt tgtgaaataa aaggaaaagt aagtaaatat tataaaattt tggacttgga 1860
aattaaaatg cattaataat aatatttagt attattgaat taaaatggac accggaaacc 1920
ctaaaagagg gagtggccac ctataaaagg gaagcactca tctcacccaa acccttgtta 1980
ttcccaattg gccgtgcggc aaagaagcct ctcaacc 2017

<210> SEQ ID NO 27
<211> LENGTH: 1353
<212> TYPE: DNA
<213> ORGANISM: Cucumis melo

<400> SEQUENCE: 27
tgagggtcaa aggaggagga agaacaagaa gtaaatgaag tggagtcatg ggaaaaggaa 60
aacaaatgtg agaaaagaaa gaaagccaga gagggaacat aaaattatta gtcagaatta 120
caacagaaaa tttctgaaga attgagtttg tatgcagcaa taatatattg aacaaataag 180
gagagaagga ggaggggaaa ttcaataaac agcagaggaa gaagaatggc gaaaacccaa 240
tatctaaaac tagttaattc aacaagaagc aacacaatca tttcattaaa aaaagaaaag 300
gtaaagagaa attcccagat tcgttactct agattggtcc aatggagtgg aaagggatgc 360
aatgaaatca gtaatagaaa agaaaagagt taaagtagta ttggtaggta ccgattaaaa 420
atggaaggcg tcggaaggaa acggagagtt caataaaagg aagattcttt gcttcctccg 480
gccatttgat gagaaacaaa aactccgcac ctccaagttc cttccggggg aaggagaaga 540
ctcttctatt ctggggtaca caccctccct tcctgctaca gaatcaaatc taaattattt 600
tggattggaa tggcatggga ttggtctaac ttccaatttc tcgacacaca accccaatct 660
acccgccacc tgtacccagt tttcccaaaa cgcaactcac attgcaattg caattcttgt 720
ctttaataaa tacaaattga tttttctttt tctttttttt ttttttttaat aacgattaac 780 cctaaaaaaa ataaagaaaa gaaagccgat cctaaaagta gaattacttt ttttttgttt 840
ttcaaggttc acgtctgtgt ttgcatagac gtgttgtagt cggtgggtgt gtaaattaga 900
gtttgttttt ctcatctctt gttcttttta acgaaatttc aaagatacaa aagcataatg 960
aagaaaagta tacaaagcaa cgtaaactta gcattttgca catgatacaa atttagtcaa 1020
actcaaaccc tggacaacct agcactctct tgggcacgtg gtagatttat gtgaatttcc 1080
ctatttttct tttgaactca caaatgggca aataataata ataaaattta ttgttgattt 1140
ttcttatatt tcaatttatt acctctagtt ttaacctaaa gtttagatgt atataattat 1200
aaatgagcgg tgaaacgggc actgattgat gaatatattg ggccttgggt tggcccaaca 1260
aacctaatgc ccaaatataa aactttggca accatagtta accctaatct gtcaatctac 1320
tctcctcgac tcggtaaacc tgcgactccc aca 1353

<210> SEQ ID NO 28
<211> LENGTH: 2005
<212> TYPE: DNA
<213> ORGANISM: Cucumis melo

<400> SEQUENCE: 28
cagtgtgctg gaattcgccc ttatccaagg agattaatgt cgagagatta ttatcgaggt 60
ttgaatttat tttgtccaat catatgattc caagagctga ccatcaattc aacagaacat 120
gaaccggaac ctcataccta ttgtaatggt tcacagcatc ctaatacaga acatgaaccg 180
aaacctctta cccattgtaa tggttcacag catctttata cgtattatag gtagtaccat 240
tgaagatgca tttaaatgct gtccatgctc tgttctctaa aaagttggac ttggacttgg 300
acgtcagctg aaagtatgaa atgcactgta gccaacgaag ctatgttttc aggcttcaac 360
atggttttag gaaagtggag gctctttggt tgaagggttg aatgaatgct tttctaattc 420
cagcatgatc ttcaaatttc gacacaaaaa gcttaagtat tttgttccgt tattctttta 480
atccttgtat tgttatatat tcttttctct gaactgaatg tacgatgatt gcaggggtcg 540
agagcaagtc cgatataatg aaacacgtaa ggacgtgatt gaatgaaaaa ctatgagcag 600
agatacaaag tctaacttac gggatgaacg atgagaggtt tgaccaagag ctgtgacgcc 660
tgtatatttc aacaaaagtt gatgactaac atcacatgtc agagtaatca aagaaatgca 720
gccgcacata tatatatcta tatatatatc gtttagtttt tttttttttt tttttatttt 780 ttttttatc taattatatt ttaattctat tttcctctgc cctcctcccc ctcctcttcc 840
cccacccttc ttctgcacat agtagccaag gattgatcgg tttcttttga ttcgggggga 900
aaatgttgta caatttttgc ttccatagaa gcttgaaagt tttgcagatt atgttgtaaa 960
attacccttg tgtactcaca ctagttcttc tcgtggaaac ttatattaca atggttgagt 1020
tttaaggggc atattcacac tggtaactac cattttctaa tttatgaatg ccgagtttct 1080
ctccatgaaa gacctttcaa atgccctttc ctccgcggtg cgtttgttgt tgtaaatgtg 1140
cagtgtcgtt ggatacacga ttgtgtgaaa gggaaaaggg aatacgatta actcttaaat 1200 tcaacccccta tctccatcag tatcaatcac atttcagcaa ctagctcttg aataacattg 1260
agattcttgt ttaatccacg tactactact actattacta ctatttgaca gccgatatct 1320
caaataacat ccatatttat caaattggta ttttaaggac ttttaatttc ttcgtacata 1380
tttcattata atttaactac tctgaccatc attgaaaatt tcacaaagaa gacattttaa 1440
attgaattga gttgaattaa gttgatataa tggttgaacg ttggatttaa tttataattt 1500
agtggtgtat gggtccattg taataattct taaaaaaaat atcatattct gaattctaaa 1560
gaaccatcta agaccaaaac taaggggtca ccaatgagta tggtaaagtc aacaaagttt 1620
gtctactttt cttatcctta tcatcaagag tgcaatatga tatcaaagat aaattgtacg 1680
tgggcgtcat ccattgggta agaccaagaa gcaaaatatc atagagaagt tgttttagta 1740
gccataggaa ggaaggaagc aaaataataa tatagatttg aaattgtgga tgataaactg 1800
ccaaatggga attcaaaata aactaaataa ataaaataaa aagagaaatc ttgggagttt 1860
ccattttagc caatgaggaa acagatagag atctcatcaa gataaggacc ctattctctt 1920
cttcatctat aaaacaaaaa caaatcaaac cctcatttca ctcattcaaa acaaaaagta 1980
ctccaaagtc aaactaacaa atacg 2005

<210> SEQ ID NO 29
<211> LENGTH: 1445
<212> TYPE: DNA
<213> ORGANISM: Cucumis melo

<400> SEQUENCE: 29
tcccttcagc cacttaacac ttaaaaatct taggaaactc cattggctcc tctttctcca 60
atgaaatttt gacatctgtg ttgttgatag ctcctatatc ctttgagaat ttgatataca 120
cctgtcattt gctgatttgt ggataactgt tagccttttg atattgatac gttccttttt 180
tatgaatttt tgtaaatcca ttcaatttta atgctgtcgt aaatgaaaag ccctttcatt 240
aatgttgttt atatacatat tttaaaatta attcaataac aagtttagtt ctgttagctt 300

```
ctaggtttgt atctatttta tctattaaag gtatgtttgg gcttcaggtt ggaatggagt    360

agaattgaat gggttgggga gtaaattttc cattcaacaa gttcaatttc aaaatggcta    420

ataagttttg aactcaattt tattttcaat aaattcctta atttttgtt ccttgtttgt    480

aaactattga cttattcgat atattttaaa attgaggtat tttaaaaaaa taatacaata    540

ttaaaattat ttataaaata taacaaaatt tatgtatagt ttatttgaaa attttactat    600

agtttcattt ttatattatt cctaaccatt tccatttaaa attatttcaa ttatttcttt    660

tattaatata attgaaattt catggattta ttagacacat gatttgaaat tttatgggtt    720

tattaagtat tttctaacac aaaatcgctt ccgcatcgtt ttcaattcat tcagtaatag    780

aagtaatttt ttaaaagaac caaatttgcc aaattttgag ttccataagg actctgaaaa    840

ctcattatgt ctattactct tcactaattg tagagactta aattcaagat aagagacact    900

aattgatgat aattgcccaa aaaataaaaa taaaaatgtt tcttccccat cctcaacctc    960

catgaattca cagagcccaa agattaatta ttgggcccca attcctactc atatatacct   1020

tacagtccct caaagaaatc ttaggaagta atcaatttct gtttattcaa gatgtagcct   1080

cccaaaagaa aaatacatca catcaaattc aaacaaaaat atctacagct agcaaaacct   1140

caaaccgtta aaatttcaag ccacataaat gaaattttca tctgaaaaaa ggacaatcta   1200

tctagacgtt agatttcagc cctaatatga atctgaagca tttggtggac gagaaagagc   1260

catgtaggaa tgcatcaaac aaaggaaaaa tctttgaact ccaatgggat tgaagataca   1320

gataccaatg gataagaatc tgttctcttt gcccactatt taaactcacc aaacccacca   1380

gtatcttcct caccacaaaa tacattccac cgttgatcac aagccttatt ccaccacctc   1440

caaca                                                               1445
```

<210> SEQ ID NO 30
<211> LENGTH: 1282
<212> TYPE: DNA
<213> ORGANISM: Cucumis melo

<400> SEQUENCE: 30

```
tgcaattaag aataagctaa tcttaatgaa gaaaagaaaa tgttctttgt atttgataaa     60

tggtggcgtt ttgggggact ttatatgctt tttttttccc atgagattgg ttatcttcat    120

ttccgtcatg atgtcgccaa gtggcgcttc attgatgata tcttaaaatc tataatgatc    180

atcctctttg ccaatggtgt ggtgacacgt ggaaggactc tccatcttct aaaagattct    240

tcaaataaaa ataaataaat aaagaaaaaa cttgtaagaa gatacatatg tacattttta    300

tatgaaatta atatgagaaa taatcgactt tacagtgact tgatcaaact ttcttatttg    360

tttcatatgt taggttaaat tactaatcaa ttcacgtact ttactagatg agatttcacg    420

tactttactc attgagtcca acggttgatt aacttatttc aagaaaattg attcattcaa    480

ggatgtttcc aactctcata taatttccat gttgttccac ttctatcaag tacaatccta    540

tcgaacacaa gtttgtttaa ctgaagttca ataatcgaga tcaagatagg ccttattatt    600

tcttctagag gttcaagtga tcaatcaaaa aaggtttatc acatgattca ttccaattca    660

actaagctaa taagtggtgt tgcatgatag agtatcggac tagctcgaac ccctatcaat    720

atgataaatg tctatgtata taaataggta cttaacccaa cgaacaatgt gtcttacgtg    780

agaaagcttt tttctaatat acataaaaag cttgcatgac tttttgatga attgtgtttt    840

gataaaacat atttgtgagt atattatctt tataaattta agttataaca acaatgtata    900

ggtgtgagta tgcttttaaa cttaataaaa aaattagaaa aaattacctt tttagtatga    960
```

```
aagttttaat gatatatcaa tttgtgtctt tatgatcaaa atgtatactt ttagtctcaa   1020

atgtttataa gaattaactc cttaataatt atcctaaaca atcatgttca aacttggatt   1080

cttattgaca catatttcat tttaatctaa gtttagaaat gaagataatt aggataagga   1140

tctttagctt atgatatctt atccaatatc ttaaataaat cttcaacacc aagaaatttc   1200

cctattgcgg atatttcaat atcgaatgcc ttggagtatc aaaggcattg gataacaagt   1260

gggacataat tgcgataaaa aa                                            1282
```

```
<210> SEQ ID NO 31
<211> LENGTH: 2002
<212> TYPE: DNA
<213> ORGANISM: Cucumis melo

<400> SEQUENCE: 31

ccgtagattg aacttatggc ttcggtcagt tattgagatt ttaattctct ttaacattag     60

gctaatccat gagtttacgt gtgctaacat gttaatatga aaagtatagt agaaaagtaa    120

aataatataa ataaataaat tggattgttt tgaaaagttg aaagattaga atatacataa    180

gattctgaaa tatctcaaat ttttgaccca gcaaactgaa attagccaaa gtaggttgtg    240

ttgtaaataa ttatacttta tattgttctt tttgtataag cttttatgtg tcaatgacaa    300

ttttaacagc taaataattt aaacagaata ttgccaagat gggtggctac aaaaataatt    360

gtaaatagaa cccaataata attagtttaa tcaattatgt ttttattaac ttgtaaatta    420

aatttacact gaaaagttga aagagtttgg aaaatatttt atttgaataa atcaaacaat    480

tgaatactaa tttgcgtaaa atacgtagtt taaaatatat atatatgtat atatatatat    540

atagtgtaat tttcaagtaa taaataaaat gaaaattaaa ggtttaaaaa taagctaatg    600

ggtgcttaaa gtatctacgg aaacgagatt gcattcgact cacgtacgac atgaaaaaga    660

tataaatgaa ttttacatta aaactattaa attgcacata tgattgtcca acaagtaaga    720

agaatcacaa tcaaagtaaa aagaatcaca atcaaaagag aatgtatcta atggatgatg    780

acaatttact taagatttaa gaattaatct aaaaatttag agagaggggt aaagatatca    840

acttttattt accagaacta aaaattatcc ttaggcctca attgctttag taatggatat    900

atatatatat atatacacat ctacctaaca aagctttaat aatagtaata ataaaaattt    960

aaataataaa taaaagaaat cgaccaatat aaaaacatat aaaaaatgta tagttaaaaa   1020

gaaagagaga aagagagaaa gagagaagag tacatgcaag agatttgatt tggaaggagc   1080

acataatagg acaagagaag ggtaattttg gaatttgggt caattattct tagtccaagg   1140

gttacactac aaaaacctaa cagccttcac aaatttttcc ctctttcgct cgcttcgctt   1200

tgcccaaaca ctcgcctcca actccacgga tcagatccga agagtttggc aaaccctagc   1260

ttcctctctt caatctccat ctttttcttc tctaacaatc cacaggtttg tttttcattc   1320

ctttctcttt cgattttgcc ttcctcttct acttattcga ctgcacgaat atggttgtat   1380

gtatgtttcc gccctctttt catatccctt tttgttcctt tagccttgaa ctactctggg   1440

ttttcttttc tttttttact tttttctatt attgtatatc tcaagatttg acgctaatct   1500

ggtctgtggt tgtgggttga gttcgttttt attcgtttgt ttgtttgttt gtttatggcc   1560

atggcttgta attgcttctg taatctacgt gaatctgttt ttgctttgga acgtttttgt   1620

tgttcaactc atacgagaat cgtcgtctat agttgggttg ggtttttttt ttcagtagca   1680

tcttgctttg ggaaaaggtt aatgcggtgt cttttttttt tttttggaga aaaaaagtta   1740
```

ttagacatcc ctcaactcct tttcctacat tgagacagaa gtttaatgct tgttttcctc 1800
tttatctgga ttgcaagttt ggcttttctg ttacagattt cctttctcag gatagctttg 1860
aacagatttg taatgttgtt ctgtttattc cttggtgggg ttgataaaat ggttatgatt 1920
ttttgtttgt tggcggcata attctggata tttttatctg tttggtctgt gttcatattt 1980
gcattgtttt ccacttacag ct 2002

<210> SEQ ID NO 32
<211> LENGTH: 2003
<212> TYPE: DNA
<213> ORGANISM: Cucumis melo

<400> SEQUENCE: 32
tggatcgacc atgacattca aaaaccttta agatatggat cttataaaat aaatgtaaag 60
ggtaaacaat tcttccttgc ttaacccaag ctatatattt tatgcactaa tttaggtatt 120
agagtatatt cagctgaaca ccacctacca atgctagtac tttaatcagt caattctaac 180
ttcgataata tatctcaacc aaattagtga aaaagagtcg taaatgaaaa actatgtacc 240
aagatattct atttgttttt tttatgttta aatatctcaa agataatacc taaaacgttt 300
tctcctcgta caaagattcc tcatttactt tttattgtcg taaactctaa tacaataaac 360
taaaacaagt acaaatacac tagctttaga aatctacttt ttattgaaac caaaaccaat 420
aattcaacat ttcattttca ccgacaaacc tttgtaaaca attgaagtaa tttttgttgg 480
tactatgaat agtaacatca agtcttcaag tgcatcatat caaccaagac atgttcttaa 540
aagcgacact aaaagattta aaaccaaaag catttatgaa atccgaactt aatcaaatcc 600
taaatatttt tcacttaaaa aaaaaaaaat aggaagaaaa attgacataa atgggatatt 660
ttcgttttca aactggcaag ccagcatgca ccacgttgtt gacgtgtcct tccacgtcgg 720
aaaaaaaaat attaccacag taaaaagaga ataaaatgaa agtcgttgac tctcccttag 780
tcggaggaag cgcgtgaagc tgaagccgga ttagaaatcg gcaataaccc cgacacgtca 840
tcgaaatgct agtatcaaat attgtccgtt ggatcttcct tcaccaactc tatttgaacg 900
gccacgatct tccaggtcca acggttcgga agaatctttt cgaaattcca tggctagtcc 960
ctacactcct ccctattggc tccctagggc atcccgaccg gttattccgg ttgccgggaa 1020
ggtggctgga cgctataaat acccgctttg ttcatctcgt agtccttgta ccgttgagct 1080
tcgccttcta atagagctct ggttcggttg gcgtattagc tcgaattctt tctctcttcc 1140
agatctacgc tgccgatttc atcaggtttg cgagctctgt tccaccattt ttcttttcct 1200
gaagctttga gcatgcttgt gattcttcat ttcctcattt ctttgatggt ttatgaaaga 1260
atttagggga attttctctt tttgtattct agtggtactg gtagatttgt ttgaagtttg 1320
tttctcttct tctgagaagt gaattcttcc agatctgaca gttgcttttg attttttctt 1380
tgggaattag tgaatgatac ttcgatactg ttttttgctc tctgagattc tggatctcgg 1440
gccttggggt tttctattgt cttttggtag ctatgtttcg tttgtcagct tgtatttgtc 1500
attgttgaat ggttcgatcc ggtttgtaaa taaaataaat tttgtaggcg cacttgtttt 1560
ccacggtttt cgtgttacgg tttcatgatt ccctagatct ctggttagaa ctaagttttt 1620
tgtcggtaat tggatttggt aagggactgt tactgtggtt gaattgtaga tccagtcatc 1680
ttctacatga gtgtagggtt ccttagggca gatcttgtgt tttataattt taattttgtt 1740
gtttccctga ttttgaacct gtttggttgt tcagattcgt cgagtcattt ccattcatta 1800
aaagtttcta taattttatt tgaatcttct gaatctgtgc ttgtattacc cagatttcta 1860
taaacctatc ttgatttcaa gtgtgctatg tggtaactgt tgatattttc aagcttaagc 1920
aatactgatg tgactaaaac ttaactaatg aactgaatgt tttttgtaca cgaactaata 1980
tggtgttttg ttatgtttca gag 2003

<210> SEQ ID NO 33
<211> LENGTH: 1372
<212> TYPE: DNA
<213> ORGANISM: Cucumis melo

<400> SEQUENCE: 33
aaataaaacg cggagacaaa cttggacttc cattcccttc ttcttccttt ttcttgtagg 60
aattcttctt tcttccttat aaaattctcg gaccctttt ttttcctttt taattttatt 120
tttccttctg tagttcgttt cttgatttag attttcgaca aaggtacctt ttacaggttt 180
gttccttctc ttcatcgttt actccgattg atgcatttcc tctattttca cttttggatt 240
ggaattatta cgatctatgt tcaatatcgt ttgatccatt ccctagatgg aaattatgtc 300
tctgtaatta tacatagtgt ttgatttgtt tgggaaattt tgtttctttg tgataatgtc 360
ttcatcgatt tgatgatgta tttgtttttt tttttttggt ggaatcgata tgatttatga 420
tttgggtgtt tttttgcttt tgagaattat gatttgatca gagtttttct tattatttct 480
gttgttttgt ttcatttcct gccgttttta aagatgtgtt tagattctgg ttgtttttgt 540
ccttttgatt atgtttttat ttttcatgta gttggaaatc aataggattt cagataattc 600
atttggttgc atagggattt gaggattgga agttcggcac tctataactt tgcagtgaat 660
gatttgggtg aagtttttcc tcttgtttgt gctttcatgc ttcagttgcc tcaaccaata 720 tcgcttttg gaagtcttga aaatctgtag ctttgagctt gtgtttagtt cgcaactgaa 780
gcttcaagga aaaagtaatt tctttcgatt ttcgtaaaag gggggaaaaa ggaagtaatt 840
ctactaaaat tttctcctat gaactcgtag gtcacatagt tgttatttgg tcagttgaca 900
ctctagacta tcttgttacc attccacata actcaaaggt tttaagaata aactcaatat 960
gggaatggtt tcattaggat tgcagagtca ggaacaagag aggttgcttt gcacaagtta 1020
catactttct attcttaggg agaaaagcca gttgtcattg ttcagggaga agattaattt 1080
ggttggaaag atttattgtc cttctgtctt taggttgtca ttggtttgtt ataattaaag 1140
tttcttgttt cctagaaaat agaagttttt ccctatgagt aatgttatac ttcattgtct 1200
tttattttgt gacaagcaaa cagtgattta ttggatgaac tacagttaaa ttctgaatcc 1260
attaattttt ctgaaatcca ttgtgattag aatcatgcaa tgccaactga agaaattttc 1320
accaattatt aaatgaatat gtttatttgc agggtgtttt aaatagatca ag 1372

<210> SEQ ID NO 34
<211> LENGTH: 1122
<212> TYPE: DNA
<213> ORGANISM: Cucumis melo

<400> SEQUENCE: 34
atatatttat tgctagggtt ttccggttcc tgtttgctcc actatttcag ccgcctaggg 60
ttgaaacaac tcattcctcc gatttcagga ttactatctt cctcctcgac cttctccggt 120
aatactttct cttcacaccc cttttgttgt ttgtgatttt taacttcctt tggattgaaa 180
tgcgagatct gtgtgtttct accactcttc tttcttaact tttcgatagt attgcatgtt 240
ccttacttat ggagaggata atgtgtactt agggatatca attttcgttc acagtattca 300
atattcatga cttactgagg tgtgaggagt tttcatttca tagaccgact gatgctatga 360
tctcaagccg agtttgaccc ctgtttttct ttttatattc tttttcttat ttttgtgtca 420
atatattagg tgatcaatga catcctaatc tattattagt gaattgagta ataagaagta 480
aagtcttgtt tatccaattt tttggtttgg atttattact attttgttgg aatgcttgaa 540
tgaattctaa tggagtccgt agaaatttgt ttcaggcgtg cgccttttct tctcactaaa 600
tttttcatta ggaatgggtg tatttatttt caggagaatt tgtcgattgg cgatagttgt 660
cttgttcttt ttcatttcct ttataaattc tttatggaaa aaatgtattt gctgcaacct 720
ctgtcttatt accoctattt gaatcaatag agttcctgat ccttcctacg atgtggtttc 780
tggggatttc tctctgggtt cgtgtgatag atgggtgacc gagggaacac cctttattgg 840
aaatgctcct attcttcaga gtcggtttct cattttctca cctttacgct ttgctgctgc 900
tctcattgac agtcgaaccg ttttggaatt cgtgatattg tgtgtatttt ggggatgaaa 960
gttttcttta ataagactag tgacagttca ttattgattg tggagaaatt tatgaccatc 1020
taattttaat ttgaacaagg gaggatgaaa atgattgggc gcattgcatg ttttatccaa 1080
ctagtactca ttttttcttt gttctgatat tcttcaggaa ca 1122

<210> SEQ ID NO 35
<211> LENGTH: 2017
<212> TYPE: DNA
<213> ORGANISM: Cucumis melo

<400> SEQUENCE: 35
actattggag acgacgaagg aaaactctaa tgtgagctta gaattgaaga tggtgaacaa 60
ttgggagtct tttttaaaaa tctttcgtcg gtatattgaa atttcctttt acactcaaat 120 aaccccccctt ttcacgcgtt caacgtcttc aaaccttcct ttttcaatta ttttttcgtt 180
tacattaatg acatttaggt aataagataa attagtggat tcttttgtga aaaatgttag 240
cccatttaag acttttatga aatatattag aaaaaaatca tatagcaatt tatattattc 300
tagttaaaag cccataatag aaactaaccc aacctaaagt aacgtaaaca ttcaataaga 360
gagacaaatt ttaaaataat ttctaattaa aaaaaaaatt gtcaagaccg tccgggtcgg 420
atccaaaata taacccgaac cggccggttt agcatctata taaatacacc tttagggttt 480
ttattctctc aagacttcac cgcatttcca cttctctgag gccacggtca gccattggag 540
cagctcaata atcctttgac tccctactac ggtaagtcga ccttactgct ttcggcttct 600 agtttttca atcctgtcat tagtcctttg gagttcttct gtacatttat gacgtttcg 660 gctcgtgttt tgtttcgcct gtatgtagtg ggtttttcga gttttgtttt tactttttt 720 tatacttgca ggaattagtt gaaatctatg tacttcatgc cttggataat actcttgatc 780
tgttgtgtta ttcaaaaatg aattgtttta agatggtatt tgagaatggt catgtgagtt 840
ttgcctactt ggttattaaa atgaattgtt ttaggatggt atttgagaat ggtcttctgg 900
gtatttggtt ggaacctttg tgctctgcta tgaattaggg tgttctcccc gttttttttt 960
ttttttttct tttggttatt aatatatctt ttatgactac ttattcatat atgatatctt 1020
ttactcgtaa attttgactc atttgaaagt tttatcctta gtcctttctc attcagggtg 1080
taaaggtatg ttgttagggt taaaatagcc tatgcaggaa agttctgtat ttgttctaat 1140
tattgcattt gtgtgcattt gtatctagtt tatttcttgc tgagagtatg cttcattttt 1200
tagtacacat cacttgtgcc actttattat agttgcacat ttttgtttat ggagaggatg 1260
aatagcattt agggatgtca attttttatt gagaaaaccc tctctcctac ttaagcttgg 1320

```
ggaatttttg ttctaaatgt ggtaaacata atacttcttc ttattttaat ttgaatggaa   1380

ggggaagacg aatactaata ttttcaacga accttcacaa cttttttttc ttatttagga   1440

agccatgttt ttcaaaattg tactgtgtga tccacatatt tatcgattat tagtgaatcg   1500

aataataatt agagttttat tggtataatt ttgaagttca gacttattac atttgtggaa   1560

agtttggtta caattttcaa ttttattgga atcctaagaa ctttgtgtta acatatattg   1620

agttttcttc tctttttttt tactcattaa gttctctatt aggaatgttt ggttcaatgt   1680

cacatagtcg atagctaaga ccagtgaccc acaaagctat gattgaacga aaaacaagcc   1740

tttcacatct tggtaggaat ttgttatttc tcaatagatt tacagagctg tttcatgtga   1800

tcacaatttt tttctatttt tctgaagttc tctattagga atgggctatc tggttagttg   1860

cttttgagag aacatgtgga ttggtgttgc tcggtttcct tgcctttgta attttgtcct   1920

tggaaaaagc aaaatgatta ggtatcctga tatgcataac atgtttaagc caactagttc   1980

tcactttttt agtgcaaata attgatcttc aggaatc                            2017
```

<210> SEQ ID NO 36
<211> LENGTH: 2000
<212> TYPE: DNA
<213> ORGANISM: Cucumis melo

<400> SEQUENCE: 36

```
aagttgttga ggctttcaat ccaaccaaat aattgtttcg ttttccacta caatttccta     60

gtactaaggt agcaatggat cgatccatag agaaccattt gatttttcac taaaatcaat    120

ggttgctaag taaccaaggg aggattggtt gaattgattc ctaatttcac ttcaataatt    180

aaagcaatgg caataaaaca aaaattggaa gattgttgaa ttaaatttag caatgagata    240

aatacctagg ccaagactta cgtaggttac tttagattca caactcaatt attgattcat    300

aatgatatta gattccttgc aacatatgaa caaaatctta gttgaccacg tctagagaag    360

ctaatgtgat gttctataaa tcaaatcaat ccttatgtct agattaaaag catcctagag    420

atgaaaatca attggcatta aggtttgagg ctaaagctaa gtcgatcaaa caatttggag    480

ttgtctaatt gattgttcga tgtgatacaa ttctaaacta gttagataaa cgtaattaga    540

atggaattgt caattcaata aatgattcta acttagctta tgttatcttg cagtctaaaa    600

ataacaatta catattagat ctagatctat aacaattaat taaacatgct tggaaaatcg    660

ccaatatttc cgaacacact caatcaaaga aataagtcca aggaaagaat tcattaaatc    720

ttaagattca caggatgaaa atgttcataa catcacacaa gtgtgtgaat caaaagataa    780

gactagaatc tcgagataat agtaccttag ctatgataca tcctcgaaaa catccaacaa    840

aatcaatgaa agtcttgagt caattcgtct agtaaaatac gaagagttca agagaaaatg    900

cctaaaattt agtgccaaaa attgtgtaaa aagtgttggc ggctagggta ataatgcaaa    960

attaagtcac agcaccgcaa caacgtgcaa aacacatgtg ctatactctc gaaaaactct   1020

atagcatcgc agtcaacacg ataccgctac acaacacgtt gtagggctga ggtgtttgca   1080

tgaaattaga ccattctacc ttacagcatc gtgccttctt cgttccattt caattttctt   1140

gccccagttg acacactaaa cctccaatta atctcgttta atataaaaga taattatgat   1200

tttctttatc tacgaacaac attattgtga aaagatataa ggatgatata tcacaatttt   1260

tagggaaaaa aggaaaatat attggcattt attatctcta tcaaatagat gattttacaa   1320

ttatatgtta agatgtttta atccttgcta atgtgaatat ttattttatt tttgttcaca   1380
```

-continued tgaaacaatg gtattttgta cactccaagt acaatagttt ctttaaaaaa atttaaaatg 1440
atacgtaaat tatctaaatt gacatcttaa ctaagcaaac aaaaatagtt gtttgaaaac 1500
tagacttatt tagtttacaa aaacatgcac cagatatcct cacttaatca ctagctctac 1560
acccaaaata tagactaaat aacttcacat ataatataca aatttaccaa actcaattcg 1620
gcatctcaat tggcgaaaga tctttttaac ccaaaagaag acgttggggc attaactttt 1680
caaaatgaac tttggcttca tagtaggaaa ttgggagtga aacatgaggc tgaaaaaggg 1740
ctaacaaaga gagcgatcgt ccacgtggtt ggcagtcaag aggtctttat agaagaggat 1800
gaagaacttg tttcccattg gtccgaaatc tatccaacac cctcctatta gatttccctt 1860
ccagattctc atcttcatga ttcctacttg gctccattta aacccacaat tcaattcaca 1920
atatctccca cacatcctct tcttcatcat atcataaaac acagtccgtt acatacctga 1980
aatcttccat ctcaaaaacc 2000

<210> SEQ ID NO 37
<211> LENGTH: 1760
<212> TYPE: DNA
<213> ORGANISM: Cucumis melo
<220> FEATURE:
<221> NAME/KEY: misc_feature
<222> LOCATION: (1)..(1760)
<223> OTHER INFORMATION: n=g, a, t or c.
<220> FEATURE:
<221> NAME/KEY: unsure
<222> LOCATION: (1)..(1760)
<223> OTHER INFORMATION: unsure at all n locations

<400> SEQUENCE: 37
ataatgaata gcaaactacg taagttaagt tttggttact caaatttaaa cgacgtaaaa 60
aaaagaagaa gaaaagaaaa aatacgatgg aaagaaatca cagagaaaaa aagaaaggaa 120
aaaaagaaag acgatggaaa gattaaacga cgtatagaaa gaagaagaaa agaagaaann 180
nnnnnnnnnn nnnnngcagc gaaaaaaaaa gaggaaaaca ataaagatga caaaagaaat 240
cggagcgaag agaagaaaaa gatggaagaa taaacttgaa ttggacaaat tttatggact 300
ttttacatag acactaattt ggttttttg ttagcttcct acaaattttc ctcttttatt 360
ttatttttgt aaaagtaaat aaatatgtgt cattagtcta attttttgaa cttattttgg 420
gagagataga ggaagacttt aaaaaattat tattactctc cattttaatt ttgagaagag 480
attgtgttgt accattcctc ttattgcttc caatttcttt gagggcagcc ctagcctttg 540
tacaacgcaa gcttcctgta gtatctctat ctctctctct ccctcttccg acggtgatct 600
cttttctctc tctcacattc atcacccgcc gccgccggta gcttctcttt ctctgacgcc 660
accgccgccg gtaatctctc actcgtcgct ctcaacacag agaaatttct gattgagcat 720
caccaggtcc ggcaactaac attccttgct tctgcatctc tttttcttca atttctggta 780
tagttttgat ggatggattg tgtgtattca atcatttatt gtgttttgat ggatgaaccc 840
gtttattatt cttttttatg acttcaagta attgcaactg ggtacttcta tctgcaactt 900
cttggctgaa gtaattttta gttaagtgca aacggacggg ctgggaccga gccaatctaa 960
cgcttatttt atcgaatttt gaggagttgg ttttgtttgg gtttatagct taggaagggt 1020
ttttggtttc gaagaaccta ccatttgaag ggttgggtct aaaatgtcgc ttaattcgac 1080
ccaatatgac tctgaatgtt aaatattgaa tagaaaagaa atgaaatact atccctaacc 1140
tgtctgccaa tttcgtgcaa aaaagcctaa tagccagttt tttctcgccg gcagtacatt 1200
cgccttcccc ttccaagcgc tacggactgt tgctcaatct ccagaatctc tcaattcgca 1260
gggggcaagt tctttccatc aatcatttta tgtatttttg cttctgccct agatcgttca 1320
tctaaagttc tttacctttt tcttctgttt tgttttttgg tgtataactt atttgatggt 1380
gatggattat gattcagtat cattttctta ttttatatca gcaacaaatt tggatttgaa 1440
atcatttttt aaatacottt tgatgttaag ggtttaggct tattattatg attcagagtc 1500
attttctacg tgttaaatta gtttactttc caagtatgca gttatgttca agcagttatg 1560
cagtcatttt ctgatgtggg agatagtgct gttttcctta aatgttttct atttaaacca 1620
ttgtgcgctt ggttggtggc cgtgcagata attgcatttc tttttttgga ttggggcagg 1680
ttggttactc tctggtttaa ctttcacaaa gaaccaagac agacatccgt aacttgtttg 1740
cataaagaca ttcaaccaag 1760

<210> SEQ ID NO 38
<211> LENGTH: 1767
<212> TYPE: DNA
<213> ORGANISM: Cucumis melo
<220> FEATURE:
<221> NAME/KEY: misc_feature
<222> LOCATION: (1)..(1767)
<223> OTHER INFORMATION: n=g, a, t or c.
<220> FEATURE:
<221> NAME/KEY: unsure
<222> LOCATION: (1)..(1767)
<223> OTHER INFORMATION: unsure at all n locations

<400> SEQUENCE: 38
aatataaata aatctcatta ctctttatga gctagaaagg atgcctaatg gacctacaga 60
ctagaagcta caacgatatg agattaattg gctaaactca ttaaccacat tatgatatat 120
ttgttaactg tgtgtacact ccactaaaga ctcgcagctg aactcttctc actgtagata 180
tatttatgtg tccacggata tagaccaata ccaataagtt agtccttcac aagtgttcat 240
aacactagct gggtcaaatt actgttttcc ccttgggtta cttctagtcc ttaaatacca 300
atgctcctct aatgaacaac ctgtttaatg tccaaccact aaacagaatc ctttctcatg 360
ccatagagag ggtaagacct tcaagtcctg gatacaccat ttaaaggagc gcttatctat 420
ttaccataaa gtcaagaagg agtgaattcc atcttnnnng attatgttcc cagctcccca 480
cccggttttg tcctcaaaat gataaatata ttgagttgac aatctgacca ctctcacccg 540
tacaaatcaa aagacaatcc ctcgcgaata ggagttcata atatactcat aattaagact 600
aagttatcca tgtcattcta atgaaataga aacccaacta gttaatggag ttacatcttg 660
tggttactat ttcgtggtcg ggtcttatgc aaactcatta catacgatac cctcactcgc 720
atgtcgctta cttgaacatg ttgaataaat gcatttatat tagatacaaa gtaagtcgta 780
tccatagtgt taccaggata agttacctag ccttaaccct atactataga cnnnttaagc 840
tgatcttgaa cattgtttcc tgtatgtctc tacatactgt tcaagactca tcaaacaact 900
caagatgtta atttattgga tttaggttat taagataaaa cgaataatat aattaataac 960
acttcttgaa attataataa tataacactt tattaataac taccaatgaa ttatatttac 1020
tatatacgag ttttaagaca taaaatccaa tataagggtg tatgaactgt taaagatgat 1080
gtgctattct tgttggatat tataggaggt atttagtgga ttatttgtga aagaataagg 1140
aggtacttat gggaagactg ctggaggtta gggaggatct ttgaaaatta ggaagtaggg 1200
atcaacaaaa aaaacgaaag ggaaagctta aagcttaaaa aagaaacgaa ataaagaaaa 1260
atgatttaga ccagcatact aaaatggcaa tgtaatctga ggctaatgta tcaattgaga 1320

-continued

```
actttgtagt cataatgatt aatcccaaac aaattagttt tcaagaaatc aaccccaaat   1380

aaaatgactt aaatattgaa gagtttaaat ggtctaaaat tattgttact gtttttttatt   1440

tttggaaaag agacgaaaaa ggaaaaataa gaaacgccca ccgtggggct cgaacccacg   1500

accacaaggt taagagcctt gcgctctacc gactgagcta gacgggcttg gtgtccaaaa   1560

atccaataat attgaaaata ccatatagtt taatgaactg ggcaattgga ataggcccaa   1620

tatattagat atagcgaccc aattgttagg cgtgtcttct tccaaaaatt ggaggcaaaa   1680

cacaaaccct agcatccgct tctgctcctt tatcgtttct ctcggcgatc aattttcacg   1740

gagctaggtt taatcaagct tcaagca                                     1767


<210> SEQ ID NO 39
<211> LENGTH: 2000
<212> TYPE: DNA
<213> ORGANISM: Cucumis melo

<400> SEQUENCE: 39

tttaaataaa aataaaaacc atctctttat tttaagtagt taaatgattg tcgtttacta     60

aattaactct agcctatttt aagacggtct ggtcaaaaaa tcgattacga ccgaccaata    120

ttcatctaac ggtcttatta tttttaaaag atatagaaat gtatctcgtt aataaagcca    180

cgacggtctt tttctaataa aaattcaact aaaccatata acaaaattat tgtaccatga    240

aaaacacttt catacataat gcaaaacaac aatagcaaaa aaccaaagag gaaggggaca    300

atttggggaa aagtaatctc aaatttccct ttttgacttt gttctaaatt agtttattga    360

aataaaatct actaatttcc catttccaaa ttaaaatgct taatctttgt ctcattagca    420

ttgctagaac aaattgtctt ctcaaaataa aaataaaaat acaatatcaa ctatttatac    480

ttaattatct aacatttctc caacataaaa agagttatat atatatccta ttttgttctc    540

taatttttcc tcttttttttg gtaattaatt ataatattgt cctaacatat tatattagat    600

agcttcgaca aaccgttgct taaaaaaaga aaagagaaat ccaacctaac tcaatccgaa    660

aatatacaaa gtacaaaata attataataa ggtagatggt atatgcatca atgaaataat    720

attgtcaact ttcctcgatg atgatggtaa taataataat aattttatat ttattaggcg    780

taatattttc ctcaatttta gtgtttgtat atactttcat atgtttaatt taagttttaa    840

aatttagtcc ctcaattaac ttgaaattaa ttaaagaatg tgaaaatgtt aatgggtgaa    900

ataaataatt tagagaaaaa ccaaaataaa ttagaggtag ggagtaattt tagaagttca    960

aaaaaaaaaa aaaaataaat tagatgtttg aaagtacaga tttgtttaaa tatgaaccaa   1020

cttcgaatag tctttccatt ttttcttata aaaagtcttt ctgatgtgga tactagttag   1080

agtatcctat caactcatcg atccaaagaa catactttca atcgtaagtc gtccattcta   1140

cttcgatcta aaatgatgct aggtttgctt caccttcacc cttcacaaag acaagtgcag   1200

gtgtgcttcg ctctatcaca tgattttgat tatgtcttca agaacttcac agcggtttta   1260

aaaaaacaag aaagaaaaga gtgagagtgt ttttatgtca gaaacatatg cccaagctta   1320

tgaaacttgt tgatcttgta gcgattgaat aacaaatgga aagtatctca tacaatttct   1380

ctatttttca cttttatcga agaactttgt ctcactaact cgtaatctaa aatacaaact   1440

cttcgactct aatatattaa ctccaaactt catttttcac atctatggaa cagataaagg   1500

tctaattttt taaaaatatg atgggaatta aagtatagta aagagattag cttcatcaat   1560

gggcttggat tggagtccaa agggttagcc caaacccaaa acatagtaaa tccaagccct   1620

ggaacaatga atagcacgga aagtttgtgc tgccggagga gcgtattgga aatgaagggt   1680
```

-continued

```
ttaggatagt tatggagcag aaaacgacac cgcatcatta aggacggatt tgggatttta   1740

agaatatatt agggacagaa taggaatttg aaaagtagcc ctagccactc aatttggtaa   1800

cagtagcaca aaaattggag gatacctaag gtaagcgaca tggggtaata cacagaattg   1860

tggctatggc agaattggat agaactccca tttgaggctc tcttttctct taccatttct   1920

acaagataac actactcttc ttcactctcc aaaaccccat cttcttcttc ttctcttagg   1980

ttcctctctc ccttcctcca                                               2000
```

<210> SEQ ID NO 40
<211> LENGTH: 2000
<212> TYPE: DNA
<213> ORGANISM: Cucumis melo

<400> SEQUENCE: 40

```
aattggaacc tgctgatatg aaatgcataa gagaactgaa cctatcagta tcatgcgaaa     60

cctgcagcat agacatacta ccgtgatgtt tcaatttttc aagcaaacaa aatatccaaa    120

aacacacaaa atagaggaaa ataaggcgaa attacaaacc tctctaggat tttcaagatc    180

ttccatattc ctctcagatc cggtgtaaa gacaaccagt tcgaagttcc aaagctgttg    240

caatactact tgtctaaacg tcatagcaag tatattttg gacgaggtac ttgaatggaa    300

atcttgagcg agagactttc tgagcttcgt ggccttttcc ttgacttctc tggcaggtaa    360

aaactgttaa cacagtcaac ttaggaatga caaatacaat cggatagcta aattttatct    420

aacgacaata ttccagagag gggagagaga cacattgttt tataacaaga ctcccaattt    480

catgagatga caacatcgca cgacagtcaa acaaaattct aagagaacat caaataatac    540

tagaaacgga catattagtg aaggagctct taaaggtagc cttgaaccag agatgggaac    600

gccatcaaat caatctcatt catcaatcat ggagttaatt gttccgatgg tggaattcaa    660

aatcggtcat agatttttat tttaagaata aaaattaaaa tggaggctcc tgaagctaac    720

atgccaggtg caaaagtttg ggagaacgcg ttcacgtcaa cattcgaatt cagtctcata    780

aatggaaatt gtagcaatga cgaaaaaatat tcatagttgt tagtcacgga aatcggttcc    840

ataatacacc accgtcgaat gcgagctaaa acgagcacca aattacgcag tcaggttaaa    900

aaataactaa ccagccgggt cgagacagtg ctgtgttcat cagaaattcc cggaaataca    960

gtctccacaa ccattgcagg catcccagaa tcaaggtgct cagtggcggt ttcaccgcca   1020

tcagccgcag ccgcagtaac agactgccgg aaatcgacgc ctccgaccag agaaagccga   1080

gacaagtcat tctcgtacgt ccggacacag ggaagaatct tctcatcgga ctccagcaca   1140

gcttgaagaa cctcttcctc ggtcgtcgga attggcctcc cagcagagca agagaaggta   1200

gaaaagcaat gccttgagtt tttcagaaca attttgggag tataaattaa gggtatagca   1260

aacagttggc gagctggtat agcctgtata ggagaataat ggataaaaga caaactcaac   1320

gccattggag aaatggccat aaacctctga gcgagtgcta gggttttcgt tttatagtgc   1380

tactagctgt gcgtcgccgg agaagcgatg tctcgtgccc acatcttttt ccctccattt   1440

cttttcgggg ttatttctct atataccctc ccaaaatatt acaattaaaa cagttccatt   1500

ttgttttaaa aaaataataa aaatttattt ctcaataatt ttttttgaaa attgaccgtc   1560

aatttcgtac aatctacttt taaagaaatg attacttcat ggatggtttc taaagggaat   1620

ccaaaattta aaagtttaat taatttagat tatgttttat ataacattga ttaaatgaaa   1680

tatgaaataa ggtgtaagtt gatattagcc ctaatatcaa agatgagggt aaaagtaaaa   1740
```

-continued taatagtgaa aagatatcca actgattctt gggtaccggt tcgggtaggg tttgggggaa 1800
tccggttggc gttttttgag cacagagaga tgtaaacggg acgggaagaa ataaaggcca 1860
acacaactat aaattctcct ctcggcggaa aggcggagca gcgtccaact tcgcctttca 1920
caaaatttac taagaggggg cttccattct acgtcgattc tgctcctctt ctactttttc 1980
ccttctgctt tttgtcgacg 2000

<210> SEQ ID NO 41
<211> LENGTH: 2000
<212> TYPE: DNA
<213> ORGANISM: Cucumis melo

<400> SEQUENCE: 41
ggtctcagac ccataggaat agatcattta ttgccttatg aattagttta tgagtacata 60
ataattgtca accgtataca aatcaacatg aaagaatata atgttgtaca tagtcattcc 120
aagtttacta atattatatt ttaggagtgt tctacaccga acctgtcaca tgtacactgg 180
gtatgctacc cctgaattca atatcataaa gcaactttaa ttgtcaagca ttctcttgac 240
catttgtgac ccatttgctc ctactttttc aatcaataac tatcacaaaa agctagatac 300
cacatgtgat aaactcactg aaatcaggta tatggttacc tgtgcttggt cagcactcaa 360
tcagattcga aggcctagtc tttgtatttc ccccctctg cacactacaa atagtcctcc 420
acgtaaagac ccataacaaa acgcaaacca agtacagaaa atctagccga aatccagacc 480
actcaaacat aacaaatctt ctggtaagtt tgaataaaat ataaaactaa cctaatttaa 540
tcaaataata caataaaatg gaagcaacta acataacata tctaaatatg atcacgtagt 600
aggaaaaaaa aaaacattcc aaaactatta acaatcattc ttaatggtat gggtcaatcc 660
ccattattta ggactataac aagaattcct catacctaat gccacatcct atgtccaacc 720
ctcgagatta cctcgtgagt aatcaatctt attcatcctt atttcaaatt atgtgaaatt 780
tctcatcagg ttgatcatat tgactttcaa tacaacttat gattaatctt tcccttgata 840
taatttcgta tgaaaaggaa gttgacatta tgtgattttc tcataaggta aaccaagtaa 900
acttgacatg acgtcttaac aagtcttggt ttctaagtgt aatttactgc agaaaaaatc 960
ctaaattcta tgacttttcc tatgagattg accaaatcaa ctttacgaga aatcttggga 1020
agccatacct acaaagtctt cccccaagaa attacaattt ctagtaaaga ttgttgaaat 1080
ttaccctcca atttttccgt gaaatttgac aaacttgtaa gaatatcaaa tttgggttgg 1140
atattgacat tccaaaataa gtagttttaa aaaggattta tccaacaata atagaagaaa 1200
aaagatagga aataacatac ccacgtaaat ggaatgtaaa tatttatata ttaggtgtct 1260
tgaacgaccg tcaaacgaaa ataaattgtt catccgaagt tgaaactctt taagtgtaca 1320
tttatctttt cgtaagaata aaatgtaaaa ttaacgtgtg aaaggttggg ttaaataagt 1380
tatgtagaga taatattgaa gatgatagaa taatcacgat cgatgaatta gtatagtccc 1440
agagcggatt taaacctctc tcactttcat gctttctata tatatcaaaa taatttcaag 1500
tagttggttt agtcgtaaaa aagtcaacca atctctttta gataaacctt gagttattaa 1560
aaaattagat caaagataat cgttgaaatt gaaattttaa gagtataatt ataacaaatt 1620
ggaaagttct aaagtagttt ttgcaatatt ctccatcaaa atagagtaga aaaatatttt 1680
agtaattttc ttatcttaat tttagttttg taatagttat taggatggtc ctaagttctc 1740
aatccgcttt tagtccataa aaagaaagaa gagagagaaa aaaagtcccc gatccgcgac 1800
acataccaat ccaaccaatt atgcacaatc catgtgatat cgaacggtca caagaataaa 1860

```
tgctttctac acacggatca ccatccaacg gcttttcctt ccatctcatc ctctatataa   1920
tctaccaact ctgtcatctt cgacacactt caattatctc agcttttatt tcatcggatt   1980
ttccatcaaa caaggcaaca                                               2000
```

<210> SEQ ID NO 42
<211> LENGTH: 2000
<212> TYPE: DNA
<213> ORGANISM: Cucumis melo

<400> SEQUENCE: 42

```
actccattat ttggtttgat taaagcttcc atctgattaa taaataataa taattataaa     60
ataaaaaaaa gcgagagttc cattaagtaa tattatctac cgaaagagag caactatcac    120
ctcaaacttc aaaaagataa aatagagacg aaacttgacc aagtcaaaca caaaccacaa    180
acaaccgatc tgacagaaag tttgccagaa tcttcaatgt acacgcgaag ataaacaaat    240
aattaaatct cgttcgtctg gataacataa cacagcaaat gaattttttt aatacatatt    300
ttaaaaaaga aatttaaaat tggtagattt tataaatcat ttccaaaggg tttttcttgt    360
tttaaaatgt ttttttgttt aaaataggca gttcatcacc acttgagaag atccaaactg    420
ggcggcaccg gttctgcgac gcttgagggc cgtctccgac tcttcgccgt aggaggccga    480
tttacgcaaa gaataaccgg acaatgttgg acagttttga cgagaagtta aaccgagtaa    540
gggcttatgc ttcttctcaa tgcgctcgtc gtcgtcgtcg gcgacggcgg cagcggtgat    600
ggggacttgc tctgttgcgg ggtgaacatt gggattccga caagaaggtg ggttcttagg    660
gttggaggga aagtggaaag cgttatgggg ttcttgatgc tgttcctgca actttttgctg   720
tttgaggaag cgcttttgga gatctaaaag agaagggcga cccttttttct tcttcttctt   780
catggtggat ttagaaacct cgcccattgt tcttcttccc tttctcgcag gaacgaagcg    840
cagggaggtt aattgatttc agttttcacg gcggagggtg caggatttct aggcacgtgc    900
gaatcgcatg accctatcac gtgcgaatca gtgacggtat aacgtgcatg caaaggaata    960
gaaacacaaa ccgctcttac aattataaaa ctctaaacta aactacgaac gcatctcata   1020
atgggcccac tccatcatcc tatgggcctt ttgaatttta tgtatactat tttttttttt   1080
tttttttttt tctttaatca caatcaattt ttctggtatt tttttaaata ttcaacaaac   1140
tttttgtttt aatgttgtgt atatctaatt aatttagttt tattggatgt catttttttct  1200
atttttgaaa aaactcttaa aaaaaatata aacaaaaaaa gaatggaaaa agaatatcaa   1260
acaaagagag gagagagcaa ccatacctaa aaagtttgaa agtaaaattg aaaaaaagaa   1320
tatacattga gggcagtgtt gaaaatgaaa ttaatgaaaa aggaaagggt acgtaacaat   1380
aaattacatt ttcttgcagg cttaaacgaa ggcccatata tgaaaaggga agcttcgatt   1440
tgggttcagt tatgcgggcc tggggttggt attgggctta attttataaa gaaggcccaa   1500
atgttggaaa gacgggcttt gagagagggt gttcggcttt tgcccgaggg gggtggggga   1560
gtggcaccgc caagcgaaga caacgaatat taggagagaa aacacaaaga ggcggagaga   1620
tggaagagaa tgaggtggac caatgagata agagtgcgca gattattgag gtggcaataa   1680
atttagaatc ccgcctaaat cccagctttc atttcatgcg caattgaatt tcaatttgcc   1740
attcccctcc atagggactt aattatcccc ttttttttac tctcataact ccctctcttc   1800
ccaccacgtt cgcttcttcc tccccccttcc tcttcaaacc ctaaacctaa cctaacctaa  1860
cctccttccc caacttcttc cgtcggtacg tttcatccat ctcctcccac ttttcatctt   1920
```

tttttccttc taatttcatc tcttttcttt gtttttcctt ccaattgttg ctgatcccat 1980
actatactgc aggattcgaa 2000

<210> SEQ ID NO 43
<211> LENGTH: 1115
<212> TYPE: DNA
<213> ORGANISM: Cucumis melo
<220> FEATURE:
<221> NAME/KEY: misc_feature
<222> LOCATION: (1)..(1115)
<223> OTHER INFORMATION: n=g, a, t or c.
<220> FEATURE:
<221> NAME/KEY: unsure
<222> LOCATION: (1)..(1115)
<223> OTHER INFORMATION: unsure at all n locations

<400> SEQUENCE: 43
aaagaaatca aagcgaaaaa acgaggagga aaagaagaaa aacgannnnn nnnnnnnnnn 60
acataaataa agaatagaaa aataaggaag atgaggaaag aaatcgcaga aaagaaaaag 120
agaaaagaat aaagacaaaa ttgcagggaa agatggagaa gatgaaataa taggaagaag 180
acgaatcgcg agaagaaaat aaagatgaga gggcaaacct gaaatattta aaaaattgct 240
aactttatgg gttttgttac acgggccgta aatagttttg ttacatttat gtaaatttac 300
aatcaattaa ttatacaatt aatcaaattt ccacaaatac aataattgga tattttccca 360
aaatatctaa taagtttcaa tttctaccca tcaaatattt caaccattat taacaccaaa 420
aaattcaaag attaaactta agataattac aaanaaatta ccttaaattt ggggcattac 480
acatttacat tgaactatac aattgtttac cataatcaaa acgatcgttt ttttatgatc 540
gacatgataa tttcctatga tcaacacgat tttttatcat atcaacacct tcatttaaat 600
ttgaagtttt tttcccatcg ttaaaaagaa gtacacgatc ttttagaaga agattacttg 660
cgcgggctga ttaatcgtct gttgactgtg acatttttta tatttttcat catgagcctg 720
tatgtctttt ttgtttttat aattgtttta catcgtgtaa atagtttgcc gattagttat 780
atttgttaga aaacactttt tcaaatgtcg aaaatttgat tttgatttat taaaacttta 840
gtaaaggata gtgtttatta cgtatagaat cccaaatttt cacaataatt tttcaaaagt 900
aatccaaaag aaaaaagcaa caataataaa aggctcaaag cgacgtcgtt tagggcaaca 960
gctggggaga agaggacgat ctgaaaaatc atttcttgag cgaagggaaa aggagctcta 1020
ctaaagcagt cgaaaaaaga aaactcaaac ctcgctgcga ctctcgacat tgattctgtt 1080
ttcaattcat tttgccaaag ttaatcgatc cgaac 1115

<210> SEQ ID NO 44
<211> LENGTH: 2000
<212> TYPE: DNA
<213> ORGANISM: Cucumis melo

<400> SEQUENCE: 44
tatagtttgt aacaatctac tctatgttct ttcaattttg atacatttga atcttaaact 60
ttattgagtt acacaatata gtccttgtat tttaaaattt ataatgactc tatttatatt 120
aatattatag aaatttttgt taaggtttaa taaaaatttt tctgtataaa taaatcgaac 180
acgaagtcta tatttagact gcaatatagt aaaacctgac atctaagttt ggtgaatttt 240
gttttgcttt aaaaactaaa ctattacaat tttaaaaata ttttaattta gttaatgcac 300
attaacttta cggagtaaat ttttacaaga ttgaatatac atagattaaa tagttataaa 360
accaaagatt agagtaaaaa catttaaata gaaagaacta agattttttt aaaacgaaaa 420

```
tgatactaga tacatatata tgtatctata ttataattac tcattttaac atatagtttt    480

gaaagaacaa agattagttg catgtgttga ttgtttttaa gaaggaaata atttttgaat    540

ggaaaatttt caaaagtttt aaatttgaca ataaactcat atttaaagtg tactacaaat    600

tttaactttt ggttaaactc cttgtttagt tcaatcatgt aataaattct cattccaaga    660

atcgttttag aaaattttat tgtgcattta ataaaatata gaacatatat ggcatataaa    720

aattgattac tttttctttt ttttgggacg aaaaacacat tagatataat ctttttgaa    780

agtttatgaa ctttaaaaat gggttatttt atacggtggt caactttatt ttattgaaat    840

tattgagttt ataaagattg ttatatcatt ttcttcttct ctttcactag aatacaatca    900

aacctatcaa actctctatg acttatttag aattcttttt gttatatttt tgaaattaat    960

aaatgaaaag cttagagtct aaattataac aattaaaatt gaaaattttg caataatttt   1020

atttttagca aaatgacgtt tggtttttgg ggattgggaa tggatcgata ctatcccgat   1080

tccggacaaa gaaaccgacc cgagattcga attttttcca ttcccaaaca gagcacttaa   1140

aatttaagca acgttataac ggcgtcaccg aactaaacgg aaaaatatga agaaaattag   1200

aaaaagaaaa acggaacagt caaacgttac ttcacgtcaa tggcaatatt catttttttt   1260

tttgtttaaa taattgaatt taattaattt ggtttataaa aatagagtcc tcatatatcg   1320

cgaatgcgca tttgatcgtg aaggacagct tctcccttgt gttcaagaga gagagatcta   1380

tcattcttat ttggggccga tctctctatt ctcctctctt ctattccgta agtttttctc   1440

attcattctc ctctctcatt tctctccgag atctgtttac aatcctttg attttcattt   1500

ttcctgcttc gatctgtgct cctggtgatt ccctttcct gttttatctt ttgttgatct   1560

tggaattgat tgttcttttg tgggttttca ttgatttgta ttttctgatc tgggtttctg   1620

ttttctcgcc ttgatgtttt gtatttggat ctgatctgac gtaccctttt tttttttttt   1680

tatttgaatt gcttttccaa tgtttatacc tggattttta ttgatgcatg ggtttaaccg   1740

attggttgga tgcgttttct ttgtgctgga tctaggtgtc cttgttttta atttgaattg   1800

tgggtaaaaa tggcattatt gtaatgtgtt tggagtttga ttttgaatct tggctagttg   1860

atttttgaat tacaaagatc ggatcctctt ctttttggg ttgtcttaag atttttggct   1920

ggtttaagta tttgatgtcg ttgtatttta aggggtaact gatgccggct tgttgtgttt   1980

gtattcagtt tacttgaaaa                                               2000
```

```
<210> SEQ ID NO 45
<211> LENGTH: 2000
<212> TYPE: DNA
<213> ORGANISM: Cucumis melo
<220> FEATURE:
<221> NAME/KEY: misc_feature
<222> LOCATION: (1)..(1115)
<223> OTHER INFORMATION: n=g, a, t or c.
<220> FEATURE:
<221> NAME/KEY: unsure
<222> LOCATION: (1)..(2000)
<223> OTHER INFORMATION: unsure at all n locations

<400> SEQUENCE: 45

attatctaaa cattaactgc aactaataca gattacagta aatttgaatt atgatgttat     60

ctagagtcat ttgtcttcaa tgatattgac tcagattcaa actttatgaa aatgttaccc    120

tggaaaatat tctaccgcaa aatttcaatc caaagttaaa ggttgaataa tttagaagtt    180

ttctgcgact tccacccact tattatttag aagacctgaa atcaaaatga tagaagatga    240
```

```
atataaatat atttttttgc tttaaaattt ataaatcaaa catttgacct agtaattgat    300
aatacataat attatgtgac tcgtaagtaa aaaagaaatt gaaataatat atatatacgg    360
agatcgcaaa aaataaaaat gaaagtaata taaagtaaac gcaaagtaag aaagcaagca    420
ttttcaagta agattgaaac ccccgtccct gggggctcca agataacacg ggtgcccaat    480
tacccggtac acgacttttg ttgaacaaca ttgaataatt agcccaaatg aaaatatttg    540
tcgacatatc tttcttataa tatgtaaatt agataccaac acaaacactt gtaacaatat    600
cctaactaac ttggttttaa atatatatat atatattatt tttttttcta tttatttatt    660
tnnnnnnnnn nnnnnnnnnn nnnnnnnnta gataccaata tttagtggcg ggtccataaa    720
ttttatatag ggttattata taataaacac taaaaattta gatattatta ttttcaaagt    780
taggccacaa gtaaaagtgg ggatataatt attatactat aaccatattt tggtaaaatt    840
aagtattaaa tatactttaa aattaatatt aaaatataaa aatcgataat gtgtgggata    900
aatttatgga tgtaaatatc aatgttttaa tgttcaaata aataaatagt aaatagaaac    960
aaaacaagaa gtcagtcttt actactaatc gggactaaaa tttgaatttg atttaaaatt   1020
taaaacttaa ataggactaa aaatgttagg acaaaatagt aacaaacacg aaatttaggc   1080
aaagaaatat aattttattt atttattatc atttttttta tatatataat tgaaaattga   1140
ttactaaaaa aaacaaagaa cggtaaaacc ctagattaaa atcaaaatag aaannnnnaa   1200
cccgaaagga gaattttgat ttccagagct aaacataaca cgatccaaac ccataaatcc   1260
cgcatcgagt ggaaccgata tcttctcccc ttcgaagttc caactctccg tttccgtctt   1320
tcttttcgat tctccttcaa accctctttt cttcgtcttc ttcaaatctc tacatttcaa   1380
aatcttcgct aatctcttct tccccttctc ttccgatctg accgtgaccc cattcgaagc   1440
ttcttctttc accaagcttt ctctccgcta tcaactttaa ctttcgtcct gtattcctta   1500
gccttccctt gcttttgcag tctccgccac cgaacaattc ctatcccgag ataatcccac   1560
ttttgggtcg tgtttctcac ttattcaaat cgctggttct ttgattttgg gcttatttca   1620
ctctgcatct gctgcgactt ggaggttata acatctctct ctcggtcttg ttaggtatga   1680
aggatttgag atattttcta atctatctga actgggtttt ctttcgcttc cgtttatgag   1740
atgtaatttg ttgttctggg aagttttcag atcctttcta atgggcttct ttaatttaat   1800
ttaaagcttc tttgtttgta cgagatgtca agtcttaatt tctagcaata tcagtatctg   1860
ggttggtggt atttaggatg atcaagtctt ttgttattta atggatgaga acaattattg   1920
tcattgttat tattattttt tggaaaaaaa atcaatgggt tttcactggt tttgttgatc   1980
tttttagata attgaagttc                                               2000
```

<210> SEQ ID NO 46
<211> LENGTH: 2000
<212> TYPE: DNA
<213> ORGANISM: Cucumis melo

<400> SEQUENCE: 46

```
cttctcgatc gcagcaattc aacttcataa acaagtccaa gaacgaagag tttgattccc     60
ctaatttaac ttaattttct ggtgaaaatg gaccatactt ttaattacat attattttgg    120
ttattgcctt ttaaatggtc tattttaatc tctaattttt tttattaaac aatgatggtg    180
aatcttttct aaaagaaaga aaaaacttct ttacaaacta tccaactcta ataacaacac    240
taattataaa ctagtctact acctttatta taacagcaat taaaagaaaa aatcgtattc    300
actgacaaaa attcgttctt ttgaatgctt atcgaatgtt ttaatttttt taaaaaaata    360
```

```
tataaatatt tgtaagggaa ggatcagaat taaaactctc tcccctcaat gaaattgaat    420

tatttgtttt tcttgttttt cttttttttaa aataaaccta tggatttagt tggtcggtcg    480

aattaaaatc gtgaggtcgc acacgcggtg tcttgtggat tcaaaattat gattatttcc    540

atcacccctt ggctttttcg ctccattcgg ccatgcctta caaatttcgc tccactccca    600

ttcttctctt cctctcctct ttcaactgca ttgaggccga tcctttaggt aaatggttct    660

ctcccatttc atctctaatt cctctgtttc tttttatttt acttgttctt tttccagccg    720

gatcctccat ttctgtggtg aaactgaatt gttcttatcg atttcttgtt tgaattctgt    780

ttttctctgt ttgtgtctgt gtgtgttttt aatttgtttt ggcatgttga agtttaaaga    840

taccaaaagt tgcgcttcac tactttccag tttcgatggt agctgctagt tgtaacgctt    900

acgttcttgg ttttttagtt aaaatttttt tgcttcttgt tgtttactgt ttagcaaaaa    960

gcatggggaa tactaccaaa gtcccgaact taatagatag atgatcatgt gctaagaagt   1020

gcgatacttt ccgtagctga tacgtgacac agtgtctgac atttgtttga cacatattag   1080

aaacttgtta gtataacata tgtgttaaac aggcatagaa cacctgttgt actaaaaaaa   1140

atatttgtat gataataata ataactttga agtgtaaaat atatccagct aagtttttttc  1200

aagtatacaa gtgcattaac tcatttcctc ttgattttct tttggtataa aaattatata   1260

tattttgaaa accgtatact ttaataaatg tatccttgtg cattatgtcc tagattttta   1320

gaatatggtg tgttgttgtg tctatatcgt gtcgtatcaa tatctcgtat tcgtatctgt   1380

gtttgttaga tcatatgtat aagcgaggac agctatttct gatgttacaa gaccttcttc   1440

aaattttaca ggaaatcatt caatttgaaa attcaagatt acaaatgcaa tctaaaccaa   1500

acttcaagaa caaaaagtgt tatttgttaa tatccttgcg acctcaccca aagtatctat   1560

tacaaacttc agaaaaaact tcataataag ggttgggttg aaaaaaaaca tgaagaagtc   1620

ccaccccaac ctaactctaa aaagcataaa aaattcaacc caacccaaac cttacaattt   1680

gggttgggta gtccgtgttg ttcgggttgt cgggttattt gaactcctag ttttagctaa   1740

gtgtaaactt atttaaggat gttgaaggtt agcattgatc tttctctctc aaatttggtc   1800

aagaggaatt attttttgag tcattcatat agttccattt tgcttttgag catttgaatt   1860

gtttgttaac tacttctttg attaatatat tcgaaagtga aatttccttg gtttacttta   1920

ttgatcagtg tcccatttta ccagttattt cagttctcct aataaccttc attggacttg   1980

agttcggtta acacaaaaca                                               2000
```

```
<210> SEQ ID NO 47
<211> LENGTH: 2000
<212> TYPE: DNA
<213> ORGANISM: Cucumis melo

<400> SEQUENCE: 47

aatgtatcgt gggcatttat tatgacaata gtgtaaaaat gttgttaaca tatctgtgta     60

ttgtcgatga tgtagatcta ctacgccaat agttatagtt tccatcggta tatctatgaa    120

atgtcaacgc cttaaaatag ttgcatgggc atagacttgt ttttttagaa aaatatgttt    180

tatatttgta ttttttttcac taacatcctt ttggttttgt atctaaacac aactcaaaat    240

atatcaaata ctgaaattca tttcctaaaa aagttacaat tgtttcaaat ataagtcacc    300

tgaatgaagt tcttaaaaca caaagaattg ttccttacaa aattaacata agcaaaatag    360

taagatcgtc caaaataaca aacattacat aaactttaga ccaacttcta atttgtttgc    420
```

caggaagtga tctccattga aagtttgtct taaaaaacaa ataaaaagaa aataatagaa 480
acatattcaa taaactagta cattttgcac cttacatata tatacaaaaa ctttacctac 540
tttaatttct tgaaaatcta aattttgaat taagaacttt tcttacaacg ccaaaacaat 600
aataacttat aaatcttagt gatggaataa taagttataa ttcattggtt gattgtatca 660
ttaaccattt ctttcttttg gtgtgagaaa cttatccaac taaaaatatt cacaatagta 720
gggcgggttt gtcgtggctt tgtctgaatt tctacaacat gtgtaaatat tttcaactgt 780
tttatcctct aagacaattt tcctaaaaac aatcatgttg ttcacacgag atttccaagg 840
aaatttaatt caaggagttg aacttgtatt tatgttgatt tgatgcctat gcttaatttt 900
aagatttgag aaagcacgtt atatttgtaa agttggagta ttggaagaaa agtttgtatt 960
ttcaaaagaa cctcaatatt cgagatcgac ggttggcttc aaaagttagg aagtctttga 1020
ctcataggag aatcctatct agactttatg caatataaag agagttctgt tttatggact 1080
tagttggata aataattaat ttgattcaac ggtcataatg aaaacatgtg acatcattat 1140
aattaaccaa tttatatctt taatacacat atcaactttt aaatagttct aaattcaatt 1200
atttgtattt atcatcatta attaaataaa taatgtgaca atttgtgatt gatccaaaaa 1260
tttcatattc aatctatact atattagtta agcttaaaat tttactaaat gcttaaagtt 1320
ttggattatc gagcttccta ccaaacaaaa gcctctattg cacatttaaa atatagaata 1380
gtaggtttat ataatatgaa agattgactc ttaagaccat actctatgac ctaatgaaat 1440
cgacatttat gtaattgata attaataatt aataaaaaaa gtgtgacaaa aaagtggaca 1500
taataaaaga aaggaaattg tgaagcatta gcatccgaat ttcgaagaaa acaaagggcg 1560
ccctcagatc aaagaggaca tactataaag tctccacgct atttcaagaa ttggcgtgat 1620
tctcaagcga catttccgta attcaccaca aaaattaaaa acaaaaaaga actcacagat 1680
tctgatttga cttttgaaac cccaaccccc atcatctccc aatttaattt tccctcgata 1740
tttatccaaa ttcagaaaca taatcttgac aattttatgc tccattcttc caatctcagc 1800
cgtacgtttc attcaaactc caattctccc ccactgcgcc ttccactacc tttttccttt 1860
ctattaaagt gtcctcacaa actcacctcc tctctctgtt tctgtctgcg gtaggatcgc 1920
cgactccgga tttacatttc aggggtcgaa gatttgttct ggggtttctt taatttcttt 1980
atatatatac acacacaatc 2000

<210> SEQ ID NO 48
<211> LENGTH: 2000
<212> TYPE: DNA
<213> ORGANISM: Cucumis melo

<400> SEQUENCE: 48
gccaaggaaa atgaattgtc taagaagaag aaagaaaaga aagaacattt tttgcaaggc 60
tacaaatcaa aacttaaatt atccacgtga cacaacaagt tcagagagga aagaaccctc 120
taaaactccc atataccttg gcaataacca tgacaatagc aataaataaa caagtccatg 180
acataaaata aatattgttt tcattaaatc tcaataattc atatgtagtc cgctccgatt 240
atgccacagt catatatcaa gttcagtatt ttaacaattc aagtagacat acataaagct 300
actatggaaa acataaacaa gaatggaaga aggagggtta aggaaacctt tatccctgat 360
ggagtttcag taaaactgag cttgtaggta ttagtacgaa agctgtgaaa tgaacaacct 420
tggccaggta attgaggcac cccaagattt cctttatcaa cactatcaaa gaaagtaaag 480
aaagttatca cttcaaaacc caactcccaa aagcagctca tcattttcca gtaagttaat 540
actttgaaag atcaaaatca aatctacaat caaattagac ttcttaatag ttattgccac 600
gaaccatgca tttgtcacgt tattaagact atggtttgca ataatctcct atctggttgg 660
atcactactt atactaggca cagcataaac taaagtagtt tcccagagaa ggaagaaaca 720
tgaacctggt tgggtccatc ttggcagtaa aggatttaag ggagaagagc aaaccaaaca 780
taagtttatg gtcttgctgg ggattcaatg tccggagagg ccgattccac tccctgtaga 840
acaagcaaac tccattccta ttgaaaatat acatcatatg cacattgttt ccagtcgctg 900
tcggtaccgg aggcgaggga ctaatttctg acccaccaaa gaactgcatg gtttctggaa 960
taaactaaac taaatcaaat caattgtcat ataaaatgat ctacgaatct aagattctaa 1020
caaacccaac atttcactca actctacaat cagtaaccta gcaaagcaac taataattca 1080
atcattccta ataattcatt gaggttaaaa ataaaatagc gaattgtcaa caggtaaaat 1140
ctaacccgac ccaaatcagg aatcactaaa gcaagaagct gtatgactcg atcaaaaata 1200
acccagatgc atttcccttt ggcctctcta cagaaccact caatatagtt agaaacaaat 1260
ctagtgtaaa attgggagtc ctattcatac ataattccaa ggaaaatgga ttttacttat 1320
gcatcgtata agagactgtg agcaggggaa aatggagaga taatcaccaa tgagctggat 1380
ggtgacagat tcaagaagaa gcatcaaaat caaacaacgg agagcagaaa gatacctcaa 1440
agagcagaga ctgcaaagta aaggaagcga tcaattcaac gacgaagctc ttgattcgtc 1500
aggcaatgat tgccggcgac aacaacgtca gcagatcgga gccttacggc accggagacc 1560
cctccgacaa ggacagagtg aacgaacgtc gtttgtgaac ggtgtaagca aatcgatctc 1620
tcggagtcca actccaaagt actgtttcga tatgcattaa tacatttgat ttttgttata 1680
tcaaaaataa atattatatt aaaatttata aacattaaca aaaaaaaatt aatttcacat 1740
aatttaaagg accatttggt aatatataca aaattgcaaa aatcaaattg ggcctatttt 1800
gttgttattg gaggcccaag atgggtggtg ataaatatgg gcctccaaaa gaataagcaa 1860
aaaaccctaa tttcctctct tcctctcttt cccaatacta taaatcttca ccattttcct 1920
gattagggtt tttgttcgtt cttggccgtc cccttcatcg ttcccagaga gagggagaga 1980
gtaagttgca atagtaaaac 2000

<210> SEQ ID NO 49
<211> LENGTH: 2000
<212> TYPE: DNA
<213> ORGANISM: Cucumis melo

<400> SEQUENCE: 49
aattagcaaa ttgtatgtaa caacgtcatg aagaggcatt tcatcgaaca atttaatagc 60
agagtcaaga tggcccagtt ttataagttt attgatttct cgattcttaa ggtaaatgag 120
atcgcgagca tggaaatgca gacccaaacg agaatatggg tgtggtaaat ggaccggtga 180
tgttgtggct acaaattcgg attttacagc agtaatagtt ctgacgaagg aagcgaattt 240
agtgaccttt cgcatcacag tttaagctta tcagagacct gaacaagggc tctagctcta 300
caacttagaa aggtttgata tggtccgtga tcgggaggga ccgaataaca ggcgcttaaa 360
ttgttgttca taaagaagag gattgtcgtt gatgtatttt aaccaagaga tgattagtta 420
tccacatcca cagagagaac agaagacggc tttctaaatc tacaccgata aaaataaccc 480
taccactttg tttctttaga aaagggtcac attctttaaa aacattagcg tcgaggatta 540
atagggtata ttgactaatg ctctgtttgg atttcgagaa ataccaattt acaattgatt 600
tcaaattaat tatgttttgt tgttgcacga aagataaaaa gaatttaaaa ttcaaaagga 660
tctcaaatct tatttttaac ttaaaaactt ttatgaccca aacggtttat gtatgattta 720
aaagtagaat acctctgtga attcttaatt tttttttctt tccaattacc acataaatat 780
gaaattttaa atacatttat tttaaatttt atatccgaaa caaaataata atttaaaact 840
atttctcata tatgaagtgt gattcgatct aaattataaa ataataaaaa tttacatcta 900
gttttgatta ttttttttcg ttagatacta aattgttaag aaaataacat ttttaatcca 960
aagttttgaa gaatatatga cttttaaaat ggtatttatc tttttagtgt ctgattttta 1020
aaaaatggat ttcaaaagtt catcaaatag cattgtattt ttattttaaa taattttgac 1080
atttaaaatt agagtaatgg tttataaaag acacttgatc tctaaaacta ttttcttaga 1140
tataaatacg tatgattatt tttaaaaatc aatcaaaata ggtaaattgt aaaaaaaaaa 1200
aaaaatcaca tgaatagtag ttgtaattat gctctcaaac tttcggttat gaaaaataaa 1260
cattttaact tttagacgtg tcaaagttga gtcaagttgg accttcaaag ttatgtagtt 1320
atataaattg taatatatgt ataagcttgt ggattcaatt ttatcattta tgggtccaat 1380
ctctacaatt atcgtaagtc tatgggtcaa ttgtaacaca tgtggagttt aagagctcaa 1440
ttttggacgt ggatgtgttt tgcaaccaac tccacacctt aaaaaggtgt ttttttttaa 1500
tttatcaaaa aacaagaatt tagaatcttt aagtttatct ttaaaaatca acggacattt 1560
tgaaaaccaa ttgaaactac tgttataaac ctaacaacta aaagtatatt ttttaagacc 1620
gaaagcataa atccataaaa aaaaaatcca gaactgaaaa tgtaactttt atagttgaaa 1680
atttagctaa attatacata ttaaaattca aggaccatat aaaattaaag tacctgatta 1740
aataataacg aattaatgtt tggtattttt aacctacatt agaaaaaaaa aacaaaagaa 1800
aaacggcata ctatttgtca agcgtccgat gggaagaaaa tccaacggtg agtgttagta 1860
ttgaaatacg cagttctcgt gaatgagcct ggcttagatt tgggaacaag agccaacccc 1920
tttcgaccga gaagccgtcg tcttcaccat attcgcctca accattcgat agccacgttt 1980
gaagaagaat taggattgcc 2000

<210> SEQ ID NO 50
<211> LENGTH: 2000
<212> TYPE: DNA
<213> ORGANISM: Cucumis melo

<400> SEQUENCE: 50
agccaatggt tcaattaaca gctctagttc tagcatggct accgctggta acctttctat 60
gactagagac gtcttggagg tggagggtag ggcacgagga ttgaaaggtg agggtttggt 120
gaaaactcaa gcctttcaaa ttcaagaaag catgcttgac ctagtagcat ctggtgatct 180
tggggaattt gcaatggata ctcataccct tagtcggcat tcgtctcttg gttctgctgg 240
tatatatttt tttctcttgt tttctagtga tattttcttt tatcaatttc cattatgaag 300
atggaatctt atgttctatt ttttcatttg gaatgtaggc tttcacaatg aaaaaattgc 360
taatacgttt ccagaagagg ttgctaaaga cccgtaagtt cttatttctt aacaatttcc 420
tcagtttaac aagttttatt tactaacata tccttagttg tataaatatg aatctattat 480
attaactatt tcatttatct atcttttaac agggtgacca ttcacaacaa agataatact 540
tcattgaaac gccctcctgt ctcacgcact tcggcatccc aggatggatt gtctgtcctg 600
attcctgatc cggttgttag aggaaagaac tcagatggta aataataagt gatccattct 660
gttatcttct ttattcattt tcaattttgt attttgtata tatttatata atattttaga 720

```
aagataaaag atccatcctg aaactttgtt tcaggtggaa gaccggaccc aactagtatc    780
ttggtgaacc aagaaaacat ggcagccatg aagaaagaga tgcgtttccg gcgctcttct    840
tcttgtagtg acagcgacgt gtcagagact tcttttattg atatgctgaa gaagacagct    900
ccacaagaat cccatttgac aacggcggga gttccagagc catctgatgg aatgcaggga    960
gggaaaggtg ggaaaaagaa agggaagaag gggagacaga tagatcccgc actactcgga   1020
ttcaaagtca ccagcaaccg aattatgatg ggtgaaatcc aacgcttaga cgattgatcc   1080
attaggcaag atatagaaca gaaattgatt tttttttttt tttttccaat catttttgta   1140
gattgtgcag ttatttgttt tcgtgtttgt ttaaccctct tgtaagttgt tgtatatagg   1200
tttcttagag ttgtcagctg cgttgaaaca tgtggccggt atatgtattc caattctttt   1260
ctttttcccc gcagttgtaa atgatcaaat ttgagttggt caaattacca aacctttgta   1320
caggaacttc gaagagagtt gaaattttat tctttttctt ttttgttctt ttatagagtt   1380
cgagattatt tgtatgaata taatcaaaag caaagcatgt aaaaataaaa tgatttgaaa   1440
gggaggtttt ctatcccatt caatgtgacg aatccaacac ttaaagtaaa tttgaaaact   1500
gtctaattta tatgtatgga atgtaatgct cttcaagaaa ttatcttatc ttctaatatt   1560
taatgggatt cacataaata tgaaatttca acgtttttct tttccttttt gttgtgagat   1620
taaggatact agataataac cgacctcaac cttttaggcc aagaggtctg gagtctttat   1680
acttgaaaaa agtttacaca tattctaaaa gattaaaagg ttaattgttt ggtaaaacat   1740
taatgatgac gatacttaag gtttcattaa aaaaatattt ggaacaattt gtttataatt   1800
taataaaatt gtaactttga acattttgaa ttacattttg tttttccatt tttacggtcc   1860
tcgaactcat cgatactcac aatggagaaa aatatcacaa tgccgaaaat acccttcttg   1920
ttcccttctt atacaaaagc aacactattg gccttatcaa cggagcagca gctactctcc   1980
tttagcacaa atctccatcc                                                2000
```

<210> SEQ ID NO 51
<211> LENGTH: 2000
<212> TYPE: DNA
<213> ORGANISM: Cucumis melo

<400> SEQUENCE: 51

```
tggtgtaccc acttggtttt ttctcttttt ttcttttagc tttttgctcc taaatttctt     60
gccttagttt tcaaaagctt gtttttattt ttgaaattta accaagtgaa tagaaaaaaa    120
aaagagaaaa caaaagcttt taaaagcttg tttttatttt tgaaatttaa ctaagtgaat    180
aggaaaaaaa gaaaaaagct tataaaattt gacgaaattt gctgtatttt gtacatttta    240
ctatttttct attttaaaaa atgtgtctga acgaaaaact tatattatga gatttaattt    300
tcaaaataaa attataccaa acagacttta gaattgtcaa tcaaatttga caatgattag    360
gtgcattttt taaagttatc ctaaagtttt tttttttttc gtagtcttgc ccttgctttt    420
atcgttaaca aataaaattt tccttatata tatatacaca tttaactact caaggtctgt    480
atttttttcca cctgatttat ttaatatttt ttttttttgc agaaaatcta tttgtatttt    540
aggggaaaca aatgagtgaa gagatcatca agcaacggtt gcgatgttgc agcggaaaaa    600
tctttggttt gtcatttctt gtgatggggg tttatagggt agtatggtta ttgtatttta    660
ggatgttgat ttttatttta atgagccaag agagagatgt ggattctaaa attgatgatt    720
gatattattg atgtgatata aatatataat tttgtgcgaa aattgctatt ttattttctg    780
```

tatgctcatt cagatcacac aataatattt gatgtagctt tacttattga caaaatatag 840
gttttaatct tgtgctcata caaacaacag ctatgggtga aattattttc tgattttatt 900
tggcaaagat gatgtcagca ttgtgtaaat ttaatgtgaa ttacacttct gatttcttcc 960
caatgtgccc tctcaaatat tggcaccaag ccatttaatt gtaaatacgg aaaggtcata 1020
aatttccatg caagatttat ttcatgttta aaatgattgt gtgaaacaaa atgaaaaaca 1080
agaaattctt acctccaacc tcaaagtagt cgatatgtca aggttcaata tcaattttaa 1140
atatccatga atagctttga tatcttttat aaatgcttgt aatatatata tactaatagc 1200
aatgtctata agttagtttt gagagtaata cttgttatag ataacaatgt tactctattt 1260
accactctac tattgaaagc ttctttttct tccatttatg aattaataac ggtcaagatc 1320
caattgcatg agttactttt aattaattac aatctaaaat gttaatataa gtctaaaatt 1380
gtccaatata tgtgattttt tttttctctc tcaaaccttc ccttcttttc attgaacttg 1440
tggttcaaat ttgatggagg acactgggaa acagcacaat tcaaagagcc aaagattgag 1500
taattttttg atttcagagt tttcatctct tcttcattct acacctttca cttctcatcc 1560
acaactatcc aatcaaccat tgccacgtgg catcaaaaat atccaaaact gaatgagatc 1620
caccacaaag ttcctctcat cactgtttgt catcaactca tcaagaactt catcatcaat 1680
cagaaatcca acatttcaac ttctcttagg aaatgacatt tttaccagtc tccaatgtca 1740
aaaactcaca caaaatccct ctttccaatc taaattttac aaagataaca ggggtaattg 1800
aagaaactta gcagtaagtt aacatattat agctttcatc aacccaagtt tttttggttc 1860
ctttctaaac tgtagtttgt tttcttgatc cattctaaat atttcctctg catgaaaaga 1920
agaaaggaaa agtgaaggcg aaacctgttt tatgcttcag aaaaccaatt cagagtaacc 1980
aaagatctga acttcagacc 2000

<210> SEQ ID NO 52
<211> LENGTH: 2000
<212> TYPE: DNA
<213> ORGANISM: Cucumis melo

<400> SEQUENCE: 52
cgctcaaatt actaacatcc ttctctttct tgttcccatt cgactagaga gacactatct 60
tatccacctc agttggctgg gtgaaatcat tgaaactaac ggttgattgt ccagattgtt 120
aaactaccct atgttttatc atcttggtta catttatagg attgtcagaa taataattcc 180
ttttgaaatc atattctaat tggcacagga ctaaaataat gcctttctta agctgtaata 240
attagaatct aaacagtgaa gttagtaact gattgatgac atttccacga ttttcattta 300
tatcctgtgc agctattctg acatcacaaa acatttcttg attttcattt ttacttgtca 360
tccatcagtc aggacgatat cggcgcgctt gttgacgacc ttgtcctaaa tacaaagagg 420
cttatccgag ctacttcaag ggagattgac aagtggaaaa gatgaaatta ctcatttgtt 480
attacattgt acaagtgatc tattaggaag aaccacaatc aaaactgaag aaaaaagaaa 540
cgtgctggct gtctacgtgg cttttagagg tagaatttat gtacaattgt ttagaaagat 600
gtatttaatt gctctaaatc tcatatgcat tggattttga gcaatcttaa aatgccgaat 660
acttaatgta ttatcgtagg ggtccctaga tggcagattt atcatgtcca ttctccagaa 720
agaaagaaaa aaaccctttt tattatactt gttcatttta agctttttct ggttgattat 780
aatgtcagta atttaaaaaa aaaaaaaaat tactgtgtat tggcatcggt tatatgttat 840
atacaaccct agttaaaagg taaagttttg ttcattcggt cattagtcat tcctatacga 900
acgtcacatt gtgctttata atttcaatag gttaaaagta ttcaatatag ttttttaagt 960
tacctagtag aggtgatcat tggttgatcg gaatcggttt tttgacaaaa ccgccactga 1020
accgatcata gtcggtttag taaatgttca aatcgacctt gacatcgatg agtaaagatc 1080
ggtcggtcgg tttttgtcgg atgggccggt ttaacacttg gaaatactat tttgaaattt 1140
ttcgaaatta atccctcttg ttttcctacc gaccgatttt gggtttggtc ggtcagttcg 1200
attttttcgg cctatcttac tcactcttat tacctaggga ttgaatttca ttttatcctt 1260
agttttaggg ttcttttttt atacttttga aatatttatg tcgatgtcta gagtttaaaa 1320
ataacacttg aaattataat ataatttttt ataattgtta gctataattt tacgtccaaa 1380
tatcaactca ctcgcaactt gtttaatcaa ccaataatat gtgtctggaa tagtaagtat 1440
ataacttgtg gaaaatgact ttaaaagact tttttaaagt atttatttaa tgccaaaata 1500
tctatattta tgtttataca ttaacataca tatccaaagt tacatattag atttgttaaa 1560
taattcaaaa tgagctaaag aaaaaaagaa gttccatata ccaaaataaa atataaaaag 1620
ttgaagacta aaatagagat tttgaaacaa ggtaagttag atttacaaat tgcaatatgg 1680
gagaccaaac caccacataa caaaaatccc aatgtccaaa tggcgcaatt ttgtttagga 1740
tagctcacgt tatccaaatc actcaatcgg agagaccaac ttaaaggcca catctgccac 1800
gtcaccatac tccaccaatc acaacacagc attggatttc tcagcttatg agaccaatca 1860
caaacctgaa tccgacgtgg catgtccaca tccaccagta ccaaccatat agcttctacg 1920
ttctccacat ctaatcttca ccatttacac aatattcttc attcttcttt cctcccttca 1980
atccttcatc ctctccgccc 2000

<210> SEQ ID NO 53
<211> LENGTH: 2000
<212> TYPE: DNA
<213> ORGANISM: Cucumis melo

<400> SEQUENCE: 53
aattctaaca actccggaac caaataattt agcatggatt gaaatataaa tcttcttgac 60
ttgcaaaaaa atcattgtaa tggtcttatg ttggttatag ttagggtatc gaaacgccat 120
acaggaatat gggattaaag ttaacttttg ttcatcaatt tcagcttatg aacttctaaa 180
atatcaattt tacctttgaa cttatatgtt attacccctt tcgattgtgg tatgttaatt 240
aatatctgaa tctcagtcct tatgaaactt ttttatactg tcacaaacat atgaagtttt 300
attgtaagtt cttagaaatc atctaaaaag agtagtttgt tggactattt attttatttt 360
ttcttattaa gttgttttca cgccatttca gtaaaataac tatagtgaat agagaatcaa 420
acttctaatc ttaagttaag gtagtagggt atatgctaat tcaataagat aatccgtgat 480
gcttgacatc tgacttaatt gttataagtt ttaaattttt tattgtaata tttaaaatac 540
tagtttttgg tttctaataa agaaataatt gaacaattac aaatatttat acaaaattaa 600
actagaatat atgatcattt tccttcgtgt tagaaaaagg gaaatatatg tgtgtattta 660
tacatattag atattgtttt actatattcc attttcctca cgggaaatgg aggattgagt 720
gggagataaa cattgtcccc aagagaattg ggaatggaaa tgcaaatgac atggccctcc 780
acaaaattgt tcgcctaaaa atgggctttc tcacttctca ctccgcaaga aaaatatcgt 840
ttcccttcga attattcggg cggcaagatc tcaaaaccac atgtttttct ttctttattt 900
ttcaagccta cattatttat aaaaatataa cttaagcaga gaattatgta aattcaagtc 960

-continued

```
cattttttcgc ttcacttagc taaatcatta acaaatctgt aattttgttc ataaattagc   1020

tcaccaatta tgttttagcc cactaaggcc cattagacat ttttattaga aaaacatgaa   1080

ccgttggatc aagatgtgtg ttttcttttc tttttctttt tattttttttt gggttttggt   1140

ggggttttgg tggatcatgg tggatcaatt cgtagcttta gcaacctatt attatatgga   1200

gggaaagggc gtattaatct gttagcgccg tccgggagtt tagctttctt ccccgagcct   1260

cggtcttatc ccctaactcc aaaaccctag cccaaaggta atccactcct tccccctccg   1320

ctcttcatct ttttctattc atcatcttta atctgttctc ccttttggtt cttagattct   1380

tcttttgttg gattctttta atctttactc atggttggcc ttgtaagttt agacgacgtt   1440

tttatacatt ggttaatcct gcttctctat ctattcgcac gctagggttt tcctattgtt   1500

ttctattctg ctctacttct gcaaggttgt gttcttcttc gttcaggtcc ctttttttaa   1560

ccgaaattaa attaatgcaa attcgtttgt gcttctaatt aggaagcctt ttggaacatc   1620

tcgacatttt gattgctgca tttcatttcg ggtatatttc tatgattgaa ggatgtgggt   1680

ctgttcactg catggtcatt acttatgcag ctatgcttat cgagtccatt atgtttgtgc   1740

aatctgtttc cggattcata attttttagt aattgatcag tagatgaaaa aagatattgt   1800

aatattcctt gagtgttgca ccagtcttgg tgggtatctg ctcctgctct ttgcttgtgg   1860

attttacttt tattatatct gtattattcg aaatgttctg ttcttgttat aacttatacc   1920

cgaagatgtg ttcctccccg cgtctagcgt tgtgggttac ttatgatgga catggttttg   1980

attctgtttg gtttgtgcag                                               2000
```

```
<210> SEQ ID NO 54
<211> LENGTH: 1547
<212> TYPE: DNA
<213> ORGANISM: Cucumis melo
<220> FEATURE:
<221> NAME/KEY: misc_feature
<222> LOCATION: (1)..(1547)
<223> OTHER INFORMATION: n=g, a, t or c.
<220> FEATURE:
<221> NAME/KEY: unsure
<222> LOCATION: (1)..(1547)
<223> OTHER INFORMATION: unsure at all n locations

<400> SEQUENCE: 54

ataatgtgtt gatgttgatg atcatgcatg gtatattaat ctcatgatta aagacgttaa     60

gattaatatt cattccatgt ttatgatggg tgttcttagg gttgtaccca tatgggtgtc    120

cctcgggatc accacctttt ttatgactgt atggttctac gagaccacca gtctgtcatg    180

atatgtttat gaatggtacg acggggtcac ttacagccca attgcttaag tgttccttcg    240

ggttcactga agacctattt ttcctaggtt ttcctttgac ttcagcaaaa atcagttttg    300

tcctaggtgt tcctcgagtt cactgaagac tagttttgtc ctaagtgttc ctttaggttt    360

atcgaagatc agatgtgttc ctacagaatc attagattgc aagtgttcgg gaacacatcg    420

gtttaggggt acttctttac atgaacccta atggaaaatt aacagacatc tagcggaatt    480

agtagttggt cccttactga gtatatattt atactcactc tttttatgtt taatatttca    540

ggcaaaggtt aaggtagagg aaagttgacg agtgatagaa aaggatctgt gacatgtcat    600

atggggactc agtttcgttt ctgcttctat gtatcagtgt ttcagtattt tgtttnntaa    660

tgaaaattta gtcttcctct attcaagaaa gtgtctcttg ttattgttta tttttagtaa    720

tgatttcaac ttagtataaa tagttggatc attacaaata atatattggt gatatacttt    780

gtaatgatac attgagttat attattcata tgtttaatat acaaaactgc aatattaaaa    840
```

```
aatgaaaatc acgtaataag tatatcaaca aaataataca tatattacaa gcacgtcaca    900
acactaatat acaaaactaa tataaagtaa gatcaaagca aaaccaacgt aaaaaataaa    960
acaaaatcat ttgaaattaa atttaactca aaatacacat cgaagaaagt ggagaaaaat   1020
cacaatagag ttaaattact ttgattaata accattatat ttcatattga aaataatatg   1080
tcattagtat tttaaaatca agattaagat aggaagaatg aattgctctt ttcgtataaa   1140
aagggatgat tggggcctta cgaaaggaga aaaatacata tgttatcgaa aaaacaaatt   1200
atttttcttg taagagagaa tgattatatc cttaaaaaaa tgaaagaaag aaacaatcat   1260
ggcattaaaa aggaaaataa ataaattatt aaagggcagt tcgataataa taacaaattc   1320
aacgagagta ttaaaagaaa atgagaattt gcaaaattta aacaaatgtg tatattaagt   1380
acagccaatg caattttcaa attttaattt atttggttta cccaaaattc aatttctaaa   1440
ttgagaggag gatatagtaa attcacacgc attatcccct tcgagtttca tcatctcacc   1500
cattcttgca tacagtgcag ttacaattcc ttcattctgg atagaca                 1547
```

<210> SEQ ID NO 55
<211> LENGTH: 2000
<212> TYPE: DNA
<213> ORGANISM: Cucumis melo

<400> SEQUENCE: 55

```
aaacacttat catgttatgt atcccacatc gaaaagataa aagagacttc atgatcttta     60
catgatatat gagttactcc ttcgactacc attggttttg gagatggatt caacccaata    120
atatgaatct gacccaacaa tggtcaactc aaagagacac catcttgaga tacatgttgt    180
gtacccatat tagatgaatg actatacctc gcaatattta taacatacat gaattacttc    240
tcttactgta atttggtttt gacgtggagc ccatgattat ctaattaacc ataactggta    300
tatgatatat tagtaggtaa cccgaagagg ttctaagata aacacagaat tcaatagaat    360
cagagccttt ccaatgatat ggctttagat gggaatgatt tgaagtataa tcattctacc    420
acaccettta tatttgtctg tcaccagaaa tctcatcttt tcttgaggta ttattcactc    480
gaaaagaggg aggcattttt gggttaccca tctaatgcac gatgaactaa gggaggtcaa    540
gttctgggaa tacagctagg caaccttcac agtggataca ttcgaacaaa tgataaatgt    600
gaaaatgaat catttcatga gtgtgactaa cccaatcatt cctccttcta tatctttgaa    660
tcccacagtg agtcagagta aaagttccag caacaagtcc tacaacccaa attctttagc    720
tatttcttcc accagaacaa aaccaagcaa aaaatcagcc acaaacacag ctcaacaatc    780
tataaaggcc aaaatactaa gacagtcacc attaccacat tgaaagccgt attttccaac    840
agactttgcc tgcaaaatag atcacaaaga cacgatttca cattggacag acgccacagc    900
tccacaatct caatttcaat caaataaaag taaatcaaag ctaaatagca agtgtatggt    960
accacgaaag cagcatggct gacgccactg aggcctgtaa gagagaaaac aaaataagtg   1020
tagaagataa agtgaaatag aaaaatcaat cgataagata gattttcaga ttaccatttt   1080
tacgggaatt gtacggaccc aaacacaaac cccatagagc gccggcctga agatgaacag   1140
gggcaggaaa ttcagaggaa gaaattaaag aaaatgaatc atagtttgag aaattattcg   1200
taaagtttac cgttccgacg cgaatgctgg attcgacggc gagggaagaa caaggaacga   1260
cgccgttgag ttcgtcttcc atcttccaat tctcaatttc cttcggaggt ccgtatgctg   1320
agagctctgt gtctaccaag ttccaaccat actacgtcgt tttggatttt tatttttatt   1380
```

```
ttctttcctc tcttttgcca aaaaagaaaa aaatagtatt ccaacctaaa acctcaaaat   1440

aacatatttg ttgtacaaat tataattagt aaacatttgt cattgtgagc ttggtatgta   1500

atattaacac gaactttatc gctaataatt tagacgttaa tgaataattt gagcattgcc   1560

ttcttatatt gttattgtgt ttataatagg attgcttaca atgtaaccta gtatgttgtt   1620

gagctcgtta actttttttgt ttttcttgaa tattcaaagt taaaaaattg tacaagtttt   1680

tggtgacgtt ttcttactac attatcggga tgaagatcaa atatagctta gattagagaa   1740

gataatcatg ttgatttatc gttaaacttt gactacaaaa tccgtttaat tttttttttgg   1800

atgaattagt tatacaattt aaacttaaaa ggggtgaatg aagaaagagg atagttttac   1860

aaattcgaag tgaaatgagt tatttctgct taaagaaaac aaatctcctt cgtgctttaa   1920

aacacaaact caaaacccta aattcagcgc cgattcttca atacatctct gcaggaagtt   1980

agggcaaagc agaagcaaaa                                               2000
```

<210> SEQ ID NO 56
<211> LENGTH: 2000
<212> TYPE: DNA
<213> ORGANISM: Cucumis melo

<400> SEQUENCE: 56

```
acttccaaaa atcagcctca tgggatattt aaagaaaacg taaattaaaa ttagcatcat     60

ttcatattga acaaactaca aaaattaact ctaaaagatg atggtaacta caactaaacc    120

ttcaattttt cattgtaaaa atcgaactct taaacttgtt caaatattaa aatttgaccc    180

tcaaacttaa aagagctaaa aaaagacctt caaatagtaa aagtagaact ctcaagctta    240

tagaattatt acggttatga ttatagccat agatgattca atcgattttc ctccaagatg    300

atggagtata attcttcaaa tctagctgct tagatgttat cacgataatg aaatcatatg    360

ggaactcaac aaaaagaaag cacttaatgt tgaaagacat tattctttgg gtgttgagtt    420

gggcgaactt gatttttatt attaatccgc aaaggacctt ttgagtaagt tgtggcaatc    480

tttattggag tgctaagatt tgttattcga aatttcttgt tttgatattt ttccaactaa    540

aactaatttt tttaagaaat gcaccttcaa ctgatttcat gcgtgtcctt ttgcaagact    600

cgcatgggac ataacacatc atcttatatg gcaaggccta tgtgtcagtg gagatttgac    660

gtcaatttct ttccactgag agtcgtcctc tttgtgatgg cagaactttg gagagtcatc    720

aaaattggtt ctttgaaaat gtttcttatt ttgatttttt tttttgaaag aaatgagagg    780

aataagatat ttttacgagg actctactag tgggtcaatt tgcccgcata tggatatgca    840

taagagtcct tttggagaga aagggtatga tggaaagaca ttgcaaaggc ccgtccacta    900

actttctatt atacaattag gtggaagcca cccatagcaa tgtcttggtt gaacactgat    960

attacttgaa accatgcatt taagatgtga aatctcgact agatgcttta ggaatttgga   1020

ttgtgtctgt tttgttgaat tcaagttcat tcctaaatac catgaagtta agatccttga   1080

agcaatgaag accatttatt tagatcctta attcaaatct ctttactaaa gatgattgtt   1140

tataaatgat caatttgttg aatgatgttc tacttgatat ctctaaagca tctcttttcg   1200

gtgagaagcc cacaacttga atagtattcc ataaatcatc tatttttagt ttctatcatg   1260

ttctttaaca tcaaaacatt ttagcgcact ctcttataac taagacttag aaaaacacga   1320

atcttccttt cttacgatat atatcctaaa tggttttcta tatttgtgcc ttacaatata   1380

atcaattctt tttctatttg atattgtcat aaaataatac tgataacata gtttttatgt   1440

tttattaaca cctaacaaga aatatggaag acgttaatat atcttcaatg tcgatattga   1500
```

atcattttat ttatgaatat atccacgcgt caaaaaatat tttaatcatt aacttctagg 1560
actaaattca aacattcttg gaaccataga caaaagaaca aaatttgcaa cctcaacaaa 1620
caaaatttta tctttacatt tgcggctaca attcacaaat tcccaaacca tgatagaaag 1680
gccccaatct cccacgtgat aaacacacat atggcacgtg accaaatcaa aatcatccac 1740
atgatgaaaa cttaatggac agctcggatc ccaacaccca ataaaaagca gccatgaagc 1800
tgacgtggca gatttccccg aaaacctttt aaataataaa caataaaaaa atatatacat 1860
aaccgttggc aacgtttttc cctccacaca ttttcccatt gccttatctt tctttccctc 1920
caaacagcga gggaagaaga atccaatcat cttcttccaa taatttctaa aacgaaattc 1980
tgctcgattt tccctctcca 2000

<210> SEQ ID NO 57
<211> LENGTH: 2000
<212> TYPE: DNA
<213> ORGANISM: Cucumis melo

<400> SEQUENCE: 57
tgggtaacat tatgagtttt attataattt aaatgaagat caaactttaa gttgtagggt 60
caccatagga ataaaatata atcaataagt tagggcccct tagtcccacc tcgtaaagga 120
gttctgtcat acatatacat tatgatatta attctatctc catgagtcat acatgtgatt 180
ttagtacttg taattttcat tctttttcct attataattc attcaagtac tgtcaatatg 240
gttaggtatt gaaattaatt atagactcag atatcatctt cattaatgga aatggaatgt 300
tatattctac ctctcatttt tacacgttga tgataaatta gaagaaaaaa aattattatt 360
tatattgttt taattgtgag atattagttc aaaatgtaat taataaaatg atacgtgtct 420
tataataaaa ttaaacaagt ataattaaat ataaaacaac atacacactc tttaactaaa 480
agacacaact cacctaatgc tcgacttaaa atcactttgt gtcgtaactt aaccatcaaa 540
gcatgttagg gtaaacacaa taaagatgat ttttgagtta tgcatgtcat ataatgtcac 600
ttccaatttg acttatcttg cttgcttgat tcatgtatat aaacaaaaac atgaaaagta 660
gtgtaaggat accaattacc tactgatttt ttttaaaagt agtttgtcta agacgtgtta 720
aattactaac ttagtcacat ttgagtttta gttctaactt attaaacata aagtaggtat 780
ctcccttact catgtgtgtt tcgataatgt caaattccaa tgtttgatta accaaattgg 840
gtaatttaac ataaatattc ataatataat attttttatg gaataccgac atctaaaaag 900
aaatcaaaat gaatattatt aggaggtgag tttttaagag agaggaaaat aataaaatat 960
ggcatcaaca agaacaataa taataagaat agaaatccga caaaggaaga agtggatgcg 1020
tgttagtact attgacattg gcatatgaac ggttgggttg ggcctcaaat aatttgcatt 1080
tctaacttcc aaacacctaa ttcctttttt tttatccata cttgcaaata tatatttata 1140
tatattcaac aagtagttta atttatttga tataccactt taagttttaa attgatggta 1200
gtgtataaat aaataattta ggattaagca tgtctatgaa ccttttgaaa tttgatggag 1260
tatatataaa acagaatact catgggttca ttataaaaat ctaatagtaa atgtattttt 1320
tatttcattt aaacattttc aaacttttaa aaattaaaat tatcttaaaa aacacgtgtg 1380
gtttcgaacc atatggttaa aaatattgag gttctctatt ttgcaaaaaa tttggaaacc 1440
ttcatggaag ttgatataaa ttgttgtaat tagttagtat tttttcttta tttgtggctt 1500
aatcatgcta tgattgatca ttttatcatc atttctataa tgtaaaacaa tatatttgat 1560
gtgtattgta aatttttatg caagagtaga aaattaataa aaaaaaaaga gagaaaaata 1620
attataaagt aatataaagc tattaacatt ttaagaaaaa taatagtgaa aatgaaagtt 1680
tcggacaata attcaataaa gaaatttgta gatttcgatt aaaatttcca aaattaagat 1740
tttcattaac acgtgtgcct cgcaaccgtc tcctacgtta tcccgtaagt agcccaatct 1800
atcccattct tacacaagcc gtcggcccaa attgattgta ggccatcggc ccactcaaca 1860
cccacaaacc ctagcccctt gctcctcctc ctcctctttt cacggctgct cactccctct 1920
ctttttacac cttctccttc tccttctccg tccctcttcc cttttctgct actatcttca 1980
gcacttgctg agcttcaacc 2000

<210> SEQ ID NO 58
<211> LENGTH: 1591
<212> TYPE: DNA
<213> ORGANISM: Cucumis melo
<220> FEATURE:
<221> NAME/KEY: misc_feature
<222> LOCATION: (1)..(1591)
<223> OTHER INFORMATION: n=g, a, t or c.
<220> FEATURE:
<221> NAME/KEY: unsure
<222> LOCATION: (1)..(1591)
<223> OTHER INFORMATION: unsure at all n locations

<400> SEQUENCE: 58
aatgttgatt tacccttgct ttgtttgaat ttcgtcctcg tggacttgac ctttggtctg 60
cttcgtatag gactatttac ggctgccctc atagtccaag tccttgtccg ccttacccta 120
tactctctat ctctagacaa tgtgaagcgg gcccttctat aatattgggc cttgaagttt 180
tgggctttgg atctgccgaa ttgtgttggg tttctctccc aatttatttc atttctttat 240
tcaaataatt ataaatatgg aattttattt tatttaaaat ataaaagtta aaattgaacg 300
aatccaaaaa taatggaatc aaatcgacgt tttaacatat ttttcaatta tgtttttaca 360
ttcattttcg tcctacaaaa atattcccac ctttatttcc tcgatatcgg aggtcacttt 420
gtatgtttca ttcgggtgat gtgatataga tcgagtttct atgcttgatt gactatggaa 480
atatatttta agaagatgtt ataaaagtaa aataaatgtt ttgattgtgg atataattat 540
attttaaaca agatgaggaa taattagatc cgaaccaata atcttgagtc aagagtgtac 600
attgaaagtc gtatattaaa taatggttga gtttataata atattgatag attgcagtta 660
accatatttt ctcaagttgt tgaccaaagt acttatttta taaacagttt agggaatgtt 720
tatgaagttt tgccaagtgt tttgaaccta tatgagtatt gacttaattg gtatataagt 780
gcattaacaa tcaagaggta tttaatttga atcgtcctac ccctatcatg ccaacaaaac 840
aattatatgt ttgtcatatt ttattgaaag tgttttcagc gcaatttagt ttgatttgcg 900
tacaaaacat gtctacacgt atcgagttag tagtaatggt tgctagttaa gactgtgaac 960
taaaacttta aatttacatt aaaaanaaaa acattatggt cgtttggtcc tcatatgtga 1020
ttgatagata ttgattaatg agtatttgtg gttgttgcca acaataaaga tgtagacaag 1080
tgaactatgt tggttgtcaa atcttgtttg tatttgttat gtgtggtttt caccaccaat 1140
gttgtagagt gtcagatcca gaatagcttg atcatttttc atatatatct acagactcaa 1200
ttagtagata aaaactataa gactttgact tatttctctt aaaatgtctc ctcgttctgt 1260
acaatcctca acaacgtttg gtgactttaa aacatcacaa gaatctaaga agaatgatga 1320
attagatgca atgcaaagat ttggacctta attttgttac tttaaacttt atatccgaac 1380
attggaagag gcaagcaaaa agcgcgcttt agaatcgcgg tttctttggg ccgagtgggt 1440

```
tgctcataac agcggaggtt tgcttttctg ccaagaaaac ccctcaaaga aaaagggctt   1500

aataagcagc tgctccattt ctaagtgggt ttagccttta gcacggaagc gccaattcga   1560

ttcaactctg atacactgca aaaattccgc c                                 1591


<210> SEQ ID NO 59
<211> LENGTH: 2000
<212> TYPE: DNA
<213> ORGANISM: Cucumis melo

<400> SEQUENCE: 59

aaagaatgga gcaagctgat attgctaagc aaaagcttct gcatgattgt gaagttcttc     60

accaccgcct tcaagattct actgtcgact ttttcattga gcaggaaaat aaactaattt    120

tggaaactgc ttcgacagct gacgacgcaa tagatctgtt ggcaacatct gataatcaca    180

ttaaccttct tttagcagag gtacttgcgt ttgtttccat tgaaatgcat ttgcatattg    240

aacttcttca tcctgaatgg cacaagtttt tgtccataca aacaggcaaa gcttctggct    300

catgatgcta acaacagcga tgacactgct ggatcagccc gtccaaatgg aactgataaa    360

ggggcagctg accaagtatt aagtaacata ctagcaaata tgcttgtcga aaatgcccga    420

ttaaggatgc agatgaacgc cgtcatccgc tgtgttctaa atgcaaatgg gacaagtgag    480

aaagatgaag atgaatctct caaggaagaa ctgttctaag caagttttta gaggaagaga    540

ttcctgaatg cacatataca atgaccttat actgtcgtgg caagaaatgg gagagctgta    600

gattttgaat aaatgcaaca gatgttgccc attaatttgc aagtcctgac aaatttggtt    660

gtcggaggtg tagaaatgat gtatcaatta aatatttaac aaagtgcctt ttggcttggc    720

taatcatggg catttgaaga ctttgcactt ggtaagagct caaacaaaat ctgggtggct    780

aaatttagtg ttgattaaat ggaatttcac tgatattcat gatctgtctc ttcttccttc    840

attgatatat tatcttctca gtaaactcct gggcctgatg cagaattgct tttaaccatc    900

tgcatacaga gaagaagtaa aaactagctc acgtggataa agggaaattt ctactgacat    960

gttggcatta gaagaaaatt ttgaaagagt tctattacca taacatcatc tacttccgtg   1020

tattattgaa actattattt ctcttacccg gagatattaa attaataaat ttctatttac   1080

attttgaaga tgctcgtgat tattgataaa aatgatgaat cattattttg attacgttac   1140

aaaaaagtca aagagagtaa caaagctatc aacaaaatat tagtaatata tacaaaaaaa   1200

gtgtaaattt aatattaaca ctgagaaata tacacttaag ctaatgggtt aaaatattta   1260

tccattgaat taaatatggt ttttctgtat ttgtgatatt ccaataaata tgaagctgtt   1320

atactgtcaa attcatattc tgcctataca atcaatttca agtcactcaa ttttgcaaaa   1380

ccatatcata ttgagttcaa ataaaatttc atatctatat acataacgaa aatgttatgt   1440

ttttgctttt aatgttttgg gtatctttct aagctacaag aaaatgtaaa aatgataata   1500

agaaatagat tatattaaaa ttattttaca aatcaaattg cggggatagc tcagttggga   1560

gagcgtcaga ctgaagatct gaaggtcgcg tgttcgatcc acgctcaccg caaatttttt   1620

tcttcttttt tttcccttgt gtatcatttt aaatgggctg ttcttacttt gaactgcgga   1680

agcccatgaa agctaggccc aatttagaaa ccgaccatct caagggtcgg ttcgtcattt   1740

atcaagatcc gataacccga ttcgctccat tttagtctct gctctttcat ctccctcacc   1800

cattctcgct tccactgagc gggcaaggga gcttaacccc tcaaagccct agaaaccgcc   1860

attggagaag ctccactagc ttcttcttct atcagcgaac gtattttcgt cttgtataga   1920
```

cctttcatct ctggaaccga tcggaagttt ggagtttctt ggtctcagtt tgtagattag 1980
ttttatcttg gcgtctcaat 2000

<210> SEQ ID NO 60
<211> LENGTH: 2000
<212> TYPE: DNA
<213> ORGANISM: Cucumis melo

<400> SEQUENCE: 60
gtgcatttaa aataatctag ttgcatgttc taggttcgat ttattatttg gggatttagt 60
tgtgtctgta tgattgaaaa aattaatgtt gatcttgtaa cacaattgtt tttccctcga 120
tgatttgaga ttatttcaac aatttagatc caatgtttaa aaagccacct tggcatcttg 180
ccttcctcat tcgcaacctg cctccagttg aagcctcgag gctcaaagcc cagtgcccta 240
ggacttcttt attaatttta cttaaaaata aagtttgtat ccctaaatgc ataaaatacc 300
cttgtgttta aggctttctg tttcttcgcg tttcacgtca ggtcagacca tgctcagcta 360
tttttccacc attcttcttc ttctctccca aagtctatca agtattttat ttccacacat 420
atattcacct acgccaattt ctttttaaaa ttttatagat atatacagtg cacctcacga 480
aaacaaagtt tgcacttctt cagttttttg tttcgcctca cacttaagct acaaaaggtt 540
attacgtttt agtaacccac tactcagctt taaaaacact atttgtatca tatgacgtcg 600
cccttatgga ataatttcac ttgattatcg ggttgtttca taaacaatct tactctgttg 660
tacctttgac aggcctggag agcatgcaac tcctctcttg cttgagtttg agtaacaata 720
aaatcggaaa ttttactgca ttggagcctc tgagactgat aaaattctta aaagttttgg 780
atatatcgta caacgagata ggttcgcatt cgatcgacac aaccagatat ctcttctcat 840
ctccactgtc gcattccgaa gaaattgatt tgagcagtga tgaaatggca acaaatttta 900
ctgatatggc aagttactgg gaagcatatt ttctattcaa agatataagc ttgatgcaat 960
tggatataga aggaaacaca atatctagtg aaagtttcaa agcatttctg gtaaagattc 1020
ttcccaaact ccactggctt gatgggaaac gggtacaata gatatggctt aatttatcta 1080
catccaatcc tctgtccatt gtggttgttc atcccctgaa tgtaaaaagg tacgctacga 1140
actagcattg atcctaaatt gaagacattg gttttgattt cttcccaatg caaggttaag 1200
aactaaggat ttgatattgc atccaataag cataggttat ttaagatttt ggtgatagtg 1260
aaaattaggt gacatgtctc gaaagcttaa agggatacat gaggtatgga gatggagatg 1320
gatgtggtta caacatggaa atgaatacgg tgcccagttt tttggactgc tctaaatcaa 1380
attttatcat atacattatg atactgtgtg ccaattgtat ttaaaaaggt actgaacttt 1440
acatttttgt tgtcccaaat tttgaaggat tgtagtttta ataattctta taataactat 1500
caatgttaat taaaaacttc agtatattta caatttttct aaaaatgttt gctatacgtt 1560
tagttattat cttgatcaat tgccccaaga gaaaaattac cctggactat ttcccaaaaa 1620
catcttctag tcgtccatca gctatagttt caaatctgtg tgggcccagt cggcccagtt 1680
cattgggcct gagaatagag atcatgaacc ggacggccca aacctttttc aggccccagc 1740
caagcctggc ctacaaactt ctaacctaaa accttatccg ttgaagcaat ccaataaaac 1800
aaagccacgt aagcacccag gatctaaaaa tgtatccaaa tccaccaatc tgaggccaca 1860
aatttagcct ctgtggctga atggatgtcg aattacaaga atctctcgat ttcttcctct 1920
taaatccatt tacccttcaa acaaataaac acaaaataaa gaaaaggaga agaaacaatt 1980
gtcgtaatta gcagcaagaa 2000

<210> SEQ ID NO 61
<211> LENGTH: 2000
<212> TYPE: DNA
<213> ORGANISM: Cucumis melo

<400> SEQUENCE: 61
acctagaact tctaaacgat aatctcggaa aaaaaattgg aacaaatcat aataatgaca 60
attaagaagc aagaaccgtt gacaaaagca agatttagag ggagtaaatt tgcatggttt 120
ggtgatgatt atttagttga atttagccta ctcttaggaa gtatccaata atcatacgca 180
aatttcacgt agcatatgaa gcaagtgcat cataataccg cataacctgc ggggttttgt 240
catctcgatt aaacacaatg tgaacatgat gatgtctatg tgtttccagc ttttgttcta 300
atgatgatag acgatagtgt ggtatagttc atatccttga tttaattgtt tccatgtata 360
ctatcgaatt tttaatatat aattaatgta tgaaatcaaa tatcaaataa tgattgtgat 420
ttaatggaat aagatcatgt ctaaaattgg taatagtaat aacgaagaag gaagagaata 480
ataaactacg atttcttgtg aatctcctag ataaattagg ataaaaacta cgagtaagaa 540
tagaataatt atactatata aaataggagt tacaaatttt gtttcttaaa ataccaagct 600
ctgttacaag aaaaaacttt aggtattata tcttcaacat tttgttaatt tgttagagat 660
tttaggatag tttgtcaact atgggtcttc taagaaactt ggtcatcaag caaatctaat 720
gactcgaatt gtccttgatc gatgtgaaag atccaatgac ttcgaattat ctttatgcaa 780
tgtgtaagat ctaattgtca taaattgatc tcatgtgcaa agtgtaagat ccaatgatcc 840
aaaattgtct ccaacaactt cttgaacaat aagataactc tttgaagaat cttgaatatt 900
aattttgaca tagatagatt gatcttgaat attaggaaat aaggaaattt tcttatgtac 960
atgcctgaac tccttcaaca tagcattttg aatcatatct cttctctagt aacttgtata 1020
gttgcaatat attttgcttc tgttgttgat atatcaacac tgattgaagt tttgaaaccc 1080
aacatatagc tctagtggca agagttaaga catatatgtg gtgaatttac ttctatcaag 1140
atcacaatct aagcagatat actttgaaaa taaagttaga ttatccatta tacaatgtaa 1200
tatttacgga ccatttaact cgcttagaaa ttagagttat tttgcaaact ttattgacaa 1260
atatcttcaa aaatttcata caccgtatag acactatcat aagatgttaa agaaaaaaaa 1320
aaggtgaatt ttccatacaa ttaaaaaaaa tcttaaacta taaaggtggt ttcgatacct 1380
ttaaactttg aaaagtttca ttttaattct cgcacttatt gttttaaaac aaacttagta 1440
aaattttcgt ataaatttag aaagaaattt tatatttaca ggtggggaaa attctaaaca 1500
catagatgaa gataaataaa aacacgatca actataaact atacctatta ttaccttcat 1560
ccttaacacc atgcactcaa atattcatta attctctata tttttttcta tcttagcctc 1620
aaaatttact ttcatcctaa acttcgagcc ctcaaatttg cgttatttca ttcacgatat 1680
tcctttttta cgttctttca tttatggtat tcttctttac gttcttctat ttacgatatt 1740
cttcttgctt ttatagtgtt ttagatttgt tcataaacaa cgtataaatt gaaaacttta 1800
taaatttagg gcattaaggt ataattgaaa ttaaaaccat atttatagtc attaaccaca 1860
gtattattta tcctttattt attaaaaaaa aaatctactt ttagttttaa atttaggcat 1920
tttacgcaaa gctaattacg acataaaaca ccaaaaggag accccgttcg atcttcacat 1980
cttctcggcc agaaacgacc 2000

<210> SEQ ID NO 62

<211> LENGTH: 2000
<212> TYPE: DNA
<213> ORGANISM: Cucumis melo

<400> SEQUENCE: 62
gcaatggcgg aaataacgta gcagagggca caaacaacga agaggagctt cgttcttcgg 60
tgcgccatct gggaaagtga gaaatggtgg acgaaacaca aacgggggaa tcggattgga 120
tctctcagaa aagaaatggt tggattcgat cacagatcaa tgaagcacat tactcggttt 180
ttcaagaaga ttacaagaac ttgcttcttg aaacctctct tcttctgttt gaaatttttg 240
ggcgtagaat tgaggaccgg agcagtcgcc tgaatttggt cgtcgaatcg attccacgga 300
aacaaaaata tgaagaaacc aaatgaatga cttagcccac tcactacgct tggcgacgtg 360
ttcttcttac gaacggacca atcaaatgcg agcctgatga atatgggcca atcatattat 420
gccacgtaag actttacttt tgcccctgac ctatgggaag aaaattgtgg tcttttctta 480
tgtcaataga agaaaaataa aattatatga aagtcttaaa aggaaaaaaa caaaccatgt 540
taatattact gtttaaaacc ataacacaaa atcaattatt gtttatgttt tgagactccc 600
ttatggtgtt tgctagatag tgtggatttt gtttttgaaa attgtttttg aattttgtta 660
ttcttaagtt tttttatccg aaaatttcat tctagaaaac aaaattatat aaaaccattt 720
taaaacataa tatatcgtgt tatagttttt taatgtaacg ggattacacg gcctattatc 780
aattatataa taagatagat taaataaaca aaaatgattt atatggcttt tttaaaaata 840
aaatttaatc tctaccgctt ataactataa ttaagtcatt ttggtttaat aaaatcatat 900
tatatagtct cactcgtatg tattatttac aaaagatgtc gactttttat caaattatag 960
actaaactat aattttcttc gaggctaaaa ttataattta accaaattta taaatgtaaa 1020
atgtatttat aaataaacga ataatagctt gtcgtcaact atattttagt ggataagtaa 1080
gattagtttt atgatttata aatatatagt ataaaacaca tttaaacatg ttttgttcat 1140
tgcgtttggt tgatatttaa acctagtaac gaaaaagtat taggtattac attaaattag 1200
catccaccta caatgttaaa tttttaagtc agttaataat ttaagagact ctcttcaaca 1260
ttgacttcat gcaacataaa atggtagaaa ttttcacacc attgtttatc gacattacta 1320
cgtaggagaa tggcaaaact ttcttatatg tatgtgtgct tttagatgtg tctttacatc 1380
ccttatcaaa acgaaaacct aattctaacc aaatcaaacc aacccgggtt gttgggttat 1440
tcttacaagc catttgttgg attaaaaaac caaaatagag gatgttcggt tcaagcattt 1500
taaagttttg ggctatttag ttcgaccact ggtttgttca aagtcgggtc ggaccaaacc 1560
gtgagcgatg taaacaacaa aggtctaaat tgggccggga tcagatgggc tgaagatcca 1620
cgattctggt ttccaaccca aggcccaatg aattacaaca aaaaagcgta ctcaggaaat 1680
ccgaatctgg atctcaacgt actctaacct ctcacagttc gccacgtcaa gaaaacacgt 1740
caatacttta ggcgaaaatc aagtgaagaa ttccccacaa taaggaatcg tatatccacg 1800
aaactatcca atcagcttac gccatcggaa gattcggaac aaagcaacag ttcaatggta 1860
tatcataggg tgagaataag tcggttccgc agactagtat ttcttagtca aactttacct 1920
gcttcaatcg gccgccgatt tcccgatatt tacaacattt agttccgatt tttccctcga 1980
agctctgaag tatcgtaaaa 2000

<210> SEQ ID NO 63
<211> LENGTH: 2000
<212> TYPE: DNA
<213> ORGANISM: Cucumis melo

<400> SEQUENCE: 63

```
gatcaacctt gaaattttcc cacatactgt gttgtaaagt tgtccccaat ttcattcaca      60
aattacctac ttgaggaatc ggcagtaaga agagatcata atgtattttt gctactacac     120
tcgcaagtct aatcagagga tttgattaca atatcttgct gctgtaatag attcgttcat     180
aaattaatcc agattgaaaa gtcaagcttt acttcatttt catcgacaat gtagaaattt     240
tgtttataac tttgtactat tgaatctatt gctcctcgat ttgccccctt ggtacgatat     300
caagccatta tttttccaac tcttactcgc aacttcaacg catgaacttg accagcttca     360
acctataatc ttatgcatgt ttttaatgat taaagctgaa atagattgtg aaacgtacct     420
tattctcact accgctgcca aagccaacca agcttccacg ggtacccata aggtccacaa     480
tcatggcact cttggatgac atgtattggt tcctactgtc tcttccgggt tctcttatta     540
atggccccga aagcaacctc tcccggcatt ctcgaaattc ggctcactaa tattctttag     600
ctactaaaac acatgtcctc aaatttctca tttaaatgtg atctgagaaa gtcattcgac     660
ccattttagt ttaaataagc atcaagtcaa aaaccattta acgtgggctt aaaaatttac     720
agcagcgcag cgtacactaa agtttatgaa cgatgaaagt gggtggcaga agaaagcaag     780
aagtccgaga gacatgccaa aaagagtaaa agtcatttgt tggggccttg acagcaaggt     840
tccatatgca tcggtccatt gcagcatggc ggctcaaaat taaattttca cccttgcttt     900
tgcttctcta acctaccctt ctacgcatcg tgtctatctt ccttcacact cattttgtgg     960
taagctttaa cgcaacattt tcttaatgta atttaagctt ggcccaccaa tccctttgaa    1020
aagtttcctc tagatggtgc gtgtcaattt caaattaaca atttgaactt atagttctaa    1080
cccccatatt gtctgccctt tttctcttct tcttcttctt cttctagttt tgttctggtt    1140
taatcttttt cggttttctc tgtgcagggt agtagctttt aagcttagtg attttctctt    1200
gttaacaact ctaagcagtg aattgttaga gacctattat ttcatataaa tactagatga    1260
cttcgactca ttgattaggc tggaagctgt caaaattaaa gagtttgaca aatacccact    1320
aatttggtaa ccaagagcca gcaggaacat ttgtatttat tgagacaagt gaaagtttgt    1380
tattttcttt actcaaaatc tctctttaat tttatagata tagacattac ttggataaga    1440
aagggagttc accggccgga ggttttcctt caaatttaac agtgactgag gtctctttca    1500
gctttgtttt tttggtgtta ttactgtttg ctcaatcctt tgaacgagtg gtgtaacttg    1560
ttaaatgccc acaaattcat gggacgcaat cctttaggag aaaggttggc cactagttat    1620
tggtggttac cgtggctctt agcaacttag catcagaatt tgtcttgaac ttctagtcgt    1680
tgaaaattct cttcatacaa agctaagtct gcttatttgt aggatccata aacatgagat    1740
gataagggtg atgggcctaa gaatgcttga tggaaacatg gtcattggac ttgcttatta    1800
attgaaaaaa ccagccccgt ctctggttag aaccctcatt aggattgtat tgtttcaatt    1860
ctttcagctt gttctggatt ttaaaggctc caatggtttg agatgatagt catggaggtg    1920
ggaaggaatg gacaatacag ttttgaagaa ctgggttatc tcaaatggga aggtgaaatg    1980
tttatgtcag tatttgcttg                                                2000
```

<210> SEQ ID NO 64
<211> LENGTH: 2000
<212> TYPE: DNA
<213> ORGANISM: Cucumis melo

<400> SEQUENCE: 64

-continued

```
atcttcaccg ttaaatcgcc gtggttgtta gcggcggcga ggagagagag tgctctttct      60
ctgagaactc ctgccatagt agacctaaag gaagaaagtg gtagtgaaac aaggaatggt     120
gaggagggtg agaattgagg aagtggttag ggctttgaag gaacggggaa ttttatttcc     180
gggaagggaa acaacagggg agaacacagc cggagcggtg tggttgtgag aaaatttaag     240
caagcagatg agacgacggc ctggcgccga ggacaggcat atgaatatca cgtggctatg     300
gctatgggaa attgaacgta ggccctttct cattcttata ccaatcttca tttttctatt     360
ttctagggtt tcttttcttt cttttttctt tttccttttt cacattttta tatgtcattg     420
aatttcgaag tttggagtta atatgttgga gtcgtgtatc tatttagctt catgggttat     480
aacattattt tggatgatgt atgatattta atctcaattt aagaaggaaa cgagtaacca     540
aaaaatctta taatgaggtt tgtccatctt ttatgtatta ttctccactt atcacatttg     600
tttgaaataa ataaataaat aaatgttgtg tcacctcaaa cacaaccata tggttcaaat     660
tgaaatttaa cacttgatgg tccctatgtt ccatacgacc taacaaggtc atcttttgat     720
tgtgaggttc atccaacata aagttgttat aaactaagaa tatttcactt atgagtgttt     780
atgtgcacgt tgttggtata ggccataatt ttcaatcatt taaaactttt attaaccatg     840
atttcacatt atcttgatct ctcccattcg aatatgattt tggttcatct atattcccct     900
tataaactca acgttacgtg cctaccagtt ttcgcttggc tcatccccaa cccatatctt     960
actgtggaat gtttttctc tgataccatt tgtattgttt cacaccttcg aatcatattt    1020
tagaatgttg atacagtacc taatgcatgt gatattcccc tccatttgtt gtgacatggc    1080
agcatttgtt cttacttgtg tttgaattgt tttctaagag aaaaaaatga tatctccaca    1140
aaccaacgca catcatttta gcatatcatg tgtctcattc acgtggttct taaaaaaaaa    1200
tcaggacatt atccaataag acgtggtcaa gggatgaacc aaatgaaaat taaaagggca    1260
tgtaatggcc gagttcatga atgcgtcata aatgaatcaa tatcacacta aaataagacc    1320
gatcacaagg gtgtgaaagc atagttaaca ataatataaa aaaaactaaa agctcatatc    1380
tatgccaaca acatacacat tattttcgat tgcttaatcg tatgaacttt aaagttaaac    1440
gtgtttattt taaagttaaa cgtgcttatc ttaaaacaat cttatgttgg acgacctcca    1500
caatttttc cattacgcat gtgagaaaca cattgaaagg actcgaatta gcatgtagag    1560
aatggtgtag cccccattct ataaaagcaa ctcaagatct gaacatgcat tgaaatttca    1620
ctcttcattc ctgacacata cataaagaga agcaagtacg agaatcatcc tctacttttt    1680
attcacaagt tttaagtcaa atttcaactt gatttgtatg tttcaaaacg acacacctac    1740
tcatttaatc ttgagcgtta cttcaattgt ttttatgttt caaaatgtta aaaaagaaaa    1800
aaaaaaaaag ttcaatagtt ttgtaaattg caaaaaaaga gaattacgag tatgcccctg    1860
tacatttaga agaagcgtaa ggtccatatg ggaatcagaa caatcaatcg acggccacat    1920
ctcacgagac ataaacaggg ggagttggag gaatcgacgg agatcggaat ctggtttagg    1980
gttttagcaa aagaagaaca                                                2000
```

<210> SEQ ID NO 65
<211> LENGTH: 2000
<212> TYPE: DNA
<213> ORGANISM: Cucumis melo

<400> SEQUENCE: 65

```
aactcagtga atacgataag aaatttaatt gaagttaaca aactcaaact taaatatttt      60
ttaacacgga caatttaaaa ccaaattcat agtctccttg tatagtgttt agagtgtgtc     120
```

gcttcattaa acctttctat cgtggaacaa atctcttcta atattttgtc aaaaacctat 180
catcacccaa aatatcatga taattatttg atgaggatca aggcttagag aggaacaagg 240
gaacttttca caagggtgga gagatttagc tattaggttt aactcgttgc ttctaatggt 300
ggatgaataa cgacaaattt taaacaatga acgttatcac gttgaaacta tctacttctc 360
tcaacctact actttatcat aaggtttgaa aagttctatc gaaaatttta aatacataaa 420
acataaaaag gaaaattttc attggagaat tttccatata tgtttaccca caaaactaag 480
gctaattaaa aagctaacct taagactaag gctaaaatgg tatcttatgc tacatttttc 540
agttgctatg ttttgaagca aaagctaatt atttgctaat aatgagatag gcatgtgggt 600
gagtgatgag cttagcctgg cctgcctttg tgtttcttct tattctctta aatatcattg 660
ttcaatcaaa atagttttgt taaatttagc ccatcctcac ttcaacctct tatatttgga 720
ttggccttct ttgtttttttg ggcttttgat atttgatgta atggacttca atcatttata 780
gaagccttac cctacagaaa caaacaaaca aaaagaggaa aaaaaaaatg gtgagttggt 840
taataacaac tttctaactc aaccaatata tggtgtgtgt atatatatat atatatcgaa 900
tacaaaatat gaatatgata tgaccacata aaattgttga aagggttgaa aattagtgaa 960
ttggactttt aaattttgta gtgtagtggt ttacctatga tgctcgtaat gttatttaat 1020
tttaaatgtg tttttttttt ttacaaaaaa aagtctcgcg gtgcaagttc aataagttga 1080
tttaaaaaca aatccatcaa aataatgttc gcttgatatg atcgagtata gagccgaatg 1140
tgtatcaaac ataaattcaa actttaatag agtgaaaaat aaatgctacg caaacaaagt 1200
ttttgtatta gcttcttaaa tgtacatata tacttttccg attcaaacac ctccaaaata 1260
aaactcaaaa gttaaaattt agactcagaa aatgagagaa aaagaaaact aaaaacgaat 1320
tctaaagata agcattttca aatataggaa aatgaacaat aaatatttac aaaatagaag 1380
aattgtaaaa aacgacaaat tgacataata cttacaaaac ataacaaaat ttcagattct 1440
atcaatgaca tacactgata tatctttatt agtcatagaa agtctatcat ttataaaatc 1500
caaatttttg ttatatattg taaatattta aatttgtttt accatattta aaaattttag 1560
atttatcacc aacaaataac catagatttc aaattttgct ataaatattt ttaaccgttt 1620
atttaccata atttttctat tataaaaaca aaaaaaacaa aaaacagata aaagcgaaga 1680
aaaagtaaga gagcagaaat attttttgat ttaggtttca tttggtaaaa aattgttatt 1740
aaaaaataca aactaatggg aaacaataat aataatttaa ttttttttaaa atctaaaaag 1800 aaaatagttg acaacaataa tttaataatt taatacacaa gccagtgtta ttaatctctt 1860
tttttctaac aacgcctttc acgagacatc ctctcaatcc tcgacatcca gtggaaaaac 1920
agtatccctc aaccctcagc tttccccaac cgccctccgt cgttcttctg atcgtcgcca 1980
ccctactccg tcatcggaaa 2000

<210> SEQ ID NO 66
<211> LENGTH: 2000
<212> TYPE: DNA
<213> ORGANISM: Cucumis melo

<400> SEQUENCE: 66
catatattta ttatgttcca cttgataacc attttgtttt tgaaaattaa gtttaaagac 60
gacactaatt ccatcttcaa ctttcttctt ttgttatcaa cattcgacca atagtccaga 120
aaaccaatta agttgttgaa aactaaaaaa aaaaaaaatt cttataaagt tgtttttttt 180

-continued

```
ttaaatttgg ttaaaaattt taatcattat acttaaaaaa tatatacacg aatcatagta    240
gaaaattgaa aacaaataaa cttaattcca aatctacttt aaaggctcac tatctgtcaa    300
gaggctttgg tatagttgtc tgtactgatt aagtgtgaga gttcttttaa tatttgtagc    360
tgaccaataa attctttcct ttctttctaa ttttgcttta actccctatc ctattcatac    420
acaataaata tacaccatat tctaattgac aatattgttt ggatttgttt gttttcttta    480
cggtaggcaa gaagttgcct agttgttgtc tgacctcaaa accctttgtt gataagagca    540
aacaaagtct agttttccaa aaaaaaaatc accaactcaa ccaaatcttg agccttttac    600
taatttccat cccaaactaa tatctaatca gtgcttacat gtttgagcct tcaactcaat    660
ttaacatcaa aacatcttgc aaccacacct tgacatgagt atgaaaacaa tataggagag    720
aactttagta ttacattgag ttccattatc attgtacatt ctcaaccaac gaaaccaacc    780
caaaacaaaa tagtttttg taacatatga gattaggtat cgtcctagtt aatgatttta    840
caaagttata tgagtattca tttgttgata tagtttgacc ggatcggaca gttggctaca    900
atggtatatt tctataaact aaggtataca atttttcatg tatgttgttt gatattgttt    960
tattattggc acatgtcttt tgtgtccaat agtaataaca aggttgtttc ttatctaaat   1020
aaaataaact cttgccagat aattgaagtt agacttttaa tcaaaacgta atattaaatg   1080
gggatgagaa ataattgatt attaggtaaa cctaacaata aaatctttaa attgtgttag   1140
aatcatttag ttagtcgagt tctacactaa aaaaaattaa aaacactaaa atcatttata   1200
aataaaatat tcaatatctt caaaatgtac taaaacattg aagctcataa aactaatcat   1260
ttttcttttg attaaatttc tctctcatat taccaagaaa cctaagataa cattaccaac   1320
gattcatacc aaaaaaattt attatcattg aacatatctc aaactagtgt attcaataat   1380
ggttagagta gtagttatat taaggtgcca tgagtttgat atttttcttt tttgcctaaa   1440
ttaggttaag ccgtagctag cttgaacaat gctaaagatc ttcttaagag tttcgtagtt   1500
taacgtttat atgataaatt ttattacatc cgaacttgat atttaatttt tgtggctctt   1560
atctgtgttt agtttttctt attctctttt aacttgtagt aatcaaatga aagccattg    1620
caaatgagga caaatgcatc tgcaagatat atattagcca atctcttgat atttttatgc   1680
tctatgagac aatatattct gccatttgcc catcaaatgg ccataatttc tcaagatttt   1740
tccatttcga gtttgtttca atcttctact ccttttgttt ttcctttgtt caatttttttg  1800
gacctttgat gaaatatctt cataactcct atgacgtggg caccatccat tggttgtcat   1860
ttgataagaa atatgtgtca atggcacaat tcccattcca tttatatatt atatagttcc   1920
taaagccata tccccatgat ttatatcctt cttcaagctc acaattgaac tttaacatta   1980
cttcttccct acacaaagat                                                2000
```

<210> SEQ ID NO 67
<211> LENGTH: 2000
<212> TYPE: DNA
<213> ORGANISM: Cucumis melo

<400> SEQUENCE: 67

```
aaataatttg tggattttat catattatgt accttagact ttgtaaggtt tataacacaa     60
gatgtggaga aatcccatga tgaacatgga cgttattata tcctttgaaa ctaaaaacaa    120
aggaaaaaaa gacaaatggc tgagtataag aaaaagagaa gaaacaacca aaaagctaaa    180
atgtcatgct ctcatatgta acatatttga attgggattg atttcaagat gtattttaaa    240
ataatttaac acacgataaa ataattctaa caaactcaaa attactctta aacatttact    300
```

-continued

```
tgatatcttc gacataatga cttttgtttt aatacaactc aaaacataat taaggttggt    360
tttaaatgac aacaaacgaa aaactcgatt ctaatttcaa tactagtctt tgaaagccct    420
aaggagcgtg gttttgaatt gtatagcaag gtttcgaaaa ttttaatcat caaacaatag    480
gtatatttac ctgttcctca agtacagtta attcatagct acttgtcgtg cttcctacga    540
caacattgta agacttgcca cacactaatt gaagccgttg ttgaaggtag ttttccatgt    600
atagcttgaa tcgacggatg accaaagagg ttgaagaagg tttgaaaaat aggggaaggg    660
atatacaaag tttgagagtg agagagggag agaaatagaa atagaagaga ctgaaaaatg    720
taaaagaaag gatgaaaaaa tgtggggtaa acgcaaattg gatttttata gtagtatttt    780
gaaaatgcta tagaaaggct atgtatagta gtgcttccaa agttctatat gaatgagaca    840
aatcaaaata tatttttttt gattaattaa ccccaaaaag actcataaaa aaatcttata    900
aatcccacta agatattgca tgttatatgt agtaaaattt atcgttcaaa taaaccttaa    960
acataattca aacgaagaaa gtaaaaattt gaatttctta tcttacatca ttcaaccaaa   1020
caatttccat ataagagatt aaacttctaa ctttaagaga gagatatcca gcatatgcaa   1080
cctaaaccaa cagtgacttt gctatatatt tgcacaaaat gtgggggaca aagttgtaat   1140
ttcggaatat caatgattaa agaaaaggta aaatttaaaa ttcggaagct tgacgtggca   1200
acacggaatg gtgatgatat ttccaactcc tcgcgacttt tagaagttgg cctcaccaac   1260
cgcatatccg cccctttgcc acgtgtcaga ctacaacaac ttccaacaat ttcctttaag   1320
aacaccaaat tatatcaata aatatttaac ttaaattaag aatatatttg ttacaatttt   1380
cctactgagt tagatagata gacagacttg tcaattaact aataagtcca aagtcaattt   1440
actcaacata gatacaattc taatttgagt gtgaaataca tattcaaatc aaaattatta   1500
ttaagaggaa aaactgattt gctttctcaa tttaaaatat aatattttga aaaagaaaca   1560
cacatgtatt atggttttca atatatttac tttcttagtc acctaatctc aaactaattt   1620
ttgaagaaat taaatatata tattatcatt tttattttct tggttatgat attggtatag   1680
aatcaacaaa actacaagtg tcctctcctc tgctatcgat ggggattaga ctctaaactt   1740
gtttagcgat tagtaattat atattagaaa aagtttatgt taatgtggac ccgacaatct   1800
caccaatagg ctcttcactt caccaacccc cgacccattc cctctaataa ttcgacacgg   1860
ctcatccccg gttcgaaccg ggccgacgtc ttcctattta acacacctcc atttcctctt   1920
ccctccgcaa cacaaacaga gacctcaccg gaaaatcaag ttaaagcaaa accaaagaga   1980
agcttcatca ctctccggaa                                               2000
```

<210> SEQ ID NO 68
<211> LENGTH: 2000
<212> TYPE: DNA
<213> ORGANISM: Cucumis melo

<400> SEQUENCE: 68

```
taatagttgc aggtcttgtt taaaatacta atctaggtgt gtaaaacata gaaagtttaa     60
tgtggaattt cttatgagaa cgattaaggc tggtgaatct cgcttggtta aatttgaagt    120
agtttcactt cgatggagac tagacgttta ggcattcgta atttcagaga caacataacg    180
aggctacgtt gggaaaatag ttatgtcatt ttatcataac tgcatacttt gtggtaagga    240
tcatactgat tagtaagtac ggtttccact ctatagtgtt tgagtcaact tctgtgcccc    300
tttactaatc tcacgagaga atccgcctgg tcctgtaaca tttgggtgtc aaagaaactt    360
```

gtaggaaaga ttccgaccac catggattga atcataagtc aagggccatt agtaaaaacc 420
tctaacttgc tcttgcttta aattttcctc tattctcctt attcgttaag cattgggtgt 480
gggtgctata ctaacttttg tgggttgtta atggcctttg tttctgtaga tagtaaggac 540
ttctactgta aacttgcttt ttgtttgcac tttctcactc tttcattttg ttaaaaaata 600
taagacaaca taacagagcg acagagagaa agagagacta accatagcaa ctggagctcc 660
ttgtgaaatt tatccaattc ctcagaagta gacaatatag gcttctttac agcaactttt 720
ctaccatcca accttccttc atacacagta ctctcggccc ctgcatcacc attcgataaa 780
aatccaatat gtcaacagaa cctctcaggc aattgaaccg gaataaatta gtgcagcgtt 840
gagtgcttac ctcgggcaat tggagagagc agcgtgaatg cggaaggttg aagatgaaga 900
ggaatcgaat tgctggagca gcagccctga tgcaggtgtt cggatccata attcccaaat 960
ccatatccgt tttcgtgaag aaatgttgag gaaaaattca ttatgcgttc agtttatacc 1020
attggagagt gggaaagttc gtattgtttt gctaatttcg tcgattctca ggtcttggag 1080
taaaaacgtt gtacccgcca cttcccattg ggccattgtc caatattgtt tgggttgggc 1140
gggtggatga cccaaatttt ggggaagata tgagatttgt ccaactctgt tatcaaatat 1200
gaccaaatga acaaaatatt gacttttttt tttctatatt tttttgaatg aagtataagt 1260
agttgtttta ttttgtttat tttaactcaa aattaccaaa tttggatttc acaaacataa 1320
aatagatttt atacttttta taattcaatc gaaagttgat cgtatatgaa aagaacaatg 1380
aataaagaaa gaaatgtaaa atttatatca acttaattaa aacctcgcaa tacaaaaatc 1440
gagtgaaata gagggtggag gatgagagga agagggagaa gacatccata ccctccatgg 1500
acatgggtag atgtatgggt tgggttgggt tgggttgaat tgggtcaacc catccactcg 1560
gttcatatag acagcattcg ttttataatt tatccaaaat aaaatataat taaaagaaga 1620
aaataaaaga aaaacgaaat ctccaattcg cgtaggaaat taaaaaggaa gagttaattc 1680
aattcgattc tctcccatct tcatcataat tttgcgaaag gatcgtaagt tgtatacttc 1740
tctccttgct gcttttcgaa tcgggataag aatattttct ttttgtcttc cccattccta 1800
ctcttcaaaa ttctctgcat tttctaccca tcacttttac ttcaaccatt tttgttgttg 1860
ggagttccat attttgattt cctctacaac gcctaaactc ttcttcttct tcttcttctt 1920
cttcttcttg gagtgatttt tcagttcaat tttggggatt tcatctattt ctttgatctg 1980
cagcgttgct ggaagttgcg 2000

<210> SEQ ID NO 69
<211> LENGTH: 2000
<212> TYPE: DNA
<213> ORGANISM: Cucumis melo

<400> SEQUENCE: 69
agtttattct gttgtagcaa ttcaaagcag tgtgatccag atgagtacat atttggtagt 60
agactcaatt atcattttat ggttgaaaac cacatcctct tctgtcattg ttcatattat 120
tacgaggaaa aaagccacgt cctctttcaa aatttcttcc acaaactctt tcttaaaagg 180
aggaattaga gtttgaaaga ctaattagat cgagaattat tcatattcag attggtacct 240
aattgagtag caaccatcgc agtaggttga agagaaaggt cctcttgttt acgatgtttt 300
gcaagagcaa attcttcaaa tttcaagaga gtatgaagtt cttcaaagat tactgattgt 360
gaacgagtgc gcatagagat gtgaaaatat tgtattcatc tagaaatcaa atgagagtat 420
agatcaacaa atcttcatcg tttactattg aaacacacat ttgcaagttt atctttgatt 480

```
tttttgcccc tcctcatgta tgaattaata gattcatcaa cttctttgaa atcgattgaa    540
gattagtttt gagattaaca atatttgatc gtaaatttga gtagtgattt tcaagtgcga    600
cccagacttc ctttgatgaa gtacaaccaa caattagggt ttttacagac atagtagcac    660
tgatcaaggt cataaaagct tgatctttag caatttaatc tttatatata aaagattcaa    720
cattgtcgtc gattgatttt gtattgtaga tgaactagtg gtcgaagaaa tcaaaatcga    780
ttttgaaatc aaaatcgatt ttgctagagc tgtacttatg tcatcaacaa atccatataa    840
atccatatag cttgtgtgct ctcaaaatag tggagaattg gaatttctaa gaaacataat    900
ttgttgattc gagtctgata aatatgaggt acatatattt gtgaggaaga tcaaaaaatt    960
gatttctttt gttcaagaag actcagcgga agccattgat ggagagaaca aaaatcggag   1020
gggatggtta atcatgggtc tttgatctgc tctaatacca tgtgatcttt accaagttgt   1080
gaaaaaataa tctctcattt tctcattaat ttacaataat agaatatggg tatctattac   1140
aacccaattt acagaggaaa tactagctga ttacaacaga atcagtgcca aatcaattat   1200
taaaactaat actcaacact aattaccaaa gaattagtgg ttttttttacc acgaatttat  1260
ggggtaaaaa aagtgaactt ttaccaaatt agtaaaataa aaaaagaaag aaaaaaaaac   1320
gtaatattca aatggatggt gaggcatgaa gaagagtagc ctaaagtaca tgaagagcta   1380
aaagacttat tatcttccat tggtcccatt gaagaccaca aagaaaatat cagtcctttt   1440
tctctttaga gacacaaacc caaagtagaa agaatctttc acaagaatta ggaatttaat   1500
gcaatttttc tttttaaaaa aaatctccaa ttttctatct cattatccac cctttccact   1560
ctaaacttca ctacaatttg atgaaatctg tttccaccaa tcagattgca ccaaattcca   1620
tcaaaaacgc cccatcagat aattatggat gtcttcttct tcctctcttc tttcgtggct   1680
gaaattgaag ctcaactcaa aaatacattt cattttcaaa attccctgat gacccaattc   1740
gccacgtgtc ccttccactc accactaccc acacaaaaca actgcttctc ttcctcttcc   1800
tcttcttctc cattaaattc ccagacccat ccctctgcaa cttcgaatgc aacagaaaga   1860
aaacggacca aaaatccctt gaggaatttc tcatttttga agcataattc aaagattaaa   1920
cccgtattaa ccctcttcat cttaccagag gtttgattta ttgatcgaat tgttttattg   1980
gttttttttc aaggtcacca                                               2000
```

<210> SEQ ID NO 70
<211> LENGTH: 2000
<212> TYPE: DNA
<213> ORGANISM: Cucumis melo

<400> SEQUENCE: 70

```
gcatcttatg gatgtagtca caacatattt atatggattt tctgataatg atatttatat     60
gaaagtccca aaaggattta agatacctaa aacatataaa tcaaattccc ataaactatg    120
ttcaataaag ttacagagat cattgtatgg attgaaaaaa tcatgacgaa tgtgatacaa    180
tcgcctgagt gaatatttag ttaaaaaaat aatatcaata taattcaata tgtccatgcg    240
tttttataaa gaaatcaccg tcaggatttg ctattataac tgtatatgtt gatgatttaa    300
atataattga aattttgaag agttttcaaa ggcaatagaa tattaagaaa gaatttgaga    360
tgaaagatct cagaaaaata aaattttgtc ttgattttca aatcgagcat ctagtaaaag    420
ggatatttgt tcatcaatta acttatacag agaaaatttt aaaaagattt tatatagata    480
aaacacattc attgaacatt ctaatgcaag ttcattcatt aaatgtgaag aaagatattt    540
```

```
ttcgacgtcg agatgataat gaagaactcc ttagtccaga agtaccatac cttaatacaa    600
ttggtgcact tattttgtca ataatcaaga ccagatattg cattttctat aaatttatta    660
gctagattca gttctccaac aaaacaacat tggaatgaag ttaaacatat acttcgttat    720
tttcgaggaa caattaatat aagattattt tattcaaata aatcaaattt taacctagtt    780
agttttgcat attcttgatt tttatctgat ccacataaat ctagatctca aacaggttat    840
ctattcacat gtggaggaac tgctatatct taacgatcag tgaaacaaat taccataaca    900
gtcaactctt caaaccgtgc tgaaattctt acaattcttg aggcattcat gaggctagcg    960
gagaatgaat atggttaagg tcgatgactc aacacattcg aaaattatgt ggtttgtctt   1020
ctagtaaact ccttccaaca acattatacg aagacaacac aacttgtata gctcaaataa   1080
aatgaggtta tattaaaagt gatagaacaa aacacatctc accgaagttt ttctatactc   1140
atgatcttga agaaaatggt gacatcacag tacaaaaaat ttgttcaaaa gataatttgg   1200
tagatttatt tacaaaatta ttacctactg caacctttga aaaattggtg cacaacattg   1260
gaacgcgacg acttagatat ctcaagtaat gttacatctt acttgccaag ttaactatac   1320
atagtgacat ttggtggagt tgtaagaaac actaatattg gagaaaaatc gaaagaaatt   1380
ggaaaatatg gagaattgaa ttttttttag attttctta ttttctaatt ttaggtttcc   1440
gtattctgat tatgcctcat tttcacaaca ttaataactt taataagatg atttcttggg   1500
ttaagggaaa aaatcatttt tttagagttg cacgtacaaa aatattatca taacatatcg   1560
attataataa accaattcac cgtcaaccta acctaggtag agtttgagtt aaatgttaaa   1620
agaatatcca cccctcaaca ttgtaatccc aactaataaa tcagcaacct aaagtttttt   1680
ttaaaaaact aaaaagaaga gcaatatatt tttttacta ttatttttt aaagagtgga   1740
tttatttatt aaattaaaaa atgaaaagaa gaaaatttgt tagtttgggt aatccgaaaa   1800
cccgattatt tgggcccgag aaaccgacgt tttgtttatt gttcctcacg gcaataagta   1860
atggcgtgaa tcgaccgcgt gcgcttcaag ctatctagac atttttatat cctccgatta   1920
gaaaccctaa ttcagattct ccgtattacc caccctggaa catctttgaa acgcgaaaag   1980
gtgacccgaa gaaacttgaa                                                2000
```

<210> SEQ ID NO 71
<211> LENGTH: 2000
<212> TYPE: DNA
<213> ORGANISM: Cucumis melo

<400> SEQUENCE: 71

```
taataaagtc gatgatatga attaattaga cggatgggtt atactatagt tattttattg     60
tcttttatag agaatttaac attggtagcg gggaaaatcc gatagatatt ggtgaagagg    120
aattcgttgg tggatgtaaa ggaaagttag tttcgccttg gcacaacgaa gggtttgaat    180
ggaaaatcat gataagttcg actgcctgtt caactaaacg aaagatacca agtcaaacct    240
tagttttctt taaggattta tgatcttagt agtgtatcta tttaaagatt caaaggtatc    300
aatagactat ttatttcaat cgttgtgttg aaatctagga gtatatttaa cgattaactt    360
aaaagatttt gctatcttgt tttgtgtttt tcattttttt gggaaaacct agtgtctttt    420
tattttattt gatacaataa gtattataaa aatgactaga atgactatat acttgatcat    480
tattttgaca tatttgcaat atattaaaaa tgactactta ttttaattac cttcatggtc    540
tttttttaat ttatgaaggg gtgggctcgt gtggcagatg aggcctgtca taattagcct    600
taccttaaat aattgggccg gttctttggg aaatatcggc ccaacctaac ttttcatggg    660
```

```
ctcaaatgat gctttatcta atacccatac tttccattac ctttgtatat tgaattagaa    720
tgatagaaaa acatactaca cagttgagtt aggatataaa taaatgcatt gaactatgta    780
ttacatagtt gagaaaaatg agaatgaagt tttgtctttt gaatatatat tctgtgaaag    840
ttagatgtat atagaaatga tgatacttcg gcgtttgttg aagattgagt ggggtgtcaa    900
cctaatcata gttggtttaa gaaaagtttt aattataaga taaccgtttt aagtgactta    960
tgccatattt tgattgcagg ttcacaatga aatgttttaa tttggtgatt agactttgac   1020
aatgtggtaa tttatgttaa gtgagttgtt gtctcgttta ccttgatcat ttgtctctac   1080
tcatttctca ttttgtttca tcccttgtta tatggcatcc attgttgttg tatttgtcat   1140
tgttcacatt cgatgcttaa ctaggtaaga acaacatttt cattttagaa ttggaacgat   1200
agaaattcat aagttttatt tttgaggcac ttggttcatt ttaatcatag aacattagtc   1260
cacaatcgtt tggaataaat ttacactcta tctagatatg gaactcttga caacctctac   1320
caaggaagga tgaaaagcaa aaaaagagta gaaaaacgaa agtagacact ataacaagcc   1380
aattagccca ttgacaaata ttaccacgtt attaaagttc attttaatca tcgtgtcaat   1440
tatcaacctt ataggtcaaa taccatttat aattatttc aaattcaatt aatgaaacaa   1500
gactcaaaaa accaaacaaa tatccaaacc caatatttga gtttagaata taataatttc   1560
atagttagac ttggagacag atttgtacgt atatgttaaa ttaaaaattt aatcaaagta   1620
taaataaatg atttggagtg gcaagaaaat attggccaaa atttcataag aaaaaggaag   1680
aaaataaaaa ggtgtattgg ctaacaaaaa cccaattcca tggggaggag aaaatttgag   1740
tcctcaaaaa aggatttcag atagggaacc aaccaatcaa aacgaaggac gtctccacgt   1800
gtcgctacaa gaggccatct ttccaaaatg agatcgcgga taaacaagcc ttttctgagc   1860
atagaaaaat ggcgaatttt aacaaaaaga aaaatctcag taaagtcatc agctacagct   1920
gctctttgac ggccacttga ttcactattt ccctctcttt ccggcgctga ttctagtgtg   1980
gttgaacttt ctgcaaagaa                                               2000
```

<210> SEQ ID NO 72
<211> LENGTH: 2000
<212> TYPE: DNA
<213> ORGANISM: Cucumis melo

<400> SEQUENCE: 72

```
attacttgaa cttaatccac atttatgtct ttatataaag ttcgaatact cataatatag     60
ccaagaaacc ttgtttattg gattttgagt tttatcataa gcaaatctct tatccaataa    120
caaattatta aacaacactt caacaataac tttattcaac aatatattag tttaacattc    180
acaaatcacg agtattagaa cataaaacgc aacaaagaat ggactaaggt actatattct    240
aacttaggtt gtttaggatt tccatatgtc aatgcttttg tgatttttga actagatttt    300
cttgttagat taattcaatt ctatttttaa atggcttaat atcttatttt cggatgcttg    360
gggattgcta gactaccgct ttgttgaagc aataagttaa atttgtttgt tacaggtatt    420
gatcaatcta acatagaatt gaatttgtat gaatatttag ttagacgctt gaaaactaat    480
tattctacca atgagccgta gatcttaatg caattgttat taatttgaac tttgtatgct    540
tctcatcgat taaatttata tcaagtagtt aattaggaca aatctattgg ctttttcatt    600
taattttgtt aagtaaaagc aacttagaat tttgaaaatg atgaacccat gatccaatac    660
attgaaagag aattttgttt aactcaaact aggattcttc tcacattgat ttcgtataat    720
```

ttaacttttt caatttatat caatcccccc agggtgaaaa aaatttgttt gaagaattca 780
tgtgctttct aaatctgatc tagacttgcc actaaaatta acttttgata tgtaatttgg 840
ttaaatattt gattcggatt tcgacgacaa acaattgatc aatgtggtat taaattctga 900
tctccatgta agaaatttac acattttcat aagttcaatg ttgacacaaa gagagtaaga 960
gcattttaaa aaaaaagata cttttaatct tttctaaaaa aacaccaaaa tgccattatg 1020
taaatgtaac ctaaataata aacatttaaa cttagaattc atgcaattag gctttgtatg 1080
ggacattgaa ttgattatta aaatcagtag ttatagaccg tgagttataa tggtttgtat 1140
tagaagcata aattatttta attttgatcg taatagcatg tatttgagat ataaattaat 1200
ttagtttggg tggcaaatag taaacagtaa agcaaaatat aaaaaaatga atttaaaata 1260
gtaagatttg taacaaatga ttaatactat aacaaacgtg gttttaaaat aacgttgatc 1320
gtagctaatt gaacattatt tattgtaaaa ttgagtgttt ttaatatttg gagcctcaaa 1380
cttcgggtgg atcaccacaa tataatcata ttcaaattta aaattttatt tttttattta 1440
attataaata ttgattgtta atagatgctc attatgggcc atctgtcact ccctccgtgc 1500
atatcctacc tgaaacatca tatatcttaa acaatgtcca ttgccatgtg tcactatttt 1560
tacatcccat ccacttgaca aatatgttga agatgcctac ttttttaggg atcatgtaat 1620
ctatctcatg cttgtcaaat tgttcgataa tagtgttaca aaaaatttag taattattat 1680
tattatattt cttcgatatt tatgcttcat atgccattgt gctctccatt tttaccatac 1740
ttaaaaaaat ttcttattat aaattttttc aaaaaaaaat ttactatata gtcatcatct 1800
ttattaaaat taaaattgag aacctgatat ttttgatatt aataatttaa aatttgaatt 1860
aatccacttt aaaattatta ataatttatt cgaatttggg ccttaaggaa gagatacgga 1920
aacaaaccct agatcccatc tatatataaa tcgccacaaa accctacctt tctctcagtt 1980
tctcgtttta gccggcaaaa 2000

<210> SEQ ID NO 73
<211> LENGTH: 2000
<212> TYPE: DNA
<213> ORGANISM: Cucumis melo

<400> SEQUENCE: 73
tgaaaaacta aattaaattg tccttacatg tgtataaaag aaaccttcgg acatttgatc 60
tgagaactat gttaaataat aagatccaaa aaactgaacc ccaacatctt cgaaatcgat 120
ttgatttcaa ttcttaagat aagctacatt caagttacct agatgatcta agaaactaat 180
gattggacaa agttagaaac tcccaataaa ccaatgatct tcaaagcact ctacgatcaa 240
gacagattaa tttttagttt gaatgctttg aacactcgtg cattctatca caagaacaaa 300
aattatacgt tttagaattt tcaaatatca ttcatcccaa tttttatttt aaacgtgaaa 360
attacaactc tatttatact aattaaaata ttaattaaca tgttacaata tttaatttta 420
tgtcatttca actaatgtaa taaataaaaa caaataagac aacgtaaata cacaatttca 480
taaacattta atttcacgac ttttaagttt tctaaataaa ttttcaactt tttcatttga 540
tttaattatg atttctcgga tcatatctat atatatatat atatatgaag ctgagtttta 600
gaaattgtaa attcaaattt ctttaaatgg tacaaattca attagtaaga ggaaaaacag 660
ctaattaaat aatgtgtgat gccccactcc ctaaaacagt gggtttggat cgattaatca 720
actaaaactg accacaaaac aatattcttc tacaacccca ttgatttttt taatcattaa 780
gtgccgattc aaagaaacaa taaacaaaag aagttgaaaa gattgagact tttaaattaa 840

```
atctgcaaga ttctctccaa actcatgttg tattcaagtg tttaaagctt aaaatatcag    900
taattatgtg ttatttaacg gtgaaaccaa tcaaatcaag caagattctt caatattcaa    960
ttccaaatcc tcaagtttcc atgaaaactt cataacgcct ttatccctcg aaagccaaaa   1020
ttcaatttcc tccattcatc ttgcagccct atctactttc caaaagccaa caaataccct   1080
tttaagcagt agccttttgt ttggttgtag taggatcttt gtttctcttc cattttaaca   1140
caagccacag gagaatctct atctctatcc tgcaaccttc atccccacat tgttcttcct   1200
ccattatcgg aaaaacccag tacagggttt gctttccggc cactatccgg ttgttctttg   1260
taagtttttt gggttttcat tatctgggtt tgtggctgct tgtggattca gggtaatgtg   1320
gccatgtttt atagtccaca gccttttttt cttcttttga catgggatta tttctgattc   1380
tatttgtcta ttgttacttt gtgctttttc tggtttgttc ttgtggtcat catttcttat   1440
gcttggaagt tcgaacatga atcaattcaa caactaagtt gagagtgttc gactctctca   1500
tctcattgac cctgatggta tatcttggct tggaagttag aacatgaatc aattgaacag   1560
cttacttgag actcgagagt gttcaactct ttcatctcat tgaccctgat gatatatctt   1620
ggctttggag ttatgaacta tgagagcttg gaggatgaac taaaaagaag ggactatttt   1680
ttgagatgga tatttagttt tagtaattta gcttttttttt tttagtacat agtacattaa   1740
ctttgttcgc gaggaaatag tggtcttgtt gacgagcatt tcttaaacaa tgtagttttt   1800
gtctcatctc tttaaaagtt tatggagggg caaacaagtg agatcaatag ttatagtatt   1860
tcaatctata actttggaac agctgatttt taacttttcc tttgtctttt ttttattata   1920
gaacacatta gagtgcgtta gattcttcag ttctgagatt ttgatctttg agtgctctct   1980
tttagcagta gaggcaaaca                                               2000
```

<210> SEQ ID NO 74
<211> LENGTH: 2000
<212> TYPE: DNA
<213> ORGANISM: Cucumis melo

<400> SEQUENCE: 74

```
actttcagta gattttatct cataaaagag tcataaagat aattagtaat gaataaagct     60
ttgtttgaag aaatgtttca ttgcaactga tatttgtcat tgatgtacaa atggctttgt    120
aactctccac tttttctaat ctaaccattt acatacaaaa tatctacgat acactaaaat    180
gaataaagaa attttttttg tcaaaaactg tggggagaat tgctccttgt tctcaaatca    240
ttcatgaact ttgcaattta gaagtaacat caatgaaggc ttcttccttg cagggaattc    300
tcaaacctcc agttgggtgg ctgaatccaa actcttcttc agccttgttg agcaagtcta    360
tgaatgaagg ctgactcaag tacgatattg gaacgaaaaa ccgctttctg tcggtttctc    420
ccacgtacac tggaatgtgg cctttgggaa caatggactg acatcttgct gagacagact    480
gcatcttgag aacttgcttg gcagcggaaa gaagaaccga aggcaaacga attcccatgg    540
ctaaattgga ttgaatcttt ttggaagtgg taaacttcaa tgcttgaatg agaatatgtg    600
aaagatttga agttggagat tagttgtttg tttagagtct atatatagaa tgagaaaaga    660
gaaggtattg tgacatatga atagaagatg ggaaaccaag aaagttgggt tcatcaatgg    720
ctcacatggg ttgctccatt ggttaaggta cattcatttt ctcattggca ccaatttctg    780
gtaagatggc cccatatgtc ataatacgtg aagtcatatt gatctaaaca aaatgggaca    840
caaaaattgt aactatttca attagcatta aaatcatgtc aagaaaacta cattaaatat    900
```

-continued agatatatta gttaatgatg taataatagt ttcatgtgag atcaaactac gattttttt 960 tataaataat gttactttta aaaaaatgtc aaaaatatgg tagaagaaaa gctattacaa 1020
aaagttaagt catctactcg gttcataatg cgttatcgtg gatcgggtac acgacaaggc 1080
aatgaagaca tagacccagt ctatgacttc gatgtaaaat gtgggttttt cctaattact 1140
cgtaaaaaaa tatttttgaa aacttttctt tttaacaaac ttaaattttg gttaattata 1200
tatataaata ccatctttac tttcttatta tccaaaacaa tttaccatat ataattatat 1260
ttattcaata aataataata taaaatattt agataaacaa aatcaattat ttcaatctta 1320
tatattttaa atatacacta agctaattta aatttacatt ctgaaaattt taattatatt 1380
tctatctaat ttaagatttt aattatattt ctatttaatt taaaatttta atggaaaatt 1440
aaattgtaaa taagaataag agtacaaact tactattttt atttcatttt taatttataa 1500
acttcatctc ttttttcata tatttttaag aaatccaacc ttatatttcg aaatttattt 1560
aaaaaaatta taaaattttt taaactatat ataaataaaa attgtaattt ttgaaataat 1620
ttattaattc ttacaacaaa cttataataa taacaataat aataataata atgagggtac 1680
tcgattctca aaaaaaccga accgatcaaa caacgttaga tcaccaacac agaagtaggg 1740
tttttcatcg gcacataaaa accctcactt cttcttcata aaaaccctca cttcttcttg 1800
acctaattcg cgccgttgat ctccggttcg atcggtttct acgctgtaat ctcaagctat 1860
ctcctacctt atccttccct ctctttttct tcttcttctt cgtatatgca tatcttcaaa 1920
tttgctgctt tttttgtctg attattcatc tgggtttgtt tgcaacagga aggaggaaga 1980
atttcaaatc aagaagaaaa 2000

<210> SEQ ID NO 75
<211> LENGTH: 2000
<212> TYPE: DNA
<213> ORGANISM: Cucumis melo

<400> SEQUENCE: 75
tttattaatc tgaatcattc tgtttcttct gagagtttta ttccttttaa gattctaatt 60
ttattttgga tagttgaatt ttggtgtgct ctctttgccc cttctttatt atacattcct 120
ttatcttaaa aaagccaaaa agttaaaaaa caaaaactaa tcaaaattgt aacatttaca 180
attttatgag catgacattt aaaatatcga ttttgaagtt aagacgttgt attctcacca 240
tcggttttta tctcttccca ttccattaga gtgataggct ttatctttca tcactgtcaa 300
aattcatcca acgtccaaga tctcttctgc aaagagttac ccacaattct ctcagactca 360
ttggcccacc ggataccgag tggatggata gaacctccaa gattgcgaga gcaaaagctc 420
agccaaaact tgcacaaact cacccatggc ttccctctct tgtactacct ccattaatct 480
caccccaaga tccttcaatt ctcgccccca ttcaaattag cttcccattt tcttggtctt 540
cagtccaacc ttcgatggct ctcacccctc tccattggac cctccaatgg gtctagagca 600
acttgctggt tcaatttaag gcaaaatgcc gagggtgcag gcatttatgg cagccagtcc 660
cgagatgatt tcaacagaga tgatgttgag caggttcttt tactaatttc tctcttcttt 720
ctttgtattt tgttttgtga ctttgattgt tgaagagtgg tgtcttttgt ttaattgctg 780
gtttgggctg attcttatgg gtttggagtt gaaattgttc ttaccctctg gctgttctgt 840
tttcttttaa gtattgtgaa ttttcaatgg ctcctttagt gaagatagat gaagaaattt 900
aaattagtaa tttttcgtac cgatgactct cttccagtgg tgttaatgtc aaactaacct 960
tttctttacg tcataaagca cttaatcggt tggaactcag tagacgtctc actcatgttt 1020
gtagccctaa cctaatgcca tggcaatcga aatttatatc gtatccctat tgcgattatt 1080
aaacatcacc ataggtgaga cattcctaac gtgatatact gagttctaga tggttaagtg 1140
ctctgacatt tcacattaac gcctcatccg cactggttag tcgaaagaag aaggtgtttc 1200
tgttatgaga ttgtgagaaa ggacctcctt aaacattata accaacctca taacttgtgc 1260
atttgtgtat caaactctgc tttcacataa agaaactaaa acaaggtatc acattgccgt 1320
tatgaaaagt gcatagaact tcctgcttcc ctcaaacaaa acttgcaaat attactgatt 1380
ggccttagcc tttaggtaag ggaagaatca aaagtattcc ttcatccttc tgctttaaaa 1440
atgtgctaaa tgacgttgtc catagtttaa aaactcgacc aaatcgcatt tgtcttacag 1500
tctctcaacc ctttttaagc actctcagag tcaatccaaa tagattccta gttcctaata 1560
tgtaacaaga agagtgatac tatgaaaacc cacaaaaaac ccacaaacat gtgacttgag 1620
ttaagatgac tcccaatccc actgtatcaa gcttttcaaa tagaggaatc acgatgagat 1680
gaacaataat atcccaacgt gctgctatcc caaattagat acagaagtct acttgtggtg 1740
ttcttaatcc aataattcat tatgaaattc ttatataatt tcttaatgag tatcttagaa 1800
ttaatgttac aacttatctc ttattctata tgatagaatc ttaacataag tattcatatt 1860
aagagcaaga ttatgttgat acttctcgaa tcataccaaa aacttggaac catgacatta 1920
acttcattcg tggaaacaag ttttgaagga aaaagaagga ttgacaaatg aacgttatgg 1980
ttgtgcagta ttttaactac 2000

<210> SEQ ID NO 76
<211> LENGTH: 2000
<212> TYPE: DNA
<213> ORGANISM: Cucumis melo

<400> SEQUENCE: 76
atctaaaact gcatttttta ctacatacag attcaccttt aggtgctggg gcttccccta 60
tttcatttta tcaatgaaat gtttcttatc tagaaataaa aagaactaca tacagattca 120
caccactgca gaaaggtcaa ataaaacatt catcataatt caaggtaagt aagcataatt 180
ttgtgaaact tatgtgatgc acttaatata tgaacgattg ccccttgttc tctcaaagtc 240
agatcttctt tttcctaaca attgaagaaa gtggaaataa gttaattacc acggccacgc 300
aataatctcc tgatggcctc caatgaaccc cccaaacata atgctgtagg gaatgtcttc 360
ttgcaatcct tcaagacgca caatgtgaga catgcaaaat attaaaaagt gacatcttca 420
aatatagcaa aagaaatcaa aatatttaca aaaaatatag caaagtttca tattttatca 480
attatacaca ctgatcgaca tattttgtaa atattttcaa tagttttgac atctacaata 540
attagttgag attttgtagt caacaggatc cagatttgtg tgttgaaagt tgaaacccat 600
gataagataa aatcccggtt aaatatttca ttttcattct taagtttttg aaaaaggaat 660
agcttggtaa gctacattcc gcatggtaaa caagcataca acttttgttt caaagaacca 720
acaagtacta caaacaaaag agtaattgat ttaatccaag ttaacaatga caaattggta 780
atatttatag gatattagtg agataataca atcaagttcc aaaagatgtt atatttacaa 840
ctatgagcat tcatcttgtt actaccacca agaaaaagta gcggttttcc aatctctgtc 900
aagtatccat ttgagttatg atttcatatt caagactgtc acaaaaattt cattaaaagg 960
tgcaagtgca acatttcctt aagaaaagga taactgagag atcaatgact ggaattcaca 1020
agttaaaatg aacacaactt cagaacatca caagctaata cctccaaacg gtccaataag 1080

-continued

```
ttttctgcaa cactgtcaac aagcgaatcc tttgggcgca tcaaccaagc agctcggtcc   1140

cgctgttacc aagaaacagc aatttcagca agaacaaaat atagaaatcc tccaagaaaa   1200

ataaacaaac aaataagttc gaaggcacca catatcagaa agcttatgga ggagtacatg   1260

tagtacaaac gctcttgcca tttagtttta cttgttaaaa gtgatttgct cagaataaac   1320

ataaccaaag cagaatccga acatatgaac caatgaatta ataaacccca tcacagaaag   1380

acaagtaata ctcccagaat tgtactctat acagacgacc actacaattt agccacacaa   1440

tatcaccatg ttctctccaa atatatttaa aaaaaaaaaa aaaaaccctc ctattgttgc   1500

ggttaacaca aatagatcaa aaagaagaaa gaaaaaacta aaaggagaca aaggtgttaa   1560

atttggttta cctgtttacg cttaagatca cgatcaaaaa ccttaacctt tgagctgtgc   1620

attccatcac cgattcttcc gtcataatta tcatcaccag tagagaaaga acaacaagga   1680

attgaatttg gaaaatctcg ccatcttgca cttctcaaca ctgagaacga tcttatgatc   1740

gtagacggcg acagccctct catttcacag tcaccgattg aacctcgccg gagagacgga   1800

gggaaatttt gtaaattttt aatgggcctg ggccgtaaag tcgtgtccaa acactcctta   1860

aacggaccaa aaccggcgta gaaatgaaac tatccagata agggacgtgc tatacattta   1920

tccaaacgag gtctcttatc gtatcttgta caagttcgtt gcttttcacg gctgtctcta   1980

gaattttggg ttgggcgaaa                                                2000


<210> SEQ ID NO 77
<211> LENGTH: 2000
<212> TYPE: DNA
<213> ORGANISM: Cucumis melo
<220> FEATURE:
<221> NAME/KEY: misc_feature
<222> LOCATION: (1)..(2000)
<223> OTHER INFORMATION: n=g, a, t or c.
<220> FEATURE:
<221> NAME/KEY: unsure
<222> LOCATION: (1)..(2000)
<223> OTHER INFORMATION: unsure at all n locations

<400> SEQUENCE: 77

aaacctactc tgtaaatgaa ggtttacatc tcttaaggca gtaccatttc tgccattact     60

tctaccattc ccacgaaacc acctcttttc tctttcattc tccccgtcag gtatgcattt    120

ctcatctcta agtccgccca ctgttttccg actgattttt cgatttttaa ttagtgagtc    180

ggttttattg tttcttattc taagctttct tttactcttt atatttttag atatttaatt    240

tcggatccat tcttcccatc atgcccaatc caaagactgt cgaaagtttt gattgttggt    300

aatgggacat taggtctggg gtttctgttt ttcttatcct ataaattggt tatccttcgt    360

ttcctctatt ttgactttat tccgtagtta ggttagaaga agaaactact gaataatgtt    420

tactatacaa acacctcaaa atagccaagc ctgtcgaaac acatttagct gataagctag    480

ggatgaagag atcaagagat ggttagctca gctgtattgc atctcatggg ggacgggtga    540

aacgaaccag agaagtaata tacacgtttt ttttttaaaa aaaaaaccga ataatttacc    600

tgttcttgct acaattacac cgataagttt tcaacttgag caattacacc gtctaatttg    660

cattgctgaa gaaattggtc tgttccatta ccactgttga ttaaaaagtt ctacttgtca    720

gcacagcatg tccatgtgcc cagatagttc ttgatctttg gaaaaagtgc tatgtttgca    780

tgcttcggta agatgtgagg ttaaaatgag gaggacataa tgttggcata gggaggtcaa    840

aatgtgttaa ttgagagaaa aaatgtggtg gatattggag aggagacatg gaagtagaga    900

gaaagagatg aggagggagg ggtgaaggta aagggaaata gacatacaga aataaagaac    960
```

```
tgtgcgagta atgtgttgcg ataagtgaaa gagagaaagc aagagaaaca gtggtagaaa   1020
attgaagtat agagagagat gtagagaggg aaaatatgga gaactacaag ataaaatatc   1080
tttattcttt ctctatctaa gtatttatct ctttagaagt tatctctctt tgtttctgag   1140
tttaccccta gtattttctt ttttctttct caagcccttc ctctctaaca caatttctct   1200
ctctctcttc tccctctctc tctgtatctg gctgtggcac tttttttgac ctcttccttt   1260
ctgtctttat ctcctttgaa gacattttga ttttcctaca cccctcaatt ggtcttctac   1320
tcaaactcat ctacttgtta ttatattaaa tgcatgaaat cctaatattt taggaagctg   1380
gagactcatt gtgcgtgcat ctgcttgctt gtagaaagtt ttaaattgaa aggcaagccg   1440
aaggggccta attattcagg ccaggacaat gatgttggtt ttagtttttt gtttttgaaa   1500
nnnnnnnnnn nnnnnnnnnn nnnnnnnnnn nnnnnnnnnn nnnnttttga aactaatttt   1560
tttcttagtt ttcaagactt ggcttggcat ttaaaaacat tggtagaaaa tggataacaa   1620
aaccaagaaa cttacatgtg gaagtagtat ttataaagct tacttatgtg tggaagtagt   1680
gtttagaagc ttaattttta aaagtctata accatatggt catcagtaga gtctcatgca   1740
acttatgttg tgacagtggt gtaattgttc taattaaaaa ttttcgggta caaatgtaaa   1800
aaacattatc gaacagtggt ggtttgtgaa atatgcatta actttttgaa aatttgatgt   1860
gtcatcatat tcattccatg ccgtgccttg tttccctccc agctccttat ccatgctaat   1920
tagattcaga ccattatccc tttggaacag ctatgcttaa ctctgttctt ttctccctct   1980
gtacaacagt atatcaaaaa                                                2000
```

<210> SEQ ID NO 78
<211> LENGTH: 2000
<212> TYPE: DNA
<213> ORGANISM: Cucumis melo

<400> SEQUENCE: 78

```
tagcttgtta attcttgtgt tgaagacgtg tttcaacaaa tctgatgggg tattcatctt     60
aagtgtccac tgaagaatgg gggttctgtg gcagatctgt atgttatgta gtgaaaacaa    120
atctgtaaag ttttttttta cttcgaattt aacgttgctt aagcttctgt gtacagtttt    180
atcactgcct cgaggttatg attattattg gattaaatta caatttagtt tacgtttacc    240
ttggaactgt gtatttcttt tgattgctca acttttctcg gggatttttc aagaattgta    300
tttttaaaat tttaatttat ttggaacatt aagaagttgg ttatttacag atgagatata    360
acactgtgat tggggtggaa aataaacaca gcttcaaaca cggagtgaga tatagttaat    420
tacattacat agtactagag attatataaa tcactccact cacatgagtt ttcatcttaa    480
aagattggaa tttacatctt aacagatgca atcttttaat gtagagttct taacgtgttc    540
tcttacggtt gtatcttttc gttttcatta ttctttggtc aaatcaaaat tagactttat    600
agtttttaat gaaatattgg acacactacg attcatcaaa gtaacccatg atcttataaa    660
gttgtgaaat gtatgtatat tgtctttgat caaactttac gtttaattat atcttgaatt    720
tataattttg tatttaagag atgaatgaat tttagaaaat tctaaagttc ctaggccaaa    780
gttgttatag aagggtaaag aatgctttaa atcatttatt ccataatcat tagttttata    840
atttttattc ttcgtaacta ttttttaaca aaaaaaaaaa aagttatgca tctcttaaat    900
actatctttt aaaagggaaa ttttcataaa taaataaaaa aagacgatag tatacacata    960
aaaaaaactc aaatgattta tagagagttt gatgaatttt gctggattta taaatagttt   1020
```

```
agaaaaataa gtattaacct aaaattttgc ctatatctca atggccttct atgtctatgt   1080
tatttcttaa ctaaaatcga aaggatatag gcttatggat tggcttaagc taaaaaatgt   1140
cggtccaaat agttgagatg tcaaacctta aaagtactac gattatgtga ttttcacatg   1200
acatagtgtt ctatggtcaa attttatagc gtacttattc caatccatca ctttttatag   1260
aactaaaatt catagttcct attttaatat atatatatat attaaaaaca cacattaaat   1320
gatgatttta tctcttctag gttgattgaa aattactaac taaaaaacac ggtgcctcaa   1380
acctccaacg taaatacgat ttctaagaac tgtgtttttt gtaaacgcca agtgactgat   1440
taaatctctc cattctctgt ttacttctat ttggggttat ttatgctaaa ggatattatt   1500
cattcaatag aataaatgtg agatagtcga gttatattca tagatgttac aatgaggtga   1560
ttcattcctt tgtcaaacaa tgctttctcg actcgtattt tactgtattg gatcgaaatc   1620
cttcttactc gcatggtttg ccttcgttga ttagttttgg tatgaattga tgctttgttt   1680
aagggggaaa atgaaaatgg ttcaattgga ggacaattgt ccaaatttcg ggacattatg   1740
ggttaaacac aaagaagaag tccaacagtg taattttgtt aaagattgcg ttacatttcc   1800
gaaatataaa tgagggtatt ttggggaaag gaaatcaata taggccttgg ccgggtgaga   1860
tgcgaaaaag tctcaaaact gagtgagaag cgtttgagct gggctcgcag ctattgaaaa   1920
agagagaaca aacccttttcg tcgctcttat tttcttcctt tgatctgaaa tttcctgttc   1980
cgatctcgct ttaggacgca                                                  2000
```

<210> SEQ ID NO 79
<211> LENGTH: 2000
<212> TYPE: DNA
<213> ORGANISM: Cucumis melo

<400> SEQUENCE: 79

```
aattcattcg ggattgttat gaggtaataa aaaatatctg agtgcgaaca tgataattgg     60
taaagtgaaa aaatgttcag ctattctgtt ctagatacag ggatggaagt gggaacaatg    120
ccaccttgct tattgacaat aaaatgagga gtggcaatat tttgtttctg aataaatatt    180
cactagcata acatattagt gatgattcaa actaaagtgc actaggtcac tagtttcttg    240
attcatcgtg tttggtagta atggtaggta ttgtatctta tagtattgga caaagcttta    300
ccgaccataa attgtggata atgtgcagag aagaattggc agttgaacgt tcctggatat    360
tcaagtgatg agtggaagaa tcacaacaaa aatgtaagaa aattatatta ccctctctaa    420
aacatcattc tattctcctc cctaaaaaat cattctgttt caatttaact ttcaaaattt    480
tgttttagtt taaccatatt gagttttttt tctttttttaa ttatcgtagt tatcatcaag    540
tgatgtccac aagaaacgtt tggacatggt aagttggact tatctcttca agtgtttgct    600
ccatttcttc ttttatcatt tgtctcaaat tttctcttct ggggtttcat cagatacgcc    660
tattgaagga agcctcctgt gtcgaaacaa atgtaaacag ccctaaagag atggtacgac    720
aaggggttgg aatgtcaatt ggtcccaaca ctctaacaag gccttcaccg agttcagaac    780
aactattatc acaaacgtct ggttcacagt tgctgcagca aatgatgagg ttttagtgta    840
ttaactacgt ttgaaactaa tgcttggtag agatcccaac tacttggtga ataaccaacc    900
ccagtgtcag ttcagggata caacaaataa aatgagattt agaggatgcc atatcagagg    960
gaacctggac tggacatctg tgtggagtgg agtgtgatga tttttagtga tacgtctttc   1020
ggaatcaatt tttttaggct gtataatatg aagttgcatt atctggaaca cgggcgtaat   1080
gttaattgta caaaatattt ggcaggtcat attagtatag gccttaagta ttgttgttgt   1140
```

ctaccatgaa ggacattttc caatttatga ttgataatct ttacttacaa tctcgagtca 1200
tatgaagttt gttgatcagg atcatagcac aattattaca aaaatgaaat agaagatatg 1260
atttttcacc cccccccac ccccccccc cccccccctc ccattcccat ccccccttt 1320 aaactgttac attacaactt gttaactgtt gattttccag atgagagaaa gggcctactt 1380
gtcttgtaca gaaaattcat ccatgacgat aaatgcagat gacctgaacc aaacgtgaca 1440
gtaggggttt cttctatgcc acaaagctcc aagccattca tggtgcgcat gtggtacaga 1500
gaggcttgat ggagcctctt caccttggtc cttagctatc taaaaattgg cttcttatgc 1560
tgatatatct cttcccatgt gcatttggtc cactccactt tcttcgtcga atatccttgg 1620
gttaatcctg aatggtaagc acaacattct tgctaattaa tccctctttt tatcctactt 1680
gccaactgta caagatgagc agaagaagaa ttgcccaatc atgaggtcat taactgcaaa 1740
aaagagaatt tatttctttc tttgagaatc tgatcttctt gagagttcat tgacagccac 1800
atgcatcaca aaatgaaatg ctgtgtggcc ctcattcatt cattcatcaa tcttcctatc 1860
ctgccatttg agtgaatgtt actccaactt gcaggaagct aaattagtac tttttatat 1920 aaaccctatg aaactcatca agaaaccaca ccatcccaaa aaggaaacga gtgaacaact 1980
agacaactca ccccgaaaaa 2000

<210> SEQ ID NO 80
<211> LENGTH: 2000
<212> TYPE: DNA
<213> ORGANISM: Cucumis melo

<400> SEQUENCE: 80
cagcgatctt cgtagaaact aattcaatgc tagctcatta tttgactttt ctcaggcaag 60
gctccgcgag gaagagaaaa ggtccaattt caggaaccaa gggcatggac aggttccggt 120
cagaagaagc tttttacgta aaccctttgc cagattgttt atgtcaagga gaattaccaa 180
atggaagtac gacttccatt ttcagatagt tcagtagaac atcaaagata aaatgctctt 240
agagagctca atgtatatgc aggcgaccac tcaacgtgtc accagctttg tacatccaat 300
aagccagcta cgatggaacg acggagtgtt tataacctga gttttggtag ttggcggagg 360
cggtgatggt ggtatagaag gaaggtcgag ggatggcaaa ccctttacgc caagtagtgg 420
aagggagtag ttggagatga acacattttg agaagtttcc aagatcactc catttggggg 480
agaggggatg ttggttattt agcacaattg ttttcatgtt ttagtaattt tatccaataa 540
tgagcgaggc attgaagcaa ttaaatttat ttttaatgat tttttcaccc ttccataggc 600
tttttctttt ttcttttcct tttagtttgc aaactttagc tccttttatc ggctgtcgaa 660
ctcatttttg aagttattga atgaaacaca gtttgggctg tgtcagatgg gtggtgaaat 720
tttatacatt ataattacta cataaaatga aatcatattg taattttcta tctatgccac 780
aatttttttt tattgcatca tgaggattaa attgtacgag tccaaatttg tacagtcatg 840
tttttaaagc tttcgagcat tgttactaat gcatggaaag gatcgattat caagtatcct 900
cccaacttca tgaaagttat tatttgtctt ctaaatttgt tttagaaaat gtttaattaa 960
ttatttgaga agaaagttta actaaatcct attggtttcc tctaaggttg tcatacttat 1020
ccaataacaa ttacgtttaa aatcaaaatt attctaatgg tataagacta atgttttaaa 1080
agcataaaat tgatgaggaa ggattggaag taatactatt tattttgaag gtaaacattc 1140
ttgaatgtct gtcctaaaat cactaatgtt ttcttagttt gagactttga gtcgttgaac 1200
ctctccatct ttataaaata taatacgagt ccttcacaat aacttaaaat atatactaaa 1260
tcctaattaa tgaaaaataa ataaataaaa ggtacaaaat cattaaagcc taaaaatcta 1320
ttactccttt aaaacttttc aagggtccct acaaccaatg agaaactacc acgtcatttt 1380
cacaatccgt tcagtgttta gaaaagtcaa atcgcaccgt ccatttatcc actcgtacca 1440
agtacggtag gaatctatct accgtccgat taagcacaaa gaagcacagt aaatgtcaat 1500
cgtgtccatc cgccgccata ccgcacatcc ttcgtccgac cggaaggccc tatataaagt 1560
cctttggttt tccgaatttc tacttcattc gcttttgaaa gatttcccaa tctcttcgtc 1620
ggccaaaatt ctctctcgct tctcaaccct tcttcggctt tttcatccag gtttgtttct 1680
cttctctttt ttcttccttt gttgttcttg gaatatgttt aatttcattt gtttttccat 1740
tcaatttcat gctagatttt acgattaggt tgattttctg ttcgtagatt gtaattgatg 1800
gttagggtta gctttttctc ccattccttc tggaatctgt ttcttgacct tcgaacttcg 1860
ttgataaatc tttagaaaca tttacataac caaacaataa ttgaacaact cgtgttgtta 1920
tgcctatata atagcggtta ggaaactgga aacgccctta taattgaaat cgccttagaa 1980
atttgttttg attcatacag 2000

<210> SEQ ID NO 81
<211> LENGTH: 2000
<212> TYPE: DNA
<213> ORGANISM: Cucumis melo

<400> SEQUENCE: 81
tgtaatgact aaacatacta tagcctattt ggaccgggtc gaaaatccaa attaaccaat 60
ctcccctcag cctcacacca aggataaatc atgtcaacct tctccatttg acatgctagc 120
tggacaaaga gaaatactaa ctcaaattcc atataaatat atctttacga ctccttatca 180
ggtaatttag actcaacaat tagtaataaa tttagtataa tgaatgatag tttccataga 240
tcaattatat catttattga tttgctagat ctagagtgaa cttattgact aatataccaa 300
atataaaata tatcaatgaa cttacccacc aaacataaaa atgtaatatt tatatctaca 360
tgaattttac aataaaaagt gtatcatata aaatacttat atacataaac cctattatat 420
atatatatat ataaaaggaa ggtaagatgg aaaaaattgg aagagaataa tttgacctaa 480
aaaaatcgaa agagaaaaga gtatttaata tataaataaa aagaaaaaga gagaaagaaa 540
aaaatcttgt tcgtcgactc ctcaaaaacc ccagcgtgta gcggttgtga gagaaggaga 600
gctcgtttcc atcacgataa aaccttatct ttctccattc ttctatcttc tcttccggag 660
ctctctccat ttctcagccg ctccccacaa tttcctctaa acacacacat acacgactat 720
ttttccattc aaattccttc acttcgtttt ccattttcct tttctttacc ccacccactc 780
acccacctct cgtcgatgga ctccatggac ttggcccaac aaccgtcgca acagaattca 840
gtctcctcag gttcttcttc cacttcctcc tcctctttta cgtcttctac cgttgattcc 900
catgtcgata ctccctctct cgatgaacct gagatggggg ttgctgaaat taaaactagt 960
gtagttgccg atgggggtgg tagtgatggt gctggttccg aaactgaagg gtttttgagt 1020
ggggaggagg aatttgagtc tgcttcagat agaccaattg tgggttatcc agaggaagag 1080
tccatcggga agtccgccca aggggctgat actggtactt cttttgtggg ttattctcaa 1140
ctttctgctc cggttagtgt taggccaatt gcgaaggttt ctgttgatag tgacgttgag 1200
gaggaggatg aggaggagga ggaggaggag gatgaccttc aggtggatga gaacttgagg 1260
ggaaaggagg aaattgagga taaagtgggt ggagaagatg tttttgttga gagtaagaag 1320

```
gggaaggaag ttgaggttcc agtggaaaag gaggagacta ttgttgtatc tgatggaaac   1380
aagaatttgg atgatgtggt gaatgatgat gatgatgcca gtcaagtgca ggaaagaaca   1440
attgagttgt cggggaactc aaaagagggc aatgtgcctg aaagcttagt agctgaagat   1500
gttggctctg tgcccgagga atctgttgat ggtgggaagc aggtgtcaga aggggatgaa   1560
ttgaatgatg tgacagttaa acagtcacaa aatgaggctt cagatggaaa aaagaagcag   1620
agttggataa agaaactctg gcgtctggga agcaggctgg taaagggatt gacttgagtg   1680
agaaggtggt tgctgaggat gtagagcaat tgaaagaaca ggaaacacct ggttcttctt   1740
ctgacgagaa agctgttttg ggagaccaag caagctctaa gcttgtgaaa ctagcagatg   1800
aaaaacaaga agaggagacc tctgcggctg agaagcaggt agatgtggag gtcaaattga   1860
atgacacggt ggctgctgct gaagatggag agcagttaaa aaatttagaa actgattctc   1920
ctgttgacga caaaattgtt ctagctgatg acgaaaactc taaggtttta gaaccagcag   1980
atggaggaca agaagcagaa                                               2000
```

<210> SEQ ID NO 82
<211> LENGTH: 1072
<212> TYPE: DNA
<213> ORGANISM: Cucumis melo

<400> SEQUENCE: 82

```
tttaatatgg tatcagagca aatggtccag agaggtcttg tgttcaagcc cctgcattta     60
cgtttccttc ccaattaaaa ttgtttccac ttgttgggct tttcaaatat ttcaagccca    120
caagtgaggg ggagtgttag tgtatataat taaatttgcc ttcttcaacc actagctgaa    180
gtttgtgggt gaattggtgg tttaatagta actatatcat gcaattagct tttttgagtt    240
caacaatatc tgtggtggag atttgaaatc gagattatga tgccttaacc atgtgaacta    300
tgcttaggtt gacaactata tcatgcaact atcgaaaaca tcatctctaa tttataggtc    360
ttttttaaca tagttgaagt ttcaatattc tatatgaaca cagctggcta tttaaattac    420
catattgaaa agcagcactt gaaatgcttc taaaaattaa tgccaattag aagtgtttat    480
gattctaatt ggttaacatt actgaacaca gattagttat agttattgaa agaataaaaa    540
ttgtaaaatg ccgaactaat accaaatgga tgggtagtct gcaaatttta ccaaatggta    600
ctacagctgg tgatgaactt agaaggggta aaggtatagt gtaactgtct aagttaatgc    660
cataaaggta tagtgtaact gtctaagtta atgccattag cagatcaagt ccgttgtatt    720
atgtactgaa cacatttttt aatcgtatag ttctaaatcc tataatctgt cgaccaagtt    780
ttaggtttgt taggctgaaa gttcatgcaa atctaggtgc ttttttgtac taattgtttg    840
agattcagaa attgtatctc aatgttctcc atgattatgt gcgtgtattt gcaaacagct    900
ctttggtttt ttcttcttct tctgacaagg atagtcaaat caattacagg acataatttc    960
aagatttaag gagagaaagc aagggaaaga ttcacgggag tggactgagt ttccaagcag   1020
agttgcagtg caattaaatg atactcatcc aacccttgca attcctgaac tg           1072
```

<210> SEQ ID NO 83
<211> LENGTH: 1730
<212> TYPE: DNA
<213> ORGANISM: Cucumis melo

<400> SEQUENCE: 83

```
gttcaactcc acaagtcaaa ttttttgga aatctcgtgt gaacacttgt gaaacacttt     60
```

-continued

```
attttatat taaaagaaac aagaagattt aagatgagaa tcccgtattt gtttggttga    120
aggacaatga aattggtaaa tatatcccat cgaaaaataa tcaaatctag acacaaaaat    180
ttaaagttaa aacttactta ataatcagct ggagcatagt ttaatttgaa tgaaaataaa    240
aatcctaaac tagagaagtt tcttatggta ttgaaaggcc agtttagaaa gcccaatagc    300
gtgggttttt cttggaccca tgtgtatgtc tcactcatga aattaaatta attggcctcc    360
acattcacct ctctcctccc aattcccata actcaatttt agacctctta aatgaaacat    420
atcatatttt cataaacttc ttttttacgt tacttatgag attaaaagac tttaaataaa    480
gtgtcaattt atattatagt agatgagatg gagtgtgtgt ctttgtgccc tccttggggc    540
ccaaggacta agtaaggatg aaagggcaaa gaaatacaaa atagaagaga gtagaaagaa    600
aatgaaatgg aatatatagt aagggttatc gtttatggtt attatgaggg aagggctgaa    660
attgataatg aacctatcct tatcttccct tcttcacctc tcattttgct tgaaattaca    720
aatgactttt ttttcaatta ttttgtgtgt acatccaaat gtggtatgca catatgggcc    780
tcccattaac ttgtgatcca aattaattct tttgcaacct aagttgaaat taaacacttt    840
tacctctctt tttttcccta acaattttac tttcattgtt agatggttga ttatcttgac    900
atgtaacaaa aagttctctc atgtcaagat agaaaaatcg aatatttgat tttgagattg    960
ataatattat aatatcagtt gagctatact cattttaact atcagtaaag cttcattaac   1020
atattttttta tttagtaaac taagattaat ataaatagaa tcttactttc attatatact   1080
ttgacgagac ttaaaaccta tttagcgcat gatttttaaa agttggtagg attttaaccc   1140
ttgaaaaatt ggtcattcgg gaatcaaaac attagtttcc ctttgagcat ttatttttaa   1200
agcacttcaa aagctaaatt agtagcatta aaaaaaaaag tcaaatagta tatatatata   1260
ccaaaacttt gtttttcaaa actatatttt aaaccaacat tctttttttt ttattattta   1320
ttactaatta agtgcagatt atagtggttc tcttttgtag ttggatcaaa tatttcattc   1380
tttttgaca ataacaaaag ttaaaatact cattaaatgc taaaaacttc catactaaca   1440
ttattgaacc attaaatata tgagcaacga aagtataggt aagaatttat attgttgttg   1500
tttagtttgg aaatagaaaa tggaccaatg ggtgagcttg gtttaagtta gggttcttgt   1560
ggttggatga taatgaaata aaatggccaa aattttaatg gagaagaaga tccctttaag   1620
ttcaaccact aatggagtct tttaggatca attcacaacc cctttctcct tctgccacgt   1680
gtcatctcag ctaatctcaa ctgtgtggtt gttgagaaat tttgaaactc              1730
```

<210> SEQ ID NO 84
<211> LENGTH: 2000
<212> TYPE: DNA
<213> ORGANISM: Cucumis melo

<400> SEQUENCE: 84

```
aactagacta gcgagtgcac aaccaaatta caaaatcctt aacagagaca accatctatc     60
tcctttaaag caacaataac atcaaccgaa ttagaatcca caatcagtaa agacgatgcc    120
gacaccaatg accaaaaccg atcaaatata gcttattacg gaccattact tcaacagtta    180
catcaacaaa aaaaaaaaat taaacattgc taataaaatc tgaaaatgag gaaaaagaga    240
ttaaaagttt tgaagataga aagaataaat ctgaaatgtt ctaatttgat atataagaaa    300
tatgaggtaa tatgacgaaa gcattttgat agttttcacc aactcccttt gtgaaaggat    360
acatccaacc aattttacaa tttctgttca aattttgtcc acctaccctt ctcttctgcc    420
ccccaaggct gctttctttc ttttattatt tgctaaatta ccaaaaacta ttttcgaatt    480
```

```
aaaccatcta tttcaattat atacgtcatt cgaattttaa cttaattaac attagtatat    540

gtttcggatc aaggatagtg gtataaatca tcctaatttc aatttgtatt tagaaaagtt    600

caattatact taaaacttct aaaaatttta tattttaaat ttggatataa attaaattta    660

agatttatgg aaggtaaata attagagcaa aacaaacttc aaactatatg gaaaatagaa    720

aaggaatatt ttagccaaac aaaaacactt attatattta ttttgttttt tgttttttttt    780

aatttaacaa ttttttttt tattggttga atgtgtttct ccactggtga gtctccaact    840

ttgacctgca aagggtctat atagcgagtt tcacgagcac ctaaccaata tctgtgtaat    900

aattcccatt tttctttcat acccacttca tttgatcatc tttttcacaa ccccggatct    960

ctaattcttg ggaatttgcc tctttctcga tccatttcca ccgtaattga aaaatattca   1020

ggtttgattt cttctgggtt ttcattcaac tgtctaactt cattatgccc tttatgtgtt   1080

tgttgaaagc cccccaccca ccatcgttca atgcggtttc tttacctttt gttcggtttc   1140

aacgatgatt tagaagttat agatggatgc taattgtttc gttgttggtt tgatccactg   1200

atctgccttt gattggcata aaaggagatt ctagatcttg ttttgatgtt gtgatttatg   1260

gatattattg ttatagtcgt ggaagttttt cttgtcgttc tgcggtatat ggttgtttta   1320

ttttttgagt ggtaaattga gcagattgtg aacttttggg ttttatggtg aaagcatgaa   1380

ttagtaaatg tagagctgct gaaacaaaat ggaggtttgc tagacctctt tgtgaattct   1440

taatggtcag cctccatctt aagaggctaa gtccaaaaat ttaaggcagt cttttgttat   1500

tgttacaaag gacaagaaat aacagaggag ttattttaat tgaatcaagt tggaaagaag   1560

tactacttca tgcttctttc aaaagcaggt caaagtgctt taaagtcttc ttatttattt   1620

attttttcct gaatcaattt aaactaatga tagaaagaag tgttttttaa tgggttatta   1680

taagtaacat caatttttaa ccattccaaa agttacatca aattcatcat agtgtgagtt   1740

tacgaatttt ggaagttgta attttaagtt aatacttctt ttaaggaaat gtacactttg   1800

catgttgtgt tcataagggg tatttctttg acaaacgcag caaccacccc ttaatgaaaa   1860

ctacaccacg gtggttggtt ttttcttgtt atttttttac ttggaattta caataagttg   1920

ttatattcgg atatatggca aagcagatat ctgtttttat ccgaaacctc ataaatcttg   1980

aatgtgcagc aggtaaaaac                                                2000
```

<210> SEQ ID NO 85
<211> LENGTH: 1020
<212> TYPE: DNA
<213> ORGANISM: Cucumis melo

<400> SEQUENCE: 85

```
tcattgatga agaaggaaac tttaagccaa ttcgacaact tatccattca acaactttcc     60

accttcagac attcagattc aactataata taacataaat tgatagtcaa gtctttttttg   120

agacaaccat aaatcatctt agcttcgaga actgtcactt ccttaaattg gtgaatatat    180

cacattccat ccattcaaaa ctttgttttc gaacttttac tgtagttatg aatcaataaa    240

ttgggagaga tattgtttaa aaagagagag catatttgtt tctattattt actctctcct    300

aagagagggt taattagtct ataaatgatc tattcttctc gtccattgaa attttgttat    360

cctaaattta tgaatacttc tacccaaaat aaagactttt ttttttgaaa agtgtcaaaa    420

aaacataaag aaattgacaa aacattcatt tttagtggat ttttacggac gtaaatagtt    480

tgttttgttt cttttaataa tacaattttt ttactttaaa aaatattttt gttataaaac    540
```

caccgtattt ttattcaatt ttaataaata aataaatgaa agaatataaa aaagaggaag 600
gaaaaagaag ccaacgaacc aacggttgcc acgtatcaaa ggtctaaagt gcgcaaaacg 660
aggccttcgg aaaccaaaat gcgtggcttc aattggagca agtaaacatg gaaaccacgt 720
ccattgtaac gcttcctgat ctcttcttta caaccgttgg attcgagtac tttttctcaa 780
cgattaacga ctgagtggac ctccacttgc ttctgttcca cgcgcgtggg attgacgtgt 840
ggtccacgca actcttctcg ataggatcat tcgagaacat cctttactta aaccgcctct 900
ctctgcctca atttctcgtc acttccttct ccttctttac cctttccact gcggctgatt 960
cttcttcgcc ttttattctc tcgtacgccg ccatattctt cacttctttt tccggcgaca 1020

<210> SEQ ID NO 86
<211> LENGTH: 2000
<212> TYPE: DNA
<213> ORGANISM: Cucumis melo

<400> SEQUENCE: 86
aaatcatctt ctcccatttg catgtgttaa cgcctaatgt agtacattta ccatgattcc 60
tagaataaga ccgattttac caacgagaag ttgctttcaa cttgctacaa tatacataac 120
atttctttgg tacgttattg atgagaagag gtataaagca tttcacagta ttctctcagc 180
aactcattag tttaaaaaaa aattaaagga atatttgaat atcgggggat gaattaagta 240
tagcctcaca atttgccagc tccttctcct tagcggctgc caacctccga agctttgcag 300
cctgtgcaaa tgtagacggt ctacaagaac ataaaagcaa atgaatacga tccccatgac 360
agccataaca gttgcaaaca atcatataga atgaatgatt tgagcctttt ttttttgtaa 420
gatgatttga gccgaattaa cagtgtctaa tgctgaatcg agctggaaaa tactacttac 480
tgagataagg tgctagcctc cctcagaagt tgctttattg atttgcgcaa ctccaattcc 540
acctggctgt tggaacctcc ctgaaaagta cacgcatgat ggaaacatga ttgtttcaaa 600
acaaacaagt tgacaagatt gaacggataa caattataac atagcaaatt cccagacatt 660
aaaactgaaa atgtcaatag atctccacat taaatgcatc acgtccctaa actaatcaaa 720
tcaaatgtct tcaatccaat atcgtaaact taacgaagca cagttaggca tattgcattc 780
tcaagtctgt caacgaaata ctgaaacgcg ctacagccca aacctcaaaa ttttcaacta 840
taaataacaa gctttgaatt gaaaaacaaa cggaatgata gaaaatacaa acacgaaaaa 900
attccgacgg gaaaaagaaa atcaaacgaa aaggcgaacc ttcttcaggt gctccagcca 960
tctagcgaga aactgaaaac cgataacgat aaagaaaata aatggagcgg caatggagct 1020
tccatgctct acgattcctt ccgcttccat ttccatttcc agaggacttt tctgccacaa 1080
cggtgaatta atcaaacaaa gaaactccgt tcatcgtcgc aattcgacgg aggttattct 1140
ggaagaagtt gagatcgtaa ttgggctacg aatatcatca aaggggcttc aataaaaggt 1200
ctctcaaaac ccaaggccca aaaaaacgaa aagcccagcc caattagtgg agaatcaaaa 1260
cgctgcgttg tagatacaaa tatcttagga aagggaacca agttacgaaa ataccccctga 1320 gtagtgagat caatgattac ctcaacgacg cgttaatcgt tttatcacgt ttattgtgat 1380
aagttccgca ctaaggaagg gacgagttgt aggaagggag gggtaaactg gtgatttcgc 1440
attcaaacaa cgggctttaa ctcacgtgtc cggatctgtt gagagggaac aattcacagc 1500
gaggaaattg caaataacac acaaaggaaa cacaaaagag cggaaagcaa atgtgaagag 1560
acgaagagta gccaatgaga aaaaaggacg aggatcgatg acatggcaaa agatttttga 1620
aatcccgcct aaacccggag tttcaattga tatcgcgatt tatctctccc tctctttaac 1680
gaaaccgact cccttcatat ccctctctct cgctccctct tcacttcaaa gggcttttcc 1740
ttctttccac ataaacacac gcactcgaag ccaatctcaa aaccgcatca cacgaaccaa 1800
actaagccta acccaatttt ttctcctcat atttcactct cacactcttt ccttatcttc 1860
ttcttccccc aaaccctaga gttttacagg taaactccca atctctccgc cgctccctcg 1920
ctcgattctc cttcgtttct ccgccttttt tcttataatc attacctgtt ttctccttcc 1980
ctctatctgc aggattcatc 2000

<210> SEQ ID NO 87
<211> LENGTH: 2000
<212> TYPE: DNA
<213> ORGANISM: Cucumis melo

<400> SEQUENCE: 87
gtgtagagtg agtgacggtg gccgacagtt cgtaacattt agttgttagt gagagacggt 60
gagacgtttg gtaacaaact ttgtttttag ttcaatcatt gctttgtttt ctctttcttt 120
tccttaatgt ctaatgtttt catcttcctt tctttatttc ttacccaatt tccgaatcaa 180
attttaattt ctaaaaaagt atttaaaaaa aaaaaaaaaa ttagtcgctt tattcgagaa 240
tttcataatc aacctaattt tcaaaattaa tcatcaatct ggaaactttt ttattttttt 300
tctcctttgg attatcctgt atgaaagtca acatactttg cactccttga gaatattttt 360
agtggtgttt ttttttctc ttaataaata aaaaagttta catctataat aatcaagatt 420
ccttggcagg tgtcactgtc aaaataattc ctatttgttg aagttgaaaa taatttaact 480
ataaacttta tttgaacgtc aaaaaaagaa aaaaaaaaga tatatgaatt cacccattcc 540
ataatttaac tatataactt tatttgaatg ttgaaaaaga aaaaaatgaa gacaaagcaa 600
attcacctgt tgccattacg acaaaatttc aaatgcgttt tattttgttt ttatgtccac 660
aagattctct atttgtattc tgcgaaatta aagtcacggg cttcgcacgt gtgtgattaa 720
tagtatttgt aaaagggcat gtagtcgaac aggatgggaa ttaaaggaga ttatgaatgg 780
gttgggtcgg gaaggcccat ttctataatg aattgatggg ccgtcaagga catttgtcta 840
cataaagggc atggaccatg aagttaagcc cacttcctaa acgagttcct tagtgtgtct 900
acattcatat ttaaatcatc tttaattcag aattttcacc atcatcaaat aatgtcttat 960
aaacctccca ttttatagtt taattatgga ttctaataaa aaatctctaa cttcaaagtg 1020
gataattttt tttttttttt aagttgaacc atgttcattc atttaattac atggaataaa 1080
aataacgtaa tttaggttaa aagttgagag gataagatga agttgaaaaa ttacaacaag 1140
ttaagaaggg aatatgaaga agaagaattc aaaattgaga acataataaa ggaattaggt 1200
ccaaagctgt aaagactagg agaaacgagt agagaaggga aggactcgtt tttcaaagaa 1260
aagaaaagtg tggaaaagga aaaaggttca ttaggggtgg tgaggaaatg gatggatatg 1320
gaatgatgat gatgagaaag aacagcacgg gaagtttccg agtagttgcc ttttgcatat 1380
accaacaagt tatctaataa aatgttttga ttaattacat taatttattc aattgattta 1440
tcggaaattt ccatactctt cacgtgatat gcacgtggtc ttcccatgtt ctaatatttt 1500
ttgtttttga aaatttgaat tcctactctg ttttgttatt ctgctcattt aactactcaa 1560
atattttagt ttgtagatat aactttgtaa atttttatta taacattttg taaatatttt 1620
aaattgtgcc catagattat gagtagataa atttacgaat taaaaaaagt ttaattctca 1680
cttcaattta attttttttt attattatcc aaatctattt gtcgcagtgg ggaaaacggg 1740
gacgtacggc cgattggagt ccaattagtg gatgtgaaac gtggacggta gagatgcaat 1800
atgaagctgg acatcaactt tgcgaaggaa ttgttccttc tttccctctg acgcttgtcc 1860
cgttattgct cgttttaaag caattcgagc tccgcgttgt ctcttccctc acgttttcct 1920
ttcaatccca ctgctcctcc tttcaccaat aaaacaaaaa cgcctcaaag aagaagaagc 1980
aacgaccaga aacctcaaaa 2000

<210> SEQ ID NO 88
<211> LENGTH: 2000
<212> TYPE: DNA
<213> ORGANISM: Cucumis melo

<400> SEQUENCE: 88
gttcgagcat gtgaatgtct tctgttgttt gatgttagaa ggaaagagat gggttaggga 60
gttcctgttg atgtctagta ggttcttttt tttttctctt gtgcaatgta acatagtaac 120
ttcgctgcaa agcagctctt atccttagaa tacgaaaatc ttctgttttt tgttatgttt 180
ctaactttat cccttcttga ttttaacttt tgagttaaat tccatctctc tgactttgct 240
ttgtggtatt ctgtttctgt tgtatgataa ttcttatgga actcctatgc tctctctcat 300
tgccttcttt ttcggctgtt acttaattac tttcttcact tgaaatttat agcttctctc 360
acaaatttga gctcattcaa gtatcaaaat tacacccatc tcataccata tttctatctc 420
tgaaggagga tttttcccct tttaaggagg gtagattgac aaagctgata gggtgagaca 480
atttaataac tcaggtcaga tgaattatac attgaagaac tctcatccag ggccagtgct 540
ttgtttataa caagatgatt aatgtgttgc tatcaaaact ttgctggttc actaaaaaaa 600
actcttggtc cttgaaagta ggcttttact agttttagct ttaatgcaca tctgtatgtc 660
aaccacgaac tccatttttc ttacttgatg catgtgcaac tttagcagct ttctaagttc 720
atatcaaagc aaatgtacct ttattcctat tgtaattcct tttctgcttt cctcttttat 780
gaattgtcaa aaatatggac aggaaagtaa gctgagcacc aacaggttgt accccttttt 840
catgtcttga aaatgaacta ccaggacaca aatcagatga tgattgttgg gagaaggaat 900
gtaagattat tcgttctgtt tgatataaga gatgtaagtt cacatgtctt acaacttttt 960
gaaatttgtg tgtcgcttat gtgcagattc ctgtatgtca ttagtggcat ttgtaagcta 1020
caattgttga atttttgtat tattatctta aaaggaaatg acaaaaggta taatcaaatc 1080
aagctgaacc taaaagaagg tacaggtttt tagtattatg catgaagaag gtttttcatg 1140
tctcttctgc catttggatt ttgtctgtga caagggacta agacactaca catgatgctg 1200
gaaactgcaa gagtgttttt accctaataa gattaaaacg tgaaaagcaa ttagattttc 1260
gtgcatatct atctttttgt gcattccacc aaactgttcg atcataactt gtcaagatct 1320
tgctttttcc ttttttttat aaatatttta atatccttct aatgtgaatg gtgaaaagag 1380
atgcacaaag ataagtgata ctatagatgt atctaagtat taccccttata cctttgccac 1440 gtaagattag atacgagaag agaaaaaaat ctatgagtta gtaatagggc aacaataaac 1500
cacagaaaaa ccaattaata cctttcctca ttgtctaata atatctaaaa gaaacttctt 1560
ttcatgttaa tgaaccaaac tatgttgtgc tatagcatga gcacattatt tctacccttt 1620
agacaagtga tgagaatgga caatatttcg actgagttca ccagaatgta accaacggtt 1680
ttgcatttgt aatatgaatt tgaaagtttg agattcctta tacgaggacc ttttttcatg 1740
tatctaacaa cacgagaacc accaaaatga gaagggagtt ggtccaagcc aaaagaattt 1800
tgacctccat gaaaatccag atagtggggc atccttatct aaacaatcag aacctgaagt 1860

```
ccgacgtagc cttatccaca tttcaacttc aaaaacactc cctctaagat cctttcgaac   1920
caccaaaatc taagaaaatt tctcttcctc atcctcctcc gacacaaaat ctagcttcaa   1980
tttcattcct ctgtaaaaac                                               2000
```

<210> SEQ ID NO 89
<211> LENGTH: 2000
<212> TYPE: DNA
<213> ORGANISM: Cucumis melo

<400> SEQUENCE: 89

```
attcgtcttc gcattatcag taaatttatc attttaagag tttgttcttt tttaaaaaaa     60
attaatcatt tcgataaagt tggagaattc aaaaatttct ccaaataatt tataaaaact    120
ttcggttata tatcgaaaaa attaacatgg tattaaaacg atcataactc aattaacata    180
aacactccct ctcaacttta ataccaaatt tctttattaa cgcaaaattt aaaatttgtt    240
tttaaaattt tcacataaca taatagaaat actttttcttt atggcaaaaa tacaataatc    300
aaaattgatt gatggtgaca ggacaccaca caatattttt aaattttgaa tatacgaact    360
atataataag atatttatga gattcccatc ctaaagattc ctagagattt ccttgtgtac    420
aatattacac aagtatcttg gaagtccaaa gtcctgagaa aaaagctatg tataaagtaa    480
tgtgtttgtc gtaggaaatt tacttcattc gtgtcattag ctttttattg aaaaaaaaaa    540
ttaggtatat cttagtgaat ctcacttaat cgttgtcgat agttattctt ttaatatcat    600
tatatactaa aatataacaa tattgaaaag ctaaaactgt atataaaaaa aatgttacct    660
ctaaactttt atcgtttatt taaaagataa atatattctt tcaaaactta caatcaacat    720
cctacgacta tcattatagg tacaaatctt ttcatgttta cacaaaaatt agatttttaa    780
atggtgtaat gatgatatat aacgaaattt tgaatgatta ctatttgagg ttaccattgt    840
aattggtcgt gttgtttgaa atttaatttt attagaaaat ttgtcaaaag tagcaaaaat    900
gaataaacta tttaaacttt aggataaaat caagtgttat gagtttttgt ctagtttata    960
tatttttatt tttattgaaa acccttttcc tatcttttca ttacttcaaa atagttttaa   1020
aatgtctatt aaggctaaag ttagtataaa taaaatttcg gaaatttttt ttcgaaaaaa   1080
attgataaat tatttatatt ttatattaaa gtcaaaattt attacgcgta gatgtttatc   1140
aaatttttctt tctttttgtt gataattttc caaaatttgg ataatttttt aaaatagtaa   1200
aattattaaa aaatgaaaac aaactattta taccttaagc aagaaatact aaaaaggcaa   1260
aaattcattt acttcatgaa gcgtaaaaat taaatatttt accacttttt gttatttttt   1320
accatctcta tcaattattt gtaaaaagaa aactacaaaa ttagatgttt tttcttttttt   1380
aaggtttaat caatattaaa atttcttaaa ttggcagaca agttggtgtt ggtaattacg   1440
aataaatccc gaattgacta aaaataaatt cttctccaag taaaatagac acgtggatga   1500
agaaataagt gaatcaaagg catccacagt tcaataaatg gaaaaaacta ctttctgctg   1560
actcattcat aagttttcat aaaatttcat aagaaaggcc aaagggctta tgaaagtgaa   1620
tgtcatagca gtaaatgaag cacagcgcca ttgaaagaca actcaaattg catgcaaacc   1680
cacataatta ttcaacaaac ccacatcaaa tttcccataa agatcaattc tttagggggt   1740
tcaattaccc aaaagtgagg tagttgaaaa ccattaaaca acaagaaatc aacaattttg   1800
taatttgttt gtacagaagt aagagataaa atcatcgtta accattcctt tatttcgtaa   1860
tacaacccat caaccatctc tctctctctc tctctctctc tctcggcctt tatctttctc   1920
```

ttcctcaatt aatttaagta ctacccaagt gagctaaaag caagttcagt ggacagtgtt 1980
gtaagaacca ctacagaaaa 2000

<210> SEQ ID NO 90
<211> LENGTH: 2000
<212> TYPE: DNA
<213> ORGANISM: Cucumis melo

<400> SEQUENCE: 90
aatcatcagg tctccttcca atgaaaccga cgacaacgac agtgtcggaa aagcgaggaa 60
gggatggcga aggcgaggaa ggagaaaacg aagtagaggg ttccggtaaa gcagaatgag 120
gagggagagg agttggggaa ggtgaagagg aagaggaagt gggagttgat aatggtggcg 180
gccggataag tactcggaca gaggaggaat tgggtacgtc catggatgag agaaaatttt 240
gagctttcag atgcaactga aaactgcttc actgctttca cttccgatga ccgccgaggg 300
gaaacttatt ttttccttgc ccttttttgcc tcctcaatat tttcctttta ccatttcctt 360
tccaaattta tttttctatg ttttgatttt atgttttgtt atatttttga tttactttta 420
cgttattttt aaatattttt gatttaattt tgttatattt gaaaacaaga tattcattat 480
atactgtaaa tcttacttta ttattgttta aatgtcgttt tggtaattca aaattaagtt 540
gaataaacac aatattttaa atattatttt agtaaaataa tttttaggtt ggagaatggc 600
aaaagaaaca aaggattgaa agactgaacc catatttgag gatagaagtc aaagccaatg 660
tcaataagtg aaactcactt ggaccaaaat accaatttta gttttatatt tttaattgtt 720
caatcttagt ttccatactt tcaatgcata ttaaacttat agttcattat tctttttcaa 780
taaatcttaa cattttacta caaattttta aaatgtttca catactttat ttttttacat 840
gaaaatgatt gttattgttt aatccatttc aataaaatta aaatttgaaa agctaaaaat 900
tcaagaatta tcgatagaca attacaattt tgtcccatta aaattatcaa attgaagtgg 960
ctacacaatg gaatggtaaa tcctttattc ttgtattggt gtgatttgga ttgagatatg 1020
aaacattata atctaaagga acatgtttaa accgaacatc acgtattttg tctttcaaaa 1080
tttcgtaagt ttgtaggttg ttttttttt gtcattttat atagttacaa ttatttaagt 1140
cagatcggat aaattttgtt atacaccaat aggaaactaa aaattccaca aggagtatga 1200
atgacctcct acgggagcat taatgaaaat gaccaagggt taaaaaatgg taagaaaaat 1260
gttcttcact aatgacaatt cctcgtgaaa gtactaacat gttcttaaaa tgcttgcaag 1320
catatatgtc accaagaatt ctcattcatt cctctggctt ctttctctca tttctcatca 1380
acattaatat gacacacttt ttccttcttc tttttgtatg tgtttataat cttactcatt 1440
ccttattctc attgtcactc aacgattcca acaagcaata tgggaacaaa cgaaggaaga 1500
agagaaaaat acactaagaa gaagagatga acaaagttgc attagaacaa ggcgtagaat 1560
atcaaagaat tcaaaataaa aaggaaaaaa agattactag acgagagaga acgagacttg 1620
aaaagaatta gaataatttc ggtaatttta cattggacga cgaaagcaaa tgacaaaaac 1680
aatttttttt tcaaaaacat agctcaaatt tcatttagat ctttcatccc aaatggcata 1740
atttctctaa tttcacatac accacaaata taatgatgac tgattaaacg aagtaaatta 1800
caataggact aaatatataa ttaaacttct taaattgagt ttgagataaa acctttgaag 1860
ccacgagggg tcgggtcggg ggcgaaagag acatgccata taagcagttg gttgctgtaa 1920
agtggcacac gcatatctac tggaagcctc catttccaat ctcccattat cccattatca 1980
tcggcagttc cccatagcta 2000

<210> SEQ ID NO 91
<211> LENGTH: 2000
<212> TYPE: DNA
<213> ORGANISM: Cucumis melo

<400> SEQUENCE: 91

```
ctttcctgac ccaataagag atcaaatcac tgtctcctgt agcctttccc ttgccgctct     60
attattgaca tttgggccta ccttcccccc cccccttct cccgattcat cacccttggg    120
ccttggccca ttaaaacatt acccagctcc ttactacttt ttaataacta tcacgtctat    180
tccttcgcaa gtgggtggaa gcgaatattt ataccaatta tcttttggtt gatcatgtag    240
ccaaaatttg gctcaccaaa ctcgtacaaa gacatttact tgttttccac tgtagatttt    300
aattttggaa gaagagatca gttgccaata gattgaatta atgcatttat gtacactttc    360
atacttaact tttggcaaag agttgaaagc aaggttttaa agaataaaat gaacttactt    420
tttttacaaa tctcatgatt tacgctagct caaacttagg atttctttcg tttgaaaaat    480
tggaccaaat atatatacaa tagattgaat aggagtcttt taaaatactg gcctcaaaga    540
aatagacaag ttagctaggt cgggataatt gcctcactca ttcttcacct cagagatgcc    600
tctcctccta ggcatgtttt ctaccctcat aatttaattc actcattttt gcttccttat    660
tgattagtaa aagtaccgat ttgccttctt ttctatgttg acaagttccc actagaaaac    720
aaattagatt atgagtttat aggaaagaat taaacacaaa tacataagtc aaattgtgaa    780
gtatcaagat aggctgttag gacagaaagt tcaaatttgg aaaacaaata tatatgttat    840
tgagttgtca tcttcttaga taatgataaa atgtgaactt ttgacacata taataaatag    900
catgttcttg ataaatagtt ttccattaaa acaataagct attattggat gatagaaact    960
cccctgggac tacaagaaaa agctaaaata gaatcagcat taaaacttcc tttaatagga   1020
tcgttatccc aaataacaac tccatctcaa aacacttcta aagaagtagt taaagaataa   1080
caatgtatat tagttatgga tgttgatgat agagaacttg gattttagct aaatttagaa   1140
tcttaaaaag ggaaggaaga aaaaaggaac aaaataaaaa gataacagta tgattactcc   1200
aacttgtgat gaacagtacc actcatggta tgtcaaacat atacatagaa tgagaacaat   1260
ttagatcaat taatttactc atttatcctt cttgctacag attgttgaga aaatagaaaa   1320
acaaattaaa gtaggaaaaa aaagaataaa tggggaatta tggaaccaaa atatcaagaa   1380
aaaggagggg caataaatta aagaggaata gtgtaggcct tctcacagtg gaagtattag   1440
cgtttaagtc agtaccttac ctttatttgt tttcatacta agttctttct ctttcatgtt   1500
aataaatttt caatcgatcc atctattcaa aatggtgtgt tttattagga agaaaggtaa   1560
tttcatacaa gaaggctaaa aaatagttga cagctgtggg atttgaaccc acgccctttc   1620
ggaccagagc ctaaatctgg cgccttagac cactcggcca aactgtcgga attgtgagtt   1680
gaataactaa gatgatcgga aatgtgacga aataaattgg gctaaagaaa agaaaagccc   1740
aaacaatgaa gaacaattcg gcccacttaa tttcacgcgc atggcacgtg taaagaaatc   1800
ccaatctgtt ctactaggtg gtggtggtgg cgaggcgaag caaagcaaag caagatcagc   1860
cttatcaaat tgtgtggtga agaatgaaga ttgtataatg tagatagaaa aagatccccc   1920
cattcccatt cccattccct tttctgaatc cgccattgtt atctctctca gacctccata   1980
acctccattt ctacccagcc                                               2000
```

<210> SEQ ID NO 92

<211> LENGTH: 2000
<212> TYPE: DNA
<213> ORGANISM: Cucumis melo

<400> SEQUENCE: 92
cttctaaaca tcctcaatgt tcgattttga tcaaggtcgt ttgcttctaa acatcctcaa 60
tgttcgattt tgatcaagag gtcgtttctc tatagtaaac atctgttaca ccttccattt 120
ctgttattca atttttccaa ttttattgag cagtttattt atttccgtaa ctactttgca 180
tcggaggcga tcatcagttt ttaaggtaca aaactagatt atatataatt atgaagcaca 240
gcaaagtata aaattttgaa gatgaaattg attggacctt gtgaacagaa ctctaaagag 300
aaaatgcatc agatagtctg gatcgttaga atttgaaatt taaatttcta tcttccacta 360
aagatatctc tgttttgcaa actaatgttc ctcattctaa acagagaatg ccagtggtat 420
tttgttcgtt ttttgcgaat atgattaaat tacccatttt atttgcatat tttatttatt 480
ctcatatcag ctccaaaaga atatgatccc tttttcctcg ataagaaaaa atatttaata 540
ctttcaactt catgcattgt gagactgccc atttgttttg tttaaagtag caccaacttc 600
tcaattgtat aagtttgtga tttttttttct atctaaattg acttgaatta tttttagata 660
taattaaatt aattgctttt aagagcaagt taaattaagg tttcgtaagg atatggatta 720
aatttaatta agaattggct tcttgctcta aatacaaatt agagtgagat ttgaaatagg 780
aggaaaaaga gagtatggtt acaaaggata tgaaagatca aatttcaaac ctttgccaac 840
tgaggctttt cagaactctt aaaccatcac agttttttct ttgcccaaat gaaatcaaac 900
attaagaaac agtgataacg aaaacgaatt atccctatgc caaccgtgac agatgatagg 960
caagaaaccc acgattagtc tctcatccgg attgttccaa caaatgaaaa agcgttttct 1020
gagactacac aaacaacaaa cacagagtta gatagttcaa gcaaatgatt ctagcagatt 1080
agaggataag gtttcttatt aaatgtttga atacattcta accaaaaacc aaaaaaccta 1140
tttgcaaatc agcttatgta aaccaaaaac atatttacta agaattcaga atttcgctgc 1200
ttgaaatttg aaggatacca tataaaacaa taatagattc ccccaatcgt gttcagtagc 1260
tcaatatagg caccgtgcaa aaggttgttt gttgtaagat taatgaacaa acacccgtgt 1320
ctgattttaa tgccaattca aactctaatt caaaaaccct acaaagacct aattgcagat 1380
aatgggatta gaaattttaa aaaatgtcga ccgggcattg tatcttaaaa ctattaagtt 1440
tcaaggatct tcctccggta acaaaatatc ggctccatgc ggcagacgga tcgccattaa 1500
aacggcgcct gctgctgact cgatgataga gccaattcag aataaccaac ccatttcatc 1560
gaaattttta aagagagaga aaataaacga ttcaagatat caaacgcatt tcgcttctat 1620
tgaaggagaa gacaatgaaa atcaaaacaa atcggaaatt aaagttaaag aagaaggaga 1680
taatctcagg acggacggaa gataattcta aaggtgcgat tcggttgaaa tttatagagg 1740
atttgtgaag gaaccctaaa ttctgattgt gaattttatc ggaaagaccg gagaggaagc 1800
ccattgtgtg aggcccaaag taactgatct gggccttttt tagtttcagc ccaaacggaa 1860
gcgacacgtc gtttctatgt agagccaaga gcgtgccacg tcaacagacg acgtcggtta 1920
gtaggaataa taccgatttg tggatttaag aattgttcat ttcggtttgt atcggaagtt 1980
ctgaatcttg atccgtggca 2000

<210> SEQ ID NO 93
<211> LENGTH: 2000
<212> TYPE: DNA
<213> ORGANISM: Cucumis melo
<220> FEATURE:
<221> NAME/KEY: misc_feature
<222> LOCATION: (1)..(2000)
<223> OTHER INFORMATION: n=g, a, t or c.
<220> FEATURE:
<221> NAME/KEY: unsure
<222> LOCATION: (1)..(2000)
<223> OTHER INFORMATION: unsure at all n locations

<400> SEQUENCE: 93

```
aagtagaaat tcagcgaaaa atgcagatgg tttcatagac aataaaaagc aggaacaagc     60

gcagagaatg gttaatcctc cagaaaatgt gataaaaggc gccaccaaga ccagtaatcc    120

ctttaccaat cacagaatac tcaacaagaa aagcgattcc agcaaaaacg aagatgaaac    180

tctcacttac aagaagaggg tcgacatttt cccgcaaaac gatgagaatg gcgagtgccc    240

agaagaagaa aatggccagt gattgctggg agaatgcgaa tctgtaagtg gggtttccgg    300

aaaaagcgag aaaaaggaaa atttcagaga aggcgacgat ggggaggagg aggatgaggg    360

aatataaatc gaaatttttc catttcggtt ctgataaata ccaggttttt gatcggtaaa    420

gagatgggtt gttgaggtaa atggaggaag aacagaggag gcgacgaagg ccaatgggga    480

tgaggaaaag ggaggcggag agatgcgttg ctagtgatgc cattgaaagg gcttttgaat    540

ttgttgaagc attcagattc ttctctgtct atggttccgt agattgttct ccaattcttc    600

cattgggaag acggagttcg gtggctgaac gttgacccta acaagtttga tcacgttgat    660

ccgttcaatg ttaaacagct cgatgatttt cgtctaaaaa agaagtgatt tttttttaa    720

ccttttttatt attgaacaaa aaaaagatct gtttatacca tagtttacgt tcttccacat    780

gagaagtttt ataatagttt atagaatcta tccaaattgt gttttattgg gtttcgattt    840

tatagaaatg tcatatcaaa aaaaaattta aaaatgataa aaatcattat aattatttta    900

tgaaattttt actgtgactt aattagatta taaaccgacc attctttaat cattattttg    960

gatgtctatc gtatgtgtat ttatagatgt caaacatgag agcatagatt taaaaaacaa   1020

atagcttaaa caaacaacaa taacttttta tctttcagaa aagnnnnnnn nnnnnnnnnn   1080

nnnnnnnnnn nnnnaagaaa agaaaagaaa agaagtcttg aaaaaagtat taaatttcac   1140

aataaatttt ttaaaataaa atacattaaa tggggatgag gaagaaacaa ctaagagtcc   1200

aagaagagaa ataaaaaatg agaggtggtg ttttttttgg tatgttaatc aaattatggt   1260

ctccacatac aagaaatgaa gccacgttaa tgacccaaca acactaacac atcaattctt   1320

aaaattcaat tccttctttt cttcccttcc aaaattatgg gtcctccaac ttacaaatta   1380

acaattgact ttagctaact atgtttttta aatataaaaa acgaatacaa gtcagtttaa   1440

taggacttga agattgtata aaccaatatt agacaatcaa aacaatcaat tttaggttca   1500

ttcccaacga tacatcaatt tggattagat taatttttca ttatggtttg atagagtgga   1560

tttagtttta gtggaatgca gggagggaaa agtaatttga aagaaaagga atgaggttgg   1620

tcaattccga agcctaggta tccaaataca agaatccata tcaaatttat gaacacctag   1680

aaaataatag taattttaat aataaaatgg agaaatgggg tccggtcgtc ctcttcctcg   1740

cggcggagat gaagccaccg cgataagaga aagagaccct tttcaataca attcaacaat   1800

cacatgaatt attccaattc acatctctgc ttttgaaact aaactaaacg ccaaaaaccc   1860

ttctgtggct cataagtttc ctctctcaaa tctccgattt ccctcaccca catcccacat   1920

ttcgcatcca aataaaaaag ggacacggac aacaagaagg agtttttaat tcagtagtgc   1980

ctctggaaga agctgtttca                                                2000
```

<210> SEQ ID NO 94
<211> LENGTH: 2000
<212> TYPE: DNA
<213> ORGANISM: Cucumis melo

<400> SEQUENCE: 94
ttagtgaaag ttcaagatgt aattcactct ctttaacaag gttgtttctt tgcttcacta 60
cgcatcaatt caaatattta gatattgatg tttaagctta atctcctatc ttagctcaga 120
acaaaattgt caaaatctca ttcttatttg tctacctggt aactttgctg ctatagttat 180
ttgtgggaga ttgtagcaaa tgactgtaga tcgaaaccat ttcagcatca atttcgaccc 240
actcttctcg tcaacaactt gatcggcagc ttcgacattc ttcaagcgcc agcttctatt 300
ggatctttag ctcaaccaca tcttcgtctt tgaattgcat gtgagctgtt gggctccttt 360
cttttgtgct tatcagttgg gagattatta ctataaatac aaagcctcac gggtatttta 420
agacacaaca aaaaattaaa agtctctcct ctgaatcacc acttccattt tctataaatt 480
ttgttctgag caacttttgt ttgtttctat ttcttattct gaagagtgca tgtttgagta 540
tggggagtaa tgttaacctt gaggaacaat tggcaacacg attggcacct cggtcaatca 600
tagttgcttt taggacagtg gttcgtcaca acacaacaat ttattttaag ttcaacattc 660
tcattctttt cttctacagt attcaaagtt atagtgttta tttctcttat tgttccttta 720
gttaacaatc taccctttaa ctaaagtaac aacttaaaag taaaatggat tattctactt 780
tttcttaatt gttactttta aaggtttaag aactgaattg ttactccgat gaaagtctaa 840
agaccaatag tggtttctat ccttaaaaaa ctattcaatg aaatttatgc taaaaaaata 900
atcactaatt catcgtgagc ttccaaacca cttgaaatta gctcaatgag attgtaactt 960
ggtcgggatc tcatcaaagg gatggtcttg gctagattct taaagatcat tttagaaagt 1020
agatcatgaa aggttgcaaa gatgctagaa acaactgggt tgtcgacgtt ttggaagcta 1080
aagcggtgat gattgacgta atagatatca ctaaacattg gcacaatcat acttggaaat 1140
agcttctata gatatattcc attttgtaag gtcttaaaga caagaacaaa gctacctata 1200
agcttgtatc ttagtttcct cttgcgatct tcttgtcgag agatgacttt ccggttttgg 1260
gttgtgtctt tgtttgtttt tctttataaa aaagtcaaaa caaaataaat ttggattaat 1320
tatcctcgta ctgaaatcaa ttggtttgga actaagtaac aataggatac atgcggcgca 1380
ccggatcatg ccattctccc tctttaaata tcaaagcaga tccctaaacc ctaacaaaga 1440
tccaaatatc aaacctcccc tcttactaca cgctccggca cctccaaaac tccatctcga 1500
ggtttgtcac ttttatgttc ttgtttttct ttatttagaa tatgatgatg attagaccga 1560
tggctatttt ctttaaatgc ctttactcct ctgactagag tggtctgtac tctgaatcag 1620
agggttcatt tcgaatcttc gaacgttgta tttcgcttca aaagctagac ttttcccaat 1680
ttacttgaac ttattgtaat tttagtgcta gcccattgat cttggtctcc aatgccactc 1740
tctgttccga ataactgccg attattgagg ggttttttt ggacttcatg atttcgagtt 1800
gttgtaaaat gattggggat tcatttaaat atgaaatata tccatcgttt atctcaaaag 1860
tatatatctt aagataaacc atgaacaaga agtttccgat ctaattccca tgggttgtct 1920
aacgagttat tctcaacaga ttacgaactg ataactagac gtttgaattt tggcacagag 1980
agaaatcgca tcactttgaa 2000

<210> SEQ ID NO 95
<211> LENGTH: 2000

<212> TYPE: DNA
<213> ORGANISM: Cucumis melo

<400> SEQUENCE: 95
taaatgggaa attggaaact aacttgaaac gaccacaaac catggggact taaaaaagtg 60
ataatctaac aaaggcttta cactcctttt tcataataaa gaacaaaaag aaagctcaag 120
agcaatcaag tttatcataa ctaattaaag tcaaacacta catttctcaa aagaatgata 180
taaaatgacc aaacatctag ctgctttaca gtgtaatgaa cacccaccat taaaggaacc 240
aaggcaactg aataaattgg taacttaatt gccctccaaa tcagagtccc cataccaaca 300
tcctcttccc cattctcttg gggcatcgaa tcaacctcca tcgctttaca ttccgataac 360
aaacctctaa aacggacatt tctgcacaac cccaattgcg ttctacgact cccgcaggca 420
aatttatgag catcagtcga caaactcgat gaatttaaac gacccagatg aaagctgtga 480
tagtagaaga gtcaagaaga taaatggggc taaacgataa ggttttgaaa gaagatgtag 540
ttgccattgt gaagtggtac ttgccttgga gtaatggtgg tgaaggagag gtggtcgttg 600
agtttgttct ttagggcgcc gagttgggtg ggtatgcaga ctatggaggc cattggcatc 660
acatagctga agatgaaact gcagagtgaa gctgcttgtt gaagcagagg atggattaat 720
taaagtggga cgattttagt tgtgtcttat cttcttcaac tttatgtttc ctcttggttt 780
gacacggttt taccattatc gctaccattt taagtaacaa tagtagtgat gaatgggtaa 840
aatataaatc ttattccatt gttagaacct tcgacaagtt ttccattatg tgtggctgtg 900
tttgacccac caactcgagt agagttgaat ttgtttggtc tactatattt acaaactaat 960
attaaataac aaaactctat taatttcatc ggtgttcact gttgaaatat atacatttag 1020
tatgaatctt tatctatttc tctcttaccc ttcctctaac atttctagtg cctccatcat 1080
caattgtcat caacgacgaa atgtgacgat aactatagtc aacgagtatt tccaccttac 1140
tttgacaata ttcattgcca caatatgctc ttgacgacct ctagcactcc acgtatgata 1200
aagactacat ttgatgacca attaaggaaa tcgtatttga caccacattc caatggctat 1260
ctctagtgat caatttcgac tatcacttgt ggttatcgac tttcaaccat ttctaacgac 1320
taacttgacg accatcttaa tcaatcatat actagaaaaa caaaaaaaaa aataactcat 1380
caaatggaaa catttttaaa tgcaattttg aaactaccac ttctctgtat ttaatagtaa 1440
tttgacatta acaaaaacac ttttaagtac ataaaaaacc aaacaaactt gtatataaaa 1500
cacttttgaa aaaaacggat gtaaccaaac acacaagtat ttttctttta gattatgttt 1560
taaaagatag aaataaaaat attaaaagaa aagcaccttt ttacaaacat gtaaatccaa 1620
atcaaacatg ctattttta atactaaaag aaatagaaaa aacatgttaa acatatccat 1680
tagcaaaata aagtgaaatt ccaagaatta gaaagatggt ttgaaaattg attttataaa 1740
gcgaagaaaa accttttcc ccaaaagaat aatattctta ttttggaaaa aacagaaaac 1800
aaaaaatgtg acaaaaagtt acattcctgc ggatttgacc ctctggtggc tgcattcgaa 1860
tctttgattt cgaataactg aagtaaacat taaccaaagt ccgtcgaaat cttccttttt 1920
ttcatttggg attccctcaa tcttcatcac caccatcacc atcctccact ttcactctgt 1980
ttccctccaa acatcaaaaa 2000

<210> SEQ ID NO 96
<211> LENGTH: 1373
<212> TYPE: DNA
<213> ORGANISM: Cucumis melo

<400> SEQUENCE: 96
tttaaatgtt actttgatat gatctatgtt tagatttgaa gtatttttct catcattaaa 60
aagaactaca cgatcgtatt catttagaag aagaattgta cgtacgcgtg tagccgatta 120
atcacgtgtt gagtgaaaca ttttttatat ttttgctaat agacctatat attgttttca 180
tttttaaaat tgatatgtaa atattttggt ttgttatata tatatatttt ttttggaaaa 240
aaaactcctt tatttatttg tcgttaagta ttaatttctt tttttagtac ttttattacc 300
attgtggcct tgttttgctc ctcaatttag atatttatta tttgtggttt atttatttct 360
tttgttttcg ggacaagtga tgtttgggat attaaagtaa aggaaaaaaa agagagatat 420
tttgattgtc aaaatgtcag aaatatctaa acccggagct tctgccacgt aggcatcact 480
ttcattacct tttataaaaa gtacgaattg aaccttcatg acactgctcc cctgctccct 540
tatataaaac ccaatcctct tccatgctca gtattatctt cactctttgc tcgaaccgcg 600
tgtttaacag ataagattca actcacaagc attcatcgct aggttcttcc aaacaaaaac 660
cctacatctt ttccatttcg cctccttaat tctctcatat ttctgtatct taatccattc 720
taaaactaca ttttaatgca ctgccttgtg ttctgtattc cactatctgt tatcgtttta 780
ttgcgttttc tttgatcaga tcgctttgtt gttgcatgaa ctgctgagtt cgtttgatga 840
ttttgtttgc gcttcagttt tcatcgtttg ccgtccagat tgtttgattg gcgagagtga 900
agtgaaaatt ctgtatgata ttggagcgtt tcgtgtaaaa tctgtcttgt ttttctatta 960
tctgtatttt agtgatttgt ttttcgttga cgattttgta tgacgtaaag atattgtcca 1020
ttttaaagga ttttcttcca ctggttacta gagatcttag attgagcttt cattcggctg 1080
tattttgatg atgcttttttg tgtttttttt tcctttcttt ctttagcttt tgcggactca 1140
tggagtcttt ttctgaacga catcttaaga tgtttaagat gcttatttgc ttttttctat 1200
ttttggtatg acggggtcga gtctgatttt gaacgacatg ttaatattta tgatattttt 1260
gaagctagtt gtgcttgatt ctgaaaattg cttttgatac acgagaaact tttttgtttt 1320
cttcaatggt aggattttga ccattattat tattattttt taaaagatca aat 1373

<210> SEQ ID NO 97
<211> LENGTH: 2000
<212> TYPE: DNA
<213> ORGANISM: Cucumis melo

<400> SEQUENCE: 97
ccgaattcgc tattgggctg cataacttta tcacttgctg ggagactgca atttgtttgt 60
ttagtgctat gtagttttca agtttactag gctagtatgt ttgtattgcc tgagagtgtg 120
catcatgagg tggataaaat tcttaggtct tatttttgga ggggtaagga ggatggtaga 180
gggggtgtta aggtggcatg agcggaggtg tgtcttcctt ttgaggaggg caggcttgcc 240
atccatgatg ggccttcttg gaaatattgc tatgtctatg aagattcttt ggtcgctatt 300
ggcgaattct ggttctcttt ggtggcttag gtggaggctt acattcttaa ggggaggtcg 360
ttatggacga ttgatagtga ggttggttga tattgtgtct tcgggctatc ttgtgtaagt 420
gggatagttt gaaagcactt gttcctatgg aggtggggga tgggagaagg tgtagagttt 480
ggcttgatac gtagttgcat ggcggtccta tccttgatta ggttggggag agggtgcttt 540
atgacgcgac gagtcggagt gaggcttgac tttctaattt tcttggtcat gatgaggagt 600
ggaggtggcc acgagtttct ttggagttgg ttaacttatg ggatacggtt cagactgttt 660
gttcgtgtct tagtgttagt gataggtgag tatgaattcc tgacagtcat ggtggttttt 720

```
cgaccgcgaa tgtgtgggat actctctgtc ctcgaagtag tcaggttcct tggactggtt    780
tattgtgggg tagggggaa ttgttttcca aaacatttct ttttgagttt gacttgccat     840
caaagatagg ttgttctttt tgtagttctt tcttttggtg ctttttgttt ctatggatcc    900
tgtgagggtt ttctgctctc gtgccttaaa ctcaggctgt gaggtcctcc ttgttatggt    960
ataataatat taccttttca aacaaaaaaa aaacaaattg attcagaatg attttttttt   1020
ctttcttttg tatttattct atgtttcctt attcaggcta ctagatttga atatgttatt   1080
tgttacttcc ttttctaaca aaattagtta taattaattt tatttggttt ctttaaaaag   1140
tgtggggttg aagcttcttg cagaatatag gatcacaaat gcctaataca cttctttcta   1200
cttctttgtt ttgcagcagg gtatgaaaaa acaaattaat atgtattttt tatacttctt   1260
tctcgtatgc attattcttc ttttgtttct gttggctttg cattgtagcc gttttcttgt   1320
tcttgtctca ttttttctct accttttgtt tcttctctaa attcctttta tgttcatttt   1380
tcataatgcg gattttttca aaaaagaaaa ttatagttgt tagttgtgtt tgatgagaaa   1440
caagaaaaga gagtgaaaag agaaaagagg tagaagagaa aagaaaagaa gaatctgagt   1500
agaggaaaaa aattgaacaa aaaagttgga attgtgttgg atgaagtgag agcaagaact   1560
aaattttgtt tgagcgtcaa gcccccaccc cacacgtttc taagaacaag atggtaattt   1620
taaatacaac taatataagc aaaatacaat ttctcgagga aataggaaac ttcattccag   1680
gcttcaaagg aaaaaagaaa aaaaaagaaa aagaaagtaa aacgattaga acgtgaattg   1740
cacgtcacta gacaaaacca tcttttggta gagaaaaaca cgtgattaca aaaaacaaac   1800
gaaacccaaa taaatatata tagaaaaaaa ataaataaaa gaaatagaaa aatctaaaaa   1860
aattgggtta gcgggcaaac aagaaaccct tgtttcgatc ccccaaaacc cccccaccct   1920
ttctcccatc ttctttcttc ttcttccctt ccccattttt gaagaaccaa ccagcacctc   1980
tgaccaacat ttgcttaccc                                               2000
```

<210> SEQ ID NO 98
<211> LENGTH: 2000
<212> TYPE: DNA
<213> ORGANISM: Cucumis melo

<400> SEQUENCE: 98

```
tagtttggtt cataggttat agtttccaaa tttgttaggc tatcattaat caaacacaat     60
acttctcttg taggatggct gcccccctata gtactttttt aacttaggag aaggatataa  120
taattatatt ccttttagaa aatataataa taattgtgta gtgctttgat ataccttaaa    180
ttagctactc acgtttttag gaggaagctt ccgttgcttt tcatggtgtt atgatctttt    240
ttattttata aaggactgaa ctttaaaatt tctctttcat ctattttgga ttggattcca    300
tctattttat acgggaagtg aactctaaga tttctcttca cctattgtga atcggactcc    360
gtcatgtagg tcaagactac gacagataag aatagacttc cacgaaagaa agtggtcaat    420
cgagatggct atatttggct ctttcagctc aatttcttct tttttccttg catgttcttc    480
cgttggtaca tttcttgcac ttttttttgtt ctcacatgac taatgtattc caagtttatc   540
attggcattg tgcctctttt aggcttgtaa actctcgatc caaaattatc taggacatat    600
gtttcctagt gaagaaatac tagtatattc cttatgtcaa tatgtcaaaa ttttcaattt    660
cttaaccttt gagtaaatca atattatatt tttatggagg ttatttataa ttggaaaaaa    720
gttacaccca tctcaaccct aattaacacc aaatgaaatt gtaccatgcg gcacaatatt    780
```

-continued

```
tttttgtgag ttttttgcaa agagaaacaa agtagcagac aaagaacaaa cattccccca    840
aaaacagcag agaataccta agagagaatg ctctctcgta aaaaataata cccaagaatc    900
ttcccaaaaa gagggagtaa aagagtccaa aacaaacgaa ccgaagattg acaagaaggg    960
cactctcgcc ctccactgcg ccgctaaatt gtaagaagca tattttcttg agttaacata   1020
ggaataggtg taactcaaga gaaatgtaat tcgtagaatt gaactttgta tattaattta   1080
tatggtgttg tagatacaat ctttagtatt tactcatttg gtgctttctc tcaaatacaa   1140
tttaaactta gaactttttg atcttcgatt ttcaggaagt tggagttgca aatcaattcg   1200
agtttcaatc tctggaattt aataaaagtt tgatcttcca agttttcaat ctttcagaag   1260
acgatgatct tgatatggat aaaaaattgc acatcatgag agctttttga agtttaaatc   1320
ttcaattctc tagagcttaa attcttcctt aaaccaaaga tcaccaaatg aatgacaaat   1380
gtctctattt atcgaaaaat ttcatagact tttagatggg cttaggcaca ttacttgttg   1440
ggcttggact tgggcttatt tgcttggcgg gctcatgctc gagcccatta tttctttggc   1500
ctatttttca tgaggggctt gaacttggtt gtatacgaaa aaacttgact acctaaatct   1560
aatcaaatta taatcatcac aattttgacg tgttacgatt taattggcca aaaattcttg   1620
ttcaacactt gtctctaatc attttcctat ataatttaac taaaatattt aactttaagt   1680
aacttaaaag atatagttta attcgaatca aaatacaaat acaatttcgt ctatctattc   1740
ccatcataaa tgttgattga gattcatatt ataaacttct ttcaggaaaa gaaagaggaa   1800
aattcaccta aaccacgttt tcctattttg gtaagaatcc ccaaaccata aatcattcca   1860
aaattatttt ttttagaaaa aagaaattca catggcgtaa aatttcagcc ccgtgagata   1920
ttttcgaacc cccagataca atctacaccg tgaaaacaaa atcggacggt ggagattgct   1980
ataatgtccg tttagaggca                                                2000


<210> SEQ ID NO 99
<211> LENGTH: 2000
<212> TYPE: DNA
<213> ORGANISM: Cucumis melo

<400> SEQUENCE: 99

acactttgaa agtccatttg agagattagg gtaaatttga gtgaggatgg cgtgatgaca     60
acgataaaag tgaaaaatgt cagatccaag agagactcaa aagtgaatga cgtgaagaca    120
atcggaatcg aaattgaaaa atcagatttt aaattatctt aaaccacata ttaattaaat    180
ttcgattcca gtttcaattt ggtttgctgt gataaaacta aattcttaat tgtacctaat    240
tttctattaa ataaataggt aaaaaaagta tagtaaaaat attggcgtcg cccggactcg    300
aaccggagac cttcagtgtg ttagactgac gtgataacca actacaccac gacaccgttt    360
tgttacatga gtaaaatgtt tcctatttgt ctaatattat tattactact actacttctt    420
cttcttcttc gagaaaaacc aatttctatg ggtttaaatt tccaaattga tgttgagtgt    480
atcaataata tagcactcac atgctactta acaaaaatca attctttctt tttagttaaa    540
accttttctt ttatatttag tgaaaggatt aagctatgtt ctacgttaaa ttgttataaa    600
caaaatttga ttgttactta tcgagattaa tttatttaag tggatatgtt ggaatatgtt    660
actaaaatga taattgatag tgatacgtcg agtttatgct aaacacattt tgatatggtt    720
ttctttttca atataataat ttgacattaa ttacattttt ttttcatata ctctcaagaa    780
tgtttatttt tattatgtac ttttaaaaat taagattttt tatggtttta tccataaatt    840
tgtttcattt tttaatcgaa attttagtat tagactttag ttgttaaaga tcctaaaata    900
```

tagtcattat attttattaa agagtctccg tcacgtgtat aaattaaaat agtcttaacc 960
gttaaaagta tagtgaacaa aatttctaac aagaattgga tcggagtaga agggtgattg 1020
attcaacatg atccttgtgc cattattgtt gttactcaag ggacgttcat caatagataa 1080
cttgaaatca aaatggcata aactattgct cagttgaaag gttgtttgtt gattgaagag 1140
ttaggtttgg atatttgggt ggaagccaat ggccttgtcg tggttaataa ggtgctttca 1200
tttaattttg cactctctcc tcatggggtt tattacacta aagtggttca tttaattgag 1260
agcatattgg acgaaaataa acaattaaga ctaaggacga aagtaatatt taaacattat 1320
tttaagaaaa agtcatttta attcctaagt tctttttttag tataattttc atttgtttgc 1380
tatattttaa aaggttacgc ttttatcaat aattctttag tttagttttc atttgaccta 1440
taaattttaa aatatcacct ttttcctttt atattttggg tttaattttc cttccttgca 1500
ttttcatatt ttacactaat acctttaaac aactaaggct tactcctagt ctttgaaggt 1560
taaacgttga gtttcaacta attgatttaa tcatctaaaa ttttgagatt tttttaaaag 1620
caatgattag gtgcagtctt ctgcttccca tttatttatc acgtaaaaaa attataaaaa 1680
aatcattttt taaaattgtt acctgacaat tttttgagtg caactcgaac tgcctatcgt 1740
tgtaacccga ctgtacctaa atattttcaa tattttaaaa cctttgatta aatgataaac 1800
aaattaaaac taagggggaa attacatttt ccttaattta aaaacaattt tgttgataag 1860
atggggcctg gcccatgagg ttttgggctg ggcctttttcg aatcgtctat ttataatgag 1920
caaacgagtc tgagcttcga agaaatcccc ttttttttcac ttgcgaaaga gacgaacaaa 1980
cgcaaaacag tcgaaggaag 2000

<210> SEQ ID NO 100
<211> LENGTH: 2000
<212> TYPE: DNA
<213> ORGANISM: Cucumis melo

<400> SEQUENCE: 100
tgttggcaat gatttctttc agaaactttt gccaccttaa tgcttgcgta gtttcaaact 60
aaatgctgat tgctgtcagt aactgattaa attttgattt aagtatagta gctgccttat 120
tgtgttaaca agtttctcca tcattttttg cattgacttg atgatttgac ttcttttggg 180
tcatatcttt gattctttcc atgtttgaaa gttctaattt agatgttggt ttgtatagcc 240
attgagaagt ttaattggca aaacatttta tagcgacctt gacatagaag aagatgatat 300
cttcgtttct gatggtgcaa aatgtgacat aacacgactt caggtatgat ttgttttagt 360
ttggaacatc tttcatccat gtaatatttt tattttcctc atttttttttg aactttaatg 420 ttggttacta accttagtta aatatgtaag atagcctggt aatcgtatct ttcatcttgt 480
tactatttaa cttctcttcc caattttggc agcttgtttt tggatccaac gtgtcgatgg 540
cagtgcagga cccatcatac ccggtgattt tctcttctca ttaatgaaaa ctttcgatga 600
ttaattggta cactaataat attttgcctg tccacctata tatcagacat ttacttaaat 660
gatcatttga aaaatatcaa gctcttgggc aatcattttg tgtgtctcat ctttactgtt 720
gtgcttgaat gagtgaccac gatggataga ctttttgaga aagatccctt tgttaatggg 780 tctttttttgt tgtattcttt gtcggaaagc ggaggaaacc cagatcatct tatttaggag 840
tcttagtttg tgaggtctat gtggaatttt ctttcaaaag ttttgatgtt gtacttgctt 900
gctagaggga tgttcatttg atgattagag agtttctcct ctagttgcct ttcaaagaga 960
aatgacaact attgtgggtt ggcctagtac taaaatagga gacatagtct caataactaa 1020
ctaagaagtc atgggttcta tccatggtgg ccacctacct aggaattaat tttctatgag 1080
tttctttgac atccaaatgt agtagggtta gacgggttgt cccgtgagat tagtttaggt 1140
gagtgtaagt tggtttggac actcatggat ataataaaag agaaatgttg ttttctattt 1200
tgtggtttgt gggtgtgtca tgtgtgcttt gttgtggaat ctttaaggaa agaggaacca 1260
caaaccctat tgaggtttgg ttcttggtga agagtgtgag gtttcatgtt ctgggcttcg 1320
gtttcaaaga ctatttgtaa ttattcactc tcacttagtt gcaaacactt tcttttgagg 1380
gtttccgtgg gcttggtttt ctgtatgctg ttgtgttttt ttcacttttt ccctcaatgg 1440
atgcaattct ttattcaaaa gaaaatcttt actcttgaat ttgcatatgc accctttgat 1500
aacttttggt aggttagtca cttcagatca aaccacaaat aataatatat tttgttttcg 1560
caaaacttag aaaatatatt tttgatatca gtctgttggt ccattctccc acttattggt 1620
ttatgttttt ttggtagtta tgaagtaaca tccaaaggcc tgtattgttt aggctgtaga 1680
actttataca aacctctgct aagtcaattc ctaatcaaga atttgtggaa ctgtaggctt 1740
atgtggactc gagtgtcatc ttggggcaga ctggacagta ccagaaggat gttgagaaat 1800
atggcaatat tgaatacatg aggtgtacac cagaaaatgg attttttccc gatctatcta 1860
aggttcctcg aacagatatc atatttttct gttcaccaaa caatcctact ggctcatctg 1920
caactaggga acagttgacc caacttgtgc agtttgacta aaagaatgga tcaattatag 1980
tctatgattc agcatatgca 2000

<210> SEQ ID NO 101
<211> LENGTH: 1078
<212> TYPE: DNA
<213> ORGANISM: Cucumis melo
<220> FEATURE:
<221> NAME/KEY: unsure
<222> LOCATION: (1)..(1078)
<223> OTHER INFORMATION: unsure at all n locations

<400> SEQUENCE: 101
ataatattaa tttcatttaa aaataacttg aattttttcc tcctatattt atcatgcatt 60
tttacaaatc cacgttcgaa aatcccatta atcataggag ttaaattgtc atcacttgat 120
ttgaatattt attttttttt aaaattaata aataaataat gtcacgaaaa tgataaaaat 180
gcaaagtatc gaatttaaaa attaaacaga acaaaattta aaaattaaat gataaaaata 240
aatataaaat ataggtggat gttaaagata ataatttaaa tctttatcta tcatcaaatg 300
acgatcctcc aatggaaaaa gaaaaaaaaa actttattct ttacctcaaa ctcctcgcta 360
aaaagtaaca atggtaagat aaaactttat tttaaattat tcttccactt gcaagcaaag 420
taaatagtta tttgattctt acacaaaaga gaatttttac tttttacttt tcattagtta 480
tatataactt tataatacat ttccctctca tggaatttaa aactaccatt tgagcaaaat 540
attttaaact aaagaaaaat atgaaactta aaactatgtg acagggatga taatgacgtt 600
tactccaaat tttcatttta aattaacgta cgttatttta taagtatatg tcaaaatttt 660
aaggatctat tttattagac aattcaaatt atatgttgtg ctttcatatt ttgttaaatt 720
caataaatat gcctttggtt gattatacta tttttctaat taactctgga gacatttcaa 780
aagatttttt atttatttat ttaagaaaat atattaatat ggtcaataga tatgtattat 840
gcacatgata taaaaannnn nnnnnnngta ataatattat tacataatta aattctttca 900
tcttcctaac agagagagag gatcgtcctc tcagcgacgc tgatcccaac tgttccagta 960
ccaaatctct gtgtcccaat ccaacagatc cttcttttaa gctaaaccca ccattttttt 1020 tttttctga aacccatttc ttatctctcg ccggaccttc agattttacc tcaaaacc 1078

<210> SEQ ID NO 102
<211> LENGTH: 2000
<212> TYPE: DNA
<213> ORGANISM: Cucumis melo
<220> FEATURE:
<221> NAME/KEY: misc_feature
<222> LOCATION: (1)..(2000)
<223> OTHER INFORMATION: n=g, a, t or c.
<220> FEATURE:
<221> NAME/KEY: unsure
<222> LOCATION: (1)..(2000)
<223> OTHER INFORMATION: unsure at all n locations

<400> SEQUENCE: 102
cactatctat catagataaa taagtgatag atctaaacga tcatttacca aagtctcaaa 60
gatcatgtac caatatctaa acgagtttgg tacaagattg tataccaaaa tcatttgatt 120
tgatacaaga tcgtgtacca aaattgttta gatttgatac aatatcatgt acaagatagt 180
gtatcaatat ttaaacaatt aatcgtctat cctagataaa caaagataaa ccactaggaa 240
atcgcacgaa gagaaataga ggaagtgaag aaaaaaatta ctcatataaa ttgatgaaaa 300
atgttatcct tctctaatat ggttttaatt tttgcactag gaaatcacac attaatgatt 360
ataatacaaa gtcctacaaa gagatctgaa ttgattcatt tgtgaaactt tacaatttta 420
atcgatacaa ttattaactt aagagtgtaa ttgatttaag ctacaaggtt taagcaaaaa 480
actaaaacat aaacagaagt caaacttttc ttaatttttg agtttagtga gctacttatt 540
tattgggtag ctttagaaaa gtcaaacttg aattgtcatt tttaagtatg atcaaactta 600
atttaaccca aacttctgtt gtaggtgaat tagcagctag tttgtatata ttgactgatt 660
tacaaattct tattttaatt aattttaacc atccattaaa atggagagtt atagttattc 720
aaggatttta actactctca aaatcatcaa gatcacttgc atatttagta taagttcaag 780
gacttaagtc cttattgata ttttcatcat catctggaaa actaatcaaa taatcatgtt 840
gatgcaactt agatgattaa gattaaagct aagacttttg aaatgataaa gaatataaat 900
aaaaaaggaa gttttttaaa aatataacaa ataggtaaaa tatttacatt atataaaaca 960
attctagaaa cgaaaaaaac ccacggtctc acaatgaaaa atacaaaaaa taccctagtc 1020
aatagcaatt aatcagccag cttgcgcgaa gaatattctt ttaaacgact gtgtactaca 1080
atttcaacga ataatccagt attgtttagg tcatgacacg atcatgtagt tctattttaa 1140
cgatgggaaa aaaggttttg aatttaaatg atcgtattga tcatgaaaaa caactatgtt 1200
gattacgata agcgatcatg tagtccaatg taaatgaatt tcaagtctaa cgatcatgtt 1260
gaccatgcta aacgattgtg ttagctatgg taagcaattg tgtagatcat gtcaacacga 1320
tcgtttagat cattttaaac gatgtgaaaa agactnnnnn nnnnnnnnnn nnnnnnnnnn 1380
nnnnnccatg ataaacgatt gtgttgacaa tggtaaaaga ttgtgttgac gatgataaac 1440
gattgtgttg ataatggtaa agatcgtgtt gacgatggta aacgatcggc taaatcatgt 1500
caaaatgata tttagacgat gtagatattt ttgaatatga gaaagatgaa gtgactttaa 1560
agatgaagta gcttttaggt caaaagcaaa taaaaacata taaaaacata cgaggaaaag 1620
ttaacatatt tttagtctat tcagactcat ccaaatttta attgtgtcat caaatctcaa 1680
tccacagctc tcaccttgat taaatacata acatatctaa gatcttataa ttaagttcat 1740

```
gaacgtatct aactttttaa ttcattgatc tgccttgctt agttcaagtt acataccctc   1800

ttgcttaaaa aaaaaagtta cataccctct tgcttaaaaa aaaaaagtta tataccctct   1860

ttgacaaata tcaaaggaga aaaagacaaa aactgacatt ggcttcccat catccagaga   1920

aaagaaagaa aagccgcgcg ggttgtttat ccacttgttt cccttattat cctcatcgat   1980

tccaagtttt gaactcaaca                                               2000
```

```
<210> SEQ ID NO 103
<211> LENGTH: 2000
<212> TYPE: DNA
<213> ORGANISM: Cucumis melo

<400> SEQUENCE: 103

ttcctattta aattaactgg ttttcttaga aaataacaga attcctgtgt ggaatcccgg     60

ctctaatcca aatttcatag ggatgaaaaa tgaaatgggg agtagacatg gagatgggga    120

gtggcattcc tgacctcacc ccgtccccgt ggacatcttt ggtgacagaa tcatcccatc    180

caaatcaatc tgtgggcaaa tttcaacact cacaacaagt tgaaagactt tgttttgtaa    240

tgtatttcga gttcaactca catgtggttg tatagtctac catttcaaac ccactccaaa    300

taagaaaaaa atataaaaaa acatatttta gaaccccaca acattttttt tatttgaaac    360

aaacaaatat ctccacgtgt ttctgtttga tctcaaattg tacaaaaggg agacaaacaa    420

gagcaactta atcgtgtggt cgaaagttca taaaaaacgt tgtttttcat tactattatt    480

acatcaacca atgcgatctc aatcttgtga agatttttct tccatgtgtg agtcatttct    540

tctcgatctt aattatcttc tcacaatcca tttattatag cataatctaa gttaatttag    600

attcaaaact atacaataat aataattaag aaaattacaa atttaaatag caaaagaacc    660

atttgttctt tatagtttct acactaactt ttgaaaaggt taaggttatt ggaaatcttt    720

ttctggggca tttttctcca attctacaat agacaatttt ttttaattaa ttaattaatt    780

aaatttaaag tttaccttgg agtagtcaat aattaatttt tatgcacatt tgtcttttat    840

atgattgaat gtaacaaaca ataacttatt cttcttcttt tattctattg ttttgatgca    900

aacccacaat atttaatgag ctcatagtta tgtgtttgct ttactaatta attattttct    960

tttcataaaa taaaaaaact tgtacaatat aaactctatt atcattgaat ttttagtact   1020

taatttaaac gtactaaaat aaaatacatc attctgactg acgatccatg taaataaaat   1080

ctaaaaataa aagaaaaatg tcagaaatag caaattgaca aaatatttac aagccatagc   1140

aaaatttcat attctaccga taacaaacat ttgatagaca ttgatattct tctgtcagtg   1200

gtattggtag acagtgatag aagtctatca atttctatca tcgatagaat tcaaaatttt   1260

gttatagatc gtaaatattt taatttattt gttactttta aaaatgtctc aatataaaaa   1320

ttattaaata aacattaatt ttttattttt caattttaat atctaagctc ataaatatta   1380

actttaccca ttatttattt ggtttcttac cgcttaaatg ttgcaaaaat attttaaatt   1440

ttatttttga aatttggtta aattcgtttt tacttaaaaa tttccgtgat aaaaatattc   1500

gaatttttta ggtttttata agatttaaaa gtaaactaca taaatgaaat cgttattttc   1560

taattctcaa tttaactttt ttatactttt taattaccaa atggaaacat gaaattttaa   1620

atatatttat tttaaatctt actcgttaca aacaaaacaa taaatttaaa attattttc   1680

cgagttttaa attacaagat ttaaaattaa tttttcaaca agaccaaaag aattgtaagt   1740

ttcgaataaa aaggtttctt tttgggctat aaagtccaat ttcctataaa agaatttgat   1800

caattggagc ccaaagtcag atccattaac ttttgggccc aaatagaaca atgaaaagaa   1860
```

agcccaaaag ctgacccacc aattaacctt attattaggg ttttgctctc tcttttaaca 1920
tccgaaaatc aggactctct tgccgctttt ctcttcgccg tcgccttctt cgagcttcaa 1980
gtctcccatc ctcttcagcc 2000

<210> SEQ ID NO 104
<211> LENGTH: 1974
<212> TYPE: DNA
<213> ORGANISM: Cucumis melo

<400> SEQUENCE: 104
tttgctattt tcgtttcatg tgggaaaaat agtatagtat gtttacgtct taaattattt 60
caaattccta gctaggaatt aaaactttaa tatatccaaa acgtttctta tttattataa 120
agatctgcaa tagcacaatg ccaatttctc ttctttgaaa tccaggttca aatcccggtt 180
gcggaataat gttttgctat tttcgtttca tgtggaaaaa atagtatagt atgtttacgt 240
cttaaattat tacaaattcc tagctaggaa ttaaaacttt aatatatcca aaacgttcct 300
tgtttattac aaagatctac actagcacaa cggtaggtag tttctcttct ttgaaatcca 360
aaatctttgc tattttcatt tcattttcaa attgaatgca tagctttaga ttgtagtaaa 420
cattgtatat atatgtttag gttgtgctaa ctttaaatgt acaaaattca aaatgtaata 480
gaattagatg tacatgataa agagttgcaa tatttagatt aaaatataag aatttaaatg 540
taagacttgc atatatcaaa aaaagatttc tttataaaca atattttttt atacaatttg 600
aaggcaactt attgttactc atgggcttga tccaaacttt tgttgtcttc actaaaattc 660
ctctaaatag ttcaacataa agttgttcat gagaaaactc attaagatat attccaacat 720
tatgaattgt ttgtccttgt attttgttaa ttgtcattgc aaagtataaa tgaatggaga 780
tttgttttct tttgaacttg aatagatatc cattatcatt tggtgggttt aatggtattc 840
atggaagaaa aatttatttt tctgcataat cacccattat tatttcagca tgtataaatat 900 ttttgctaaa taattgacat actaatcttg tctcgttaca caatccatta gatgaatcca 960
aatttttcaa taacaacgtt ggtaaaaaaa atcaagacag ccttttatat agtaaaaaaa 1020
atgttacaac aacttttcaa cgttcaagtc tttaaatttg tattgttgat tagaattaat 1080
aagatatttg atttgcaaca aatttctaaa atgtaaataa aaaaccattt gcattcaaac 1140
tctttacatc caatacttta attccttcgc atcctatact ttaattccac tcacttaaat 1200
ataattaatt aaaaatatag tggataaatg aaaaccaatt tgcatttaat ttttatatat 1260
gcatacttta attccactaa acttcgttag aattaattca aaaagttgtg ggagagaatg 1320
tgcattttat catattacaa gaaaaataaa attaaaaaag aatttaccat aaagtcatta 1380
aacaaaattc aaaggttgaa tggagagaat aaaatttctg cacgctttga tatatacaag 1440
atatttaaaa ttaaaaaaat agttttaaag agaatgtttc taaattatta ttctaacttt 1500
aaatataatt actcataatt atacttattt ttttttaaat ttagaaacta aaatgataca 1560
ttctcgaaaa ctataatcaa acgagttaat gttataaact ttgaaaacta ttttttgttt 1620
ttaaactctg catagcaaat agcatataga ggttttttaa aaaataataa taattaaaaa 1680
aacattaaag gcaaaatcta ttattccttg atttgtgtat agggtgtaaa tattttgtta 1740
ctgtgttatt tttaaccatt tgcgcactga tacggactaa aaggtaaaaa cataattttc 1800
tcgaattgtt attagaaaac tggggaagaa aaaggaaatc aaatcgcgcg aggtgggatt 1860
tgacccggga acctaagact agctcggtgt ggtgttgaaa tccacgcgtt gttcaccgat 1920

-continued

```
tttcttcata acaaacgcac ccaggctacg gcagtcttcg aagctctctc aatc        1974
```

<210> SEQ ID NO 105
<211> LENGTH: 2000
<212> TYPE: DNA
<213> ORGANISM: Cucumis melo

<400> SEQUENCE: 105

```
gtcgtcgagc agagctctgg cagttaccct acaacccgga gcacgataac tgcagtgatc     60
cctatcctca gcatcagtta aatgggccga ttcaaaactt ttatgggcct cagcccactt    120
ccacttacaa ctattacaaa catggatacg atagtcacga tcaggcccat catcttaatt    180
actccacaca ttccaatatc ttcggccgcc aaactgcctc cgtttttagc gacgaaaatg    240
tccataattg ctctattatg taataaggct aaacactaat catctatccc tttaaatctt    300
gaatttttgt aataaaacca atctatactt tttgccatag tttatttcta gaaaagttta    360
gaatacattg aagatttgag aaacttgtct acaaggcatc aacaaaacta cgtgaaaatg    420
acaaattgga aacaaataaa aatatcttat gtttgagtat atggaatgaa gggattgatg    480
taataaaact taacgtcaag tgttaatatt acgctatagt tattttcttg ttgtagtaat    540
tttctcttag ttaatttttt tattattgaa ataagtgata aattttctaa taagaacgta    600
aagatttaaa cctctaatta agttaaaaaa aaaaacttga attattgttt gagttatgag    660
gtaacgtaaa agacaactta aattttaaag tcaaaccgaa aggaaaagag ttaaataccc    720
acaaatggat caaagaagtt aataacacac acgcacgttg ggaagcttaa aaattagcaa    780
caaacaagca atcattggtg tgggacagta ttgaaattcc acaaaactac aagggtatat    840
tggaaaatcc aatttattta tttatttttt aataggaatt aaatttactg taaaaaaatg    900
taagaccgtc gattgacaat tggtggactg tgaaacgtgg caaaagttaa ttggcgaaaa    960
ggagaggaaa gattttctct tttcattata atgaaaaaaa ttaatgatag tacacgtggc   1020
aaaaaagtat tggagagaaa tttccgggaa ttatctctaa tacgcggcta atttggatgt   1080
caattttgca aagaccagaa tctttttgaa cagcgaagaa gaacaaatat atagacatac   1140
aataataaat aaaaataaaa atatattaag cataagagaa aaagaagatt tgaaggttat   1200
attgaagtga tattgttggt ttctccattt ctgtgggtct gactctgcct ctctcttttc   1260
gagccagaac caccaaaacg aaaaaaccca cacactgtat agcaaaccct aattctttgg   1320
tctcagatcg cccatggctt ccactaaaga acgcgacaac ttcgtttaca tcgctaagct   1380
cgccgagcag gccgagcggt ttattgtatt ggttttccta ccttcctttc cacttttttt   1440
ttttgggttt gcttctcatt tctattttat gcttttctta atttgtgttt tacttttcac   1500
tctctctttg ctcagatcgt atttcttctg gttgtttaat tttgtgttta tgttttttga   1560
cttcggattt aagccacgat cgcttgcctt tttgtgtact attttcagaa gtgttgttat   1620
gtttatccgt ttacacgatc tgtttgaaat ttatggaaat ttagtttgct tataattttg   1680
ctacatttct attgtttagc ttctcgagca gttttttttt tttttggccg atccattgat   1740
ttatactgtt tttctgtctg atctgtttta tttaatggag aatactcttt ttttgcgaag   1800
cttggtagct catttttcac tcatacttac acagactact tggtcattgt ttttatctgt   1860
aagcacaaag caaattcaag tttctgcctg ttctttcttt gcttgtcaaa cgacaaaact   1920
atgtttgtag ttgcttttgg atgatagatg gtgattctga ttttaattta cgttttcctg   1980
ctgttttttt tttaaaagaa                                                2000
```

<210> SEQ ID NO 106
<211> LENGTH: 1643
<212> TYPE: DNA
<213> ORGANISM: Cucumis melo

<400> SEQUENCE: 106
tccattggcc ctctcaaacc tttatgtgca tatcactaat atggttgaat atgtatatct 60
tctttctcga atagatgatt cttggtggtt tcaataatca tttagcaaat ccagaaattg 120
ggacctcaag ttcggttgcc gtggaaatag ctaaattaac tctgaaatcc tcaaactgaa 180
atgtgagaat aatcacgatg aatctgaacc gtcaacggcg gaacatagca acagtaatca 240
gaattaccaa atttcaattg ggggaattcc tttgtatgat ccttccttgg gcctaacagg 300
gattcttgat ttgaacctct cttcttcgta aaaattacac aaaatattta gctgctagag 360
ctagacaaaa caagatttag attggaaaaa caacaatgca gctcccaaat tgcaatccta 420
attccactat ttcttttttc tttttctttt ttttaatctt aggattcaat tcatcattca 480
tcaattttat tgttactgct cattgatgac caatgttttg gattttgtgt gtcaaatatt 540
ttagtttata tatggtgaaa agataaaatg aatagtttca aattttgtgt tttatgaatt 600
cctcactacc tctttctttc actaatacgt atgaaatgtg tatggttgtt tataaataag 660
atggatggat gttttgattt tgatttgaat gttaatgtta cttaaattat agattttaac 720
catttgaatg aaatatggag agaacagttt ttatatgtaa aaacaaatta atgtgagaaa 780
gaaataaata gcaatgcctt tcttcactaa taaatgtatt tatatttttt attaacaaaa 840
taaaatttat attaattatt agtgtatgag gtgtgttctt gtacaaagga aagtattgca 900
aaattacaaa aatggaaagt tgaaattact gcactcattt gctaaaatca aattagttaa 960
ttatagaacg aaaaataaat aaataagttg tatttgatga tcctagataa ataacttttg 1020
aagaataaag atcaactatt taaaaaaaat atgtgtatca caaaaaagaa tagagaaaaa 1080
aatcacaaaa atcacatccc aaattataat aattcatatt ataataattt atataccaaa 1140
cataaactat aataatcacg tattattata actcatagac tataataact cactccacgt 1200
cccgtagtta ttaaataaaa gaaagtaacg gtaacattaa cattataact tcgccctcat 1260
ttatggcaag gaaaaattgg ggggattggc aagtattata tttgtttatg gaaaactttt 1320
gtgaaggtgg aaaatagaga gagccaaatt aacaaaaata ataacaaaat caaagggtgt 1380
agaattcatc cagtttgaga gcggaagatt agatgggtga agaaaggatt attctagaac 1440
cctagcccac gtgtcataat ccaaccctca cctttttcttc aaaaaccctt tctttcttct 1500
ccctccccta tatctccttc ttcgaccacc aaactctttt ctctcaattt cccagcatct 1560
tcttcatttt tcattcttaa ttcaacccat ttcttctctc ttttcgtttc tattttcatc 1620
gtttctctat aatttctccc tta 1643

<210> SEQ ID NO 107
<211> LENGTH: 2000
<212> TYPE: DNA
<213> ORGANISM: Cucumis melo

<400> SEQUENCE: 107
ggatgggcaa tcgtgcgaca cttgttctac tcgattaaca aattagccgt gtaaaatcca 60
aaaattgtgg acaatttacg gtatgatgta gcccctcttc acgttcttaa gaaatttttt 120
ataaaatgag aaagggaaag gaaatcattg aaaagatcat aaaagaaagc attgaagact 180
gttaattgca aagaaagctt agcttaaaaa gagtgcaaca aggcttagtt ggggatttaa 240

-continued

```
ctactatgtc tcccttattg tacattttga atatttttat ccttggcaga cttgcatatg    300
aaaatgtcga aacgtcacac actaggtcga caacataaaa atgaaagcaa tagagcaata    360
gattaaacta agtagaaaac ataaagacaa ggtgatttga aggtatttgg atatgtggcc    420
ataggcaaat aacgcgctgg acaagcatgt tcatgacata tgacactttg cacgcatgct    480
caatgtggat atatcagcat ggcgcacgtg cctcactcgg acacataaac atggtatgcg    540
cggcatcatg tgcgcacgcc ttacacgacc aacgagctag gtgtagtcca agcacacacg    600
cgatgggcaa acgtgcctat ggctgcccct ggcgcagaca gtctcgaaag atgcatgtcc    660
atcctaggcc catctagaca cgtccaaaag ttccaatgac ggtccaaaag gatacaatac    720
ctttagaagt gtcatggtag gtctagaatg ttctagagtc atttgtaaat tgttaaactg    780
ccttatatct tctagatata caggtcctcg gccgaccttc aaagcaccta ggtcggttag    840
gaaagctata aatagatgta aggtggctta tttgtaatca ccctaaaatc ttggcataac    900
ctagccaagt aagacaacct tgcctcatca tttgtacaca aggtaccttt acaaatggta    960
ataccctggc aaaggactac actcatttgt atacaacttg tacacaagca atcttggaac   1020
gcaaagtact cttccaagaa gtgtcaagct aagctccatc attctcacaa aatgatctct   1080
cttgcctttc aactatctta aatcttctac tgccatattc tttctcatag tgcttagtgc   1140
actaacctct caaaggctta cttggctacg tgggcgttaa tattagtcaa gtgttgtacg   1200
tttggttagt tgaaaaatct aaccacgtga caatagacaa acatcaattt tattttattt   1260
tagagtctca ccaagttctt aaataaaatg tttattgtaa gacaaacaaa aatgaaaata   1320
tgttattata gtgatataga attttcacta ttagtacaag atataaaagc gaaaggaaga   1380
atgaatgaac actcaacatt tagaaagtgt tttgagtaaa gaagtaaata gtgagaaata   1440
acgagtacaa atgtgtggaa agttataaac ttctaagatc tacagaacaa aagattgata   1500
agatataaaa ttgatgttag gataggagct acaaactcct ttgaccaaat atcgagcagg   1560
attcacaagt catactctct tactctacca aattcattag aagtacataa tgggcatgca   1620
tgtgaacgaa ttaaaaaatt ggtatttttta tttttatatt ttaaaaaaat tggatgaatt   1680
ggcaatggcc atgaatgaac cagttgttaa agtttagagg acaaaaccca aaagagagaa   1740
gtgtacctca taaaaaacaa atccaccaat tgagaatcac ataaattata ggaagacgtg   1800
tcactctatc ggccgatcct caaactcttc caccaaatcc acatgcacaa tctccttctc   1860
ttcccttcca ccatacactc aaaatcccac tgatcttctt cttcataaaa acccatataa   1920
tcataaatta atttcctcaa gtttttcttt tccaattaaa caaacaactc tgcaaaagag   1980
gcctttcttc caccatttcc                                               2000

<210> SEQ ID NO 108
<211> LENGTH: 2000
<212> TYPE: DNA
<213> ORGANISM: Cucumis melo

<400> SEQUENCE: 108

agacgaagaa gaagacaggg tgtgatcatt taagaatatg cgttttaact ctgccctttt     60
tagggctttt ttcttttatt tatttgcctt ttttctcgct cctagggttt ttccctccat    120
tgaattagaa ggatgactgg gccacagact tatgatgggc ttcacggtca ttatttgaaa    180
gtgtgatatt ctaaaaaaaa taaaaactca tttgaattaa aatagggttt ccctccatgg    240
gagtatgaaa gacttttaat tgaattgggg tttttaaacc ctaaattgaa ctaaatatat    300
ttttatgatt tttacaaaaa ttaatactac aaaacaaatt atgattaata aaatttgttg    360
```

```
atatttttca aaaaacaatt atataataaa acaaactaaa tattcaattt ggtattttta    420

accatgctat aggaaaagat tcatatgggc atcaaaatga agcaagaaca tggcaaagca    480

agttgggtga agataagtat tgtcctaaat cgaaggacga ggcaataaac tcgatatctc    540

gaagagtctc caggtcaaca tcacaacgcc tgcacaaacc aaatattatt atatatatag    600

ccatcgttta ctataagact atgtatttac gaaaaattct atattgtttt cgacgattac    660

atttatatta tataggaata aaatacaaac ttttcgaaaa gtcatatatc ccaccatata    720

aagatcaaac gtggtagatt gaaaacatta tacagtatat tctctatttt tttctcataa    780

aacttattac gctttgtcaa gttataaaga ttaatggttt tggtatattg tgctaacttc    840

gtccatttgt tgtgaaatta cattttcact actttttttcc acattgcacc atttttcata    900

tgttttattt ccattatctc gtagaatatg agcaaagaaa aagattaaag atgaaatttt    960

tcaacgtgtg agagaaacat cattaaaggt tacttaataa ggaattagaa aaaagagcat   1020

gaacctagaa caacaagata caaaatatca aagacaaaag agttcgatgg agagctagaa   1080

agataaatca agattttgta aaagaaaagt gctcggtggg gaactagaaa aatgttatag   1140

aagctagaaa gataagccga taatttgtaa actataagag gccgtttaga ggaagagttg   1200

ggttgtgaaa tgttagtgtt atgataaaac tattgttatg tttggggaaa gagtttaaaa   1260

aggtactttt atgataaaat atgtctggga taagagttga aaaacgtagt tttatgggag   1320

agttgaagat atagggttat gaagagttaa aaaaggtata agaaaaggag agagagagag   1380

ggaatagggg ttatgatcat agtcttaaaa cagaattatc ataacccaat ccaagtgata   1440

acccttggac caaacgacct aaaatatcaa agagaaaact gtttggtgag gaactataaa   1500

aatgttatag aagctaaaaa tacgaactag aaagataagc ggagccaatt ataagggttg   1560

gttaagtgta gggtttattt atttgagggg aatgataatt taagatataa attaatagaa   1620

tggcaagttt tgtaagaaaa attaataaca actcgataaa cttttgtttg tgttggtaga   1680

gaaaacatgg gccacaaaca tgagcccaaa tgtggagaag cccagctgat aatttaattt   1740

taaaaataat aaagattaga ttatttttgt tcgcccaaaa ttcggcgcgg ctaggaggtt   1800

gcttataaat ggaaataaat ggaaagggtg ttaggtctcg aacaagtgtg cgacggtatt   1860

ttaaaggtcg gccacgttga ggcggccctt ttcactcctt tttcctcgct cgtattcaat   1920

ctagggtttt aggtttccaa cttctcttcc tccccttccc cttccccttc cccttccttc   1980

tctactcatc actattctca                                                2000
```

<210> SEQ ID NO 109
<211> LENGTH: 2000
<212> TYPE: DNA
<213> ORGANISM: Cucumis melo

<400> SEQUENCE: 109

```
atgggtagtt ttcaaattaa tccgaccttt gaagtacttt ggtttttaaa ataatttttt     60

atcatctgaa atcactccat agacttatgt taccgtaaat cattattctt tacaaatgat    120

ttgattttac ttaaaagtat attatttcaa acacgttata ggtattatga agttttaccg    180

tcaacaatta tagttagtaa gccaactatt tataaaaatt taaaaaggaa tatttgaagc    240

atggtgcatg atgtatgttc ttctctctct taagttgact atcaaaactt aatcatgctc    300

agaataacat acctcacata gcatgtgcaa tttaatctaa gcaattcaaa attcattaac    360

aataattcat acacactaca aagtcatacc acctatgtca cccaagaact actattattg    420
```

-continued

```
taacaagtca aataagaagt ccctatccta tccatcctaa gatggagtaa tttttctttt    480

ccttaaattt ttggaaagaa gaatattgaa attcaggaca ttaaatcaaa gctgttcgga    540

gataaatgaa ccattcttca agtaaaattc atatttgtca tcatgcaaac aaatattgaa    600

aacatgatat caagaaaaag aacaaattat ttaaaaacat cataccgcac atcaaactta    660

aaataacctt ttgtgcatat caaacttaaa ataacttttc tcaacaaatt aaagcgacat    720

aaaattgata atttttgttt ttttttaaa tatatattca agaaaatcga caaatccaaa    780

tgacaagttg ttcacctgta tattaaaaaa aacaataatg aaaatttgaa aggagagatg    840

agaaaaaaaa aatcaatcca tcaatccaac ttgaattttt gggtcgacag catatcccta    900

attataatag gaagcaccct acttttttta caaaagtatc gaaattatta gtcgaaaatc    960

ttaattagag tccaaattgg atgcagcaag gatagtttta aatccaatta atagcatgcc   1020

taatgctatt acaaatatat tttggattat acataaatag aaaaaaaaaa gtgaacttcc   1080

agactcaaat agattttact ctattgttat aaaaactata cattaaaatt agatgtagag   1140

aatgagagct caaaaccaag aaaagtaaat gataaaaggg aaacaggagg tgaaaagaaa   1200

aggtgatacc gcggatttga tgtggctctc ggtttttgcc tcccaagcaa tccccattgc   1260

ccatctcctc tacaccaacc cacttttctc cctttctttc tttctttctt tctaaaactt   1320

ttgttttcca attttgacct ctcttcttgg gcccacttac taacaaatca aaaccaattt   1380

tcattttttt ttcttttctc tattcccttc cacaaataag aaaaaacttt atataaatca   1440

atacaagaat gacatttatt ataatagtat atactataag gtgggaggga tggcaattgc   1500

caattgtata agtaactatt aatagacagt aaaactttga aatagaaggt atttagatgt   1560

ctgagggtaa acttataaca ttttatgaaa tctaaaaact aaaattaaaa ttattgggac   1620

aatataaact ttagacataa gaagaaaaca tatttttgtt aataatttaa caaagaacac   1680

aacaagaatg gtagagtgtt gattaagagt gagcataata gacaaaaaaa aatatagtca   1740

atcagccaaa atagacggtg gttggtcgga gatgaagaga gtttcaatct aatcagttgg   1800

taaaaaattc aaacatcgtc acattcttta aaactttttaa aggtttaaat ctgctaagat  1860

ttatcgaaca atgacctatt tgtactactt tatgattgac atcaatttaa atatttaccg   1920

gtgaatttag taacgattag ggcgagagcg gttttaaaaa caggagtgga gtagtggaca   1980

aggagggggc ggaccaaccg                                               2000
```

```
<210> SEQ ID NO 110
<211> LENGTH: 2000
<212> TYPE: DNA
<213> ORGANISM: Cucumis melo

<400> SEQUENCE: 110

ataatactat aaaacaaata aattttaatt aagttgtttt tactttcata ttatactaac     60

aagaacagtt tgttaagttt tatatgtatt tataaaagat atatgagtta ttggttaatc    120

tataatatca atgtcgaatc tctaacaaat attttagtgt ctagacctta tgtaaaaatc    180

agaagtgacg ctcaatattt ggaaacagga atcattggga tacgtggaaa tcaatctttc    240

tgacattgtt acaaacaaaa gaataaacga aaagtatcac cttatagact caaagaatgg    300

aaggattcag attgagttgc aatggaggac ttcatcctga agtacctata tatttttctt    360

cttggttagt tttcagtctt tctcttctat ggatcaagtg gggaatacag caagagacaa    420

gaaagacatt ttcctataca aattcatttt attattcttt cattgtctct ataaataaag    480

aggcatttaa atccttttcc taatttaggt ttggtatcaa tattttgttt gtaacagagt    540
```

```
aatagaacca aaatatttca ttatgttact tgaaatgttg atttttttgt gcccattctc    600
ttctgagtcg acaagtgaga gtagatatga aagtagctta catttatatt ttaagagttt    660
ggaatctctt accttaaata ttttctaaaa gaatatcgtt gtgggaatat gatttttcta    720
ttttataaat ttgacactat cgatcaattt aaacacgacg tataatttta gttttatttt    780
tagaaaaata agctttttag tttaagtttt tttttacgta attactattg aatccctaaa    840
gttttaaaat gctatagctt tactcttata ctttgagttt agtttgtata tatggtcgat    900
aaattttaag attatgtacc gtaattctaa gttaaaacat tgctcacctc ttgtcctcaa    960
agttaatgta aatgaaatta taatactcat acataataga actttttttt attcttaatt   1020
atgcaaaaag aatagtgaag gttaatttag ttataatcag ttctagaaaa ttaacacaaa   1080
cattctaaaa gtagtttgaa attgagataa aatgaaagtc aaattcaaaa caacgaaata   1140
aagttataaa tatgaaactt tgaaaaatat agataaaatt agaactacgc atgaaaactc   1200
taagacaaat agacaattct cgagatagaa gtttgaaatc gaaatctggg gaaggaaaaa   1260
tctttacatt tccattttat tcctatatct actaataagt tttgtattaa aaaagaacat   1320
caaatagagt aaataactgc acactaaaca acactcaccc aaccacccca tatctcaatg   1380
agaaatctta atgtgaacta caaagctagg gacagaaaaa tgattcatta gattccagaa   1440
caataataat tatgattaca ttttggattc attagattcc aaaataataa taattatgat   1500
tacatttggt gtttgaccta tttatttatt tattttatat aaatattttg tcgaagagat   1560
agaaaaaagg atgcatttaa attaaaaaag aaaaattata ttgataaaga agaagatggc   1620
gggctgacaa gagaagaccg ggaggctgat gtggcaatgg gaattccaat tttccaatca   1680
aaaactaaaa acaaaaaaga aaaaaaaaaa gcaaaataat tttggttcac tgaaaatttt   1740
catataaata catgtggcgg ttgatggccc aaaggatgag ctttgaaggt cgcattatca   1800
aaagtttggg gaagcagatt tttgctaact tcgaggtact ctcctctcct ctcctctcct   1860
cactttcctt tctctctata ctaactataa tttccattcc tcctccatca ataatttctt   1920
catcctcttc cttagctaat ctctctcttc tctaccagtc aaacgccctc ccttttggtg   1980
ctctctagcc tcctcctccc                                               2000
```

```
<210> SEQ ID NO 111
<211> LENGTH: 2000
<212> TYPE: DNA
<213> ORGANISM: Cucumis melo

<400> SEQUENCE: 111
```

```
ttctctctct cttttaatct acaacgtatc caattatatg gagaaagttg aggttgttgg     60
atttaattca ttttttcaca ttttttaggg ttaaaatcta aaaacacatt tcgattttgc    120
gactgttcaa ggcgtatatg tttctttaaa tattatagtt gaaattacga tcaaattctt    180
acgctggtta agaaagagaa aatcgtagga gagaaattgt gagcatataa gtgaaaataa    240
cctcctagag ttttttggat ttttgagcga aacaaaagta aggttgtaac gatttatgtc    300
taaaatgaac aatgtcatat cattgtggga atatgtgtga atgataaatt atcacaactt    360
ccaacaatga gtatcacaat acatatcatt gatgggtttt gagaaaatga gggttgactt    420
ggacatgaca acttgataga cttataactg tgtggtgtac ttataagaaa tcggaagttg    480
gtttaaaagg agaatcattt gcgtcgacaa gatgattatt attgcaaaag atgcaaccaa    540
ggtatgtcga tacataggct agataaaaag aagatcaagt aatgatataa ctatgtctct    600
```

gttgatatgt ttttaagtga aataaaaaac aaaactatta atcctatacc taaaatgaac 660
catatcgtac tatattagaa aagaataatg tacctcttga tagaaactta tagtaaaagt 720
gattaataaa atatcactag agagatacgt aaatacttcg ttatcataat ttattttact 780
tataaatgaa ctataacaaa aagtatttat atccacaaaa tcaacgttaa gaatattagg 840
gcgtcgaaga agacgccaaa ctattttaat ataggttacg tttggtatct catctacata 900
acaatctttt gctttcaaat acactcaata aagtaaatgg aatgattttt tgttttctaa 960
ttttgtcatt aaaaacagtg ttttacattg tacttgaatt tgtgacatat aatgatatat 1020
ttctttttac aatacccaaa atcaacagta aaaaaacaaa tacttacttc ttttcattca 1080
aatttttcat atgcttttga ccgttattag cctttagtag tttatcgtaa atagattgtg 1140
atatttttat caagaagttt tattttttaa aataaatttc ctttttcata accacaaaaa 1200
gcacccttgc aaaatcaata tttcattttg gaccgggttg acattaggtg ctttaaggat 1260
cggcccaatc tagattcaat aatctcagta aggcccactt gtaaaccaca aaaaggcatg 1320
gcccaccgag cccactatgc caatagttgg gcctttcttt cgcaaatgca cgcagctaat 1380
taaggcttca ttacttaata atcagtaatt aattttgctc caaaacgggt caaagagcga 1440
cccgacccgc gaatatgtat ctgggccgtt gattatttta gtagtaatct caaccgttca 1500
gtcggtcctt ttatatgtct gtcctccctc gtaatcaatt cttagggttt tctagggttt 1560
ttagttcttc tctacgcttg gttggaagtg cccttcctct cattcttcct gctttactac 1620
aggttttcaa tcttcaacaa tttaaatctc aacatttaat ttgttttgca cattgattca 1680
agtgtgtttt ttttctttcg tttgggcttt tgttgattga aattactcaa gaaattgcag 1740
ccacaaggat agtctaaaaa tgcatttgat ttagtgtagg tgctgctctc ttttttgtga 1800
ttgttcttag cttacttgga gctgtatgtt aatgctagag ttcattgagt atcaatgctc 1860
aattacagat agttttgttt tgtaatttcc acatatattt tcgtatttgt gaaattaagc 1920
tcgtttgttt tcattgtttg ttggcaattt atgttttatg ttatgccaac gattcatgat 1980
ttgtagcttg actcgaaagg 2000

<210> SEQ ID NO 112
<211> LENGTH: 1027
<212> TYPE: DNA
<213> ORGANISM: Cucumis melo

<400> SEQUENCE: 112
ggggggggtt gtcttcctca aactctgtta tcgaaattag gtttacattt agtatctggt 60
tgacgttttg attgtattcc tgggcctgaa atatgataaa taaatatgac cattgaagtt 120
ggtgtttatt ctgggtttct atcattaaga gggtgtgaac ttacgaggga accaagaaag 180
ggatggaaat aggaatattt agaatagtag gaagctcaaa tgaattattt cgttcgataa 240
ggcggagtga atataaataa tatgcaagga gatgcggaga atattaccca ccttatgaga 300
gagagccaca aatcagaaaa cagtaacaaa tataacaaat caaacaacac catttgcaag 360
cgaattcaaa cgtttttcgg gtatgttgtt ccattaccac attcaaacat gaattgaaac 420
ctgagctctt gggcacttta attttatttt caacacatta cgtttaaatt gccgagtggt 480
caatatcatg tattgcttag tactaggtgg atacaaacct tacatataag gtcaaagtat 540
tgtgggcatg atataaatgc tctagcatat tggtctcata gagtttttta tacttttaca 600
tatccattaa tgagataagt taatgtttca acattaaatt tttagttaat atgaattcta 660
gatgcatttg ttatacaaat ggtctgatgt atttgaggtt ctgaatgtca aataggattg 720
tagtttattc acgttgaata ttgtaaagag ttaggacgtt tttttaagat tagatgatgg 780
gtgccatatg ctaccccata cgccaacaat tataatgaaa attatatttt gtcatttggt 840
atttaacaat ttttttaaa aaataagcta ataacgcata gaattcctga gatttaaaca 900
actttctgta atttcttttc tatgtactaa ttgttataga acctgtgatg tgcttgtcca 960
tcatgcagat tacaacgact ttgaacataa cttcaaaatt gttgataatg gtagccgagt 1020
ttttgcc 1027

<210> SEQ ID NO 113
<211> LENGTH: 2000
<212> TYPE: DNA
<213> ORGANISM: Cucumis melo

<400> SEQUENCE: 113
agccaaagtt taatatgatt caatcttgca caaatgcagg ttacccaaat ggttaaggtt 60
aagacaggca acaccactct agcagttggt gatggtgcaa acgatgttgg aatgatccaa 120
gaagcggata tcgggatcgg tattagtggt gtagaaggga tgcaggtaaa tttaaaacag 180
atcccagctg gagtgataaa atatagcttt cattcatctc aattttgttt tatacttctt 240
atctttctga atttcaggcg gtcatgtcaa gtgatattgc aatcgcacag ttccgatact 300
tggagcggct gctccttgtg catggacatt ggtgttacag aaggatctct tccatggtac 360
attatgatct ataaatatta ctttatatta gcttcttagt gagaatcatc cagattaatg 420
tgcaactata cagtctcaac atcattttca gcttgaaaat ctttgaaata tgtcgaactc 480
atcgcatttt atatatggca gatatgctat ttcttctaca agaacattgt ttttgggttc 540
actctattct tctttgagat gtatgcatca ttctccggcc aaactgtata caacgactgg 600
ttcctttctt tgtataacgt ctttttttact tctctccctg tgattgcttt gggagtgttt 660
gaccaagacg tctcatcccg gtactgtctt aaggtaagtt caactttcct ttatttcatt 720
ggtgcaatct tttgccttcc ttaagtacaa tatcaaatgg ctcattgccc tcaacatttt 780
tggattttca gttctcactt ttataccaag aaggtgtcca aaatgtgtta tttagttggg 840
ttcgaatttt cggatgggtg ttcaatgggc tactcagttc tgtcatcata ttcttctttt 900
gtgttggggc aatggaccat caagctttcc gcaacagcgg agaggtcgtc gggctggaaa 960
ttcttggtgc caccatgtac acttgtgttg tttgggttgt aaactgccaa atggcattgt 1020
ccatcagtta cttcacctat attcaacatc tcttcatctg gggcagcatc attctttggt 1080
atttattcct catggcatat ggagctataa acccagccat atccaccaca gcatttcagg 1140
tattcattga ggcctgcgcc ccggcaccat cattttggat cctcacacta ttggctcttg 1200
gagcttccct tcttccatac ttcgtctttt catcgatcca aatgcgattc ttcccaatgt 1260
atcatcaaat gattcaatgg ataaaagctg acggacaatc gaacgatcca gaatactgtc 1320
aggtagtgag acagaggtca ttacgtcaca caaccgtcgg ttacacagct cggttcgaag 1380
catcaaagca ttttgaagaa ttctcagaaa tcaagagtca ctaggtttga tgattagatc 1440
gtagaaagat tcaaaacatt ttttctacgt aaagtttctt ctcagtgtat atatatatat 1500
acatttatat atttatacaa catgtgtaca taagattctt gtgtagtttt gatctccttg 1560
tagcttaagt gaccattccc aattcaaatg gtcaaaaatt ttcttccttt catgaaattt 1620
ttaggaaata agccaattgt agtattcaat cgtatatttc aaatagtcat tgagaagttc 1680
taactctact atagttctca attataagta tgatggtttt gtcttattca tcttgtagta 1740
gaaacaaaag aataaattta cgaaggatga agcattgtta ttttaattat aatttgggaa 1800
atttggagcc acgaaatgaa atccaatttt gtgccaagta gatgtgcaac aatgggcaaa 1860
gaatcacttt ttctttttca taattttccc ttccaacact caccactaat tcatcacctc 1920
aatcctcttc ttcttcttct tcttcttctt cttcttcttc actcgccttt gggttgaggt 1980
tggctctgtt acagtcatcc 2000

<210> SEQ ID NO 114
<211> LENGTH: 2000
<212> TYPE: DNA
<213> ORGANISM: Cucumis melo

<400> SEQUENCE: 114
aaaagagtca tagtgaaaaa agctgagatc ataatagttt caccctaaac acaacttata 60
ataacacata ctatcataat atacacacca aacacagact ctatagtctt cactctaaac 120
gcagattaca atagtctgca ccccaaacgt agactattat aatcttctga ctattataat 180
actcttttca cttatcgccc caaacgtccc ctaagagaac aaagataggt tataaaagag 240
agatgagggt ttatattatg caacaagtat aaggttctag aacgatgtag tcttcaaagt 300
aacgaaagca ataggctaca cgagaaaaat atttttaaaa tatagtgctt tccctaaact 360
agatttcaat gacaaattat tataaaaaat agaatcatta atccaacatg gcttgcatgt 420
cacaccttgg ccaaaactga agacggatgt catactcgac ttcaatatat ttttttaatt 480
aattttcatg tgacaacaca taaatattta aaatttagat tgggttggat ttttttttcaa 540 gtgggtccca aaatactctt caaacccaaa ccaacccaac ttgtttaccc atctaataat 600
aacccaccag gttcaagaag acgaaccgaa ccgaaccgat ccggtctaac tttgtttcat 660
acttaagtcg aacttagcgg tacttttggt tcggttctcg gtttccccaa acagagccac 720
tcaaaattag atttagggtt ccgttcgcaa ttttcagcgc atttttattt gaatcggtcg 780
tttgttgaac acgttctctc tcagctggtt tagggttcat cgttctctct tctcgcgcta 840
tatctttctc tctctcaggt tcgtttcttt ctcttaggcc attttatcag aaagatcctc 900
ttcgtttctc cgattttctt tccgtgttcg ccctcggttt ctcagcagac gtaggaagtt 960
tggtttccgt ttagtgaatc tgtttggggt attacgaatg atattttgta ctgggctttc 1020
cgcatagtct ttttctttct aggaatatat gcatctgaga atttatttgt ttggcttttc 1080
tttataaagt atgaggacat atacatctcg attgctaatc cttgattata atcttttttt 1140
ttctatgttg tttgaatctg tttttttttt tttaatttct aggttttttg aatctaaaaa 1200
tgtatttctt ggatgaattg catactgttg aattagaagt ttattgatta gattgttgat 1260
atttgcccta agttccatgg ataggtttgc gtctttcacc ttttcgtttg ctttttcttt 1320
tggctgacga catcttacat agcctctgct ctaaaaggtg ccatgatttt ttttcctggc 1380
tttatctgag tttgcgcaat ttagatttga agtgatgatt tgtctaaata taaatatcta 1440
tcggccatac tattttttgt tattttgagt ttttcaagga tgactgctag agaatgaaaa 1500
atcttgaaaa cattgtgttt tgaagttcaa ggatcttgta gttttgttct tttctagact 1560
atctcatttg atatagccct ttaaatttaa tcaaaatttg ttaatattca aatcctcgga 1620
cattttaatt atttatctaa atagttgttt aggcattact caggttgccc actattttaa 1680
gcttagaagc ctactctggt tgacctaaag tttgcatgct atttgcctta tttcgcacga 1740
ctctaaactg ttatagacat ctttttttcag ccttcaggta aatgaacaca aaaaggagtg 1800
aaagtctgac ttctgtgtga tggtctttta atcaattata gggattaaga tggttttttt 1860

```
attcattgta taaatattaa attagaatga tgacaaccaa taatattaaa actgacaatg   1920

gaaggttcct tatattattt ggagtgtaca ttacaacagc ctgattcttg gcttggcagg   1980

ttcctgatca ccttgtaaac                                               2000
```

```
<210> SEQ ID NO 115
<211> LENGTH: 2000
<212> TYPE: DNA
<213> ORGANISM: Cucumis melo

<400> SEQUENCE: 115

aatgtaaata gtttataaac ttaagataaa attggtaatt gtttaataca aatacaaatt     60

gttaaatgaa atgacacacc ttgagcaatt ttcttttcta atcttctctt atagattaat    120

tttatttaat catgaaggtt agaatttctt tagcattatt tatttattta tttattagaa    180

aaagatagtt tgtgtatatt ttatatcata aagtttcaga agaaaccata aaattaatgg    240

agaataataa aaggtgggga tctctaacat ttttgccata aacaaatcac taagttaaga    300

atatgacact aaacttcttc taatttaata ttatatacaa agattttaaa attataaagt    360

aagagccttg aattgtagct aatttaagaa tatgctctaa gttttttaaa atcacttttg    420

ccctacggtt attatttatt tttttgttga aatatgttta atccaaatca atttcaatcg    480

aacatagtca aggatatgac tgcggattcg tatattagtt gattttgaaa cgattaaatg    540

tttgaaatat tgtagtttag gaacaattac aattataaca atcagattca aaattttagt    600

atatacagta acatttaaaa gaataataaa tatatcaaaa tctatcgaca atagacttct    660

cttcatagat aaattatcag ggtctgactt ctctcataga taaattatca gggtctatta    720

gcaatagact aaatccttga tggtttatca ttggtagacc aaaagagttt attagtgtga    780

tagactttac tacataattt gcaatttgtt taaaatgttg ttatacattt ggttgctatc    840

cttaacatta caatccataa catttgtcgt gtctttaact tgaattgatt gttatctgtg    900

ataaaaagag atgatcactt tttgtcatga gatttgaaca attgatgtta aaagtggtaa    960

ttaatgtacc attcactaac caatgtcaat atttattttg tttaataaaa agaaaaagga   1020

gattgtgaca ttagttttat actcttttct aaacataggt ttggtttgtg ttagatttgg   1080

cctacactta gctcaaatcc actctttata aaattccctt acttattaca agttatattt   1140

tcactccaat cataatcttt taaaggataa tatttgtatt agaagatacg acacatgtag   1200

aagataattc ttttttaacc aaaacaacat acaatttcga ggatatgaca aattaccttt   1260

tctattttta actatttgat cttcaagtcc catctaaaca tcaaatgaaa gttgattagg   1320

ttaaagaatt ggacaattag agaaggaatg gagaatcaaa cctctaactt ttaaggaatt   1380

aggtcattca catttttcatt gagctaagct cacattaaca agatcaatat tacttgtatg   1440

tagttaattc agatgtgaat ccttgaggtt tcaaaagtga cactttagtt cgaggtttaa   1500

aaaatattta tatatataca catgttacaa cccaaattta aggtatatat ataaatatat   1560

ataatttaat tatcttgaat tataattacc ttaaattact taaagtaaag attggtttat   1620

ttatgattaa gttatgatga atgttaagta atttgaaaat ttgaagttta gaggattgtt   1680

aattcacttc attgtgggcc tcattaattg gcccattaaa tctccatatg ggcctgtcta   1740

gggcttcatt tccccaagct tccaactgta atggcggcca cagttctctc ctccatctcc   1800

tctcttctta cctacttatt atgttaatat ctacgttttc cagattcatt ttctttttat   1860

ttgtattatt ctaaatctcc agaactgctt agctgctctg gtttttgggg attttagggg   1920
```

gctcgatctg gtgggtttac ggttaaattt tgcagctttt cgaggtcctt ttcggcttcc 1980
attttgtcgg aagttacaaa 2000

<210> SEQ ID NO 116
<211> LENGTH: 2000
<212> TYPE: DNA
<213> ORGANISM: Cucumis melo

<400> SEQUENCE: 116
acacttgtaa tgttgagcag ggtaacttat ggtaaatttg acatgagctg gcgcacaaag 60
gcctagcatg ctcggagctg tttttccatg gagtcaatgc ttgatcgcat tattggctat 120
attctaaatg aaactaaaat tattgatggg ttccatctgt ttggatacca actttataca 180
caggtgtttt tctatttatg agtgtaaagt ttgatttgct tcatcatcgt atattcaacg 240
tagagtttct tagttaatcc aatccatatg cctcaactat catgctcttt tccctgtaat 300
tgaatgtttt ttttggtgtc cacatggtca tggaggtttt gttctgcact agcttcacga 360
tgctactaaa catgatgatg aagcttgagt ttatttattt cttagtactt tgtgatgaaa 420
aaaaagtaga agaaaacggt agaaaattgg aatggatacg gtacaatgga tgggttgtgc 480
taagtcacgt ctcgtggata caactacaat tagttatttt gttttgtaga tttcatatta 540
gcatttcctt ctgaatagtt gaaatcacca tagaatgtgt actgatgttt tgtgatttta 600
gtgcttcggt ataatttgaa cgctttacaa gtaaaaattt cctcaggtaa acgagtcttc 660
cgaagtactt gttcataaaa tgttcttgtg tgggagagtt gattggagag gatcatggtc 720
aaattcttct tggtgtgttt tatataaggt tttaatgatt ctttgaaatt gtaatgtttc 780
cttagttttt ttaagtgata ctggtgggtt ttccttggaa taaatattaa gggctgaaac 840
ttaggaatta tatggatttg agggaggttt gtggattctc aaatcaaatc aaaccaaaac 900
cagataattt taaattctag aattttgaag ttactatttg tgtttagaaa taaaaagaaa 960
gaatatcgct tctttgtcct tccaatattc tttagaacca aaagagaacc aaaattatat 1020
ataaaagagt cgataaaatc aaatatatat ctataatata gtttattatt atttttcatt 1080
tgctatcaat aagaatttttg aaatgtaata tttgctccaa attatattaa aaacagctgt 1140
tgaaatttca acaaaatgag aatttgtact ctggattttg ttattagttt ttttttcaat 1200
atcttaaact atttcttaaa tattctcatt gcgagtcctt ccatttacat agaactaaaa 1260
atggattgag tttggttaga gaataatccc aatcttactc atatttttag gttgattaga 1320
ttggtaattt gattagcggt taagttattg ggttgtattg tttcataaat tcgatagatt 1380
acatcgatgg caatgtagtg tggaacataa aaaataatga aataccagcg gaacacaatg 1440
gagactgaaa aggatagacg atcgaagatg atgaaatgag aagctgacaa caatgagggg 1500
cgtgagttga gaagccgaga caagagggag agagtgagtc ggaaagagat gtggggcgtt 1560
acaagttgtg ttgaacaaag tgaggtcaaa tttaaattta ctatttgcta aattaataat 1620
aaaataaaat ataaatataa acatataaat atatatatga ttgggttggg ttgatacaaa 1680
atttctaacc ctaactcgat aaagcaaaat gcaacccaaa ttttaaatta accagatcgg 1740
gttattctta tcctaacctt aggacagtga ttacttaatc tgtacgcagg ggcaattttg 1800
acctttgata aactctccca ttttgttttc ttttttcggc aattttccct ccctctctag 1860
tctcttctgt tctcagttca gctctctagg gttttgtcga acagccattt ctaagtgtac 1920
atctcctctc aatttccctc gctttattcc attttttcac gtactatcgg cggatccttt 1980
gagctccaac tctctcatcc 2000

<210> SEQ ID NO 117
<211> LENGTH: 1025
<212> TYPE: DNA
<213> ORGANISM: Cucumis melo

<400> SEQUENCE: 117

```
tttttcttac ttcattatcg aacaataatt tgatttccaa gcgacccttt caaattcaaa     60
caaacccatt tctcctctca gccagagcaa gtgattgaac tgctgcgctg cgcgtgacct    120
gttatcttct ccgtttttct taccgccgcc cgcccctcac ggcggagtag tttcaccgcc    180
gacccatttc gccggccgcc ggcggtgttt cgattcctct tgttttgtcc cttttcgtct    240
taccagtttt ctctctgtct acattgtgtg ctcgttaaca gccagctgta tagccactgc    300
ttttttattt gactcttgaa acagagagat aggggagatt ctgtatagtc ccactgtttc    360
tgctcaactt tttcggttta atgtctgttt ctatattcga ttcttcgttt tatgttcgtg    420
attcgatatt gcttttgctt ggaatcgttt agaggcaagt gattgtctct gcttttgcta    480
tgtagttact ctgttttttt tccctttctc tctctctctc tctccccccc tctttctcaa    540
aagggggttg gtttttttat cgtcggagga tgttgggttg atcttttgat agggtctgtt    600
gactaattta gctggtgttc ttggtctgct gaatccgaac ttctcttagt tttagagttt    660
tcgatgttgt tggtttacac tgattcttct tcgtttgttt gggattattt ttgacaggac    720
tatagtgttt aactgctagc tgccatggaa catgcagaat ctgcggtgag tttttagaat    780
aaacttgttc ggttggtgag aaaagcatgg gaaagaggag ggggaggttt ttctttatgt    840
caaatatttt ctcaaactca ggttttagaa taaaaaagcc tttgtttctt aaccaaatag    900
tttatttgat aatcagctgt tttgttttag ctccctcatc tcattttcgg aaatcttagt    960
tatcagttta atcaactctg tgttctatga tgctcatttg tacttaggca aaggttataa   1020
agaac                                                               1025
```

<210> SEQ ID NO 118
<211> LENGTH: 2000
<212> TYPE: DNA
<213> ORGANISM: Cucumis melo

<400> SEQUENCE: 118

```
tgcattttat cagagatgaa attgaaaaag gaagaataaa cacgtactgt aaaatcaaaa     60
cataagaaac ccagctgact tagcttgtta attaaccaaa caaagtttga gcattgtcta    120
aattaaagtt gttcaacttg actgttgtag ggttattaat ttttcttgaa aagaaaacgc    180
agcatataat attaaaggag tattttgtct cgagggggaa gattattggt taaaagtata    240
tatggtgtga cataattaaa tactttgtaa ctaaaaaata aaacataatg ggaagttatc    300
tctaccaatt tttttgttaa agggctgaat atataacctc caacattact tagttactga    360
tatatcagtt tctctagccg tcaacagtac tacatagttg ctgatcataa atagaagaaa    420
caagttagaa attttgtgaa gagaaaggcg agattatgtg atttttgctt tgtataattt    480
tgaaaaccct tgatataagg aagttccttg ttgctgcatg ccttcttaga gatcagcagt    540
tactgtatgt ctatatataa ttctctctct caatattttt ttctgttctt gagcttgatt    600
gtttactgct tcagaaatct tctttacaac tactactgta tttggaagtt ttagttccat    660
atatatttct attttttaa tgatttcaaa tcttgttgtt tcaaacagta ctctcctaat    720
tacaaataca ataaaattat atctagcatt acaattttac aaagtccttt tcttgtgaaa    780
```

```
aataaattac gtgagacttt gtaaatggta ttttgaatgt attaaggtac tatatgacac    840

ttagaattgc tttgctttag ctctaaccat gggttcaaat gtaaagttaa aaataaaaca    900

atcaactatt taaggtttta cttaaaaatg taattatttg tcaaaataag cataataatt    960

gagtagtaat ttacatatat tgcctccaca tttgagatca aaactagaga tgttcatttt   1020

cttagatata ttattaagct aagaatgaga gaatgggtga ggggaaaagt gaacggaggc   1080

aggaagacca aatcacccat tcctgaaaat ggaaggatta aaattgcaat tttccttgca   1140

atttaatacc aacatgattt tgtatatata tatttgaaga ggggttttaa aaaaatataa   1200

caaactgtta aaatatttac actatataca acaatcgtta agataaaaaa actcataggt   1260

ccacaatgaa aaatataaca aatgtcatag tcaacacgcg attaatcagc cacactcacg   1320

ttcgagtaat cttcttctga atgattgtgt attacagtca aaatacacaa tcgtagagtt   1380

cttttctaat gatgttgaaa aatacttcaa atttagggtt tagggtttag ggtttaatga   1440

tcgtgttaac cgtgaaaaat aatcgtgtta atcaatggaa aacgatcgtg ttgattatga   1500

taagtgatcg tgtagtccaa tgtaaacgat cgtgtttgac tatgttaaat gatcactatg   1560

gtaagtgatc gtttaaatca tataaacacg acgatcatgt agttcttttt aaaagatgga   1620

aaaagaattc aaatgcaaac gttcgtgtta acaatgacaa atcattgttt agatcatgtc   1680

aaaattaata tttaaacgat ctattgatat tcttaaatag gaggaagatg aagtagttct   1740

aaagaatact gtcgaaaaca ataaagatag aatatgatat ttaaattaaa aaataaatga   1800

tatcggaaga gaagatgaat aaatcagaga aacagatata aaaggggaag tgactgatcc   1860

tccaaatcta aaagataaaa atattttaca tgactctgta aactttggtt tcttttgcta   1920

ggcagtaaat atttgagggt tttggtattg tatttgtggc ggaatggagt aagtgggcct   1980

ggcattgggc cgtatacgta                                               2000
```

<210> SEQ ID NO 119
<211> LENGTH: 2000
<212> TYPE: DNA
<213> ORGANISM: Cucumis melo

<400> SEQUENCE: 119

```
tcattccaga aaaggtaatc tttgattttg agaagttaat ttgaatttta ttttaaggga     60

attcaggcag caagattaat catctggctt cctggaaaaa ggtcaagttt tctcaatcag    120

aagggggggct aggtttgggc agtttaaaaa ataaaaaaaa taaggccctc tttctttact    180

aaataaatgg tgttggaggt ttttgaaaga agactccaca ttgtggggta agttatcaaa    240

agtatccatg gcttcaaaaa aatttaattg gcagactcta aacaaactag aaaatagcct    300

tagaagttcg tggatcatgg gaaagttgag ttggcaactt tcaaaacaga gaacgaaagg    360

agagtaactt tctggacaga ttcgtggatt agtgatctcc ctcttaaata tccatttcca    420

aatatattca gattagctca acaacccaat gattcaatta ctgcgcactg ggattatgtc    480

actaattctt ggtcattagt attttgaaga ttgctaaaag atgaagaaat tcaagatttc    540

caaaggcttt taacactcaa atcctagaaa gtaatagact tggatgatag aagagtttgg    600

tcattaaaaa cctcaggcca tttttcagtt aagtcccttt cgaagcacct ctctccttct    660

tcacctttgg aaaaagatta ctttaaagca ccttggaaaa ccaggagtcc aagaagaata    720

aatgttctgg tttggattat agcagtgggt tctctaaact gttatgagac tatataaagg    780

aagcttccta atatgtgttt actaccttta gtgtgctcca tttgcttgaa aaacagtgag    840

ctcctaatac acttattcat tttttgtccc ttctcatcta cttgttggtt tagcatattt    900
```

tctatgctca aacaacttgg gtctttgatg gttcattaaa caccaacgtt gttcctaatt 960
ttttaggggg tccttattta tatatatata tataaaaaaa acttttctaa tttgggttaa 1020
tttgataaaa gcactcctag ctgagatttg gtttgaatgt aaccaatgca tcttccatga 1080
taaaagagag agagagagat tgggttgaca ttgtagacaa ttctaaaaga aacgtggtag 1140
cttggtgttc ttcaaatgca gaattcaaat gcaggatatc tacttattgg actaccttca 1200
tatgaagaga ttcaatgcag tttcccccga ctactagttt agaatttgtg tttttgtagt 1260
tttaatgggc tgtaatatgt atttctacct ttaagttttt acttttcagt cttgcttctg 1320
tctaccatag gtagtattgt tattttgggt atttactttt gtcttttcat gaccttagtc 1380
ttgttcttgt attttggata taatgagggt gctatcgggg tatcaaccta gttgagatgt 1440
tcgagtgcac ctactgatcc ccttatttgt aggcttctct attattctca atgtataact 1500
ctcttgtact ttgagtttat caataataaa gaagcttgtc tcattctaaa aaaacaaaaa 1560
ggaaaaggaa gataattgct cctaatcgtt gaaattacta ctaattactc ttaattactc 1620
caaatgatcg tataacatac atttataatt tttaactttc ttttcctttt taaataccaa 1680
cattaaattt taaatacatc cattaatttg aaattagttt tcaaattcca aatcgaaaga 1740
tttaaagtcc tttgaatcca aagggagaat gagcccatcc aagcaagttt ttgtgtcgta 1800
gttgcatatt ttaagtcgtt tcatattagc ctcgagtttg gcttaatgac ttggtggtgt 1860
ctagtgcagg cttgtggcga ctggcgagcg tggttctaaa gataaggttt gcattcgctc 1920
cttctccctc cctttcacta cttcatatcc atttcctttc tcgatttctc gtcttccctt 1980
ctgaattccc cattccagcc 2000

<210> SEQ ID NO 120
<211> LENGTH: 2000
<212> TYPE: DNA
<213> ORGANISM: Cucumis melo

<400> SEQUENCE: 120
atttatttgt ttagagataa gacgcacatg agaatatgag atggattcca ctccactcac 60
actccaattt ctacctatcc tattactgtt tactattatc attccacccc tcgacccctc 120
attcttcttc tcaccttact tttttatgat ttactactac ttcattttgg atcacaatct 180
gatcaatgct gggtgggctg ccctcggcct gtcaccaggc ccagcccact tccaaattaa 240
acctcttggc ccaccgccca ttgtccccat cccattccat ttaatattcc caaccttccc 300
tttttctttc ccaatgcgat gcttctccaa tatacctttc ctgccctcca tgtttccttt 360
ttactgcttt cttatattta taacacacct tctacagtct tttggctggg aatgctgcgt 420
atgtgaatga gattcaagat ttcgttgatg ttatttgagt ctctatattc ataagttttg 480
ttcttagttt tctctagacc aactgcaaga gttagcgttc catatgctca taagtttcag 540
atttctgctg tgtggtttga agacagtcat cgatccatgg gtgaattcgg ctttttatta 600
ttattattat tattatttat tgttgtctta cttttctatt tgaatcttcc tatcttttta 660
ctcattgttg gactctaata attcttgcta aacacaatct ccatttttat tggacatttt 720
aaatcccatc tcaactcata attttagtta ccttccacca tcaccatatc caaatccgaa 780
ataaactcaa ataaaatcct tcacgtgcat gtgctctcca tatatttttt ctacatggta 840
aaaataaaat gaaaacaatc taaatttaat aaaataacat atatggcaga cttttattga 900
tgtagagact gggtgttgta caagaacagt gcagccaaga aaaaaaaaat acttccaatg 960

```
aatcgtacat tttaaggatt atgaaactaa ctagttccaa ccattttttc acgaccacgt   1020

gcttgttaaa cacgcaagta gaatcaaaat gtgggcttct tcgctttata taactgtgaa   1080

tcattctcca aaaagggaag gggatctcat tccctaattc aataaagaaa aagaaaaatg   1140

ctagcgaact tcatccatct cattcctttt acctatttca tgagatgccc attgtatata   1200

agtatttttt tttttttat ttcattttac ttagtttact cctcacctct aaaaaaaatt   1260

aggagagttt gctaaatcca ttctcaaact tagctttatt tttttaattt tatttaacct   1320

cgtcgtggat gttaacctca aatgtcagtt ctttttattc tatttattga tgttataatt   1380

tactttagga ttccaatttt ataaaaataa gaatacaaat aaagataaag agtgtgaaag   1440

ccagaaagaa aaaaaggaaa tcgtaatatg ggtaaaattg gtacaaattg ggtcccgtta   1500

aatattaact caaaaaatgc gagaaaatgg tagaaaagga aatagggggt aagagcaaag   1560

tagtggaagg agagcattga acatattctc tagtttttgc acttggatct aaacacgagg   1620

aattataggt ttattcattt actaattaca taaataggat tggattttaa aatttgaccg   1680

agtgattatg catatttgat agagttagaa aatagtggtg gggcaggtac aagttacaag   1740

taatgtataa gagatatgat gagcatatta ggaaactata gatttaaatt cgtccgtaaa   1800

taaataatta gaaatataat attcgagtgg aagggtatta gggttaggcg aaaccaattg   1860

cagttgcacc tataaaaccc cttttacgcc tccacccgct tcaacagcgg tctcggcgtc   1920

tacaactaca cactacacac tacacactac acactacaca gttgcagacc agaagcataa   1980

cgtaacgccg gtccacaaaa                                               2000
```

<210> SEQ ID NO 121
<211> LENGTH: 2000
<212> TYPE: DNA
<213> ORGANISM: Cucumis melo

<400> SEQUENCE: 121

```
tgaagagccg gaaaagcatg gcaaggtcaa ggcatttcag caagaatacg aggatgaatt     60

ctgggtttgt aagtccggtt cttcttcgga gttgtggttc gaatttcaaa cggccatgag    120

gagccctaca gcttaggaag cttcaggtct gagactctga ctccgacaga aattgctgat    180

ttttgtgtgt gttttgaata accattgtat gagtatgatt ggttgtatag gtttgaaatg    240

agggaaagtg atccatctcc ttgttgtctt tgcaggaaag gctcatattc gaccaagaac    300

gctttgtcat tgctttcgat aatcatagaa tccacaatgg tttggcatat tagcaaacaa    360

atcttcttta ggcattgcag acagaaaatt ggagagtaag ttattataat taaggattct    420

aaatgagtaa gaataataag atcaggcaaa gattggaaga actaaagcgt ttagtatttt    480

gtgtggtaca gaagaattgt aattagatac gtagtctaga gaagcagatg gtgagatttg    540

tgaaagacaa atgttagtgg agagtgaaga gtgtttctca acaaccgaca tagaaggatt    600

ctcagaaaat gagaaagatt tttattgcgc aaaatagctc ccatatcatc atatgccgtt    660

gccattccct ctggggttgc atgtaatgag taatggaaag ctgtagacag gctaacttca    720

ccctttgtct tgggtatagg gtgcattttt ggtcactcca ttttaagttt tctaataata    780

aaaggatgaa gaaaagatat tgaaaaacag ctcaggtttt aaagttgtca cacttgagaa    840

taatgcattt aacagttaga attttgcatc aacgtctttc aaatagaaaa gtaaaggaga    900

gtctagtttg agctggatag ctaaactggt ttaatcatat cttctatcaa gtggttagag    960

ttttagacct cccaacttta tatgtcgttg ccctaacaat gttgatggat gtttagtcct   1020

aagctctaac attgtccccg tatcatattt cataatagaa tgtactgagt aatggaaaac   1080
```

tagagaggta ggaagttgga cgaactttga atctatattg attttactat agtctttctt 1140
ccaagtctta atgagagctt tagctaaagt ttttcaaaaa ctcaaaagaa gtttttgttt 1200
tccaattctt cgatccatag attgtcaaga tggctataat atccttgaag ttaatagcct 1260
tcaaagtttc atagctttta tcctatgatc tttagaaatt caagagttat attctttaga 1320
actacagaac tttgatcttc gattcttcac ctcttccaga acctttatag tagagtttct 1380
tgaccttaca tgggcttggg attgggcctg gctacttatg ggcttagaga ttgaccttgg 1440
gtttaagcac attcgtttta cttggcccaa ttttcttaaa cttctgcaaa atcctaatta 1500
actaacacct caacaaaagt ccagtattaa atggggcata taaacaaaag ttaaacaaaa 1560
ttgtcgtaca gaatcctaat ttgctaacct cagcaaattt tatgccattc gtccttgtgt 1620
atctaattag tgttaatttg aggaaatata ataatataga cgtaggacgg atattggtat 1680
ttggtgcaac atcctccgaa ccaattcctg gaaagtaatt ggggcaacaa gataatgtta 1740
tcgtcagttt caagtgcaaa acttgccacg tggaacagcg gcaacatgat atctcaaata 1800
tggacctctc acccggtcaa gcttccacca ccaccaccac ctccgtattc taaaataaag 1860
tcaggaacaa gaacagacac accttaacaa aaccaatatt cttcatctct atctctctct 1920
catttcagca tagaagagag ctgagtaaaa ggaaaaaact tcaatcaaat ttgacagaga 1980
agagcccaag agaaaaccaa 2000

<210> SEQ ID NO 122
<211> LENGTH: 2000
<212> TYPE: DNA
<213> ORGANISM: Cucumis melo

<400> SEQUENCE: 122
agatgaacca gaaagatgga aaatctactt ggggttcagc agtgagtttg gaaaagagag 60
aactatttga agaaagagca gaaaccatct tgctaatact taaacaccgc ttccctggaa 120
ttccacaatc ttcactagac atcagcaaaa ttcagttcaa ccgggtaaaa gaacgctcct 180
tccttgtcta taatctcatc taaaattatc aacaatccaa acacaattta tacaaactaa 240
aatgaaagct tctcaacttt aggctacaaa aacagatgct tattataatt ctgcccaaca 300
atatcttctc ctaaataaga tgatatatgt tttttgccca tataatcaaa taggaaataa 360
caatcctgtg cccatttctt tggagtgtga gatcataaaa cactgtctaa aacaacatgt 420
ccaaacatat cgtaaatacc tagtttcata gtgtgatgaa ccaccacaaa caaacttact 480
ctttggtgaa ctgcaggacg tggggcacgc cgttttagag agctactcca gaatactgga 540
aagcttagcc ttcacagtga tgtcacgaat tgaagacgta ctccacgccg ataggttaac 600
tcagaaccca tcacaaatag caacaaggag gaaaccgacg agcgaacccc caatggagaa 660
atcagaagag ttgaacaaca acggcccaga aacgccagct tcaatgacgc tgttggattt 720
catggggtgg ggacaggatc aaaacgagtt ggagatgaag aaggaatggt ttgggaattc 780
agatgattta aacgcggatt cagatctgaa acaagggaat aagccaggga atatagtgac 840
gaacaagagg gtttcatacc tggagaattt gagcgctgtg agaagtccaa cggcgcgcca 900
ttgaagaaga agaatagata gagagatgat ttggaggcaa aattccatga tttcagttat 960
atacattcct tttgtgtaaa taggaagaag aagaaggaga atgagatcaa ccccattttt 1020
ttctctcttc tttttttaat ttggattttg gaatcacaac tctttgtgtt tgtgtaaaac 1080
caaaattgtt ctatgtatca tttgtatcaa ttaatgtagt cattttagat tcatacattc 1140

```
aaaaatatca actccatttt ccaactacta tcttcctcca tctcacctct aatcataatt   1200
caaagcggat acaaattcat gttagaatga aagattcgag tatagcctat tccattgatc   1260
aaatgcatgt atctatacta ttgacacttt tcaactcaag tcatgcttga acaattgttt   1320
tttataaatg ttaattacaa gagtgtacac aaatcgagtt gggaaaaaat atgaaccaac   1380
ccaaaccaaa aactttgagt tggaccgaat ttgaataaat aattcaattt tcattatttt   1440
tatatagttt ttcaaccaaa ttttttatct tttttttctc aaatttcaag tttacaataa   1500
tgtccattca aaagtttaaa ttttcatatt tcgaacattg aagttggaag gtccaaacga   1560
aagaactaaa tgattatgac acatgtctag ggtttatata tattgttgag ttgagtaatc   1620
caagtttttg aaacaccact agttatttat gttaaataat taactgagta ctcgactttc   1680
ttagttcgag aatatttttt agaaaaaaga agagaggatg tgtttagaaa taatagcaag   1740
ttagggtgtt ggtgagtgag aaatattttg ggatcttctt gtaatagtta ttaagaagat   1800
ttttcaaaga atttgagagt taaagaaata ataataataa ataagtaaac atttaatagt   1860
aaacgacatg tcgttttata cagcatcgta tttacttacc atgtgctcat tcacacacga   1920
ttcctcctcc tcctcctccc gttcatctct tcttatcttc gtcttcttca tttcggataa   1980
cacaaaaatc cctaaaaaaa                                                2000
```

```
<210> SEQ ID NO 123
<211> LENGTH: 2000
<212> TYPE: DNA
<213> ORGANISM: Cucumis melo

<400> SEQUENCE: 123
```

```
tcattttcgt ttggttaaag aatatatcat cgtttctttt ataaaatgtt tttgtagaat     60
taatcttcga gtacttctca taaaaacatt ttttttaatt acatagagtc agtaataatt    120
agaactatct caaaccaaag tactataaca tttcaaacca taacactgta ttttttagaa    180
aagttattgt aaaggataga attacaaaaa tattatagca tatgaaacat tattgttata    240
ttttataaat attccatata caatataatt gattctagat gtctctaaaa atagggaagc    300
atatgtgtta ataactaaat ttaaaaatta aaaaattact cgattactgt ttatttattt    360
atgtgttgag gctatacata ctatatttta gtaattattt taaaattaaa aacaaaatca    420
catggctaat agaaacgata gatatctagt agtaaaattt tgttatattt ataataagtt    480
gtcttatttt acttaatgta actacaaata tctcactgtt attttccttt ttttttcagc    540
ttattggttt atatgtttag aaaatttggt aaaatatttg tgtagctgcg gttatcatgt    600
atcaacttaa ctatgtaatc tatgaaaaaa tagtcattct ttaaaaaaaa aatgaaaagt    660
taaaaaagaa aaaaaggata aatttataac aatattcttt aattgaattt tatcatttga    720
ttcaaagata ttcttatact tttaaaagct gcaatgttat ttatgaaatt gttttaaaat    780
tacatttata atgaaaaaat ctttaaaaat gtagaaaaat caaggcttag aattgtattg    840
tcatttccat caaggagagg atgtaatttt ttctttatca ctttatttga atcctcaaat    900
tttcgataag tatatatttt gacatttgag aatatttttg tttactttaa atttaaagtt    960
atttttaaaa caaatgaaac aaaatattca taacgtggat caaatcacca taatttagaa   1020
agcgttcttt tgaaacatga ccccaaaact ttagaagata aattacaatt tgaactattt   1080
tgaaaatggt agcaaggaga caggtaaaaa aagaccacat aaatcacttt aggctttaaa   1140
gaaacaatgt taattggaga aagattcatt ggcatataat tttgaaatat gattgtattt   1200
tatatttcaa atcatattcc atgaatttat ctatctttgc ttgtagtcta aatcatgcaa   1260
```

actttgaaaa taacaatgtt attgtatcaa aatttaaaag tttaaaacat ataattgatt 1320
aaataaagaa aaatatttag aaatgttgta tgccaatagg tattatgtaa taaattataa 1380
atgatataat attaaaaaca ataattcata ccatttttta aacataaaaa catgcttagt 1440
agattagtta taaacagttt caagtaatat ttaaaagaga gtcataagta gttttataat 1500
ttataaaata caatatcaaa cgtacttaaa actaattgct tttaacttca aatctaaatt 1560
aagaataaga aaagggagag tgggaaagag caaaatgaga gaaaatgtcg aaaatacgcc 1620
caacggttcg gaccggtcca tttttgtccc gcgcaatggt aaaaatagat taggttacga 1680
caatcaccat gatgatgagg atgatgatga tcatagcaat tcaagaagca tagggcccca 1740
cttttggccc tcttatttc tcttctctta cttactttaa agaatctaac tgtcctccat 1800
taccccgccg atcaatgctc tatttttctc tctctttttt cttttcttta ttaaacaata 1860
ataacaaaaa ccatcaaatt ttcaaaattt tgaattatat tcccttaaca caaaacactc 1920
tcctcttttc ctttctctta taaatacaag tggagctcca cacacttgtc attttgtacc 1980
cttcttcccc aacctcccaa 2000

<210> SEQ ID NO 124
<211> LENGTH: 2000
<212> TYPE: DNA
<213> ORGANISM: Cucumis melo

<400> SEQUENCE: 124
gggcttccat tggcctcctt cccgtcgccg tagtgagaga aaaaagaaag aaaggggaga 60
ggcagaagaa tttgagagat ggatcgagga gaggttttgg aatgaatggg aaatttgaag 120
gaagaggttt aaacataaaa gtgaggcacg tgcgagaatg caaatattta cggggctaaa 180
aatgggagag ccaacggatt caccccagta aaaaggtaaa ttcaaacacg tttatgcctt 240
tttacctttt tctttctttt tttaacacct atagatgtaa gatatttcat attcttaact 300
ttctctttct cttttctttt ttgttttact atttcccttt cgttggctaa taataaaaat 360
tgatggatac agtatatttg gtatgtcatc ataaatttag agaaggtatt aagattttgt 420
gacataaaaa cccaatttct tttaatgaga ttcttagaaa ttttattgaa gagaattata 480
aactttacgt aaattaggta aagtctttcc ctccttctcg atagaagttg ataataaaca 540
tagcatacct agataaaagt ttgggaacat ttttgttgtt tggagggttg aaaaaaatta 600
agaaatttca atttggttag gatttgatgt cttgattttt tgaaatataa actttcaatt 660
ccaaatggtc ggacttggaa cctaacaaat cgtgttttca attttacctt gatattttag 720
atgtgtgaga ctccattaag tattctcttc gctctcttct tactatttct ctgttttgct 780
atcgaacgat atttttttta aaagatttat tttttaattg gtggaatgtt tgtatgagag 840
tatataagtt aaggtaaaca aataataatt ggttatttag caatcttcct agtcaataag 900
caaaacagac ctaacatgca tcaaagaaac aaaatcaaaa ccttaaaata tcatggttgg 960
gcgttgattt tttttttctt ttaatgtttg aaaatgtggg ctttgggtgc cgcagtcgta 1020
tggttgtagg gatttctttt aagaaaatta ttttatattg tattcgtttt gatctgaaga 1080
tatcaattat acaataattg gaatataagg agtaatttaa ctttgttcgt gattgttttc 1140
tactttattc gatgtgtatt ttggaattaa atatgatttc aaatgatttt gtttatttct 1200
ttttattgat tttgttttga ttttactttg tatcaatttt gaatatcaat gtagtgatgt 1260
gcttgtatta aatgtattgg ttgataaatt tactatgcaa atttttttc aaaatttatg 1320

```
caattcattg tagtattatt aactatatca acacatcagt aaagtgaatc attatcaagt   1380
atatcaatta agttacaaag tgtatatatc aataatgtat caagtttatc agtagcactt   1440
taagcatata aagtgtattt aatcaattaa ctgtaccagt gaatcttact agatgtattt   1500
gcagtacatc cgacgtatca aacatatcat gtgtatcata tgtttaaatt tgttgagtat   1560
attagtgaaa cataacaagt ttattagtag tgcatcaagt atatcaaatt tatcagttaa   1620
acatttaagt ctactaagaa aaaatgagtg caataaaaat tatttttcgg atatataaaa   1680
aaatattgag tgtatcgaag agttccatgg tgcatcaaat atataaagat aaaaaaatat   1740
caagaaatat taaatgtata tccatatatc aagaaacaaa cctaacatgt atttcgtgat   1800
ccaacaaccg gactggaaga caaatttcgg cccgggactt tcatagtcca aataaaggcc   1860
cattaaactt aacctgggcc caaattaatt tgtaaatttt aagtataaaa agaagagaaa   1920
ccctagggtt tccttcattc accaggcctt cctatcccct tcccttcccc ccctccccat   1980
tcccattttt gccggccgcc                                                2000
```

<210> SEQ ID NO 125
<211> LENGTH: 2000
<212> TYPE: DNA
<213> ORGANISM: Cucumis melo

<400> SEQUENCE: 125

```
ggacttatgg ggaatgggtt caagtgatgg taactagcta cttcagattt aatatcctaa     60
attgccttgg caacccaatt caaatgtatt aggattagat aggtgttttg tgaggatagt    120
taataaggtg cttgcaagtt ggtgtcgaca ttcccaaatg tgaagggaaa aaaaccccaa    180
tctttggtct caactggact ttggttcatt gcagttgaaa ataaattatt ttagttcaaa    240
ccaataaaac acatttttta aaatctttgg atatttgttt cttaaagttc ctgaaacagc    300
ccaccaagtc catagcaatt aggaaggcat aagttagagc tagtatgctt ggcatggttg    360
ggggtgggtt accttgttat gtaaattcat agaaatattc atatcttgtg ctaaaagtca    420
aatggaaaga gggtgattgc tgtgatgctg tctaatacaa agtgctagaa gccatatgga    480
gaaagggtat ttctacagtg tctaataagt taattacata ataaatttct aggttatgag    540
aatccaatcc gcatgaattt aaggactgca cacttgctcc atttgcaaca tgtgtaccac    600
tttagaatca tatttcacct gagttcatta ttcaactaga ttaatgtatc tcttttggtg    660
ttacatgttt ttaagaacat aattatttta gtttactgtc ggagagaagc aagtactggt    720
tatgcatggt tctagtgagc ctaatagagt aaggctatgg tttgggcatt tggaagtttt    780
agtggattag aattttgaag gcaaagctaa ggatcataca cgcccttctt cccttttgac    840
cagttggaga tctatcatgt aactctattg tcttgggctt cggccttatt tttataaattt    900
catatatcaa tgaaatttat ttcctataaa aaaaagaaaa aagaaaaaaa gctaaggatt    960
ttaatatcat tgttagtttc tttaattttt ttctttggga agtgtgcatg tagagctcct   1020
ttgaaagaga aaaagcaaag aactcttgaa tgtaaaatct ctatgtttga gttttatagt   1080
agcgtaccac attcacttca tggtgatgta gttatagttt tcctatggaa tatggctatt   1140
aatttttgcg aggctcttat tttatagttc ttttggggtg ttctttcctg taccccctcc   1200
cctttttgtg agaaggggag gtttctgtgg ctagctgggt tggtttagat ttgtggacct   1260
tttttgtgag aggaaccata gaaccttttg atgaggacct cgagcactat ttgatcattt   1320
ataagtttcc ataggctttt gtaattacct ttttggtctt attttaattg gagtcccctt   1380
cctccccttt tgttggcttt tttgttgtat ggttgggcat tctttcgtta gggaagtttg   1440
```

```
ataattcaca taataaacat acaataaaca accatcaata caatcaacaa gcaggattag   1500

tgtaatactg taaatgtctt ttattttctt tactcctttt ttcttttgag gtctatgata   1560

attgatatcc aacagtgtat tggccaaaat gatttatcat ggtcagtacc ttaggggttt   1620

gacttccaat ccaggattta aggtttgaga ccagatattc tgtgcctcaa ggccctcaac   1680

aaccttctca tggcttttc ctgtatacat attattatat aaagttataa ccaataaaag   1740

ggacaggtca aatcctctta atatatgcga aaatcaacct aatgtctact gtataccttc   1800

tcaatcgcca ccttcctcct gctgtcatcc aaggtagggc cttattgtat cagctagctc   1860

cctttactta tttatttatt ttttgaagtg cgcagtttgt ttgtttacct tgttatagga   1920

aattcaatct attctcattt tattggtgca ttcgtctcag aaattcttgt acggtttcag   1980

gttatcatct acccttgtag                                               2000
```

```
<210> SEQ ID NO 126
<211> LENGTH: 1397
<212> TYPE: DNA
<213> ORGANISM: Cucumis melo

<400> SEQUENCE: 126

tatatatatt aacttttaaa attttgaaaa cgtcatagat aaattatata caaaataaaa     60

agtttgatta tttacgaaag ttaaaaagtt tatccgaaag ttgactcaac gataaaaaca    120

ctaaatatca cttttagaga tgatgatatt atacataaac atacgaactt acgcgtcaaa    180

cttttatact aacacaagat caaaacaact ttgttgagta gtgagaattt tatctgctga    240

tatggttgaa acttgggaag caagcagagg aagttccatt cattaccaaa atccattttg    300

tattcatcaa aatatgaagt ttagcgactt gataaagtca agtcaagtgg tcctatcgat    360

ttgttaatgt caatgtttgg ttttgaattt gatacctatt agacaatgat atataatttt    420

aagtatggtt tacactgtga tgctttatat atttttaaat gtaaaatatt agaacttgta    480

atttcaataa attttaaaaa tgattttgtg ttatttcctt ttttaaattg aaatatcaat    540

gtatcaatat tgcgtcatag agtattgcaa cacaacctta tgttaaattg tttattgctt    600

attgctctaa ttcaactcct tcatcaaatg tgcacagaat ttaaacaaga aaaagagtag    660

gtgctttttt actaaaatat actaaaagct ttttatacca aatcttatga caaaatcatt    720

ccaacaaaat gactatttaa atataagatc gaatccctaa tttaaaaaaa aaaaatcaaa    780

gatgttaatt tctattatta aactcacttt agcgtagcta acaaaaaaag gaaaaatgag    840

aggctacaaa gcttgagccc tctgcctccc tttattgcat tgtttgaaat tagatcaata    900

ctttgtattt ttttcaaaat gaaaaatcgt acatagaatt aattctatgg acaaaaaatc    960

agagaaggaa ataatctaga ataaaattcg atttttaacc caaaaaaaaa aaaaaaactc   1020

gattctgatt tttgtaagca atcacccaaa ttaccataaa taaatggtat tcaattactc   1080

aattatggat attttagaaa tgataaattt ttattcataa actcttttct ttctctttca   1140

aaaagaaaaa aattagcata aacttcaatg acatttattt attcttcttc gtttggagtc   1200

aaaagtttaa attgagcatc agtccagccc aaaagcccac gaagaagccc aagaatcttc   1260

agctttttcg ttcaaacgtc cctttttggt ttataaaatt aaagaaaata aaaactaaat   1320

ttatttgtta tttaacaaaa catttttggt taagacattc tctttgatta tttttcttcc   1380

attcttcgtc gtcaatc                                                  1397

<210> SEQ ID NO 127
```

```
<211> LENGTH: 2000
<212> TYPE: DNA
<213> ORGANISM: Cucumis melo
<220> FEATURE:
<221> NAME/KEY: misc_feature
<222> LOCATION: (1)..(2000)
<223> OTHER INFORMATION: n=g, a, c or t.
<220> FEATURE:
<221> NAME/KEY: unsure
<222> LOCATION: (1)..(2000)
<223> OTHER INFORMATION: unsure at all n locations

<400> SEQUENCE: 127

tttatattta tgaaaatgaa gtctctaaac aatttttcta ctcccaaatt tgttgatttt     60
tctgcctatt ctttatcggt gctttaaaaa atgaaaccaa atttcaaaac taaaaaaacc    120
aagcttttaa aaaaatgtta ggttattttt gaaattcaac taaatgttga actcttttac    180
ttattaaata ggcaaattat tgaaataaat ttagagcaag taagcttaat ttttaaaact    240
aatatactta ccaaatcgag gactaaaata ttcaaatact ctttaaaatt aagattaaca    300
ttaatcactt tgttatgttt aaaaagttgc agtgtcactt gaacettttt aaattaatat    360
aatgaaaatg aatccaactc aatatatata atatctatat tattaatctc gatgtcagat    420
gtttgatacg cacatatctc aaaaaattata cctcaactaa catcggtgca cgatgtatta    480
tttcgtgagg ataaaaatcg tttttagtat aaattgatgg aaagattatt tgaattactg    540
aaaaatgcac cggtacatta tttgaaactt ccccttcatt taaagaggct aatattagaa    600
aaagacacgc tgaggctatt tttacaatta atgtgggctg ttgacttggc ccagcccaaa    660
acataaaccc taaagtagca caaacaaacg cctctttctt cttgaaaccg catattaagc    720
gttttatcac ttctcaccac ctctcattcc tcctcttccg cacgttgttt cgctcctcaa    780
cgggagtgcc ttccctttgc tctccctcca ggttcttctt ccttctcatc tcatttccaa    840
gtaatttcat tccgtttctt ttctcttaat cgtatcttgt tcagactctt tcgcgttttt    900
ttttagttgc gccttaccag atctgtgttt tcactcgttt ctattcgata catgcttcca    960
agatccattt cttaatcgca tgtattcggt tgattggatg attgtctttt tgtaagtttt   1020
gattactttt ttggaatgga tcggttgaac caacggggtt taagtcgatg gaagtaggtt   1080
atgttaaaga tttgcttctt ttttttatg aagatgtgtg tgttcttttt ctttgctaga   1140
tgatgttatt atttgattgt tttaacagtc gtgttttgtt tttctgcagt ttatagtcct   1200
cggtcttttg aagacttgtc aagatggtta gtacacctct tgtcatcgtg attttgattg   1260
agtgatgtgt taagtgcttc tttaggttac agctaacgcg attttttata ttcaattgtg   1320
cctgtgcagg tgaagtttac agcagaagag ctccgtcgga ttatggacta taagcataac   1380
attcgtaata tgtctgttat tgctcacgtc gatcatggta agctacttag tttaagttta   1440
tttatgccga gcgtctattt aagaagatta acatcttagc tttcatttat tgtttatttg   1500
gtaagcatcg tttcttttc tccgaggaac tgtacatgtc agttcacatg acaataaaac   1560
gatcttcctt ggacattagt ttttgaagtt caattagacg ccaaattttg ttggttaaaa   1620
gatgcttgtg gagcatatgg acctaatgga atcagtactt tttgatggat ggacttgtct   1680
tttgttcttt tattttcaaa agaaattgca tgtgcaatta catcatcttt gatcgaaaga   1740
ttgggtaatt gggtaattgg ggtaaagaca tgttgtaaaa actaatgtta attatcaatt   1800
accattatat accttattta gtgcttattt atatcctttt tccccatttc agggaagtcc   1860
actctcacag attctcttgt ggctgctgcc ggtatcattg cacaagaagt tgcnnngatg   1920
tacgaatgac agatactcgt caagatgagg cagagcgtgg tatcaccatt aaatctactg   1980
```

gaatctccct ctactatgag 2000

<210> SEQ ID NO 128
<211> LENGTH: 1657
<212> TYPE: DNA
<213> ORGANISM: Cucumis melo

<400> SEQUENCE: 128
ggcaaaatgg agagaaaaaa gtttctccct attgccacat ttatatatag tatatagata 60
tatactatag acatgatgga gaatcataag ataaggtaag gctgaggaag attttgacga 120
tatagaatgg aaaattttga agatataaaa tggaagattt tgaaaatata gaataagatc 180
atcaaatgat agcaaaaaaa tccaaatgag tcagatgaaa cactacgcca aattttcatc 240
actccaaaat tgttgcaaag gagattgatt aatagggtat tatacacaat catatttttc 300
gtagcatgat aattggttaa taattagaca taatggcaat caattagtta actaatacaa 360
cattttaggt agcaatatta aaattggaga tccggaaaaa aactaaaaac tcagaaaaat 420
cttgggcaaa atgagcacgg tttatcaaat ttttaggctt ttttggtaca attttgtcta 480
ggatgaaacg agatccataa ttttctttga gaagataaaa aaaattaaga tttggtgtaa 540
gatttgggaa gatttgaata attttttaa aagaaaaaat aagatttgga aaatggtaga 600
ataacggtct aatgtctccc aagatgcacc gggaaagcaa aaaacaacca aaacaataaa 660
taaattggaa aattttaata ttttaggaaa atctcgatgt caatttcgtc taagattgga 720
tcgagaaaaa cagttttacg agtttttaaa aaatgtgtta tatttaaaaa taaaatcaaa 780
attgtgctac ttttgtcaat ttcccaagat aaaaatgtat gcttccacgt aaaaagtaac 840
attactaccc ttctttcatt taatctctat atttggaaat gtcgcactag ttcttggtag 900
ctaatatttg gatactaatt atcttatatg acaaaatatt taatgtactt tttttttaca 960
acaaatattg aatgaactta aataatcttt tcactgcaat gaaaaaagat aaattagagc 1020
atcccaaaaa gatgaaaagt tcgaaagtct gctaactaca ttgaaaaaca aagcatttaa 1080
ttcttcaaac ttgatagttc aattaaattt ctaccaacta actcaagtaa atctattatt 1140
agtgtttgag tgaggctatg aactctaaga ctaagcctat aagtttggtt aaatttaatt 1200
ataccagccc ttttgtaagt aatttgattt gaaaggtaag acgtaatacc gattacccaa 1260
cccaaaatta ctgtgaatga gttaaaaaat aaaattagtt gaattttaaa taaaaagcat 1320
accaataaga cgatgacaca tgtacaaaat cttagaagga gaagcttcat ttgaggacaa 1380
aaaagagtgt gtggagtgag aagaaagaat agtcacgaat attgctgact gtgcaacaaa 1440
tgtacatttg gcaccaatca aaacctataa aaccttatcc aaaaatcaat aatctcatcc 1500
cttcttcgct gttcttcccc aatccaaacc ccaaccattc tcctccacac acacacacac 1560
tcacatacac aaatccttcc aacattattc tatacccact tcccaattct cattgcattt 1620
cacaatcatt gttctaactc acttacaacc tccatca 1657

<210> SEQ ID NO 129
<211> LENGTH: 2000
<212> TYPE: DNA
<213> ORGANISM: Cucumis melo

<400> SEQUENCE: 129
atgaacgaag gagaatatcg gataatgaag aggagatcca tgaatcacag agaatgaatg 60
aaggagaccc acgtgaatta aatagaacga aggagaatga agagaaagga tgaatacttc 120

```
ttttctttaa ttttaaccta atcgggtgaa tcaaactcaa atcgaaactg gtttagttcg    180
attatgtttg gtaccattgt cttttaaacc gatcaaacct gaaccaaacg aatcggtacg    240
gtttttttgca cccctaattt atatcatgtg aaaggtttta agttaagggt cagctagtgt    300
cgtttagagg gaatgatatt ggttgacttc atgtcgtctc ttggatcaag agtaggagat    360
tcgggagggg tgtgacgaaa tcaaccccga gattgtccta cagatggcat gtaaaatgca    420
tcatatctcg ggactccttc tacaaactcg agaaaaatgt ctcttgagat tcttcttcta    480
cacagcccca aattgatgaa atgactgaga ttctttgaaa gacaccacat gcattaactg    540
aaactaatgt tgtacatcta aaaaactaca tcacgccacc aactaaaaag ttttccattt    600
gcctgatttc aaactaaaaa caaaagactt aaacgataaa ctaaaaacta aaccacaaac    660
aatgaaatcg ttaaaagtgc accttgagag atttaagaga gtaaatgagt tcacatagtt    720
ttttgaagga aaaatcacta aaacaagttg gattgtagga gcgaaattgt tcactcctta    780
accgaaatta gcaaaatgtt tggagtttag cgtttttaga gaatatgtaa cgttatgaat    840
aataagggta ttttggtaat ttgatatatc cctttatttt caaattttta ataaaaaaca    900
cacatcttgg tgacacactc gactgaaaag gaccaagata tttccttgaa agattttttt    960
ttttaaattg ggaaagaatc ttggggtcga tctcgatcga gattgatcga gaaaaataga   1020
attacgagtt ttctaaaact gtgcttttga aatatcacac caaaaaagcg ttatttctca   1080
aaatttccca agtttatatg tggggggtat tgcgagttag cttttgatgg gtttgctttt   1140
gggtgtttgt atataggttt gaaatgtacc tttaatgtcg atttttgaag aaaggtacct   1200
ttattgttta aaattgacat tgtaccttca tatttgattt cagtttaaaa ttgatattaa   1260
ttatccgcat tttaaaaacc aacatcaaac atccatgttc atttcttttc aaatttaagc   1320
ttgaggatga cttcgtgaaa ctttttgagc aaacacgttt atcggttgtt caaagtaaat   1380
caccttcaca aatttaagct tgaggacgac tttgtgaaat ttcggcaagc aaaaatcaga   1440
caaatctctt caatcttttt tgagcaaaca cactttatct ctgctgaaat gagcacaagg   1500
tttagggttt tgagaatatc tagcatttag gctttcaatg gtattttggt catttgagaa   1560
taccatttat tttgaaattt taaaacaaaa acctaccatc ttggtgacga tcatttaggc   1620
cgagatgtat tgaaaaatta tgttaaaatg agtttttcaa atttgattag aacctcgtgt   1680
tgaggtcgac cgaaattgac cgagaaaaat aaatttacga attttttttc aaaatgtgct   1740
acttttaaaa tataaaacta aatgggttac ttctcaaaag ctaaccgaaa ctattagtta   1800
tattgcggaa atatcaattt cgcccaattt tagtcatcca gagcctgact catcgaattt   1860
aggagattct agacgttgca ttcaggagat ttttatccgt tgtcgccgac tctctttact   1920
gatctacatt gtacttcatt gctgaactca acgagtcaac tcaatcgttt ctagatttgg   1980
aagaatctgc ttcagcgacg                                                2000
```

<210> SEQ ID NO 130
<211> LENGTH: 2000
<212> TYPE: DNA
<213> ORGANISM: Cucumis melo
<220> FEATURE:
<221> NAME/KEY: misc_feature
<222> LOCATION: (1)..(2000)
<223> OTHER INFORMATION: n=g, a, t or c.
<220> FEATURE:
<221> NAME/KEY: unsure
<222> LOCATION: (1)..(2000)
<223> OTHER INFORMATION: unsure at all n locations

<400> SEQUENCE: 130
aaaaggcgaa aaaaaagtta gcttcccgag aaggagaaga cgaggaagag tttgacttcc 60
cggggagata aagtttgtgt ctcgagggaa tctctaatct ggagttgacc gtcgacttat 120
gtgtcgagcc tggatttagt tgcatggtgc gacaaagcga taaggcggca tatgtaaagt 180
agtaattcaa aactagcggt taaagaaata atcagccaaa aaatttagta caaatacggg 240
tggaggccct aagtgaagtg ctgctattca gaggttttgg caaaagagtg caaagagttg 300
agttgtgcag agaaagtact aggtgaggag aggcgtttgg aaaagaaaag gatcaaacat 360
ttgcatgagt gatattctta aactaaacac tcttgtgtga gtgacttgcc taagctaaac 420
actcttgcat gagtaacttt cttaaactaa acgttttgta atgttttctt aatggattct 480
tttcgagtct gagttatgct taacacgttt tgtttctctc gtgttattgt tgttgttgtt 540
tgaaaagaga aaactattgt tttctatgtg ctgattgtga tgaatgtgtg cgaaccatta 600
gccttaatcc tatcaagtga atagtgatta tgtggtgtgt gcacataatg taaatgacat 660
tgtgtggatg gccagtgcaa caagaaatga atcagaaagc ttcccaaata ctgtgaatgg 720
agtgaacatc acactagctc aatggcaaga tattggcgat agtgaatcac aataggcttg 780
acaaggggaa ggattcatgt tcttggttga aaggaataag agaggctaat gtgagatttc 840
tgtgatttgc aaaatgaggc gttggaagac acgtttgaga aatgaaaacg aattagtgct 900
tgacttgtat tcctaaaaaa gttgtccaat atcttcaatc actaaatatt tgatgtgcct 960
aagttttcct tccttagttg ttgaggcgtt gaggccgagt aaggaaagat aagataatta 1020
tgacgttgaa aagctggtca agttatccat ctttggatgg tttaaagtta ttacatgtag 1080
ggagggttgc attccaattt tgtgtgtgag atgagtctta ttttcgagat gggttgctag 1140
gcgatcaagg agaagtataa gaaatgagtt cttatactct tgaacaactt gacacgaaga 1200
ataacatcct agtggatgaa ggaaggtgat ggaacttaaa gtttaggttt tattttnnnn 1260
nnnnnnnnnn nnnnnaaatg taattgtaaa gtattagatc aagtaataaa acagagttgt 1320
gttttctatt tttgctgtgt tgggttgtgt atctttattg tgcttatggc ctagttgcta 1380
aagagttaag gttattacct aaatgtttta cggtgtgttg agttgtaaag atctcctgag 1440
ttaaagttgg aattttgtat tggagattgt tttgagaagt ttagcttact aattgtttaa 1500
ctcattaggt gtctaagcga cacgcctcct tttggtcgca tgaagtggct agcagggtgg 1560
ggcggaccgg ggtggggtgt gataataaac ctaaaaaatc acccagataa gcctaaatta 1620
tacgttgaag ttaaacttac aatttgatta gaagaagaag gaatatctga tttggacatg 1680
aattaattac aaatacggcg ccaatcatac aaagcacatg taagatcaac gcattctaca 1740
ctcaatctca gccgttgatt gctttcaatc cttcaaaaag aaaaaaagaa gggcagttcg 1800
ggcagagtca tacctacccg ttgactataa aagcaactac aaatcgaaaa cctccatttc 1860
tccgttacca ttacagagaa aatcaaagaa atttggcgtt gagagattgg gagagaggtt 1920
tctctttcta gggttgcttc ttcttcttca tcctccattg ttgcaaattt cacttccttc 1980
tcctcttgtt ctcatctccc 2000

<210> SEQ ID NO 131
<211> LENGTH: 2000
<212> TYPE: DNA
<213> ORGANISM: Cucumis melo

<400> SEQUENCE: 131
atagagtaac caatatgccc ttttcagcag ccaaagtttt ctatgggcag acttaatcaa 60

-continued

```
ttaaggttcc tattgaggcc ccactcttag tgaaaagcct agacccttct ttccaacatg    120
tctcaattgg tcacctccat caaaagcttc tatcatttaa tctaaaagca tactcttttt    180
tcctttttaa atttcatttt gatggtctat atttgaaaat aataatcact acaacgacga    240
cacgttgttt tcaaactatt attttgtatg aattaataat ttttttaata gtatagttgt    300
tttacttatg gaatctatac gtttaatcga ttcggtcaca tctatttact ttgatgtttt    360
tgttatttta tttagacgtg gttgtaaaga gtttaaagca atggagaaga aattgatgct    420
ttccaaagca atacaaattt atatatacct tcaaatgaga ctaacattag acaatacata    480
aactataata aacattttga aagtacatag atcaaaatga accaaagtcg aaaaagtaca    540
attatcaaat tagtttttaa accttggata aacttcagca ttcaaacttt gtatttcttt    600
tttttttcga tcgatatata tagtgataga agattttttt tttctgttta ttatttttga    660
cgatacgttg agtagaagaa tcgaacatca aacctttaaa tcaataatat atattttacg    720
actcaatatc tagccatcaa tattttaaaa tagcaattat tattcactaa attatgttag    780
agattggatg tcatacaaca attgttaaag attatttgtc tagtttgttc aattaatcaa    840
gagagcatta agcattaaag tcaattattg tgataagatg cttttgcact atgtaactaa    900
aaatagttgg atacaccatt taaggcccta catgcaaacc atgataggcc cacaaaaaaa    960
aatctctttt tggaaacaat ggtcaaataa tttctttcaa ataataataa taattacaac   1020
aaataaatac ataaaccaaa ttactaaact aatgtatcaa gttctagaga aaacaaaatt   1080
atgccctttc aagttgcaac atcccctact ataatttttc ttcaaatttt ccatttaata   1140
taatccaatt ctaaacatgg aaaagaaatg taacaatatt tacattattt caatctttcc   1200
tatattcatc gactaatttt aataagacgt gaaatcaaca tttttctaaa ctcgttgatg   1260
tcataaaaaa taaacttaaa ttatgtacaa gatcgtctat taaattatgt ataacacgtg   1320
tggtgtatga gtaatagaaa ctttaaactc ttgatcaagg acatgtacct ataaataaat   1380
agatttcttt aagtcttgac tattaaccaa cttgtattca gtaaggttaa agtgatctat   1440
tatcatacta aatacacaag tttatttcga gtatgaatgc aaagaatcaa agatatatgg   1500
tttaaacaaa atctattata ccaataaaaa aggttaacca tatgcaataa aaactaaaaa   1560
gtctattgct caaatctctt tcgagaccat attaaaaatg ttagtttaat tgacgtatgt   1620
atttattgga tttatctaat aacattttaa gagattgttg caaatatagc tattagattc   1680
aaaataatta agtatatagc aaagtctgtc aaattctatc gatgatagga ctatgttaaa   1740
attgttgttc gatcgttggt aaactataaa aatctacgac aataaactac tattcaaaaa   1800
tttttttacta cccaaatttt aaatccatct catggatcga gtcaagccca cttctaaatt   1860
gggccacgaa tattgattgt gaagctcaat aatcccatac gtatggctga aaacgcatta   1920
cgaacgaacg cccttcaact atccaaatcc gaacccaccc aaattccggt taggcttctt   1980
ctccgagatc gacgaccgcg                                                2000
```

<210> SEQ ID NO 132
<211> LENGTH: 2000
<212> TYPE: DNA
<213> ORGANISM: Cucumis melo

<400> SEQUENCE: 132

```
tgcagctgca caaaagattc caaatgatat aacataatag tttatgaaaa tttaatgcat     60
ttaatttccc cttccacaga agacactata tttttcaact acccaacaat accaataatt    120
atcattatta ttatacctct aattagtaat tagtcacaac ataaacagct attctcatta    180
```

```
atacatataa tcaacaactt cataaattct taaatttgta tgtgtacttg atgggtgtag    240
atttaagaag tccaagagtt tgacaccctt tgttaaaatg atatacaaat tcctgcaaat    300
taaatttacc attggtatga ttgttgttgg agtggtcaca acactaattt actaattagc    360
ttcgtattta acatagttgg ccatgcgagg aggtagcttt tgaacttcca ataacctggc    420
ttggaaggac gtcgataaac agaataacaa ctatgctaaa ttttgaataa tatactttat    480
atatattata taaagacgac aaagttgagg agcatccgtc ccctacattt gttggtgctc    540
atatcatcct attgcatatg ccttttacca atgaaaccct atctccttaa ttatttctac    600
tccacactca taattatcat tcatttattt tcatgcatga ctttctttta ccaaatttag    660
tttccaatta aactccatta actaccaaca atcaactcca ataacgtaac tcacattcat    720
tctaaccaat tgtttggatt gactcgagaa aaaaaaatgt tttttctaac tcatttttac    780
ttatacattt aaaaattctt ttggaagtga tcgtcaaaca ttttgatatt tttttccttt    840
taaaatgact tattttttaa aaaacttaaa tattcaaaaa ggttttccaa atgaatgtaa    900
ttaattactc aacatagatc tccattaatc attattatat gtaacaatag taattcaaag    960
taaaaaaaaa attatgtgga gtgcaaagat gaaaattttg acctatttta catgatttga   1020
actatatgtt tatgcgtacc tatgatttaa ctcttatata cacatatttt tgtctcaatt   1080
taatttaatt ttacgatttt cttgaataat tttattctct aaccactttt gaaaaacatt   1140
ttttaaactt tagaaaagaa tatctttacc aaacttaatt caatatatga aaatagctaa   1200
ataaaattta aaaaacagat aaccaccctt tgataactgt agctgatatt attaattaat   1260
tgtcatattt atatttgcaa tatgaaaaag gagatgtcat gagttttttt ttttttaatc   1320
aatctaatgc aattttctta aatttaatta atgtgaaggt gagagagaga ggcaatttca   1380
aattttaggt aagtattatg aataaggtta cttaacatta ttttaattta attttacatt   1440
atgttttatt tgaatttttt taaagactct catttttcca ttttggaact tttggaaaag   1500
aaaattttac ttcaatctct tatgcaagca agttaaaact acatttgtct tttcatggga   1560
tttttaagga gatgtgtggg gaaatacaat aagccttttt ttatttgcaa tttgctaaat   1620
gtgtattctt ccaattggct aattattaaa gtgaaattta gattgaaaaa agagataaaa   1680
ttgaattgaa gttgtataga tgggttagga atatgaaaat tgtttgagat atagtgagta   1740
ttggttttat ccaatgccat gtcatagggg tggaatccaa atgaaccaat gagaatcact   1800
caaaagaaaa cagatataat gcactatcca aacctaaaac taaaagccac acattgctca   1860
tccattcact cccattctca aaaccacaca aaaataaata tcaaatcaat ctctttccct   1920
tttccatata taccactttc ccctctcttc gcctctttga ttattaccca ccaaatattc   1980
ccatatatct tacaacaacc                                               2000
```

<210> SEQ ID NO 133
<211> LENGTH: 2000
<212> TYPE: DNA
<213> ORGANISM: Cucumis melo
<220> FEATURE:
<221> NAME/KEY: misc_feature
<222> LOCATION: (1)..(2000)
<223> OTHER INFORMATION: n=g, a, t or c.
<220> FEATURE:
<221> NAME/KEY: unsure
<222> LOCATION: (1)..(2000)
<223> OTHER INFORMATION: unsure at all n locations

<400> SEQUENCE: 133

-continued

```
aagcttgttt gaccctattt ttaatgtctt aacacaggat tatgaacaaa agaagaaact     60
agtgaatcac agaggaactc acgcaaagac taggtgagaa gatcatatca aaatgagaga    120
ataagttcgc tagaagataa aagtggtagt tgaagttgat gtgacttgac caagaggcag    180
cttctggtgt tgatatattc agaagactag atttcctgcc taaatctacc tatataaaga    240
actccatctc cattaagaaa atgaggcctg aatggaccac ccaagtggtc gactgtgtga    300
agagccaaat gtttgtgaac tgcccatgag tgcctgaaag gcccgatcct agagagtggt    360
gggaaggagc agcctttcca ccatctgtaa agtctttctt catcttctcc agttagttta    420
agagtgaaag tttgaggttg agtgaagaag attccattcc tatctttttc taactggtaa    480
tgtcatttct attctttcca tttttgtata tttctttgta atgtatttnn ncatattgta    540
cagtggccta agacctatat tctttaatac atttcatgtt tatatctttt caatctatca    600
cgtttgttat tattcatctg tccttgtgct attggtagct taagatttat gataagttct    660
tgataagaag gttagcttat atttcttatg tgtgttagtt gtgagctatt ttcatcacct    720
ggctagtgta tattgcaaac tacctgagag ggtaagtagc aaagatatgg cttaggcgca    780
caaggaggag tttggagaca aaatccacat tggcaagata acttccatca tttgtgtctc    840
aaaaggagaa caagtgtggg tattaagcat tgagatgttg tgacccttaa acgagaagct    900
atataagtct tagtgaaggt cgtttggatc tcgagaggtg agcaagtgtg gtgtttaaag    960
acaccgagag gtgctcgtct taatcataag ctcgttaact aagttatatt gcattaggga   1020
tattttattg cttaatttct tggtaatgca cgaacttttt ttcacccatt cttttatgcc   1080
agctagttca caattccatc tcgcatccat tttaatcccc ctttacagat tctccggtgt   1140
agataagtag atatagttta aacttacatg ctttcacact atatatttta ttcttttata   1200
ctacctaaat gcctagtgaa gcctagaact aagctttgat atcgattccc tgcattcgac   1260
tctaaatcgc ccatataaac ctattgtttc gcttacactt gggcaagcaa taggaaaact   1320
tgtactcaac gaggacttat gagttacatg atgacgagat acatagagag catctaatat   1380
gcattgacca tgatcattga ctcttcatgt agatttaaat acctttcagc ttaattagat   1440
agaagatata taataaagcc attccattag tttaaaagaa ttaagttaga ggtagttgaa   1500
atgctttata agtgggggtt aattctattt tagctgtaat gctgagctga tctcaagcca   1560
aggttgcctt gagatatccc cgagtttaaa aacagaagct aaaatggaaa ctaaaaacta   1620
agacatataa actttttagt tacttttagg gaaatatctt agctataaat taaagaatat   1680
gaccaacatg gaagttcctc catcactttt ccaccaactc attttattgg gggttagtca   1740
ttttaaggcc aattagttta aattaaagtt caatctcagt gatgcactag gccgagagag   1800
accgagataa atcattcaaa tattttttta aatttgggaa gaatcttgag gtcgagattg   1860
atcctgagaa aaacaaaatt acgagttttt taaaactgtg aaatataaaa caaaaaagtg   1920
ctagttttgt caattcccat ttatcttgct cattgttgat acaagatcat taaaagttta   1980
tggataaatg ttggttgaga                                               2000
```

<210> SEQ ID NO 134
<211> LENGTH: 1696
<212> TYPE: DNA
<213> ORGANISM: Cucumis melo

<400> SEQUENCE: 134

```
tatatatata tataaaaaga ggaatacaat taagacatcc cattgttaat aaggggtgga     60
ataaattggg aaattaccat tcgagaaatc attgacgaga gcaaatatgt caaagtagaa    120
```

```
aattagtcat ctcaaaagaa tgtaatcgtt acaaaaatta aaagtacgta aatttaatca    180

tcgttacaaa aattaaaaga atataaatta caccgttaca caataatacc aacaatccat    240

ttataatatg ttgtttttat ttcaactttg aataaaattt gaactctttg ataaaatttg    300

tttaaaataa atttaaaacc atttcaaaag ctatttttat attatccaaa tacatatatt    360

cttttctttt tccaaaatga cttgtttcta aattcgaaca tccaaaaatt aaaacataac    420

atttttagta tattaagaat tataaattaa gagataaaat attcaatact attataataa    480

aatcggtgtt ttcagtaatt gtatttgtac aagtaaataa aattaatagt aaaattttta    540

atatataaac aagttttaaa agaaacttaa agatataaaa aataaattga aataaaattc    600

aaacccatca acaaataaag aaaataaaga tggttttatt gaaatgaatg aactaaaatt    660

tgaaggaggc aaaagtaagt acaccaaaaa tagaatacta aaatggtaga ggacaataat    720

tgcatatgtt tggtagattt ttcattaact atcataccaa ttaacaataa tgaaataaac    780

tttctcgttg atattgatta caatcgtaat agggcaaccc actgtttaac ttgtcaaagt    840

tttcttaact ttattatttt tgactttatt tgtttgtttt attgattaga ttgatagatt    900

atatatttta atcatattat ttatagtaca acaactacga ggtaagtgat tgaagcttta    960

gtctctaaga acaaaggttc gacctaattt tttagtctgt ttttatttga catattttgt   1020

ccattgatag aattactatc acttaagtta aatgtattat tattgcaaac cactaattct   1080

acgtaaaatc tctaagtagc aagtgttatg tcaataaaat agcaattttt tttttaccaa   1140

ttacacacat catggtgata attattatca tgcacgggta aatttttaat tataaaattt   1200

caactttcaa aattatacca atactaaatt tattacaaaa gttattttag gtaaattata   1260

aaaacttgat aacaattaca agtacattct aaaactttca ataataaaga ttgaatcatc   1320

caattcatcc aaatgttaaa tttataatcc gatttcaaga agaaaattaa aaactcaatt   1380

tttatgaaaa tgtaactaca accacaacca tattaaacaa aaactcacaa tttgtccata   1440

ttttttaagt taaaaatata ggtttaggat tcaaatattt ataaaataaa ataaaatgaa   1500

actatttgaa aacatagttt aaaaaagaag aagaagaagt gttaaataaa gtcccatttt   1560

ttaaaaaaat atcaagaccg atattaatat tatatatata tagaaatgta cacaaagtta   1620

aaaaaaagta tcctataaat atctaagttt ctccccgtct agccttcgcc aaccttatct   1680

caaaaactcg gaagcc                                                    1696
```

<210> SEQ ID NO 135
<211> LENGTH: 2000
<212> TYPE: DNA
<213> ORGANISM: Cucumis melo

<400> SEQUENCE: 135

```
tttacatatt tatgaacatt ttcctatttt tgtaaatatc ttgattcaag atttttgttc     60

gatatattta aaaataaact tattttaaat tcatacttct ttctccttct atatgattat    120

ataagtattg tagttactat agattaaact cataacctcc tagttagata ttgagattat    180

tactttcttt tattatcggg ccagtacaga aacgctttta tgacgattac attcgtcatt    240

cgtcacttat ttgtgcatta aagttggcat tgtaatgttt gtttttacat gattctctat    300

tccatagatt tcctttatcc ttttccttgc atttgagtgg ccctttccta agatgtattc    360

ttcggacttt caaataaata aagattagaa gcatttttct cttcaatatt gacttcatcc    420

ttaatcctta agccttaagc ggaggctaaa aaggctttat ttgcctcgaa tcccaactaa    480
```

```
ttctccctct catgcccatt tcaatctctt gcctaattgt taattaatgg gtcaaatttc    540

gtattgaatt tcaattttgg atcaatccta cgattatctc aattaggggt caaaattaat    600

ggttgatgta ggagcaagtg gaagacacaa ttttggtgta gcaattggag cttcatcatc    660

aacaacatga gatttaatcc cgtggttgca gttaaatggt gtagaagaag tagtcaacac    720

aacccaaggt gaagaagagg gagacaagag aagtggttga ggttgtggct ctatttgcct    780

atggcagcct tcacctcttc tctctcgctc cctctccgtt tcaatccctt atccccttcc    840

tctccccgcc attttcttct tctcttcttc ttccctccac caatttcacc tcccgattct    900

ctgccctaac catctcttcc tcctccttgc actccgcctc cgacaatttc gatcatgcca    960

aaagctcccc tttttcatct aaggtctgat tcatttctgt tgtttgttta actcaatttg   1020

tcttagttat attcaatcgg gattttgctt gcttgtggaa ttaattttcg tttattaagt   1080

ggaagatatg ggtatgcttg gtgacactgt atttactgtt aaatttcaaa caatcctacc   1140

aaattttggt ttaaattgag tatttttagt tccttcttgg taaattggat ttgcgaatga   1200

ttaacttaac tatgttggca cttcgttgta agaccgttaa ctatttagct tccttacggg   1260

taatgatgtt tagaaggggg gtgcttggtc cactaagtgg agttaagtct atggtaaaca   1320

tgttggcatt agtaagtttt tggtaaacat gttggcatta gtaagttttt ggtaaacacg   1380

ttggcattag taagtttttg gtaaacatgt tggcattagt aagtttttgt ttgtgatgta   1440

gagttgtaag attgagttct ttaataattt gagttgtaag attgaattct tcgataactg   1500

tgaaaagtat attaagaaag taagatagag ttacttgata aatttgaata gtggagatag   1560

gggcaagatt gagttccttg ataaaagtat aataaagtaa atgtgcaact cttgcctata   1620

tacagcttag caggaactct tacttttgtg tgtcatgtat tcttattggt tcgttcttat   1680

tgcatttagt agatagtgga tcccagtgaa ctttttaat  cgctagaatg gcgccttaaa   1740

aagttagttg gagcttctac ttgttggttg gtatggtgcg gttgcaagta tttttccttt   1800

ctatgattat gtttttagat ctaaatttta aagcactcga tgaatgctga tgcttgatat   1860

gttttctgtg ttaaattctt ttgttgatga atattatttc cattttttcag aaatcagttc   1920

tttcatcttt gatacaagag atagagccgt tagatgtaag cttaattcaa aaagatgttc   1980

cacctactac tgtggatgct                                               2000
```

```
<210> SEQ ID NO 136
<211> LENGTH: 2000
<212> TYPE: DNA
<213> ORGANISM: Cucumis melo

<400> SEQUENCE: 136

ttcttgatta gcttggtgtg ctgttgtata tcatatttgg tgcgagcata acttaccctt     60

ggctaccttg catctaccct aagtggttta gtcagattgt atgatttgag gtatttcgtt    120

tctttgttgc tctaagtggc tttgagcttc tactgaggga acctaggacg tctcttcttt    180

ttgggatctt ttttctcgag tagttggatg cctagttggt ttttttgttc ctttactcaa    240

gtcctttgtt tgtcatttga tcgtgtcaaa gtccaaatgc tttctattgc aattcagtat    300

cttaaaaaac tgttctttgt tgatttatgt aaatgacata ctgtatgtat aaaaggacag    360

aatgctacca tttcttgaag tttctggcac ttaccctgat aatcgttacg gtaattatta    420

tgtgcagatt gacggcaata acgcagctag cacatcatgg tatgatattt gtacctcttg    480

ggtacacatt tgggagtaag atgatggaaa tgaatgaggt gaaaggtggc tctccttatg    540

gtgctggaac ctttgcagcc gatggaactc gacacccgac tgagttggag cttgaacagg    600
```

```
cttttttacca aggtaagtat gttgctgagt taaccaagaa actcaaaaac taatgccatg    660
tttgaaatgt tgttgggtat ttgaaaacgt gttattacac tagcacactt ttactgtact    720
tccttccaac atctattatt cagcttctca catcatggct atataaataa aggttaatgg    780
aagttactaa aaatgatgta aatctatcac attgttaata ctcctgtaat tatattgatt    840
gatgaacaat tcgatcacca tcttttgtta tttaaaatta aacttgtaat atgtattcga    900
acgtttttag ctttattgca tgcttattat ttcactgttt taaaactatc tttagacttc    960
aaatcaaatt ctgaaaaaca aaattaagtt ttcacataca ttatgtcatg aatataaaat   1020
tttagatatt ttagttcatt ttactatatt taaaaatgtt ttattattat taattttgta   1080
aaacaaccat gatcgtttat taattgaatt gtcacaatta agccattatt ttttttttta   1140
ctttcctttt tcccatcaat ttctttattt tctaaaaatt attggcctcc cagactcttt   1200
gttatttgca aataatgagt ctaatcataa tagaatttca ttgataaaac caatcatagc   1260
gagtcttaaa accaatcata gcgagtcgta attataaata ttattgaatt gctcttggtc   1320
cagtttagct agaattatga atttgatcaa attttctgtt atcattaccg tataacaata   1380
aatgataaaa ttcaaaaaaa aaaaagaaag aaaattgata tgttaacgac aatggtaatg   1440
ataaccataa ttgtaatggt aaccgtaact acaatacata atttttgaat ccaatgagat   1500
gaatcactta cttagttgat ttgcgtacca aattatagaa caccaatcat ttttgtaatt   1560
aggattgatt tactagcgtt agattagaga aaagcttggc ttatttctaa ttcctcctcc   1620
ctcttccact cattttgtcc ttaactaaaa catagtgata gttccctttt tcttttagag   1680
aaaagaaaag aaaagaaaag aaaaagagtg ttaattggta atacataata acatatcaca   1740
tacataaata aatcatgccg agttcgcctt agaaacgacg ccgtttaaag taagtcaaca   1800
agtcaacact gacagctaat ttccgcaata aatacgtaaa aatgaaaaga aaattaaaaa   1860
acgatataat ataaatagaa gcaagaggct cccatcacaa gatcccattc gcaaccacat   1920
tccggccttg aggcttcaaa aaatcgaagg aaaacactct ctgtatctct cccctctacc   1980
caccgattcc gtcgcggccg                                                2000
```

<210> SEQ ID NO 137
<211> LENGTH: 1575
<212> TYPE: DNA
<213> ORGANISM: Cucumis melo

<400> SEQUENCE: 137

```
atatatatat atataattta actaaataaa caaatgaaag aaaaaagtga gttcccattc     60
ggaaaatgca gatggatcca tttcttcaaa tattaaaaaa taaaaaataa aataaaataa    120
cttaaatatg caaatagaaa gaattttaat ttctggatta tccatatggg acaattttta    180
aaactcattt attttatttt ttttatttat ttgattttga tatatctatg gggaaatttt    240
tcgtaataat tttcgaaaaa atattgcaat atatcatttg atcagatcgg tattattaaa    300
tctctatcac atttggtctt aaattatcca aagattcctt taagataatt tagataacca    360
tctacagatc actactataa tcaacaaaag gaacaactta aattatttaa acaaattcat    420
taatattaga ctttgtgctt cattagaaaa tgatcttatc acaaccacaa ccatagtggt    480
ggtttaaaat tttattttaa actcttatta gtattatttt aattcatact taatcaaact    540
aattacttta aaaaacatat atatataaat aagttaaatc attcccccctt atctaaataa    600
cataaaaaaa aattgtttac tctacaagaa gtttgtatat atatatgctc ggtactattt    660
```

```
agcatcttta taataaaatt tctaaatcaa ttttttatat ctctttatta aatgtatagt    720

catcaaaaaa tttaacgaga taatgtgtca aagatttatt ttattaacgt tcataaatat    780

caaattatac ttagcttata attgaaaaca tgttcgataa atataagtaa ataaaatttt    840

attttttta aatattacaa aataaactaa ataagttata aatatgacaa taaacattat    900

atattttatt atatttataa atacttaata atttagtcgt ttaaaataat tttcttaatt    960

ttcaaaacat gtttcatatg ttaataataa ataaatggaa aaccttccaa aagaagaaaa   1020

aaagatatct taaaatttaa aaattgagat tttgaggatc aataattaat aaaagaagga   1080

ttaataaggg tgaaattaaa tcccaaaaag aaaattgaaa atgaagaaaa gaaaagtgaa   1140

gaaataattg aacgtgggaa gtggattcga tgtctccaga gaacaagcga aaggagacga   1200

aatccacata atttgcacgt tacgtgtccc tatcaaccgt agacacgtgt caacatctca   1260

acaccctacg ccgaattgct tcgctggatc tggacggtca tcggataaca gcggcaacca   1320

attaatattt ccccttatat ttcacagcct ggccatgtcc accaatcacg ttcaactatt   1380

aattcatttt tcatttcctt tttcttttt tttttaattc ccctcaatta ttaccgacaa   1440

cctgttgtag ccggttaacc ctaccctcca acgttccatt ataaggccta gaaaatggac   1500

gtgaaaatgg agtactacaa actacaatta attttaaaga attttaattt taaagttctc   1560

taattactat tagcc                                                    1575
```

```
<210> SEQ ID NO 138
<211> LENGTH: 2000
<212> TYPE: DNA
<213> ORGANISM: Cucumis melo
<220> FEATURE:
<221> NAME/KEY: misc_feature
<222> LOCATION: (1)..(2000)
<223> OTHER INFORMATION: n=g, a, t or c.
<220> FEATURE:
<221> NAME/KEY: unsure
<222> LOCATION: (1)..(2000)
<223> OTHER INFORMATION: unsure at all n locations

<400> SEQUENCE: 138

ccgtcgggaa cctctgctct gacataatta atattcatgt atttcctgat acccatgcaa     60

gtcgtcggga aatatgttac caattttcga cgccagacga gaatcgttag gaacaagtgt    120

caccatgccc aacttcttgt atggggcatc aggataagtt aaatttcttt tttagttgtg    180

aactattccc gacgccataa acctagatgt cggaaatgtc ttcttgtttt tcgacggctt    240

cgtgaatctt cgaaaaaacg taagattaaa ataatgtttt cgacgagttc cgacctgtgc    300

aaaacgacat cgggaatagg tatttattcc aacgttctag cttctgacat ctagaaccct    360

tcaatttctt gtagtgccag tgcaaagatt gacactctta aacgatggga cttgtcaaat    420

agatgttgcg cagatatcca taggttatct aaggttttgt tttgttacct aagttatcat    480

caaacttctt catgaattct cttagctatt tctaagtacc taagttctcc tctatccact    540

aggattgtct ctcttaaagt caagggtggc tgttggtagg atgtagactt tgtcggcatt    600

ggtctaccaa tttaatctct tatatcccta aagacctaga ctccatggtc tccacctatt    660

tccataaatg tacccataac atcattaaat gaaattatta ctcaagtaca aaaaaattgt    720

ttaattttat tgataaaaac catatgtgaa aaaatagatg acatttttaa aagcttgtaa    780

acagtgtgtg aaataagtat cctaagtgaa ggctattaat ttaacttaaa cacaataatt    840

attattgttt taatgatgaa aataattaac ttatataacc aattttcatc aacacataca    900

taccttttgt ataaacattt atttgaacac aaatgagaga caaatagaca tttttatttg    960
```

-continued

```
gtaattttct cagcattatt aattatcatt ttcagatatc ttaattgaaa tttctgaata   1020

atttttattt tttcggattt tcacattata atattttgaa ttagttagtt gaaaaccaaa   1080

gccagcatca gtgaaaactc attaatacat gtaaaatact aaaattgttt ttttaaactt   1140

ctcaaagaaa aaaagtctta atttttattt tcttaacttg acataaaaat cattggtgtt   1200

gtttttaata aagtaaatgt taaagtagac tcagttaaaa acgaaaaaaa aagttaaagt   1260

ggactcaaca cttggagtaa acattttttt taaaaaaaat taatcctaaa attatgatta   1320

taatttttat ttggcttaaa tatttcaaaa tgtgttacac atggtttagt ttcaatttag   1380

ttgttacaaa atttattatt gtatttgaat ttttgataga ctaattaaaa tttgaaaatc   1440

aatttattta tacagttgtt tttcttttaa tgatgtaaat agaggtctaa tgattttaac   1500

ttgtaagggt taatttttct tatgatctaa tgtaattcaa tgagcattaa ttttagaaga   1560

aaatgtgtac ttattttgtg taaaaataaa ttataataac aatttttttca ttttggtata   1620

acgtatgatt aagttccatg aaaaaacaaa ataaaaaaga ataaaatatt tttccattta   1680

aagaaaaaca ataataaaaa tggagggatt caataggaat ttcggagggc ccacttccca   1740

attccaactc cccactcact cactcactca cnnnnnnnnn nnnnnnnnnn nnnnnnnnnn   1800

nnnnnnnnnn nntttttttt attattatat tagaaattaa taattattgt ttatttcgct   1860

gtcaaataaa aataaaattg tggggcaggt gcagctcacg tgcctcctca cattgacacc   1920

acatttaaac actttcattt tcaaaggctg ctgctttata ttcttcacaa aaacttcctc   1980

ttccctttct cacactacta                                                2000


<210> SEQ ID NO 139
<211> LENGTH: 1006
<212> TYPE: DNA
<213> ORGANISM: Cucumis melo

<400> SEQUENCE: 139

ataataataa taaatacata aaataaaaaa ataataatag taatgaaaat caatagaata     60

attttaaaat cgggaaggaa gtcgtgtaca atccttgcac gttggagagt caaatggcct    120

aagtggtgat gtggaagtcg tgtaccgggt acacgatttt cctacaagtc aataataata    180

atatggttat ttttttttcta gtttagggtt catgacaaaa gattgttcag tcgactggat    240

gtagacaaat ctaaaaaata aattaaaatc taatatgaaa actagtttta atttccaaat    300

tattaagggt tgaattcgac caataaataa taataatacg gttattttga aatttaggaa    360

attgaataaa gttgttaaaa tcttcaagca aattgttaag ccccgagata ttaagaagag    420

gtaataatag aggattctat atttataaca tgttaaaatt aattgcaaac tcataaatgc    480

atcacacaga ttaacaacat aggagggact tccgataaaa gtgcaaatat tgaaataatt    540

acagttcgcg aacatgagta ttttaatatt ttataaaata gtatgcacgt gtatttttgc    600

caaaagaaaa aaagaataga ttttgccatt tttcaaagtg actctcggtt atatctttta    660

tggcgattgt attttatagc gtatgttgtt tgtagttaac ccatttctca ttggcaaatt    720

caatcgtggg ccacaacgtt tgggcatagc ttcaatttgg attaactcaa ttatgtctga    780

atgggttgga ctagttcgga ctcttcggct gggccagaat cagattcggg ccgcaatctg    840

ttcatttcac acctatatcc aaacaccccc aaaatcgata cccatcaaac cctaactctc    900

aataaccccc atatataaat tccttcttta gggtttttca tcctcataca ctctcaaacc    960

tccggtcatt ctcattttcc ctgccgcttc ttcaataacc ctaatc                  1006
```

<210> SEQ ID NO 140
<211> LENGTH: 2000
<212> TYPE: DNA
<213> ORGANISM: Cucumis melo

<400> SEQUENCE: 140
aaggagtaga ctctcaagtc cactattcta acttcttacc cgaaagagcc aaaacttttc 60
attcaaattc aactagaaag ttattattga tctatcaatt tgattttaat ctacaggcgt 120
gcgttgcaat ttgggaaggg attgagtttg taactggagt acgggcaacc tcattgaatt 180
ctcttcgatc aacgtgggga tgaagttctt tcaccagttg gagtctggaa aaacttttgc 240
tagactaacc tattgctact gccttttggt gaaatctttg tgctctaata ttaaaaagac 300
tccaactttg aatcgttaat tataaactag tgttatttgc ttgtaaatct tacttatagt 360
ttgaaatgag tgcttggcga aagtgttgtt caaatcggta cgtgtaagtt taaagattct 420
tatttcagct ttgaatcaga tcagagtctt ttaaacttaa tcaaccgaca ccaccacacc 480
ccactcttgt tcttctccac gtgggagttc ccaaattggt tgatttgtta tctctttgaa 540
tcatctcaaa tcaagaaatt tcagaacagg tttggggaaa tttgataaac tacactctct 600
tgctcgaact ttgcaaggtt tttactgttt gttatatgat tcaatattcc catttcttct 660
aattggatga actgttgaaa attggaaatg ctcagctgcc aagttttttt ccgaaatagg 720
tataaattca aagattcaat cagtgtgggt ttacccaaaa aaccaatggg gtaagtccat 780
tttggactca tgtggagggc acatgtttag gcaaagcctt atctctttgc cagtgggctc 840
acaatcaata cggacaagac aagaaatgct tcctaacacc gtcattgtca gcgaccatgt 900
gagctttcag caaattggat ccttcaagta actcacgtga aagatattta gtgattgact 960
taattactct ccccttcctg tttatctaaa ttaggcgaat agatccaaag tgggtatttt 1020
tggagatcat ttatctgttt cctgttcttg tttatcgttt ataattattg attgtttttc 1080
tggctcaagt aaaacgagga ctttgacatt tcaatacccc ctttttttgtt ttctggtagg 1140 tagcgctaag tgggtttctg atatcgtact gaaaaagtta tagttttgct agaacactcg 1200
atagatttta gcttttgtat tgattttttt gttgatattt cctggtttca gtgaatgaat 1260
gatattcttt tatgacggtt gttgtgaaga ctcataagtt tgtctcagat cttcagttat 1320
actcttgaag cttcttcgtt catacttcaa cagttcttgt acattttacc ccctctgttc 1380
ctctttccat cggcttgtga atctgtgatt gtaaattgtg ctgatgattg tttttaagct 1440
gttgagatgg cgttggggtt gtgtcctaat ttgagactgg tcaacttgat catttggggt 1500
agtgatggcc ttcttttcta tatcattctg tgaagagtac tttctaaccg attttgttaa 1560
aaacacatgt cggattgctt gcttgttttg tggtgtttct gatttgtgat atgatttgat 1620
taatctctga tcgagttgtt atgaatttga ttgacagcaa ttgggggacc atggaatcat 1680
tgtggttcct ctcatagatt ttgatttctg aggtgttgag aaggctttaa cctttttgtc 1740
actgaaatgg atggtggaag ctctgaatcc ccagatatgg gttgtaacaa gaccatagta 1800
tggtttcgta ggacctcagg attgaggaca accctgcttt agctgctgct gctaggaatg 1860
gttttgtata tcctgtgtac atatggtgtc ctaaagaaga gggacaattc tatcctggtc 1920
gggtatcgag gtggtggttg aagcaatccc ttgcccattt gaaacagtct cttaaatcac 1980
ttggtgctga cctagtgctg 2000

<210> SEQ ID NO 141
<211> LENGTH: 1556

<212> TYPE: DNA
<213> ORGANISM: Cucumis melo

<400> SEQUENCE: 141
ttttagtcat tatacttcaa catctcgttg gttttaggtt tttggaaagc aaacctacaa 60
aacacactct ttcattcatt ggttttaagt tttgttgaca actttttagg agtgctttga 120
ctaagatttc aaagtcttgt acttaaaatg atgcatacta tcgtaaaatt agtataagag 180
actagatttt taaaaaagaa gaagatcggt ggaagtatgt tctaatttct aagtttttca 240
acacttacaa atttattgaa aaacagctgt cggtacatgc acacatacta tttatggatc 300
tacaattcca agcatagaag agtttagtat atatccaaat tcttattttt aaggggaaaa 360
aatgaacgaa agaatgcatt gtattctcgc ttttgtcgtg ataacgtatg attttcaagc 420
tctttcgtcg aaaaacatca acaaacaaac aagctaagtg taatctaaat aatcttcaac 480
atccttggaa atttattgaa aaataaagat ggctagcaat gcatactttt tatggatcta 540
tatcccattt caaccgtaga agattcaaag tattcgaatt cttaaaaaaa caaaacaaac 600
tgccttgtta agataaaatg gaattagaat gaaattttca aaattgaagt ggggccttgt 660
aaaagaataa actttgtttg aaaattaatt tccatcgttg gttggtagat gtgtccttaa 720
ttgaaaaagt ggaagaaatg aaggatgaat atgaaagttc tgaaaagaat atggacggaa 780
ttggaaaaaa caaaaaacct aatttcataa attaaccaga atctaaacat tgggggatga 840
agggagcgga ggccattcat gtaattggcc gtacagattc atggtttaac aaaagccaca 900
acgactccca ttcttccacc acagaaattt cctctcctcc taaattcact tatctctttc 960
tatataattg cttcgttccc caactttcta tcttcgtgca gccccattca atcccccatt 1020
ttacccactt cgtcttctcc tttctccttc gtcttccagt tccgttttcc ccatctgggt 1080
tctcctgatt tctctttaaa atcaactacc catgttcgac tttgaggaac tggtgcgttg 1140
gaattgagct ttcgaaggag atttattgtt tttatcacaa cccatctgct cgaggtaagg 1200
ggtaaaaccc gggttcgtca ggctgtagac atcacggcta tacacgtagt ttcccggtcg 1260
ttctttcatg tccgggctgt acgacggaag ggttgtataa ctccgacaaa cccttcgccg 1320
cacggcggac gtggtgcttt gccttccgaa ggtggtagtc cttctgatct tctttttctc 1380
gccggcggtg gattctcttg cttcttctct tcttcgtatt agctttgcaa cgagtccgtt 1440
tgtgttttag ctctaccggt ttaggatttg acatcagcaa gtttctgttt tgcgtttctt 1500
tgttttgggt ggggagattt tggtgttggg tttggtttga attagaagca gacgat 1556

<210> SEQ ID NO 142
<211> LENGTH: 2000
<212> TYPE: DNA
<213> ORGANISM: Cucumis melo

<400> SEQUENCE: 142
gagtacctaa tctaaactaa ttaactcgct caccctctta tttactgccc catactaatg 60
atcctaatag attgtttggt tgggttgata aattctcttt aaaattatca agtttccaa 120 tttttgccac ctaagttgtt ttcttacaaa aaataaaaaa taaaaaaagg caatgttatt 180
tctcgtatgc attaattgat tgattttctc aactaaccct tcaatttgac tttatatgta 240
ataatagtgt aaaatatata cgcacatacc tacatatgac caacaataaa aacgataaca 300
ttaaattcag acagaaataa aaattacgat tatgatttta ataaatataa atgcacataa 360
ataaaattta cagttcatag aaaaatccga tgtaatgaag tttaaatcgt tagttatttt 420

```
atttcgtaaa ataccaattt atgatttgca tgacaaattt ttaaaatata acttatgaaa    480
ttaaaagttg gttttgagaa aacattcaag actttattac aaccaaacaa aaattttatt    540
gagttttgtt tcattaaaaa aattattaaa ttacaaatat ttggacttac gtaatttgtt    600
ttctttcttt ttagggtaga aaaatatgat agattaaaag gattcgaaat caaactttat    660
atcaatttcc ttttaaataa ttatttcttt ccaaatttag tttttatatg atagcctaag    720
tctccatcat aagaaacaac gttaattata ataaaaaatg gatgtagatt caccaatatt    780
ttccaactat attattactt tcacgtttac attaaaatta aatccacaca ataatataat    840
agttttcttt gtttgattca aagtttctct tggttaaaat taaatttcga aatgataata    900
aataaactcg tgattaataa actttaattt aaatttcaaa cttaggtgtc taataaattc    960
ctatattttg tatcacaact tttcaattat gtgcaataaa ttttctaatg atttattatt   1020
ttttttaaga atgtaaagtt gattatattc atattaaaca taagattgaa aagagagagt   1080
tgattatata ccgagtagcc gacagtcatt ggaagcatta acccattatc atctccggcg   1140
agcaaaagca aggatctaca aacaaacatg acaattaata tgaaactcat caatccacgt   1200
atccaaacat tccatatgtt agacatggaa gagcaataat tacaaagctc tctcatcgtc   1260
tccgatcact ccatttatcg tacaaatccg tctttcttca ccttaatcat tttccccgaa   1320
attcatccca ctgtttcgca acaaaatcca agtttggaaa gatgagtttg tttttagtga   1380
tcaaggaaag gacaaagaat gtagcattgg caatgacggg caaacaagag aggtgtggct   1440
aaacttatac atgcttttgt ttggtgaaag gttaaagcga agaacgccaa agacagagga   1500
aaccgtataa aatatgagta aatgtcaatg ctaatgaatg ggcagaggtg aagcggtcgt   1560
ctatggctgg agaagggcag atgtgaaaca atatgaggta gacgaaggtg gagacaaaac   1620
aatttagtaa agtcaaaaca attcatccat atcctaatcc aattatattt ctttaaaaag   1680
tttaagtatc aaaattggac tgcttgatca tctatcaagt tatttttgaa ctttatttta   1740
aaaagtttaa gattattaat aaaaatgtaa tgtttaaagt ggttagtgct ttggaagcca   1800
ttacgtccta tggattatgt ggtgtgttgg gctactctct atttggacat gttttgacgt   1860
accgtgcgaa gtcctgactc tatttgtaaa acgtcacccg gcaaaaaccc aacttaaaaa   1920
acagaacttt atttcattta atttgcgggg tttatccgga aagaattgtg agagctctct   1980
tgtgtttggt ttgcttatct                                               2000
```

```
<210> SEQ ID NO 143
<211> LENGTH: 2000
<212> TYPE: DNA
<213> ORGANISM: Cucumis melo

<400> SEQUENCE: 143
```

```
gtaatgcaat attagcaatt attttggagc aatacaaaca actaggtttg gatcaaatat     60
cacgaaatac aggagcaata acattaacaa caaataaatg cacgaagttt tttttttga    120
acaaacactt aactctctcc aaaccaaaac gagctaagtt agacctaaaa aaacaaagta    180
tcggaataca atatagctta aacaaaaatc atgtttagat tattggttag gttcatctaa    240
actagtggtt agccattttt caaaagaaaa atatgatttg tccttgctaa ttttccaaat    300
ctatatttta aaagtatcac tctcgtcata attttccata gctcaattaa tactaatctc    360
acggtagctt ttaattgttc ttgacaagta atggattaac ttaaaacatt tatataactt    420
tgtaggtatt attttataga aaaattagtt tatacgtgaa aacttcttaa atatctaact    480
acaatcaaat acctagatta cataatgtat ttttcataat atttatacat tatatttgaa    540
```

```
aaaggactct catttctttt attggtatct acgcagaaat taagattttc gagttgcgac    600

atctcaatca acgaaccagc taagaagacc ggcaaattcc aaacgtatcc ttcgggaagc    660

actgagtgtt tccacgtcaa taacaaaata ttgacccaat aaatttcagc cacgtagaaa    720

caaagcaatg aaagccgtcg gattctccac atcggctacc gtatgccgtt aagatcatca    780

agtagacttc taattcccat gtcttccgtg ggggccagaa atggaaaatt gaaatcgctt    840

tatccacgtc aagctaacaa aaaacaacca ataataattc gccacgtttt ctcattagaa    900

aagtgcaccg ttggatcatc cacgttggca acatagatcg atccgatgga cttatataaa    960

tttgggtagc tcgtcgagaa atcagatcag tgatcgaagc tactggaagt tttgctaag    1020

aaccatgagg aagtggacga tcgcttctgc tcttctcctt ctttgcattc tctctctcgt   1080

tcccgatgaa ggtgtgattt cgtttcttcc ttcagcagtt tgatttattt gttggaatgt   1140

aaactgaatg cattgcatta tcttaatcac gagggctgat gctttaattt ttgggggttc   1200

gaggagaaat ttggatgaga ttcgagcttc gtttgaactg cgaaggtttg atggtgatat   1260

ttctattgtg tttgaatttt caggtcctag atttcatgcc aaggccgacg gtgatgccga   1320

cgaggttgta gatccaccaa aggttgagga aaaaatcggc gccgttccac atggtctttc   1380

cactgattct gatgttgtta agaggttcgt gaatgtctaa tctcgttgat acacgcttca   1440

agtatagatt tgtccacttc gggaaaaaaa attatcgaac cttcttttga atgttgattc   1500

agagagtcgg agtcaatctc gaagagatct cttcgcagta gcggggagaa atttgagttc   1560

caagctgagg tgtctcggct catggatatt atcatcaatt ccttatatag taacaaagac   1620

attttcctaa gagaattgat ctccaacgct tctgatgtaa gttcactctg cctcttctca   1680

cttcattaga tctagtaatc tcattgttag atttgtgtta gttaataatg gcgtctctgc   1740

atttcaggcg ttggataaga ttaggttcct ttccctaacc gacaaagaga tattgggtga   1800

gggagacaac tcgaagctgg agattcaagt gagttcgacc ttcatactga catattgttt   1860

tcttattacc tcgctgaaaa aagctgctcg ttctggttga tgaaccttgc atacttttat   1920

tgttgtccat aaatcaaata tcgcagatta agttggacaa agcaaacaaa atcctttcaa   1980

ttcgcgacag aggtattggt                                               2000
```

<210> SEQ ID NO 144
<211> LENGTH: 1337
<212> TYPE: DNA
<213> ORGANISM: Cucumis melo

<400> SEQUENCE: 144

```
ttttttttaa ttttcttttt gcagattgtg gggctgatcg tccacgatat gattccactt     60

tggctacgag gggtgtcggg caccttgtcc gtaagggcac tggtgggaga tcgtctgtta    120

ggtaacctag ccctagcttt ttcgtgtttg gattcttcta tttaattgtt ggcttgatgt    180

tgtagatgta atgctgggtt tgagtgcttt gaaatgttga gggaaattta agaaatttaa    240

tgggatgaag atgaacagtg gtacttcaag cctcaaattg aattaaaatt attttaaaca    300

tcctaaattg gtatgactaa gtattgctaa acatgatagt catataaaag cgcaaaagaa    360

aagaaaaatc acccctctac taggattggt ttattctatg gatttttgcc ttcagtgttc    420

ttgaagtcac aataataaaa gtagtaatag ttgcagtcac aactcaaacc tttatatgtt    480

ttttaagatt gtggtaaata ttgttttgat cattagacaa gacatagaga ttttaagtct    540

ctgggccttt tcacgaagcc ataagcctct tatggttcag caaaggcata ctcaaggcta    600
```

gaagttaaaa aagccttgcc ttgagatgta attctgaata ccttttttaaa acatttggta 660 cttcaaattt ataagtttat tagtggaaaa tataatcttt cagtctcttt tttagctgaa 720
atacttatac cttttttccc cattgtcatt gatttcttaa ttcatatgca gaggaaagga 780
ctaattagat atactttgtt ttattgagta atctaaaaga tgtggcacta cccactatga 840
acattttgac gtcattccag cttttatggg atattgaagc aggcaatttt aatctgagct 900
ggtttctctg tcgctgtcag ataatccttg tttgtgctta tgtgttctct ttcaagcatg 960
cacattagga ttctcaggca gatcagatca ttgatattta attcaatttg tggatttagt 1020
ttgtagtgaa tacactaaat tctgtctctg gtttctctga tcttactgtt ttattacaaa 1080
attgttttgc agtgggattg ttgctactgt cttcggagct actggattcc ttggccgata 1140
tgttgtacag caactaggta ataggtgaac ataaatggta ctagcattcg actttctttt 1200
tgcttagata tgtaatttat tacgtttctc tataccttct actactagtg ggttttggca 1260
gctttggctc tattcttgat ttttatatca attttatgct aagcatgatt ttggaaatga 1320
attgtgtttc agctaaa 1337

<210> SEQ ID NO 145
<211> LENGTH: 2000
<212> TYPE: DNA
<213> ORGANISM: Cucumis melo

<400> SEQUENCE: 145
atatgtgacg attaattacc taaaaattaa ttatttacat agggttagtc aagttgtccc 60
gtgagactag ttgaggtgag cataagttga tccgaaagct cacaaaaata taaaatacgt 120
caatctccat gctttcataa aaataacaat ttgattctca tgactactca ttcacttatc 180
gtaaactctt ttaaagaata ttaagagcgt attagtgtag tgggctagtt tgttacaaaa 240
gttggcgaca aatagatgaa attagagtta tctcgagatt cgacgagggt taaaaagagc 300
atttgcttta ccctgtattt tcatcgtagt tcatatttat ttatattcaa attctatcaa 360
gttaaggcca cgtatattcc aagaaaacat aatccattaa tggtaatatg aaaaatgagt 420
tttaatttga tcatgttgtc ggcattatgt aatcacaaag atatctaaag ctcaatgtta 480
aatctaatta atggaggccg ataatccaat tatatttgaa aattaagtgg aacctacggt 540
gagatatttg tactatcaca attacaatta ctcttacttg ttcggaaaag aaattttgta 600
aacatgtcaa aattatcgtt actattccaa atattgtcac tgacctgaac attgtcaaaa 660
agaaataaat aaataaaata atattagata atgtaaaata aaccacctaa actttaatct 720
attatggtcg caaatgcttt gataacacat aaaccgattg atccgtcaat gaaattttac 780
cataatcttt attatggatc gataaatatg acttaatttt cttttaaaaa agtgtttttt 840
aatttaaaaa aaaaaaagga aaggaaaggg ggaggggcaa aggttctaga gtgttccaaa 900
taggacaatg gaggagggtc tccaatggag ggaggagcca aatccaacgg ccaacaattg 960
ctggaagctt caggagccta catgattctt gggttcgttt ttctctcctc ttcctatcca 1020
tccttttgaa atttgctata aagaaaccta cttctcttct ccttacaaaa aatccatttt 1080
acactctctg taataccccc agttttgcct cactcgcagc gctcatttct caccctctta 1140
tccaaatcaa tccttctccc tctaaaccct aaaacccctt tgcacctccg ccgttttctt 1200
gtaagattcc ccctctcttt tcattctgtt ggactttctt atccttttac tttactgggt 1260
catgcttaca tttctatttg ggttttgttt ttgcttgccg attcagtctt ctgtattgtg 1320
ttttgagctt tctgactgtt ttggctttct gggtttcaat tgttggtgta gacttatcga 1380

```
ttgattcgtt tgttttgtgt cctttcattt ctgggttttg atttctttaa cattttcttc   1440

atgggttttg gattttgggt cttcttcttg tgtgcatctc tgtagcttgc tgattcattt   1500

gtatctcgtg tttatctatt tgtttgagtt cctgacatgt gggtttttgt tgttgtctga   1560

gaattatgtg tcaaatgtca attgtcaatt cctatgttct tgaatttgtt tatgtcattt   1620

cctttctggg ttttctctgt tcaatcttgc tacatgggtt ttgggttttc ttacccttgt   1680

tgtgtgtagt tttagctgat ttttgtttat gcttactgat tcggttctgt attctcgatg   1740

atttgcttac ctggtttttt atgtcgtttg agaattgtgt gtcaattcct ttgttgttga   1800

ttttgtttgt catttctggt ttgacattcc atccaatcct ctctgctcta agtctacttg   1860

gttttcaatt catgaatttc catcagacgc attgtcggcc ccctgctcta tttgtttaca   1920

attctggttg tgaagttgtt tcagtttgaa ctaattgatg gtctggtgat tacgttctgt   1980

atcagtttgg aagagggtaa                                               2000
```

<210> SEQ ID NO 146
<211> LENGTH: 1212
<212> TYPE: DNA
<213> ORGANISM: Cucumis melo

<400> SEQUENCE: 146

```
atatatatat atataatgga ataggctatt tgatttagat gaaagctatt acgtcctggg     60

gtttacatca taatctctat tataatgtta atcgagaaac tttataaagg ttaactcatt    120

atctctcttg tcttcagttt attattgttg tttttatatc ggtggaattc cacctttcac    180

caactctcaa gctgtggtgt gaatctatgg gattaatcta gggcgaataa gggagctgag    240

tattttctat ttgtggaatt aaatctatag tacacaaaac atttgctcaa ctactaagga    300

tatgaaaacc cttggctctg ccaacatggc ttatagaaag tatctgaaaa cgttcaccac    360

tttgcaattt caacaataag tgtaaattct tttcctattg ttgttattta gtcgatttga    420

tcgttgtaca atatttgctg taacatgttt gatttttggc cattttagtg ttcacaagaa    480

gatattgttt gttataagaa tctacctgat ccttttcaat tgttattcaa tatattgcct    540

actccgttga cagcaggtcc atgcagagga acaagttcta aagttcaaac tcgatgctga    600

tattcttcag gtactacttt tctgttttca caagtttgtt gtttcaatag ttctaagaca    660

gtgacactca tccctttatc tccgtaaccc aattcattaa cgatgacttt tgatcggttt    720

gaagaaaaaa tttataacac tttctcatct cgttcccttt ggattttcag tttttaaaat    780

tgcatctata tgtattcttt tgttatcaaa ttttacttga taatgacttt taaattgtac    840

taactcattt agatgtgaat attaataatt ttaaacttca tttctgacgt ctaatactaa    900

taaaataata ataacaatta tccttcttaa ttaaatatgg tttacctacc ggtctattgt    960

tctgaactgg atatattcaa tttgttttat ctgaataatc ttttgaggtt gagttatcaa   1020

gagcctgttt aacttaccta aagcatttct aacctgaact atgccccata tgaatacttc   1080

attttcttta ttctattgta aaacattgtt gttattataa tttgaaacgc ctgtaatagt   1140

ttttacgatg tcttgcagga gtctatcgtt cggcatgtaa acgaacaccc acaggctggc   1200

tggaaagcta cc                                                       1212
```

<210> SEQ ID NO 147
<211> LENGTH: 2000
<212> TYPE: DNA
<213> ORGANISM: Cucumis melo
<220> FEATURE:

<221> NAME/KEY: misc_feature
<222> LOCATION: (1)..(2000)
<223> OTHER INFORMATION: n=g, a, t or c.
<220> FEATURE:
<221> NAME/KEY: unsure
<222> LOCATION: (1)..(2000)
<223> OTHER INFORMATION: unsure at all n locations

<400> SEQUENCE: 147

```
acatagtatt aataaattag ggaatgactt agttatttaa tttaagcggt agtaaatatt     60
attaactttt gttcgttgtg ttattttact ttcaaaacgt tcatcttgat ctttatcctt    120
tctaatattt atttatttta gttaatatca aaaaactaaa tttaatttat acgttaagtt    180
acaacttcat ttatttcaat ctaaaacttt tagaattaca ctttattcac taaaaaatta    240
ctcgtaaatg caaccattcc aaaaaggttt caatattata taaaatatca taatttttcg    300
aacattctta aaataaatta aacaaaatag tagttttcat atacataaaa ttcgaataaa    360
tcctcataca aaaattttaa atttgaatca tcacattgtt ttattttaga taatcaatca    420
aataatttag gaaaagagaa gaaagaaaag taaaaggaag ttgaaggtat tttatttagt    480
gatagaatta taaaataggg tattttagaa ataaaaacac aaatatataa aaatacagaa    540
attgatgcat ttaatggaac actatttgac aatcaataag aaagaaaaaa aagaannnnn    600
nnnaaaaaaa gaaaaaagag aaaaggtttg gtattgggtt tgtgggattt tattaataaa    660
tgaaataaaa aaaaaagaaa gaaaaattta attgattaat ttggtgggag aatattacaa    720
tgaaacccca ctttgtgaac aaatacattg catttgggtt gtaatcaagt gtacatgcat    780
ctacccaaac ctttcttgaa ctcaccataa atccttcttt tagaccgctt cgacttccca    840
atttttcttc acttttttc cccttctct ctcttcctcc gtttcccccc cccttttttt    900
tccctatctc atagggtttc catccacctt cttcttcttc cgttctctca tgcattgtca    960
ttcacaatct cattctgaat tcctcttgat cttcttcatc ttcatttcct ccttattttt   1020
tgctctcttt cgagggtttt tcggttcatt tccgtccaga ttccaccacc tcccgtggtt   1080
ttttcaccca tactcatgtc gaagctcttc gccttttccg gtaagtttat ggatttttac   1140
tgattttttt tttttgtttg ttttgccttt ctttggattt gacttagatt gggtagctgg   1200
tagggttaag cgtcgtgttt tgtatgggtg tttggattgt tatttggatc gtagggaaag   1260
atttggaatt attggtttta gtttttgggg gtttcttgat tcgccaggtg gcggatcatg   1320
gcttggtatg aattgtgagg gaatatggat ttgggtttct ttctattagg attgttttat   1380
tgtgttgatt gattggctat tttattgtct tgaacagtcc atgccagatg taagtttctt   1440
gaaaagagat atcgtagttt gaagatgggt ttacctttta agtgatgtgt atgtgttgtt   1500
gatctgtcgt tcccgtacag atttagattt gaggtttaga ataagagagc acatcaatag   1560
taaatattaa agggtcaaat atagttttgc agagattgct tcttgttttt ctctgttgat   1620
aaattttcga tcttttgatc tagaagttga ggggtatttt ggtctgagga tttatttgtg   1680
atgttggatg atgtatctaa cttgtagttc ttgttgttga aatttcaggt agtgaagatt   1740
tttgcactgg agggtcaata tacccaaatc ccaaggactc cagtttattc ttgtcccttc   1800
ctcaccacgt tgatgtctat tttcctcctc gaaagaggtc tcgcatcact gctccatttg   1860
tgtttggtgg agaagaagtt gaatcaaaag caaatgtttc tatcgagatt cttccggatg   1920
agtgcctgtt tgagattttc agacggttgt ctggtggcaa agaaaggagt gcctgcgcaa   1980
ccgtttctaa acgatggcta                                               2000
```

<210> SEQ ID NO 148
<211> LENGTH: 1254
<212> TYPE: DNA
<213> ORGANISM: Cucumis melo
<220> FEATURE:
<221> NAME/KEY: misc_feature
<222> LOCATION: (1)..(1254)
<223> OTHER INFORMATION: n=g, a, t or c.
<220> FEATURE:
<221> NAME/KEY: unsure
<222> LOCATION: (1)..(1254)
<223> OTHER INFORMATION: unsure at all n locations

<400> SEQUENCE: 148

```
tcataaatat atatataaaa aaacaaatat tataacctac cttttgcaaa tgataaaatt     60
gtaaagtctc gtgccgataa tgtgttataa aataaaagaa caaagaaact aaataagaac    120
aatgcaacaa nnnnnnnnnn nnnaatagag aagagaggaa gaaggggaaa caattaaaaa    180
ctcaattgta gtgtgactta cacaaatgca acacatatat ctatttatag gacatatcat    240
ggtatatgtt atattatgaa attcaatgaa atgaatgtta caataaagaa ttgaatgaga    300
gttgtatgaa aattgtaacc ttcataaatt atggatatct actcttataa tatatcatta    360
tatttataat gtatactata tgtttgtatt ttaataagaa aattatccca ttggatttgc    420
gatcttagat ctaacctact aaacaaatat tccaacgaag aggaacgaga tgagaacgcc    480
gttctaacct acgcaatatc aatcgtttct tcgctgctac tttacgcctc aagttcctac    540
ccttcaagtt tcatcttcaa cgatcaaccc aacgattaac ccactgcacc accttatctc    600
ttgttggtgt catctaatcc atcttcttcc tgcatcttct gcaaatgctc tcaggttctt    660
tcctctctct tgtgcacaaa ctgatcaccc atgttgttcg ccggaaaatg attcagattc    720
ttcgtatctt gcctgcattg tctttgacta taatatgatt gaaattcact tgttgattgg    780
ttttcaattg ttaattaccg ttggttttgc tgtttagtga tagtatatta tgaggttttt    840
gttcgttttc gggtttttgg atgtgatttc atcctataga atgaagagta tgcaacgtat    900
gctgtcacct tgcgggggaa atggtacacg tggacccgaa atggagctag gttttgatac    960
gtgcagtttg agttttggtt ttgggaggat ttggcattcg ttatatgaat tttgtaatta   1020
actatgccgt ttgattgtta tttataacgg tgcattgctt tttgaggttt agaatttgga   1080
cttaacgcct ctttctattc atggttattg gttttatttc ttcctttttg ttgactgaga   1140
ttggtcgtag aactcgttgc ctgtctatgt tttaatgttg gcctgatttt gaatttctaa   1200
tccatgacta agtatttctt tattgtcttg atatagttga ttgaatcatc aatc         1254
```

<210> SEQ ID NO 149
<211> LENGTH: 2000
<212> TYPE: DNA
<213> ORGANISM: Cucumis melo

<400> SEQUENCE: 149

```
cattttaaat tgacctttca tgaaaaatcg tatgtttttg gtgtgatttt gagtataata     60
aaaatgattt taaccatttg aaaatcactt taaattacac ctaatgggtg actgaggttt    120
tagctttcgt ctttgtttag ctctaaattt gcatggcaag ttttccattc caatgattga    180
tgtggcttgt aatagttgaa atatatatat atatatatga ggtatcaaaa tccccagcct    240
tgtgttaggt tgaatatgga gggagtgggg agttattttt cctgctctta ccccgttcct    300
aattcccacc ttgtttacta tgtgttattg ttattgccat atttactatg tacataatat    360
ttcgattaga aattttattg tttaaccatt agacaatttt atatgtctaa accataggtt    420
```

tgaacaaacc atttagatta tatatatgtt gacaattaga ttgatagggc aattattttg 480
tttatcctaa aaatggtaaa taatgttctt aaacttggtt ctttgtgaaa taccttcaac 540
tttcaaagtt tttaataata ttcttacgct tataaaaaga aaaaaaggat aagttgaaaa 600
aagaatactt ctatgataag ttttagatgg aaactattta ctttttcatt taaaaaatac 660
ttttcaaatt tatgaagttc caaaagtatg acttaaagaa atagttatac ccttattgat 720
aatatacgac aaaaacaacg caatatttcg ttacaaaaat aaatctagct gcattactat 780
cttactttaa agatactctt atcgtctatc taaactacct tactctagaa ttaataatta 840
agttcctttt actttataaa tataacttat tcctactatt agtatatatt tatattggta 900
tctaatagct aattttgaat tttgttccaa aaaaaaaata tcgctgagtt ttgttttgaa 960
gtcttttttt ttttttaaat atatattttc gattaaagct agatgttgca gttgatatgt 1020
agatttaaaa gaaatgtgtg agatcgttta taactatata gaagattaag catttattac 1080
ttcaaaatat atcgttaaaa ttattcacat aaccaatttt tactcatcaa atattatgtc 1140
agagaaaaga aaaacgaaaa agaaaaccta cttcaacgga caaagaagtc cttagttcaa 1200
atcttcaaac ctttatttgt attaaaaaat ggcatataaa ttttttcaat ttttacgcat 1260
tacctgttgc gtgaaaaaca ttgatttaat agaaaagaac tgtcctttca gttttgtttt 1320
tttaaaacca atttcgaaat tcaagaatag aaacaaaact ttaagtctag aggatcacta 1380
aaatctatca taaggctaga aatacatctt gtaatctgca gtaggcattt gccgggatga 1440
caattttctg gtgcttggat taagaaaaaa gaaaaaaaga aaaaagaaaa aaaaatggtg 1500
aggacttaga ggccataatg agtttggcat tgggcccaca gtaggatgag taaattataa 1560
ttgggagaaa atgagcatag ggtgtggagg ggaaaaggag aaggctaaaa cactatcaca 1620
aatcacacag tagaagatac acagaagaag taaccacagc cattcattga gtgagaggct 1680
atccataatc tcatcctctt acccttctca tcattcattc aaagccattc aactcaacat 1740
cccactctta gttaaccaac aaaatatata tacatccttc tcaatttccc ttctctctac 1800
tgctttaatc ttttgcttct tcttcttctt cttcttcttc ttctgctttc tcaataccct 1860
caaccatggc tacggctact ctatcagtag ccaaaccatc tattcaggtt cctccattac 1920
taaacaccat cctctttccc ttccactctt ctttaatttt ttgtatctga taaacattac 1980
tgcattttct tgcatagcag 2000

<210> SEQ ID NO 150
<211> LENGTH: 1680
<212> TYPE: DNA
<213> ORGANISM: Cucumis melo

<400> SEQUENCE: 150
tttttatgaa gggagttgtt attttccttt gggatttgga gggatatgat atatatcctt 60
tttttgcaat ttgatgacag aattctgctt ttagagactt ttcaaactgt ttcgtaatga 120
atttgatggg ttgggggtgg cttagttcaa tactttgtgg gttgaaaatt ttgatttgca 180
ataaatgaaa gccaaaaatg tggggaagct ttcagttcaa gtaagttaag ggaaaactgc 240
agaatatctg gcttgaaata agagatgtct tcgaaggtta atagttttac attgactttt 300
ttaaaaaaaa gattatatta taagtacaaa tatgggtgga tgtgaactta tattattcaa 360
agagactaat ataagtttttg ggcgcttaat attttatatt ttcatttagc agtcaaagat 420
gtataagaaa actttggtaa tgcattttat actagtttat ttatgtagga tgtaggatct 480
atcgaataat acaacatatt tttaaatgat gtgtacaatt gtgaaaaaaa aaggaacata 540

```
cagtattgta gaaactaaaa tattttctaa gatatatcga gatgtaaaaa aaatgaatgg    600
atgtcaattc cagcataact taattgttga actaaaaaca aaaagaagaa ataaaggggg    660
caatggtttg atcctcatgc cccacatgaa agtcaaagtt atgtaaaggt tccgtgtagg    720
atatccttcc tcctaataag gggagatagg attttatgag ggtgccaaca gctcagaatt    780
ccaaattccc aaaataccct cttgcttgaa aatttcaaac tcttctgttt ttgccttgtg    840
taccattcac tattccgatg cgtacagttc attaaccaca caagttctcc ttttgcaggc    900
aggtttagct aaacttattg gacttgctgg agagaccaat gttcaggtaa gatcttattt    960
gttataatga actcacaaac taatttagat tagccaaaga attctgtttc tgaagaaaga   1020
gaggatgaaa atcatctcat accaaatttc tttctttttt tggaattatg tcttcacatt   1080
tattcatttt ccttgtcaac agggtgaaga gcaaaagaaa ctggatgtgc tctcaaatga   1140
agtctttatc aaagctttgg tcagcagtgg cagaactgta agctgctatc taatcataca   1200
aatgacacga caaaaatatc tggtgactta ctctaatagt tgacaaattg gtggcagtgt   1260
attcttgttt ctgaagaaga tgaagagcca acatatgtcg agccatctcg gcgtggaagg   1320
tttgttttcc attcttgatg atttttgtct aatgcttaca attatcatca gtatcaactc   1380
ctcttacttt gttttaattt taatgttatt tcttcttatt ttccaatgac aaaggtattc   1440
tgtggtgttc gatccactgg atggttcctc caacattgat tgtggtgttt ccattggaac   1500
ggtaacatcc ctatgctacc ttctgaatga gatttcaaat atttttggta taatttcttt   1560
ccaataagct gagtgtatga ttgtttgaat atctactttt tcatgtagat ttttggaatt   1620
tatcacttga acgacagcca cgaacctaac ctagaagacg tcttgcaacc tggaaagaat   1680
```

<210> SEQ ID NO 151
<211> LENGTH: 1524
<212> TYPE: DNA
<213> ORGANISM: Cucumis melo

<400> SEQUENCE: 151

```
tatatatata tatataggta atgagtaaag aaatgaaaaa gaatgagttg aagaatcaca     60
cccttaccat tctatttgaa actcgtgagt cttgtagact tttacatgtc ttctccttca    120
cttaatatca ttctggattt tgattatatg tatctttatt tctaaacagc ttggacagat    180
ttattattgt tagaatacct tgaatatgtt ttctggtgct tagaacgatc atacatgggt    240
ttttctaggg ttagaggagt gcgctataca taaactttct agttctagag gcattgctgt    300
aatcttaagt ttaacagttt ctctttaata acaaaaactg ctcttcccct acggtttaag    360
ttttctcctt atcttaacag ttataattat gaaaaatgat ggaaccaaaa caaagttctg    420
ttaaaatttg actaattgat tgaatgaact tttgtttcca agattcttaa tttgtaaagt    480
aataatgttc ttacaaatca ttattttgat gtctgagtta taacccttaa gcttggtggt    540
tcatattcca ttcaggtgaa gaagattgtg agtgaaagct gttcccaaga ggttttagaa    600
gtggcgttaa actccatctc atccctaatt accatcctct cctccatgtc atcgtctacc    660
aaactccatt cttcactttg atggtataag aaagtgaatt agatttggga ttgagcttca    720
aaacatgtat gatgatgtga atatttactc gtgtaaataa tataacatgt tgtattcttg    780
cttgtttctc tttgctcatc ttcgttttgt taagagcaaa gaaaagctta cgagcatgaa    840
catgtgcaaa tttatgaagg tcaatgggct tcgtaatttt ttttccccat tgatttaacg    900
atttatggaa gatggatata gtaaatttag gttaagctgt acaaaaccag agaattttca    960
```

ttatagtaaa tactttacaa ttttcaatta gctacaataa acaccgtttc aaaatctccc 1020
tcatttgcta ccatatttac tattcgatat ttatcatttt ttttattcct gttgtaatgt 1080
ctactatttt tcttttaaac tattacacca caaacacata ctattataat tcaaattaaa 1140
ataatcacta gtataactca actataataa ctcagatgat ttcattccat gaaagtggta 1200
attataaata tttaatatct tatatgataa ggataactat ctatttggtg aaaccaaatc 1260
acaatgatgc agtggtaagt gctttggact ttgaatctct tttttatagt atttcattct 1320
tttttcaacg aagcagcatc atgggccttg aatggaggcc agctagaacg agcccattac 1380
atttgacaga gcatctcttc ggcccatgag cccaaacact attcatcttg ttaaaccacg 1440
aacaaatcga gactgccgag agtgtaagag aattgagtaa tttttttcga gacacaggga 1500
gtttagagag taagtcggag aaca 1524

<210> SEQ ID NO 152
<211> LENGTH: 1851
<212> TYPE: DNA
<213> ORGANISM: Cucumis melo

<400> SEQUENCE: 152
ttgggtcgtt acaatatcac tgtttaaact taagtttatt tttatttatt tttttatttt 60
ttaatctttt tcccttcttc ctttcatctt ccattcattt atacaaaaat aaataatgag 120
aaaattactt ttcacttttg agtttaatta tttttaagtt ctaaaatcta cattttaatc 180
tttaaattta aaaaaaaaag gatttacaag attcttgagt aatttattat tattattatt 240
ttgaacgtaa atataacctt ttacaaaatc taaatgagtg tttgggacaa tgagttgatt 300
attataagta ttgaattata ataatttttt gtggggtata gactatttta atttgaagaa 360
taataggtac gtgtttgaaa tataaattat gttagttggg aaagaaaata gtaaatatcg 420
tagaaaaaaa taaaataaat gaacaataag aatataaaat atggtaataa attgggactt 480
tgaaataatg gtaataatta attaattaat tgaaagctac aaaacaatgt tcacttcatt 540
gctatagttc taaacagact aacaatctca atcaatgacc taatgggtca ggccattata 600
ttgggctcaa atagattttg gcaaaacgaa tcgaaagccc aatggggcct atattatgta 660
gggccgaaat gaatttcaac gaaaggaacc caaagcccaa taggcccaaa ttgagactta 720
caaaggcgca tgttagcatg aagagagaat tgaaagctta aacagcgcca tcacaaaaca 780
tttgcatttt cgtgttgaaa tcgcatttgg gccgtaaacc aatgaaacac aaaacaaaca 840
aatcctggaa tagcctcaac ggttctggaa gaagaagaat cttctggaac ctccaatccc 900
acaataaaaa tcaaacccta aactcttaca ttcagctctt tgcttacctt atcccaacaa 960
accttcacca acgctctacc ggaactaaaa cccctccgac ctcccacttc cgacttacga 1020
cctctgttgc ctgaacatgg cgtctgccaa tgctctttct tccgcttcta ttctatgttc 1080
ttctcacaag gtacttcact tataaccccc tcatttcttc cttgtatttt tcacaattcc 1140
tctttggaaa tgatgatatc tagattgtag tagttgggat tgtatgttag gtagagattt 1200
tgtggagtta gctgagagcg gctgagaata ctaatatatc gtttccagta gcttacgttg 1260
cgtttttcta atgttgcaga gcttgagaaa ggtgaatcaa acgcagaaca acagagtaaa 1320
ttacagacag gctggtagta gatttgttgt gagagccact gcaaaggaga tagcattcga 1380
ccagagttct agaactgcac ttcagtctgg gattgataag cttgctaatg cagttggttt 1440
gactcttgga cctaggggta actttctgtt tatatttatt tatgaattgg ttagtattgg 1500
atgttgttct aatattgaaa tccctacagg atatattcat cacatttata gattcgtgtt 1560

```
atggttatgt tgagaaattt gggttcttca cataattctc aatcttgttg tgatattttg   1620

tatttgaagg gaggaatgtg gtgttggatg agtttggtag tcccaaagtg gttaatgatg   1680

gtgtgacaat tgctcgggca attgagttac ctgatcccat ggaaaatgct ggtgcagctt   1740

taattagaga ggttggtttt ttatactttg ttatgaagca aaattttctc atctatcgat   1800

tattgaagtc ttattagttc ttacattgcg ttgacaagta ttctatatgt c            1851
```

<210> SEQ ID NO 153
<211> LENGTH: 2000
<212> TYPE: DNA
<213> ORGANISM: Cucumis melo

<400> SEQUENCE: 153

```
actaattaat agtaatttgt atgggatata tgtatatgtg tgtataacag gaactacaga     60

gatagagatt cactttctag aaataaagtt gactgccatt ggagtttatt tggagccttc    120

agttgtggag catttgcaac aatggaaggg aaaagctgct aaggacttag tggaagatga    180

tgacttcttt caggctattg tttctggtat ctccctagtt atcctatttt taactatact    240

atctcatcac attcctaaat gtgaattact tgacgatctg ttcaaacata tatatttcat    300

tgtttgatcg taatgtttca tatttatgat gtttcatata ctacctcgtc acacgtgcaa    360

aggatttaga tccgttcaaa catatttcat tattggatcg taatgtttca tatctatgat    420

gtttcttata ctatcgcatc acacatgaga tccattcaaa catatctcat tgttagaaag    480

attatacatt atttcaattc aaatagctct aaccaatgac aaaattagat tcgtcccgtt    540

tagcttattc tatatatata gatagataga tagatagata gtatggatat gcttgtgata    600

agtgtttttt tcttcttttt tttttctttt tttgtttttt ttctttttttt gtcactttct    660

aaattatcta tctcacagtt agctagttgg cggggtgatg acttttggtg tgtcagtcta    720

gtgagaagtt tgggggttat ttttatttc gaaagcttcc taattgaatg acttgtaaag    780

gttaatgttt atgtttttgt acatgttttt catgaactat tggttttaca agagttacaa    840

ttctatttat ttgtgtaaga aagatcatat cacattttta cccctggtgt gttcgtttta    900

tgttcttgat ttgcttttttg tttttcaata atttacgggg aaagagagaa taaaattttc    960

tttctccgat ctccgcattc aattttttttt tttttgaaag gtgcattcaa ttttttttgtg   1020

cttattaaat attcacttac atcttttgtt ttgtttattt ttttattttc atctttctta   1080

tatgaaaata aaatattttt tagtacaaca atagaacctc ttgttaccat tgaaatgaat   1140

tacaggaaat taaaactttt actttttatt tgagagaatt aaaagagtag tttttaaata   1200

taacaaaacg actttcgcaa tagatccaga tgatcattta ttaacaattt tctaattaaa   1260

attgttacta aattttaaca attattaaaa aatattaatt gaaaaacacg tgtatatata   1320

taggaacatt ttcaattata gccaaaagtt ataattattt actctataaa attctttaga   1380

gtctatttaa cctttttgtt aaattttgtt aatagtttta ctttgccatt cataaaaatt   1440

tctcatatta tatacagtga gaattttata agtctcaaaa gtcaaagatt tgattaaaaa   1500

aaaaagaaat gaaagcatat ctaaatatat tatttatact ttgaaaatta cttccgaagc   1560

aaaatgtaaa accgttataa gtgaacttag aatccaaaaa catatattaa attaagttta   1620

aattatataa caacaccttt ggattttgtc attttctaaa ataccttttta tcatttcaat   1680

aattgtaaaa tgagtcctaa attttcacaa atgtttcaaa aatatttgga ggagacaatt   1740

ccttgagaat ttcaaagata tattaaagag gacgtattga cccaaatctt ttgttctatg   1800
```

```
tcactatgat caccctttta tatcacaatt tatttccatc tacaattcta aagaatttat   1860

aatttaaaag tagtttcaaa atgtttctaa attttcgagg gtaatatttt aacttttgga   1920

agtacggaaa gttaatcaaa tctttgtctc aaaatctcaa ctaataactg gaattgggaa   1980

agctaaagtc tagaccttaa                                                2000
```

<210> SEQ ID NO 154
<211> LENGTH: 1288
<212> TYPE: DNA
<213> ORGANISM: Cucumis melo
<220> FEATURE:
<221> NAME/KEY: misc_feature
<222> LOCATION: (1)..(1288)
<223> OTHER INFORMATION: n=g, a, t or c.
<220> FEATURE:
<221> NAME/KEY: unsure
<222> LOCATION: (1)..(1288)
<223> OTHER INFORMATION: unsure at all n locations

<400> SEQUENCE: 154

```
cgagaagtac ccggcgttgg tcaccggatt tttcttcttc atgtggtggg tttaattgtt     60

ggtcacgtgt tttgcacggc gaaggccggg tggtaattat tacgttgcgg caagtttgag    120

cttggttgtg tgaaattacc gtgttgtcct ttctgttttg taggtacttt ttgaacgtga    180

ttttcaatat cctcaataag aagatatata attacttccc ctatccatag tatgtatttc    240

caatttacat tttcatccct gtatttttct tcttcttctt cttnnnnttt tttttttaat    300

attgttatta atatttgttt acgttccagt tttgtgtcgg tgatccattt agttgttggg    360

gttgtgtact gtttgataag ctgggcagtg ggtcttccta agcgagcagt aagtcaactc    420

tttctatagc ccaatatgcc aattttgtct ttttctttca ttaaaattgt tatttttaac    480

tttttcatac ccaatttagt ttttttagtc tgtttattag tcttgttttc ttcaaattta    540

gtagtattgg tagtctaatt ggtagggctg ttttgaaagt aattacctaa tataatgagt    600

atttagattg agacagtact atagtctaaa cgatgtcatt gcagttttga ttgaaatttt    660

ttctccttta tttatttcga aaatgacaat ataacttctg taatctttgt aaccatgttt    720

atttgaagct acgttgtaaa ggggaaaaag aaaaggaaag tgtaaaatgg tcaaataaat    780

tatattttta agtgaataga ttatataatg tgcggtaaaa tatagcactc acaagtaaat    840

gcaacttagt aatctaaaga ttgaactatc aattcatgaa ttttttttata attagcatgg    900

ttttctatag tttttgggag tctgtttttc aatgaaaata ttgccagtat ggtaatcttg    960

tatgacaatg tattttctaa agtatggata taattaaatt ttctttaatt tatcggctta   1020

aacttttcgt tgtactaaaa atctaggata ggacgtttaa tatttgaacc tttgtaatgc   1080

catttaatca ccgattaata tagatctaac tattgaaact tcttcaaaag ttttaatcca   1140

acggatggct aagagtgtta aaatattgat acaattaaat ttatcgtagc ttaagctttg   1200

acagtgtcaa aagctaattc agttattttc tctgcccttg gtataagggt aactctgttc   1260

tctctatttc acacaagtga ttgctaac                                       1288
```

<210> SEQ ID NO 155
<211> LENGTH: 2000
<212> TYPE: DNA
<213> ORGANISM: Cucumis melo

<400> SEQUENCE: 155

```
ttatgtttta ttaactccat agttttacta accccatttc acgggaaagt acaataaaac     60

atttgtgtta aaaaggagtt gtttgtatag atcgaataaa cattttgtac taattccaat    120
```

catattacca aatgttttaa gagcatgcgt tcttgtgtgc ttgaataggg gtgatcatca 180
attgagtggc gtcagattta aatttaaagt ggcaccaatc atcgacttgt tggtttagat 240
cgatcggtag ttgttgtttg tgggacaatc atagttatca tttttctcct tctatatgaa 300
taatagtcaa ctagatagaa ttgacatttc ttagtattaa aaaaacgacc actgacctgt 360
ctatatcact aaactgcttg acctaagtga gtttggttgg acttgattgc ttcgttgtgg 420
tctaattcac ttaaccctac ttgaaagtaa aggtagaata taacatgatt ctttccaaat 480
tggcaagttg tgacttgatt tatgcatgca cgaagattct tccactctcc acctaactag 540
tactcgatca cattggaaaa tggatctgtc ccgtgaagga tcgcaatatt acatgccttc 600
ctactttttt cttttcttcc accaaagaaa aagaaaacgg gacacacaat aactatacat 660
tatcaataat aattaaacga atcatcccac caaatgtaaa ccatgaatat tgaaatcatc 720
atgttttaag aatcatttta ataattatgt tatttcattg ttttatatag aacacaccgt 780
tcatgaaatc aaacaaagag agagaaatta taattttgta acaaattacc aacattcttt 840
ttctttctat ttttcataaa tgagcatatg tttgtgtata tatacatact gttatttgat 900
ctccacattg ttgaacaaaa aagttggtgt tcttgaaaat agctatcacc gaaaatacgt 960
catatactgg gttgttatgt accaaggccc agaagaaagc ccaaaatcac cggcccatga 1020
gcagtgaaca aataattggg ctaaaagccc aatatacgtg atgatgggcc aacccagaga 1080
agtttatagt tatgttatta tagaattcca gatcagggag tatcgaaaca aaagcctcca 1140
ttgtcctcgt tctcttctcc ttgtgctctc tctctctctc tcttgctctt ttctctttct 1200
ctttctctcc gacgacaggt tcctgaagct cgaccagcca agggcattga tctaggtgag 1260
tccgctttca cttttccact ttcctctgcc gtttttcttg tcatttccaa ttctccattc 1320
tttgttctgg atttcacttc tttacttcgt cgttgattag aagataatag tgagatcgaa 1380
ttctatgtct cgcatacctt cagtttcaag gaacaagaca atgattcaac cgcgccgtcc 1440
acgttatgga tagagggttt tgattctcac ctttatagct gcataacacc gttcttaggg 1500
ttcggacctt tgaatctgcg atatttctca cactgttttg gacgttttta ccgttttcct 1560
atggttcttt agccttacct tatcttgcct tcagatcttc gattgcggat ctgattcgtt 1620
catttctact tgttactttt tcttggaagt cgaggattat aaatcaacaa caaagcattc 1680
aaaatctcta gtgcaattag tgttttccat ctagttattg gagatcgttt gtagctttga 1740
ttttgtccac tttcttattt tgaacgtctg gaagacgttt tatacatgtt ctttgggtaa 1800
agttgcgttt gggcactgtt cttcacctct gggttttcgt tcttatgcta tgtttcatga 1860
tttcttttga tatctttgtt attgtttccc catcatcgag tatctgattc ttattcggaa 1920
gccgtcttct tgaagctgcg aaccggtttt ctttttctcc ctcatcaagt ctttaatttt 1980
acaggaaagc gctgaataag 2000

<210> SEQ ID NO 156
<211> LENGTH: 2011
<212> TYPE: DNA
<213> ORGANISM: Cucumis melo

<400> SEQUENCE: 156
ttgttagagg agttagcttt tcagggagtc ggttacaact tacaagacag acaaccatac 60
tgtacaatca atcactactg cctcaaagtc gaaaccattt aataccagtt gagcctcatt 120
gtgactgcat aattttgacc cctaccacga ggtaatttca gttcaaatca attgtatctc 180
tcttctggat atcagtcaag aatctcatgt tctcaagtta tagtacattg ataattactg 240
tgcattttta ttaatttatg agttaaaatc ctgctgatta attcaactaa aggaataaaa 300
tagttattgg catttggatg agaatagaat gtgaatccca tcattcatcg ctagattgga 360
ccgtaattat aagtgagagg gagaaacttc tgttgctatt cccttttat ttcttaattc 420
atttataaat tgtttttagg ccttttatat atatatattt ctaccatttt tacatttaaa 480
attcttttaa ctttattatg tatggactca aactaacaag ctttatttga taaaattgtt 540
caaactatta tattagtttt atatttgtaa accataaaac aaatccataa aattccacct 600
gcatcactca ctcatgttgt tgaatggtac gaaataaaca atacatgtga aagatgaaaa 660
taagaattgt tctcttatta aatctaaaat ctagattttc tttttagtac atttaacact 720
tcaatgaaag gtctaaaaca ttattgaatg acgtcacgaa ctattacaaa agattattcc 780
gatttatctc aaaaggggtc tatttcacta attttggtgt cccacatctg taaagagaat 840
tttcgtgata tgtgtagata tttaaatata attgaattcg atgaaagcaa agcaagaatc 900
gatatccgta gttattttga tatagatcgg tgataaataa aagacaatat gcataaagtt 960
tgtgggtaca gagtcggcta gttgcaatga ggggtatggc cccaagactt ttccccaacc 1020
ccaacggtca attaatcacc ccaatggggc atcgaatctt ccccaccatt ttccttttct 1080
tcgccgactc ttctacccat ctcttttgcc gactctttct cacaggtttg attaaatccc 1140
attcatattc agatacacta tttcaaaata ctcgcaaatt aatttgtttt tttaaatatt 1200
ggtataataa taaaattaat tataaattgt gacctaaaaa gtactttgtg gaagagggga 1260
tatagtctgt ctaatatatt attgattaaa tatataatag aaccataaat gcaaaccact 1320
agaattgtta ataaaaatca acgctctttt aagtctttcc atagaaagaa aggcaaagac 1380
gcgcaacgtc tagaatttc tttataacgg aagctaactc tgttataacg gccgtccaca 1440
taatatggta gatttaaaat gacgtcagca tgtcgcttct aaatttgggt ccaaaggggg 1500
gattcattta tagggaaggg aaacggcaaa tgcaagcata gtgagtaaat acgtggcggc 1560
aaagtaatgg ataattctgc ctctgccgtg acgacattgc ccttccattt cactataaat 1620
acacctcctc tatccctcga tttcttcgca attgaatttc tcttctcatc tctgtcgtag 1680
caaaccaaat cgatttcttc aaaggtattt cttcctttcc ttttttttt ttttttttt 1740
tttttaaatc atgttgttca aactttgaga gatgaaatga ttaggggctt tcaaagtggt 1800
tttcgtttga tatgtttctt agatcgatag ggtttagaat cgagcatcct tgtaggtatc 1860
ctgaggtttg gtggttggat ctgcttaatt tttatgtggt tgcatggaaa attgggattt 1920
ttttttcta attacgtgat tctggaaata ttgatctgtg gttcagatgg aattgaatct 1980
gatctttctg ttttgttctg tataggtggg c 2011

<210> SEQ ID NO 157
<211> LENGTH: 1698
<212> TYPE: DNA
<213> ORGANISM: Cucumis melo

<400> SEQUENCE: 157
ttgttagagg agttagcttt tcagggagtc ggttacaact tacaagacag acaaccatac 60
tgtacaatca atcactactg cctcaaagtc gaaaccattt aataccagtt gagcctcatt 120
gtgactgcat aattttgacc cctaccacga ggtaatttca gttcaaatca attgtatctc 180
tcttctggat atcagtcaag aatctcatgt tctcaagtta tagtacattg ataattactg 240
tgcattttta ttaatttatg agttaaaatc ctgctgatta attcaactaa aggaataaaa 300

```
tagttattgg catttggatg agaatagaat gtgaatccca tcattcatcg ctagattgga    360
ccgtaattat aagtgagagg gagaaacttc tgttgctatt ccctttttat ttcttaattc    420
atttataaat tgtttttagg ccttttatat atatatattt ctaccatttt tacatttaaa    480
attcttttaa ctttattatg tatggactca aactaacaag ctttatttga taaaattgtt    540
caaactatta tattagtttt atatttgtaa accataaaac aaatccataa aattccacct    600
gcatcactca ctcatgttgt tgaatggtac gaaataaaca atacatgtga aagatgaaaa    660
taagaattgt tctcttatta aatctaaaat ctagattttc tttttagtac atttaacact    720
tcaatgaaag gtctaaaaca ttattgaatg acgtcacgaa ctattacaaa agattattcc    780
gatttatctc aaaaggggtc tatttcacta attttggtgt cccacatctg taaagagaat    840
tttcgtgata tgtgtagata tttaaatata attgaattcg atgaaagcaa agcaagaatc    900
gatatccgta gttattttga tatagatcgg tgataaataa aagacaatat gcataaagtt    960
tgtgggtaca gagtcggcta gttgcaatga ggggtatggc cccaagactt ttccccaacc   1020
ccaacggtca attaatcacc ccaatggggc atcgaatctt ccccaccatt ttccttttct   1080
tcgccgactc ttctacccat ctcttttgcc gactctttct cacaggtttg attaaatccc   1140
attcatattc agatacacta tttcaaaata ctcgcaaatt aatttgtttt tttaaatatt   1200
ggtataataa taaaattaat tataaattgt gacctaaaaa gtactttgtg gaagagggga   1260
tatagtctgt ctaatatatt attgattaaa tatataatag aaccataaat gcaaaccact   1320
agaattgtta ataaaaatca acgctctttt aagtctttcc atagaaagaa aggcaaagac   1380
gcgcaacgtc tagaattttc tttataacgg aagctaactc tgttataacg gccgtccaca   1440
taatatggta gatttaaaat gacgtcagca tgtcgcttct aaatttgggt ccaaaggggg   1500
gattcattta tagggaaggg aaacggcaaa tgcaagcata gtgagtaaat acgtggcggc   1560
aaagtaatgg ataattctgc ctctgccgtg acgacattgc ccttccattt cactataaat   1620
acacctcctc tatccctcga tttcttcgca attgaatttc tcttctcatc tctgtcgtag   1680
caaaccaaat cgatttct                                                 1698
```

<210> SEQ ID NO 158
<211> LENGTH: 313
<212> TYPE: DNA
<213> ORGANISM: Cucumis melo

<400> SEQUENCE: 158

```
tcaaaggtat ttcttccttt ccttttttt ttttttttt tttttttaaa tcatgttgtt      60
caaactttga gagatgaaat gattaggggc tttcaaagtg gttttcgttt gatatgtttc    120
ttagatcgat agggtttaga atcgagcatc cttgtaggta tcctgaggtt tggtggttgg    180
atctgcttaa tttttatgtg gttgcatgga aaattgggat tttttttttc taattacgtg    240
attctggaaa tattgatctg tggttcagat ggaattgaat ctgatctttc tgttttgttc    300
tgtataggtg ggc                                                        313
```

<210> SEQ ID NO 159
<211> LENGTH: 2010
<212> TYPE: DNA
<213> ORGANISM: Cucumis melo

<400> SEQUENCE: 159

```
tagaaaaaaa ttgaagatct tcttaatgct aataataaaa gcatatataa aaaggcttca     60
```

```
tattacacaa gcatcttaaa accaaaccga acttgatttg aaattatccc actaattctg    120
tagatttcac caaagtcctt aacctttata ctaacatctg catttgactc tttcatttga    180
cctccaacat attctttctc attttccttc cattcaccac aaaaaccaac aaatacaaaa    240
aaccacaaat acatagaaaa ttaataaaaa aatcaaaatt tcgagatgaa atcattataa    300
actcatccga taactttgag atttgaaacc ttacactata taaagaaact catccgataa    360
ctttgaattc gcatcgaaat tacgtaagtg aagacgaaaa tgtaaatgat tagatgcgaa    420
taacaaaaaa aacataattt ctaaacgtaa aacactatat tcaccttatt atacttgatt    480
attttggaaa agtatgaaat ttgagtgtgg gagaggagcc aaagaattgg aaacttgtta    540
ttaggagtcg ttatgaaaca ttttcaacaa gccaatattc tttcacatac tataatgata    600
tacatagaaa taatacaata atatttttga aattgaggca tttttgtcgt aatttatcta    660
aaaatgtcag ggtagattca tcatgtatac aaatctctcg ctatcaaaac tatataaaaa    720
tcttgtgaat gatttcaatc gaaatggacc gagaaaaaac atcgtaacca cctctaaaat    780
cgataaattt gtttcaattt caaatcccta aaactaaagg tgctactttg tacaatttcc    840
cctgattagg gtgctaaagt taaaccctaa ataaaggtgt gtacgtttcc ggaagtttct    900
agaatcccca gcgaagttct ccaaatcgtg gcttgcagac caaggacccc cattaaaatt    960
cgtttcttcc tctaaacctc ctcccttaat tttggcattt tggtattttg gctcctataa   1020
attcaccccc tccttatccc taatcctttg tcttccaaat tttccttcaa agcctgcttt   1080
tcccatttcg tcgtgctttt tcttcatcta aaggtatatt tcagttctag ttttctttct   1140
ctgttgatct cttggatttg agggacgttt gaagttggct ttgtttaatt ctttgttatt   1200
caatctcttt ttttgttaga gttgttgttt aatcgtttcc cttgttgttt ttctcccttc   1260
tagttcgatt ttagaacgct ttttgtgggt tgattttaat ttctccgttt tcttacatct   1320
ttcacaaaga aacgattgaa atcgtgtttg tttttttttcc cacggcatac gttattagat   1380
cttgtagata atgatctcaa tctattgttt agtttttgca aataagaagt tggtttttta   1440
tctccaactt ttatatattc gattcgatga gatgttctac accgttagga tggaaccaag   1500
aagtgaggta agggtgtttg attgaaaaat tgaactgaga agttaaagtt ccttcctaac   1560
tttttaatgg attgtataat tcgttcaatt ccttgtcgtt ccatttttat ttctgtttcg   1620
tttttcgtgt tgctgcgtat cgcttccctt gttgttttcc tcccctattg attttgcgtt   1680
tcttggagtt tctctgtttt ctctcttcat ttttctacaa aaatcaattc tatttttatt   1740
cgttttcaat tcccgagctc cttggaatgt tatccttttc tcctgtgtaa ataagaaccc   1800
gtattcaatc ccagttcata gtttggcttt cccaaataag agcaaaaaga ttgtactgag   1860
aagttgaaga tttcaaaatt ttgtacatga tttcttctaa tttatcaatt tgattggact   1920
ttttgtatat agatttggtt cttgagctat ttatgttatg acgttttcat attgaggcca   1980
tgcgttgaat tggtttctta acaggtgggc                                    2010
```

<210> SEQ ID NO 160
<211> LENGTH: 1107
<212> TYPE: DNA
<213> ORGANISM: Cucumis melo

<400> SEQUENCE: 160

```
tagaaaaaaa ttgaagatct tcttaatgct aataataaaa gcatatataa aaaggcttca     60
tattacacaa gcatcttaaa accaaaccga acttgatttg aaattatccc actaattctg    120
tagatttcac caaagtcctt aacctttata ctaacatctg catttgactc tttcatttga    180
```

cctccaacat attctttctc attttccttc cattcaccac aaaaaccaac aaatacaaaa 240
aaccacaaat acatagaaaa ttaataaaaa aatcaaaatt tcgagatgaa atcattataa 300
actcatccga taactttgag atttgaaacc ttacactata taaagaaact catccgataa 360
ctttgaattc gcatcgaaat tacgtaagtg aagacgaaaa tgtaaatgat tagatgcgaa 420
taacaaaaaa aacataattt ctaaacgtaa aacactatat tcaccttatt atacttgatt 480
attttggaaa agtatgaaat ttgagtgtgg gagaggagcc aaagaattgg aaacttgtta 540
ttaggagtcg ttatgaaaca ttttcaacaa gccaatattc tttcacatac tataatgata 600
tacatagaaa taatacaata atatttttga aattgaggca tttttgtcgt aatttatcta 660
aaaatgtcag ggtagattca tcatgtatac aaatctctcg ctatcaaaac tatataaaaa 720
tcttgtgaat gatttcaatc gaaatggacc gagaaaaaac atcgtaacca cctctaaaat 780
cgataaattt gtttcaattt caaatcccta aaactaaagg tgctactttg tacaatttcc 840
cctgattagg gtgctaaagt taaaccctaa ataaaggtgt gtacgtttcc ggaagtttct 900
agaatcccca gcgaagttct ccaaatcgtg gcttgcagac caaggacccc cattaaaatt 960
cgtttcttcc tctaaacctc ctcccttaat tttggcattt tggtattttg gctcctataa 1020
attcaccccc tccttatccc taatcctttg tcttccaaat tttccttcaa agcctgcttt 1080
tcccatttcg tcgtgctttt tcttcat 1107

<210> SEQ ID NO 161
<211> LENGTH: 903
<212> TYPE: DNA
<213> ORGANISM: Cucumis melo

<400> SEQUENCE: 161
ctaaaggtat atttcagttc tagttttctt tctctgttga tctcttggat ttgagggacg 60
tttgaagttg gctttgttta attctttgtt attcaatctc ttttttgtt agagttgttg 120 tttaatcgtt tcccttgttg tttttctccc ttctagttcg attttagaac gctttttgtg 180
ggttgatttt aatttctccg ttttcttaca tctttcacaa agaaacgatt gaaatcgtgt 240
ttgttttttt tcccacggca tacgttatta gatcttgtag ataatgatct caatctattg 300
tttagttttt gcaaataaga agttggtttt ttatctccaa cttttatata ttcgattcga 360
tgagatgttc tacaccgtta ggatggaacc aagaagtgag gtaagggtgt ttgattgaaa 420
aattgaactg agaagttaaa gttccttcct aactttttaa tggattgtat aattcgttca 480
attccttgtc gttccatttt tatttctgtt tcgtttttcg tgttgctgcg tatcgcttcc 540
cttgttgttt tcctccccta ttgattttgc gtttcttgga gtttctctgt tttctctctt 600
catttttcta caaaaatcaa ttctattttt attcgttttc aattcccgag ctccttggaa 660
tgttatcctt ttctcctgtg taaataagaa cccgtattca atcccagttc atagtttggc 720
tttcccaaat aagagcaaaa agattgtact gagaagttga agatttcaaa attttgtaca 780
tgatttcttc taatttatca atttgattgg actttttgta tatagatttg gttcttgagc 840
tatttatgtt atgacgtttt catattgagg ccatgcgttg aattggtttc ttaacaggtg 900
ggc 903

<210> SEQ ID NO 162
<211> LENGTH: 1235
<212> TYPE: DNA
<213> ORGANISM: Cucumis melo

<400> SEQUENCE: 162
aaattttaat aattaaaatg aacaattttt caagagtaat agagtttgag agatgtcaga 60
gaagtttgag gaagaagata acaagtggga gaagagaata agtttgttgt gtgaaagaga 120
aggggaaatt tcattcaagg gtatattgaa ctttttactc aaattttgta agtctatttt 180
ttccgatcaa tcctaaaatc acacacaccc ttaaaaaatg gattatattt ggcaattttc 240
catgataaac tcatttttaa tttagagtta ttttttcaac gagatattaa cagttttagt 300
tcatatacta attgtaagaa tagtttcttt taagttgaat agaatttttg aaacttttaa 360
tagttcaaaa ggtatttttg aaacaaaata agaatgtttt tgaacttttt ataaaaagaa 420
ttgagatttt tttgaaattt ttgataaaga gaaaagaaaa gaagaaagaa aaaagaaaaa 480
caagtttgta gaactccgtg ggaaaatcgt cgagggccct gtgaaggaat tttgaaatta 540
taatgagggt attttcgtca acaagggaat ttagacatcg tatataagca tcctcaaacc 600
ctataattaa gcccttcaat ccaattgcca ttctccatct ctcgccgcaa gggtttaaga 660
gcagcttctc tcctcaggtt ggggtttccc cctatcttct tcattcttcc tcttctcgat 720
ttctttcttc tatttgctcg atagtctctt atttcttgag cttttgctgt ttttctcctg 780
tacatcctaa catgaattat aacttggttt tgattttgtc ttttacttct gtattaaaca 840
acttttctta cccttttatt cttctcttct tcttcgtgtc cctgcccttt tgtttttatg 900
ctaattttat gtttctgttt atcaatctat cgaggcgtga cctgtcgttc ttccaatagc 960
gtagatctgc acttaatcta ttctagctga ttggattggt cgtttttcgt ttttttaatt 1020
tattttctct gttctagttc cgataaattt ttttatatat aattaacaag ttctccagcc 1080
aaaagggtta atattgcgtt ggatatttta atttttacgt tatttagatg tgtgaatcta 1140
ataaaattag ggttattcat aaatttcagt aatgatattt tggttatctg ttcttgctgt 1200
tcctgtttcg cagttctttt acctaatatt caagc 1235

<210> SEQ ID NO 163
<211> LENGTH: 617
<212> TYPE: DNA
<213> ORGANISM: Cucumis melo

<400> SEQUENCE: 163
aaattttaat aattaaaatg aacaattttt caagagtaat agagtttgag agatgtcaga 60
gaagtttgag gaagaagata acaagtggga gaagagaata agtttgttgt gtgaaagaga 120
aggggaaatt tcattcaagg gtatattgaa ctttttactc aaattttgta agtctatttt 180
ttccgatcaa tcctaaaatc acacacaccc ttaaaaaatg gattatattt ggcaattttc 240
catgataaac tcatttttaa tttagagtta ttttttcaac gagatattaa cagttttagt 300
tcatatacta attgtaagaa tagtttcttt taagttgaat agaatttttg aaacttttaa 360
tagttcaaaa ggtatttttg aaacaaaata agaatgtttt tgaacttttt ataaaaagaa 420
ttgagatttt tttgaaattt ttgataaaga gaaaagaaaa gaagaaagaa aaaagaaaaa 480
caagtttgta gaactccgtg ggaaaatcgt cgagggccct gtgaaggaat tttgaaatta 540
taatgagggt attttcgtca acaagggaat ttagacatcg tatataagca tcctcaaacc 600
ctataattaa gcccttc 617

<210> SEQ ID NO 164
<211> LENGTH: 54
<212> TYPE: DNA
<213> ORGANISM: Cucumis melo

<400> SEQUENCE: 164
aatccaattg ccattctcca tctctcgccg caagggttta agagcagctt ctct 54

<210> SEQ ID NO 165
<211> LENGTH: 545
<212> TYPE: DNA
<213> ORGANISM: Cucumis melo

<400> SEQUENCE: 165
cctcaggttg gggtttcccc ctatcttctt cattcttcct cttctcgatt tctttcttct 60
atttgctcga tagtctctta tttcttgagc ttttgctgtt tttctcctgt acatcctaac 120
atgaattata acttggtttt gattttgtct tttacttctg tattaaacaa cttttcttac 180
ccttttattc ttctcttctt cttcgtgtcc ctgccctttt gtttttatgc taattttatg 240
tttctgttta tcaatctatc gaggcgtgac ctgtcgttct tccaatagcg tagatctgca 300
cttaatctat tctagctgat tggattggtc gtttttcgtt tttttaattt attttctctg 360
ttctagttcc gataaatttt tttatatata attaacaagt tctccagcca aaagggttaa 420
tattgcgttg gatattttaa tttttacgtt atttagatgt gtgaatctaa taaaattagg 480
gttattcata aatttcagta atgatatttt ggttatctgt tcttgctgtt cctgtttcgc 540
agttc 545

<210> SEQ ID NO 166
<211> LENGTH: 19
<212> TYPE: DNA
<213> ORGANISM: Cucumis melo

<400> SEQUENCE: 166
ttttacctaa tattcaagc 19

<210> SEQ ID NO 167
<211> LENGTH: 2003
<212> TYPE: DNA
<213> ORGANISM: Cucumis melo

<400> SEQUENCE: 167
cagtgtgctg gaattcgccc ttatccaagg agattaatgt cgagagatta ttatcgaggt 60
ttgaatttat tttgtccaat catatgattc caagagctga ccatcaattc aacagaacat 120
gaaccggaac ctcataccta ttgtaatggt tcacagcatc ctaatacaga acatgaaccg 180
aaacctctta cccattgtaa tggttcacag catctttata cgtattatag gtagtaccat 240
tgaagatgca tttaaatgct gtccatgctc tgttctctaa aaagttggac ttggacttgg 300
acgtcagctg aaagtatgaa atgcactgta gccaacgaag ctatgttttc aggcttcaac 360
atggttttag gaaagtggag gctctttggt tgaagggttg aatgaatgct tttctaattc 420
cagcatgatc ttcaaatttc gacacaaaaa gcttaagtat tttgttccgt tattctttta 480
atccttgtat tgttatatat tcttttctct gaactgaatg tacgatgatt gcaggggtcg 540
agagcaagtc cgatataatg aaacacgtaa ggacgtgatt gaatgaaaaa ctatgagcag 600
agatacaaag tctaacttac gggatgaacg atgagaggtt tgaccaagag ctgtgacgcc 660
tgtatatttc aacaaaagtt gatgactaac atcacatgtc agagtaatca aagaaatgca 720
gccgcacata tatatatcta tatatatatc gagttttttt tttttttttt tttttttttt 780 ttttttttatc taatatattt taatctattt tcctctgccc tcctccccct cctcttcccc 840

-continued

```
caccccttctt ctgcacatag tagccaagga ttgatcggtt tcttttgatt cggggggaaa    900

atgttgtaca atttttgctt ccatagaagc ttgaaagttt tgcagattat gttgtaaaat    960

taccccttgtg tactcacact agttcttctc gtggaaactt atattacaat ggttgagttt   1020

taaggggcat attcacactg gtaactacca ttttctaatt tatgaatgcc gagtttctct   1080

ccatgaaaga cctttcaaat gccctttcct ccgcggtgcg tttgttgttg taaatgtgca   1140

gtgtcgttgg atacacgatt gtgtgaaagg gaaaagggaa tacgattaac tcttaaattc   1200

aacccctatc tccatcagta tcaatcacat ttcagcaact agctcttgaa taacattgag   1260

attcttgttt aatccacgta ctactactac tattactact atttgacagt tgatatctca   1320

aataacatcc atatttatca aattggtatt ttaaggactt ttaatttctt cgtacatatt   1380

tcattataat ttaactactc tgaccatcat tgaaaatttc acaaagaaga cattttaaat   1440

tgaattgagt tgaattaagt tgatataatg gttgaacgtt ggatttaatt tataatttag   1500

tggtgtatgg gtccattgta ataattctta aaaaaaatat catattctga attctaaaga   1560

accatctaag accaaaacta aggggtcacc aatgagtatg gtaaagtcaa caaagtttgt   1620

ctacttttct tatccttatc atcaagagtg caatatgata tcaaagataa attgtacgtg   1680

ggcgtcatcc attgggtaag accaagaagc aaaatatcat agagaagttg ttttagtagc   1740

cataggaagg aaggaagcaa aataataata tagatttgaa attgtggatg ataaactgcc   1800

aaatgggaat tcaaaataaa ctaaataaat aaaataaaaa gagaaatctt gggagtttcc   1860

attttagcca atgaggaaac agatagagat ctcatcaaga taaggaccct attctcttct   1920

tcatctataa aacaaaaaca aatcaaaccc tcatttcact cattcaaaac aaaaagtact   1980

ccaaagtcaa actaacaaat acg                                             2003
```

<210> SEQ ID NO 168
<211> LENGTH: 2004
<212> TYPE: DNA
<213> ORGANISM: Cucumis melo

<400> SEQUENCE: 168

```
tggatcgacc atgacattca aaaacccttta agatatggat cttataaaat aaatgtaaag     60

ggtaaacaat tcttccttgc ttaacccaag ctatatattt tatgcactaa tttaggtatt    120

agagtatatt cagctgaaca ccacctacca atgctagtac tttaatcagt caattctaac    180

ttcgataata tatctcaacc aaattagtga aaaagagtcg taaatgaaaa actatgtacc    240

aagatattct atttgttttt tttatgttta aatatctcaa agataatacc taaaacgttt    300

tctcctcgta caaagattcc tcatttactt tttattgtcg taaactctaa tacaataaac    360

taaaacaagt acaaatacac tagctttaga aatctacttt ttattgaaac caaaaccaat    420

aattcaacat ttcattttca ccgacaaacc tttgtaaaca attgaagtaa tttttgttgg    480

tactatgaat agtaacatca agtcttcaag tgcatcatat caaccaagac atgttcttaa    540

aagcgacact aaaagattta aaaccaaaag catttatgaa atccgaactt aatcaaatcc    600

taaatatttt tcacttaaaa aaaaaaaaat aggaagaaaa attgacataa atgggatatt    660

ttcgttttca aactggcaag ccagcatgca ccacgttgtt gacgtgtcct tccacgtcgg    720

aaaaaaaaat attaccacag taaaaagaga ataaaatgaa agtcgttgac tctcccttag    780

tcggaggaag cgcgtgaagc tgaagccgga ttagaaatcg gcaataaccc cgacacgtca    840

tcgaaatgct agtatcaaat attgtccgtt ggatcttcct tcaccaactc tatttgaacg    900

gccacgatct tccaggtcca acggttcgga agaatctttt cgaaattcca tggctagtcc    960
```

ctacactcct ccctattggc tccctagggc atcccgaccg gttattccgg ttgccgggaa 1020
ggtggctgga cgctataaat acccgctttg ttcatctcgt agtccttgta ccgttgagct 1080
tcgccttcta atagagctct ggttcggttg gcgtattagc tcgaattctt tctctcttcc 1140
agatctacgc tgccgatttc atcaggtttg cgagctctgt tccaccattt ttcttttcct 1200
gaagctttga gcatgcttgt gattcttcat ttcctcattt ctttgatggt ttatgaaaga 1260
atttagggga attttctctt tttgtattct agtggtactg gtagatttgt ttgaagtttg 1320
tttctcttct tctgagaagt gaattcttcc agatctgaca gttgcttttg attttttctt 1380
tgggaattag tgaatgatac ttcgatactg ttttttgctc tctgagattc tggatctcgg 1440
gccttggggt tttctattgt cttttggtag ctatgtttcg tttgtcagct tgtatttgtc 1500
attgttgaat ggttcgatcc ggtttgtaaa taaaataaat tttgtaggcg cacttgtttt 1560
ccacggtttt cgtgttacgg tttcatgatt ccctagatct ctggttagaa ctaagttttt 1620
tgtcggtaat tggatttggt aagggactgt tactgtggtt gaattgtaga tccagtcatc 1680
ttctacatga gtgtagggtt ccttagggca gatcttgtgt tttataattt taattttgtt 1740
gtttccctga ttttgaacct gtttggttgt tcagattcgt cgagtcattt ccattcatta 1800
aaagtttcta taattttatt tgaatcttct gaatctgtgc ttgtattacc cagatttcta 1860
taaacctatc ttgatttcaa gtgtgctatg tggtaactgt tgatattttc aagcttaagc 1920
aatactgatg tgactaaaac ttaactaatg aactgaatgt tttttgtaca cgaactaata 1980
tggtgttttg ttatgtttca gagg 2004

<210> SEQ ID NO 169
<211> LENGTH: 1067
<212> TYPE: DNA
<213> ORGANISM: Cucumis melo

<400> SEQUENCE: 169
tggatcgacc atgacattca aaaaccttta agatatggat cttataaaat aaatgtaaag 60
ggtaaacaat tcttccttgc ttaacccaag ctatatattt tatgcactaa tttaggtatt 120
agagtatatt cagctgaaca ccacctacca atgctagtac tttaatcagt caattctaac 180
ttcgataata tatctcaacc aaattagtga aaaagagtcg taaatgaaaa actatgtacc 240
aagatattct atttgttttt tttatgttta aatatctcaa agataatacc taaaacgttt 300
tctcctcgta caaagattcc tcatttactt tttattgtcg taaactctaa tacaataaac 360
taaaacaagt acaaatacac tagctttaga aatctacttt ttattgaaac caaaaccaat 420
aattcaacat ttcattttca ccgacaaacc tttgtaaaca attgaagtaa tttttgttgg 480
tactatgaat agtaacatca agtcttcaag tgcatcatat caaccaagac atgttcttaa 540
aagcgacact aaaagattta aaaccaaaag catttatgaa atccgaactt aatcaaatcc 600
taaatatttt tcacttaaaa aaaaaaaaat aggaagaaaa attgacataa atgggatatt 660
ttcgttttca aactggcaag ccagcatgca ccacgttgtt gacgtgtcct tccacgtcgg 720
aaaaaaaaat attaccacag taaaaagaga ataaaatgaa agtcgttgac tctcccttag 780
tcggaggaag cgcgtgaagc tgaagccgga ttagaaatcg gcaataaccc cgacacgtca 840
tcgaaatgct agtatcaaat attgtccgtt ggatcttcct tcaccaactc tatttgaacg 900
gccacgatct tccaggtcca acggttcgga agaatctttt cgaaattcca tggctagtcc 960
ctacactcct ccctattggc tccctagggc atcccgaccg gttattccgg ttgccgggaa 1020
ggtggctgga cgctataaat acccgctttg ttcatctcgt agtcctt 1067

<210> SEQ ID NO 170
<211> LENGTH: 92
<212> TYPE: DNA
<213> ORGANISM: Cucumis melo

<400> SEQUENCE: 170
gtaccgttga gcttcgcctt ctaatagagc tctggttcgg ttggcgtatt agctcgaatt 60
ctttctctct tccagatcta cgctgccgat tt 92

<210> SEQ ID NO 171
<211> LENGTH: 845
<212> TYPE: DNA
<213> ORGANISM: Cucumis melo

<400> SEQUENCE: 171
catcaggttt gcgagctctg ttccaccatt tttcttttcc tgaagctttg agcatgcttg 60
tgattcttca tttcctcatt tctttgatgg tttatgaaag aatttagggg aattttctct 120
ttttgtattc tagtggtact ggtagatttg tttgaagttt gtttctcttc ttctgagaag 180
tgaattcttc cagatctgac agttgctttt gattttttct ttgggaatta gtgaatgata 240
cttcgatact gttttttgct ctctgagatt ctggatctcg ggccttgggg ttttctattg 300
tcttttggta gctatgtttc gtttgtcagc ttgtatttgt cattgttgaa tggttcgatc 360
cggtttgtaa ataaaataaa ttttgtaggc gcacttgttt tccacggttt tcgtgttacg 420
gtttcatgat tccctagatc tctggttaga actaagtttt ttgtcggtaa ttggatttgg 480
taagggactg ttactgtggt tgaattgtag atccagtcat cttctacatg agtgtagggt 540
tccttagggc agatcttgtg ttttataatt ttaattttgt tgtttccctg attttgaacc 600
tgtttggttg ttcagattcg tcgagtcatt tccattcatt aaaagtttct ataattttat 660
ttgaatcttc tgaatctgtg cttgtattac ccagatttct ataaacctat cttgatttca 720
agtgtgctat gtggtaactg ttgatatttt caagcttaag caatactgat gtgactaaaa 780
cttaactaat gaactgaatg ttttttgtac acgaactaat atggtgtttt gttatgtttc 840
agagg 845

<210> SEQ ID NO 172
<211> LENGTH: 2018
<212> TYPE: DNA
<213> ORGANISM: Cucumis melo

<400> SEQUENCE: 172
actattggag acgacgaagg aaaactctaa tgtgagctta gaattgaaga tggtgaacaa 60
ttgggagtct tttttaaaaa tctttcgtcg gtatattgaa atttcctttt acactcaaat 120 aaccccccttt ttcacgcgtt caacgtcttc aaaccttcct ttttcaatta ttttttcgtt 180
tacattaatg acatttaggt aataagataa attagtggat tcttttgtga aaaatgttag 240
cccatttaag acttttatga aatatattag aaaaaaatca tatagcaatt tatattattc 300
tagttaaaag cccataatag aaactaaccc aacctaaagt aacgtaaaca ttcaataaga 360
gagacaaatt ttaaaataat ttctaattaa aaaaaaaatt gtcaagaccg tccgggtcgg 420
atccaaaata taacccgaac cggccggttt agcatctata taaatacacc tttagggttt 480
ttattctctc aagacttcac cgcatttcca cttctctgag gccacggtca gccattggag 540
cagctcaata atcctttgac tccctactac ggtaagtcga ccttactgct ttcggcttct 600

```
agtttttca atcctgtcat tagtcctttg gagttcttct gtacatttat gacgttttcg     660
gctcgtgttt tgtttcgcct gtatgtagtg ggtttttcga gttttgtttt tacttttttt    720
tatacttgca ggaattagtt gaaatctatg tacttcatgc cttggataat actcttgatc    780
tgttgtgtta ttcaaaaatg aattgtttta agatggtatt tgagaatggt catgtgagtt    840
ttgcctactt ggttattaaa atgaattgtt ttaggatggt atttgagaat ggtcttctgg    900
gtatttggtt ggaacctttg tgctctgcta tgaattaggg tgttctcccc gttttttttt    960
tttttttct tttggttatt aatatatctt ttatgactac ttattcatat atgatatctt    1020
ttactcgtaa attttgactc atttgaaagt tttatcctta gtcctttctc attcagggtg   1080
taaaggtatg ttgttagggt taaaatagcc tatgcaggaa agttctgtat ttgttctaat   1140
tattgcattt gtgtgcattt gtatctagtt tatttcttgc tgagagtatg cttcattttt   1200
tagtacacat cacttgtgcc actttattat agttgcacat ttttgtttat ggagaggatg   1260
aatagcattt agggatgtca attttttatt gagaaaaccc tctctcctac ttaagcttgg   1320
ggaattttg ttctaaatgt ggtaaacata atacttcttc ttattttaat ttgaatggaa   1380
ggggaagacg aatactaata ttttcaacga accttcacaa ctttttttc ttatttagga   1440
agccatgttt ttcaaaattg tactgtgtga tccacatatt tatcgattat tagtgaatcg   1500
aataataatt agagttttat tggtataatt ttgaagttca gacttattac atttgtggaa   1560
agtttggtta caattttcaa ttttattgga atcctaagaa ctttgtgtta acatatattg   1620
agtttcttc tcttttttt tactcattaa gttctctatt aggaatgttt ggttcaatgt     1680
cacatagtcg atagctaaga ccagtgaccc acaaagctat gattgaacga aaaacaagcc   1740
tttcacatct tggtaggaat ttgttatttc tcaatagatt tacagagctg tttcatgtga   1800
tcacaatttt tttctatttt tctgaagttc tctattagga atgggctatc tggttagttg   1860
cttttgagag aacatgtgga ttggtgttgc tcggtttcct tgcctttgta attttgtcct   1920
tggaaaaagc aaaatgatta ggtatcctga tatgcataac atgtttaagc caactagttc   1980
tcactttttt agtgcaaata attgatcttc aggaatcg                           2018
```

<210> SEQ ID NO 173
<211> LENGTH: 565
<212> TYPE: DNA
<213> ORGANISM: Cucumis melo

<400> SEQUENCE: 173

```
actattggag acgacgaagg aaaactctaa tgtgagctta gaattgaaga tggtgaacaa     60
ttgggagtct tttttaaaaa tctttcgtcg gtatattgaa atttcctttt acactcaaat    120
aacccccctt ttcacgcgtt caacgtcttc aaaccttcct ttttcaatta ttttttcgtt    180
tacattaatg acatttaggt aataagataa attagtggat tcttttgtga aaaatgttag    240
cccatttaag acttttatga aatatattag aaaaaaatca tatagcaatt tatattattc    300
tagttaaaag cccataatag aaactaaccc aacctaaagt aacgtaaaca ttcaataaga    360
gagacaaatt ttaaaataat ttctaattaa aaaaaaaatt gtcaagaccg tccgggtcgg    420
atccaaaata taacccgaac cggccggttt agcatctata taaatacacc tttagggttt    480
ttattctctc aagacttcac cgcatttcca cttctctgag gccacggtca gccattggag    540
cagctcaata atcctttgac tccct                                           565
```

<210> SEQ ID NO 174

<211> LENGTH: 1453
<212> TYPE: DNA
<213> ORGANISM: Cucumis melo

<400> SEQUENCE: 174
actacggtaa gtcgacctta ctgctttcgg cttctagttt tttcaatcct gtcattagtc 60
ctttggagtt cttctgtaca tttatgacgt tttcggctcg tgttttgttt cgcctgtatg 120
tagtgggttt ttcgagtttt gtttttactt ttttttatac ttgcaggaat tagttgaaat 180
ctatgtactt catgccttgg ataatactct tgatctgttg tgttattcaa aaatgaattg 240
ttttaagatg gtatttgaga atggtcatgt gagttttgcc tacttggtta ttaaaatgaa 300
ttgttttagg atggtatttg agaatggtct tctgggtatt tggttggaac ctttgtgctc 360
tgctatgaat tagggtgttc tccccgtttt tttttttttt tttcttttgg ttattaatat 420
atcttttatg actacttatt catatatgat atcttttact cgtaaatttt gactcatttg 480
aaagttttat ccttagtcct ttctcattca gggtgtaaag gtatgttgtt agggttaaaa 540
tagcctatgc aggaaagttc tgtatttgtt ctaattattg catttgtgtg catttgtatc 600
tagtttattt cttgctgaga gtatgcttca ttttttagta cacatcactt gtgccacttt 660
attatagttg cacatttttg tttatggaga ggatgaatag catttaggga tgtcaatttt 720
ttattgagaa aaccctctct cctacttaag cttggggaat ttttgttcta aatgtggtaa 780
acataatact tcttcttatt ttaatttgaa tggaagggga agacgaatac taatattttc 840
aacgaacctt cacaactttt ttttcttatt taggaagcca tgtttttcaa aattgtactg 900
tgtgatccac atatttatcg attattagtg aatcgaataa taattagagt tttattggta 960
taattttgaa gttcagactt attacatttg tggaaagttt ggttacaatt ttcaatttta 1020
ttggaatcct aagaactttg tgttaacata tattgagttt tcttctcttt ttttttactc 1080
attaagttct ctattaggaa tgtttggttc aatgtcacat agtcgatagc taagaccagt 1140
gacccacaaa gctatgattg aacgaaaaac aagcctttca catcttggta ggaatttgtt 1200
atttctcaat agatttacag agctgtttca tgtgatcaca attttttttct attttttctga 1260 agttctctat taggaatggg ctatctggtt agttgctttt gagagaacat gtggattggt 1320
gttgctcggt ttccttgcct ttgtaatttt gtccttggaa aaagcaaaat gattaggtat 1380
cctgatatgc ataacatgtt taagccaact agttctcact tttttagtgc aaataattga 1440
tcttcaggaa tcg 1453

<210> SEQ ID NO 175
<211> LENGTH: 1999
<212> TYPE: DNA
<213> ORGANISM: Cucumis melo

<400> SEQUENCE: 175
ggtctcagac ccataggaat agatcattta ttgccttatg aattagttta tgagtacata 60
ataattgtca accgtataca aatcaacatg aaagaatata atgttgtaca tagtcattcc 120
aagtttacta atattatatt ttaggagtgt tctacaccga acctgtcaca tgtacactgg 180
gtatgctacc cctgaattca atatcataaa gcaactttaa ttgtcaagca ttctcttgac 240
catttgtgac ccatttgctc ctactttttc aatcaataac tatcacaaaa agctagatac 300
cacatgtgat aaactcactg aaatcaggta tatggttacc tgtgcttggt cagcactcaa 360
tcagattcga aggcctagtc tttgtatttc cccccctctg cacactacaa atagtcctcc 420
acgtaaagac ccataacaaa acgcaaacca agtacagaaa atctagccga aatccagacc 480

```
actcaaacat aacaaatctt ctggtaagtt tgaataaaat ataaaactaa cctatttaat    540
caaataatac aataaaatgg aagcaactaa cataacatat ctaaatatga tcacgtagta    600
ggaaaaaaaa aaacattcca aaactattaa caatcattct taatggtatg ggtcaatccc    660
cattatttag gactataaca agaattcctc atacctaatg ccacatccta tgtccaaccc    720
tcgagattac ctcgtgagta atcaatctta ttcatcctta tttcaaatta tgtgaaattt    780
ctcatcaggt tgatcatatt gactttcaat acaacttatg attaatcttt cccttgatat    840
aatttcgtat gaaaaggaag ttgacattat gtgattttct cataaggtaa accaagtaaa    900
cttgacatga cgtcttaaca agtcttggtt tctaagtgta atttactgca gaaaaaatcc    960
taaattctat gacttttcct atgagattga ccaaatcaac tttacgagaa atcttgggaa   1020
gccataccta caaagtcttc cccaagaaa ttacaatttc tagtaaagat tgttgaaatt   1080
taccctccaa tttttccgtg aaaatttgac aaacttgtaa gaatatcaaa tttgggttgg   1140
atattgacat tccaaaataa gtagttttaa aaaggattta tccaacaata atagaagaaa   1200
aaagatagga aataacatac ccacgtaaat ggaatgtaaa tatttatata ttaggtgtct   1260
tgaacgaccg tcaaacgaaa ataaattgtt catccgaagt tgaaactctt taagtgtaca   1320
tttatctttt cgtaagaata aaatgtaaaa ttaacgtgtg aaaggttggg ttaaataagt   1380
tatgtagaga taatattgaa gatgatagaa taatcacgat cgatgaatta gtatagtccc   1440
agagcggatt taaacctctc tcactttcat gctttctata tatatcaaaa taatttcaag   1500
tagttggttt agtcgtaaaa aagtcaacca atctctttta gataaacctt gagttattaa   1560
aaaattagat caaagataat cgttgaaatt gaaattttaa gagtataatt ataacaaatt   1620
ggaaagttct aaagtagttt ttgcaatatt ctccatcaaa atagagtaga aaaatatttt   1680
agtaattttc ttatcttaat tttagttttg taatagttat taggatggtc ctaagttctc   1740
aatccgcttt tagtccataa aaagaaagaa gagagagaaa aaaagtcccc gatccgcgac   1800
acataccaat ccaaccaatt atgcacaatc catgtgatat cgaacggtca caagaataaa   1860
tgctttctac acacggatca ccatccaacg gctttccttc catctcatcc tctatataat   1920
ctaccaactc tgtcatcttc gacacacttc aattatctca gcttttattt catcggattt   1980
tccatcaaac aaggcaaca                                                1999
```

<210> SEQ ID NO 176
<211> LENGTH: 2004
<212> TYPE: DNA
<213> ORGANISM: Cucumis melo

<400> SEQUENCE: 176

```
tatagtttgt aacaatctac tctatgttct ttcaattttg atacatttga atcttaaact     60
ttattgagtt acacaatata gtccttgtat ttttaaaatt tataatgact ctatttatat    120
taatattata gaaatttttg ttaaggttta ataaaaattt ttctgtataa ataaatcgaa    180
cacgaagtct atatttagac tgcaatatag taaaacctga catctaagtt tggtgaattt    240
tgttttgctt taaaaactaa actattacaa ttttaaaaat attttaattt agttaatgca    300
cattaacttt acggagtaaa tttttacaag attgaatata catagattaa atagttataa    360
aaccaaagat tagagtaaaa aacatttaaa tagaaagaac taagattttt ttaaaacgaa    420
aatgatacta gatacatata tatgtatcta tattataatt actcatttta acatatagtt    480
ttgaaagaac aaagattagt tgcatgtgtt gattgttttt aagaaggaaa taatttttga    540
```

atggaaaatt ttcaaaagtt ttaaatttga caataaactc atatttaaag tgtactacaa 600
attttaactt ttggttaaac tccttgttta gttcaatcat gtaataaatt ctcattccaa 660
gaatcgtttt agaaaatttt attgtgcatt taataaaata tagaacatat atggcatata 720
aaaattgatt actttttttct ttttttggga cgaaaaacac attagatata atctttttttg 780 aaagtttatg aactttaaaa atgggttatt ttatacggtg gtcaacttta ttttattgaa 840
attattgagt ttataaagat tgttatatca ttttcttctt ctctttcact agaatacaat 900
caaacctatc aaactctcta tgacttattt agaattcttt ttgttatatt tttgaaatta 960
ataaatgaaa agcttagagt ctaaattata acaattaaaa ttgaaaattt tgcaataatt 1020
ttatttttag caaaatgacg tttggttttt ggggattggg aatggatcga tactatcccg 1080
attccggaca aagaaaccga cccgagattc gaatttttttc cattcccaaa cagagcactt 1140
aaaatttaag caacgttata acggcgtcac cgaactaaac ggaaaaatat gaagaaaatt 1200
agaaaaagaa aaacggaaca gtcaaacgtt acttcacgtc aatggcaata ttcatttttt 1260
tttttgttta aataattgaa tttaattaat ttggtttata aaaatagagt cctcatatat 1320
cgcgaatgcg catttgatcg tgaaggacag cttctccctt gtgttcaaga gagagagatc 1380
tatcattctt atttggggcc gatctctcta ttctcctctc ttctattccg taagtttttc 1440
tcattcattc tcctctctca tttctctccg agatctgttt acaatccttt tgattttcat 1500
ttttcctgct tcgatctgtg ctcctggtga ttccctttttc ctgttttatc ttttgttgat 1560
cttggaattg attgttcttt tgtgggtttt cattgatttg tattttctga tctgggtttc 1620
tgttttctcg ccttgatgtt ttgtatttgg atctgatctg acgacccttt tttttttttt 1680
tttttatttg aattgctttt ccaatgttta tacctggatt tttattgatg catgggttta 1740
accgattggt tggatgcgtt ttctttgtgc tggatctagg tgtccttgtt tttaatttga 1800
attgtgggta aaaatggcat tattgtaatg tgtttggagt ttgattttga atcttggcta 1860
gttgattttt gaattacaaa gatcggatcc tcttcttttt tgggttgtct taagattttt 1920
ggctggttta agtatttgat gtcgttgtat tttaaggggt aactgatgcc ggcttgttgt 1980
gtttgtattc agtttacttg aaaa 2004

<210> SEQ ID NO 177
<211> LENGTH: 2005
<212> TYPE: DNA
<213> ORGANISM: Cucumis melo

<400> SEQUENCE: 177
aattagcaaa ttgtatgtaa caacgtcatg aagaggcatt tcatcgaaca atttaatagc 60
agagtcaaga tggcccagtt ttataagttt attgatttct cgattcttaa ggtaaatgag 120
atcgcgagca tggaaatgca gacccaaacg agaatatggg tgtggtaaat ggaccggtga 180
tgttgtggct acaaattcgg attttacagc agtaatagtt ctgacgaagg aagcgaattt 240
agtgaccttt cgcatcacag tttaagctta tcagagacct gaacaagggc tctagctcta 300
caacttagaa aggtttgata tggtccgtga tcgggaggga ccgaataaca ggcgcttaaa 360
ttgttgttca taaagaagag gattgtcgtt gatgtatttt aaccaagaga tgattagtta 420
tccacatcca cagagagaac agaagacggc tttctaaatc tacaccgata aaaataaccc 480
taccactttg tttctttaga aaagggtcac attctttaaa aacattagcg tcgaggatta 540
atagggtata ttgactaatg ctctgtttgg atttcgagaa ataccaattt acaattgatt 600
tcaaattaat tatgttttgt tgttgcacga aagataaaaa gaatttaaaa ttcaaaagga 660
tctcaaatct tatttttaac ttaaaaactt ttatgaccca aacggtttat gtatgattta 720
aaagtagaat acctctgtga attcttaatt tttttttctt tccaattacc acataaatat 780
gaaattttaa atacatttat tttaaatttt atatccgaaa caaaataata atttaaaact 840
atttctcata tatgaagtgt gattcgatct aaattataaa ataataaaaa tttacatcta 900
gttttgatta ttttttttc gttagatact aaattgttaa gaaaataaca tttttaatcc 960
aaagttttga agaatatatg acttttaaaa tggtatttat ctttttagtg tctgattttt 1020
aaaaaatgga tttcaaaagt tcatcaaata gcattgtatt tttattttaa ataattttga 1080
catttaaaat tagagtaatg gtttataaaa gacacttgat ctctaaaact attttcttag 1140
atataaatac gtatgattat ttttaaaaat caatcaaaat aggtaaattg taaaaaaaaa 1200
aaaaaaatca taaaacatga tagtagttgt aattatgctc tcaaactttc ggttatgaaa 1260
aataaacatt ttaactttta gacgtgtcaa agttgagtca agttggacct tcaaagttat 1320
gtagttatat aaattgtaat atatgtataa gcttgtggat tcaattttat catttatggg 1380
tccaatctct acaattatcg taagtctatg ggtcaattgt aacacatgtg gagtttaaga 1440
gctcaatttt ggacgtggat gtgttttgca accaactcca caccttaaaa aggtgttttt 1500
ttttaattta tcaaaaaaca agaatttaga atctttaagt ttatctttaa aaatcaacgg 1560
acattttgaa aaccaattga aactactgtt ataaacctaa caactaaaag tatatttttt 1620
aagaccgaaa gcataaatcc ataaaaaaaa aatccagaac tgaaaatgta acttttatag 1680
ttgaaaattt agctaaatta tacatattaa aattcaagga ccatataaaa ttaaagtacc 1740
tgattaaata ataacgaatt aatgtttggt atttttaacc tacattagaa aaaaaaaaca 1800
aaagaaaaac ggcatactat ttgtcaagcg tccgatggga agaaaatcca acggtgagtg 1860
ttagtattga aatacgcagt tctcgtgaat gagcctggct tagatttggg aacaagagcc 1920
aacccctttc gaccgagaag ccgtcgtctt caccatattc gcctcaacca ttcgatagcc 1980
acgtttgaag aagaatagga ttgcc 2005

<210> SEQ ID NO 178
<211> LENGTH: 1978
<212> TYPE: DNA
<213> ORGANISM: Cucumis melo

<400> SEQUENCE: 178
aattctaaca actccggaac aaataattta gcatggattg aaatataaat cttcttgact 60
tgcaaaaaaa tcattgtaat ggtcttatgt tggttatagt tagggtatcg aaacgccata 120
caggaatatg ggattaaagt taacttttgt tcatcaattt cagcttatga acttctaaaa 180
tatcaatttt acctttgaac ttatatgtta ttaccccttt cgattgtggt atgttaatta 240
atatctgaat ctcagtcctt atgaaacttt tttatactgt cacaaacata tgaagtttta 300
ttgtaagttc ttagaaatca tctaaaaaga gtagtttgtt ggactattta ttttattttt 360
tcttattaag ttgttttcac gccatttcag taaaataact atagtgaata gagaatcaaa 420
cttctaatct taagttaagg tagtagggta tatgctaatt caataagata atccgtgatg 480
cttgacatct gacttaattg ttataagttt taaatttttt attgtaatat ttaaaatact 540
agtttttggt ttctaataaa gaaataattg aacaattaca aatatttata caaaattaaa 600
ctagaatata tgatcatttt ccttcgtgtt agaaaaaggg aaatatatgt gtgtatttat 660
acatattaga tattgtttta ctatattcca ttttcctcac gggaaatgga ggattgagtg 720
ggagataaac attgtcccca agagaattgg gaatggaaat gcaaatgaca tggccctcca 780
caaaattgtt cgcctaaaaa tgggctttct cacttctcac tccgcaagaa aaatatcgtt 840
tcccttcgaa ttcgggcaag atctcaaaac cacatgtttt tctttcttta tttttcaagc 900
ctacattatt tataaaaata taacttaagc agagaattat gtaaattcaa gtccattttt 960
cgcttcactt agctaaatca ttaacaaatc tgtaattttg ttcataaatt agctcaccaa 1020
ttatgtttta gcccactaag gcccattaga catttttatt agaaaaacat gaaccgttgg 1080
atcaagatgt gtgttttctt ttctttttct ttttattttt tttgggtttt ggtggatcaa 1140
ttcgtagctt tagcaaccta ttattatatg gagggaaagg gcgtattaat ctgttagcgc 1200
cgtccgggag tttagctttc ttccccgagc ctcggtctta tcccctaact ccaaaaccct 1260
agcccaaagg taatccactc cttccccctc cgctcttcat ctttttctat tcatcatctt 1320
taatctgttc tcccttttgg ttcttagatt cttcttttgt tggattcttt taatctttac 1380
tcatggttgg ccttgtaagt ttagacgacg tttttataca ttggttaatc ctgcttctct 1440
atctattcgc acgctagggt tttcctattg ttttctattc tgctctactt ctgcaaggtt 1500
gtgttcttct tcgttcaggt cccttttttt aaccgaaatt aaattaatgc aaattcgttt 1560
gtgcttctaa ttaggaagcc ttttggaaca tctcgacatt ttgattgctg catttcattt 1620
cgggtatatt tctatgattg aaggatgtgg gtctgttcac tgcatggtca ttacttatgc 1680
agctatgctt atcgagtcca ttatgtttgt gcaatctgtt tccggattca taatttttta 1740
gtaattgatc agtagatgaa aaaagatatt gtaatattcc ttgagtgttg caccagtctt 1800
ggtgggtatc tgctcctgct ctttgcttgt ggattttact tttattatat ctgtattatt 1860
cgaaatgttc tgttcttgtt ataacttata cccgaagatg tgttcctccc cgcgtctagc 1920
gttgtgggtt acttatgatg gacatggttt tgattctgtt tggtttgtgc agggtacc 1978

<210> SEQ ID NO 179
<211> LENGTH: 1263
<212> TYPE: DNA
<213> ORGANISM: Cucumis melo

<400> SEQUENCE: 179
aattctaaca actccggaac aaataattta gcatggattg aaatataaat cttcttgact 60
tgcaaaaaaa tcattgtaat ggtcttatgt tggttatagt tagggtatcg aaacgccata 120
caggaatatg ggattaaagt taacttttgt tcatcaattt cagcttatga acttctaaaa 180
tatcaatttt acctttgaac ttatatgtta ttaccccttt cgattgtggt atgttaatta 240
atatctgaat ctcagtcctt atgaaacttt tttatactgt cacaaacata tgaagtttta 300
ttgtaagttc ttagaaatca tctaaaaaga gtagtttgtt ggactattta ttttattttt 360
tcttattaag ttgttttcac gccatttcag taaaataact atagtgaata gagaatcaaa 420
cttctaatct taagttaagg tagtagggta tatgctaatt caataagata atccgtgatg 480
cttgacatct gacttaattg ttataagttt taaatttttt attgtaatat ttaaaatact 540
agtttttggt ttctaataaa gaaataattg aacaattaca aatatttata caaaattaaa 600
ctagaatata tgatcatttt ccttcgtgtt agaaaaaggg aaatatatgt gtgtatttat 660
acatattaga tattgtttta ctatattcca ttttcctcac gggaaatgga ggattgagtg 720
ggagataaac attgtcccca agagaattgg gaatggaaat gcaaatgaca tggccctcca 780
caaaattgtt cgcctaaaaa tgggctttct cacttctcac tccgcaagaa aaatatcgtt 840
tcccttcgaa ttcgggcaag atctcaaaac cacatgtttt tctttcttta tttttcaagc 900
ctacattatt tataaaaata taacttaagc agagaattat gtaaattcaa gtccattttt 960
cgcttcactt agctaaatca ttaacaaatc tgtaattttg ttcataaatt agctcaccaa 1020
ttatgtttta gcccactaag gcccattaga catttttatt agaaaaacat gaaccgttgg 1080
atcaagatgt gtgttttctt ttctttttct ttttattttt tttgggtttt ggtggatcaa 1140
ttcgtagctt tagcaaccta ttattatatg gagggaaagg gcgtattaat ctgttagcgc 1200
cgtccgggag tttagctttc ttccccgagc ctcggtctta tcccctaact ccaaaaccct 1260
agc 1263

<210> SEQ ID NO 180
<211> LENGTH: 715
<212> TYPE: DNA
<213> ORGANISM: Cucumis melo

<400> SEQUENCE: 180
ccaaaggtaa tccactcctt cccctccgc tcttcatctt tttctattca tcatctttaa 60
tctgttctcc cttttggttc ttagattctt cttttgttgg attcttttaa tctttactca 120
tggttggcct tgtaagttta gacgacgttt ttatacattg gttaatcctg cttctctatc 180
tattcgcacg ctagggtttt cctattgttt tctattctgc tctacttctg caaggttgtg 240
ttcttcttcg ttcaggtccc tttttttaac cgaaattaaa ttaatgcaaa ttcgtttgtg 300
cttctaatta ggaagccttt tggaacatct cgacattttg attgctgcat ttcatttcgg 360
gtatatttct atgattgaag gatgtgggtc tgttcactgc atggtcatta cttatgcagc 420
tatgcttatc gagtccatta tgtttgtgca atctgtttcc ggattcataa ttttttagta 480
attgatcagt agatgaaaaa agatattgta atattccttg agtgttgcac cagtcttggt 540
gggtatctgc tcctgctctt tgcttgtgga ttttactttt attatatctg tattattcga 600
aatgttctgt tcttgttata acttataccc gaagatgtgt tcctccccgc gtctagcgtt 660
gtgggttact tatgatggac atggttttga ttctgtttgg tttgtgcagg gtacc 715

<210> SEQ ID NO 181
<211> LENGTH: 2000
<212> TYPE: DNA
<213> ORGANISM: Cucumis melo

<400> SEQUENCE: 181
aaataatttg tggattttat catattatgt accttagact ttgtaaggtt tataacacaa 60
gatgtggaga aatcccatga tgaacattgg acgttattat atcctttgaa actaaaaaca 120
aaggaaaaaa gacaaatggc tgagtataag aaaaagagaa gaaacaacca aaaagctaaa 180
atgtcatgct ctcatatgta acatatttga attgggattg atttcaagat gtattttaaa 240
ataatttaac acacgataaa ataattctaa caaactcaaa attactctta aacatttact 300
tgatatcttc gacataatga cttttgtttt aatacaactc aaaacataat taaggttggt 360
tttaaatgac aacaaacgaa aaactcgatt ctaatttcaa tactagtctt tgaaagccct 420
aaggagcgtg gttttgaatt gtatagcaag gtttcgaaaa ttttaatcat caaacaatag 480
gtatatttac ctgttcctca agtacagtta attcatagct acttgtcgtg cttcctacga 540
caacattgta agacttgcca cacactaatt gaagccgttg ttgaaggtag ttttccatgt 600
atagcttgaa tcgacggatg accaaagagg ttgaagaagg tttgaaaaat aggggaaggg 660
atatacaaag tttgagagtg agagagggag agaaatagaa atagaagaga ctgaaaaatg 720
taaaagaaag gatgaaaaaa tgtggggtaa acgcaaattg gatttttata gtagtatttt 780
gaaaatgcta tagaaaggct atgtatagta gtgcttccaa agttctatat gaatgagaca 840
aatcaaaata tatttttttt gattaattaa ccccaaaaag actcataaaa aaatcttata 900
aatcccacta agatattgca tgttatatgt agtaaaattt atcgttcaaa taaaccttaa 960
acataattca aacgaagaaa gtaaaaattt gaatttctta tcttacatca ttcaaccaaa 1020
caatttccat ataagagatt aaacttctaa ctttaagaga gagatatcca gcatatgcaa 1080
cctaaaccaa cagtgacttt gctatatatt tgcacaaaat gtgggggaca aagttgtaat 1140
ttcggaatat caatgattaa agaaaaggta aaatttaaaa ttcggaagct tgacgtggca 1200
acacggaatg gtgatgatat ttccaactcc tcgcgacttt tagaagttgg cctcaccaac 1260
cgcatatccg cccctttgcc acgtgtcaga ctacaacaac ttccaacaat ttcctttaag 1320
aacaccaaat tatatcaata aatatttaac ttaaattaag aatatatttg ttacaatttt 1380
cctactgagt tagatagata gacagacttg tcaattaact aataagtcca aagtcaattt 1440
actcaacata gatacaattc taatttgagt gtgaaataca tattcaaatc aaaattatta 1500
ttaagaggaa aaactgattt gctttctcaa tttaaaatat aatattttga aaaagaaaca 1560
cacatgtatt atggttttca atatatttac tttcttagtc acctaatctc aaactaattt 1620
ttgaagaaat taaatatata tattatcatt tttattttct tggttatgat attggtatag 1680
aatcaacaaa actacaagtg tcctctcctc tgctatcgat ggggattaga ctctaaactt 1740
gtttagcgat tagtaattat atattagaaa aagtttatgt taatgtggac ccgacaatct 1800
caccaatagg ctcttcactt caccaacccc cgacccattc cctctaataa ttcgacacgg 1860
ctcatccccg gttcgaaccg ggccgacgtc ttcctattta acacacctcc atttcctctt 1920
ccctccgcaa cacaaacaga gacctcaccg gaaaatcaag ttaaagcaaa accaaagaga 1980
agcttcatca ctctccggaa 2000

<210> SEQ ID NO 182
<211> LENGTH: 2000
<212> TYPE: DNA
<213> ORGANISM: Cucumis melo

<400> SEQUENCE: 182
gcatcttatg gatgtagtca caacatattt atatggattt tctgataatg atatttatat 60
gaaagtccca aaaggattta agatacctaa aacatataaa tcaaattccc ataaactatg 120
ttcaataaag ttacagagat cattgtatgg attgaaaaaa tcatgacgaa tgtgatacaa 180
tcgcctgagt gaatatttgt taaaaaaata atatcaatat aattcaatat gtccatgcgt 240
ttttataaag aaatcaccgt caggatttgc tattataact gtatatgttg atgatttaaa 300
tataattgaa attttgaaga gttttcaaag gcaatagaat attaagaaag aatttgagat 360
gaaagatctc agaaaaataa aattttgtct tgattttcaa atcgagcatc tagtaaaagg 420
gatatttgtt catcaattaa cttatacaga gaaaatttta aaaagatttt atatagataa 480
aacacattca ttgaacattc taatgcaagt tcattcatta aatgtgaaga aagatatttt 540
tcgacgtcga gatgataatg aagaactcct tagtccagaa gtaccatacc ttaatacaat 600
tggtgcactt attttgtcaa taatcaagac cagatattgc attttctata aatttattag 660
ctagattcag ttctccaaca aaacaacatt ggaatgaagt taaacatata cttcgttatt 720
ttcgaggaac aattaatata agattatttt attcaaataa atcaaatttt aacctagtta 780
gttttgcata ttcttgattt ttatctgatc cacataaatc tagatctcaa acaggttatc 840

```
tattcacatg tggaggaact gctatatctt aacgatcagt gaaacaaatt accataacag    900
tcaactcttc aaaccgtgct gaaattctta caattcttga ggcattcatg aggctagcgg    960
agaatgaata tggttaaggt cgatgactca acacattcga aaattatgtg gtttgtcttc   1020
tagtaaactc cttccaacaa cattatacga agacaacaca acttgtatag ctcaaataaa   1080
atgaggttat attaaaagtg atagaacaaa acacatctca ccgaagtttt tctatactca   1140
tgatcttgaa gaaaatggtg acatcacagt acaaaaaatt tgttcaaaag ataatttggt   1200
agatttattt acaaaattat tacctactgc aacctttgaa aaattggtgc acaacattgg   1260
aacgcgacga cttagatatc tcaagtaatg ttacatctta cttgccaagt taactataca   1320
tagtgacatt tggtggagtt gtaagaaaca ctaatattgg agaaaaatcg aaagaaattg   1380
gaaaatatgg agaattgaat tttttttaga tttttcttat tttctaattt taggtttccg   1440
tattctgatt atgcctcatt ttcacaacat taataacttt aataagatga tttcttgggt   1500
taagggaaaa aaatcatttt tttagagttg cacgtacaaa aatattatca taacatatcg   1560
attataataa accaattcac cgtcaaccta acctaggtag agtttgagtt aaatgttaaa   1620
agaatatcca cccctcaaca ttgtaatccc aactaataaa tcagcaacct aaagtttttt   1680
ttaaaaaact aaaaagaaga gcaatatatt tttttacta ttattttttt aaagagtgga    1740
tttatttatt aaattaaaaa atgaaaagaa gaaaatttgt tagtttgggt aatccgaaaa   1800
cccgattatt tgggcccgag aaaccgacgt tttgtttatt gttcctcacg gcaataagta   1860
atggcgtgaa tcgaccgcgt gcgcttcaag ctatctagac atttttatat cctccgatta   1920
gaaaccctaa ttcagattct ccgtattacc caccctggaa catctttgaa acgcgaaaag   1980
gtgacccgaa gaaacttgaa                                               2000
```

<210> SEQ ID NO 183
<211> LENGTH: 1989
<212> TYPE: DNA
<213> ORGANISM: Cucumis melo

<400> SEQUENCE: 183

```
attacttgaa cttaatccac atttatgtct ttatataaag ttcgaatact cataatatag     60
ccaagaaacc ttgtttattg gattttgagt tttatcataa gcaaatctct tatccaataa    120
caaattatta aacaacactt caacaataac tttattcaac aatatattag tttaacattc    180
acaaatcacg agtattagaa cataaaacgc aacaaagaat ggactaaggt actatattct    240
aacttaggtt gtttaggatt tccatatgtc aatgcttttg tgatttttga actagatttt    300
cttgttagat taattcaatt ctatttttaa atggcttaat atcttatttt cggatgcttg    360
gggattgcta gactaccgct ttgttgaagc aataagttaa atttgtttgt tacaggtatt    420
gatcaatcta acatagaatt gaatttgtat gaatatttag ttagacgctt gaaaactaat    480
tattctacca atgagccgta gatcttaatg caattgttat taatttgaac tttgtatgct    540
tctcatcgat taaatttata tcaagtagtt aattaggaca aatctattgg ctttttcatt    600
taattttgtt aagtaaaagc aacttagaat tttgaaaatg atgaacccat gatccaatac    660
attgaaagag aattttgttt aactcaaact aggattcttc tcacattgat ttcgtataat    720
ttaacttttt caatttatat caatcccccc agggtgaaaa aaatttgttt gaagaattca    780
tgtgctttct aaatctgatc tagacttgcc actaaaatta acttttgata tgtaatttgg    840
ttaaatattt gattcggatt tcgacgacaa acaattgatc aatgtggtat taaattctga    900
```

-continued

```
tctccatgta agaaatttac acattttcat aagttcaatg ttgacacaaa gagagtaaga    960
gcattttaaa aaaaaagata cttttaatct tttctaaaaa aacaccaaaa tgccattatg   1020
taaatgtaac ctaaataata aacatttaaa cttagaattc atgcaattag gctttgtatg   1080
ggacattgaa ttgattatta aaatcagtag ttatagaccg tgagttataa tggtttgtat   1140
tagaagcata aattatttta attttgatcg taatagcatg tatttgagat ataaattaat   1200
ttagtttggg tggcaaatag taaacagtaa agcaaaatat aaaaaaatga atttaaaata   1260
gtaagatttg taacaaatga ttaatactat aacaaacgtg gttttaaaat aacgttgatc   1320
gtagctaatt gaacattatt tattgtaaaa ttgagtgttt ttaatatttg gagcctcaaa   1380
cttcgggtgg atcaccacaa tataatcata ttcaaattta aaattttatt tttattataa   1440
atattgttaa tagatgctca ttatgggcca tctgtcactc cctccgtgca tatcctacct   1500
gaaacatcat atatcttaaa caatgtccat tgccatgtgt cactattttt acatcccatc   1560
cacttgacaa atatgttgaa gatgcctact tttttaggga tcatgtaatc tatctcatgc   1620
ttgtcaaatt gttcgataat agtgttacaa aaaatttagt aattattatt attatatttc   1680
ttcgatattt atgcttcata tgccattgtg ctctccattt ttaccatact taaaaaaatt   1740
tcttattata aatttttttca aaaaaaaatt tactatatag tcatcatctt tattaaaatt   1800
aaaattgaga acctgatatt tttgatatta ataatttaaa atttgaatta atccacttta   1860
aaattattaa taatttattc gaatttgggc cttaaggaag agatacggaa acaaacccta   1920
gatcccatct atatataaat cgccacaaaa ccctaccttt ctctcagttt ctcgttttag   1980
ccggcaaaa                                                           1989
```

<210> SEQ ID NO 184
<211> LENGTH: 1463
<212> TYPE: DNA
<213> ORGANISM: Cucumis melo

<400> SEQUENCE: 184

```
ttttcttctt gatttgaaat tcttcctcct tcctgttgca aacaaaccca gatgaataat     60
cagacaaaaa aagcagcaaa tttgaagata tgcatatacg aagaagaaga agaaaaagag    120
agggaaggat aaggtaggag atagcttgag attacagcgt agaaaccgat cgaaccggag    180
atcaacggcg cgaattaggt caagaagaag tgagggtttt tatgaagaag aagtgagggt    240
ttttatgtgc cgatgaaaaa ccctacttct gtgttggtga tctaacgttg tttgatcggt    300
tcggtttttt tgagaatcga gtaccctcat tattattatt attattgtta ttattataag    360
tttgttgtaa gaattaataa attatttcaa aaattacaat ttttatttat atatagttta    420
aaaaatttta taattttttt aaataaattt cgaaatataa ggttggattt cttaaaaata    480
tatgaaaaaa gagatgaagt ttataaatta aaaatgaaat aaaaatagta agtttgtact    540
cttattctta tttacaattt aattttccat taaaatttta aattaaatag aaatataatt    600
aaaatcttaa attagataga aatataatta aaattttcag aatgtaaatt taaattagct    660
tagtgtatat ttaaaatata taagattgaa ataattgatt ttgtttatct aaatatttta    720
tattattatt tattgaataa atataattat atatggtaaa ttgttttgga taataagaaa    780
gtaaagatgg tatttatata tataattaac caaaatttaa gtttgttaaa aagaaaagtt    840
ttcaaaaata tttttttacg agtaattagg aaaaacccac attttacatc gaagtcatag    900
actgggtcta tgtcttcatt gccttgtcgt gtacccgatc cacgataacg cattatgaac    960
cgagtagatg acttaacttt ttgtaatagc ttttcttcta ccatattttt gacatttttt   1020
```

```
taaaagtaac attatttata aaaaaaaaat cgtagtttga tctcacatga aactattatt   1080

acatcattaa ctaatatatc tatatttaat gtagttttct tgacatgatt ttaatgctaa   1140

ttgaaatagt tacaattttt gtgtcccatt ttgtttagat caatatgact tcacgtatta   1200

tgacatatgg ggccatctta ccagaaattg gtgccaatga gaaaatgaat gtaccttaac   1260

caatggagca acccatgtga gccattgatg aacccaactt tcttggtttc ccatcttcta   1320

ttcatatgtc acaatacctt ctcttttctc attctatata tagactctaa acaaacaact   1380

aatctccaac ttcaaatctt tcacatattc tcattcaagc attgaagttt accacttcca   1440

aaaagattca atccaattta gcc                                           1463
```

<210> SEQ ID NO 185
<211> LENGTH: 2006
<212> TYPE: DNA
<213> ORGANISM: Cucumis melo

<400> SEQUENCE: 185

```
cagcgatctt cgtagaaact aattcaatgc tagctcatta tttgactttt ctcaggcaag     60

gctccgcgag gaagagaaaa ggtccaattt caggaaccaa gggcatggac aggttccggt    120

cagaagaagc tttttacgta aaccctttgc cagattgttt atgtcaagga gaattaccaa    180

atggaagtac gacttccatt ttcagatagt tcagtagaac atcaaagata aaatgctctt    240

agagagctca atgtatatgc aggcgaccac tcaacgtgtc accagctttg tacatccaat    300

aagccagcta cgatggaacg acggagtgtt tataacctga gttttggtag ttggcggagg    360

cggtgatggt ggtatagaag gaaggtcgag ggatggcaaa ccctttacgc caagtagtgg    420

aagggagtag ttggagatga acacattttg agaagtttcc aagatcactc catttggggg    480

agaggggatg ttggttattt agcacaattg ttttcatgtt ttagtaattt tatccaataa    540

tgagcgaggc attgaagcaa ttaaatttat ttttaatgat tttttcaccc ttccataggc    600

tttttctttt ttcttttcct tttagtttgc aaactttagc tccttttatc ggctgtcgaa    660

ctcatttttg aagttattga atgaaacaca gtttgggctg tgtcagatgg gtggtgaaat    720

tttatacatt ataattacta cataaaatga aatcatattg taattttcta tctatgccac    780

aatttttttt tattgcatca tgaggattaa attgtacgag tccaaatttg tacagtcatg    840

tttttaaagc tttcgagcat tgttactaat gcatggaaag gatcgattat caagtatcct    900

cccaacttca tgaaagttat tatttgtctt ctaaatttgt tttagaaaat gtttaattaa    960

ttatttgaga agaaagttta actaaatcct attggtttcc tctaaggttg tcatacttat   1020

ccaataacaa ttacgtttaa aatcaaaatt attctaatgg tataagacta atgttttaaa   1080

agcataaaat tgatgaggaa ggattggaag taatactatt tattttgaag gtaaacattc   1140

ttgaatgtct gtcctaaaat cactaatgtt ttcttagttt gagactttga gtcgttgaac   1200

ctctccatct ttataaaata taatacgagt ccttcacaat aacttaaaat atatactaaa   1260

tcctaattaa tgaaaaataa ataaataaaa ggtacaaaat cattaaagcc taaaaatcta   1320

ttactccttt aaaacttttc aagggtccct acaaccaatg agaaactacc acgtcatttt   1380

cacaatccgt tcagtgttta gaaaagtcaa atcgcaccgt ccatttatcc actcgtacca   1440

agtacggtag gaatctatct accgtccgat taagcacaaa gaagcacagt aaatgtcaat   1500

cgtgtccatc cgccgccata ccgcacatcc ttcgtccgac cggaaggccc tatataaagt   1560

cctttggttt tccgaatttc tacttcattc gcttttgaaa gatttcccaa tctcttcgtc   1620
```

-continued

```
ggccaaaatt ctctctcgct tctcaaccct tcttcggctt tttcatccag gtttgtttct   1680
cttctctttt ttcttccttt gttgttcttg gaatatgttt aatttcattt gtttttccat   1740
tcaatttcat gctagatttt acgattaggt tgattttctg ttcgtagatt gtaattgatg   1800
gttagggtta gctttttctc ccattccttc tggaatctgt ttcttgacct tcgaacttcg   1860
ttgataaatc tttagaaaca tttacataac caaacaataa ttgaacaact cgtgttgtta   1920
tgcctatata atagcggtta ggaaactgga aacgccctta taattgaaat cgccttagaa   1980
atttgttttg attcatacag ggtacc                                       2006
```

<210> SEQ ID NO 186
<211> LENGTH: 1664
<212> TYPE: DNA
<213> ORGANISM: Cucumis melo

<400> SEQUENCE: 186

```
cagcgatctt cgtagaaact aattcaatgc tagctcatta tttgactttt ctcaggcaag     60
gctccgcgag gaagagaaaa ggtccaattt caggaaccaa gggcatggac aggttccggt    120
cagaagaagc tttttacgta aaccctttgc cagattgttt atgtcaagga gaattaccaa    180
atggaagtac gacttccatt ttcagatagt tcagtagaac atcaaagata aaatgctctt    240
agagagctca atgtatatgc aggcgaccac tcaacgtgtc accagctttg tacatccaat    300
aagccagcta cgatggaacg acggagtgtt tataacctga gttttggtag ttggcggagg    360
cggtgatggt ggtatagaag gaaggtcgag ggatggcaaa ccctttacgc caagtagtgg    420
aagggagtag ttggagatga acacattttg agaagtttcc aagatcactc catttggggg    480
agaggggatg ttggttattt agcacaattg ttttcatgtt ttagtaattt tatccaataa    540
tgagcgaggc attgaagcaa ttaaatttat ttttaatgat tttttcaccc ttccataggc    600
tttttctttt ttcttttcct tttagtttgc aaactttagc tccttttatc ggctgtcgaa    660
ctcatttttg aagttattga atgaaacaca gtttgggctg tgtcagatgg gtggtgaaat    720
tttatacatt ataattacta cataaaatga aatcatattg taattttcta tctatgccac    780
aatttttttt tattgcatca tgaggattaa attgtacgag tccaaatttg tacagtcatg    840
tttttaaagc tttcgagcat tgttactaat gcatggaaag gatcgattat caagtatcct    900
cccaacttca tgaaagttat tatttgtctt ctaaatttgt tttagaaaat gtttaattaa    960
ttatttgaga agaaagttta actaaatcct attggtttcc tctaaggttg tcatacttat   1020
ccaataacaa ttacgtttaa aatcaaaatt attctaatgg tataagacta atgttttaaa   1080
agcataaaat tgatgaggaa ggattggaag taatactatt tattttgaag gtaaacattc   1140
ttgaatgtct gtcctaaaat cactaatgtt ttcttagttt gagactttga gtcgttgaac   1200
ctctccatct ttataaaata taatacgagt ccttcacaat aacttaaaat atatactaaa   1260
tcctaattaa tgaaaaataa ataaataaaa ggtacaaaat cattaaagcc taaaaatcta   1320
ttactccttt aaaacttttc aagggtccct acaaccaatg agaaactacc acgtcatttt   1380
cacaatccgt tcagtgttta gaaaagtcaa atcgcaccgt ccatttatcc actcgtacca   1440
agtacggtag gaatctatct accgtccgat taagcacaaa gaagcacagt aaatgtcaat   1500
cgtgtccatc cgccgccata ccgcacatcc ttcgtccgac cggaaggccc tatataaagt   1560
cctttggttt tccgaatttc tacttcattc gcttttgaaa gatttcccaa tctcttcgtc   1620
ggccaaaatt ctctctcgct tctcaaccct tcttcggctt tttc                    1664
```

<210> SEQ ID NO 187
<211> LENGTH: 342
<212> TYPE: DNA
<213> ORGANISM: Cucumis melo

<400> SEQUENCE: 187
atccaggttt gtttctcttc tcttttttct tcctttgttg ttcttggaat atgtttaatt 60
tcatttgttt ttccattcaa tttcatgcta gattttacga ttaggttgat tttctgttcg 120
tagattgtaa ttgatggtta gggttagctt tttctcccat tccttctgga atctgtttct 180
tgaccttcga acttcgttga taaatcttta gaaacattta cataaccaaa caataattga 240
acaactcgtg ttgttatgcc tatataatag cggttaggaa actggaaacg cccttataat 300
tgaaatcgcc ttagaaattt gttttgattc atacagggta cc 342

<210> SEQ ID NO 188
<211> LENGTH: 2003
<212> TYPE: DNA
<213> ORGANISM: Cucumis melo

<400> SEQUENCE: 188
aactagacta gcgagtgcac aaccaaatta caaaatcctt aacagagaca accatctatc 60
tcctttaaag caacaataac atcaaccgaa ttagaatcca caatcagtaa agacgatgcc 120
gacaccaatg accaaaaccg atcaaatata gcttattacg gaccattact tcaacagtta 180
catcaacaaa aaaaaaaaaa ttaaacattg ctaataaaat ctgaaaatga ggaaaaagag 240
attaaaagtt ttgaagatag aaagaataaa tctgaaatgt tctaatttga tatataagaa 300
atatgaggta atatgacgaa agcattttga tagttttcac caactccctt tgtgaaagga 360
tacatccaac caattttaca atttctgttc aaattttgtc cacctaccct tctcttctgc 420
cccccaaggc tgctttcttt cttttattat ttgctaaatt accaaaaact attttcgaat 480
taaaccatct atttcaatta tatacgtcat tcgaatttta acttaattaa cattagtata 540
tgtttcggat caaggatagt ggtataaatc atcctaattt caatttgtat ttagaaaagt 600
tcaattatac ttaaaacttc taaaaatttt atattttaaa tttggatata aattaaattt 660
aagatttatg gaaggtaaat aattagagca aaacaaactt caaactatat ggaaaataga 720
aaaggaatat tttagccaaa caaaaacact tattatttta ttttgttttt ttgttttttt 780
tttaatttaa caattttttt ttttattggt tgaatgtgtt tctccactgg tgagtctcca 840
actttgacct gcaaagggtc tatatagcga gtttcacgag cacctaacca atatctgtgt 900
aataattccc atttttcttt catacccact tcatttgatc atctttttca caaccccgga 960
tctctaattc ttgggaattt gcctctttct cgatccattt ccaccgtaat tgaaaaatat 1020
tcaggtttga tttcttctgg gttttcattc aactgtctaa cttcattatg ccctttatgt 1080
gtttgttgaa agccccccac ccaccatcgt tcaatgcggt ttctttacct tttgttcggt 1140
ttcaacgatg atttagaagt tatagatgga tgctaattgt ttcgttgttg gtttgatcca 1200
ctgatctgcc tttgattggc ataaaaggag attctagatc ttgttttgat gttgtgattt 1260
atggatatta ttgttatagt cgtggaagtt tttcttgtcg ttctgcggta tatggttgtt 1320
ttattttttg agtggtaaat tgagcagatt gtgaactttt gggttttatg gtgaaagcat 1380
gaattagtaa atgtagagct gctgaaacaa aatggaggtt tgctagacct ctttgtgaat 1440
tcttaatggt cagcctccat cttaagaggc taagtccaaa aatttaaggc agtcttttgt 1500
tattgttaca aaggacaaga aataacagag gagttatttt aattgaatca agttggaaag 1560

-continued

```
aagtactact tcatgcttct ttcaaaagca ggtcaaagtg ctttaaagtc ttcttattta   1620
tttatttttt cctgaatcaa tttaaactaa tgatagaaag aagtgttttt taatgggtta   1680
ttataagtaa catcaatttt taaccattcc aaaagttaca tcaaattcat catagtgtga   1740
gtttacgaat tttggaagtt gtaattttaa gttaatactt cttttaagga aatgtacact   1800
ttgcatgttg tgttcataag ggtatttct ttgacaaacg cagcaaccac cccttaatga   1860
aaactacacc acggtggttg gtttttttctt gttatttttt tacttggaat ttacaataag   1920
ttgttatatt cggatatatg gcaaagcaga tatctgtttt tatccgaaac ctcataaatc   1980
ttgaatgtgc agcaggtaaa aac                                          2003
```

<210> SEQ ID NO 189
<211> LENGTH: 1024
<212> TYPE: DNA
<213> ORGANISM: Cucumis melo

<400> SEQUENCE: 189

```
tcattgatga agaaggaaac tttaagccaa ttcgacaact tatccattca acaactttcc     60
accttcagac attcagattc aactataata taacataaat tgatagtcaa gtcttttttg    120
agacaaccat aaatcatctt agcttcgaga actgtcactt ccttaaattg gtgaatatat    180
cacattccat ccattcaaaa ctttgtttcg aactttactg tagttatgaa tcaataaatt    240
gggagagata ttgttaaaaa gagagagcat atttgtttct attatttact ctctcctaag    300
agagggttaa ttagtctata aatgatctat tcttctcgtc cattgaaatt ttgttatcct    360
aaatttatga atacttctac ccaaaataaa gacttttttt ttttttgaaa agtgtcaaaa    420
aaacataaag aaattgacaa aacattcatt tttagtggat tttttacgga cgtaaatagt    480
ttgtttttgt ttcttttaat aatacaattt ttttttactt taaaaaaatat ttttgttata    540
aaaccaccgt atttttattc aattttaata aataaataaa tgaaagaata taaaaaaagag   600
gaaggaaaaa gaagccaacg aaccaacggt tgccacgtat caaaggtcta aagtgcgcaa    660
aacgaggcct tcggaaacca aaatgcgtgg cttcaattgg agcaagtaaa catggaaacc    720
acgtccattg taacgcttcc tgatctcttc tttacaaccg ttggattcga gtactttttc    780
tcaacgatta acgactgagt ggacctccac ttgcttctgt tccacgcgcg tgggattgac    840
gtgtggtcca cgcaactctt ctcgatagga tcattcgaga acatccttta cttaaaccgc    900
ctctctctgc ctcaatttct cgtcacttcc ttctccttct ttaccctttc cactgcggct    960
gattcttctt cgccttttat tctctcgtac gccgccatat tcttcacttc tttttccggc   1020
gaca                                                               1024
```

<210> SEQ ID NO 190
<211> LENGTH: 2001
<212> TYPE: DNA
<213> ORGANISM: Cucumis melo

<400> SEQUENCE: 190

```
attcgtcttc gcattatcag taaatttatc attttaagag tttgttcttt tttaaaaaaa     60
attaatcatt tcgataaagt tggagaattc aaaaatttct ccaaataatt tataaaaact    120
ttcggttata tatcgaaaaa attaacatgg tattaaaacg atcataactc aattaacata    180
aacactccct ctcaacttta ataccaaatt tctttattaa cgcaaaattt aaaatttgtt    240
tttaaaattt tcacataaca taatagaaat acttttcttt atggcaaaaa tacaataatc    300
aaaattgatt gatggtgaca ggacaccaca caatattttt aaattttgaa tatacgaact    360
```

```
atataataag atatttatga gattcccatc ctaaagattc ctagagattt ccttgtgtac    420

aatattacac aagtatcttg gaagtccaaa gtcctgagaa aaaagctatg tataaagtaa    480

tagtgtttgt cgtaggaaat ttacttcatt cgtgtcatta gctttttatt gaaaaaaaaa    540

attaggtata tcttagtgaa tctcacttaa tcgttgtcga tagttattct tttaatatca    600

ttatatacta aaatataaca atattgaaaa gctaaaactg tatataaaaa aaatgttacc    660

tctaaacttt tatcgtttat ttaaaagata aatatattct ttcaaaactt acaatcaaca    720

tcctacgact atcattatag gtacaaatct tttcatgttt acacaaaaat tagattttta    780

aatggtgtaa tgatgatata taacgaaatt ttgaatgatt actatttgag gttaccattg    840

taattggtcg tgttgtttga aatttaattt tattagaaaa tttgtcaaaa gtagcaaaaa    900

tgaataaact atttaaactt taggataaaa tcaagtgtta tgagtttttg tctagtttat    960

atatttttat ttttattgaa aaccctttttc ctatcttttc attacttcaa aatagtttta   1020

aaatgtctat taaggctaaa gttagtataa ataaaatttc ggaaattttt tttcgaaaaa   1080

aattgataaa ttatttatat tttatattaa agtcaaaatt tattacgcgt agatgtttat   1140

caaattttct ttctttttgt tgataatttt ccaaaatttg gataattttt taaaatagta   1200

aaattattat aaaaatgaaa acaaactatt tataccttaa gcaagaaata ctaaaaaggc   1260

aaaaattcat ttacttcatg aagcgtaaaa attaaatatt ttaccacttt ttgttatttt   1320

ttaccatctc tatcaattat ttgtaaaaag aaaactacaa aattagatgt tttttctttt   1380

ttaaggttta atcaatatta aaatttctta aattggcaga caagttggtg ttggtaatta   1440

cgaataaatc ccgaattgac taaaaataaa ttcttctcca agtaaaatag acacgtggat   1500

gaagaaataa gtgaatcaaa ggcatccaca gttcaataaa tggaaaaaac tactttctgc   1560

tgactcattc ataagttttc ataaaatttc ataagaaagg ccaaagggct tatgaaagtg   1620

aatgtcatag cagtaaatga agcacagcgc cattgaaaga caactcaaat tgcatgcaaa   1680

cccacataat tattcaacaa acccacatca aatttcccat aaagatcaat tctttagggg   1740

gttcaattac ccaaaagtga ggtagttgaa aaccattaaa caacaagaaa tcaacaattt   1800

tgtaatttgt ttgtacagaa gtaagagata aaatcatcgt taaccattcc tttatttcgt   1860

aatacaaccc atcaaccatc tctctctctc tctctctctc tctctcggcc tttatctttc   1920

tcttcctcaa ttatttaagt actacccaag tgagctaaaa gcaagttcag tggacagtgt   1980

tgtaagaacc actacagaaa a                                              2001
```

<210> SEQ ID NO 191
<211> LENGTH: 4175
<212> TYPE: DNA
<213> ORGANISM: Cucumis melo

<400> SEQUENCE: 191

```
tagtttggtt cataggttat agtttccaaa tttgttaggc tatcattaat caaacacaat     60

acttctcttg taggatggct gccccctata gtactttttt aacttaggag aaggatataa    120

taattatatt ccttttagaa aatataataa taattgtgta gtgctttgat ataccttaaa    180

ttagctactc acgtttttag gaggaagctt ccgttgcttt tcatggtgtt atgatctttt    240

ttattttata aaggactgaa ctttaaaatt tctctttcat ctattttgga ttggattcca    300

tctattttat acgggaagtg aactctaaga tttctcttca cctattgtga atcggactcc    360

gtcatgtagg tcaagactac gacagataag aatagacttc cacgaaagaa agtggtcaat    420
```

```
cgagatggct atatttggct ctttcagctc aatttcttct tttttccttg catgttcttc    480
cgttggtaca tttcttgcac ttttttgtt ctcacatgac taatgtattc caagtttatc    540
attggcattg tgcctctttt aggcttgtaa actctcgatc caaaattatc taggacatat    600
gtttcctagt gaagaaatac tagtatattc cttatgtcaa tatgtcaaaa ttttcaattt    660
cttaaccttt gagtaaatca atattatatt tttatggagg ttatttataa ttggaaaaaa    720
gttacaccca tctcaaccct aattaacacc aaatgaaatt gtaccatgcg gcacaatatt    780
tttttgtgag ttttttgcaa agagaaacaa agtagcagac aaagaacaaa cattccccca    840
aaaacagcag agaataccta agagagaatg ctctctcgta aaaaataata cccaagaatc    900
ttcccaaaaa gagggagtaa aagagtccaa aacaaacgaa ccgaagattg acaagaaggg    960
cactctcgcc ctccactgcg ccgctaaatt gtaagaagca tattttcttg agttaacata   1020
ggaataggtg taactcaaga gaaatgtaat tcgtagaatt gaactttgta tattaattta   1080
tatggtgttg tagatacaat ctttagtatt tactcatttg gtgctttctc tcaaatacaa   1140
tttaaattta gaacttttg atcttcgatt ttcaggaagt tggagttgca aatcaattcg    1200
agtttcaatc tctggaattt aataaaagtt tgatcttcca agttttcaat ctttcagaag   1260
acgatgatct tgatatggat aaaaaattgc acatcatgag agctttttga agtttaaatc   1320
ttcaattctc tagagcttaa attcttcctt aaaccaaaga tcaccaaatg aatgacaaat   1380
gtctctattt atcgaaaaat ttcatagact tttagatggg cttaggcaca ttacttgttg   1440
ggcttggact tgggcttatt tgcttggcgg gctcatgctc gagcccatta tttctttggc   1500
ctatttttca tgaggggctt gaacttggtt gtatacgaaa aaacttgact acctaaatct   1560
aatcaaatta taatcatcac aattttgacg tgttacgatt taattggcca aaaattcttg   1620
ttcaacactt gtctctaatc attttcctat ataatttaac taaaatattt aactttaagt   1680
aacttaaaag atatagttta attcgaatca aaatacaaat acaatttcgt ctatctattc   1740
ccatcataaa tgttgattga gattcatatt ataaacttct ttcaggaaaa gaaagaggaa   1800
aattcaccta aaccacgttt tcctattttg gtaagaatcc ccaaaccata aatcattcca   1860
aaattatttt ttttagatta gaaaagaaaa aagaaaaaaa gaaattcaca tggcgtaaaa   1920
tttcagcccc gtgagatatt ttcgaacccc cagatacaat ctacaccgtg aaaacaaaat   1980
cggacggtgg ttgctataat gtccgtttag aggcaatggc agggatgaaa ttgccaacgc   2040
aagataagga acgaataaga gaaggacacg taagtacaag tttaggatgg gcgggcccac   2100
agccacaagt gccgttcgtg cttatataca agtcgctcat attcctagaa gtgtctccaa   2160
ataaaggaaa gaaaagttca ctcatagaga gaaagagaaa aataaagctt cgttgccggc   2220
gatctgaagg cggcggccat ttctctcggg agagagaaag agagagattg atagagcgga   2280
gagttcgagg ctctctcaaa cttcggtcct cttcttctct ttcaggtatc gttcttctct   2340
atcccttcgt attctgtttc ctcttttctc tttcttcgcc atcatgctct ttctcttgtt   2400
ttgtactcac tcaatgtgat tgactttatg ttgtttttct gttttatttt tccattaatg   2460
ctcgttgtaa tgtgtagatc tatgataaga tttgaattat tgctcattaa tgtgttgcat   2520
gcttttgatt tcattttaaa aacagagatt actttctcta tattgattaa atcgttggat   2580
tttaggttct tacagagttt gtaaacagtg atgttaagga ttgctgagat ttatgactga   2640
tgagagttag tgtttgtctt ttagcttgtc gttttcctct ttgaaatcac atggattcga   2700
tctggatatc tgggtttggc tcgtctgaaa tggctacact atagcatatt tgagtttgtg   2760
atgttgaaga tttgttaatt tcttggaaaa tcgggagttc gttttgtttt tcctcttttt   2820
```

acaggtttta ttgattggtt tattgatcgg cgatatctcg ttttcaactt ccgaaatgct 2880
atttttcata agaagaaatt gtggatgtct ttttctactc gattagagat ccttgaaact 2940
atgccaaaaa aaattggttc tttcaccaaa ttgtttttg tcgtttgtga tattaatgca 3000
ttttcttatt cttaattaag ttcaagtatt cttttattat tttttaatga tggttgttgt 3060
aatggttttt tccctttac taaaagcttt ttccatgtga ttcaaaggtg tacttggggt 3120
ttcccggtct ttgttcccaa gtcaattagg atgggcgcca attcgatttt agcttctgta 3180
tcattggtgt atattctgtt ctggggagga aaaaaaaaaa gaaaaaaatc ttccgtccta 3240
cagtgtgctg agtaacaatt tgaccagcct tttctgccga aaactttttg aaattatttt 3300
ttaattgtga tttggtgaac ttaaattgtt ttaataaata aggtggattg aatcttaaca 3360
gaaacatcaa ataaaatcga gttttaaaaa aaaaacatat ttttagtgaa tgtttatttt 3420
atttaaaaga tctccatcag tcctgatgtt tcctagaaaa cttatacatc ataggtcttg 3480
attaacaaat ttggaggaag tcaataggtt attctttttt tctttttcca ttctagtttg 3540
aaacaatttt cttttctttt ttaacttaga aaataatggg tagctagaaa tatggaaatc 3600
aatgtatttt gggcttctcc ttgaaactgg agcagcggtc aatttctctt tcgtttgtat 3660
agatgtgata gaaatagaat gtttccttcg cttacggcat cagagagttg gaattggtct 3720
ttctcaacct caatatcaat taaatcaagt ttcgtcataa acaggttttt tttttcttcg 3780
tttcaaatgt ttggtagggt caaataattt gtaaaatacc tagccgtcca atatgataca 3840
aactggagga tttcacttgc tcttttaaat tacaaaaaat attttatcat tgatgttgcc 3900
tgtctgtgtt tatcttttct ctttccgcct caagtaggcg tctaattgtc ttggcaagtt 3960 ggtttttgt acttccgccc cttgtccttt ggcccttttg attaagtttt tcatttaatt 4020
ttctggtcgg cgtacgttga attattaggt ttgcatttaa tgtggtacct ggtgctttga 4080
ctcttatttg ataaggtatt ttgaagtcta aaacgttaaa ccctttgttt gatgtttatt 4140
tttttatcgt tccaggacaa tatcctttgg aaaaa 4175

<210> SEQ ID NO 192
<211> LENGTH: 1999
<212> TYPE: DNA
<213> ORGANISM: Cucumis melo

<400> SEQUENCE: 192
aaaagagtca tagtgaaaaa agctgagatc ataatagttt caccctaaac acaacttata 60
ataacacata ctatcataat atacacacca aacacagact ctatagtctt cactctaaac 120
gcagattaca atagtctgca ccccaaacgt agactattat aatcttctga ctattataat 180
actcttttca cttatcgccc caaacgtccc ctaagagaac aaagataggt tataaaagag 240
agatgagggt ttatattatg caacaagtat aaggttctag aacgatgtag tcttcaaagt 300
aacgaaagca ataggctaca cgagaaaaat atttttaaaa tatagtgctt tccctaaact 360
agatttcaat gacaaattat tataaaaaat agaatcatta atccaacatg gcttgcatgt 420
cacaccttgg ccaaaactga agacggatgt catactcgac ttcaatatat ttttttaatt 480
aattttcatg tgacaacaca taaatattta aaatttagat tgggttggat ttttttttcaa 540 gtgggtccca aaatactctt caaacccaaa ccaacccaac ttgtttaccc atctaataat 600
aacccaccag gttcaagaag acgaaccgaa ccgaaccgat ccggtctaac tttgtttcat 660
acttaagtcg aacttagcgg tacttttggt tcggttctcg gtttccccaa acagagccac 720

```
tcaaaattag atttagggtt ccgttcgcaa ttttcagcgc atttttattt gaatcggtcg    780
tttgttgaac acgttctctc tcagctggtt tagggttcat cgttctctct tctcgcgcta    840
tatctttctc tctctcaggt tcgtttcttt ctcttaggcc attttatcag aagatcctct    900
tcgttctccg attttctttc cgtgttcgcc ctcggtttct cagcagacgt aggaagtttg    960
gtttccgttt agtgaatctg tttggggtat tacgaatgat attttgtact gggctttccg   1020
catagtcttt ttctttctag gaatatatgc atctgagaat ttatttgttt ggcttttctt   1080
tataaagtat gaggacatat acatctcgat tgctaatcct tgattataat cttttttttt   1140
tctatgttgt ttgaatctgt tttttttttt ttaatttcaa taggtttttt gaatctaaaa   1200
atgtatttct tggatgaatt gcatactgtt gaattagaag tttattgatt agattgttga   1260
tatttgccct aagttccatg gataggtttg cgtctttcac cttttcgttt gctttttctt   1320
ttggctgacg acatcttaca tagcctctgc tctaaaaggt gccatgattt tttttcctgg   1380
ctttatctga gtttgcgcaa tttagatttg aagtgatgat ttgtctaaat ataaatatct   1440
atcggccata ctattttttg ttattttgag tttttcagga tgactgctag agaatgaaaa   1500
atcttgaaac attgtgtttt gaagttcaag gatcttgtag ttttgttctt ttctagacta   1560
tctcatttga tatagccctt taaatttaat caaaatttgt taatattcaa atcctcggac   1620
attttaatta tttatctaaa tagttgttta ggcattactc aggttgccca ctattttaag   1680
cttagaagcc tactctggtt gacctaaagt ttgcatgcta tttgccttat ttcgcacgac   1740
tctaaactgt tatagacatc ttttttcagc cttcaggtaa atgaacacaa aaaggagtga   1800
aagtctgact tctgtgtgat ggtcttttaa tcaattatag ggattaagat ggttttttta   1860
ttcattgtat aaatattaaa ttagaatgat gacaaccaat aatattaaaa ctgacaatgg   1920
aaggttcctt atattatttg gagtgtacat tacaacagcc tgattcttgg cttggcaggt   1980
tcctgatcac cttgtaaac                                                 1999
```

```
<210> SEQ ID NO 193
<211> LENGTH: 2000
<212> TYPE: DNA
<213> ORGANISM: Cucumis melo

<400> SEQUENCE: 193

atttatttgt ttagagataa gacgcacatg agaatatgag atggattcca ctccactcac     60
actccaattt ctacctatcc tattactgtt tactattatc attccacccc tcgacccctc    120
attcttcttc tcaccttact tttttatgat ttactactac ttcattttgg atcacaatct    180
gatcaatgct gggtgggctg ccctcggcct gtcaccaggc ccagcccact tccaaattaa    240
acctcttggc ccaccgccca ttgtccccat cccattccat ttaatattcc caaccttccc    300
tttttctttc ccaatgcgat gcttctccaa tatacctttc ctgccctcca tgtttccttt    360
ttactgcttt cttatattta taacacacct tctacagtct tttggctggg aatgctgcgt    420
atgtgaatga gattcaagat ttcgttgatg ttatttgagt ctctatattc ataagttttg    480
ttcttagttt tctctagacc aactgcaaga gttagcgttc catatgctca taagtttcag    540
atttctgctg tgtggtttga agacagtcat cgatccatgg gtgaattcgg ctttttatta    600
ttattattat tattatttat tgttgtctta cttttctatt tgaatcttcc tatctttttt    660
actcattgtt ggactctaat aattcttgct aaacacaatc tccattttta ttggacattt    720
taaatcccat ctcaactcat aattttagtt accttccacc atcaccatat ccaaatccga    780
aataaactca aataaaatcc ttcacgtgca tgtgctctcc atatattttt tctacatggt    840
```

aaaaataaaa tgaaaacaat ctaaatttaa taaaataaca tatatggcag acttttattg 900
atgtagagac tgggtgttgt acaagaacag tgcagccaag aaaaaaaaaa tacttccaat 960
gaatcgtaca ttttaaggat tatgaaacta actagttcca accatttttt cacgaccacg 1020
tgcttgttaa acacgcaagt agaatcaaaa tgtgggcttc ttcgctttat ataactgtga 1080
atcattctcc aaaaagggaa ggggatctca ttccctaatt caataaagaa aaagaaaaat 1140
gctagcgaac ttcatccatc tcattccttt tacctatttc atgagatgcc cattgtatat 1200
aagtattttt tttttattt cattttactt agtttactcc tcacctctaa aaaaaattag 1260
gagagtttgc taaatccatt ctcaaactta gctttatttt ttttaatttt atttaacctc 1320
gtcgtggatg ttaacctcaa atgtcagttc tttttattct atttattgat gttataattt 1380
actttaggat tccaatttta taaaaataag aatacaaata aagataaaga gtgtgaaagc 1440
cagaaagaaa aaaaaggaaa tcgtaatatg ggtaaaattg gtacaaattg ggtcccgtta 1500
aatattaact caaaaaatgc gagaaaatgg tagaaaagga aatagggggt aagagcaaag 1560
tagtggaagg agagcattga acatattctc tagtttttgc acttggatct aaacacgagg 1620
aattataggt ttattcattt actaattaca taaataggat tggattttaa aatttgaccg 1680
agtgattatg catatttgat agagttagaa aatagtggtg gggcaggtac aagttacaag 1740
taatgtataa gagatatgat gagcatatta ggaaactata gatttaaatt cgtccgtaaa 1800
taaataatta gaaatataat attcgagtgg aagggtatta gggttaggcg aaaccaattg 1860
cagttgcacc tataaaaccc cttttacgcc tccacccgct tcaacagcgg tctcggcgtc 1920
tacaactaca cactacacac tacacactac acactacaca gttgcagacc agaagcataa 1980
cgtaacgccg gtccacaaaa 2000

<210> SEQ ID NO 194
<211> LENGTH: 2000
<212> TYPE: DNA
<213> ORGANISM: Cucumis melo

<400> SEQUENCE: 194
tgaagagccg gaaaagcatg gcaaggtcaa ggcatttcag caagaatacg aggatgaatt 60
ctgggtttgt aagtccggtt cttcttcgga gttgtggttc gaatttcaaa cggccatgag 120
gagccctaca gcttaggaag cttcaggtct gagactctga ctccgacaga aattgctgat 180
ttttgtgtgt gttttgaata accattgtat gagtatgatt ggttgtatag gtttgaaatg 240
agggaaagtg atccatctcc ttgttgtctt tgcaggaaag gctcatattc gaccaagaac 300
gctttgtcat tgctttcgat aatcatagaa tccacaatgg tttggcatat tagcaaacaa 360
atcttcttta ggcattgcag acagaaaatt ggagagtaag ttattataat taaggattct 420
aaatgagtaa gaataataag atcaggcaaa gattggaaga actaaagcgt ttagtatttt 480
gtgtggtaca gaagaattgt aattagatac gtagtctaga gaagcagatg gtgagatttg 540
tgaaagacaa atgttagtgg agagtgaaga gtgtttctca acaaccgaca tagaaggatt 600
ctcagaaaat gagaaagatt tttattgcgc aaaatagctc ccatatcatc atatgccgtt 660
gccattccct ctggggttgc atgtaatgag taatggaaag ctgtagacag gctaacttca 720
ccctttgtct tgggtatagg gtgcattttt ggtcactcca ttttaagttt tctaataata 780
aaaggatgaa gaaaagatat tgaaaaacag ctcaggtttt aaagttgtca cacttgagaa 840
taatgcattt aacagttaga attttgcatc aacgtctttc aaatagaaaa gtaaaggaga 900

-continued

```
gtctagtttg agctggatag ctaaactggt ttaatcatat cttctatcaa gtggttagag    960
ttttagacct cccaacttta tatgtcgttg ccctaacaat gttgatggat gtttagtcct   1020
aagctctaac attgtccccg tatcatattt cataatagaa tgtactgagt aatggaaaac   1080
tagagaggta ggaagttgga cgaactttga atctatattg attttactat agtctttctt   1140
ccaagtctta atgagagctt tagctaaagt ttttcaaaaa ctcaaaagaa gtttttgttt   1200
tccaattctt cgatccatag attgtcaaga tggctataat atccttgaag ttaatagcct   1260
tcaaagtttc atagctttta tcctatgatc tttagaaatt caagagttat attctttaga   1320
actacagaac tttgatcttc gattcttcac ctcttccaga acctttatag tagagtttct   1380
tgaccttaca tgggcttggg attgggcctg gctacttatg ggcttagaga ttgaccttgg   1440
gtttaagcac attcgtttta cttggcccaa ttttcttaaa cttctgcaaa atcctaatta   1500
actaacacct caacaaaagt ccagtattaa atggggcata taaacaaaag ttaaacaaaa   1560
ttgtcgtaca gaatcctaat ttgctaacct cagcaaattt tatgccattc gtccttgtgt   1620
atctaattag tgttaatttg aggaaatata ataatataga cgtaggacgg atattggtat   1680
ttggtgcaac atcctccgaa ccaattcctg gaaagtaatt ggggcaacaa gataatgtta   1740
tcgtcagttt caagtgcaaa acttgccacg tggaacagcg gcaacatgat atctcaaata   1800
tggacctctc acccggtcaa gcttccacca ccaccaccac ctccgtattc taaaataaag   1860
tcaggaacaa gaacagacac accttaacaa aaccaatatt cttcatctct atctctctct   1920
catttcagca tagaagagag ctgagtaaaa ggaaaaaact tcaatcaaat ttgacagaga   1980
agagcccaag agaaaaccaa                                               2000
```

<210> SEQ ID NO 195
<211> LENGTH: 1400
<212> TYPE: DNA
<213> ORGANISM: Cucumis melo

<400> SEQUENCE: 195

```
tatatatatt aacttttaaa attttgaaaa cgtcatagat aaattatata caaaataaaa     60
agtttgatta tttacgaaag ttaaaaagtt tatccgaaag ttgactcaac gataaaaaca    120
ctaaatatca cttttagaga tgatgatatt atacataaac atacgaactt acgcgtcaaa    180
cttttatact aacacaagat caaaacaact ttgttgagta gtgagaattt tatctgctga    240
tatggttgaa acttgggaag caagcagagg aagttccatt cattaccaaa atccattttg    300
tattcatcaa aatatgaagt ttagcgactt gataaagtca agtcaagtgg tcctatcgat    360
ttgttaatgt caatgtttgg ttttgaattt gatacctatt agacaatgat atataatttt    420
aagtatggtt tacactgtga tgctttatat atttttaaat gtaaaatatt agaacttgta    480
atttcaataa attttaaaaa tgattttgtg ttatttcctt ttttaaattg aaatatcaat    540
gtatcaatat tgcgtcatag agtattgcaa cacaacctta tgttaaattg tttattgctt    600
attgctctaa ttcaactcct tcatcaaatg tgcacagaat ttaaacaaga aaaagagtag    660
gtgctttttt actaaaatat actaaaagct ttttatacca aatcttatga caaaatcatt    720
ccaacaaaat gactatttaa atataagatc gaatccctaa tttaaaaaaa aaaaaaaatc    780
aaagatgtta atttctatta ttaaactcac tttagcgtag ctaacaaaaa aaggaaaatg    840
agaggctaca aagcttgagc cctctgcctc cctttattgc attgtttgaa attagatcaa    900
tactttgtat ttttttcaaa atgaaaaatc gtacatagaa ttaattctat ggacaaaaaa    960
tcagagaagg aaataatcta gaataaaatt cgatttttaa cccaaaaaaa aaaaaaaaaa   1020
```

```
ctcgattctg atttttgtaa gcaatcaccc aaattaccat aaataaatgg tattcaatta   1080

ctcaattatg gatattttag aaatgataaa tttttattca taaactcttt tctttctctt   1140

tcaaaaagaa aaaaattagc ataaacttca atgacattta tttattcttc ttcgtttgga   1200

gtcaaaagtt taaattgagc atcagtccag cccaaaagcc cacgaagaag cccaagaatc   1260

ttcagctttt tcgttcaaac gtcccttttt ggtttataaa attaaagaaa ataaaaacta   1320

aatttatttg ttatttaaca aaacattttt ggttaagaca ttctctttga ttatttttct   1380

tccattcttc gtcgtcaatc                                               1400


<210> SEQ ID NO 196
<211> LENGTH: 2019
<212> TYPE: DNA
<213> ORGANISM: Cucumis melo

<400> SEQUENCE: 196

tttatattta tgaaaatgaa gtctctaaac aatttttcta ctcccaaatt tgttgatttt     60

tctgcctatt ctttatcggt gctttaaaaa atgaaaccaa atttcaaaac taaaaaaacc    120

aagcttttaa aaaaatgtta ggttattttt gaaattcaac taaatgttga actcttttac    180

ttattaaata ggcaaattat tgaaataaat ttagagcaag taagcttaat ttttaaaact    240

aatatactta ccaaatcgag gactaaaata ttcaaatact ctttaaaatt aagattaaca    300

ttaatcactt tgttatgttt aaaaagttgc agtgtcactt gaaccttttt aaattaatat    360

aatgaaaatg aatccaactc aatatatata atatctatat tattaatctc gatgtcagat    420

gtttgatacg cacatatctc aaaaattata cctcaactaa catcggtgca cgatgtatta    480

tttcgtgagg ataaaaatcg tttttagtat aaattgatgg aaagattatt tgaattactg    540

aaaaatgcac cggtacatta tttgaaactt ccccttcatt taaagaggct aatattagaa    600

aaagacacgc tgaggctatt tttacaatta atgtgggctg ttgacttggc ccagcccaaa    660

acataaaccc taaagtagca caaacaaacg cctctttctt cttgaaaccg catattaagc    720

gttttatcac ttctcaccac ctctcattcc tcctcttccg cacgttgttt cgctcctcaa    780

cgggagtgcc ttccctttgc tctccctcca ggttcttctt ccttctcatc tcatttccaa    840

gtaatttcat tccgtttctt ttctcttaat cgtatcttgt tcagactctt tcgcgttttt    900

ttttagttgc gccttaccag atctgtgttt tcactcgttt ctattcgata catgcttcca    960

agatccattt cttaatcgca tgtattcggt tgattggatg attgtctttt tgtaagtttt   1020

gattactttt ttggaatgga tcggttgaac caacggggtt taagtcgatg gaagtaggtt   1080

atgttaaaga tttgcttctt ttttatgaag atgtgtgtgt tctttttttct ttgctagatg   1140

atgttattat ttgattgttt taacagtcgt gttttgtttt tctgcagttt atagtcctcg   1200

gtcttttgaa gacttgtcaa gatggttagt acacctcttg tcatcgtgat tttgattgag   1260

tgatgtgtta agtgcttctt taggttacag ctaacgcgat tttttatatt caattgtgcc   1320

tgtgcaggtg aagtttacag cagaagagct ccgtcggatt atggactata agcataacat   1380

tcgtaatatg tctgttattg ctcacgtcga tcatggtaag ctacttagtt taagtttatt   1440

tatgccgagc gtctatttaa gaagattaac atcttagctt tcatttattg tttatttggt   1500

aagcatcgtt tctttttctc cgaggaactg tacatgtcag ttcacatgac aataaaacga   1560

tcttccttgg acattagttt ttgaagttca attagacgcc aaattttgtt ggttaaaaga   1620

tgcttgtgga gcatatggac ctaatggaat cagtactttt tgatggatgg acttgtcttt   1680
```

```
tgttctttta ttttcaaaag aaattgcatg tgcaattaca tcatctttga tcgaaagatt   1740

gggtaattgg gtaattgggg taaagacatg ttgtaaaaac taatgttaat tatcaattac   1800

cattatatac cttatttagt gcttatttat atccttttc cccatttcag ggaagtccac   1860

tctcacagat tctcttgtgg ctgctgccgg tatcattgca caagaagttg ctggtgatgt   1920

acgaatgaca gatactcgtc aagatgaggc agagcgtggt atcaccatta aatctactgg   1980

aatctccctc tactatgagc agaagagctc cgtcggatt                          2019
```

<210> SEQ ID NO 197
<211> LENGTH: 1999
<212> TYPE: DNA
<213> ORGANISM: Cucumis melo

<400> SEQUENCE: 197

```
aaaaggcgaa aaaaaagtta gcttcccgag aaggagaaga cgaggaagag tttgacttcc     60

cggggagata aagtttgtgt ctcgagggaa tctctaatct ggagttgacc gtcgacttat    120

gtgtcgagcc tggatttagt tgcatggtgc gacaaagcga taaggcggca tatgtaaagt    180

agtaattcaa aactagcggt taaagaaata atcagccaaa aaatttagta caaatacggg    240

tggaggccct aagtgaagtg ctgctattca gaggttttgg caaaagagtg caaagagttg    300

agttgtgcag agaaagtact aggtgaggag aggcgtttgg aaaagaaaag gatcaaacat    360

ttgcatgagt gatattctta aactaaacac tcttgtgtga gtgacttgcc taagctaaac    420

actcttgcat gagtaacttt cttaaactaa acgttttgta atgttttctt aatggattct    480

tttcgagtct gagttatgct taacacgttt tgtttctctc gtgttattgt tgttgttgtt    540

tgaaaagaga aaactattgt tttctatgtg ctgattgtga tgaatgtgtg cgaaccatta    600

gccttaatcc tatcaagtga atagtgatta tgtggtgtgt gcacataatg taaatgacat    660

tgtgtggatg gccagtgcaa caagaaatga atcagaaagc ttcccaaata ctgtgaatgg    720

agtgaacatc acactagctc aatggcaaga tattggcgat agtgaatcac aataggcttg    780

acaaggggaa ggattcatgt tcttggttga aaggaataag agaggctaat gtgagatttc    840

tgtgatttgc aaaatgaggc gttggaagac acgtttgaga aatgaaaacg aattagtgct    900

tgacttgtat tcctaaaaaa gttgtccaat atcttcaatc actaaatatt tgatgtgcct    960

aagttttcct tccttagttg ttgaggcgtt gaggccgagt aaggaaagat aagataatta   1020

tgacgttgaa aagctggtca agttatccat ctttggatgg tttaaagtta ttacatgtag   1080

ggagggttgc attccaattt tgtgtgtgag atgagtctta ttttcgagat gggttgctag   1140

gcgatcaagg agaagtataa gaaatgagtt cttatactct tgaacaactt gacacgaaga   1200

ataacatcct agtggatgaa ggaaggtgat ggaacttaaa gtttaggttt tatttttggc   1260

cttgtgataa aaaaaatgta attgtaaagt attagatcaa gtaataaaaa cagagttgtg   1320

ttttctattt ttgctgtgtt gggttgtgta tctttattgt gcttatggcc tagttgctaa   1380

agagttaagg ttattaccta aatgttttac ggtgtgttga gttgtaaaga tctcctgagt   1440

taaagttgga attttgtatt ggagattgtt ttgagaagtt tagcttacta attgtttaac   1500

tcattaggtg tctaagcgac acgcctcctt ttggtcgcat gaagtggcta gcagggtggg   1560

gcggaccggg gtggggtgtg ataataaacc taaaaaatca cccagataag cctaaattat   1620

acgttgaagt taaacttaca atttgattag aagaagaagg aatatctgat ttggacatga   1680

attaattaca aatacggcgc caatcataca aagcacatgt aagatcaacg cattctacac   1740

tcaatctcag ccgttgattg ctttcaatcc ttcaaaaaga aaaaaagaag ggcagttcgg   1800
```

gcagagtcat acctacccgt tgactataaa agcaactaca aatcgaaaac ctccatttct 1860
ccgttaccat tacagagaaa atcaaagaaa tttggcgttg agagattggg agagaggttt 1920
ctctttctag ggttgcttct tcttcttcat cctccattgt tgcaaatttc acttccttct 1980
cctcttgttc tcatctccc 1999

<210> SEQ ID NO 198
<211> LENGTH: 1578
<212> TYPE: DNA
<213> ORGANISM: Cucumis melo

<400> SEQUENCE: 198
atatatatat atataattta actaaataaa caaatgaaag aaaaaagtga gttcccattc 60
ggaaaatgca gatggatcca tttcttcaaa tattaaaaaa taaaaaaata aaataaaata 120
acttaaatat gcaaatagaa agaattttaa tttctggatt atccatatgg gacaattttt 180
aaaactcatt tattttattt tttttattta tttgattttg atatatctat ggggaaattt 240
ttcgtaataa ttttcgaaaa aatattgcaa tatatcattt gatcagatcg gtattattaa 300
atctctatca catttggtct taaattatcc aaagattcct ttaagataat ttagataacc 360
atctacagat cactactata atcaacaaaa ggaacaactt aaattattta aacaaattca 420
ttaatattag actttgtgct tcattagaaa atgatcttat cacaaccaca accatagtgg 480
tggtttaaaa ttttatttta aactcttatt agtattattt taattcatac ttaatcaaac 540
taattacttt aaaaaacata tatatataaa taagttaaat cattccccct tatatctaaa 600
taacataaaa aaaaattgtt tactctacaa gaagtttgta tatatatatg ctcggtacta 660
tttagcatct ttataataaa atttctaaat caatttttta tatctcttta ttaaatgtat 720
agtcatcaaa aaatttaacg agataatgtg tcaaagattt attttattaa cgttcataaa 780
tatcaaatta tacttagctt ataattgaaa acatgttcga taaatataag taaataaaat 840
tttatttttt ttaaatatta caaaataaac taaataagtt ataaatatga caataaacat 900
tatatatttt attatattta taaatactta ataatttagt cgtttaaaat aattttctta 960
attttcaaaa catgtttcat atgttaataa taaataaatg gaaaaccttc caaaagaaga 1020
aaaaaagata tcttaaaatt taaaaattga gattttgagg atcaataatt aataaaagaa 1080
ggattaataa gggtgaaatt aaatcccaaa aagaaaattg aaaatgaaga aaagaaaagt 1140
gaagaaataa ttgaacgtgg gaagtggatt cgatgtctcc agagaacaag cgaaaggaga 1200
cgaaatccac ataatttgca cgttacgtgt ccctatcaac cgtagacacg tgtcaacatc 1260
tcaacaccct acgccgaatt gcttcgctgg atctggacgg tcatcggata acagcggcaa 1320
ccaattaata tttcccctta tatttcacag cctggccatg tccaccaatc acgttcaact 1380
attaattcat ttttcatttc ctttttcttt ttttttttaa ttcccctcaa ttattaccga 1440
caacctgttg tagccggtta accctaccct ccaacgttcc attataaggc ctagaaaatg 1500
gacgtgaaaa tggagtacta caaactacaa ttaattttaa agaattttaa ttttaaagtt 1560
ctctaattac tattagcc 1578

<210> SEQ ID NO 199
<211> LENGTH: 1023
<212> TYPE: DNA
<213> ORGANISM: Cucumis melo

<400> SEQUENCE: 199

```
ataataataa taaatacata atagtaataa taataaaaaa aataaaaaaa taataatagt     60
aatgaaaatc aatagaataa ttttaaaatc gggaaggaag tcgtgtacaa tccttgcacg    120
ttggagagtc aaatggccta agtggtgatg tggaagtcgt gtaccgggta cacgattttc    180
ctacaagtca ataataataa tatggttatt tttctagttt agggttcatg acaaaagatt    240
gttcagtcga ctggatgtag acaaatctaa aaaataaatt aaaatctaat atgaaaacta    300
gttttaattt ccaaattatt aagggttgaa ttcgaccaat aaataataat aatacggtta    360
ttttgaaatt taggaaattg aataaagttg ttaaaatctt caagcaaatt gttaagcccc    420
gagatattaa gaagaggtaa taatagagga ttctatattt ataacatgtt aaaattaatt    480
gcaaactcat aaatgcatca cacagattaa caacatagga gggacttccg ataaaagtgc    540
aaatattgaa ataattacag ttcgcgaaca tgagtatttt aatattttat aaaatagtat    600
gcacgtgtat ttttgccaaa agaaaaaaag aatagatttt gccatttttc aaagtgactc    660
tcggttatat cttttatggc gattgtattt tatagcgtat gttgtttgta gttaacccat    720
ttctcattgg caaattcaat cgtgggccac aacgtttggg catagcttca atttggatta    780
actcaattat gtctgaatgg gttggactag ttcggactct tcggctgggc cagaatcaga    840
ttcgggccgc aatctgttca tttcacacct atatccaaac acccccaaaa tcgataccca    900
tcaaacccta actctcaata acccccatat ataaattcct tctttagggt tttttcatcc    960
tcatacactc tcaaacctcc ggtcattctc attttccctg ccgcttcttc aataacccta   1020
atc                                                                 1023
```

<210> SEQ ID NO 200
<211> LENGTH: 1654
<212> TYPE: DNA
<213> ORGANISM: Arabidopsis thaliana

<400> SEQUENCE: 200

```
tgatgattct tgttgttgta gttcttttta aaagtcccac ctgagcctct atagactctg     60
attctctttt aagttactat tttcaccgct ctctaataag gctcgtgatt ttttgggagc    120
catactgtat actcgccggc cctctcacga tgttgttcaa ttcacagact aaatttgatt    180
tatctatttc gccaaaacat aacttcatta aaaaatgttc tccaaataac taaacgaatt    240
aaataaaaga aacctttcat gtaaagttaa aggtatgaga ctttaagggc agttgctgaa    300
cattcgtaac acatgggaga acaatagaga aagttgaaaa gaaacgtagc atatagaaaa    360
attatctttg taaccaagtt gatttagaaa aatatcacta tttgtgaaaa atactagatc    420
agtttattat tacttttttt tttttgtata ttcacaaata tcatattcat atagaagaaa    480
ataaacaaag ttgtaaaaat ctggcattta aaataaaatt gaacacttca atttatttcc    540
tttcataata ataattttgg cataagatat ttgcaaattg atctggttcg gtatggtcga    600
caaaataatt ttccacgcta cccttccagc cgtccattca ctatttgccc tcaacgttac    660
caaataacgg tccagattcc tagggcaaga tctaacggtt agcaagtaaa gtcgtaccat    720
cagaaagaat aacaattctt tcacaaagta aacataacca acggttaaca agttcttagg    780
gttaaatcag taagatccaa cggatattaa attgcaaggc ccaaatagtt tttttgcagc    840
agataataac tcgtccccac tggcgagtga cgaccgagac tctgtgaccc tatttttcga    900
gacgataaaa gggcaaacaa tcgctctttt caaagctcgc ctcttcacca cagagaaaac    960
ttcgtctctc ttctctgctt cgccctctca tttcctgtga gataaaggcg gagtctctct   1020
ccagttattt tgctcatcca tcgattctta ggtatgactc gtttctctca gatctgtgat   1080
```

```
tctttataat ctcgtcgttc ttcaaatcat tgttatattc gtttcttcga tctgtgtttt   1140

ttagatctgt aaggtaaatg agacgtttcg atctgtagat ctgattgtta tattgataga   1200

ttatgttatc tgctttgctt aaagtccgat cggaatgttt tgtgctcatt gtcgaatatc   1260

tgatgtatcg gtttcataga tctgcttctt tttgtgcgtt tcgttgatct gataatcttc   1320

tagtgatcaa aatcgtttgg atctgttgac tttagtttaa aatgtatccg atctgatgtc   1380

gaggcttcat tattggaagt tgttattgtt gtaatcctga tttaagttgc tgttcttaaa   1440

tttatatgat ctttgcgtta taatatgaca tggtagatct tggttcatgg ttcactgttt   1500

tccaataaac ttggtttgtt tggttggata gcgttctgtg atacgaccat gtcttgtgtt   1560

ggataagaat tctctgaatt tccttggctg gtttgtagta tgttattcac gtctggtttc   1620

tcatcaatga ttatgtgatt ttgcagagtt cacc                              1654
```

<210> SEQ ID NO 201
<211> LENGTH: 712
<212> TYPE: DNA
<213> ORGANISM: Artificial sequence
<220> FEATURE:
<221> NAME/KEY: misc_feature
<222> LOCATION: (1)..(712)
<223> OTHER INFORMATION: Chimeric transcriptional regulatory expression element.

<400> SEQUENCE: 201

```
ggtccgatgt gagacttttc aacaaagggt aatatccgga aacctcctcg gattccattg     60

cccagctatc tgtcacttta ttgtgaagat agtggaaaag gaaggtggct cctacaaatg    120

ccatcattgc gataaaggaa aggccatcgt tgaagatgcc tctgccgaca gtggtcccaa    180

agatggaccc ccacccacga ggagcatcgt ggaaaaagaa gacgttccaa ccacgtcttc    240

aaagcaagtg gattgatgtg atggtccgat tgagactttt caacaaaggg taatatccgg    300

aaacctcctc ggattccatt gcccagctat ctgtcacttt attgtgaaga tagtggaaaa    360

ggaaggtggc tcctacaaat gccatcattg cgataaagga aaggccatcg ttgaagatgc    420

ctctgccgac agtggtccca aagatggacc cccacccacg aggagcatcg tggaaaaaga    480

agacgttcca accacgtctt caaagcaagt ggattgatgt gatatctcca ctgacgtaag    540

ggatgacgca caatcccact atccttcgca agacccttcc tctatataag gaagttcatt    600

tcatttggag aggacactct agacagaaaa atttgctaca ttgtttcaca aacttcaaat    660

attattcatt tatttgtcag ctttcaaact ctttgtttct tgtttgttga tt            712
```

<210> SEQ ID NO 202
<211> LENGTH: 938
<212> TYPE: DNA
<213> ORGANISM: Arabidopsis thaliana

<400> SEQUENCE: 202

```
caaaagccga gccgataaat cctaagccga gcctaacttt agccgtaacc atcagtcacg     60

gctcccgggc taattcattt gaaccgaatc ataatcaacg gtttagatca aactcaaaac    120

aatctaacgg caacatagac gcgtcggtga gctaaaaaga gtgtgaaagc caggtcacca    180

tagcattgtc tctcccagat tttttatttg ggaaataata gaagaaatag aaaaaaataa    240

aagagtgaga aaaatcgtag agctatatat tcgcacatgt actcgtttcg ctttccttag    300

tgttagctgc tgccgctgtt gtttctcctc catttctcta tctttctctc tcgctgcttc    360

tcgaatcttc tgtatcatct tcttcttctt caaggtgagt ctctagatcc gttcgcttga    420
```

ttttgctgct cgttagtcgt tattgttgat tctctatgcc gatttcgcta gatctgttta 480
gcatgcgttg tggttttatg agaaaatctt tgttttgggg gttgcttgtt atgtgattcg 540
atccgtgctt gttggatcga tctgagctaa ttcttaaggt ttatgtgtta gatctatgga 600
gtttgaggat tcttctcgct tctgtcgatc tctcgctgtt atttttgttt ttttcagtga 660
agtgaagttg tttagttcga aatgacttcg tgtatgctcg attgatctgg ttttaatctt 720
cgatctgtta ggtgttgatg tttacaagtg aattctagtg ttttctcgtt gagatctgtg 780
aagtttgaac ctagttttct caataatcaa catatgaagc gatgtttgag tttcaataaa 840
cgctgctaat cttcgaaact aagttgtgat ctgattcatg tttacttcat gagcttatcc 900
aattcatttc ggtttcattt tacttttttt ttagtgaa 938

<210> SEQ ID NO 203
<211> LENGTH: 633
<212> TYPE: DNA
<213> ORGANISM: Pisum sativum

<400> SEQUENCE: 203
agctttcgtt cgtatcatcg gtttcgacaa cgttcgtcaa gttcaatgca tcagtttcat 60
tgcgcacaca ccagaatcct actgagtttg agtattatgg cattgggaaa actgtttttc 120
ttgtaccatt tgttgtgctt gtaatttact gtgtttttta ttcggttttc gctatcgaac 180
tgtgaaatgg aaatggatgg agaagagtta atgaatgata tggtcctttt gttcattctc 240
aaattaatat tatttgtttt ttctcttatt tgttgtgtgt tgaatttgaa attataagag 300
atatgcaaac attttgtttt gagtaaaaat gtgtcaaatc gtggcctcta atgaccgaag 360
ttaatatgag gagtaaaaca cttgtagttg taccattatg cttattcact aggcaacaaa 420
tatattttca gacctagaaa agctgcaaat gttactgaat acaagtatgt cctcttgtgt 480
tttagacatt tatgaacttt cctttatgta attttccaga atccttgtca gattctaatc 540
attgctttat aattatagtt atactcatgg atttgtagtt gagtatgaaa atattttta 600 atgcatttta tgacttgcca attgattgac aac 633

<210> SEQ ID NO 204
<211> LENGTH: 315
<212> TYPE: DNA
<213> ORGANISM: Gossypium barbadense

<400> SEQUENCE: 204
tgatcacctg tcgtacagta tttctacatt tgatgtgtga tttgtgaaga acatcaaaca 60
aaacaagcac tggctttaat atgatgataa gtattatggt aattaattaa ttggcaaaaa 120
caacaatgaa gctaaaattt tatttattga gccttgcggt taatttcttg tgatgatctt 180 ttttttatt ttctaattat atatagtttc ctttgctttg aaatgctaaa ggtttgagag 240
agttatgctc tttttttctt cctctttctt ttttaacttt atcatacaaa ttttgaataa 300
aaatgtgagt acatt 315

<210> SEQ ID NO 205
<211> LENGTH: 315
<212> TYPE: DNA
<213> ORGANISM: Gossypium barbadense

<400> SEQUENCE: 205
accatatgac actggtgcat gtgccatcat catgcagtaa tttcatggta tatcttaatt 60
atatggttaa taaaaaaaag atggtgagtg aataatgtgc gtgcattcct ccatgcacca 120
atggtgaatc tctttgcata catagagatt ctgaatgatt atagtttatg ttgtagtgaa 180
attaattttg aatgttgttt ttaaatttta atgtcacttg gcttgattta tgttttaacg 240
aagcttatgt tatgtatttt actttaatga tattgcatgt attgttaatt taacattgct 300
tgatcagtat actct 315

<210> SEQ ID NO 206
<211> LENGTH: 2001
<212> TYPE: DNA
<213> ORGANISM: Artificial sequence
<220> FEATURE:
<221> NAME/KEY: misc_feature
<222> LOCATION: (1)..(2001)
<223> OTHER INFORMATION: Codon redesigned coding sequence.

<400> SEQUENCE: 206
atggtccgtc ctgtagaaac cccaacccgt gaaatcaaaa aactcgacgg cctgtgggca 60
ttcagtctgg atcgcgaaaa ctgtggaatt gatcagcgtt ggtgggaaag cgcgttacaa 120
gaaagccggg caattgctgt gccaggcagt tttaacgatc agttcgccga tgcagatatt 180
cgtaattatg cgggcaacgt ctggtatcag cgcgaagtct ttataccgaa aggttgggca 240
ggccagcgta tcgtgctgcg tttcgatgcg gtcactcatt acggcaaagt gtgggtcaat 300
aatcaggaag tgatggagca tcagggcggc tatacgccat ttgaagccga tgtcacgccg 360
tatgttattg ccgggaaaag tgtacgtaag tttctgcttc tacctttgat atatatataa 420
taattatcat taattagtag taatataata tttcaaatat ttttttcaaa ataaaagaat 480
gtagtatata gcaattgctt ttctgtagtt tataagtgtg tatattttaa tttataactt 540
ttctaatata tgaccaaaat ttgttgatgt gcaggtatca ccgtttgtgt gaacaacgaa 600
ctgaactggc agactatccc gccgggaatg gtgattaccg acgaaaacgg caagaaaaag 660
cagtcttact tccatgattt ctttaactat gccggaatcc atcgcagcgt aatgctctac 720
accacgccga acacctgggt ggacgatatc accgtggtga cgcatgtcgc gcaagactgt 780
aaccacgcgt ctgttgactg gcaggtggtg gccaatggtg atgtcagcgt tgaactgcgt 840
gatgcggatc aacaggtggt tgcaactgga caaggcacta gcgggacttt gcaagtggtg 900
aatccgcacc tctggcaacc gggtgaaggt tatctctatg aactgtgcgt cacagccaaa 960
agccagacag agtgtgatat ctacccgctt cgcgtcggca tccggtcagt ggcagtgaag 1020
ggcgaacagt tcctgattaa ccacaaaccg ttctacttta ctggctttgg tcgtcatgaa 1080
gatgcggact tgcgtggcaa aggattcgat aacgtgctga tggtgcacga ccacgcatta 1140
atggactgga ttggggccaa ctcctaccgt acctcgcatt acccttacgc tgaagagatg 1200
ctcgactggg cagatgaaca tggcatcgtg gtgattgatg aaactgctgc tgtcggcttt 1260
aacctctctt taggcattgg tttcgaagcg ggcaacaagc cgaaagaact gtacagcgaa 1320
gaggcagtca acggggaaac tcagcaagcg cacttacagg cgattaaaga gctgatagcg 1380
cgtgacaaaa accacccaag cgtggtgatg tggagtattg ccaacgaacc ggatacccgt 1440
ccgcaaggtg cacgggaata tttcgcgcca ctggcggaag caacgcgtaa actcgacccg 1500
acgcgtccga tcacctgcgt caatgtaatg ttctgcgacg ctcacaccga taccatcagc 1560
gatctctttg atgtgctgtg cctgaaccgt tattacggat ggtatgtcca aagcggcgat 1620
ttggaaacgg cagagaaggt actggaaaaa gaacttctgg cctggcagga gaaactgcat 1680
cagccgatta tcatcaccga atacggcgtg gatacgttag ccgggctgca ctcaatgtac 1740
accgacatgt ggagtgaaga gtatcagtgt gcatggctgg atatgtatca ccgcgtcttt 1800
gatcgcgtca gcgccgtcgt cggtgaacag gtatggaatt tcgccgattt tgcgacctcg 1860
caaggcatat tgcgcgttgg cggtaacaag aaagggatct tcactcgcga ccgcaaaccg 1920
aagtcggcgg cttttctgct gcaaaaacgc tggactggca tgaacttcgg tgaaaaaccg 1980
cagcagggag gcaaacaatg a 2001

<210> SEQ ID NO 207
<211> LENGTH: 1653
<212> TYPE: DNA
<213> ORGANISM: Artificial sequence
<220> FEATURE:
<221> NAME/KEY: misc_feature
<222> LOCATION: (1)..(1653)
<223> OTHER INFORMATION: Codon redesinged coding sequence.

<400> SEQUENCE: 207
atggaagacg ccaaaaacat aaagaaaggc ccggcgccat tctatcctct agaggatgga 60
accgctggag agcaactgca taaggctatg aagagatacg ccctggttcc tggaacaatt 120
gcttttacag atgcacatat cgaggtgaac atcacgtacg cggaatactt cgaaatgtcc 180
gttcggttgg cagaagctat gaaacgatat gggctgaata caaatcacag aatcgtcgta 240
tgcagtgaaa actctcttca attctttatg ccggtgttgg gcgcgttatt tatcggagtt 300
gcagttgcgc ccgcgaacga catttataat gaacgtgaat tgctcaacag tatgaacatt 360
tcgcagccta ccgtagtgtt tgtttccaaa aaggggttgc aaaaaatttt gaacgtgcaa 420
aaaaaattac caataatcca gaaaattatt atcatggatt ctaaaacgga ttaccaggga 480
tttcagtcga tgtacacgtt cgtcacatct catctacctc ccggttttaa tgaatacgat 540
tttgtaccag agtcctttga tcgtgacaaa acaattgcac tgataatgaa ttcctctgga 600
tctactgggt tacctaaggg tgtggccctt ccgcatagaa ctgcctgcgt cagattctcg 660
catgccagag atcctatttt tggcaatcaa atcattccgg atactgcgat tttaagtgtt 720
gttccattcc atcacggttt tggaatgttt actacactcg gatatttgat atgtggattt 780
cgagtcgtct taatgtatag atttgaagaa gagctgtttt tacgatccct tcaggattac 840
aaaattcaaa gtgcgttgct agtaccaacc ctattttcat tcttcgccaa aagcactctg 900
attgacaaat acgatttatc taatttacac gaaattgctt ctgggggcgc acctctttcg 960
aaagaagtcg gggaagcggt tgcaaaacgc ttccatcttc cagggatacg acaaggatat 1020
gggctcactg agactacatc agctattctg attacacccg agggggatga taaaccgggc 1080
gcggtcggta aagttgttcc atttttttgaa gcgaaggttg tggatctgga taccgggaaa 1140
acgctgggcg ttaatcagag aggcgaatta tgtgtcagag gacctatgat tatgtccggt 1200
tatgtaaaca atccggaagc gaccaacgcc ttgattgaca aggatggatg gctacattct 1260
ggagacatag cttactggga cgaagacgaa cacttcttca tagttgaccg cttgaagtct 1320
ttaattaaat acaaaggata tcaggtggcc cccgctgaat tggaatcgat attgttacaa 1380
caccccaaca tcttcgacgc gggcgtggca ggtcttcccg acgatgacgc cggtgaactt 1440
cccgccgccg ttgttgtttt ggagcacgga aagacgatga cggaaaaaga gatcgtggat 1500
tacgtcgcca gtcaagtaac aaccgcgaaa aagttgcgcg gaggagttgt gtttgtggac 1560
gaagtaccga aaggtcttac cggaaaactc gacgcaagaa aaatcagaga gatcctcata 1620
aaggccaaga agggcggaaa gtccaaattg taa 1653

<210> SEQ ID NO 208
<211> LENGTH: 936
<212> TYPE: DNA
<213> ORGANISM: Artificial sequence
<220> FEATURE:
<221> NAME/KEY: misc_feature
<222> LOCATION: (1)..(936)
<223> OTHER INFORMATION: Codon redesigned coding sequence.

<400> SEQUENCE: 208
atggcttcca aggtgtacga ccccgagcaa cgcaaacgca tgatcactgg gcctcagtgg 60
tgggctcgct gcaagcaaat gaacgtgctg gactccttca tcaactacta tgattccgag 120
aagcacgccg agaacgccgt gatttttctg catggtaacg ctgcctccag ctacctgtgg 180
aggcacgtcg tgcctcacat cgagcccgtg gctagatgca tcatccctga tctgatcgga 240
atgggtaagt ccggcaagag cgggaatggc tcatatcgcc tcctggatca ctacaagtac 300
ctcaccgctt ggttcgagct gctgaacctt ccaaagaaaa tcatctttgt gggccacgac 360
tggggggctt gtctggcctt tcactactcc tacgagcacc aagacaagat caaggccatc 420
gtccatgctg agagtgtcgt ggacgtgatc gagtcctggg acgagtggcc tgacatcgag 480
gaggatatcg ccctgatcaa gagcgaagag ggcgagaaaa tggtgcttga gaataacttc 540
ttcgtcgaga ccatgctccc aagcaagatc atgcggaaac tggagcctga ggagttcgct 600
gcctacctgg agccattcaa ggagaagggc gaggttagac ggcctaccct ctcctggcct 660
cgcgagatcc ctctcgttaa gggaggcaag cccgacgtcg tccagattgt ccgcaactac 720
aacgcctacc ttcgggccag cgacgatctg cctaagatgt tcatcgagtc cgaccctggg 780
ttcttttcca acgctattgt cgagggagct aagaagttcc ctaacaccga gttcgtgaag 840
gtgaagggcc tccacttcag ccaggaggac gctccagatg aaatgggtaa gtacatcaag 900
agcttcgtgg agcgcgtgct gaagaacgag cagtaa 936

<210> SEQ ID NO 209
<211> LENGTH: 253
<212> TYPE: DNA
<213> ORGANISM: Agrobacterium tumefaciens

<400> SEQUENCE: 209
gatcgttcaa acatttggca ataaagtttc ttaagattga atcctgttgc cggtcttgcg 60
atgattatca tataatttct gttgaattac gttaagcatg taataattaa catgtaatgc 120
atgacgttat ttatgagatg ggtttttatg attagagtcc cgcaattata catttaatac 180
gcgatagaaa acaaaatata gcgcgcaaac taggataaat tatcgcgcgc ggtgtcatct 240
atgttactag atc 253

<210> SEQ ID NO 210
<211> LENGTH: 622
<212> TYPE: DNA
<213> ORGANISM: Cauliflower mosaic virus

<400> SEQUENCE: 210
ggtccgattg agacttttca acaaagggta atatccggaa acctcctcgg attccattgc 60
ccagctatct gtcactttat tgtgaagata gtggaaaagg aaggtggctc ctacaaatgc 120
catcattgcg ataaaggaaa ggccatcgtt gaagatgcct ctgccgacag tggtcccaaa 180
gatggacccc cacccacgag gagcatcgtg gaaaaagaag acgttccaac cacgtcttca 240
aagcaagtgg attgatgtga tggtccgatt gagacttttc aacaaagggt aatatccgga 300
aacctcctcg gattccattg cccagctatc tgtcacttta ttgtgaagat agtggaaaag 360
gaaggtggct cctacaaatg ccatcattgc gataaaggaa aggccatcgt tgaagatgcc 420
tctgccgaca gtggtcccaa agatggaccc ccacccacga ggagcatcgt ggaaaaagaa 480
gacgttccaa ccacgtcttc aaagcaagtg gattgatgtg atatctccac tgacgtaagg 540
gatgacgcac aatcccacta tctagacgca agacccttcc tctatataag gaagttcatt 600
tcatttggag aggacacgct ga 622

<210> SEQ ID NO 211
<211> LENGTH: 1446
<212> TYPE: DNA
<213> ORGANISM: Cucumis melo

<400> SEQUENCE: 211
tcccttcagc cacttaacac ttaaaaatct taggaaactc catgggctcc tctttctcca 60
atgaaatttt gacatctgtg ttgttgatag ctcctatatc ctttgagaat ttgatataca 120
cctgtcattt gctgatttgt ggataactgt tagccttttg atattgatac gttccttttt 180
ttatgaattt ttgtaaatcc attcaatttt aatgctgtcg taaatgaaaa gccctttcat 240
taatgttgtt tatatacata ttttaaaatt aattcaataa caagtttagt tctgttagct 300
tctaggtttg tatctatttt atctattaaa ggtatgtttg ggcttcaggt tggaatggag 360
tagaattgaa tgggttgggg agtaaatttt ccattcaaca agttcaattt caaaatggct 420
aataagtttt gaactcaatt ttattttcaa taaattcctt aattttttgt tccttgtttg 480
taaactattg acttattcga tatattttaa aattgaggta ttttaaaaaa ataatacaat 540
attaaaatta tttataaaat ataacaaaat ttatgtatag tttatttgaa aattttacta 600
tagtttcatt tttatattat tcctaaccat ttccatttaa aattatttca attatttctt 660
ttattaatat aattgaaatt tcatggattt attagacaca tgatttgaaa ttttatgggt 720
ttattaagta ttttctaaca caaaatcgct tccgcatcgt tttcaattca ttcagtaata 780
gaagtaattt tttaaaagaa ccaaatttgc caaattttga gttccataag gactctgaaa 840
actcattatg tctattactc ttcactaatt gtagagactt aaattcaaga taagagacac 900
taattgatga taattgccca aaaaataaaa ataaaaatgt ttcttcccca tcctcaacct 960
ccatgaattc acagagccca aagattaatt attgggcccc aattcctact catatatacc 1020
ttacagtccc tcaaagaaat cttaggaagt aatcaatttc tgtttattca agatgtagcc 1080
tcccaaaaga aaaatacatc acatcaaatt caaacaaaaa tatctacagc tagcaaaacc 1140
tcaaaccgtt aaaatttcaa gccacataaa tgaaattttc atctgaaaaa aggacaatct 1200
atctagacgt tagatttcag ccctaatatg aatctgaagc atttggtgga cgagaaagag 1260
ccatgtagga atgcatcaaa caaaggaaaa atctttgaac tccaatggga ttgaagatac 1320
agataccaat ggataagaat ctgttctctt tgcccactat ttaaactcac caaacccacc 1380
agtatcttcc tcaccacaaa atacattcca ccgttgatca caagccttat tccaccacct 1440
ccaaca 1446

<210> SEQ ID NO 212
<211> LENGTH: 2018
<212> TYPE: DNA
<213> ORGANISM: Cucumis melo

<400> SEQUENCE: 212

-continued

```
actattggag acgacgaagg aaaactctaa tgtgagctta gaattgaaga tggtgaacaa     60
ttgggagtct tttttaaaaa tctttcgtcg gtatattgaa atttcctttt acactcaaat    120
aacccccctt ttcacgcgtt caacgtcttc aaaccttcct ttttcaatta ttttttcgtt    180
tacattaatg acatttaggt aataagataa attagtggat tcttttgtga aaaatgttag    240
cccatttaag acttttatga aatatattag aaaaaaatca tatagcaatt tatattattc    300
tagttaaaag cccataatag aaactaaccc aacctaaagt aacgtaaaca ttcaataaga    360
gagacaaatt ttaaaataat ttctaattaa aaaaaaaatt gtcaagaccg tccgggtcgg    420
atccaaaata taacccgaac cggccggttt agcatctata taaatacacc tttagggttt    480
ttattctctc aagacttcac cgcatttcca cttctctgag gccacggtca gccattggag    540
cagctcaata atcctttgac tccctactac ggtaagtcga ccttactgct ttcggcttct    600
agtttttca atcctgtcat tagtcctttg gagttcttct gtacatttat gacgttttcg    660
gctcgtgttt tgtttcgcct gtatgtagtg ggtttttcga gttttgtttt tactttttt    720
tatacttgca ggaattagtt gaaatctatg tacttcatgc cttggataat actcttgatc    780
tgttgtgtta ttcaaaatga attgttttaa gatggtattt gagaatggtc atgtgagttt    840
tgcctacttg gttattaaaa tgaattgttt taggatggta tttgagaatg gtcttctggg    900
tatttggttg gaacctttgt gctctgctat gaattagggt gttctccccg ttttttttt    960
ttttttctt ttggttatta atatatcttt tatgactact tattcatata tgatatcttt   1020
tactcgtaaa ttttgactca tttgaaagtt ttatccttag tcctttctca ttcagggtgt   1080
aaaggtatgt tgttagggtt aaaatagcct atgcaggaaa gttctgtatt tgttctaatt   1140
attgcatttg tgtgcatttg tatctagttt atttcttgct gagagtatgc ttcattttt    1200
agtacacatc acttgtgcca ctttattata gttgcacatt tttgtttatg gagaggatga   1260
atagcattta gggatgtcaa ttttttattg agaaaaccct ctctcctact taagcttggg   1320
gaatttttgt tctaaatgtg gtaaacataa tacttcttct tattttaatt tgaatggaag   1380
gggaagacga atactaatat tttcaacgaa ccttcacaac tttttttttc ttatttagga   1440
agccatgttt ttcaaaattg tactgtgtga tccacatatt tatcgattat tagtgaatcg   1500
aataataatt agagttttat tggtataatt ttgaagttca gacttattac atttgtggaa   1560
agtttggtta caattttcaa ttttattgga atcctaagaa ctttgtgtta acatatattg   1620
agttttcttc tcttttttt tactcattaa gttctctatt aggaatgttt ggttcaatgt   1680
cacatagtcg atagctaaga ccagtgaccc acaaagctat gattgaacga aaaacaagcc   1740
tttcacatct tggtaggaat ttgttatttc tcaatagatt tacagagctg tttcatgtga   1800
tcacaatttt tttctatttt tctgaagttc tctattagga atgggctatc tggttagttg   1860
cttttgagag aacatgtgga ttggtgttgc tcggtttcct tgcctttgta attttgtcct   1920
tggaaaaagc aaaatgatta ggtatcctga tatgcataac atgtttaagc caactagttc   1980
tcactttttt agtgcaaata attgatcttc aggaatcg                          2018
```